United States Patent
Feng et al.

(10) Patent No.: US 10,596,234 B2
(45) Date of Patent: Mar. 24, 2020

(54) COMPOSITIONS AND METHODS TO INHIBIT VIRAL REPLICATION

(71) Applicants: Pinghui Feng, Los Angeles, CA (US); Jun Zhao, Los Angeles, CA (US)

(72) Inventors: Pinghui Feng, Los Angeles, CA (US); Jun Zhao, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/798,388

(22) Filed: Oct. 30, 2017

(65) Prior Publication Data

US 2018/0193430 A1  Jul. 12, 2018

Related U.S. Application Data

(60) Provisional application No. 62/414,592, filed on Oct. 28, 2016.

(51) Int. Cl.
*A61K 38/46* (2006.01)
*C12N 15/10* (2006.01)
*A61K 47/64* (2017.01)
*C12N 9/14* (2006.01)

(52) U.S. Cl.
CPC ............ *A61K 38/46* (2013.01); *A61K 47/646* (2017.08); *C12N 9/14* (2013.01); *C12N 15/1096* (2013.01); *C12N 2710/16663* (2013.01); *C12Y 306/04013* (2013.01)

(58) Field of Classification Search
CPC ............ A61K 48/0066; A61K 2039/53; A61K 38/00; A61K 39/0011; A61K 2039/572; A61K 2039/575; A61K 38/193; A61K 38/212; A61K 35/76; A61K 35/763; A61K 38/162; A61K 38/21; A61K 38/46; A61K 47/646; A61P 35/00; A61P 31/20; A61P 31/14; A61P 31/12; A61P 31/00; A61P 37/02; C12N 15/117; C12N 2310/17; C12N 9/14; C12N 15/1096; C12N 10/16663; C07K 14/4705; C12Y 306/04013
See application file for complete search history.

(56) References Cited

U.S. PATENT DOCUMENTS

2015/0017207 A1* 1/2015 Gale, Jr. ............... C07H 21/04
424/211.1

FOREIGN PATENT DOCUMENTS

CA 2660622 A1 * 9/2010 ........... C07K 14/705

OTHER PUBLICATIONS

Anchisi, et al. "RIG-I ATPase Activity and Discrimination of Self-RNA versus Non-Self-RNA", mBio, vol. 6, Issue 2, Mar./Apr. 2015, e02349-14.
Chan, et al., "RIG-I-like receptor regulation in virus infection and immunity", Current Opinion in Virology, 2015, 2, pp. 7-14.
Dong, et al., "Murine Gamma Herpesvirus 68 Hijacks MAVS and IKKbeta to Abrogate NFkappaB Activation and Antiviral Cytokine Production", PLoS Pathogens, Nov. 2011, vol. 7, e1002336.
Dong, et al., "Murine Gammaherpesvirus 68 Evades Host Cytokine Production via Replication Transactivator-Induced ReIA Degradation", Journal of Virology 86, 2012, pp. 1930-1941.
Feng, et al., "Evasion of adaptive and innate immune response mechanisms by gamma-herpesviruses", Current Opinion in Virology, 2013, 3, pp. 285-295.
He, et al., Viral Pseudo-Enzymes Activate RIG-I via Deamidation to Evade Cytokine Production, Molecular Cell 58, Apr. 2, 2015, pp. 134-146.
Kato, et al., "Differential roles of MDA5 and RIG-I helicases in the recognition of RNA viruses," Nature, vol. 441, May 4, 2006, pp. 101-105.
Kawai, et al., "IPS-1, an adaptor triggering RIG-I- and Mda5-mediated type I interferon induction", Nature Immunology, vol. 6, No. 10, Oct. 2005, pp. 981-988.
Lassig, et al., "ATP hydrolysis by the viral RNA sensor RIG-I prevents unintentional recognition of self-RNA", elife, 2015, 4, e10859.
Luo, et al., "Duplex RNA activated ATPases (DRAs): Platforms for RNA sensing, signaling and processing", RNA Biology, 10:1, 2013, pp. 111-120.
Meylan, et al., "Cardif is an adaptor protein in the RIG-I antiviral pathway and is targeted by hepatitis C virus", Nature, vol. 437, Oct. 20, 2005, pp. 1167-1172.
Seth, et al., "Identification and Characterization of MAVS, a Mitochondrial Antiviral Signaling Protein that Activates NF-kappaB and IRF3", Cell, vol. 122, Sep. 9, 2005, pp. 669-682.
Sun, et al., "The Specific and Essential Role of MAVS in Antiviral Innate Immune Responses", Immunity 24, May 2006, pp. 633-642.
Takahasi, et al., "Nonself RNA-Sensing Mechanism of RIG-I Helicase and Activation of Antiviral Immune Responses", Molecular Cell 29, Feb. 29, 2008, pp. 428-440.
Xu, et al., "VISA is an Adapter Protein Required for Virus-Triggered IFN-beta Signaling", Molecular Cell, vol. 19, Sep. 16, 2005, pp. 727-740.

* cited by examiner

*Primary Examiner* — Rachel B Gill
(74) *Attorney, Agent, or Firm* — Foley & Lardner LLP; Antoinette F. Konski; Peter Diez

(57) ABSTRACT

This disclosure provides vaccine and therapeutic active against viral infections such as herpes simplex virus 1 (HSV-1) infections.

36 Claims, 68 Drawing Sheets
Specification includes a Sequence Listing.

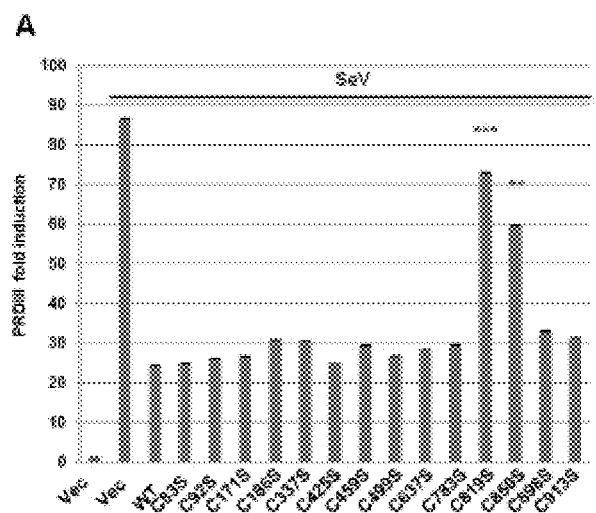
FIG. 7A
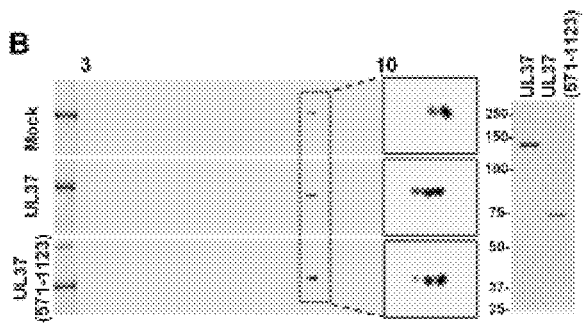
FIG. 7B
FIG. 7C

COMPOSITIONS AND METHODS TO INHIBIT VIRAL REPLICATION

CROSS-REFERENCE TO RELATED APPLICATION

This application claims the benefit under 35 U.S.C. 119(e) of U.S. Provisional Ser. No. 62/414,592, filed Oct. 28, 2016, the contents of which is hereby incorporated by reference into the present disclosure.

STATEMENT OF GOVERNMENT SUPPORT

This invention was made with government support under the Grant No. DE021445, awarded by the National Institute for Health. Accordingly, the U.S. Government has certain rights to the invention.

SEQUENCE LISTING

The instant application contains a Sequence Listing which has been submitted electronically in ASCII format and is hereby incorporated by reference in its entirety. Said ASCII copy, created on Jan. 31, 2018, is named 064189-0551_SL.txt and is 233,889 bytes in size.

BACKGROUND

Throughout this disclosure, various patent and technical publications are identified by an identifying citation or an Arabic numeral, the full citations for which are found immediately preceding the claims. These citations and the publications referenced within the present specification are incorporated by reference into the present disclosure to more fully describe the state of the art to which this invention pertains.

Innate immunity is the first line of host defense. In response to invading pathogens, pattern recognition receptors (PRRs) sense pathogen-associated molecular patterns (PAMPs) that are structural components or replication intermediates (Medzhitov, 2007; Takeuchi and Akira, 2010; Ting et al., 2010). PRRs include the cytosolic receptors (e.g., cGAS, IFI16, RIG-I-like and NOD-like receptors) and the membrane-anchored Toll-like receptors (TLRs) and C-type lectins. Upon binding to PAMPs, PRRs recruit cognate adaptor molecules that signal to activate two closely-related kinase complexes, IKKα/β and TBK-1/IKKε. IKKα/β phosphorylates and induces the degradation of the inhibitor of NF-κB (IκBs), leading to the nuclear translocation of NF-κB (Chen et al., 1996; Zandi et al., 1997). TBK-1/IKKε can directly phosphorylate interferon regulatory factors (IRFs) to induce its dimerization and translocation into the nucleus (Fitzgerald et al., 2003; Sharma et al., 2003). Along with other transcription factors, nuclear NF-κB and IRFs coordinate to up-regulate the expression of many immune genes to engender an antiviral state (Bhatt and Ghosh, 2014). The cytosolic RIG-I receptor is a genuine RNA sensor that, in response to viral infection, activates NF-κB and IRFs through the mitochondrion antiviral signaling (MAVS) protein (Kawai et al., 2005; Meylan et al., 2005; Seth et al., 2005; Xu et al., 2005). Studies entailing gene knockout mice demonstrate that loss of RIG-I or MAVS severely impairs host innate immune response and greatly increases viral replication (Kato et al., 2006; Sun et al., 2006). Not surprisingly, viruses have evolved diverse strategies to halt or hijack antiviral signaling downstream of RIG-I and MAVS (Chan and Gack, 2015; Feng et al., 2013).

Post-translational modification (PTM) is a major means to regulate protein function and underpins diverse fundamental biological processes. First reported more than five decades ago (Mycek and Waelsch, 1960), deamidation of asparagine/glutamine in protein has long been regarded as a non-specific process associated with protein "aging". Early protein deamidation research surveyed the overall deamidation of the cellular proteome, and led to the postulate that non-enzymatic protein deamidation serves as a biological clock for protein "aging" (Robinson and Robinson, 2001; Weintraub and Deverman, 2007). As such, research in protein deamidation is scarce and accordingly Applicant's understanding is rudimentary at best. A few proteins (e.g., Bcl-$x_L$ and 4EBP2) were shown to be regulated by deamidation in mammalian cells, which was postulated to be the consequence of an increase in cellular pH (Bidinosti et al., 2010; Deverman et al., 2002; Dho et al., 2013). Recent studies demonstrate that pathogenic bacteria secrete effectors to deamidate key signaling molecules to evade host immune defenses (Cui et al., 2010; Sanada et al., 2012) and manipulate cellular signaling (Flatau et al., 1997; Schmidt et al., 1997), indicating that protein deamidation can be catalyzed by bacterial enzymes and is highly regulated. The roles of protein deamidation in metazoan remain largely unclear.

SUMMARY

It has been reported that gamma herpesviruses, including human Kaposi's sarcoma-associated herpesvirus (KSHV) and murine gamma herpesvirus 68 (γHV68), deploy vGAT pseudo-enzymes to induce RIG-I deamidation (He et al., 2015; Kolakofsky and Garcin, 2015). Though lacking intrinsic enzyme activity, vGAT proteins recruited cellular phosphoribosylformylglycinamidine synthetase (PFAS, also known as FGARAT) to deamidate and concomitantly activate RIG-I. Activated RIG-I was harnessed by γHV68 to evade antiviral cytokine production (Dong and Feng, 2011; Dong et al., 2012). Applicant reports here that herpes simplex virus 1 (HSV-1) induces RIG-I deamidation to prevent RIG-I activation by viral dsRNA. The UL37 tegument protein was sufficient to deamidate RIG-I in cells and in vitro, making it the first viral protein deamidase to be identified. Site-specific deamidation within the helicase 2i domain impaired the RNA detection and ATP hydrolysis of RIG-I. Uncoupling RIG-I deamidation from HSV-1 infection restored RIG-I activation and anti-viral cytokine production, thereby reducing HSV-1 replication. This work delineates a pivotal role of protein deamidation in sensing nucleic acid by a PRR and demonstrates that HSV-1 exploits protein deamidation to evade innate immune defense.

The therapeutic and prophylactic interventions and screens disclosed herein are derived from Applicant's disclosed discoveries. As background, RIG-I detects double-stranded RNA (dsRNA) to trigger antiviral cytokine production. Protein deamidation is emerging as a post-translational modification that chiefly regulates protein function. Applicant reports here that UL37 of herpes simplex virus 1 (HSV-1) is a protein deamidase that targets RIG-I to block RNA-induced activation. Mass spectrometry analysis identified two asparagine residues in the helicase 2i domain that were deamidated upon UL37 expression or HSV-1 infection. Deamidations in the helicase 2i domain rendered RIG-I unable to sense viral dsRNA, trigger antiviral immune responses and restrict viral replication. Purified full-length UL37 and its carboxyl terminal fragment were sufficient to deamidate RIG-I in vitro. Uncoupling RIG-I deamidation from HSV-1 infection, via engineering deamidation-resistant RIG-I or introducing deamidase-deficient UL37 into the HSV-1 genome, restored RIG-I activation and antiviral immune signaling. This work defines the first viral deamidase and a pivotal role of protein deamidation in sensing microbial pathogens by a pattern recognition receptor.

This disclosure provides an isolated polynucleotide encoding a RIG-I mutant and equivalents thereof as well as compliment thereto. In one aspect, the RIG-I mutant is RIG-I-QQ. A non-limiting example of this polypeptide is SEQ ID NO. 4, and equivalents thereof and complements thereto. An equivalent is one or more polypeptide that retains amino acids at positions 495 and/or 549 that make the protein deaminase resistant, e.g., a substitution of Q at positions 495 and/or 549. Vectors and host cells are further provided herein. Complementary polypeptides to these are further provided herein.

Further provided are polypeptides are encoded by polynucleotides.

Compositions containing one or more of the polynucleotides, proteins, vectors and host cells and one or more carriers, are further provided herein. In one aspect, the compositions contain buffers, stabilizers and/or preservatives. In a further aspect, the compositions are lyophilized for ease of transport, storage and use.

The compositions can be formulated for administration as a vaccine or therapeutic composition and contain an effective immunity-inducing amount of the active components and optionally an adjuvant. The compositions can be further formulated into dosage units that can be packaged into kits with instructions for use.

The compositions are useful in methods to inhibit viral replication by contacting the virus in a cell, tissue or subject in need thereof by with an effective amount of an agent that inhibits the deamidation activity of UL37. Also provided is a method to abolish 5'-ppp-RNA-binding and ATP hydrolysis is a cell, tissue or subject infected with the virus, as well as to inhibit or "switch off RIG-1 by contacting the cell, tissue or administering to the subject an effective amount of a composition as provided herein. In another aspect, provided herein is a method to block RNA-induced activation by a cell, tissue or subject in need thereof by contacting the cell, tissue or administering to the subject. In a further aspect, this disclosure also provides a method to induce an anti-viral immune response in a subject in need thereof by administering an effective amount of a composition as described herein.

In one aspect, the virus is an virus that exhibits these activities such as a DNA virus, e.g., a virus of the class Herpesviridae, e.g., HIV-1 or HSV-2 virus.

Methods to determine if the methods are effective are known in the art and disclosed herein, e.g., a reduction in viral load, deamination assay, ATPase activation assay, enhanced immunity, e.g., B-cell or T-cell adaptive immunity, etc.

The contacting can be in vitro or in vivo, and the administration can be effected by methods known in the art, e.g., injection or oral administration. Multiple administrations can be provided as necessary.

For in vivo methods, the subject to be treated is any subject at risk of or having a viral infection, e.g., a pet, sports animal or human patient.

BRIEF DESCRIPTION OF THE FIGURES

(FIG. 1A) HEK293/Flag-RIG-I cells were mock-infected or infected with HSV-1 (MOI=2) or Sendai virus (SeV, 100 HAU/ml) for 4 hours. Whole cell lysates (WCLs) were analyzed by two-dimensional gel electrophoresis. (FIGS. 1A-1B) HEK293 cells were mock-infected or infected with HSV-1 (MOI=2) for 1 h and super-infected with SeV (100 HAU/ml) for 8 (FIG. 1B) or 16 h (FIG. 1C). The expression of the indicated antiviral genes was analyzed by real-time PCR using total RNA (FIG. 1B). Supernatant was collected to determine IFN-β by ELISA (FIG. 1C). (FIG. 1D) HEK293/Flag-RIG-I were mock-infected or infected with HSV-1 for 1 h, followed by SeV infection (100 HAU/ml) for 4 h. RIG-I was purified and analyzed by gel filtration and immunoblotting. Numbers indicate the size of RIG-I in kDa and $V_0$ denotes void volume. For FIGS. 1B-1D, WCLs were analyzed by immunoblotting with antibodies against SeV, HSV-1 UL37 and β-actin. ***, p<0.001 was calculated in reference to cells infected with SeV. For FIGS. 1B-1C, data are presented as mean±SD.

(FIG. 2A) 293T cells were transfected with plasmids containing GST-RIG-I and the indicated open reading frames of HSV-1. WCLs were precipitated with the indicated antibody. WCLs and precipitated proteins were analyzed by immunoblotting. (FIGS. 2B-2C) 293T cells were infected with recombinant HSV-1 UL37-Flag at MOI of 30 for 1 h (FIG. 2B) or MOI of 1 for 8 and 16 h (FIG. 2C). WCLs were precipitated with anti-Flag (M2) antibody. RIG-I and WCLs were analyzed by immunoblotting with indicated antibodies.

(FIGS. 3A-3F) Whole cell lysates (WCLs) of 293T cells stably expressing UL37 were analyzed by immunoblotting with anti-V5 (UL37) and anti-β-actin antibodies (FIG. 3A). Cells were infected with Sendai virus (SeV) (100 HAU, 8 h) and total RNA was analyzed by real-time PCR with primers specific for the indicated genes (FIG. 3B). WCLs were analyzed by immunoblotting with antibodies against V5 (UL37), SeV and β-actin (FIG. 3C). Supernatant was harvested for cytokines determined by ELISA at 16 hpi, and WCLs were analyzed by immunoblotting with antibodies against SeV and β-actin (FIG. 3D). Cells were transfected with poly [I:C] and the PRDIII-luc reporter. Activation of the PRDIII promoter was determined by luciferase reporter assay (FIG. 3E). 293T stable cells were infected with SeV (100 HAU/ml) for 1 and 3 h, and WCLs were analyzed for the phosphorylation of TBK-1 and IRF3 by immunoblotting (FIG. 3F). (FIGS. 3G-3H) 293T cells stably expressing Flag-RIG-I and RIG-I-V5 were transfected with an empty or UL37-containing plasmid. At 30 h post-transfection, cells were infected with SeV (100 HAU/ml) for 4 h. WCLs were precipitated with anti-Flag. Precipitated proteins and WCLs were analyzed by immunoblotting with the indicated antibodies (FIG. 3G). 293T/Flag-RIG-1 cells, without or with UL37-V5 expression (by lentivirus), were mock-infected or infected with SeV (100 HAU/ml) for 4 h. Purified RIG-I was analyzed by gel filtration and immunoblotting. Numbers at the top indicate the size of RIG-I in kDa and $V_0$ denotes void volume (FIG. 3H). (FIG. 3I) Diagram of key components of the RIG-I-mediated IFN induction pathway. (FIG. 3J) 293T cells were transfected with plasmids containing MAVS, TBK1 and the constitutively active IRF3-5D, along with the IFN-β reporter plasmid and a UL37-containing plasmid. Activation of the IFN-β promoter was determined by luciferase assay. WCLs were analyzed by immunoblotting with anti-Flag (M2) (MAVS, TBK-1 and IRF3-5D) and anti-V5 (UL37) antibodies (right panels). ***, p<0.001. For FIG. 3B, FIG. 3D, FIG. 3E and FIG. 3J, data are presented as mean±SD.

(FIG. 4A) HEK293/Flag-RIG-I cells were transfected with an empty or UL37-containing plasmid. Whole cell lysates (WCLs) were analyzed by two-dimensional gel electrophoresis and immunoblotting with the indicated antibodies. (FIGS. 4B-4C) HEK293/Flag-RIG-I cells were transfected with a UL37-expressing plasmid or infected with HSV-1 (MOI=1) for 12 h. RIG-I was purified and analyzed by tandem mass spectrometry. Two peptides (SEQ ID NOS 50-51, respectively, in order of appearance), containing deamidated asparagines were identified. D495 and D549 (in red) were shown (FIG. 4B). Deamidated peptides were quantitatively determined by tandem mass spectrometry analysis and data represents one of two independent experiments (FIG. 4C). (FIG. 4D) HEK293/Flag-RIG-I or HEK293/Flag-RIG-I-DD cells were transfected with an empty or UL37-containing plasmid. WCLs were analyzed by two-dimensional gel electrophoresis and immunoblotting. (FIG. 4E) GST-RIG-I and UL37 were purified from transfected 293T cells and $E.$ $coli$, respectively, and analyzed by silver staining (right panels). Deamidation reaction was analyzed by two-dimensional gel electrophoresis and immunoblotting with anti-RIG-I antibody.

(FIG. 5A) $N^{955}$ and $N^{549}$ are located in the helicase 2i domain of the RIG-I structure (PDB ID: 3TMI). dsRNA is shown as helices in dark yellow. (FIG. 5B) Purified RIG-I and RIG-I-DD were incubated with [$^{32}$P]-labeled 5'-triphosphate 19mer dsRNA and analyzed by electrophoresis mobility shift assay. (FIGS. 5C-5D) Purified RIG-I and RIG-I-DD were used for in vitro ATP hydrolysis with increasing amount of ATP (FIG. 5C) or 5'-triphosphate 19 mer dsRNA (FIG. 5D). (FIG. 5E) 293T cells stably expressing RIG-I-WT and RIG-I-DD were mock-infected or infected with Sendai virus (SeV, 100 HAU/ml) for 4 h. Purified RIG-I was analyzed by gel filtration and immunoblotting. Numbers at the top indicate the size of RIG-I in kDa and $V_0$ denotes void volume. (FIGS. 5F-5H) Rig-i$^{-/-}$ MEFs "reconstituted" with RIG-I-WT or RIG-I-DD were analyzed by immunoblotting with the indicated antibodies (FIG. 5F). Cells were infected with recombinant eGFP VSV (Indiana Strain, MOI=20) for 8 h, and total RNA was analyzed by real-time PCR (FIG. 5G). Cells were infected with VSV (MOI=0.05) and viral titer in the supernatant was determined by plaque assay (FIG. 5H) hpi, hours post-infection. For FIG. 5C, FIG. 5D, FIG. 5G and FIG. 5H, data are presented as mean±SD.

(FIG. 6A) N549 forms two hydrogen bonds with the backbone of T504 within the helicase 2i domain of the RIG-I structure (PDB ID: 4A36). (FIG. 6B) HEK293/Flag-RIG-I-WT or HEK293/Flag-RIG-I-QQ cells were transfected with an empty or UL37-containing plasmid. Whole cell lysates (WCLs) were analyzed by two-dimensional gel electrophoresis. (FIG. 6C) HEK293/Flag-RIG-I-QQ cells were mock-infected or infected with HSV-1 (MOI=5) or Sendai virus (SeV, 100 HAU/ml) for 4 h. Purified RIG-I was resolved by gel filtration and analyzed by immunoblotting. (FIGS. 6D-6F) Control HEK293 (Vec) or HEK293 cells stably expressing RIG-I-WT, RIG-I-DD or RIG-I-QQ were infected with HSV-1 (MOI=5) for 4 h and WCLs were analyzed by immunoblotting with the indicated antibodies (FIG. 6D). Total RNA was analyzed by real-time PCR (FIG. 6E). Supernatant was collected at 16 hpi and cytokines (IFN-β and RANTES) were quantified by ELISA (FIG. 6F). M, mock-infected; numbers on the top indicate hours post-infection in (FIG. 6D). (FIG. 6G) Stable HEK293 cell lines as above were infected with HSV-1 at MOI=0.5 and viral titer was determined by plaque assay. For FIG. 6E, FIG. 6F and FIG. 6G, data are presented as mean±SD.

FIGS. 7A-7H: A cysteine is required for UL37 deamidase activity. (FIG. 7A) 293T cells were transfected with plasmids containing UL37 wild-type or mutants, along with the PRDIII-luciferase reporter. Cells were infected with Sendai virus (SeV, 100 HAU/mL) at 30 h later for 15 hours. Activation of the PRDIII promoter was determined by luciferase reporter assay. (FIG. 7B) UL37 and UL37 (571-1123) were purified from $E.$ $coli$ and analyzed by silver staining (right panel). In vitro RIG-I deamidation reaction was analyzed by two-dimensional gel electrophoresis and immunoblotting. (FIG. 7C) UL37C (571-1123) was reacted with CNM (1 and 10 µM) for 45 minutes and analyzed by tandem mass spectrometry. The ratio of peptide containing the indicated cysteines is shown as the percentage of the CNM-modified peptide to total peptide. Data represents one of two independent experiments. (FIGS. 7D-7E) HEK293/Flag-RIG-I cells were infected with recombinant HSV-1 UL37-WT or HSV-1 UL37-C819S (MOI=5) for 4 h. WCLs were analyzed by two-dimensional gel electrophoresis and immunoblotting (FIG. 7D). RIG-I was purified and analyzed by gel filtration and immunoblotting (FIG. 7E). Numbers indicate the size of RIG-I in kDa and $V_0$ denotes void volume. (FIGS. 7F-7G) THP-1 cells were harvested at 8 h after HSV-1 infection (MOI=2) and total RNA was analyzed by real-time PCR (FIG. 7F). Supernatant was collected at 16 hpi to quantify cytokines by ELISA (FIG. 7G). (FIG. 7H) HFF cells were infected with HSV-1 UL37-WT and HSV-1 UL37-C819S at MOI of 0.1. Viral replication was determined by plaque assays. , p<0.01 and *, p<0.001. For FIGS. 7A, 7F, 7G and 7H, data are presented as mean±SD.

(FIG. 8A) HFF cells stably expressing control, IFI16 or RIG-I shRNA were prepared by lentiviral transduction. RNA was extracted and cDNA was prepared to determine IFI16 and RIG-I mRNA expression by real-time PCR analysis. Stable cells were then infected with HSV-1 (MOI=5) for the indicated hours. RNA was extracted and cDNA was prepared to determine IFN-β mRNA expression by real-time PCR analysis. (FIG. 8B) 293T cells stably expressing control or RIG-I shRNAs were prepared by lentiviral transduction. WCLs were analyzed by SDS-PAGE and immunoblotting with the indicated antibodies. (FIG. 8C) Control and RIG-I knockdown 293T cells were mock-infected or infected with HSV-1 of indicated MOI for 24 h. RNA was extracted and cDNA was prepared to determine IFN-β and ISG56 mRNA expression by real-time PCR analysis. (FIG. 8D) Control and RIG-I knockdown HeLa cells were mock-infected or infected with HSV-1 of indicated MOI for 24 h. RNA was extracted and cDNA was prepared to determine IFN-β and ISG56 mRNA expression by real-time PCR analysis. (FIG. 8E) THP1 cells stably expressing control or RIG-I shRNA were prepared by lentiviral transduction. Cells were then infected with HSV-1 (MOI=5) for the indicated hours. RNA was extracted and cDNA was prepared to determine IFN-β and ISG56 mRNA expression by real-time PCR analysis. (FIG. 8F) 293T cells were infected with HSV-1 (MOI=5) for 2 h and then transfected with LMV Poly [I:C] for 8 h. RNA was extracted and cDNA was prepared to determine IFN-β and ISG56 mRNA expression by real-time PCR analysis. (FIG. 8G) 293T cells were transfected with a plasmids containing RIG-I and those containing indicated ORFs of HSV-1. Whole cell lysates (WCLs) were harvested and RIG-I was immunoprecipitated, followed by SDS-PAGE analysis and immunoblotting with the indicated antibodies. (FIG. 8H) 293T cells were transfected with plasmids containing UL37 and RIG-I/MDA5. RIG-I/MDA5 was immunoprecipitated. Precipitated proteins and WCL were analyzed by immunoblotting with indicated antibodies. (FIG. 8I) 293T cells were infected by HSV-1 (MOI=5) for 15 h. WCLs were analyzed by gel filtration and immunoblotting with indicated antibodies. p<0.01, *p<0.001, error bars denote SD (n=3).

(FIG. 9A) 293T cells were transfected with a PRDIII (ISRE) reporter cocktail and increasing amounts of a plasmid containing UL37. Transfected cells were subsequently infected with Sendai virus (SeV, 100 [HAU]/ml) for 15 h. Fold induction of the PRDIII reporter was determined by luciferase assay. (FIG. 9B) 293T cells were transfected with an IFN-β reporter cocktail and increasing amounts of a plasmid containing UL37. Transfected cells were subsequently infected with SeV (100 [HAU]/ml) for 15 h. Fold induction of the PRDIII reporter was determined by luciferase assay. (FIG. 9C) Control 293T and 293T cells stably expressing UL37 were infected with SeV (100 [HAU]/ml) for 10 h. RNA was extracted and cDNA was prepared to determine IL8 and CXCL2 mRNA expression by real-time PCR analysis. (FIG. 9D) 293T cells were transfected with an NF-κB reporter cocktail and increasing amounts of a plasmid containing UL37. Fold induction of the NF-κB reporter was determined by luciferase assay. (FIG. 9E) 293T cells were transfected with PRDIII reporter cocktail and increasing amounts of a plasmid containing UL37. Fold induction of the PRDIII reporter was determined by luciferase assay. (FIG. 9F) (Left) Rig-i$^{+/+}$ and Rig-i$^{-/-}$ MEF cells were transfected with an NF-κB reporter cocktail and a plasmid containing UL37 via NEON transfection system. Fold induction of the NF-κB reporter was determined by luciferase assay. (Right) 293T cells were transfected with a PRDIII reporter cocktail and a plasmid containing MDA5, with increasing amounts of a plasmid containing UL37. Fold induction of the PRDIII reporter was determined by luciferase assay. (FIG. 9G) Control 293T and 293T cells stably expressing UL37 were infected with SeV (100 [HAU]/ml) for 8 h. WCLs were analyzed by native PAGE and immunoblotting with anti-IRF3 antibody. (FIG. 9H) HeLa cells were transfected with a control plasmid or a plasmid containing UL37, and then infected with SeV (100 [HAU]/ml) for 8 h. IRF3 nuclear translocation was analyzed by immunofluorescence microscopy with anti-IRF3 antibody. p<0.01, *p<0.001, error bars denote SD (n=3).

(FIG. 10A) 293T cells were transfected with a plasmid containing MDA5 and either a vector or a plasmid containing UL37. WCLs were analyzed by 2-dimensional gel electrophoresis (2DGE) and immunoblotting with indicated antibodies. (FIG. 10B) 293T/RIG-I cells were mock-infected or infected with HSV-1 (MOI=5) or transfected with a plasmid containing UL37. RIG-I was purified and analyzed by SDS-PAGE and coommassie staining. (FIG. 10C) 293T/RIG-I cells were transfected with a plasmid containing UL37 and subsequently treated with or without DON (10 μM). WCLs were analyzed by 2DGE and immunoblotting with indicated antibodies. β-actin served as an internal control.

(FIG. 11A) 293T cells were transfected with a PRDIII reporter cocktail and plasmids containing RIG-I, RIG-I-N495D, RIG-I-N549D, RIG-I-DD and RIG-I-N(1-200), respectively. Fold induction of the PRDIII reporter was determined by luciferase assay. (FIG. 11B) 293T cells were transfected with an NF-κB reporter cocktail and plasmids containing RIG-I, RIG-I-N495D, RIG-I-N549D, RIG-I-DD and RIG-I-N(1-200), respectively. Fold induction of the NF-κB reporter was determined by luciferase assay. (FIG. 11C) RIG-I WT and the indicated mutants were purified from transfected 293T cells and analyzed by SDS-PAGE and silver staining. (FIG. 11D) Purified RIG-I, RIG-I-N495D, RIG-I-N549D and RIG-I-DD were incubated with $^{32}$P-labeled 5'-triphosphate dsRNA (20 nM), with and without a 500-fold excess of cold 5'-triphosphate dsRNA. RNA-RIG-I complex was analyzed by PAGE and autoradiography. (FIG. 11E) Purified RIG-I and RIG-I-DD were incubated with $^{32}$P-labeled 5'-triphosphate dsRNA (20 nM) or $^{32}$P-labeled control dsRNA, with and without a 500-fold excess of cold dsRNA. RNA-RIG-I complex was analyzed by PAGE and autoradiography. (FIG. 11F) Purified RIG-I, RIG-I-DD and RIG-I-K270A were incubated with $^{32}$P-labeled 5'-triphosphate dsRNA (20 nM), with and without a 500-fold excess of cold 5'-triphosphate dsRNA. RNA-RIG-I complex was analyzed by PAGE and autoradiography. (FIG. 11G) Purified RIG-I, RIG-I-N495D, RIG-I-N549D and RIG-I-DD (20 nM) were incubated with increasing concentrations of ATP in the presence of 5'-triphosphate dsRNA (80 nM) and analyzed by ATP hydrolysis assay. (FIG. 11H) Purified RIG-I, RIG-I-N495D, RIG-I-N549D and RIG-I-DD (20 nM) were incubated with increasing concentrations of dsRNA in the presence of ATP (1000 μM) and analyzed by ATP hydrolysis assay. (FIG. 11I) "Reconstituted" MEFs as shown in FIG. 5G were infected with Sendai virus (100 [HAU]/ml) for 10 h. RNA was extracted and cDNA was prepared to determine IFN-β and ISG56 mRNA expression by real-time PCR analysis. p<0.01, *p<0.001, error bars denote SD (n=3).

(FIG. 12A) 293T cells were transfected with a PRDIII reporter cocktail and increasing amount of a plasmid containing UL37-WT, UL37-C819S or UL37-C850S. Transfected cells were subsequently infected with Sendai virus (SeV, 100 [HAU]/ml) for 15 h. Fold induction of the PRDIII reporter was determined by luciferase assay. (FIG. 12B) 293TRex/RIG-I cells were transfected with a plasmid containing UL37-WT, UL37-C819S or UL37-C850S. WCLs were analyzed by 2-dimensional gel electrophoresis and immunoblotting with indicated antibodies. (FIG. 12C) 293T cells were transfected with the ISRE reporter plasmid cocktail and increasing amounts of a plasmid containing UL37 (1-1123), UL37 (571-1123) or UL37 (730-1123). At 16 hours later, cells were infected with SeV (100 HAU) for 14 hours. Fold induction of the ISRE promoter was determined by luciferase assay. (FIG. 12D) Recombinant HSV-1 carrying flag-tagged wild-type UL37 or C819S UL37 was generated by homologous recombination. Viral DNA was extracted from infected Vero cells and digested by BamHI. DNA fragments were analyzed by agarose gel electrophoresis. (FIG. 12E) 293T cells were infected with HSV-1 (KOS), HSV-1 UL37-WT or HSV-1 UL37-C819S (MOI=5) for 20 h, respectively. WCLs were analyzed by immunoblotting with indicated antibodies.

(FIG. 13A) HeLa cells were infected with recombinant HSV-1 UL37-WT or HSV-1 UL37-C819S (MOI=5) for the indicated hours. RNA was extracted and cDNA was prepared to determine IFN-β and ISG56 mRNA expression by real-time PCR analysis. (FIG. 13B) HeLa and 293T cells were infected with recombinant HSV-1 as in (A). Supernatant was harvested and IFN-β was quantified by ELISA. (FIG. 13C) (Top) HFF cells stably expressing control or STING shRNA were prepared by lentiviral transduction. WCLs were analyzed by immunoblotting with the indicated antibodies. (Bottom) HFF stable cells were infected with recombinant HSV-1 (MOI=5) as in (A). RNA was extracted and cDNA was prepared to determine IFN-β mRNA expression by real-time PCR analysis. (FIG. 13D) HeLa cells were infected with recombinant HSV-1 (MOI=0.1/1) as in (A) for the indicated hours. Supernatant was harvested and HSV-1 viral titer was measured by plaque assay. (FIG. 13E) Vero cells were infected with recombinant HSV-1 (MOI=0.1) as in (A) for the indicated hours. Supernatant was harvested and HSV-1 viral titer was measured by plaque assay. (FIG. 13F) HFF cells stably expressing control or RIG-I shRNA were prepared by lentiviral transduction as in FIG. 8A. Cells were then infected with recombinant HSV-1 (MOI=0.1) as in (FIG. 13A) for the indicated hours. Supernatant was harvested and HSV-1 viral titer was measured by plaque assay. $p<0.01$, $*p<0.001$, error bars denote SD (n=3).

(FIG. 14A and FIG. 14B). Human THP-1 monocytes were infected with HSV-1 UL37 wild-type (HSV-1 WT) or HSV-1 containing the deamidase-deficient UL37C819S mutant (HSV-1 C819S) at MOI=5. The expression of inflammatory cytokines was determined by real-time PCR at the indicated time points (FIG. 14A). Medium was collected at 16 hours post-infection and IFN-β was determined by ELISA (FIG. 14B). In FIG. 14C, THP-1 monocytes were infected as described in (FIG. 14A). Whole cell lysates prepared at various time points post-infection were analyzed by immunoblotting with the indicated antibodies. p- indicates phosphorylated TBK1 or IRF3. In FIG. 14D, wild-type and cGAS knockout L929 mouse fibroblasts were infected with HSV-1 WT and HSV-1 UL37C819S at MOI=5. L929 cells were harvested at 8 hours post-infection and the expression of the indicated cytokine genes were analyzed by real-time PCR. In FIG. 14E, THP-1 monocytes were infected as described in (FIG. 14A). cGAMP was extracted and quantified using permeabilized THP-1 reporter cells. For FIGS. 14A, 14B, 14D and 14E, $p*<0.5$, $p***<0.005$.

In FIG. 15A, THP-1 monocytes infected with control (Vector) or UL37-expressing lentivirus were selected with puromycin and whole cell lysates (WCLs) were analyzed by immunoblotting with the indicated antibodies. FIG. 15B shows stable THP-1 cell lines as described in (FIG. 15A) were transfected with HT-DNA. Cells were harvested at 6 hours post-infection (hpi) and the expression of IFNB1 and ISG56 were analyzed by real-time PCR (FIG. 15B). Medium was harvested at 16 hpi and IFN-β was determined by ELISA (FIG. 15C). In FIG. 15C, stable THP-1 cell lines were transfected with cGAMP (2 µg/ml). Cells were harvested at 8 h post-transfection, and the expression of IFNB1 and ISG56 were analyzed by real-time PCR. In FIG. 15D, control (V) or UL37-expressing (U) THP-1 cells were left non-transfected (NT), or transfected with HT-DNA or cGAMP. Cells were harvested at 3 h post-transfection and WCLs were analyzed by immunoblotting with the indicated antibodies. In FIG. 15E, THP-1 cells were infected with control (Vector) or UL37-expressing lentivirus to establish stable cells lines as in (FIG. 15A). WCLs were analyzed by immunoblotting with the indicated antibodies. In FIG. 15F, stable THP-1 cell lines were transfected with HT-DNA. Cells were harvested at 6 h post-transfection. The relative mRNA quantity of IFNB1 was determined by real-time PCR (FIG. 15G), while intracellular cGAMP was extracted and the concentration was determined (FIG. 15H).

FIG. 16A shows that human THP-1 monocytes were infected with HSV-1 carrying Flag-tagged UL37 at MOI=0.5. At 16 hours post-infection (hpi), cells were harvested and whole cell lysates (WCLs) were precipitated with anti-FLAG (UL37). Precipitated proteins and WCLs were analyzed by immunoblotting with antibody against cGAS or FLAG (UL37). In FIG. 16B, 293T cells stably expressing FLAG-tagged cGAS were transfected with vector or vector containing UL37. At 30 h post-transfection, WCLs were prepared and analyzed by two-dimensional gel electrophoresis (2-DGE) and immunoblotting with the indicated antibodies. In FIG. 16C, cGAS-expressing 293T cells were mock-infected or infected with HSV-(MOI=10). At 4 hpi, WCLs were analyzed by 2-DGE and immunoblotting with the indicated antibodies. In FIGS. 16D and 16E, purified cGAS was analyzed by tandem mass spectrometry. The m/z spectrum of a deamidated peptide (SEQ ID NO: 52) containing Q451 and Q454 is shown. Es in darker color indicates deamidated residues (FIG. 16D). The relative deamidation efficiency was calculated by number of deamidated peptides and total number of peptides. Data represents results of two independent experiments (FIG. 16E). In FIG. 16F, 293T cells stably expressing wild-type cGAS or the deamidated cGAS-DDEE mutant were transfected with vector or vector containing UL37. WCLs were prepared, and analyzed by 2-DGE and immunoblotting as described in (FIG. 16B). In FIG. 16G, purified cGAS or deamidated cGAS-DDEE mutant (as fusion constructs with maltose-binding protein from E. coli), UL37 and its deamidase-deficient UL37 C819S mutant were analyzed by silver staining (left panels). In vitro deamidation reactions were analyzed by 2-DGE and immunoblotting (right panels).

In FIG. 17A, 293T cells were transfected with an IFN-β reporter plasmid cocktail with plasmids containing cGAS wild-type or the deamidated cGAS-DDEE mutant. At 30 h post-transfection, IFN-γ activation was determined by luciferase assay (top panel), while whole cell lysates (WCLs) were analyzed by immunoblotting with the indicated antibodies (bottom panels). In FIG. 17B, the N196 residue is located in proximity to the catalytic active site, consisting of E211, D213 (not shown) and D307 (PDB: 4K9B). cGAMP, in relation to E211 and D307, is also shown. In FIG. 17C, in vitro cGAMP synthesis was measured with purified cGAS or its deamidated mutants, including N201D and DDEE, with or without HT-DNA. Reactions were analyzed by thin layer chromatography (left panel). The relative intensity of cGAMP was determined by densitometry analysis (right panel). Data represents more than three independent experiments. In FIG. 17D, cGAS-deficient L929 cells were infected with control (Vector) lentivirus or vector containing cGAS wild-type (WT) or the deamidated cGAS-DDEE mutant (DDEE). WCLs prepared from stable L929 cells were analyzed by immunoblotting with the indicated antibodies. In FIG. 17E, "reconstituted" cGAS stable cell lines as described in FIG. 17D were transfected with HT-DNA. Cells were harvested at 6 h post-transfection and the expression of the indicated inflammatory genes was analyzed by real-time PCR. In FIGS. 17G-17H, "reconstituted" cGAS stable cell lines were infected with HSV-1 (MOI=0.01) (FIG. 17G) or murine herpesvirus 68 (MHV68) (H) (MOI=0.05). Viral titers in the supernatant at the indicated time points were determined by plaque assays. For C, E, G and H, p<0.01; p*<0.005.

In FIGS. 18A-18B, age (10-12-week old) and gender-matched BL6 mice were intravenously infected with HSV-1 UL37 wild-type (WT) or HSV-1 UL37C819S (C819S) ($5 \times 10^7$ PFU). Blood was collected at 8 hours post-infection (hpi) and cytokines in sera were determined by ELISA (FIG. 18A). In FIGS. 18C-18E, mice were sacrificed at 3 days post-infection and the viral genome copy numbers in the brain were determined by real-time PCR analysis (FIG. 18B). In FIGS. 18C-18E, mice infection with HSV-1 was carried out as in FIG. 18A. Mouse survival was recorded over time (FIG. 18C). Infected mice were sacrificed at the indicated days post-infection (dpi). The spleens were harvested and isolated T cells were analyzed by flow cytometry after staining with gB-specific tetramer (FIG. 18D). Sera were collected at the indicated time points and antibody titer was determined by ELISA. In FIG. 18F and FIG. 18G, (FIG. 18F) or STING (FIG. 18G), were infected with HSV-1 UL37 wild-type (WT) or the deamidase-deficient HSV-1 UL37C819S (UL37C819S) ($5 \times 10^7$ PFU).

FIG. 19A is diagram of the experimental design for immunization and challenge with HSV-1 wild-type. Wk, week. In FIG. 19B and FIG. 19C, age-(10-12-week old) and gender-matched BALB/c mice were intraperitoneally infected with HSV-1 UL37C819S (C819S) ($1 \times 10^6$ PFU) twice at an interval of two weeks or received PBS injection (control). Mice were intravenously challenged with lethal doses of HSV-1 wild-type ($5 \times 10^6$ PFU) and survival was recorded (FIG. 19A). No mouse died up to 20 days post-infection (dpi) in the vaccinated group. Mouse body weight was determined and recorded (FIG. 19B). In FIG. 19D and FIG. 19E, mock-infected mice and mice vaccinated with PBS or HSV-1 UL37C819S were challenged with lethal doses of HSV-1 as described in (FIG. 19A), and sacrificed at 3 dpi. Mouse brains were collected and fixed. Brain sections analyzed by Haematoxylin & Eosin staining. Representative images are shown (FIG. 19D). Boxed regions have been amplified and are shown below the original images. Scale bars denote 100 μm (top) and 50 μm (bottom). In FIG. 19F and FIG. 19G, brain sections as described in FIG. 19D, were stained with anti-UL37 rabbit serum and representative images are shown (FIG. 19F), with boxed regions amplified and displayed below. UL37-positive cells were counted from five randomly selected fields and the percentage of HSV-1-positive cells was semi-quantitatively determined (FIG. 19G). In FIG. 19H, brain sections were also stained with antibody against NeuN (a neuron marker), and representative images are shown in FIG. 19F.

SEQUENCE LISTING

Figure 1A:
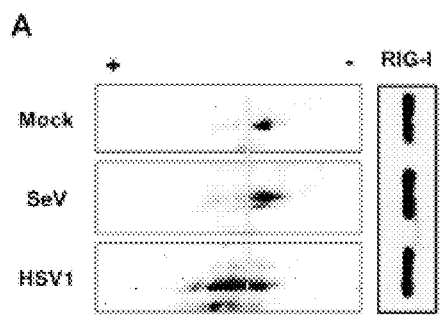
FIGS. 1A-1D: HSV-1 evades RNA-induced activation of RIG-I.

Attached are nucleotide sequences that are relevant to disclosure;

SEQ ID NO.: 1 is the wild-type polynucleotide sequence of UL37.

SEQ ID NO.: 2 is the mutated polynucleotide sequence designated UL37 C819S.

SEQ ID NO.: 3 depicts wild-type RIGI polypeptide.

SEQ ID NO.: 4 depicts mutated RIG-I-QQ polypeptide.

SEQ ID NO.: 5 depicts the polynucleotide sequence of Strain KOS of HSV-1, a mutated HSV-1 having mutated UL37.

DETAILED DESCRIPTION

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides, antibodies, proteins, host cells and polynucleotides that are isolated from other cellular proteins or tissues and is meant to encompass both purified and recombinant polypeptides, antibodies, proteins and polynucleotides. In other embodiments, the term "isolated" means separated from constituents, cellular and otherwise, in which the cell, tissue, polynucleotide, peptide, polypeptide, protein, antibody or fragment(s) thereof, which are normally associated in nature and can include at least 80%, or alternatively at least 85%, or alternatively at least 90%, or alternatively at least 95%, or alternatively at least 98%, purified from a cell or cellular extract. For example, an isolated polynucleotide is separated from the 3' and 5' contiguous nucleotides with which it is normally associated in its native or natural environment, e.g., on the chromosome. An isolated cell, for example, is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

The term "binding" or "binds" as used herein are meant to include interactions between molecules that may be detected using, for example, a hybridization assay. The terms are also meant to include "binding" interactions between molecules. Interactions may be, for example, protein-protein, antibody-protein, protein-nucleic acid, protein-small molecule or small molecule-nucleic acid in nature. This binding can result in the formation of a "complex" comprising the interacting molecules. A "complex" refers to the binding of two or more molecules held together by covalent or non-covalent bonds, interactions or forces.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment" as used herein, also refers to a peptide chain.

The phrase "equivalent polypeptide" or "biologically equivalent peptide or peptide fragment" or "biologically equivalent polynucleotide" refers to a protein or a peptide fragment which is homologous to the exemplified reference polynucleotide, protein or peptide fragment and which exhibit similar biological activity in vitro or in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence identity or homology. Percentage homology can be determined by sequence comparison using programs such as BLAST run under appropriate conditions. In one aspect, the program is run under default parameters.

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Homology" or "identity" or "similarity" are synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

The term "non-contiguous" refers to the presence of an intervening peptide, nucleotide, polypeptide or polynucleotide between a specified region and/or sequence. For example, two polypeptide sequences are non-contiguous because the two sequences are separated by a polypeptide sequences that is not homologous to either of the two sequences. Non-limiting intervening sequences are comprised of at least a single amino acid or nucleotide.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product such as RNA or a polypeptide or protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced there from.

Applicant have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "composition" is intended to mean a combination of active polypeptide, polynucleotide or antibody and another compound or composition, inert (e.g. a detectable label) or active (e.g. a gene delivery vehicle) alone or in combination with a carrier which can in one embodiment be a simple carrier like saline or pharmaceutically acceptable or a solid support as defined below.

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Cell," "host cell" or "recombinant host cell" are terms used interchangeably herein. It is understood that such terms refer not only to the particular subject cell but to the progeny or potential progeny of such a cell. The cells can be of any one or more of the type murine, rat, rabbit, simian, bovine, ovine, porcine, canine, feline, equine, and primate, particularly human.

Because certain modifications may occur in succeeding generations due to either mutation or environmental influences, such progeny may not, in fact, be identical to the parent cell, but are still included within the scope of the term as used herein.

Herpesviridae is a large family of DNA viruses that cause diseases in animals, including humans. Non-limiting examples of the members include HSV-1, HSV-2, varicella zoster virus, Epstein-Barr virus, cytomegalovirus, varicella-zoster virus, human herpesvirus 6A and 6B, and Karposi's sarcoma-associated herpesvirus.

"Treating," "treatment," or "ameliorating" of a disease includes: (1) preventing the disease, i.e., causing the clinical symptoms of the disease not to develop in a patient that may be predisposed to the disease but does not yet experience or display symptoms of the disease; and/or (2) inhibiting the disease, i.e., arresting or reducing the development of the disease or its clinical symptoms; and/or (3) relieving the disease, i.e., causing regression of the disease or its clinical symptoms.

The term "suffering" as it related to the term "treatment" refers to a patient or individual who has been diagnosed with or is predisposed to a disease or infection by a virus. A patient may also be referred to being "at risk of suffering" from a disease or infection by a virus. This patient has not yet developed characteristic disease pathology, however are known to be predisposed to the disease due to family history, being genetically predispose to developing the disease, or diagnosed with a disease or disorder that predisposes them to developing the disease to be treated.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific compound employed, bioavailability of the compound, the route of administration, the age of the animal and its body weight, general health, sex, the diet of the animal, the time of administration, the rate of excretion, the drug combination, and the severity of the particular disorder being treated and form of administration. In general, one will desire to administer an amount of the compound that is effective to achieve a serum level commensurate with the concentrations found to be effective in vivo. These considerations, as well as effective formulations and administration procedures are well known in the art and are described in standard textbooks.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell.

A "probe" when used in the context of polynucleotide manipulation refers to an oligonucleotide that is provided as a reagent to detect a target potentially present in a sample of interest by hybridizing with the target. Usually, a probe will comprise a detectable label or a means by which a label can be attached, either before or subsequent to the hybridization reaction. Alternatively, a "probe" can be a biological compound such as a polypeptide, antibody, or fragments thereof that is capable of binding to the target potentially present in a sample of interest.

"Detectable labels" or "markers" include, but are not limited to radioisotopes, fluorochromes, chemiluminescent compounds, dyes, and proteins, including enzymes. Detectable labels can also be attached to a polynucleotide, polypeptide, antibody or composition described herein.

A "primer" is a short polynucleotide, generally with a free 3'—OH group that binds to a target or "template" potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or a "set of primers" consisting of an "upstream" and a "downstream" primer, and a catalyst of polymerization, such as a DNA polymerase, and typically a thermally-stable polymerase enzyme. Methods for PCR are well known in the art, and taught, for example in MacPherson et al. (1991) PCR 1: A Practical Approach (IRL Press at Oxford University Press). All processes of producing replicate copies of a polynucleotide, such as PCR or gene cloning, are collectively referred to herein as "replication." A primer can also be used as a probe in hybridization reactions, such as Southern or Northern blot analyses. Sambrook and Russell (2001), infra.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^2$ normally found in a cell.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

The term "propagate" means to grow a cell or population of cells. The term "growing" also refers to the proliferation of cells in the presence of supporting media, nutrients, growth factors, support cells, or any chemical or biological compound necessary for obtaining the desired number of cells or cell type.

The term "culturing" refers to the in vitro propagation of cells or organisms on or in media of various kinds. It is understood that the descendants of a cell grown in culture may not be completely identical (i.e., morphologically, genetically, or phenotypically) to the parent cell.

A "viral vector" is defined as a recombinantly produced virus or viral particle that comprises a polynucleotide to be delivered into a host cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

In aspects where gene transfer is mediated by a lentiviral vector, a vector construct refers to the polynucleotide comprising the lentiviral genome or part thereof, and a therapeutic gene. As used herein, "lentiviral mediated gene transfer" or "lentiviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. Retroviruses carry their genetic information in the form of RNA; however, once the virus infects a cell, the RNA is reverse-transcribed into the DNA form which integrates into the genomic DNA of the infected cell. The integrated DNA form is called a provirus. As used herein, lentiviral vector refers to a viral particle capable of introducing exogenous nucleic acid into a cell through a viral or viral-like entry mechanism. A "lentiviral vector" is a type of retroviral vector well-known in the art that has certain advantages in transducing nondividing cells as compared to other retroviral vectors. See, Trono D. (2002) Lentiviral vectors, New York: Spring-Verlag Berlin Heidelberg.

Lentiviral vectors of this invention are based on or derived from oncoretroviruses (the sub-group of retroviruses containing MLV), and lentiviruses (the sub-group of retroviruses containing HIV). Examples include ASLV, SNV and RSV all of which have been split into packaging and vector components for lentiviral vector particle production systems. The lentiviral vector particle according to the invention may be based on a genetically or otherwise (e.g. by specific choice of packaging cell system) altered version of a particular retrovirus.

That the vector particle according to the invention is "based on" a particular retrovirus means that the vector is derived from that particular retrovirus. The genome of the vector particle comprises components from that retrovirus as a backbone. The vector particle contains essential vector components compatible with the RNA genome, including reverse transcription and integration systems. Usually these will include gag and pol proteins derived from the particular retrovirus. Thus, the majority of the structural components of the vector particle will normally be derived from that retrovirus, although they may have been altered genetically or otherwise so as to provide desired useful properties. However, certain structural components and in particular the env proteins, may originate from a different virus. The vector host range and cell types infected or transduced can be altered by using different env genes in the vector particle production system to give the vector particle a different specificity.

"RNA interference" (RNAi) refers to sequence-specific or gene specific suppression of gene expression (protein synthesis) that is mediated by short interfering RNA (siRNA).

"Short interfering RNA" (siRNA) refers to double-stranded RNA molecules (dsRNA), generally, from about 10 to about 30 nucleotides in length that are capable of mediating RNA interference (RNAi), or 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, or 29 nucleotides in length. As used herein, the term siRNA includes short hairpin RNAs (shRNAs).

"Double stranded RNA" (dsRNA) refer to double stranded RNA molecules that may be of any length and may be cleaved intracellularly into smaller RNA molecules, such as siRNA. In cells that have a competent interferon response, longer dsRNA, such as those longer than about 30 base pair in length, may trigger the interferon response. In other cells that do not have a competent interferon response, dsRNA may be used to trigger specific RNAi.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides in length. For example, the stem can be 10-30 nucleotides in length, or alternatively, 12-28 nucleotides in length, or alternatively, 15-25 nucleotides in length, or alternatively, 19-23 nucleotides in length, or alternatively, 21-23 nucleotides in length.

Tools to assist siRNA design are readily available to the public. For example, a computer-based siRNA design tool is available on the internet at www.dharmacon.com, Ambion-www.ambion.com/jp/techlib/misc/siRNA_finder.html; Thermo Scientific-Dharmacon-www.dharmacon.com/DesignCenter/DesignCenterPage.aspx; Bioinformatics Research Center-sysbio.kribb.re.kr:8080/AsiDesigner/menuDesigner.jsf; and Invitrogen-maidesigner.invitrogen.com/maiexpress/.

As used herein, the term "purification label" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly(NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

MODES FOR CARRYING OUT THE ASPECTS OF THE DISCLOSURE

Applicant has identified a mechanism by which certain virus evade a host's innate immune response. Provided herein are compositions and methods that build upon this discovery. To that end, in one aspect provided herein is an isolated polynucleotide encoding a RIG-I-QQ mutant and equivalents thereof. Non-limiting examples of equivalents include polynucleotides that hybridize under stringen conditions to the polynucleotide (e.g., a polynucleotide encoding SEQ ID NO. 4) and sequences having at least 70% sequence identity to a polynucleotide encoding SEQ ID NO. 4). In one aspect, the isolated polynucleotide encodes the polypeptide shown in SEQ ID NO. 4, and equivalents that retain amino acids at positions 495 and/or 549 that make the protein deaminase resistant, e.g., substitution of Q at position positions 495 and/or 549. The isolated polynucleotides can be included within a vector or other gene delivery vehicle or isolated host cell. The RIG-I-QQ polypeptide and equivalents thereof can be combined or contained with a host cell and/or with a carrier, such as a pharmaceutically acceptable carrier. The polypeptide and proteins can be chemically and/or recombinantly produced using methods known in the art, using host cells containing the polynucleotides and culturing the cell under conditions for expression and/or replication of the polynucleotides or polypeptides. The polypeptides and polynucleotides can be further combined with a detectable label or a purification label and used for purification and/or in drug development screens. Compositions containing the RIG-I-QQ mutant or an equivalent thereof can be combined with other antiviral agents and immune enhancing compositions such as an vaccine adjuvant.

Also provided herein is an isolated mutated UL37 polynucleotide that fails to deaminate RIG-I polypeptide. Non-limiting examples of such is the polynucleotide is a modified wild-type UL 37 mutated at positions 819 and 850, e.g., identified herein as UL 37 C819S (SEQ ID NO.: 2) and C850S, and equivalents thereof. The isolated mutated UL37 polynucleotides fail to deaminate RIG-I polypeptide. The mutated polynucleotides can be combined with a label, e.g., a detectable or purification label for screening, probes, primers or other assays. The polynucleotides can be chemically or recombinantly produced using methods known in the art. In one aspect, they are combined within an HSV vector or virus and are useful in vaccine compositions. In one aspect, they are combined with a carrier, such as a pharmaceutically acceptable carrier and/or adjuvant. The compositions can be incorporated into a kit and can further contain instructions for use, e.g., in the methods disclosed herein.

The agents and compositions of the present disclosure can be used in the manufacture of medicaments and for the treatment of humans and other animals by administration in accordance with conventional procedures, such as an active ingredient in pharmaceutical compositions.

Also provided are methods for one or more of:

a. inhibiting viral replication in a cell or tissue;
b. abolishing 5'-ppp-RNA-binding and ATP hydrolysis is a cell or tissue;
c. switching off RIG-1 in a cell or tissue;
d. blocking RNA-induced activation in a cell or tissue;
e. inhibiting the deamidation activity of UL37 in a cell or tissue; or
f. inducing an anti-viral immune in a tissue;
g. inducing expression of anti-viral cytokine genes; or
h. enhancing adaptive immunity, by contacting the cell, virus or tissue or surface containing the virus with an effective amount of a composition as described herein, e.g., an agent that inhibits the deamidation activity of UL 37. Non-limiting examples of agents that inhibit the deamidation activity of UL 37 polynucleotide include, for example, antisense UL37 polynucleotides and UL37 interfering RNA molecules, e.g., siRNA, dsRNA, and shRNA, mutated RIG-I-QQ polynucleotide or an equivalent thereof, a mutated RIG-I-QQ polypeptide or an equivalent thereof, a mutated UL37 polynucleotide or an equivalent thereof, or a virus containing mutated UL37 polynucleotide or an equivalent thereof. Virus that are inhibited by the method includes virus that deaminate RIG-I, e.g., a virus of the class Herpesviradae, e.g., HSV-1, HSV-2, Varicella Zoster Virus and HCMV. The agents can be combined with a carrier for ease of administration.

The contacting can be performed in vitro or in vivo. When performed in vivo, the agent is administered to a subject infected with the virus or for whom prophylaxis is desired. Any suitable method of administration can be used in the method, e.g., topical, intravenous, by inhalation therapy. The subject is any animal that is susceptible to the viral infection e.g., a mammal or a human. The method can further comprise administration of an effective amount of an antiviral agent.

Administration can be effected in one dose, continuously or intermittently throughout the course of treatment. Methods of determining the most effective means and dosage of administration are known to those of skill in the art and will vary with the composition used for therapy, the purpose of the therapy, the infection being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intraperitoneal, intravenous and by inhalation.

Also provided herein is a method for one or more of:

a. inhibiting viral replication in subject infected with a virus;

b. abolishing 5'-ppp-RNA-binding and ATP hydrolysis in a subject;
c. switching off RIG-1 in a subject;
d. blocking RNA-induced activation in a subject;
e. inhibiting the deamidation activity of UL37 in a subject; or
f. inducing an anti-viral immune in a subject;
g. inducing expression of anti-viral cytokine genes; or
h. enhancing adaptive immunity, comprising administering to the subject an effective amount of the composition as described herein. In one aspect, the composition comprises an effective amount of mutated RIG-I polypeptide as described above (e.g., RIG-I-QQ or an equivalent thereof) or a virus containing a mutated UL37 polynucleotide that lacks the ability to deaminate RIG-I polypeptide. Any suitable method of administration can be used in the method, e.g., topical, intravenous, by inhalation therapy. The subject is any animal that is susceptible to the viral infection e.g., a mammal or a human. The method can further comprise administration of an effective amount of an antiviral agent. The virus and viral infections include virus that deaminate RIG-I, e.g., a virus of the class Herpesviradae, e.g., HSV-1, HSV-2, Varicella Zoster Virus and HCMV. The agents can be combined with a carrier for ease of administration.

"Administration" can be effected in one dose, continuously or intermittently throughout the course of treatment. Methods of determining the most effective means and dosage of administration are known to those of skill in the art and will vary with the composition used for therapy, the purpose of the therapy, the virus being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intraperitoneal, intravenous and by inhalation.

Materials and Methods
Experiment No. 1
Cell Lines and Viruses

HEK293T, HeLa, Vero, HCT116, BHK21, mouse embryonic fibroblasts (MEFs) and human foreskin fibroblasts (HFF) were cultured in Dulbecco's modified Eagle's medium (DMEM, Corning) supplemented with 10% heat-inactivated fetal bovine serum (FBS; HyClone), penicillin (100 U/mL) and streptomycin (100 µg/mL). Wild-type and Rig-i$^{-/-}$ MEFs were described previously (Kato et al., 2005). Wild-type HSV-1 (KOS strain), GFP HSV-1 and HSV-1 recombinant viruses were amplified in Vero cells, with viral titers ranging from $10^7$ to $10^8$ pfu/ml. eGFP VSV (Dr. Sean Whelan) was amplified in BHK21 cells, with viral titer of $10^9$ pfu/ml. Sendai virus was purchased from Charles River Laboratories.

Constructs

Luciferase reporter plasmids for the NF-κB, IFN-β promoter, PRDIII (ISRE) promoter, mammalian expression plasmids for RIG-I and their truncated mutants, MDA5, MAVS, IKKβ, TBK1, IRF3-5D, RelA were described previously (Dong et al., 2010; Dong and Feng, 2011; Dong et al., 2012; He et al., 2015; Seth et al., 2005). The non-silencing (control) shRNA and shRNA against human RIG-I, human IFI16 and human STING were purchased from Thermo Scientific. HSV-1 expression library was described previously (Sen et al., 2013). Mammalian expression plasmids for truncated RIG-I and UL37, lentiviral expression plasmids for RIG-I and UL37 were generated by standard molecular biology techniques. All point mutants, including those of RIG-I and UL37, were generated by site-directed mutagenesis and confirm by sequencing. HSV-1ΔUL37 (KOS) and HSV-1(KOS) Bacmid was a gift from Dr. Thomas C. Mettenleiter.

Antibodies and Reagents

Antibody against UL37 was a gift from Dr. Weiming Yuan. Antibodies against GST (Z-5), IRF3 (FL-425), TRAF6 (D10) and RIG-I (H-300) were purchased from Santa Cruz Biotechnology. Antibodies against FLAG (M2, Sigma), V5 (A190-220A, Bethyl Group), RIG-I (SS1A, Enzo Life Sciences), STING (ab92605, Abcam), dsRNA-J2 (SCICONS), Sendai Virus (PD029, MBL), P-S172 TBK-1 (D52C2, Cell Signaling) and β-actin (Ab8226, Abcam) were purchased from the indicated suppliers. The glutamine analog 6-Diazo-5-oxo-L-norleucine (DON) was purchased from Sigma. Low molecular weight Poly [I:C] (31852-29-6), ppp-dsRNA (tlrl-3prna) and control-dsRNA (tlrl-3prnac) were purchased from InvivoGen Lipofectamine 2000 was purchased from Life Technologies.

DNA and RNA Transfection

For plasmid transfection in HEK293T cells, calcium phosphate transfection method was applied. 293T cells were plated at around 50%-60% confluence. For dsRNA and Poly [I:C] transfection in 293T cells and plasmid transfection in HeLa cells, Lipofectamine 2000 transfection reagent was used according to the manufacturer's instructions. Both cells were prepared at around 80%-90% confluence prior to transfection.

Lentivirus-Mediated Stable Cell Line Construction

Lentiviruses were produced as previously described (Dong and Feng, 2011; Feng et al., 2008). Briefly, HEK293T cells were transfected with the packaging plasmids VSV-G and DR8.9 and the pCDH lentiviral expression vector or lentiviral shRNA plasmids. At 48 h post transfection, supernatant was harvested and filtered (and concentrated by centrifugation if necessary). HEK293T cells, MEFs, HeLa, HCT116 or HFF cells were infected with the supernatant in the presence of polybrene (8 µg/ml) with centrifugation at 1800 rpm for 45 minutes. Cells were selected at 48 h post infection and maintained in 10% FBS DMEM supplemented with puromycin (1~2 µg/ml).

Dual-Luciferase Reporter Assay

HEK293T cells, seeded in 24-well plates (~50% cell density), were transfected with IFN-β, PRDIII (ISRE) or NF-κB reporter plasmid cocktail (50 ng of luciferase reporter plasmid and 5 ng of pRL *Renilla* luciferase control vector) and expression plasmid (empty plasmid, one or multiple plasmids depending on the experiment) by calcium phosphate precipitation. Cells were infected with SeV (100 HA/ml), HSV-1 for 16 h, transfected with Poly [I:C] for 16 h or directly harvested 30-36 h post transfection. Whole cell lysates were used to determine the activity of firefly luciferase and *renilla* luciferase by a microplate reader (FLUOstar Omega).

Plaque Assay

HSV-1 and VSV titer were determined by plaque assay on Vero monolayer essentially as previously described (Lieber and Bailer, 2013). Briefly, 10-fold serially-diluted virus-containing supernatant was added onto Vero cells and incubated for 2 h at 37° C. Then, DMEM containing 2% FBS and 1% methylcellulose (Sigma) was added after removing the supernatant. Plaques were counted at day 3 post-infection.

Confocal Microscopy

HFF cells were infected with HSV-1 for 8 h (MOI=50). HeLa cells were transfected with expression plasmid containing UL37 and subsequently infected with Sendai Virus for 6 h (200 HA/ml). Cells were fixed, permeabilized, stained with indicated primary antibody (1:100 dilution) and Alexa Fluor 488/594-congugated goat secondary antibody (1:200 dilution), and analyzed with confocal microscope (Leica). Representative images were shown for all analyses.

Protein Expression and Purification

HEK293T cells were transfected with expression vector containing Flag-tagged gene of interest. Cells were harvested and lysed with Triton X-100 buffer (20 mM Tris, pH 7.5, 150 mM NaCl, 1.5 mM $MgCl_2$, 20 mM β-glycerophosphate, 1 mM sodium orthovanadate, 10% glycerol, 0.5 mM EGTA, 0.5% Triton X-100) supplemented with a protease inhibitor cocktail (Roche). Whole cell lysates were sonicated and centrifuged at 12,000 rpm for 15 min. Supernatant was harvested, filtered, pre-cleared with protein A/G agarose beads at 4° C. for 1 h and then incubated with anti-Flag agarose beads at 4° C. for 4 h. The agarose beads were washed extensively and eluted with 0.2 mg/ml 3× Flag peptide. The eluted proteins were analyzed by SDS gel electrophoresis and silver staining.

For recombinant protein expression and purification, *E. coli* B121(DE3) was transformed with pGEX-4T-1 or pET28 plasmid containing UL37. Recombinant GST-UL37 expression was induced by 0.1 mM IPTG at 20° C. Bacteria were harvested, lysed and incubated with glutathione sepharose 4B (GE) for 4 h at 4° C. Sepharose beads were washed extensively and GST-UL37 was eluted with 10 mM reduced glutathione. UL37 was then cleaved and purified from the fusion protein by TEV protease treatment at 4° C. overnight.

Co-Immunoprecipitation (Co-IP) and Immunoblotting

For Co-IP using exogenous protein, HEK293T cells were transfected with indicated expression plasmids for 48 h. For Co-IP using endogenous proteins, cells were directly harvested. Whole cell lysates were prepared with NP40 buffer (50 mM Tris-HCl, pH 7.4, 150 mM NaCl, 1% NP-40, 5 mM EDTA) supplemented with 20 mM β-glycerophosphate and 1 mM sodium orthovanadate. Whole cell lysates were sonicated, centrifuged and pre-cleared with protein A/G agarose for 1 h. Pre-cleared samples were then incubated with indicated antibodies overnight and protein A/G agarose for 1 h at 4° C., or with antibody/glutathione-conjugated agarose for 4 h at 4° C. The agarose beads were washed extensively and samples were eluted by boiling at 95° C. for 10 min. Precipitated proteins were analyzed by SDS gel electrophoresis and immunoblotting.

All immunoblottings were performed using the indicated primary antibodies (1:1000 dilution) and IRDye800-conjugated secondary antibodies (1:10,000 dilution, Licor). Proteins were visualized by Odyssey infrared imaging system (Licor).

Gel Filtration

Virus-infected HEK293T/Flag-RIG-I or HeLa/Flag-RIG-I stable cells were harvested and lysed in cold Triton X-100 buffer (20 mM Tris, pH 7.5, 150 mM NaCl, 1.5 mM $MgCl_2$, 20 mM β-glycerophosphate, 1 mM sodium orthovanadate, 10% glycerol, 0.5 mM EGTA, 0.5% Triton X-100, 1 mM PMSF and 10 μg/ml leupeptin). Centrifuged supernatant was filtered and subjected to incubation with anti-Flag-conjugated agarose beads for 2 h at 4° C. Beads were then extensively washed and proteins were eluted with 3× Flag peptide at 0.2 mg/ml.

Gel filtration with superose 6 was performed as described previously. Briefly, eluted proteins (200-300 μl) were loaded to superose 6 column and subjected to gel filtration analysis with Buffer B (20 mM Tris-HCl, pH 7.6, 150 mM NaCl, 1 mM EDTA, 0.5 mM EGTA, 0.5% Triton X-100, 20 mM NaF, 20 mM β-glycerophosphate, 1 mM $Na_3VO_4$, 2.5 mM metabisulphite [sodium salt], 5 mM benzamidine). Elution was collected in 0.5 ml fractions and aliquots of fractions were analyzed by immunoblotting.

Mock- or HSV-1-infected cells ($2\times10^7$) were harvested and lysed in 300 μl cold Triton X-100 buffer. Samples were sonicated briefly and centrifuged. Supernatant was filtered and loaded to superose 6 column and subjected to gel filtration analysis with Buffer B. Elution was collected in 0.5 ml fractions and aliquots of fractions were analyzed by immunoblotting.

Quantitative Real-Time PCR (qRT-PCR)

Quantitative Real-time PCR was performed as previously described. Cells were infected or treated with viruses or agents for indicated time period. Total RNA was extracted using TRIzol reagent (Invitrogen). Complementary cDNA was synthesized from DNase I-treated total RNA using reverse transcriptase (Invitrogen). cDNA was diluted and qRT-PCR was performed using SYBR Green Master Mix (Applied Biosystems) by real-time PCR instrument (Applied Biosystems). Relative mRNA expression for each target gene was calculated by the $2^{-\Delta\Delta Ct}$ method using β-Actin as an internal control. The sequences of qRT-PCR primers are as follows:

| | | | |
|---|---|---|---|
| Human β-actin | forward | 5'-CTGGCACCCAGCACAATG-3' | (SEQ ID NO: 6) |
| | reverse | 5'-GCCGATCCACACGGAGTACT-3' | (SEQ ID NO: 7) |
| Human IFN-β | forward | 5'-AGGACAGGATGAACTTTGAC-3' | (SEQ ID NO: 8) |
| | reverse | 5'-TGATAGACATTAGCCAGGAG-3' | (SEQ ID NO: 9) |
| Human ISG56 | forward | 5'-TCTCAGAGGAGCCTGGCTAA-3' | (SEQ ID NO: 10) |
| | reverse | 5'-TGACATCTCAATTGCTCCAG-3' | (SEQ ID NO: 11) |
| Human IL8 | forward | 5'-GGCACAAACTTTCAGAGACAG-3' | (SEQ ID NO: 12) |
| | reverse | 5'-ACACAGAGCTGCAGAAATCAGG-3' | (SEQ ID NO: 13) |
| Human CXCL2 | forward | 5'-GGGCAGAAAGCTTGTCTCAA-3' | (SEQ ID NO: 14) |
| | reverse | 5'-GCTTCCTCCTTCCTTCTGGT-3' | (SEQ ID NO: 15) |

| | | | |
|---|---|---|---|
| Human IFI16 | forward | 5'-ACAAACCCGAGAAACAATGACC-3' | (SEQ ID NO: 16) |
| | reverse | 5'-GCATCTGAGGAGTCCGAAGA-3' | (SEQ ID NO: 17) |
| Mouse β-actin | forward | 5'-ACGGCCAGGTCATCACTATTG-3' | (SEQ ID NO: 18) |
| | reverse | 5'-CAAGAAGGAAGGCTGGAAAAGA-3' | (SEQ ID NO: 19) |
| Mouse IFN-β | forward | 5'-TCCGAGCAGAGATCTTCAGGAA-3' | (SEQ ID NO: 20) |
| | reverse | 5'-TGCAACCACCACTCATTCTGAG-3' | (SEQ ID NO: 21) |
| Mouse ISG56 | forward | 5'-ACC ATG GGA GAG AAT GCT GAT-3' | (SEQ ID NO: 22) |
| | reverse | 5'-GCC AGG AGG TTG TGC-3' | (SEQ ID NO: 23) |

Cytokine ELISA

Commercial cytokine ELISA kits used in this study include: human IFN-β (PBL Assay Science) and human RANTES (R&D Systems). Cytokine levels in the supernatant from cultured cells were assessed according to manufacturer's instruction. Absorbance was determined with FLUOstar Omega (BMG Labtech.).

In Vitro ATPase Activity Assay

Purified RIG-I or RIG-I mutants were incubated with 5'-ppp-dsRNA (Invivogen) at 37° C. for 20 min in ATPase reaction buffer (50 mM Tris-HCl, pH 7.5, 2.5 mM $MgCl_2$, and ATP. Released phosphates were measured using a PiColorLock™ phosphate detection reagent (Innova Biosciences). For reactions with varying concentrations of ATP, the concentrations of RIG-I proteins and RNA were 20 nM and 80 nM, respectively. For reactions with varying concentrations of the RNA, the concentrations of RIG-I proteins and ATP were 20 nM and 500 μM, respectively.

Mass Spectrometry Analysis

For identification of deamidation sites, HEK293T/Flag-RIG-I stable cell line was transfected with an expression plasmid containing UL37 or infected by HSV-1 for 10 h (MOI=10). Flag-RIG-I was purified by anti-Flag-conjugated agarose beads for 4 h at 4° C. Beads were then extensively washed and RIG-I was eluted with 3× Flag peptide at 0.2 mg/ml. Purified RIG-I was subjected to SDS page electrophoresis and gel slices were prepared for in-gel digestion and Mass Spectrometry analysis (Harvard Taplin Mass Spectrometry Facility).

For Cysteine labeling experiment, bacterial purified UL37 (571-1123) was treated with N-methylacetamide (Alfa Aesar) (1 μM) at room temperature for 45 min. Samples were then blocked with Iodoacetamide (Sigma) (50 mM) at room temperature for 1 h and subjected to Mass Spectrometry analysis (Poochon Scientific).

Statistical Analysis

Statistical analysis was performed by unpaired two-tailed Student's t-test. *, $p<0.05$; , $p<0.01$; *, $p<0.001$. A p-value less than 0.05 is considered statistically significant.

Experimental Methods

HSV-1 Evades RNA-Induced RIG-I Activation

Applicant previously reported that the vGAT proteins of human KSHV and murine γHV68 recruit PFAS to deamidate RIG-I. In addition to these gamma herpesviruses, HSV-1 infection also increased negative charge of RIG-I as analyzed by two-dimensional gel electrophoresis (2-DGE), indicative of deamidation (FIG. 1A). However, genomes of HSV-1 and other alpha-herpesviruses contain no homologue of gamma herpesvirus vGAT proteins, suggesting a distinct mechanism of RIG-I deamidation. Additionally, the antiviral roles of RIG-I against DNA viruses, such as herpesviruses, are not well defined. Thus, Applicant investigated whether HSV-1 infection induces RIG-I deamidation and determined the functional consequence of RIG-I deamidation on host immune responses.

Figure 5A:
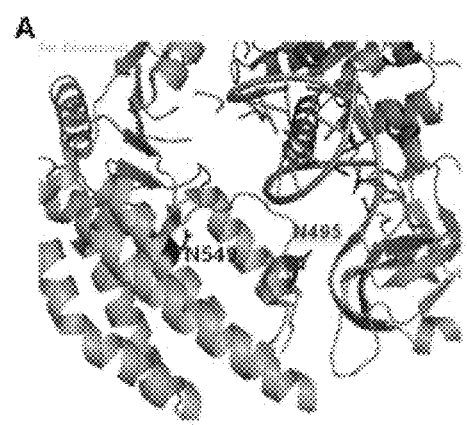
FIGS. 5A-5H: The deamidated RIG-I-DD mutant fails to sense viral dsRNA.
Figure 5B:
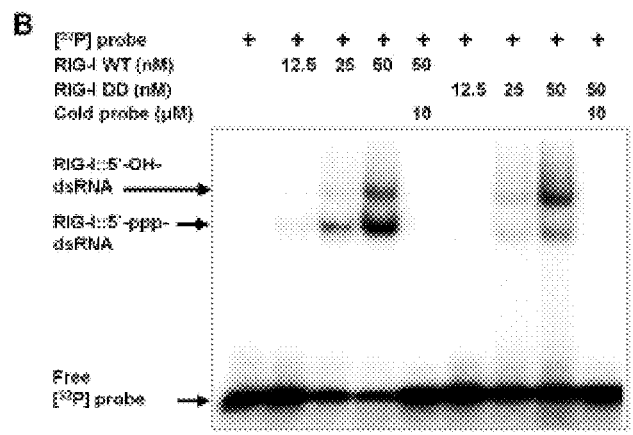
Figure 5C:
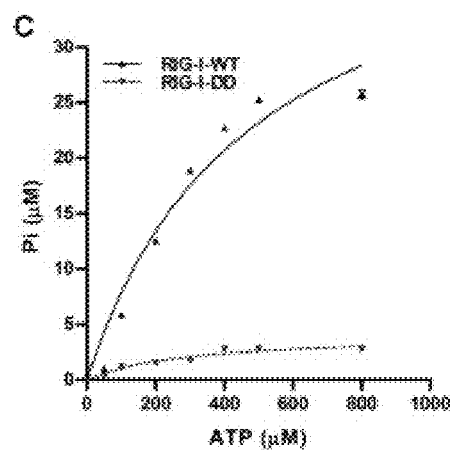
Figure 5D:
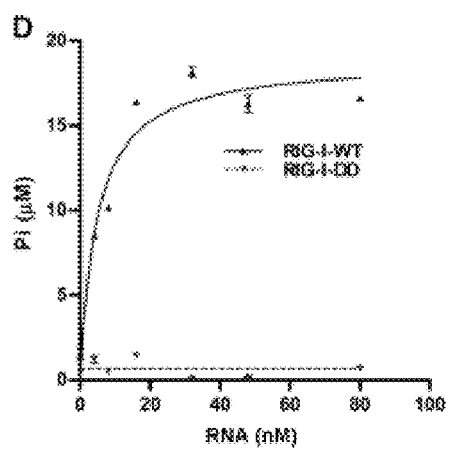
Figure 8A:
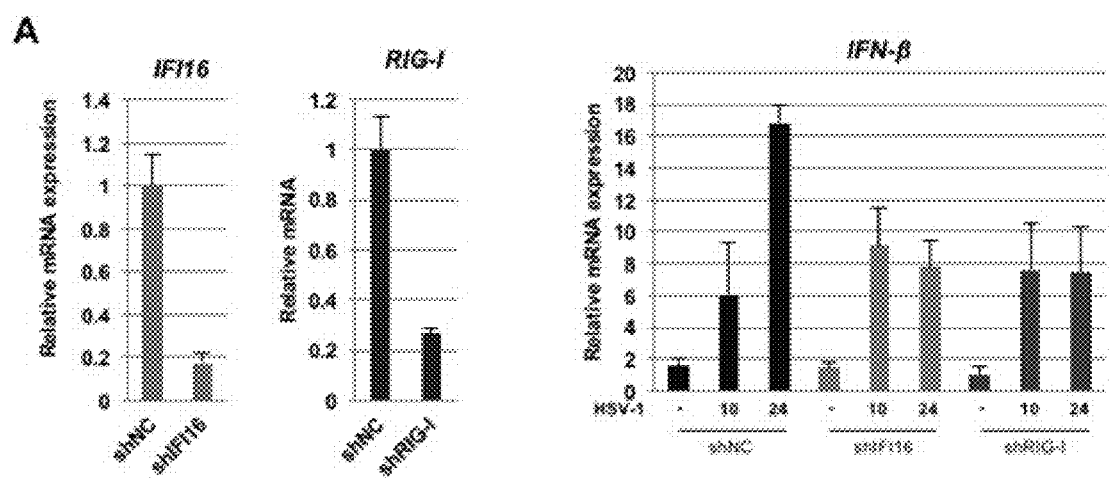
FIGS. 8A-8I: HSV-1 evades RIG-I-mediated antiviral immune responses.
Figure 8B:
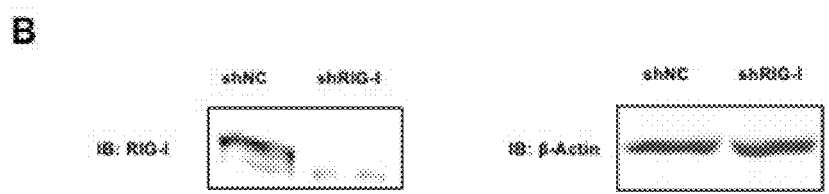
Figure 8C:
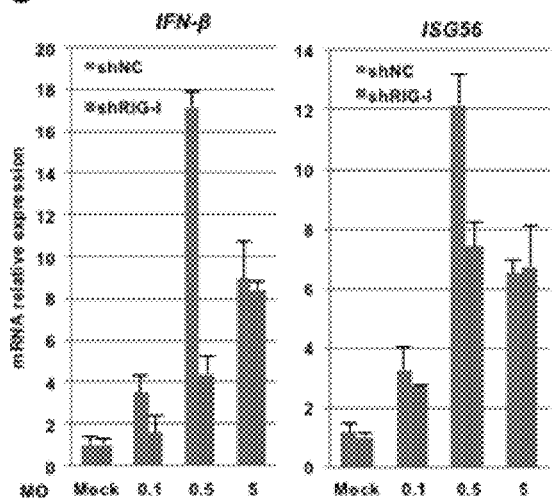
Figure 8D:
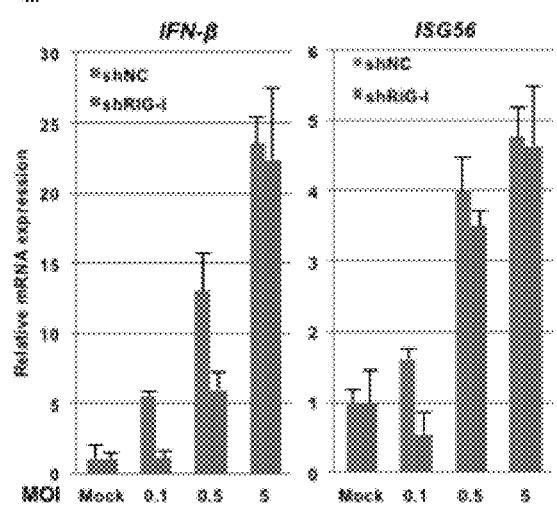
Figure 8E:
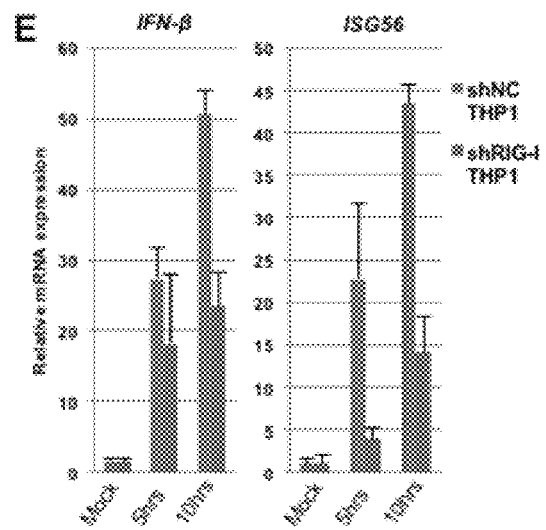
Figure 8F:
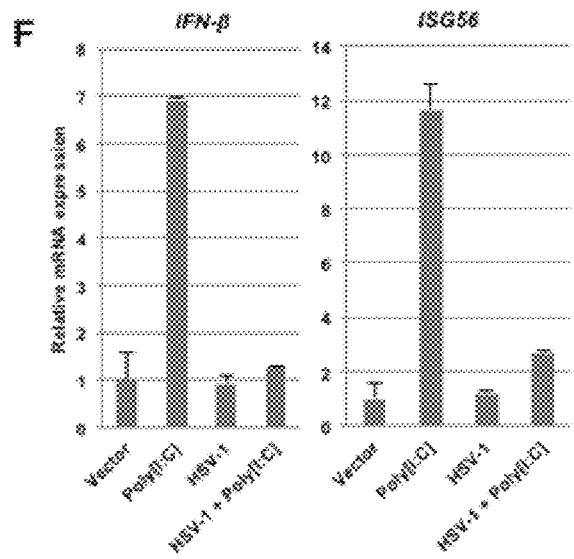
Figure 8G:
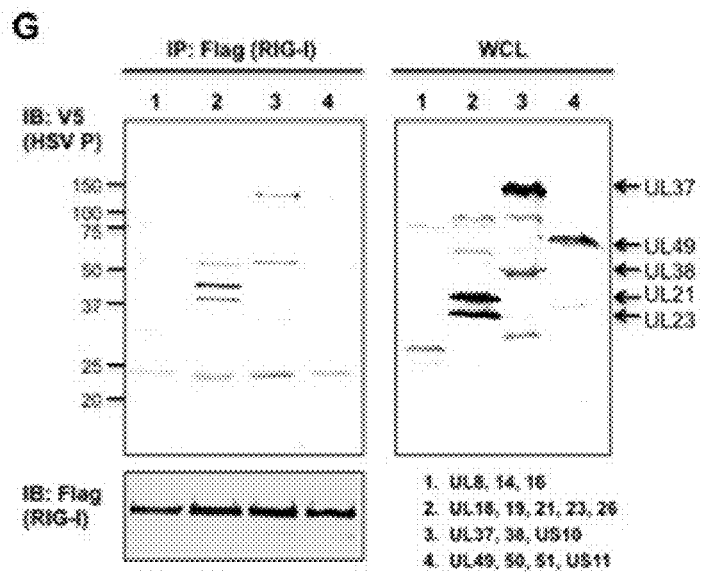
Figure 8H:
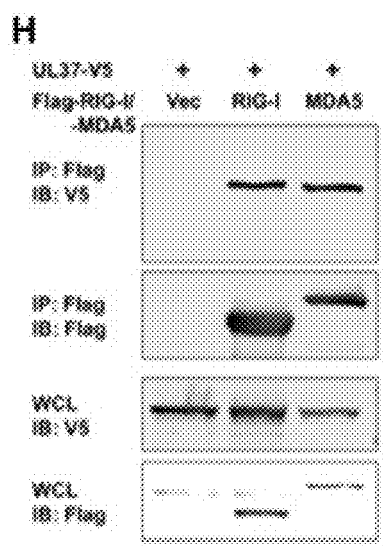
Figure 8I:
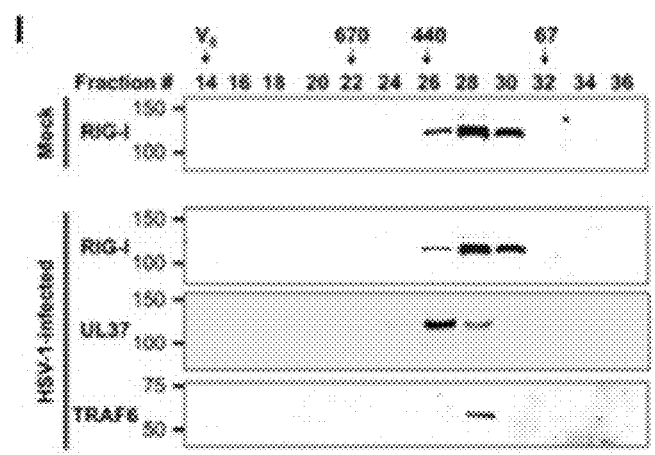

To probe the roles of RIG-I in host defense against HSV-1, Applicant depleted RIG-I expression and assessed the IFN-β mRNA in primary human foreskin fibroblasts (HFF). Applicant found that knockdown of RIG-I reduced IFN-β mRNA at 24 h induced by HSV-1 infection (FIG. 8A). A similar effect was observed with knockdown of IFI16, a DNA sensor implicated in detecting herpesviruses (Kerur et al., 2011, Unterholzner et al., 2010). In 293T and HeLa cells that HSV-1 replication is very robust, Applicant observed that RIG-I depletion impaired IFN and ISG56 induction at multiplicity of infection (MOI) of 0.1 and 0.5 (FIG. 8B, FIG. 5C). No difference in IFN and ISG56 induction was observed in RIG-I knockdown cells upon high MOI (=5) HSV-1 infection, suggesting that HSV-1 can blunt IFN induction. Moreover, RIG-I depletion in human THP-1 macrophages also reduced IFN-β and ISG56 mRNA induced by HSV-1 infection (FIG. 5D). These results indicate that RIG-I senses dsRNA produced by HSV-1-infected cells and contributes to the IFN induction by HSV-1 infection.

Figure 1B:
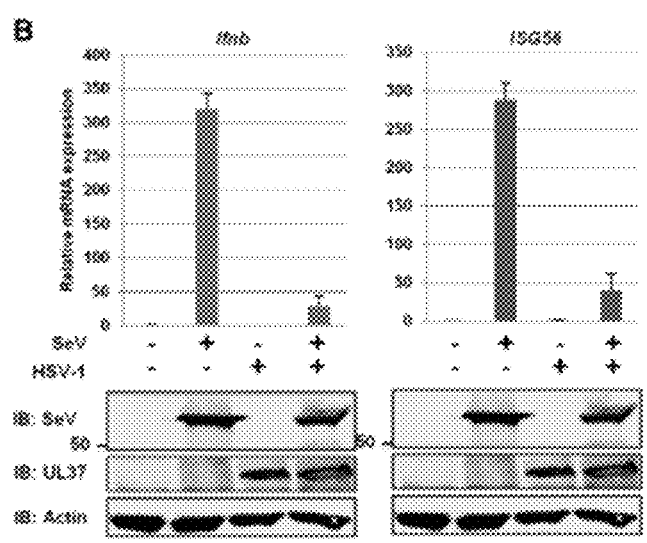
Figure 1C:
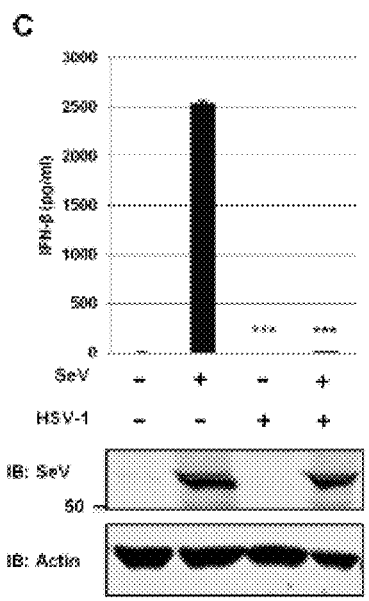
Figure 1D:
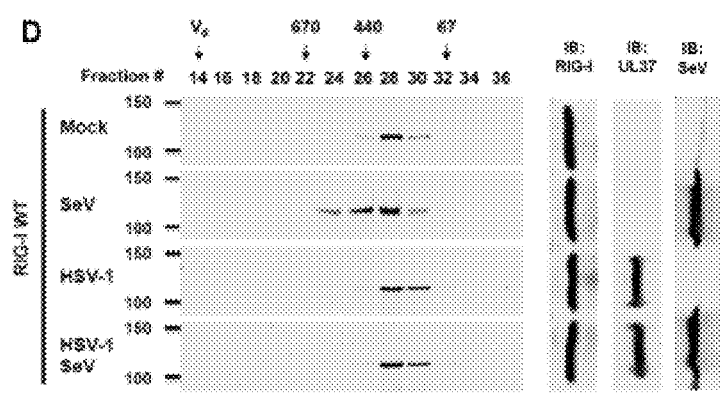
Figure 5E:
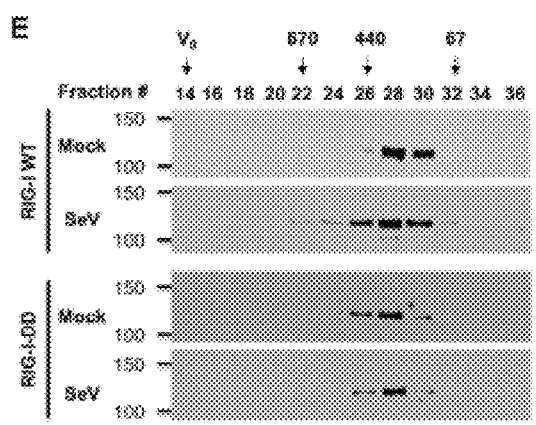

To determine whether HSV-1 infection inhibits RIG-I activation, Applicant sequentially infected 293T cells with HSV-1 and SeV, and determined IFN-β and ISG56 expression. Applicant found that HSV-1 infection significantly reduced IFN-β and ISG56 mRNA induced by SeV (FIG. 1B), which correlated with minimal IFN-β secretion (FIG. 1C). Importantly, HSV-1 infection did not significantly reduce SeV replication as evidenced by expression of the major protein of SeV (FIG. 1B and FIG. 1C). Furthermore, SeV infection induced the oligomerization of RIG-I that eluted in fractions corresponding to protein sizes between ~440 kDa and ~670 kDa, while RIG-I eluted in fraction corresponding to ~230 kDa in mock-infected cells or cells that were infected with HSV-1 (FIG. 1D). Strikingly, RIG-I purified from HSV-1- and SeV-infected cells had an elution pattern identical to that of mock-infected cells. Finally, HSV-1 infection completely blunted the induction of IFN and ISG56 mRNA in 293T cells transfected with LMW poly [I:C] (FIG. 5E). These results show that HSV-1 inhibits RIG-I activation triggered by SeV, a prototype RIG-I activator.

HSV-1 UL37 Interacts with RIG-I

Figure 2A:
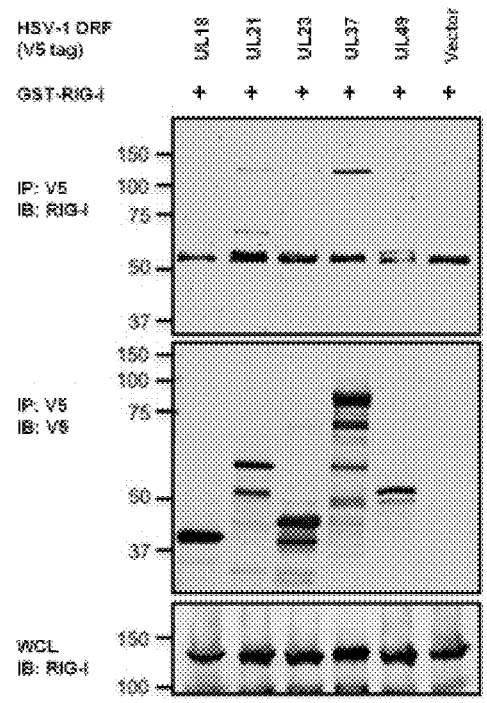
FIGS. 2A-2C: HSV-1 UL37 interacts with RIG-I.
Figure 2B:
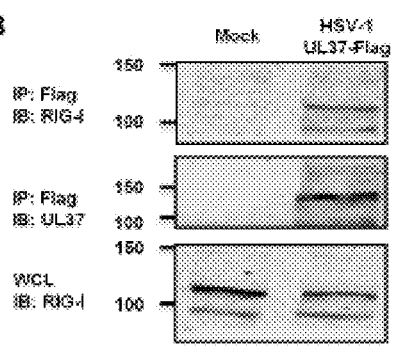
Figure 2C:
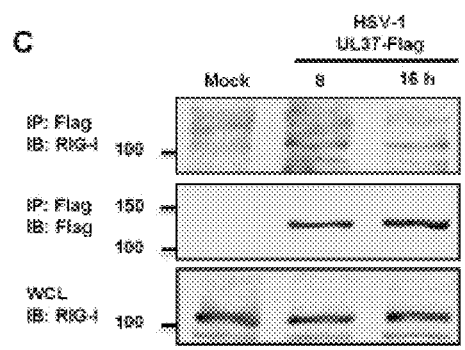
Figure 9A:
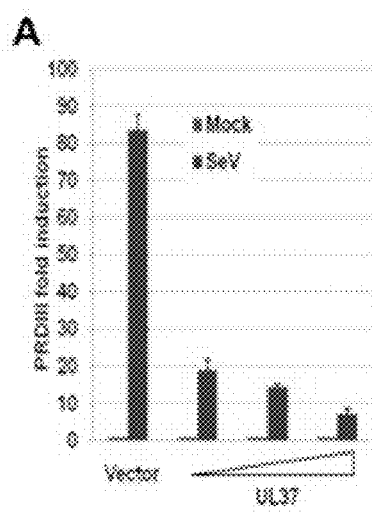
FIGS. 9A-9H: UL37 inhibits RIG-I-mediated antiviral immune responses.
Figure 9B:
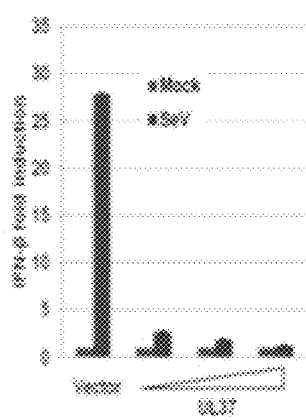
Figure 9C:
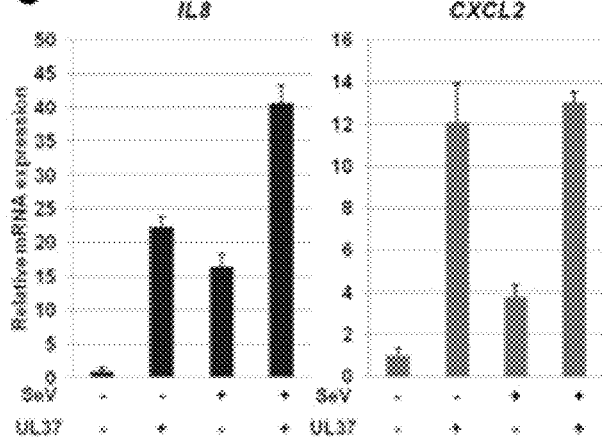

To delineate the mechanism by which HSV-1 abrogates RIG-I activation, Applicant screened for RIG-I-binding proteins by co-immunoprecipitation (Co-IP) using a HSV-1 expression library, with a particular focus on gene products that operate in the early phase of infection. Co-IP assays identified open reading frames UL21 and UL37 as RIG-I-interacting proteins (FIG. 2A and FIG. 9A). Although UL37 has no sequence homology with gamma herpesvirus vGAT proteins, it shares multiple functions with the vGAT proteins, e.g., activating NF-κB and promoting viral replication (Desai et al., 2001; Full et al., 2014; Gaspar et al., 2008; Liu et al., 2008). Thus, Applicant examined whether UL37 evades RIG-I-dependent immune defense. Indeed, UL37 was readily detected in protein complexes precipitated by antibody against RIG-I in HSV-1-infected 293T cells as early as 1 hour post-infection (hpi) at high MOI (=30) (FIG. 2B) and during late lytic replication at lower MOI (=1) (FIG. 2C). When expressed in 293T cells, UL37 co-precipitated with RIG-I (FIG. 9B), indicating that UL37 interacts with RIG-I in the absence of any other viral proteins. Interestingly, UL37 also interacted with MDA5 in transfected 293T cells (FIG. 9B). Gel filtration analyses further showed that UL37 co-eluted with RIG-I in fractions corresponding to ~220-440 kDa, supporting that these proteins form a complex in HSV-1-infected cells (FIG. 9C). UL37 also partly co-eluted with its interacting partner TRAF6 by gel filtration analysis. Thus, UL37 interacts with RIG-I in HSV-1-infected or transfected cells.

HSV-1 UL37 Inhibits RIG-I Activation

Figure 3A:
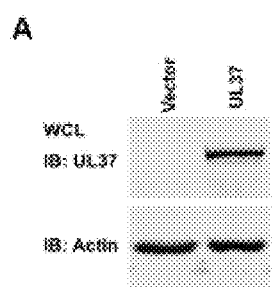
FIGS. 3A-3J: UL37 inhibits RIG-I activation.
Figure 3B:
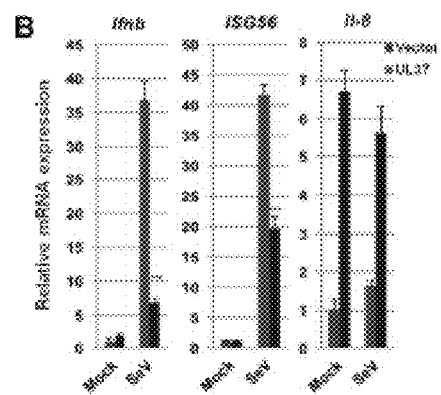
Figure 3C:
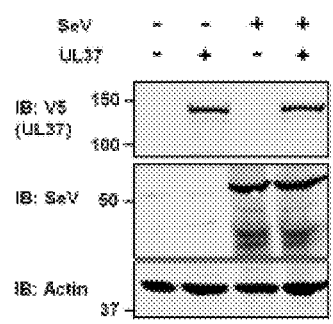
Figure 3D:
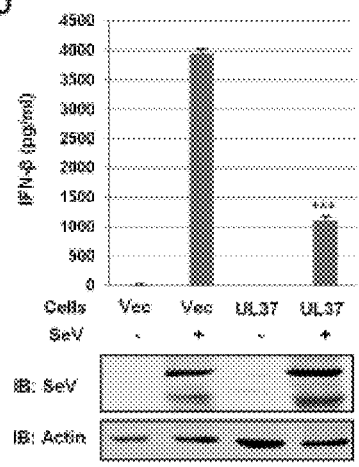
Figure 3E:
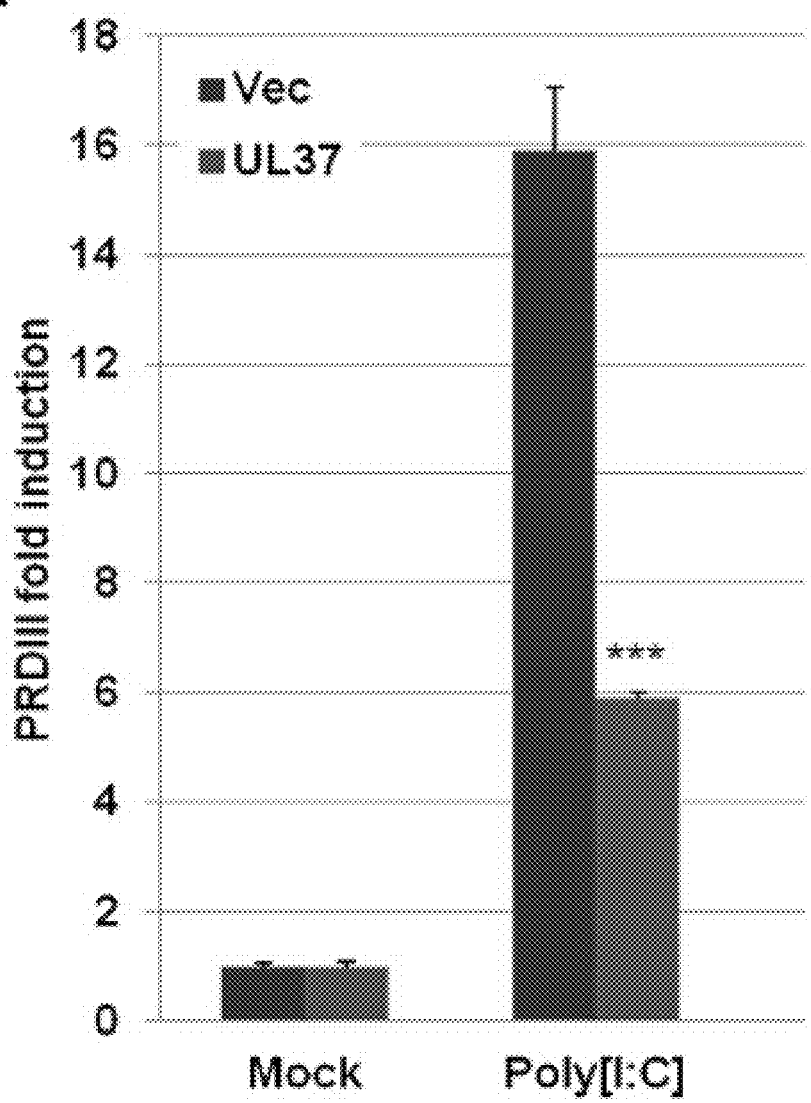
Figure 9D:
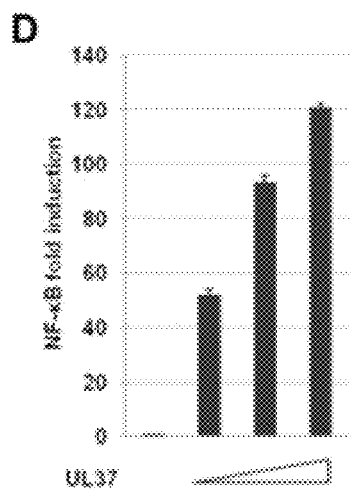
Figure 9E:
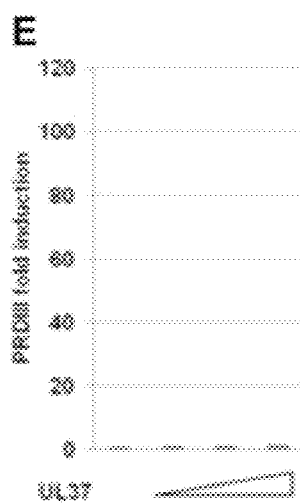
Figure 9F:
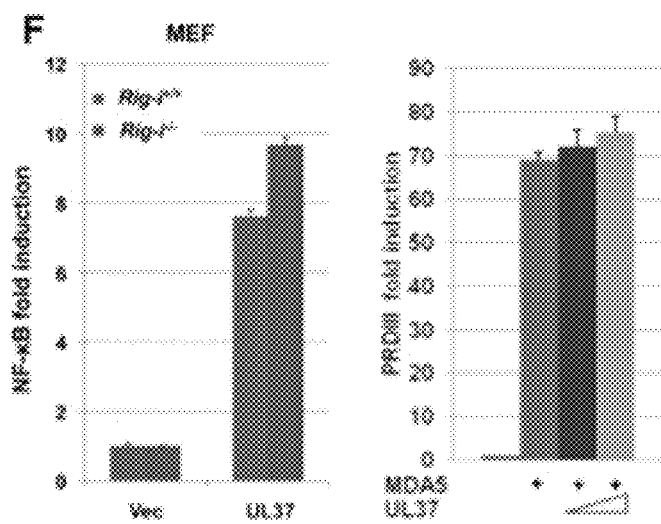

Applicant established 293T cells stably expressing UL37 (FIG. 3A). Upon SeV infection, UL37 expression significantly reduced IFN-β and ISG56 expression by real-time PCR analysis (FIG. 3B) and reporter assays (FIG. 9A, FIG. 9B). UL37 did not reduce SeV protein expression (FIG. 3C). UL37 significantly up-regulated IL-8 and CxCL2 expression (FIG. 9C), likely due to the NF-κB activation by UL37 (Liu et al., 2008), while had a marginal effect on IL-8 expression upon SeV infection (FIG. 3B). ELISA further confirmed that UL37 expression reduced IFN-β secretion by ~75% in response to SeV infection (FIG. 3D). Moreover, UL37 expression inhibited IFN induction upon LMW poly [I:C] transfection (FIG. 3E). Over-expression of UL37 was sufficient to activate NF-κB (FIG. 9D), but had no detectable effect on PRDIII, an IRF-responsive element of the IFN-β promoter (FIG. 9E). Loss of RIG-I in mouse embryonic fibroblasts (MEFs) had no effect on UL37-induced NF-κB activation (FIG. 9F). UL37 expression did not alter the transcription of the PRDIII promoter induced by MDA5 over-expression (FIG. 9F). These results collectively show that UL37 specifically inhibits RIG-I-dependent IFN-β induction.

Figure 3F:
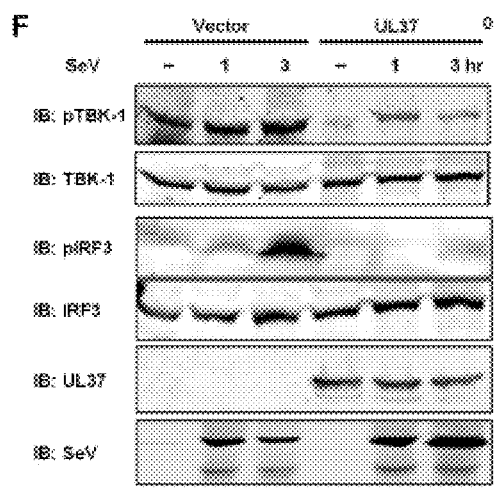
Figure 3G:
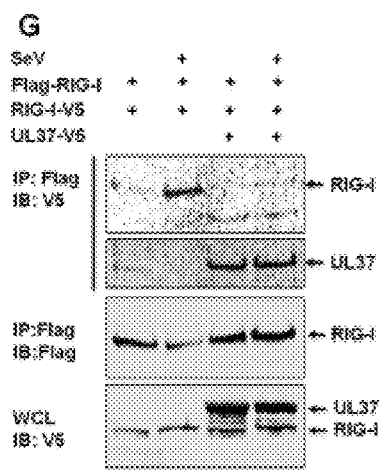
Figure 3H:
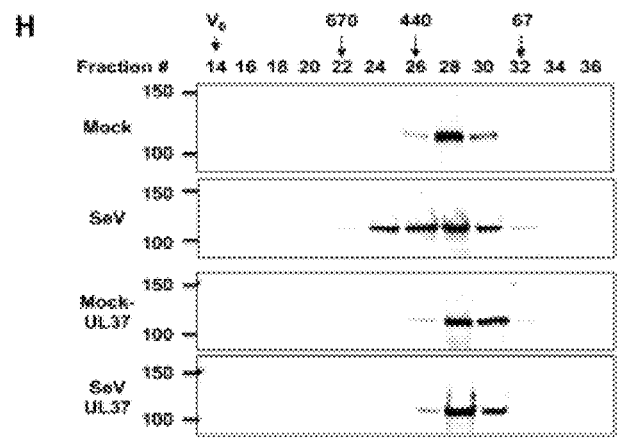
Figure 3I:
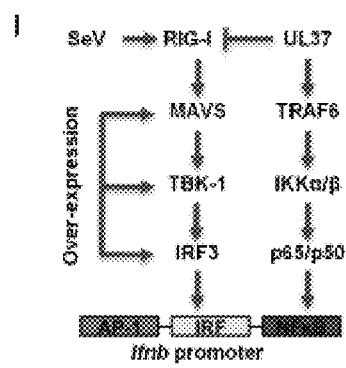
Figure 3J:
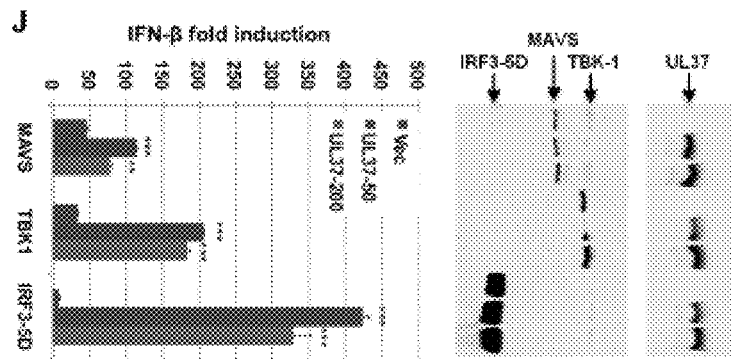
Figure 9G:
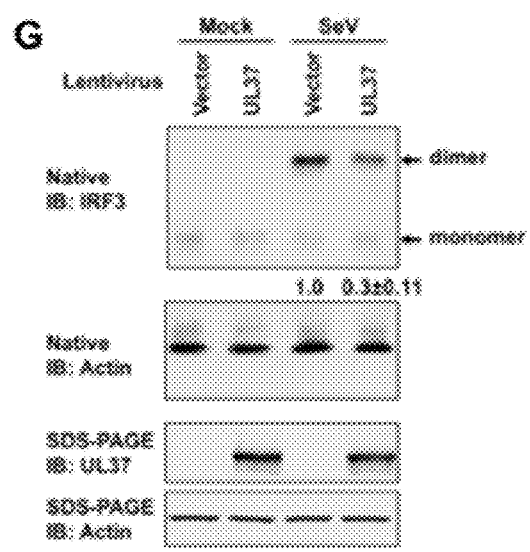
Figure 9H:
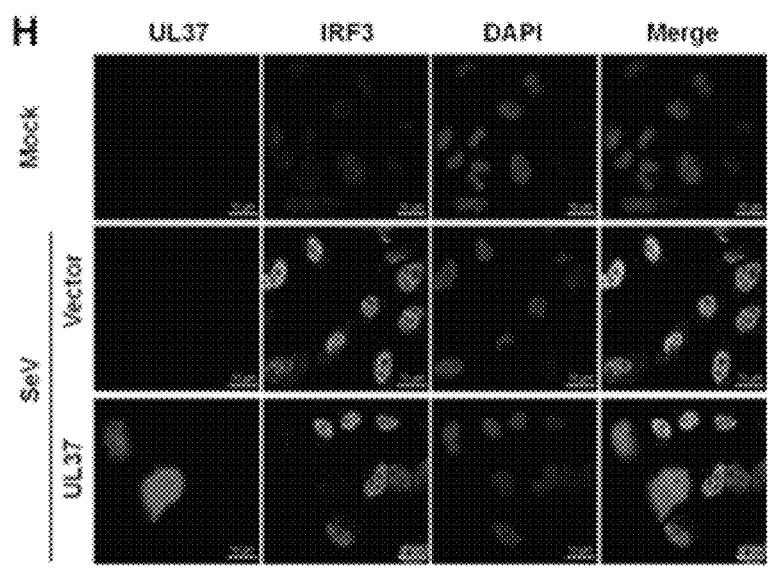

To probe the effect of UL37 on signaling events downstream of RIG-I, Applicant analyzed the phosphorylation of TBK-1 (Ser172) and IRF3 (Ser396), markers of activated TBK-1 and IRF3, respectively. As shown in FIG. 3F, UL37 expression inhibited the phosphorylation of TBK-1 and IRF3 upon SeV infection. Moreover, UL37 expression reduced the dimerization and nuclear translocation of IRF3 (FIG. 9G and FIG. 9H). Using 293T cells stably expressing Flag-RIG-I and RIG-I-VS, Applicant found that UL37 expression abolished RIG-I dimerization upon SeV infection by Co-IP assay (FIG. 3G). Furthermore, UL37 diminished the SeV-induced oligomerization of RIG-I as analyzed by gel filtration (FIG. 3H). To test whether UL37 inhibits key components of the IRF-IFN pathway downstream of RIG-I, Applicant over-expressed MAVS, TBK-1 and the constitutively active IRF3-5D mutant (FIG. 3I) and examined the activation of the IFN-β reporter. Consistent with NF-κB activation by UL37 (FIG. 9D), Applicant found that UL37 enhanced, rather than inhibited, the transcription of the IFN-β reporter in a dose-dependent manner with all three components (FIG. 3J). UL37 did not alter the protein level of MAVS, TBK-1 and IRF3-5D. These results conclude that UL37 specifically targets RIG-I to block IFN induction by viral dsRNA.

UL37 Deamidates RIG-I

Figure 4A:
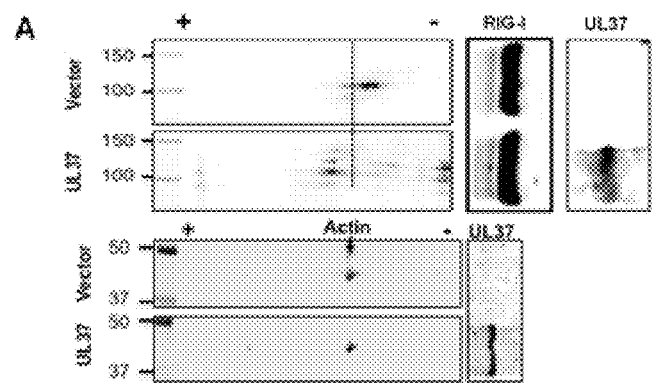
FIGS. 4A-4E: UL37 deamidates RIG-I in cells and in vitro.
Figure 4B:
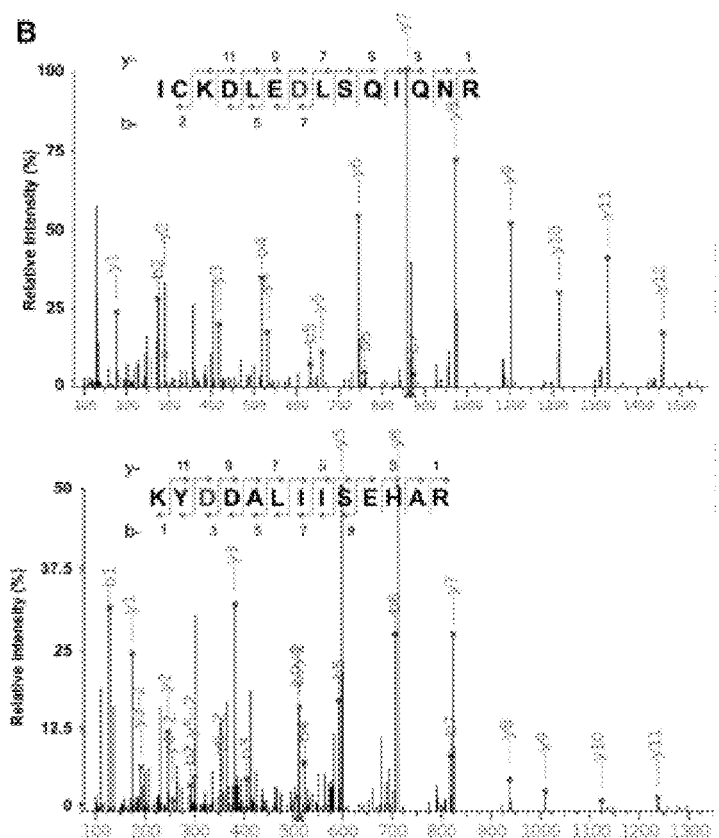
Figure 4C:
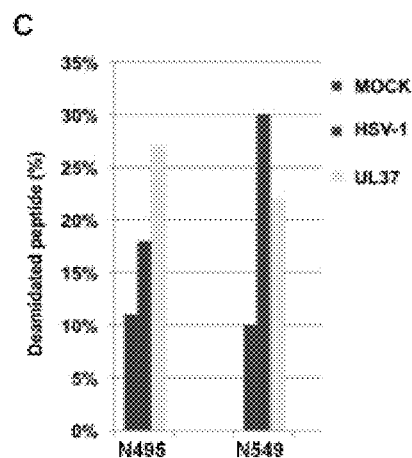
Figure 4D:
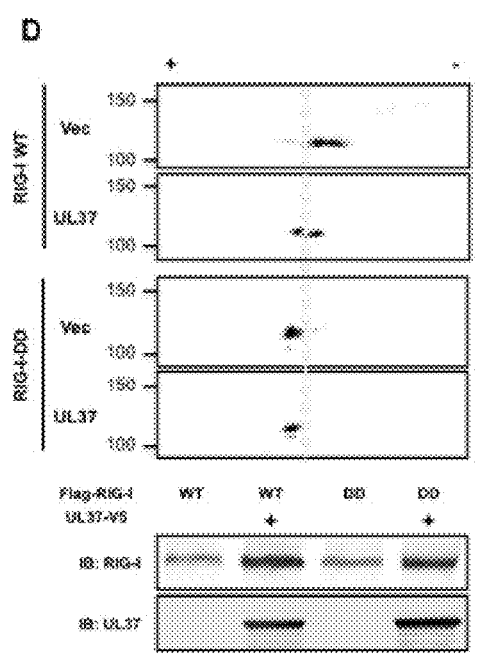
Figure 10A:
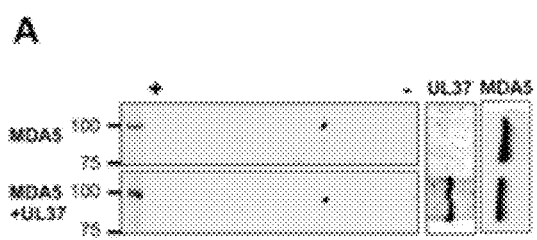
FIGS. 10A-10C: UL37 deamidates RIG-I.
Figure 10B:
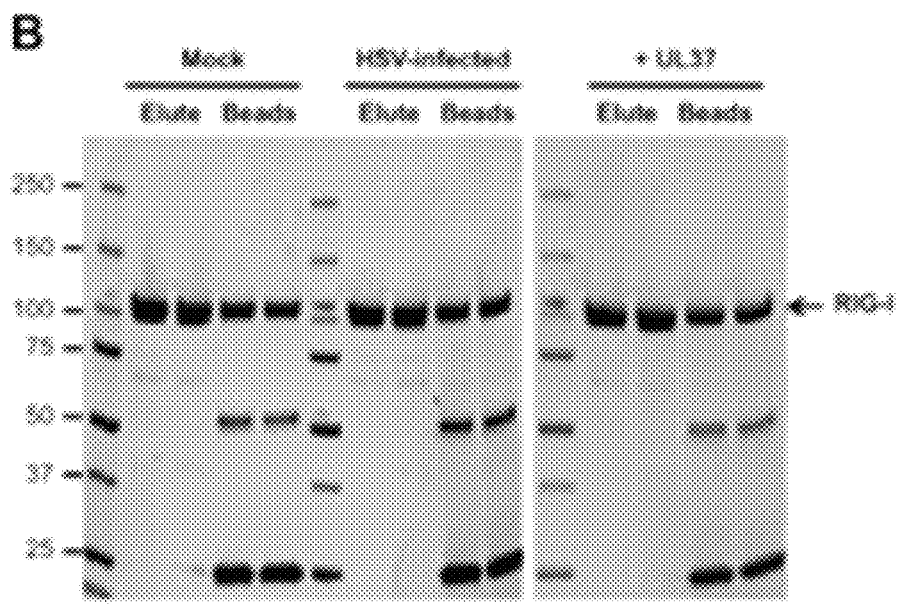

HSV-1 infection reduced the charge of RIG-I, suggesting that HSV-1 induces RIG-I deamidation. Applicant found that UL37 expression was sufficient to reduce the charge of RIG-I, but not that of R-actin (FIG. 4A). Furthermore, UL37 expression did not alter the charge of MDA5, an RNA sensor akin to RIG-I (FIG. 10A). Applicant thus purified RIG-I 293T stable cells upon HSV-1 infection or UL37 expression (FIG. 10B). Tandem mass spectrometry analyses of both samples identified two peptides that contained aspartates at residue 495 and 549, indicative of deamidation of N495 and N549 (FIG. 4B). HSV-1 infection and UL37 expression had similar effect on the deamidation of N495 and N549 (FIG. 4C), suggesting that UL37 is responsible for RIG-I deamidation during HSV-1 infection. When N495D and N549D were introduced into RIG-I, designated RIG-I-DD, Applicant found that RIG-I-DD migrated toward the positive end of the strip, to a position identical to that of RIG-I-WT when UL37 was expressed (FIG. 4D). Moreover, UL37 expression did not further shift RIG-I-DD by 2-DGE analysis, indicating that N495 and N549 are the two sites of deamidation by UL37.

Figure 4E:
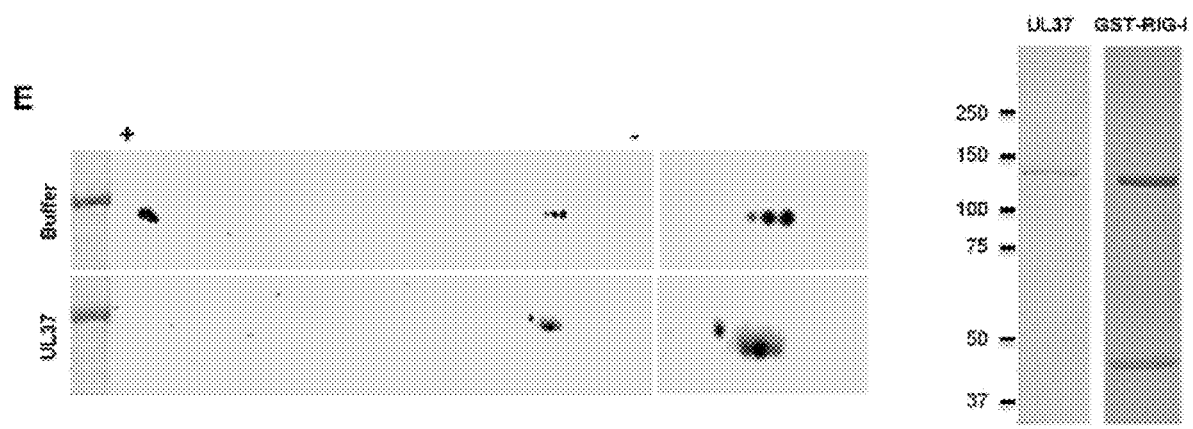
Figure 10C:
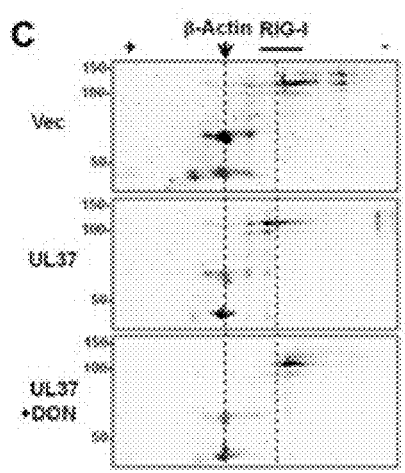

To probe the mechanism of UL37-induced deamidation, Applicant first determined whether a specific inhibitor of glutamine amidotransferase, 6-diazo-5-oxo-L-norleucine (DON), can block UL37-induced RIG-I deamidation. Indeed, DON inhibited RIG-I deamidation in cells expressing UL37 (FIG. 10C). This result suggests that UL37-mediated deamidation of RIG-I depends on an enzymatic activity akin to glutamine amidotransferase. Thus, Applicant sought to determine whether UL37 is intrinsically a protein deamidase. Applicant purified UL37 full-length from E. coli to homogeneity and examined RIG-I deamidation in vitro. Analysis by 2-DGE indicated that UL37 was sufficient to reduce RIG-I charge, suggestive of deamidation (FIG. 4E). These results indicate that UL37 deamidates RIG-I in cells and in vitro.

Deamidated RIG-I Fails to Sense RNA and Hydrolyze ATP

Figure 11A:
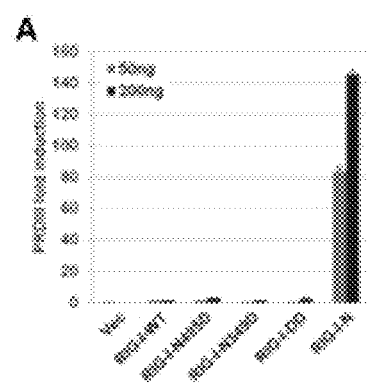
FIGS. 11A-11I: Deamidation inactivates RIG-I to sense dsRNA.
Figure 11B:
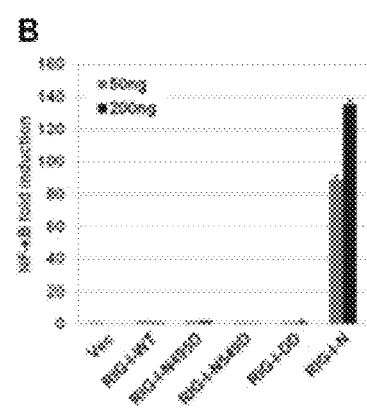
Figure 11C:
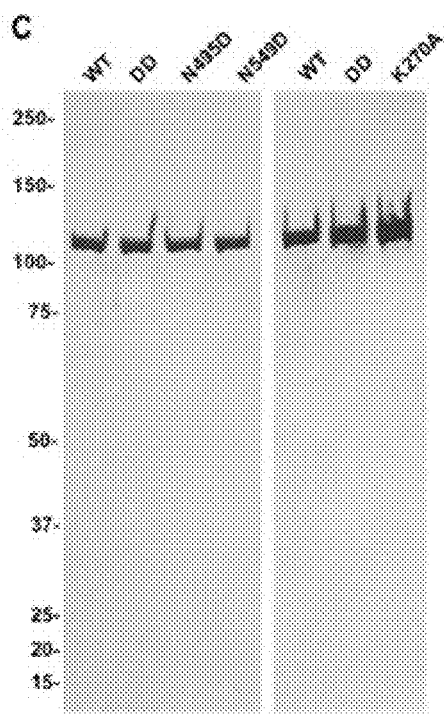
Figure 11D:
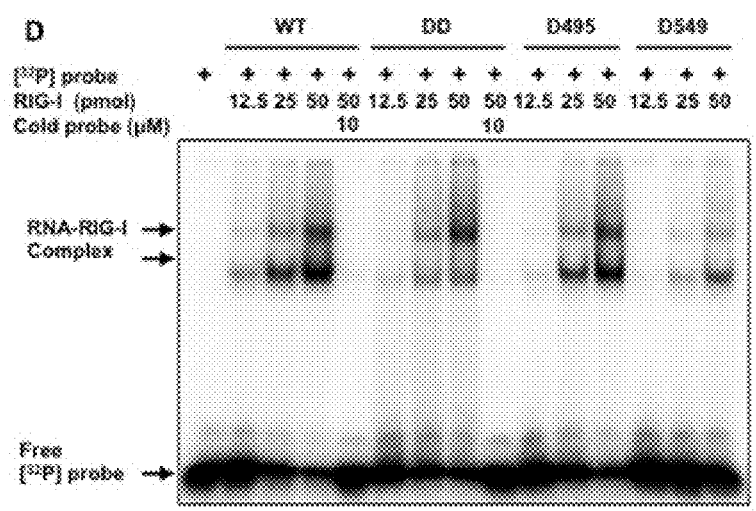
Figure 11E:
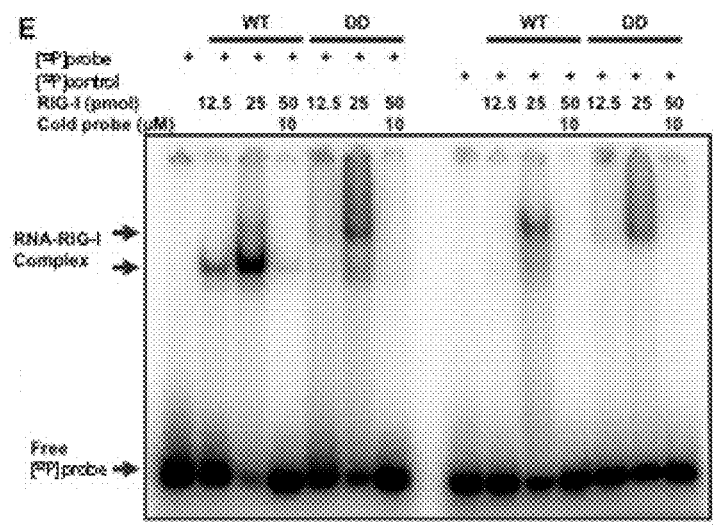
Figure 11F:
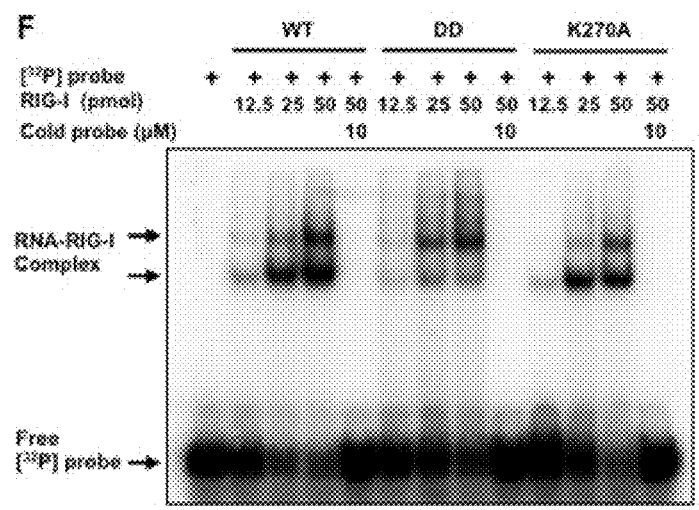
Figure 11G:
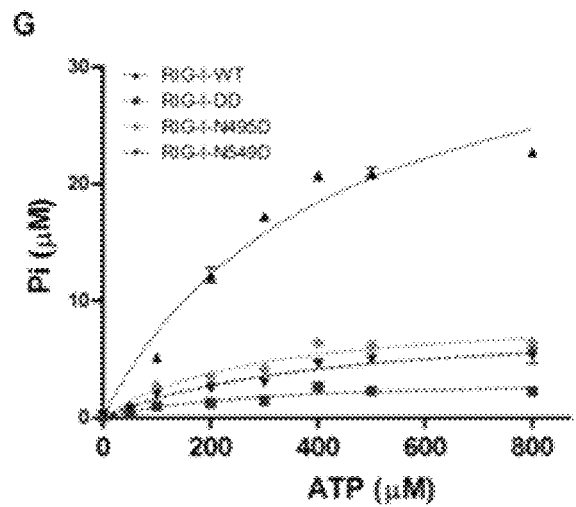
Figure 11H:
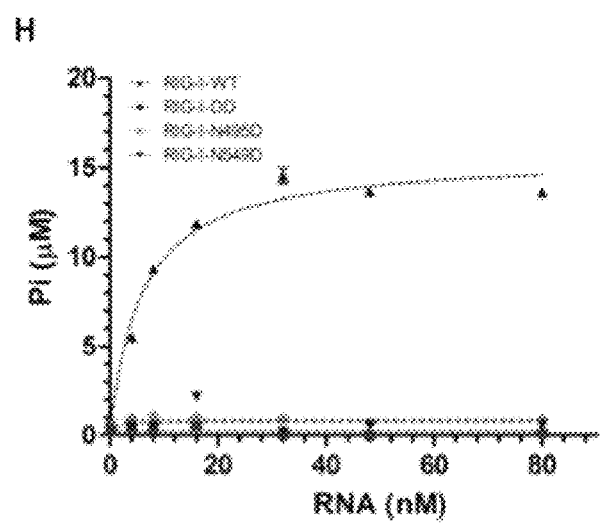

Applicant previously showed that m-vGAT induced deamidation and concomitant activation of RIG-I. However, the RIG-I-DD mutant failed to activate NF-κB and IFN-β reporters (FIG. 11A, FIG. 11B). N495 and N549 reside in the helicase 2i (Hel2i) domain that specializes in duplex RNA recognition (Luo et al., 2013). Previous structural analyses of RNA-bound RIG-I showed that these two residues flank the dsRNA-binding α-helix, α23 (FIG. 5A) (Kowalinski et al., 2011; Luo et al., 2011). Residues of the α-helix (α23), specifically K508 and Q511, make direct contact with dsRNA. While N495 precedes the α23 helix, N549 is located in the middle of a spatially adjacent α-helix (α24). Thus, Applicant opted to determine whether deamidation of N495 and N549 affects the RNA-binding ability of RIG-I, an important function for RNA detection by RIG-I. Applicant purified RIG-I-WT and its mutants to homogeneity from transfected 293T cells (FIG. 11C) and performed electrophoresis mobility shift assay (EMSA). Applicant found two distinct RIG-I:RNA complexes that correlated with increasing doses of RIG-I (FIG. 5B and FIG. 11D). The RIG-I-DD mutant was significantly impaired in forming the fast migrating RIG-I:RNA complex, while formed higher levels of the more slowly migrating RIG-I:RNA complex compared to RIG-I-WT (FIG. 5B). EMSA also showed that the deamidation of N549 had a major effect on the RNA-binding ability of RIG-I, while RIG-I-N495D demonstrated comparable RNA-binding affinity to RIG-I-WT (FIG. 11D). Using a control dsRNA 19 mer lacking the 5'-triphosphate, Applicant found that the more slowly migrating RIG-I:RNA complex consisted of RIG-I and dsRNA without 5'-triphophate (FIG. 11E). Interestingly, the K270A mutant previously shown to have impaired ATPase activity, bound to the 5'-triphosphate 19mer dsRNA (5'ppp-RNA) with affinity similar to RIG-I-WT (FIG. 11F). Although ATP hydrolysis is not required for RIG-I signaling, it has been proposed that ATPase activity is necessary for recycling of RIG-I from RNA-bound complexes and critical for RIG-I-mediated innate immune signaling against nonself RNA (Anchisi et al., 2015; Lassig et al., 2015; Luo et al., 2013). Applicant thus examined the ATP hydrolysis activity using purified RIG-I proteins. An in vitro ATPase assay showed that RIG-I-DD completely lost its ability to hydrolyze ATP (FIG. 5C). RIG-I-WT and RIG-I-DD demonstrated ATPase activity with kcat of 944 and 32.6 sec$^{-1}$ at physiological ATP concentrations, respectively. Furthermore, RIG-I-DD failed to hydrolyze ATP upon 5'ppp-RNA stimulation (FIG. 5D). RIG-I-N549D and RIG-I-N495D demonstrated basal or no ATPase activity similar to RIG-I-DD, with or without 5'ppp-RNA (FIG. 11G, FIG. 11H). These results indicate that deamidation of N495 and N549 abolishes RIG-I activity to bind RNA and hydrolyze ATP.

Figure 5F:
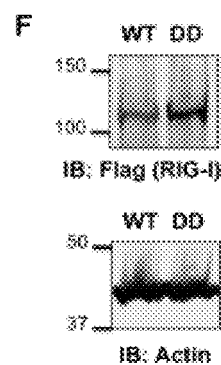
Figure 5G:
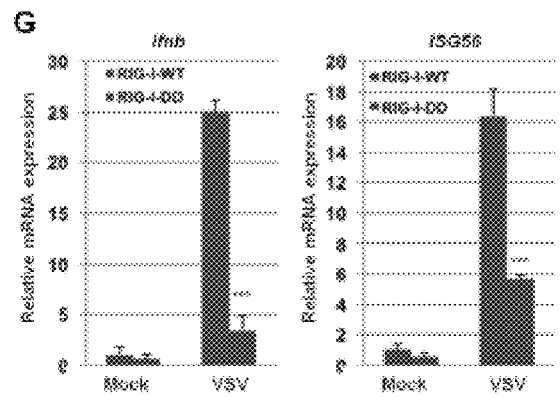
Figure 5H:
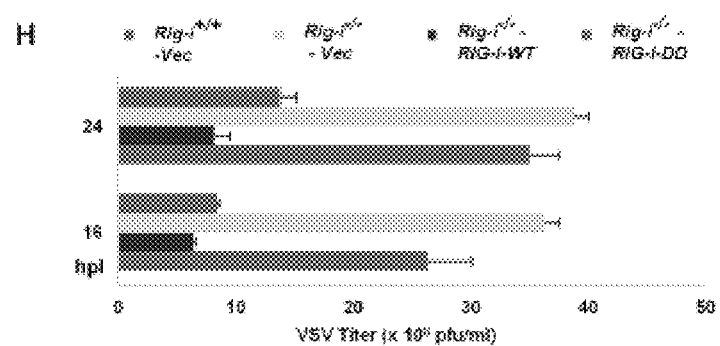
Figure 11I:
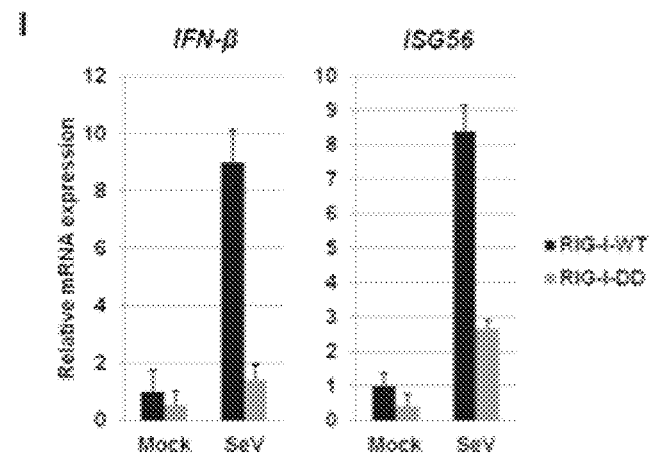

To assess the functional consequence of RIG-I deamidation, Applicant examined RIG-I activation by gel filtration. SeV infection induced oligomerization of RIG-I-WT as evidenced by fractions corresponding to protein complexes of ~440-670 kDa sizes, while RIG-I-WT in mock-infected cells eluted in fractions corresponding to ~130-230 kDa (FIG. 5E). However, SeV infection failed to induce the oligomerization of RIG-I-DD. Notably, a low level of RIG-I-DD was detected in fractions corresponding to protein sizes of ~440 kDa regardless of SeV infection. Applicant then "reconstituted" RIG-I expression in Rig-i$^{-/-}$ MEF with RIG-I-WT or RIG-I-DD (FIG. 5F), and examined host immune responses and viral infection. Compared to RIG-I-WT, RIG-I-DD induced basal or lower expression of IFN-β and ISG56 upon vesicular stomatitis virus (VSV) infection (FIG. 5G). Similar results were observed in SeV-infected cells (FIG. 11I). Consequently, RIG-I-WT, but not RIG-I-DD, reduced VSV replication in Rig-i$^{-/-}$ MEFs (FIG. 5H). These results demonstrate that deamidation of N495 and N549 eliminates RIG-I detection of viral RNA and restriction of viral replication.

Figure 6A:
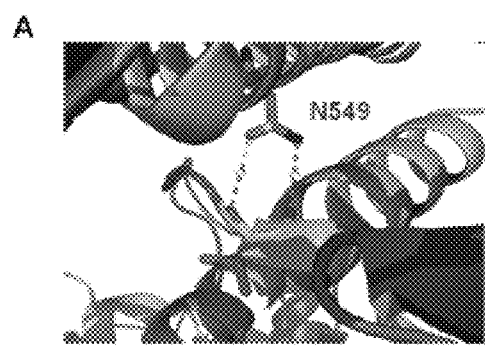
FIGS. 6A-6G: The deamidation-resistant RIG-I-QQ restores antiviral cytokine production in response to HSV-1 infection.

A Deamidation-Resistant RIG-I-QQ Mutant Restores Antiviral Immune Responses Against HSV-1 Infection Applicant's mutational analysis indicates that N549 is critical for the RNA-binding and ATPase activities of RIG-I. Previously solved crystal structure of RIG-I showed that the amide group of N549 (within α24) forms two hydrogen bonds with the backbone of threonine 504 of the RNA-binding α-helix (α23) (FIG. 6A) (Kowalinski et al., 2011; Luo et al., 2011). The RIG-I-N549A mutant failed to trigger IFN induction by SeV infection (data not shown), suggesting that the hydrogen bonds between N549 and T504 of the two neighboring helices are critical for RIG-I immune signaling. The side chain of glutamine contains a primary amide functional group as asparagine does. Applicant hypothesized that a glutamine residue at position 549 might conserve hydrogen bonds with T504, which translates to a predicted ~1 angstrom short difference in hydrogen bonds formed by Q549 than N549, thereby potentially resisting deamidation.

Figure 6B:
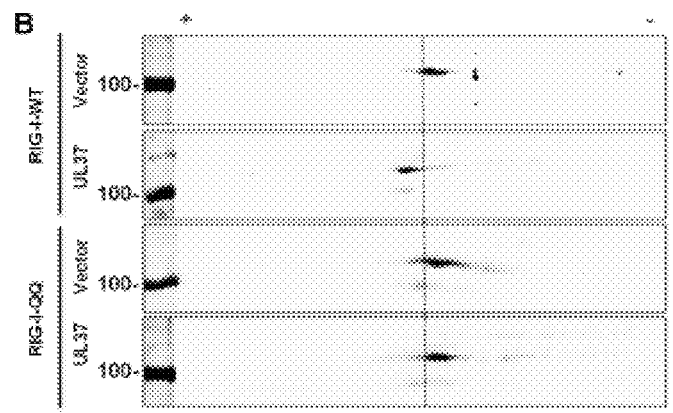
Figure 6C:
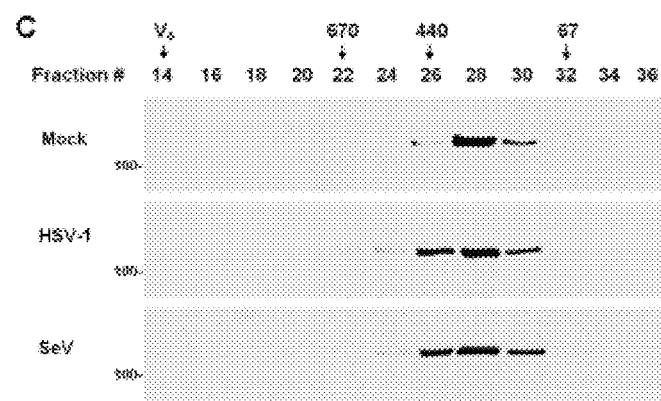

Applicant then generated a RIG-I mutant containing Q495 and Q549, designated RIG-I-QQ. In 293T cells stably expressing RIG-I-WT or the RIG-I-QQ mutant, UL37 expression shifted RIG-I-WT, but not RIG-I-QQ, toward the positive end of the strip, indicating that RIG-I-QQ is deamidation-resistant (FIG. 6B). Furthermore, RIG-I-QQ was eluted in fractions corresponding to sizes of ~440-670 kDa in cells infected with HSV-1, demonstrating similar levels of oligomerization as RIG-I-WT (FIG. 1D) and RIG-I-QQ (FIG. 6C) induced by SeV infection. These results indicate that RIG-I-QQ is refractory to deamidation, and therefore, restores RIG-I activation induced by HSV-1 infection.

Figure 6D:
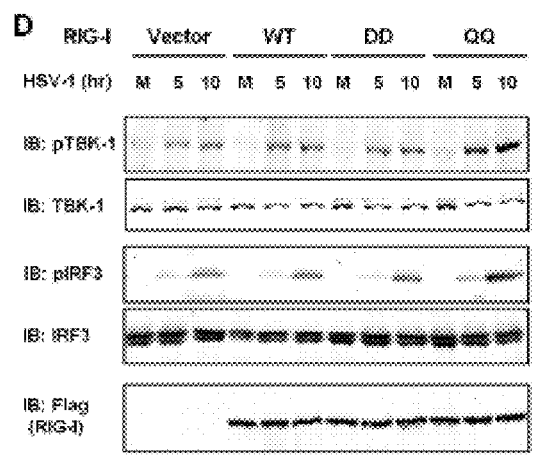
Figure 6E:
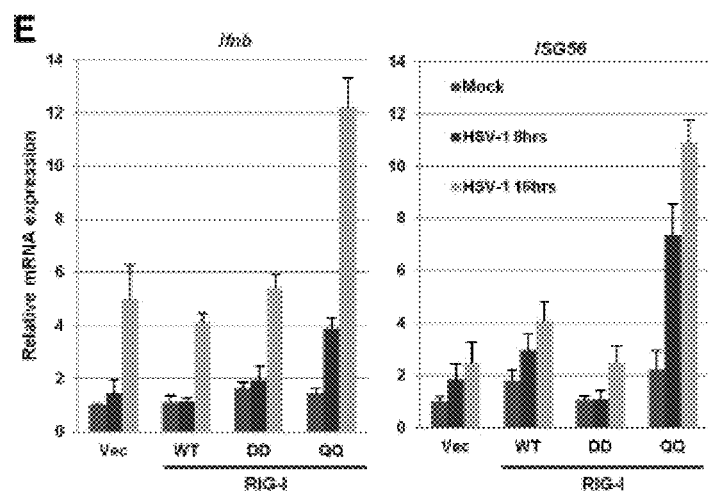
Figure 6F:
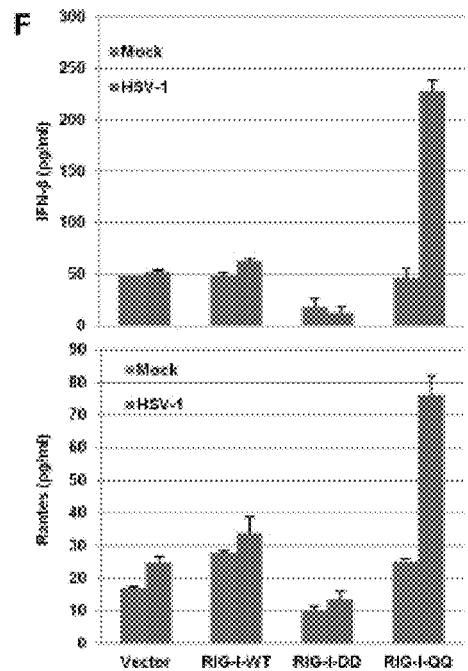
Figure 6G:
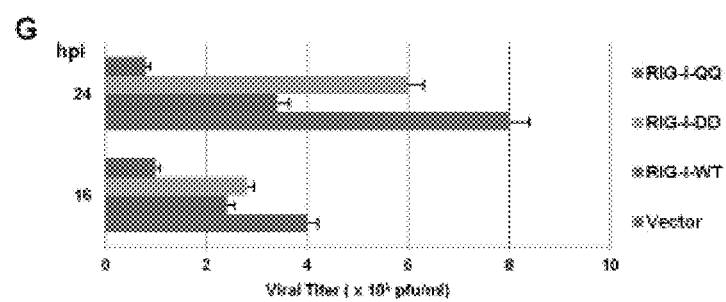

Applicant reasoned that only the deamidation-resistant RIG-I-QQ mutant will confer gain-of-function in RIG-I-mediated innate immune response, thus Applicant used wild-type HEK293 to establish stable cell lines expressing RIG-I wild-type and mutants. In resting cells, the level of phosphorylated TBK-1 (Ser172) was below detection in all four cell lines. HSV-1 infection increased the phosphorylation of TBK-1 to similar levels in control cells and cells expressing RIG-I-WT or RIG-I-DD (FIG. 6D). Remarkably, HSV-1 infection induced TBK-1 phosphorylation to much more pronounced levels in cells expressing RIG-I-QQ than the other three cell lines. Similar results were observed for phosphorylated IRF3. Consistent with this, HSV-1 infection also more significantly up-regulated IFN-β and ISG56 expression in RIG-I-QQ cells than control cells and cells expressing RIG-I-WT or RIG-I-DD (FIG. 6E). The low levels of IFN-β and ISG56 induction in the other three cell lines are likely due to activation of innate sensors other than RIG-I. Increased IFN-β and RANTES expression were detected only in the supernatant of HSV-1-infected 293T cells expressing RIG-I-QQ, but not the other three cell lines (FIG. 6F). To determine the antiviral activities of RIG-I wild-type and these mutants, Applicant examined viral replication in HEK293 stable cells. As shown in FIG. 6G, RIG-I-WT reduced HSV-1 replication by ~50%, while RIG-I-DD had a marginal effect on HSV-1 replication. Consistent with the robust antiviral response induced by RIG-I-QQ, RIG-I-QQ reduced HSV-1 titer by ~75-90% in HEK293 cells. These results show that the deamidation-resistant RIG-I-QQ restores RIG-I antiviral activity against HSV-1 and efficiently restricts HSV-1 replication.

The Carboxyl Terminal of UL37 Contains a Deamidase Domain

Figure 12A:
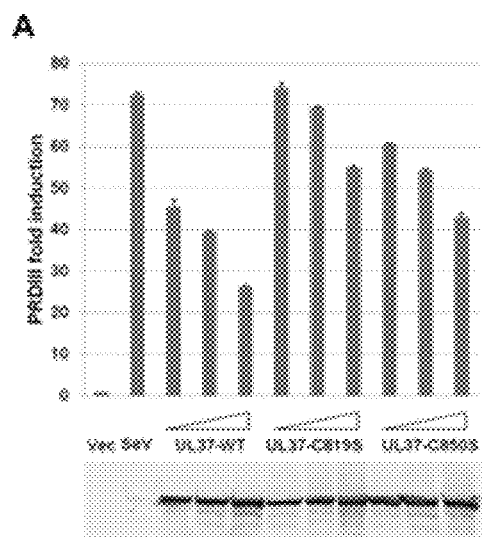
FIGS. 12A-12E: The carboxyl terminal half of UL37 contains a deamidase domain.
Figure 12B:
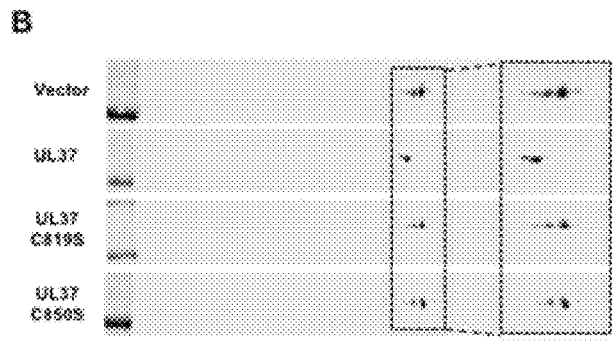
Figure 12C:
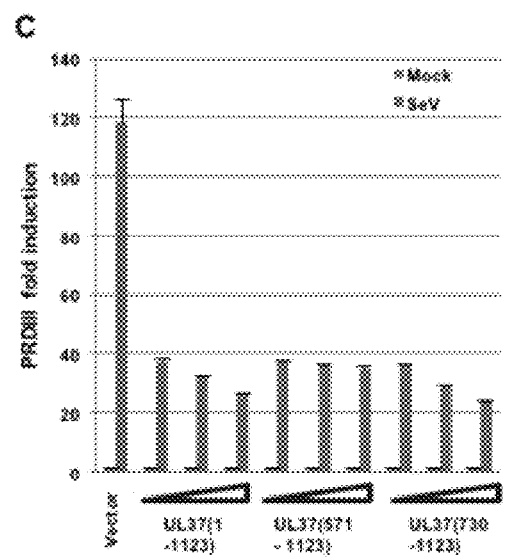

UL37 purified from *E. coli* is sufficient to deamidate RIG-I, implying that UL37 is a bonafide protein deamidase. Because all known protein deamidases (e.g., PFAS) are cysteine hydrolases (Zhao et al., 2016), Applicant suspect that UL37 also contains a catalytic cysteine residue. Thus, Applicant mutated all 14 cysteines of UL37 individually to serines and screened for the loss of inhibition of RIG-I-mediated activation of the PRDIII promoter upon SeV infection. The C819S and C850S mutants were identified to have greatly impaired blockade of PRDIII induction by SeV (FIG. 7A and FIG. 12A). Analysis by 2-DGE also showed that the C819S and C850S mutants of UL37 failed to induce RIG-I deamidation in transfected cells (FIG. 12B), indicating that these cysteines are required for the deamidase activity of UL37. Previous crystallography analysis showed that the N-terminus of UL37 adopts a helical bundle structure similar to multisubunit tethering complexes involved in intracellular trafficking (Pitts et al., 2014). Coupled with the observation that C819 and C850 are required for UL37 to deamidate RIG-I, Applicant reasoned that the C-terminal half (571-1123, designated UL37C) contains a protein deamidase domain. Applicant first determined whether UL37C was sufficient to block RIG-I-dependent IFN induction. Indeed, UL37C expression inhibited the SeV-induced transcription of PRDIII (FIG. 12C). Applicant then expressed and purified UL37C from *E. coli* to homogeneity for RIG-I deamidation studies. Consistent with results from transfected cells, UL37C was sufficient to deamidate RIG-I in vitro, demonstrating that UL37C contains intrinsic protein deamidase activity (FIG. 7B).

To pinpoint the cysteine residue of the active site. Applicant employed a small molecule electrophile for mass spectrometry analysis, an approach that was successfully used to quantitatively profile functional cysteines in proteomes (Weerapana et al., 2010). The rationale is that functional cysteines, such as those in enzymatic active sites, are hyper-reactive and react with small molecule electrophiles independent of concentration. As such, a ratio of the percentage of labeled peptides at high concentration to that at low concentration near 1 predicts functional cysteines. After reacting with 2-Chloro-N-(hydroxymethyl) acetamide (CNM), mass spectrometry analysis identified that C819 was primarily labeled by CNM within UL37C. Specifically, 38.3° % and 42.5% of C819 were labeled by CNM at 1 and 10 μM, respectively (FIG. 7C). C850 was labeled at minimal level (<10%) by CNM, suggesting that C850 is largely inaccessible. Taken together, these results support the conclusion that C819 is the active site of the catalytic triad.

Figure 7D:
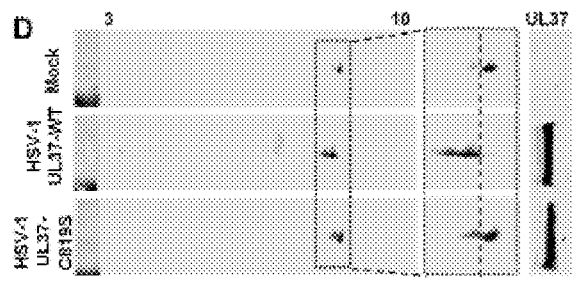
Figure 7E:
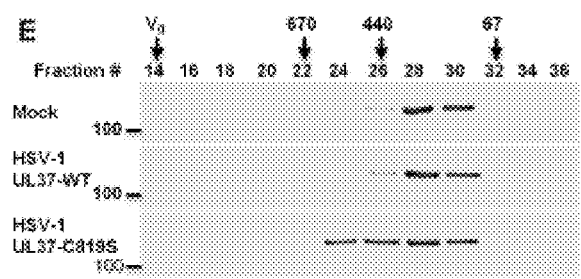
Figure 7F:
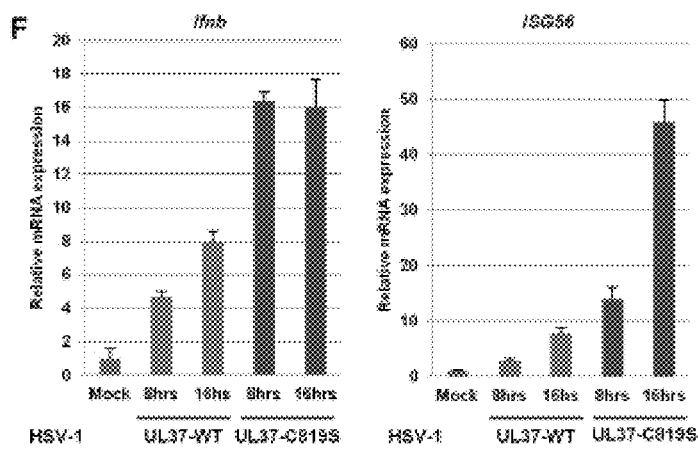
Figure 7G:
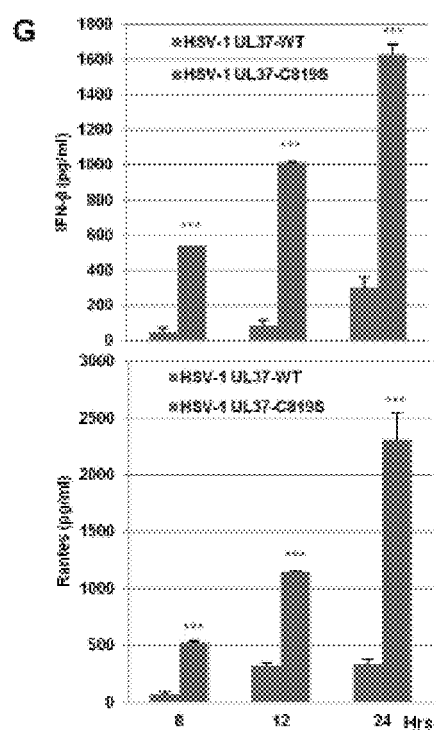
Figure 12D:
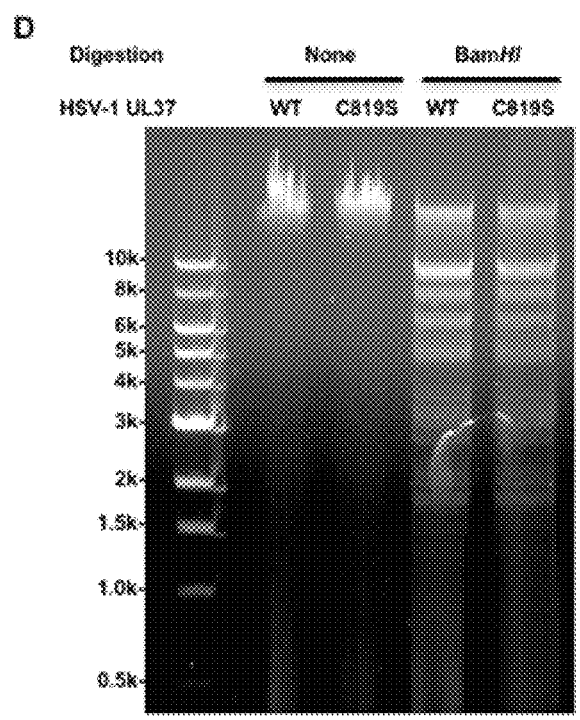
Figure 12E:
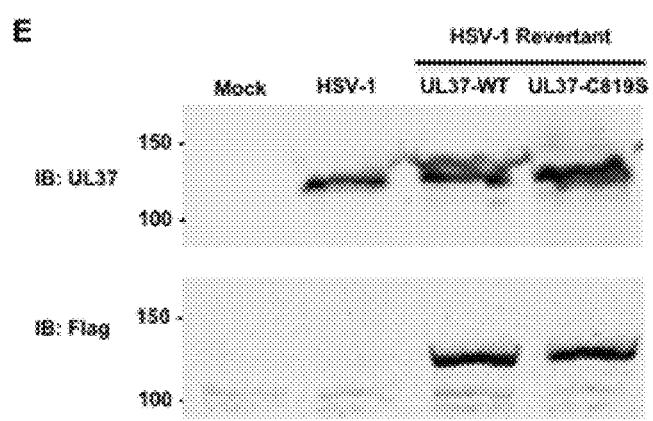
Figure 13A:
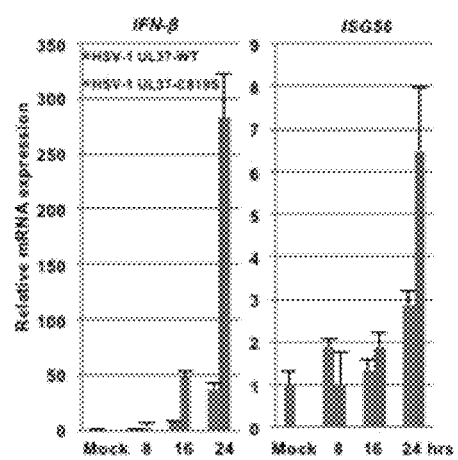
FIGS. 13A-13F: The carboxyl terminal half of UL37 contains a deamidase domain.
Figure 13B:
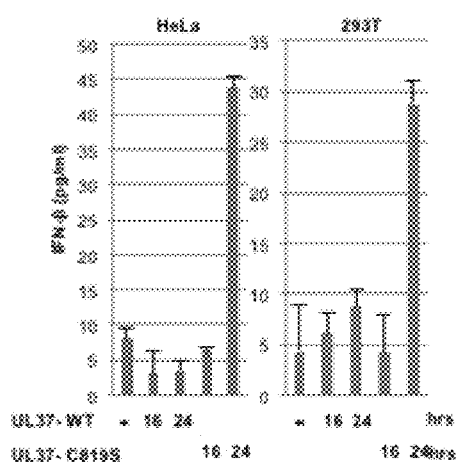
Figure 13C:
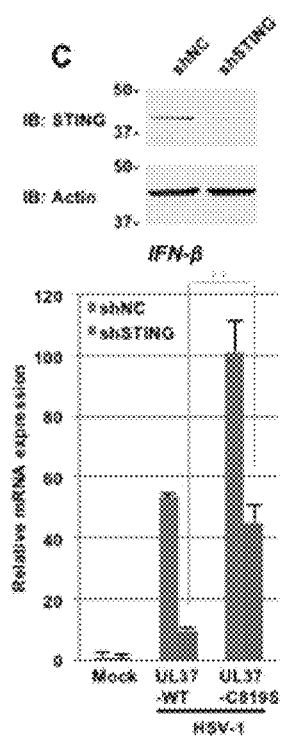

To probe the roles of UL37-mediated deamidation in viral infection, Applicant introduced UL37 wild-type (UL37-WT) and UL37-C819S into the HSV-1 genome (designated HSV-1 UL37-WT and HSV-1 UL37-C819S) and examined RIG-I-mediated innate immune signaling. Gel electrophoresis of viral genomic DNA after BamHI digestion revealed identical pattern of migration, indicative of lack of large chromosome rearrangement (FIG. 12D). Immunoblotting analysis showed that UL37-WT and UL37-C819S were expressed at similar levels in 293T cells (FIG. 12E). Compared to HSV-1 UL37-WT, HSV-1 UL37-C819S failed to deamidate RIG-I by 2-DGE analysis (FIG. 7D). Infection of HSV-1 UL37-C819S, but not HSV-1 UL37-WT, induced RIG-I oligomerization corresponding to protein sizes of ~440-670 kDa analyzed by gel filtration (FIG. 7E). Moreover, HSV-1 UL37-C819S induced higher levels of IFN-β and ISG56 expression (FIG. 7F), and IFN-β and RANTES secretion (FIG. 7G) in THP-1 macrophages. Similar results were obtained in HSV-1-infected HeLa, HFF and 293T cells (FIGS. 13A-13C). These results show that the deamidase activity of UL37 is critical for HSV-1 to evade RIG-I-mediated immune response.

Figure 7H:
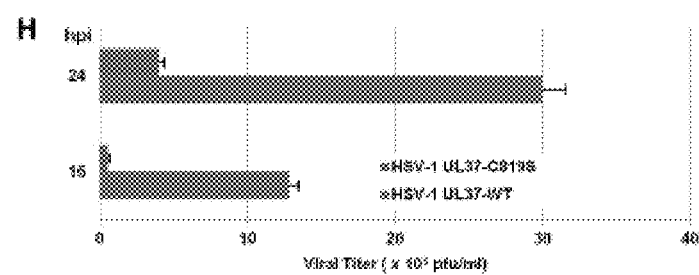
Figure 13D:
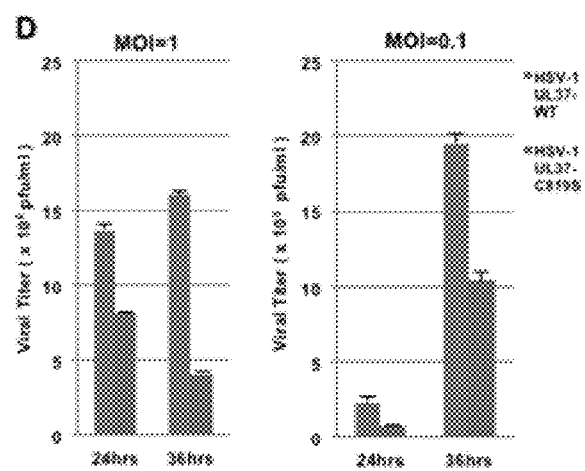
Figure 13E:
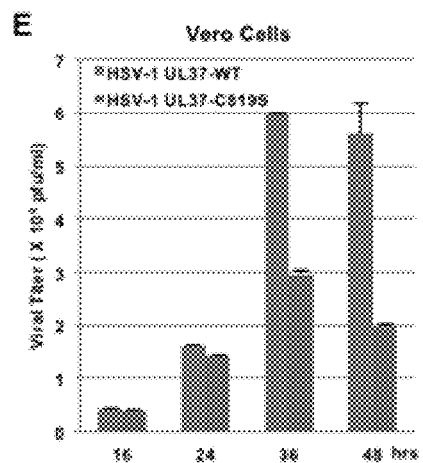
Figure 13F:
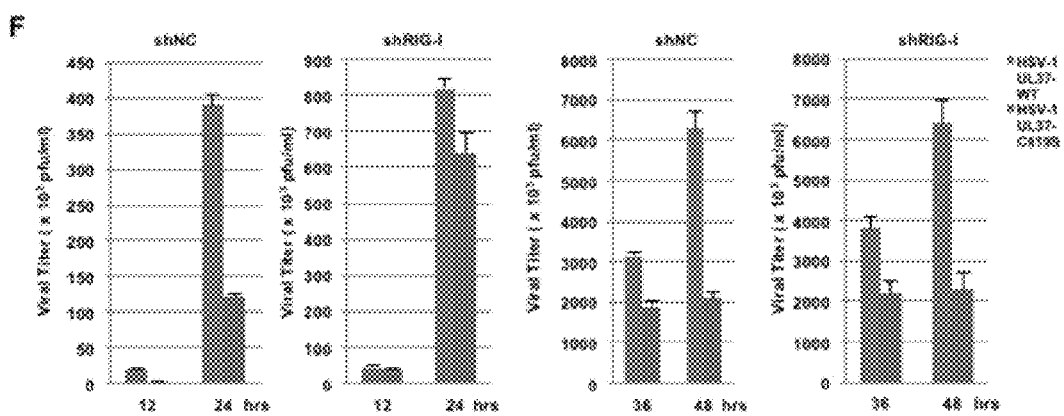

Applicant then analyzed HSV-1 lytic replication and found that HSV-1 UL37-C819S produced ~10% of virion progeny of HSV-1 UL37-WT in HFF (FIG. 7H). In HeLa cells, HSV-1 UL37-C819S was more impaired at 36 than at 24 hpi compared to HSV-1 UL37-WT with the MOI of 1, whereas the impaired replication phenotype of HSV-1 UL37-C819S was more pronounced at 12 than 24 hpi with the MOI of 0.1 (FIG. 13D). To determine whether the reduced replication of HSV-1 UL37-C819S is due to the elevated IFN response, Applicant characterized HSV-1 replication in Vero cells that are deficient in IFN induction. Compared to HSV-1 UL37-WT, HSV-1 UL37-C819S showed identical viral replication at 12 and 24 hpi (FIG. 13E). However, HSV-1 UL37-C819S produced ~50% and 35% as many virion progeny as HSV-1 UL37-WT at 36 and 48 hpi, respectively. To further corroborate the roles of RIG-I in inhibiting HSV-1 replication, Applicant knocked down RIG-I and examined HSV-1 replication. As shown in FIG. 13F, RIG-I depletion restored the lytic replication of HSV-1 UL37-C819S to levels of HSV-1 UL37-WT, at 12 and 24 hpi. However, RIG-I knockdown had no effect on the difference in lytic replication between HSV-1 UL37-WT and HSV-1 UL37-C819S, at 36 and 48 hpi. These results show that RIG-I-mediated antiviral activity suppresses HSV-1 lytic replication during early infection and that UL37 deamidase activity is important to antagonize RIG-I-mediated antiviral defense. Furthermore, UL37 deamidase activity is important for late stages of HSV-1 lytic replication.

Applicant previously reported that vGAT pseudo-enzymes of human KSHV and murine γHV68 recruited cellular PFAS to deamidate RIG-I and evade antiviral cytokine production (He et al., 2015). Interestingly, HSV-1 infection also induced RIG-I deamidation, despite the fact that genomes of alpha herpesviruses do not contain sequence homologues of vGAT proteins. Herein, Applicant identified UL37 as a viral deamidase that targets RIG-I for deamidation and inactivation, thereby preventing RIG-I from sensing viral dsRNA. To Applicant's knowledge, this is the first viral protein deamidase identified thus far. Previously reported protein deamidases contain either a cysteine-protease fold or a GAT domain (Cui et al., 2010; He et al., 2015; Sanada et al., 2012; Wang et al., 2009). UL37-mediated deamidation of RIG-I disarms downstream innate immune signaling, suggesting the critical, and likely more ubiquitous, roles of protein deamidation in signal transduction. UL37 is a large tegument protein that is implicated in viral trafficking, egress and innate immune regulation (Desai et al., 2001; Liu et al., 2008; Pitts et al., 2014). Taken together, UL37 inhibits the IRF-IFN branch of innate immune signaling through deamidation of RIG-I, while activating the NF-κB cascade, sharing functions similar to the gamma herpesvirus vGAT proteins.

Applicant's biochemical analyses show that UL37 is intrinsically a protein deamidase. UL37 and its carboxyl terminal fragment (571-1123) purified from *E. coli* were sufficient to deamidate RIG-I in vitro. Mutational analysis and electrophile reaction profiling of hyper-reactive cysteines identified C819 as the single residue critical for the deamidase activity, implying that C819 is the active cysteine of the catalytic triad of UL37. Interestingly, C850 is more conserved in alpha herpesviruses than C819 (data not shown). The fact that C850 is largely inaccessible suggests that it may be required for the structural integrity of the deamidase domain. It is unclear whether other UL37 homologs are deamidases. Future structural studies of the UL37 deamidase domain may define a new fold catalyzing protein deamidation and "visualize" the catalytic cysteine.

Although previous studies implicated RIG-I in sensing dsRNA produced by herpesviruses (da Silva and Jones, 2013; Jacquemont and Roizman, 1975; Rasmussen et al., 2009; Weber et al., 2006), Applicant's work provides further credence concerning the RIG-I-mediated immune defense against a model DNA virus and viral immune evasion thereof. HSV-1 infection prevents RIG-I activation and innate immune responses triggered by subsequent SeV infection. These phenotypes were recapitulated by UL37 expression, pointing to the key roles of UL37 in evading RIG-I activation by viral dsRNA. The deamidated RIG-I-DD (D495 and D549) mutant, failed to sense 5'ppp-RNA and SeV, which correlated with its inability to initiate host immune signaling and control VSV replication. Comparing HSV-1 replication kinetics in IFN-competent 293T and HeLa cells to that in IFN-deficient Vero cells, Applicant found that the deamidase activity of UL37 is critical in negating RIG-I-mediated inhibition of the early steps of HSV-1 lytic replication. The mutation abolishing UL37 deamidase activity, notably, also impaired HSV-1 replication during late stages of replication in an RIG-I-independent manner, implying the existence of other viral and cellular targets in addition to RIG-I. Nevertheless, uncoupling RIG-I deamidation from UL37, via either introducing the deamidation-resistant RIG-I-QQ into cells or engineering the C819S mutation of UL37 into the HSV-1 genome, restored RIG-I activation and downstream innate immune signaling, thereby reducing HSV-1 productive infection. These results unambiguously demonstrate the antiviral activity of RIG-I against a DNA herpesvirus and elucidate a new mechanism of viral immune evasion.

N495 and N549 reside in two α-helices that constitute the RNA-binding interface of the Hel2i domain. Interestingly, N549 forms hydrogen bonds with the backbone of T504 that ends the N495-containing α23 helix, providing a physical link between these two neighboring helices that are located immediately proximal to the RIG-I-bound dsRNA. These observations suggest that the two α-helices constitute a region responsible for regulating RNA-binding/sensing by RIG-I. The susceptibility of the hydrogen bonds between N549 and T504 to the deamidase activity of UL37 underpins the inactivation of RIG-I by HSV-1 infection. Remarkably, the N549Q mutation appears to conserve hydrogen bonds, and confers resistance to UL37-mediated deamidation, demonstrating the exquisite specificity of UL37-mediated deamidation. Deamidation of N495 and N549 within the Hel2i domain, unexpectedly, abolishes 5'ppp-RNA-binding and ATP hydrolysis of RIG-I, uncovering a simple but powerful mechanism to switch off RIG-I. Although the CTD of RIG-I is responsible for sensing viral dsRNA, emerging studies support the regulatory role of helicase domains in RNA-sensing by RIG-I. It was previously reported that Hel2i "measures" the length of dsRNA stem during RNA-binding by RIG-I (Kohlway et al., 2013). Structural analysis also highlighted the direct contact between Hel2i and dsRNA (Kowalinski et al., 2011; Luo et al., 2011). Moreover, mutations within a helicase domain reduced the ATPase activity of RIG-I, increased its association with cellular dsRNA and activated downstream signaling (Lassig et al., 2015). Together with these observations. Applicant's work further lends credence to the pivotal roles of Hel2i of RIG-I and site-specific deamidation thereof in interacting with and sensing viral dsRNA, suggesting more ubiquitous roles of protein deamidation in fundamental biological processes.

Two-Dimensional Gel Electrophoresis

Cells ($1\times10^6$) were lysed in 150 µl rehydration buffer (8 M Urea, 2% CHAPS, 0.5% IPG Buffer, 0.002% bromophenol blue) by three pulses of sonication and whole cell lysates were centrifuged at 20,000 g for 15 min. Supernatants were loaded to IEF strips for focusing with a program comprising: 20 V, 10 h (rehydration); 100 V, 1 h; 500 V, 1 h; 1000 V, 1 h; 2000 V, 1 h; 4000 V, 1 h; 8000 V, 4 h. After IEF, strips were incubated with SDS equilibration buffer (50 mM Tris-HCl [pH8.8], 6 M urea, 30% glycerol, 2% SDS, 0.001% Bromophenol Blue) containing 10 mg/ml DTT for 15 min and then SDS equilibration buffer containing 2-iodoacetamide for 15 min. Strips were washed with SDS-PAGE buffer, resolved by SDS-PAGE, and analyzed by immunoblotting.

In Vitro Deamidation Assay

GST-RIG-I was purified from transfected 293T cells to homogeneity as determined by silver staining. In vitro on-column deamidation of RIG-I was performed as previously reported (He et al., 2015). Briefly, ~0.2 µg of His-tagged UL37/UL37 (571-1123) expressed and purified from E. coli, and 0.6 µg of GST-RIG-I (bound to glutathione-conjugated agarose) were added to a total volume of 30 µl. The reaction was carried out at 30° C. for 45 min in deamidation buffer (50 mM Tris-HCl, pH 7.5, 100 mM NaCl, 5 mM $MgCl_2$). Protein-bound GST beads were washed with deamidation buffer and GST-RIG-I was eluted with rehydration buffer (6 M Urea, 2 M Thio-urea, 2% CHAPS, 0.5% IPG Buffer, 0.002% bromophenol blue) at room temperature. Samples were then analyzed by two-dimensional gel electrophoresis and immunoblotting.

Constructing Recombinant HSV-1

Recombinant HSV-1 was engineered as previously described (Dong et al., 2010). Briefly, DNA fragments containing UL37 WT and C819S were amplified using overlapping primers. First round PCR products of ~500 bp fragment upstream of UL37, UL37 open reading frames (WT and C819S) and ~500 bp fragments downstream of UL37 were used as the template for second round PCR amplification. Purified PCR products of the second round, along with HSV-1 ΔUL37 (KOS) Bacmid, were transfected into 293T cells to generate recombinant HSV-1. The revertant (containing wild-type UL37, designated wild-type) and UL37-C819S mutant were plaque purified and validated by restriction digestion of viral genomic DNA and sequencing of the UL37 open reading frame.

RNA Electrophoresis Mobility Shift Assay (EMSA)

RNA EMSA was performed as previously described (Takahasi et al., 2008). 5'-ppp-dsRNA and control dsRNA were purchased from Invivogen and bottom strands were labeled with γ-[$P^{32}$]ATP by T4 polynucleotide kinase (NEB). Purified RIG-I and RIG-I mutants were incubated with dsRNA at room temperature for 15 min. Binding buffer contains 20 mM Tris-HCl (pH=8.0), 1.5 mM $MgCl_2$ and 1.5 mM DTT. Unlabeled ppp-dsRNA was used as competitor at 500-fold in excess. The reaction mixtures were run on 5% native polyacrylamide gels at a constant voltage of 200 V. Gels were dried and subjected to phosphorimaging.

| Labeled 5'-ppp-dsRNA | Top Strand | 5'-ppp-GCAUGCGACCUCUGU UUGA-3' (SEQ ID NO: 24) |
|---|---|---|
| | Bottom Strand | 3'-CGUACGCUGGAGACAAACU-5'-32P (SEQ ID NO: 25) |
| Labeled 5' control dsRNA | Top Strand | 5'-GCAUGCGACCUCUGUUUGA-3' (SEQ ID NO: 26) |
| | Bottom Strand | 3'-CGUACGCUGGAGACAAACU-5'-32P (SEQ ID NO: 25) |

In Vitro ATPase Activity Assay

Purified RIG-I or RIG-I mutants were incubated with 5'-ppp-dsRNA (Invivogen) at 37° C. for 20 min in ATPase reaction buffer (50 mM Tris-HCl, pH 7.5, 2.5 mM $MgCl_2$, and ATP). Released phosphates were measured using a PiColorLock™ phosphate detection reagent (Innova Biosciences). For reactions with varying concentrations of ATP, the concentrations of RIG-I proteins and RNA were 20 nM and 80 nM, respectively. For reactions with varying concentrations of the RNA, the concentrations of RIG-I proteins and ATP were 20 nM and 500 µM, respectively.

Experiment No. 2

Upon infection, eukaryotic cells immediately respond with innate immune activation to defeat the invading pathogens. Cyclic GMP-AMP (cGAMP) synthase (cGAS) is an essential cytosolic sensor that detects double-stranded (ds) DNA of microbial origin or aberrantly localized cellular DNA. Other DNA sensors, including AIM2, DAI, DDX41, RNA polymerase III, DNA-PK and IFI16, may play redundant roles in a tissue- or ligand-specific manner in detecting cytosolic dsDNA. Upon binding dsDNA, cGAS catalyzes the synthesis of cGAMP, which induces the dimerization and activation of the ER-anchored STING (also known as MITA). Within close proximity to the ER membrane, STING recruits TBK-1 and interferon regulatory factor 3 (IRF3) to assemble into a signaling complex that phosphorylates and activates IRF3. Along with NF-κB and AP-1, nuclear IRF3 potently up-regulates the gene expression of interferons (IFNs). IFNs, via autocrine and paracrine mechanisms, stimulate the expression of hundreds of genes, known as ISGs, which establish an immune defensive state of the cell. Parallel to the TBK-1-IRF3-IFN pathway, IKK kinase, consisting of IKKα, IKKβ and IKKγ (also known as NEMO), phosphorylates and induces the degradation of inhibitor of NF-κB (IκB). This enables NF-κB activation that induces the expression of inflammatory cytokines, such as interleukins and chemokines. The primary role of inflammatory cytokines is to attract professional immune cells to the site of infection. Thus, the innate immune system defends the host from infection via direct anti-microbial activities and enables the establishment of adaptive immunity in tissue local to the infection.

Though key steps of the cGAS-STING pathway are well established, the regulatory mechanisms governing cGAMP synthesis of cGAS to induce STING-dependent innate immune activation is not well understood. Studying viral immune evasion allows us to interrogate mechanisms regulating host immune responses. As one of the most successful pathogens, herpesviruses have evolved numerous intricate strategies to manipulate, evade and exploit host immune response to benefit their infection. The most common viral mechanism is to encode proteins that physically interact with central cellular signaling nodes of immune defense to derail host immune response. Viral proteins efficiently regulate cellular immune signal transduction by microbial enzyme-mediated reactions, such as proteolytic cleavage or post-translational modifications (PTMs). Virally encoded proteases cleave various adaptor molecules and effectively dampen innate immune signaling, while host cells often deploy reversible PTMs (phosphorylation, ubiquitination and sumoylation) to regulate immune response.

Protein deamidation is emerging as a key PTM that regulates immune responses against infecting microbes. First reported more than half a century ago, protein deamidation was regarded as a marker associated with protein "aging" or functional decay. Though initial studies focused on non-enzymatic protein deamidation, recent findings from bacterial effectors and mammalian cells imply that protein deamidation can be enzyme-catalyzed and thus highly regulated. Applicant has identified viral pseudo-enzymes and bona fide deamidases that target cellular innate immune RIG-I sensor to evade antiviral cytokine roduction. While gamma herpesvirus vGAT pseudoenzymes recruit cellular PFAS to deamidate RIG-I, the UL37 tegument protein of herpes simplex virus 1 (HSV-1) is a bona fide protein deamidase that deamidates RIG-I in vitro and in cells. While further characterizing the in vivo roles of UL37 deamidase in HSV-1 infection, Applicant discovered that UL37 antagonizes cGAS-mediated innate immune activation via deamidating cGAS. Moreover, HSV-1 carrying deamidase-deficient UL37 was highly attenuated, and more robustly induced innate and adaptive immune responses in mice than wild-type HSV-1. Vaccination with HSV-1 carrying deamidase-deficient UL37 protected mice from lethal dose challenge with wild-type HSV-1. These results imply that interfering with protein deamidation can boost antiviral immune responses and thwart viral infection.

Results

Figure 14A:
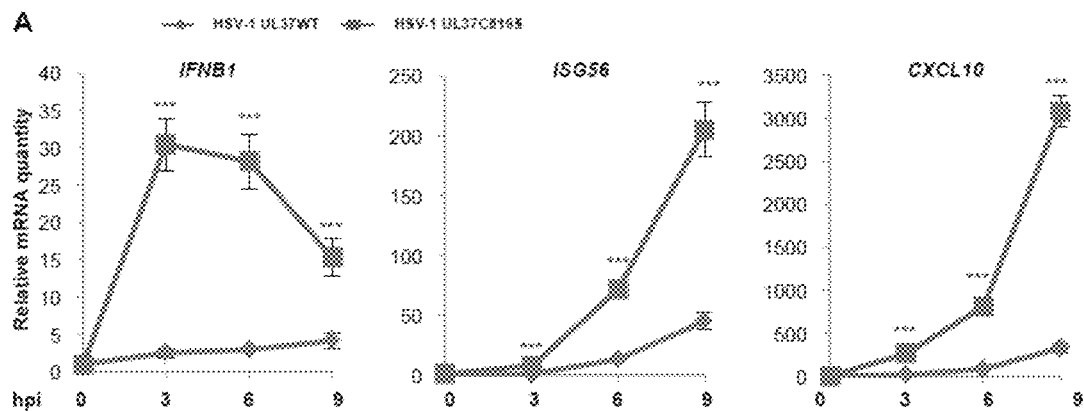
FIGS. 14A-14E show that HSV-1 carrying deamidase-deficient UL37C718S more robustly induces cytokine production in THP-1 cells than wild-type HSV-1.
Figure 14B:
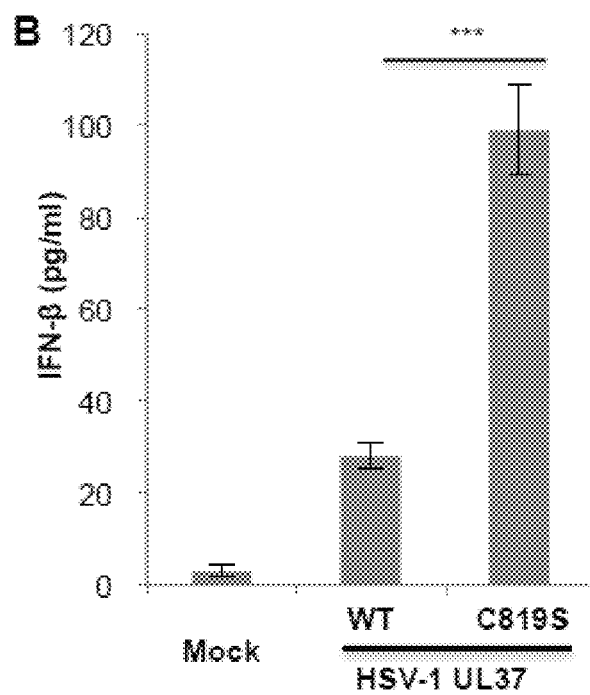
Figure 14C:
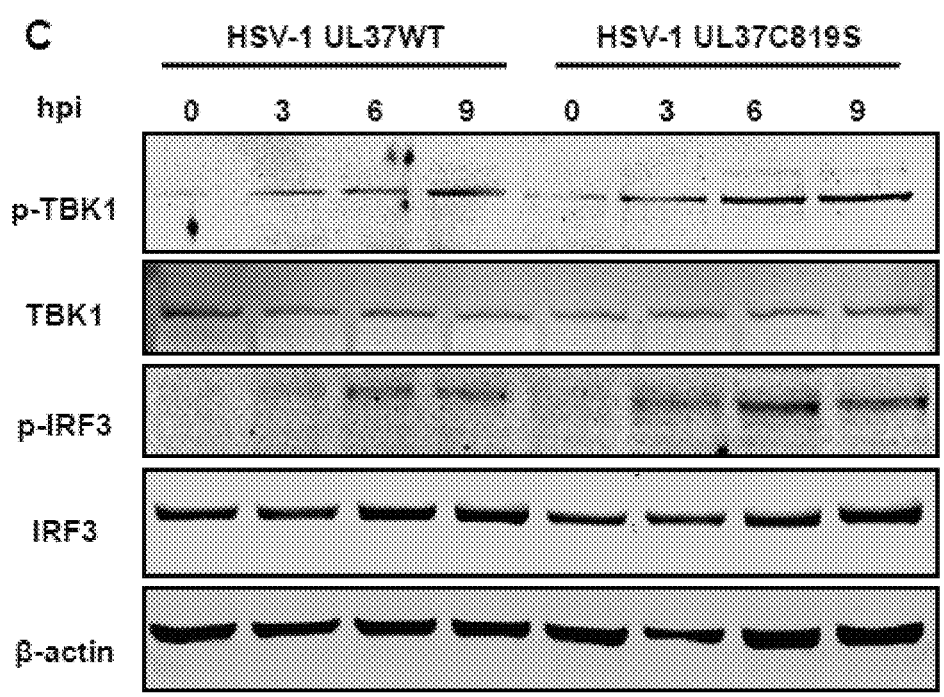
Figure 14D:
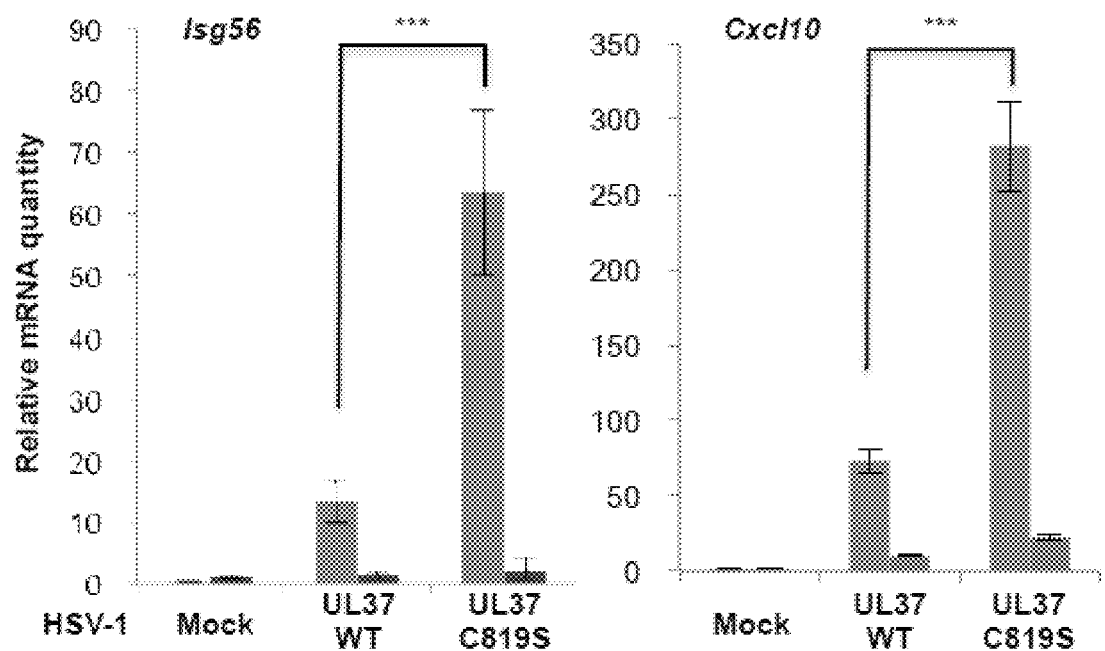

Applicant reports herein that the UL37 tegument protein of HSV-1 deamidates RIG-I to avoid dsRNA-induced innate immune activation. Recombinant HSV-1 carrying deamidase-deficient UL37C819S mutant (HSV-1 UL37C819S) more robustly induced antiviral cytokines than HSV-1 containing wild-type UL37 (HSV-1 UL37WT). To further characterize this recombinant HSV-1, Applicant examined antiviral immune responses in human THP-1 monocytes upon HSV-1 infection. Real-time PCR analysis of representative antiviral cytokines (IFNB1, ISG56, CXCL10, MX1, IFIT3 and IL6) indicated that HSV-1 UL37C819S virus induced ~5-10-fold higher expression of cytokine genes than HSV-1 UL37 wild-type (WT) in THP-1 cells during early viral infection (FIG. 14A). Enzyme-linked immunosorbant assay (ELISA) further showed that THP-1 cells infected with HSV-1 UL37C819S virus secreted significantly higher IFN-β than those infected with HSV-1 UL37WT (FIG. 14B). Consistent with these results, HSV-1 UL37C819S virus more robustly induced activation of the IRF-IFN pathway than HSV-1 UL37WT virus in THP-1 cells, as evidenced by the elevated phosphorylation (and activation) of TBK-1 (Ser172) and IRF3 (Ser396) (FIG. 14C). These results clearly demonstrate that HSV-1 UL37C819S more robustly induces innate immune activation than HSV-1 UL37WT in human THP-1 monocytes.

cGAS is a crucial DNA sensor that detects cytosolic DNA of diverse human pathogens, including herpesviruses. Thus, Applicant assessed whether cGAS is required for effective antiviral immune responses against HSV-1 UL37C819S virus. Applicant infected wild-type and cGAS-deficient L929 fibroblasts with HSV-1 UL37WT and HSV-1 UL37C819S, and determined antiviral gene expression. In wild-type L929 fibroblasts, HSV-1 UL37C819S virus more robustly induced Isg56 and Cxcl10 expression than HSV-1 UL37WT virus, recapitulating the phenotype that was observed in human THP-1 monocytes. Remarkably, loss of cGAS abolished Isg56 and Cxcl10 expression in response to HSV-1 UL37WT and HSV-1 UL37C819S (FIG. 14D). Furthermore, similar levels of residual expression of Isg56 and Cxcl10 were detected in cGAS-deficient L929 cells infected by HSV-1 UL37WT and HSV-1 UL37C819S (FIG. 14D). These results indicate that induction of elevated antiviral cytokine expression by deamidase-deficient HSV-1 UL37C819S virus is dependent on cGAS.

Figure 14E:
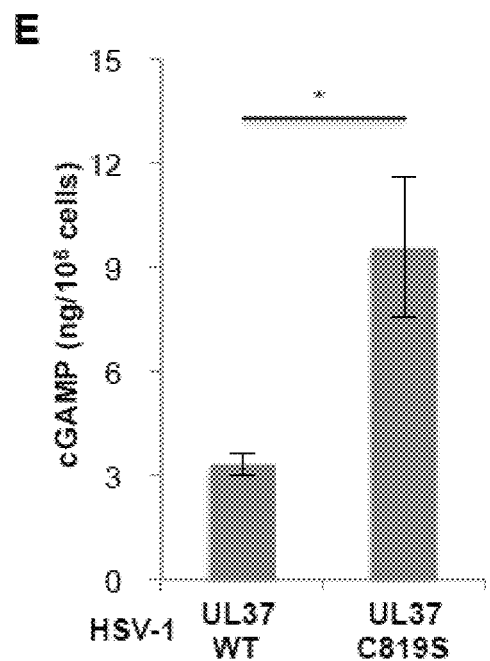

To probe the effect of HSV-1 infection on the DNA-cGAS pathway, Applicant determined intracellular cGAMP concentrations using the THP-1/Lucia reporter cell line. Applicant applied known concentrations of cGAMP to establish a standard that demonstrated a high correlation between cGAMP concentration and luciferase activity with 0-30 ng/ml of cGAMP. Applicant determined that HSV-1 UL37WT induced approximately 3.5 ng of cGAMP per one million of THP-1 cells, while HSV-1 UL37C819S infection increased cGAMP production to ~10.5 ng per one million of THP-1 cells (FIG. 14E). Enhanced activation of the DNA-cGAS pathway by HSV-1 UL37C819S than HSV-1 UL37WT is further supported by elevated levels of intracellular cGAMP, phosphorylated TBK-1 and IRF3, and the expression of antiviral cytokines.

UL37 Targets cGAS to Dampen Antiviral Cytokine Production

Figure 15A:
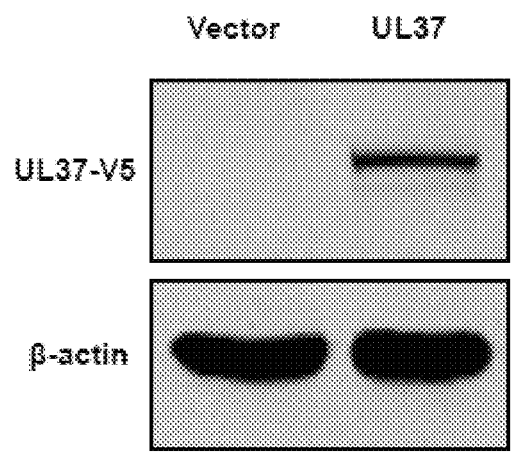
FIGS. 15A-15H evidence that UL37 targets cGAS to inhibit innate immune activation.
Figure 15B:
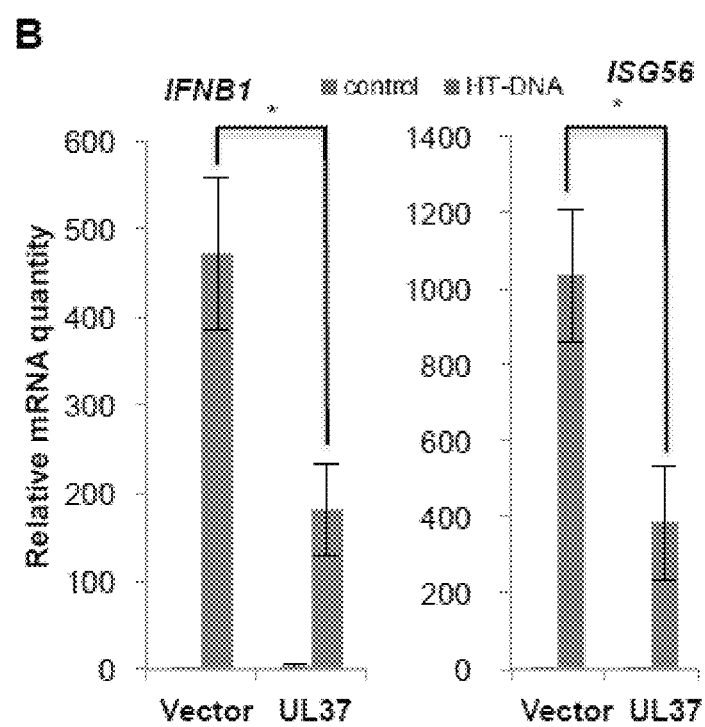
Figure 15C:
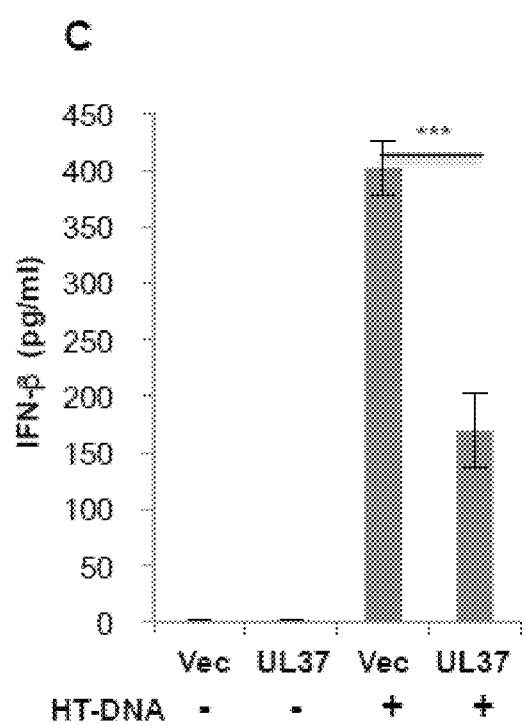
Figure 15D:
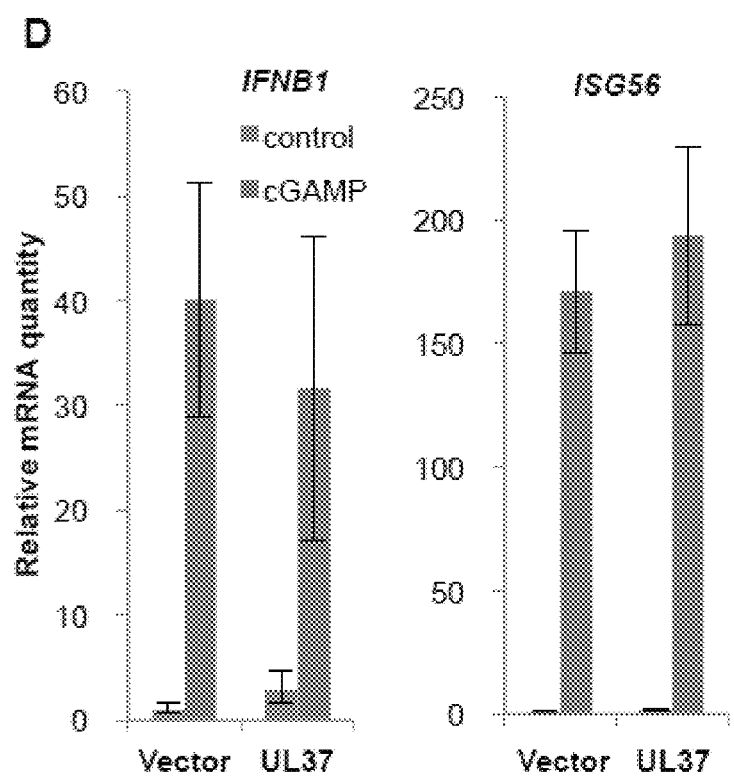
Figure 15E:
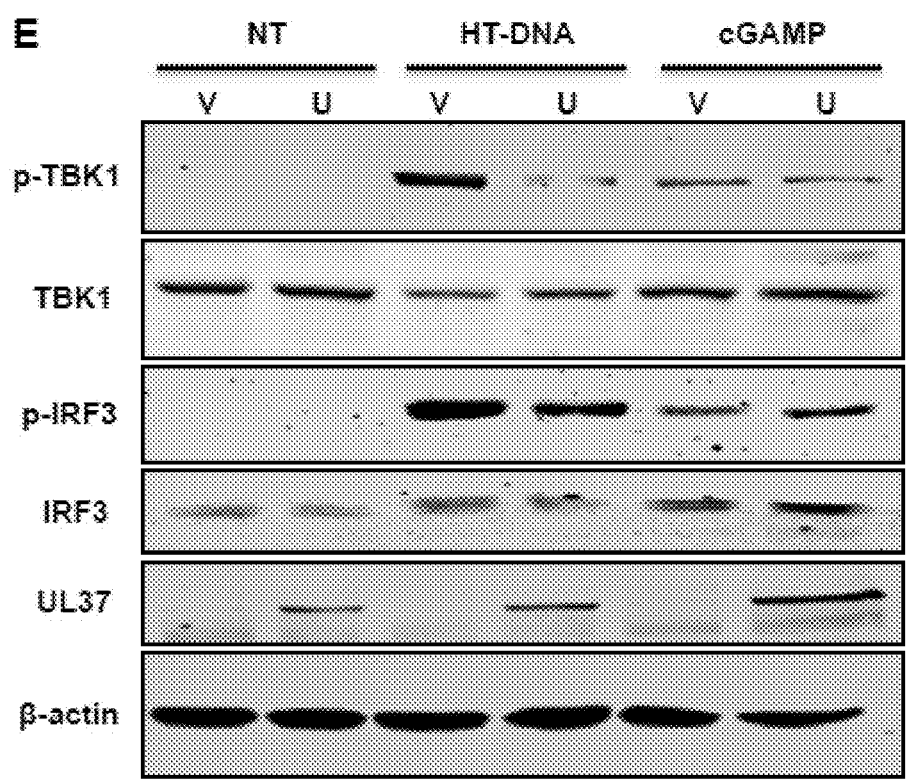
Figure 15F:

To determine whether UL37 is sufficient to inhibit cGAS-mediated innate immune responses, Applicant established a THP-1 cell line stably expressing UL37 by lentiviral transduction (FIG. 15A). When THP-1 cells were transfected with herring testis DNA (HT-DNA) that activates cGAS, Applicant found that UL37 expression reduced IFNB1 and ISG56 expression by ~60% as analyzed by quantitative real-time PCR (FIG. 15B). A similar level of reduction in secreted IFN-β in THP-1 cells was also observed upon UL37 expression (FIG. 15C). Interestingly, the induction of IL6 and IL8 by HT-DNA transfection was not affected by UL3 expression. Moreover, CXCL10 and ISG56 expression induced by LPS was significantly increased by UL37 expression. This is likely due to the ability of UL37 to activate NF-κB, as evidenced by the slight elevation of CXCL10 and ISG56 in THP-1 cells expressing UL37 at baseline without stimulation. Upon sensing cytosolic DNA, cGAS catalyzes the synthesis of cGAMP, which subsequently activates the STING adaptor. To determine the mechanism of inhibition by UL37, Applicant assessed IFNB1 and ISG56 gene expression in THP-1 cells upon cGAMP transfection. Interestingly, UL37 expression did not significantly affect neither the expression of IFNB1 and ISG56 (FIG. 15D), nor the secretion of IFN-β, in THP-1 cells transfected with cGAMP. Applicant further examined the effect of UL37 on DNA-induced innate immune signaling in wild-type and cGAS-deficient L929 cells. UL37 expression reduced the mRNA levels of Ifnb1 and Isg56 in L929 cells transfected with HT-DNA. Consistent with previous reports, loss of cGAS abolished Ifnb1 and Isg56 gene expression induced by HT-DNA in L929 cells. UL37 expression in THP-1 cells inhibited the phosphorylation of TBK-1 and IRF3 induced by HT-DNA, but not those induced by cGAMP (FIG. 15E). Similar results were obtained in L929 cells. Interestingly, HT-DNA induced TBK-1 and IRF3 phosphorylation in cGAS-deficient L929 cells, which were not affected by UL37 expression. The cGAS-independent activation of TBK-1 and IRF3 by HT-DNA in L929 cells remains to be investigated. Similar to what was observed in THP-1 cells, UL37 expression didn't affect the induction of Ifnb1 and Isg56 by cGAMP in L929 wild type and cGAS-deficient cells. As previously reported, cGAMP-induced expression of Isg56 in cGAS-deficient L929 cells was significantly lower than that in wild-type L929 cells. These results collectively indicate that UL37 antagonizes cGAS to inhibit DNA-induced innate immune signaling.

Figure 15G:
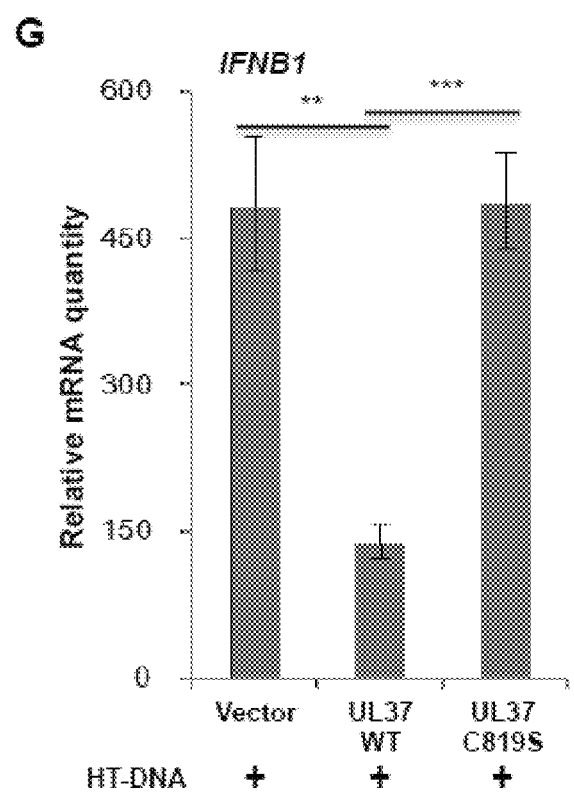
Figure 15H:
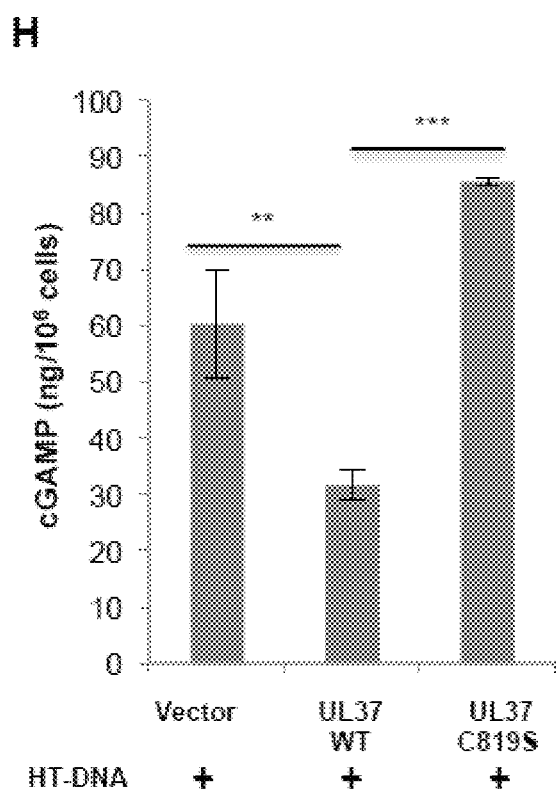

Given that recombinant HSV-1 UL37C819S virus more robustly induced antiviral cytokine production in THP-1 cells (FIG. 14), Applicant sought to determine whether the deamidase activity of UL37 is necessary to suppress cGAS-mediated innate immune activation using the deamidase-deficient UL37C819S mutant. UL37WT potently reduced the expression of IFNB1, ISG56 and CXCL10 induced by HT-DNA in THP-1 cells, whereas UL37C819S mutant had no detectable effect on IFNB1 and ISG56 expression and increased CXCL10 expression (FIG. 15G). To test whether UL37 impacts the enzymatic activity of cGAS, Applicant determined intracellular cGAMP concentrations in THP-1 cells transfected with HT-DNA. This assay showed that HT-DNA induced approximately 60 ng of cGAMP per one million THP-1 cells (equivalent to 0.5 million molecules of cGAMP per cell), while UL37WT expression reduced cGAMP to ~35 ng per one million THP-1 cells (FIG. 15H). The expression of UL37C819S slightly increased cGAMP production to ~85 ng per one million THP-1 cells. These results collectively indicate that the deamidase activity of UL37 is required to suppress cGAMP synthesis catalyzed by cGAS.

UL37 Deamidates cGAS In Vitro and in Cells

Figure 16A:
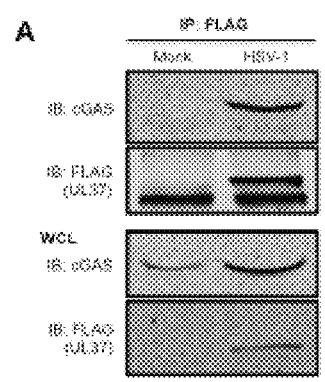
FIGS. 16A-16G show that UL37 interacts with and deamidates cGAS.

UL37WT, but not the deamidase-deficient UL37C819S mutant, reduced cGAS-mediated cGAMP synthesis. Moreover, HSV-1 UL37C819S virus more robustly induced antiviral cytokines in THP-1 monocytes than HSV-1 UL37WT. These results imply that UL37 targets cGAS for deamidation. To test this hypothesis, Applicant first determined whether UL37 interacts with cGAS in HSV-1-infected cells. Using recombinant HSV-1 carrying FLAG-tagged UL37, Applicant demonstrated that cGAS precipitated with UL37 in HSV-1-infected THP-1 cells (FIG. 16A). Applicant noted that HSV-1 infection increased cGAS protein expression, consistent with established knowledge that cGAS is an interferon-inducible gene. Mutational analysis showed that the Mab21 enzyme domain (residue 162-522) of cGAS interacts with UL37, and both the N-terminal and C-terminal domains of UL37 are sufficient for binding cGAS.

Figure 16B:
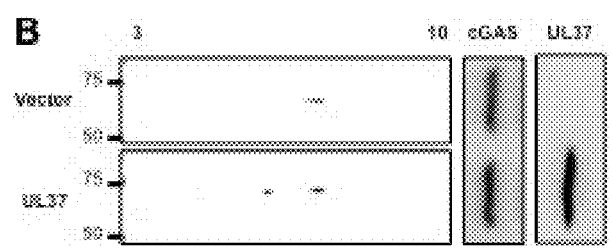
Figure 16C:
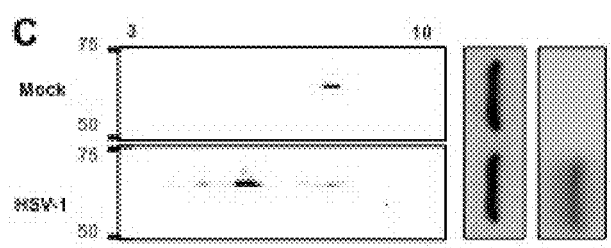
Figure 16D:
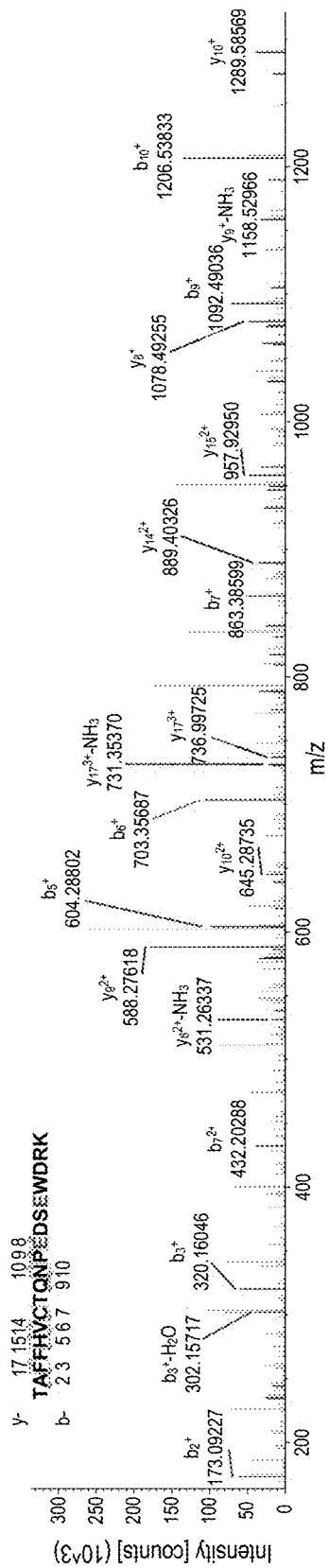
Figure 16E:
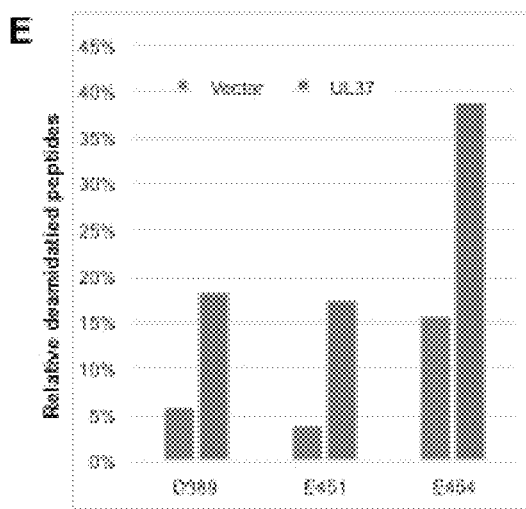
Figure 16F:
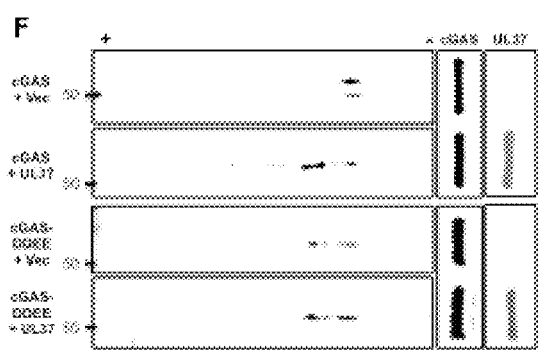

To assess whether UL37 induces cGAS deamidation, Applicant analyzed the charge status of cGAS without or with UL37 expression by two-dimensional gel electrophoresis (2DGE). As shown in FIG. 16B, UL37 expression shifted cGAS toward the positive side of the gel strip, indicative of reduced charge due to potential deamidation upon UL37 expression. This directional shift of cGAS was recapitulated by HSV-1 infection (FIG. 16C). To identify sites of deamidation in cGAS, Applicant purified cGAS in 293T cells without or with UL37 expression and conducted tandem mass spectrometry (MS). Additionally, Applicant performed in vitro deamidation assays to augment the protein coverage of cGAS analyzed by tandem MS. MS analysis using purified cGAS deamidated in cells and in vitro identified a total of four sites of deamidation, all located within the Mab21 enzyme domain of cGAS: N196, N377, Q436 and Q439 (homologous to hcGAS N210, N389, Q451 and Q454) (FIG. 16D). Quantification of deamidated peptides indicated that UL37 expression increased the deamidation of these four sites by ~2-3-fold (FIG. 16E). To validate the deamidation sites of cGAS, Applicant generated a deamidated mutant of all four deamidated residues, designated cGAS-DDEE. UL37 expression shifted cGAS-WT toward the positive side of the strip and to the position that was identical to that of cGAS-DDEE (FIG. 16F). Expression of UL37 did not further shift cGAS-DDEE, implying that there are no other deamidation sites in addition to the four identified. There was a residual amount of cGAS-WT and cGAS-DDEE that was not shifted by UL37 expression; this species may represent cGAS with other PTMs that counteract the charge change of deamidation.

Figure 16G:
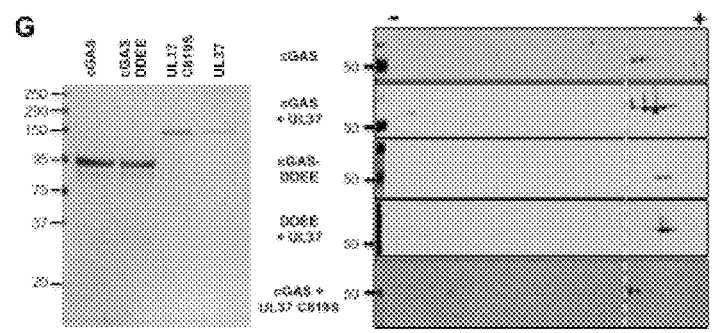

Applicant has previously shown herein that UL37 is a bona fide protein deamidase of RIG-I. Thus, Applicant sought to determine whether UL37 is sufficient to deamidate cGAS in vitro. Applicant purified cGAS, UL37WT and UL37C819S mutant from bacteria to high homogeneity (FIG. 16G). There were two major species and one minor species of the purified cGAS as analyzed by 2DGE, likely due to deamidation or other modifications. Analysis of in vitro cGAS deamidation reactions by 2DGE showed that UL37WT shifted cGAS toward the positive end of the gel strip to a position of the deamidated cGAS-DDEE mutant, while the deamidase-deficient UL37C819S failed to do so (FIG. 16G). Again, UL37WT failed to further shift the deamidated cGAS-DDEE mutant. Taken together, UL37 is a bona fide protein deamidase that deamidates cGAS in cells and in vitro.

Deamidation Impairs the cGAMP Synthase Activity of cGAS

Figure 17A:
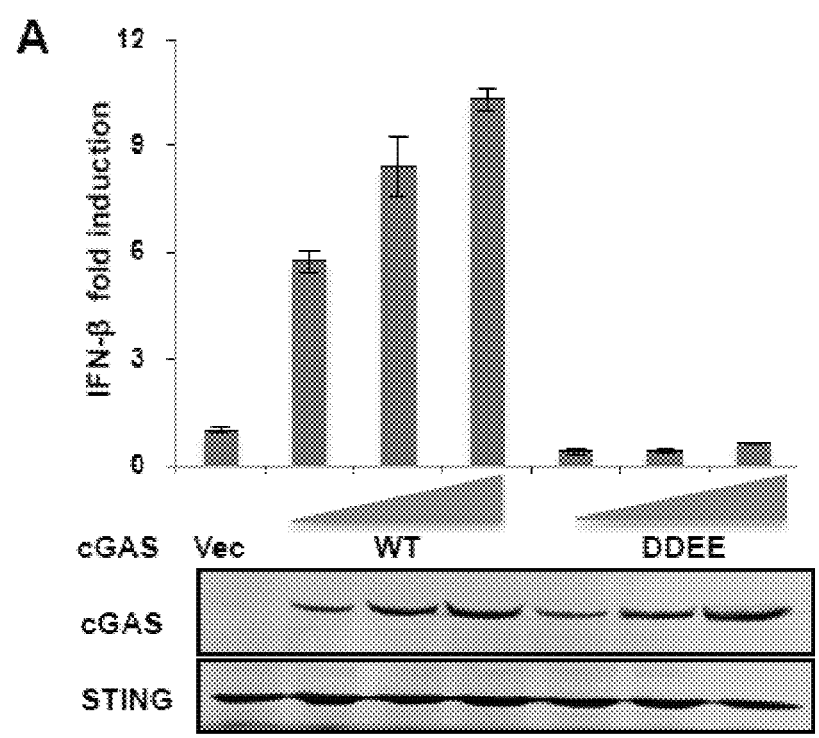
FIGS. 17A-17H show that deamidated cGAS fails to synthesize cGAMP, trigger innate immune response and restrict viral replication.

To probe the role of protein deamidation in cGAS-mediated antiviral immune response, Applicant first performed reporter assays to analyze the ability of various deamidated cGAS mutants in activating the IFN-β and NF-κB promoters. Applicant also has also generated mutations of all N and Q residues that are conserved within the Mab21 enzyme domain of human and mouse cGAS for these reporter assays. These reporter assays showed that N210D reduced cGAS-mediated gene expression by 50%, while the other three deamidations had marginal effects. The other deamidated residues did not significantly impair cGAS to activate the IFN-β promoter. However, combining the three mutations in NQQ389,451,454DEE modestly reduced cGAS-induced gene expression. When all four deamidated residues were introduced into cGAS, Applicant found that the cGAS-DDEE mutant failed to activate the IFN-β and NF-κB promoters by reporter assay (FIG. 17A). Thus, these deamidations negatively regulate cGAS-induced innate immune activation.

Figure 17B:
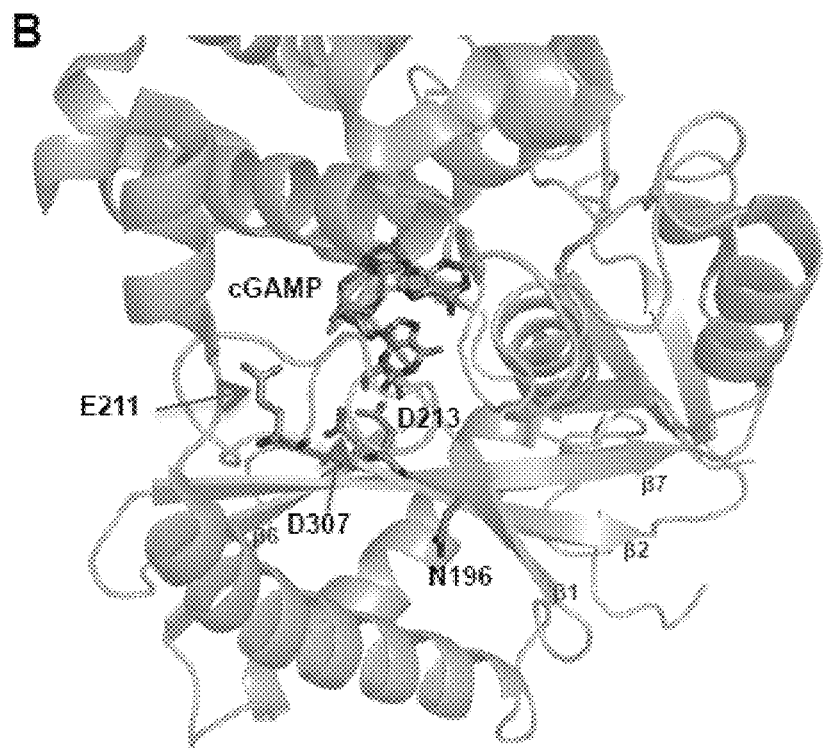

All four deamidation sites, N210, N389, Q451 and Q454, are conserved between mouse and human cGAS. These four sites correspond to N196, N377, Q436 and Q439 of mouse cGAS (mcGAS). Previous structural studies revealed an active site of mcGAS that catalyzes the synthesis of cGAMP, consisting of two parallel β-sheets (32 and 37, PDB: 4K9B) (FIG. 17B) that provide E211, D213 and D307 to form a catalytic triad. Additionally, 31 and 36 sheets sandwich the two core β-sheets. Linking the 31 sheet and the activation loop, N196 also is proximal to a hydrophobic pocket.

Interestingly, this hydrophobic pocket is formed by residues from core β-sheets (F212, V214 and F216 of β2, V306 and 1308 of 07) and a neighboring α-helix (V171, L175 and L179 of α2). In the cGAS structure bound to dsDNA, N196 lies between the hydrophobic cluster and the backbone of the dsDNA†(PDB:4K9B). Moreover, structural analysis by others show that, similar to other nonpolar residues with small side chain, N196 (or N210 of hcGAS) confers flexibility to the activation loop of cGAS. Thus, deamidation of N196 of mcGAS is expected to impinge on the nearby hydrophobic cluster and the flexibility of the activation loop that collectively enable the proper coordination of the catalytic triad.

Figure 17C:
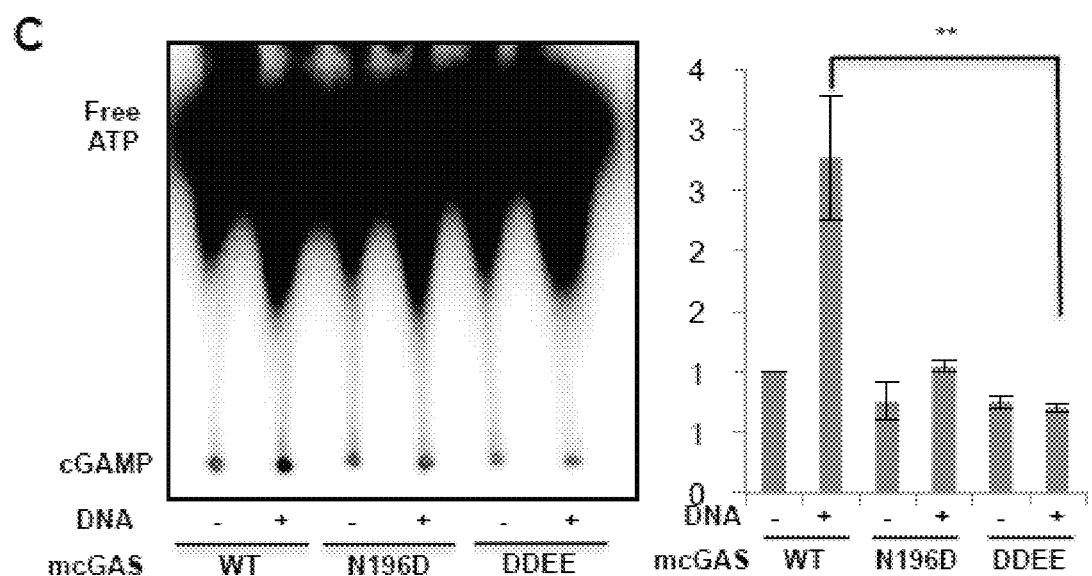

This is supported by the structure wherein N196 is close to the catalytic residue D213. In fact, the three catalytically residues E211, D213 and D307 form a highly negatively charged spot on protein, whose structure and physical chemical properties are likely very sensitive to alternation of nearby electrostatic potential induced by the damindation of N196. Applicant therefore assessed the effect of N196 deamidation on the enzyme activity of cGAS. As shown in FIG. 17C, HT-DNA stimulated cGAMP synthesis catalyzed by cGAS, but had no significant effect on cGAMP synthesis catalyzed by hcGAS-N196D or cGAS-DDEE. Furthermore addition of UL37 to the cGAMP reaction greatly reduced cGAS-mediated cGAMP production, while the deamidase-deficient UL37C819S mutant had less, albeit still significant, inhibition of cGAMP production. These results collectively show that UL37-mediated deamidation inhibits the cGAMP synthase activity of cGAS.

Structural analyses also indicate that the side chain of N376 and N377 of mcGAS (corresponding to N388 and N389 of hcGAS) project toward the minor groove of the dsDNA helix, suggesting that deamidation of these residues potentially interferes cGAS ability to sense dsDNA. However, precipitation of biotinylated interferon-stimulating DNA (ISD) demonstrated that neither UL37-WT, nor UL37C819S diminished cGAS co-precipitated with ISD. In fact, UL37WT, but not UL37C819S, increased the interaction between cGAS and ISD by ~50%. Similar results were recapitulated with the deamidated cGAS-DDEE mutant, which demonstrated slightly enhanced interaction with ISD. Given that all four deamidation sites reside in regions proximal to the dimerization interface of cGAS, Applicant sought to determine whether UL37 influences cGAS self-dimerization. Co-IP assay showed that expression of UL37WT or UL37C819S did not alter cGAS dimerization. Taken together, these results suggest that UL37-mediated deamidation does not impair either the dsDNA-binding or dimerization of cGAS.

Figure 17D:
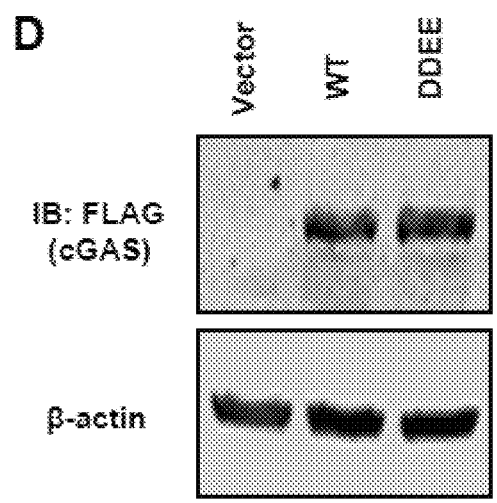
Figure 17E:
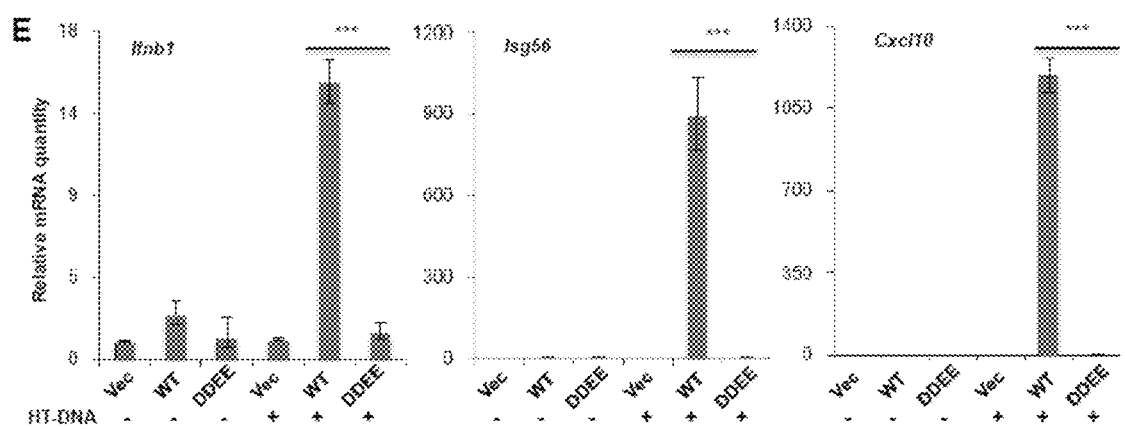

Deamidated cGAS Fails to Activate Innate Immune Signaling and Restrict DNA Virus Replication To probe the role of deamidation in regulating cGAS-mediated immune signaling and restricting viral replication, Applicant "reconstituted" cGAS-deficient L929 cells with cGAS wild-type and the deamidated cGAS-DDEE mutant (FIG. 17D). In response to HD-DNA transfection, L929 cells "reconstituted" with cGAS wild-type up-regulated the expression of Ifnb, Isg56, Cxcl10 and Ifit3 genes (FIG. 17E). In contrast, L929 cells "reconstituted" with the deamidated cGAS-DDEE mutant failed to induce the expression of these innate immune genes upon HD-DNA transfection. Applicant further "reconstituted" cGAS-deficient L929 cells with cGAS carrying individual deamidated residues. When these cells were transfected with HT-DNA, Applicant found that cytokine gene expression was significantly and most reduced in L929 cells "reconstituted" with cGAS-D210 compared to L929 "reconstituted" with cGAS wild-type. D389 and E454 also consistently reduced cGAS-dependent expression of cytokines, including Ifnb1 and Cxcl10. E451 had a minor effect on the expression of Ifnb1, but had no effect on other cytokines. These results collectively show that the deamidation of N210, N389 and N454 reduces the activity of cGAS in innate immune signaling.

Figure 17F:
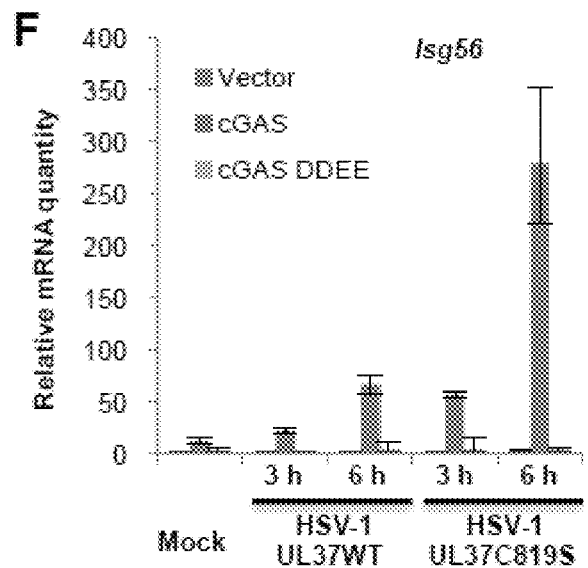
Figure 17G:
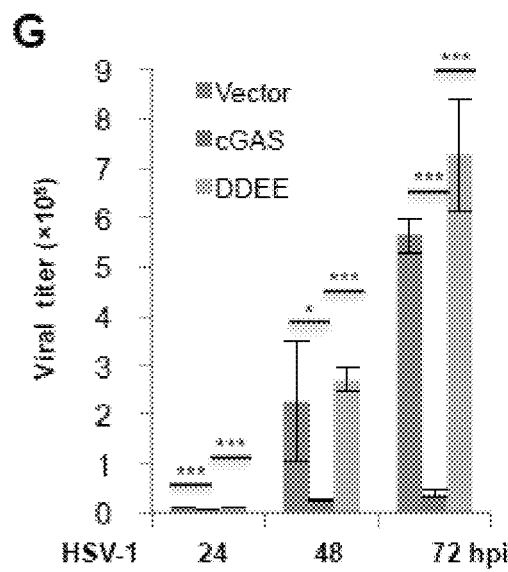
Figure 17H:
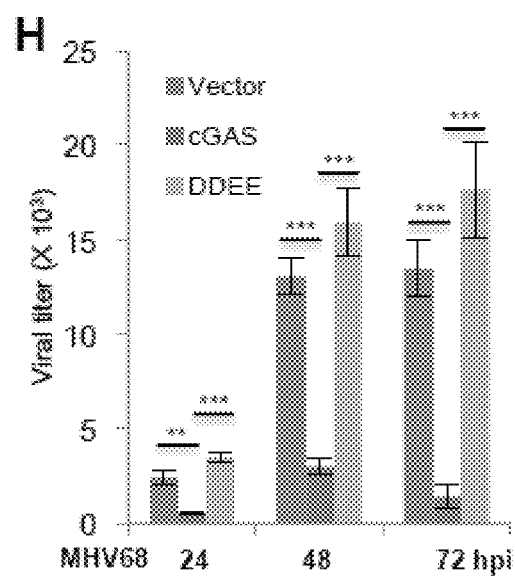

When infected with HSV-1 UL37WT or HSV-1 UL37C819S virus, L929 cells "reconstituted" with cGAS wild-type up-regulated the expression of inflammatory genes as potent as wild-type L929 cells. L929 cells "reconstituted" with cGAS-DDEE essentially behaved like cGAS-deficient L929 cells, demonstrating no induction of immune gene expression in response to HSV-1 infection (FIG. 17F). Applicant further tested the ability of cGAS wild-type and cGAS-DDEE in restricting DNA virus replication. Applicant found that "reconstituted" expression of cGAS wild-type reduced the replication of both HSV-1 and murine gamma herpesvirus 68 (MHV68) by >95% (FIGS. 4G and 4H). The expression of cGAS-DDEE had no effect on HSV-1 and MHV68 replication in L929 cells compared to cGAS-deficient L929 cells. These results demonstrate that deamidated cGAS fails to induce innate immune activation and to restrict DNA virus replication.

HSV-1 UL37C819S Virus More Robustly Induces Innate Immune Activation

Figure 18A:
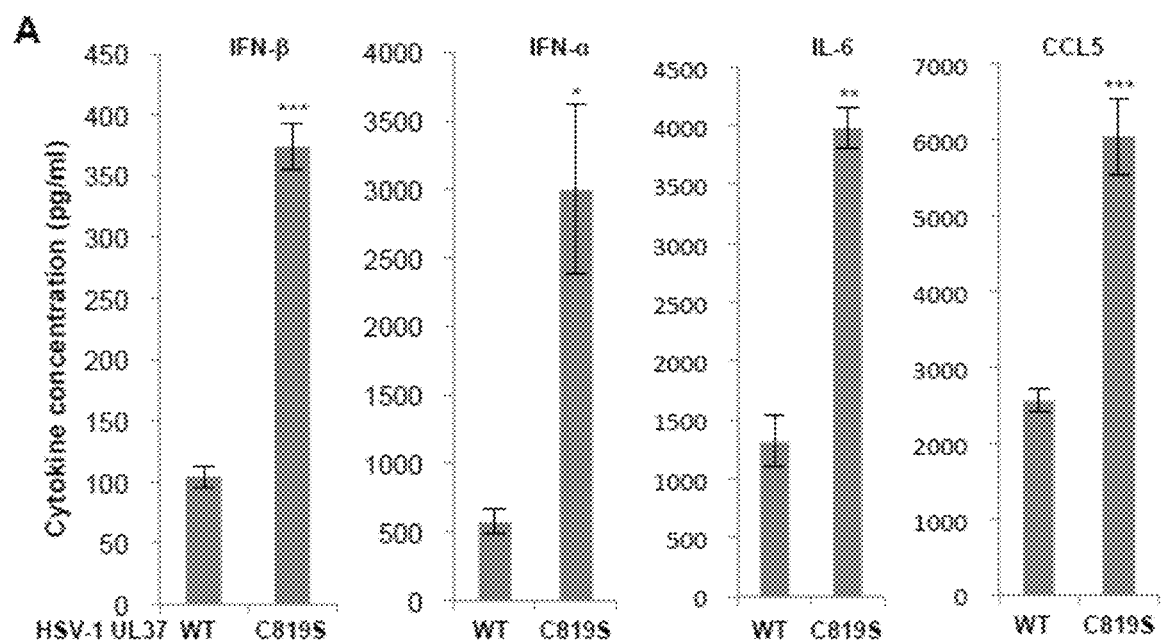
FIGS. 18A-18G show that HSV-1 carrying deamidase-deficient UL37C819S more robustly induces innate and adaptive immune responses.
Figure 18B:
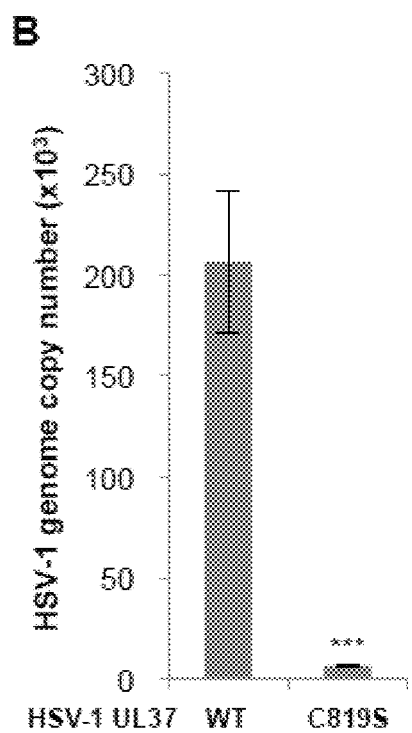
Figure 18C:
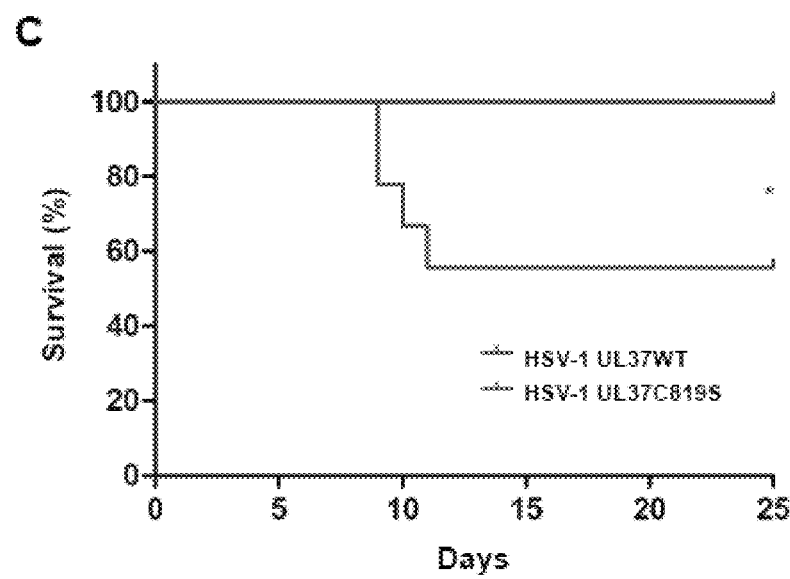

To characterize the in vivo function of the deamidase activity of UL37, Applicant infected mice with HSV-1 UL37WT and HSV-1 UL37C819S virus. At 8 hours post-infection, HSV-1 UL37C819S virus induced ~2-5-fold more cytokines in the sera of infected mice than HSV-1 UL37WT (FIG. 18A). For example, IFN-α and IFN-β were increased by 5- and 3.5-fold, respectively, in mice infected with HSV-1 UL37C819S than those infected with HSV-1 UL37WT. Conversely, the viral load of HSV-1 UL37C819S in the brain was reduced by >97% compared to that of HSV-1 UL37WT, as assessed by real-time PCR of viral genome copy number (FIG. 18B). When BL6 mice were inoculated with high dose ($5 \times 10^7$ PFU) of HSV-1 UL37WT or HSV-1 UL37C819S virus, approximately 50% mice succumbed to HSV-1 UL37WT infection, while none of the mice infected with HSV-1 UL37C819S died or otherwise demonstrated apparent disease (FIG. 18C). These results show that HSV-1 carrying the deamidase-deficient UL37 is highly attenuated, while more robustly inducing innate immune responses in mice.

Figure 18D:
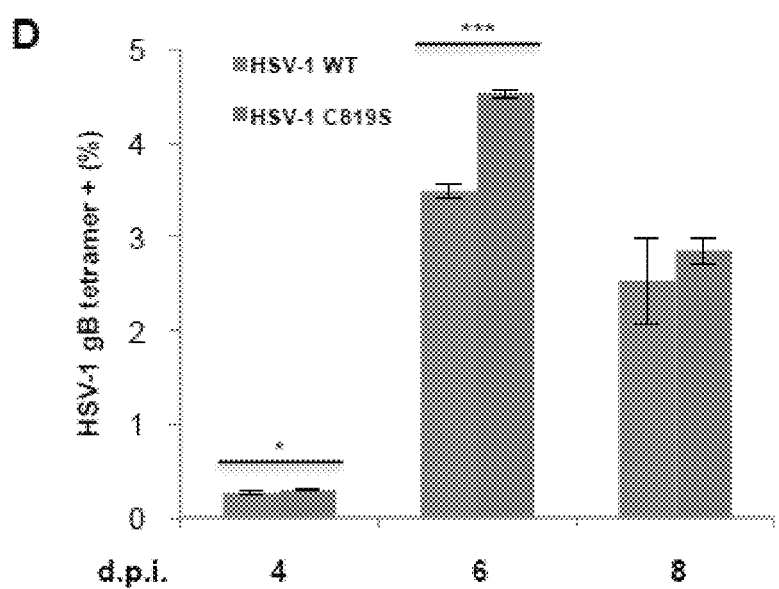
Figure 18E:
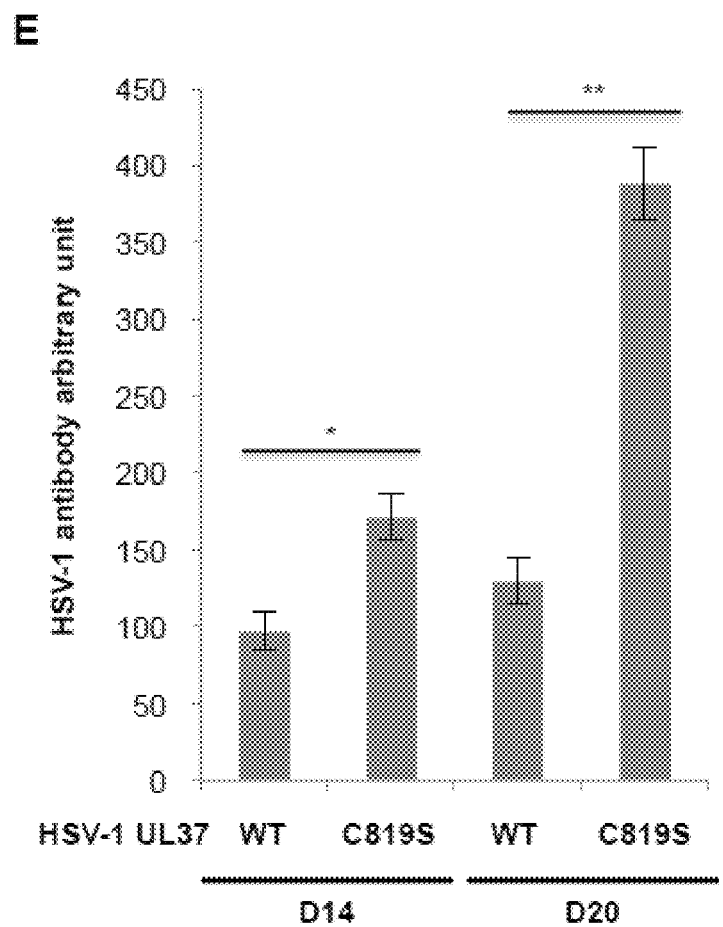

Previous studies have implicated the cGAS-STING pathway in promoting adaptive immune responses. Thus, Applicant tested whether the increased innate immune activation by HSV-1 UL37C819S virus translated into enhanced adaptive immunity. To quantify T cell immunity, Applicant analyzed virus-specific CD8+ T cells by tetramer staining against the most abundant epitope of glycoprotein B (gB, 498-505, SSIEFARL (SEQ ID NO: 27)). This analysis showed that both HSV-1 UL37WT and HSV-1 UL37C819S induced similar CD8+ T cell response kinetics, peaking at 6 days post-infection (dpi) (FIG. 18D). At 6 dpi, HSV-1 UL37WT and HSV-1 UL37C819S induced ~3.5% and 4.5% gB-specific CD8+ T cells, respectively (FIG. 18D). Additionally, when antibody against HSV-1 was quantified using whole virion-coated plates, Applicant found that HSV-1 UL37C819S virus induced as much 170% and 300% of HSV-1-specific antibody as HSV-1 UL37WT did at 14 and 20 dpi, respectively (FIG. 18E). These results indicate that HSV-1 containing the deamidase-deficient UL37C819S more robustly induces adaptive immunity, as evidenced by increased virus-specific CD8+ T cell response and antibody production.

Figure 18F:
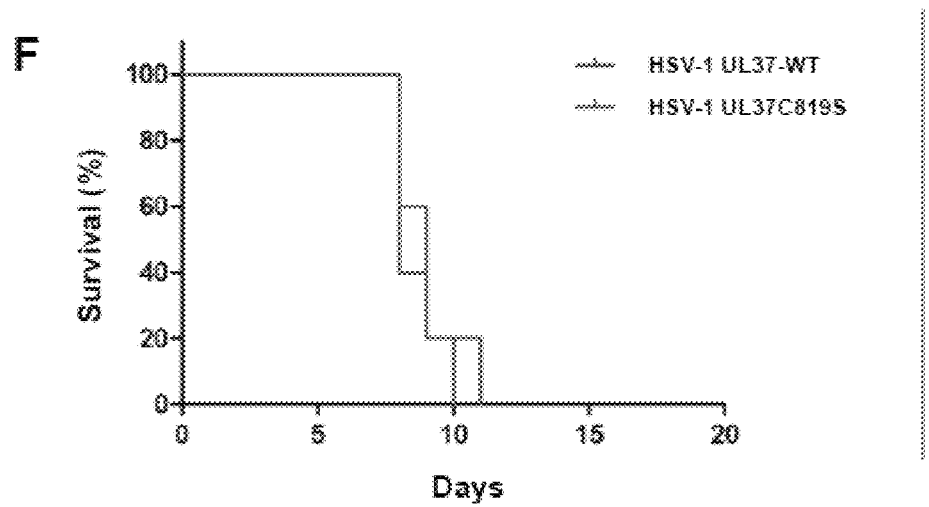
Figure 18G:
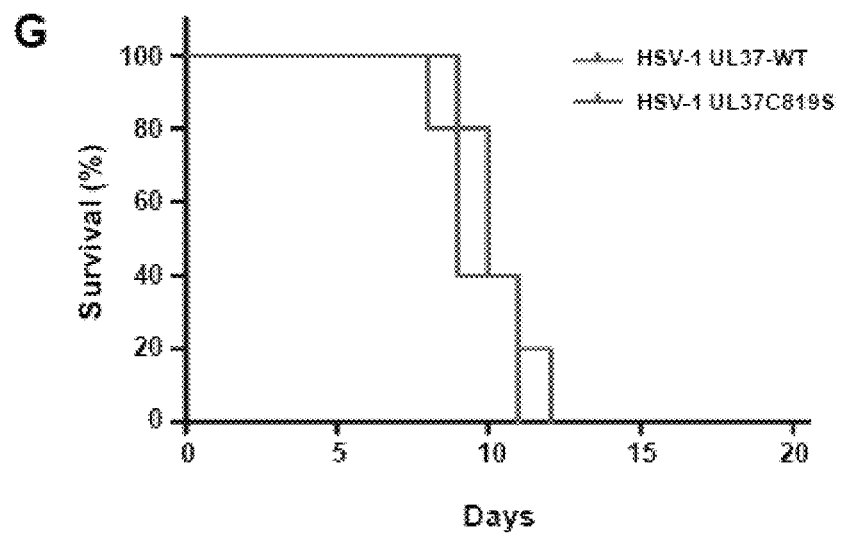

To determine whether the elevated virulence of HSV-1 UL37WT is dependent on its ability to evade cGAS-mediated innate immune activation, Applicant analyzed the pathogenesis of HSV-1 UL37WT and HSV-1 UL37C819S in mice deficient in cGAS or STING. Mice deficient in cGAS or STING were highly susceptible to HSV-1 infection, demonstrating 100% lethality by 11 dpi. Importantly, cGAS-deficient mice infected with HSV-1 UL37C819S succumbed to death as rapidly as those infected with HSV-1 UL37WT (FIG. 18F). Consistent with this, HSV-1 UL37WT and HSV-1 UL37C819S mutant induced similar levels of inflammatory cytokines in the sera of cGAS-deficient mice. The concentration of these cytokines in the sera was dramatically lower than those in wild-type mice infected with either HSV-1 UL37WT or HSV-1 UL37C819S (FIG. 18A), supporting the conclusion that cGAS is critical for immediate innate immune responses against DNA viruses. Furthermore, viral loads in the brain of cGAS-deficient mice were similar to mice infected with HSV-1 UL37WT or HSV-1 UL37C819S. In mice deficient in STING, infection of HSV-1 UL37WT and HSV-1 UL37C819S resulted in mouse lethality of similar kinetics and serum levels of inflammatory cytokines as cGAS-deficient mice (FIG. 18G). Viral loads in the brain of STING-deficient mice infected with HSV-1 UL37WT and HSV-1 UL37C819S were identical as determined by plaque assay. Thus, mouse deficient in STING recapitulate phenotypes of cGAS knockout mice, when infected with HSV-1 UL37WT and HSV-1 UL37C819S. Taken together, these results show that the UL37 deamidase antagonizes the cGAS- and STING-mediated innate immune response in vivo.

Immunization with HSV-1 UL37C819S Protects Mice from HSV-1 Lethal Dose

Figure 19A:
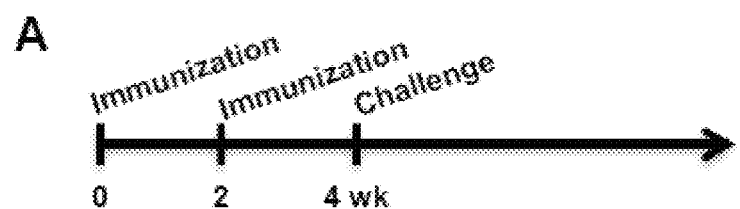
FIGS. 19A-19H show that vaccination with HSV-1 carrying deamidase-deficient UL37C819S protects mice from lethal HSV-1 challenge.
Figure 19B:
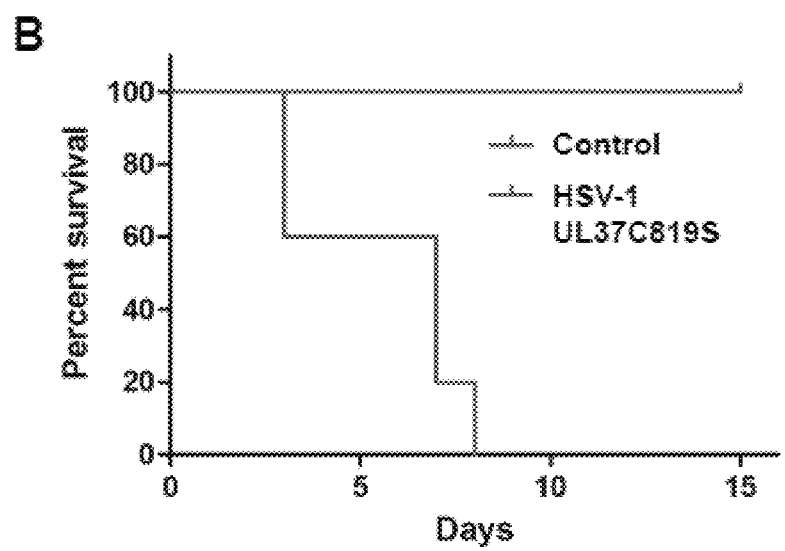
Figure 19C:
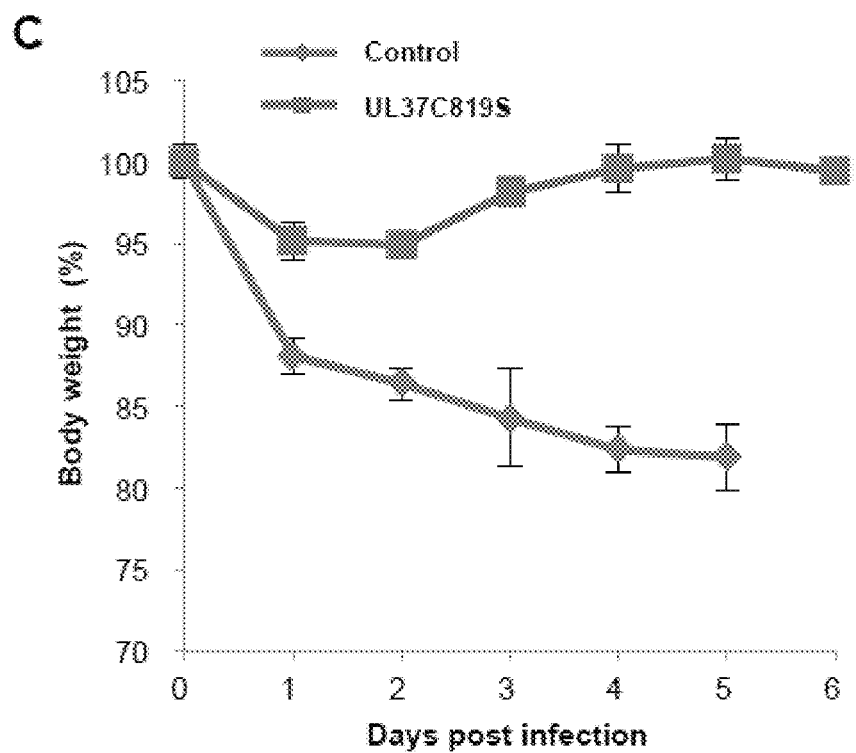

Considering that HSV-1 UL37C819S more robustly induces immune responses and is highly attenuated in mice, Applicant explored the possibility that immunization with HSV-1 UL37C819S protects mice from pathogenesis induced by wild-type HSV-1 infection. For this experiment, Applicant used BALB/c mice, which are more susceptible to HSV-1 infection than BL/6 mice. After two rounds of HSV-1 UL37C819S infection at an interval of two weeks (FIG. 19A), Applicant challenged mice with a lethal dose of HSV-1 wild-type ($5 \times 10^6$ PFU) via intravenous injection. Naïve mice all succumbed to HSV-1 infection by 8 dpi. All mice immunized with HSV-1 UL37C819S survived the challenge (FIG. 19B). Additionally, naïve mice demonstrated significant weight loss that peaked at ~20% reduction when mice were euthanized at 5 dpi, while vaccinated mice had a decrease of ~5% in body weight at 1 and 2 dpi, and quickly recovered to baseline body weight by 4 dpi (FIG. 19C). These results show that immunization with the deamidase-deficient HSV-1 UL37C819S potently protects mice from lethal challenge of wild-type HSV-1 infection.

Figure 19D:
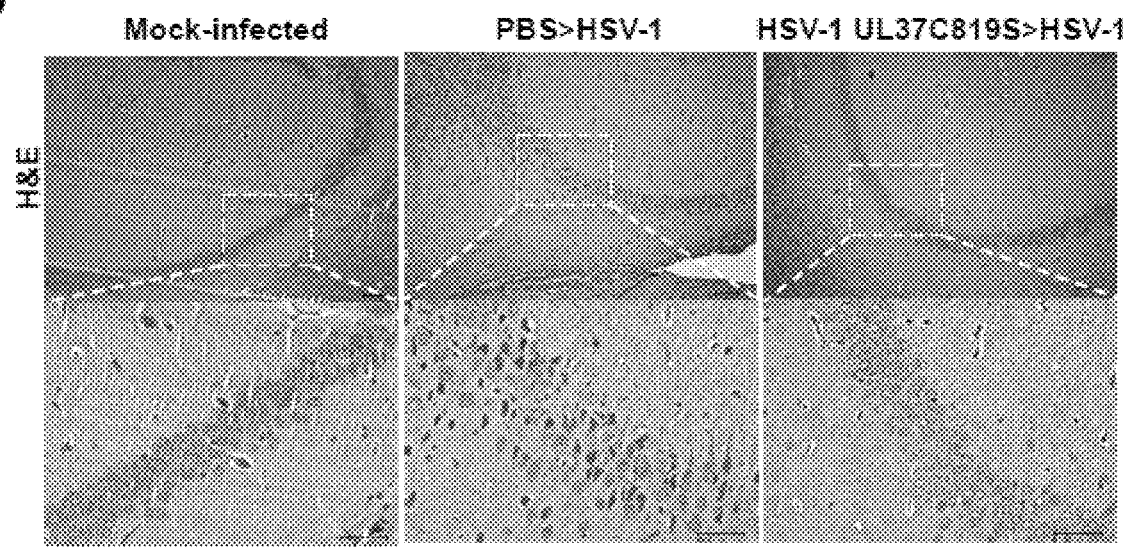
Figure 19E:
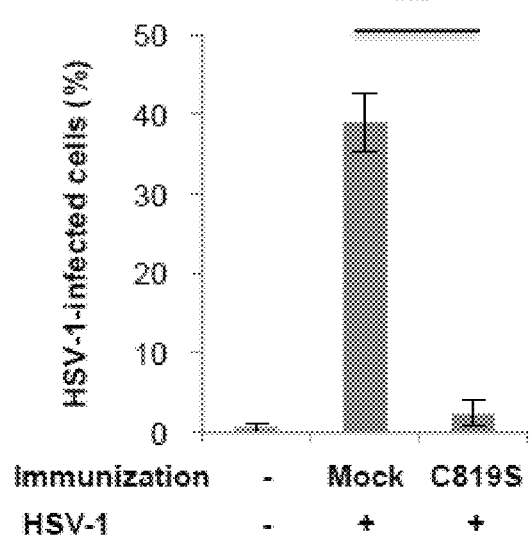
Figure 19F:
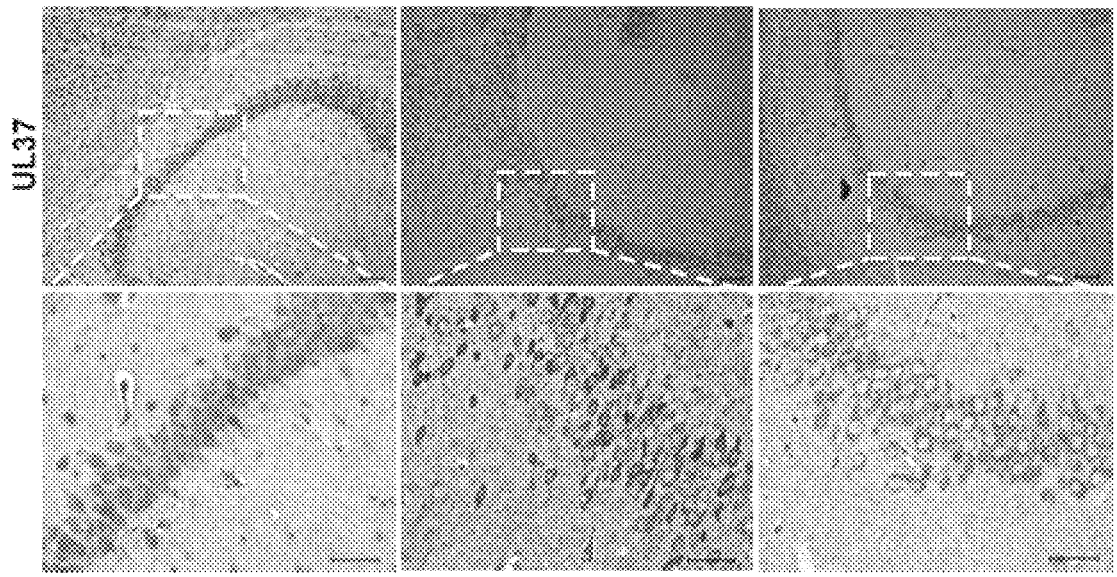
Figure 19G:
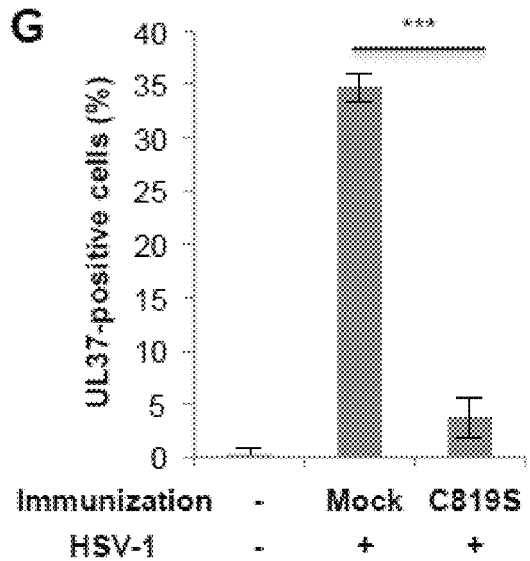
Figure 19H:
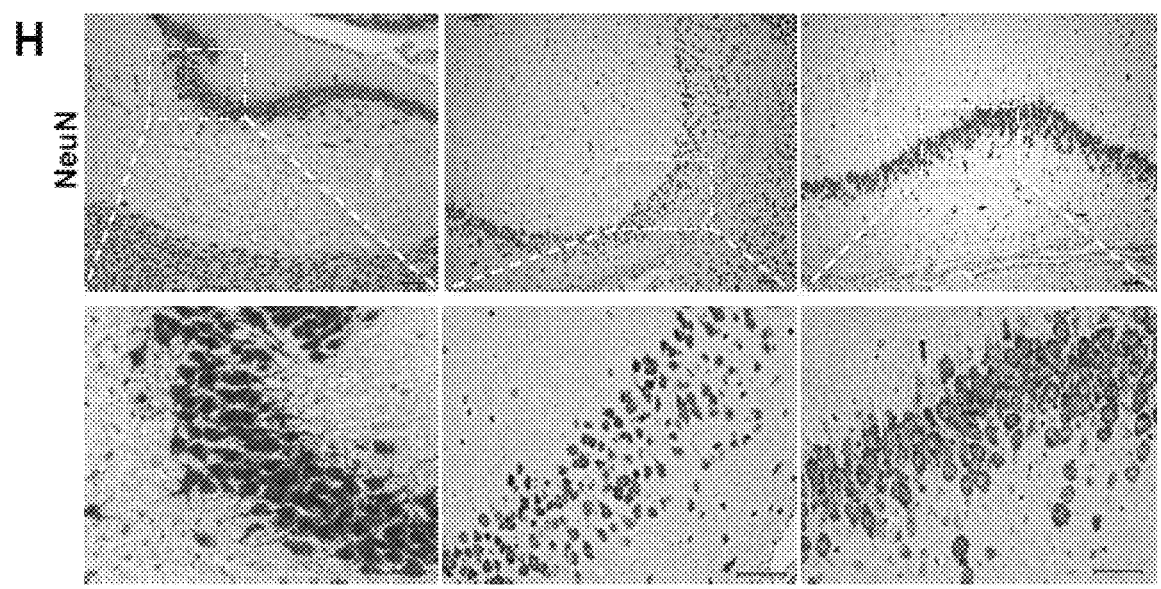

To further characterize the pathology of HSV-1 infection, Applicant analyzed the brain of mice infected with HSV-1. Haematoxylin & Eosin (H&E) staining showed a significant fraction of cells had apparent morphology changes only in mice immunized with PBS and challenged with wild-type HSV-1 (FIG. 19D). A remarkable phenotype of the brain tissue of infected mice is the stark contrast of dark nuclear staining by H&E and the relatively small cell body compared to neighboring cells (FIG. 19D). The heavy stain by H&E and reduced cell size are likely due to the massive accumulation of viral proteins and nucleic acids from HSV-1 replication. Immunohistochemistry (IHC) staining with an antibody against UL37, a lytic protein, revealed a pattern similar to the morphological change revealed by H&E staining (FIG. 19F). Staining of the horizontal sections showed UL37-positive cells in the cortex, hippocampus and cerebellum. In the hippocampus, UL37-positive cells concentrated in CA3 and dentate gyrus (DG) regions. Consistent with the morphological analysis, IHC staining identified ~35% brain cells expressing UL37 antigens (FIG. 19G). Immunization with HSV-1 UL37C819S mutant virus significantly reduced the number of UL37-positive cells similar to mock-infected mice (FIG. 19G). UL37-positive cells were observed in Purkinjie neurons that line the cerebellum (S6 Da), and were sporadically distributed in the cortex and stratum regions. IHC staining using anti-Vhs serum revealed significantly more viral replication in the brain of naïve mice than that of mice immunized with HSV-1 UL37C819S. Importantly, although low levels of HSV-1 replication were detected in mice immunized with HSV-1 UL37C819S, these mice were healthy and showed no diseased behavior. IHC staining with antibody against NeuN (a marker for neurons) and GFAP (a marker for astrocytes) showed that these HSV-1-infected cells were neuronal cells (FIG. 19H). Close inspection revealed that many neuron cells in the DG region of PBS-immunized mice were significantly smaller than that in HSV-1 UL37C819S immunized mice, after lethal dose challenge of wild-type HSV-1 (FIG. 19H). Comparing the IHC staining against NeuN to that against UL37 suggests that these smaller neurons are infected with HSV-1. These results collectively show that immunization with HSV-1 UL37C819S virus potently protects mice from acute HSV-1 infection and its pathogenesis.

Discussion

As innate immunity is essential to defeating pathogen infection, pathogens have evolved diverse mechanisms to evade host defense, providing a physiological system to examine host immune regulation. Employing HSV-1 for monocyte and mouse infection, Applicant discovered that the UL37 tegument protein of HSV-1 deamidates cGAS to abrogate its cGAMP synthesis activity, without diminishing the DNA-binding or dimerization. Site-specific deamidation of all four amide-containing residues distributed throughout the relatively large enzyme domain reveals an exquisite specificity of deamidation on the enzyme activity of cGAS. The physiological role of the deamidase activity of UL37 in counteracting cGAS-mediated immune defense is substantiated by significantly elevated levels of inflammatory cytokines in THP-1 monocytes and mice infected with the deamidase-deficient HSV-1 UL37C819S than those infected with HSV-1 UL37WT. Applicant further showed that elevated antiviral cytokines translated into more robust adaptive immunity against HSV-1 in mice, including CD8+ cytotoxic T cell response and serum antibody. These findings agree with a previous report that cGAMP and activation of cGAS-mediated innate immune signaling play an adjuvant role in immunization. In support of this conclusion, immunization with the highly inflammatory deamidase-deficient HSV-1 UL37C819S that had attenuated replication in vivo protected mice from challenge with lethal dose of wild-type HSV-1, representing a new vaccine candidate.

Applicant has shown that UL37 deamidates RIG-I to prevent dsRNA-induced activation. This work identifies cGAS as an additional target of UL37 in HSV-1-infected cells. In cGAS- and STING-deficient mice infected with HSV-1, Applicant found that the deamidase-deficient HSV-1 UL37C819S virus was as pathogenic as wild-type HSV-1, as measured by survival rates of mice infected with HSV-1 UL37WT and HSV-1 UL37C819S. These results clearly support the crucial role of UL37 in antagonizing the cGAS-STING pathway, but do not address the role of UL37-mediated RIG-I deamidation, previously shown to diminish antiviral cytokine production, in host defense against HSV-1 infection in mice. The identical pathogenesis of HSV-1 UL37WT and HSV-1 UL37C819S virus in mice deficient in cGAS or STING suggests that UL37 fails to antagonize mouse RIG-I in vivo. N495 of human RIG-I is not conserved in mouse, so it is possible that mouse RIG-I is resistant to UL37-mediated deamidation and inhibition. Although the roles of RIG-I in HSV-1 infection in vivo remain undefined, RIG-I is possibly important for innate immune defense against HSV-1 in cell types with limited or minimal cGAS expression, such as epithelial cells and keratinocytes. Previous studies demonstrating the antiviral activities of RIG-I against various herpesviruses primarily used mouse fibroblasts or human cells deficient in RIG-I.

Remarkably, all four cGAS deamidation sites impinge on cGAMP synthesis activity despite being located within three structurally distinct surfaces of cGAS. Two structural studies highlighted the importance of the N210 of hcGAS (or N196 of mcGAS) in regulating cGAS enzymatic activity. Specifically, others showed that N210 is located within the first half of the so-called activation loop. The sequence of this short loop features residues that have small and non-charged side chains. Additional mutational and functional analysis of G211 and S212 of hcGAS in this structural study demonstrated that the flexibility of the activation loop underpins the conformational change and subsequent coordination of the catalytic triad of cGAS upon DNA-binding and dimer formation. Thus, deamidation of N210 of hcGAS is expected to compromise the free rotation of the activation loop and proper formation of the catalytic triad.

Surprisingly, collective deamidation of N389, Q451 and Q454 reduced cGAMP synthesis, but not DNA-binding and dimerization, of cGAS. N389 and N388 lie at the center of the dsDNA-binding surface of cGAS and directly point to the minor groove of dsDNA. Deamidation of N389, and more so that of N388, are expected to diminish the DNA-binding ability of cGAS. However, Applicant's reporter assay showed that N388D and N389D mutations had no detectable effect on the ability of cGAS to activate the IFN-β promoter. Moreover, UL37WT expression and the deamidated cGAS mutant (cGAS-DDEE) appeared to slightly increase the DNA-binding of cGAS. Q451 and Q454 reside in a short α-helical structure that forms the front edge of the butterfly-shaped cGAS dimer. The expression of UL37WT and UL37C819S mutant had no detectable effect on cGAS dimer formation upon HT-DNA transfection. These results indicate that deamidation of cGAS does not impair the DNA-binding and dimerization of cGAS upon sensing dsDNA. On the other hand, cGAS-deficient L929 cells "reconstituted" with cGAS mutants harboring single deamidated residues, demonstrated lower activity to induce Ifnb1 expression in response to transfected HT-DNA, suggesting that these sites are important for cGAS signaling. Thus, Applicant's reported methods are perhaps not sufficiently sensitive to accurately quantify the dsDNA-cGAS interaction, especially given the observation that the DNA-binding of cGAS appears to be of low affinity. If indeed the deamidation of these Gln and Asn residues do not impair the dimerization and DNA-binding of cGAS, it is possible that the deamidated surfaces of monomeric or dimeric cGAS serve as binding sites for cellular factors that regulate cGAS enzymatic activity. For example, cGAS sensing of HIV DNA requires the PQBP1 cofactor for innate immune activation. Whether deamidation impacts cGAS interaction with its cofactors remains to be determined. Nevertheless, the conformational changes induced by deamidation of these residues likely impact the active site and reduce cGAMP synthesis by cGAS. The molecular details of how these deamidations affect cGAS enzyme activity calls for further investigation. It is clear that these deamidations dampen the cGAMP synthesis activity of cGAS with explicit specificity.

cGAS is a cytosolic DNA sensor crucial for innate immune defense and aberrant activation of cGAS can lead to autoimmune diseases. Thus, the cGAS activity is tightly regulated. PTMs, such as phosphorylation, glutamylation, sumoylation and ubiquitination, play important roles in regulating the activity of cGAS. Phosphorylation of hcGAS S305 by AKT potently inhibits the enzymatic activity of cGAS. Glutamylation of cGAS by the enzymes TTLL6 and TTLL4 dampens the DNA-binding and synthase activity of cGAS, while the removal of glutamylation by CCP5 and CCP6 enhances cGAS activity.

Similarly, TRIM38 targets cGAS for sumoylation to prevent its polyubiquitination and degradation that is facilitated by SENP2-mediated desumoylation. Interestingly, sumoylation of cGAS at different residues suppresses its DNA-binding, oligomerization and synthase activities, and desumoylation by SENP7 increases cGAS activity. Thus, the activity of cGAS is dynamically regulated by sumoylation and desumoylation during infection. In this study, Applicant provides evidence that the activity of cGAS can be modified through deamidation, adding another PTM to the dynamic and complex regulation of cGAS.

Due to its core function in innate immune response against microbes, cGAS is often targeted by diverse pathogens to prevent innate immune activation. Human kaposi's sarcoma-associated herpesvirus (KSHV) notably deploys three distinct molecules, ORF52, LANA (ORF73) and vIRF1 (K9), to disable cGAS and its downstream signaling. The E7 oncogene of human papillomavirus and E1A of adenovirus utilize a common L×C×E motif to antagonize the DNA-sensing of cGAS. Recently, the protease cofactor NS2B of Dengue virus was shown to promote the lysosomal degradation of cGAS, thereby suppressing the induction of type I interferon production in infected cells. Applicant found that HSV-1 UL37 tegument protein deamidates cGAS to block cGAMP synthesis, revealing an efficient means of antagonizing the cGAS-STING pathway. Applicant and others have reported that herpesviruses and bacteria deploy deamidation to modify key signaling molecules to manipulate host immune responses.

In conclusion, Applicant has identified multiple sites of deamidation within cGAS targeted by HSV-1 UL37 deamidase. Deamidation of cGAS specifically ablates the cGAMP synthesis activity of cGAS. HSV-1 containing the deamidase-deficient UL37C819S is highly attenuated in mice and more robustly induces antiviral cytokines. Immunization with the deamidase-deficient HSV-1 virus potently protects mice from lethal dose challenge of HSV-1 wild-type. Collectively, these studies provide evidence that deamidation modifies protein function.

Experiment No. 3

The genetic data disclosed in this experiment shows that the cGAS and STING pathway is the primary target of UL37. Moreover, recombinant HSV-1 containing the deamidase-deficient UL37C819S is highly attenuated in mice, but induced much more robust antiviral immune response (innate arm and adaptive as well). Thus, these proteins are shown to be effective as a prophylactic vaccine. Indeed, mice vaccinated with the recombinant HSV-1 containing the deaminase-deficient UL37C819S potently protected mice from lethal dose infection of wild-type HSV-1.

Antibodies and Reagents

Commercially available antibodies used for this study include mouse monoclonal FLAG M2 antibody (Sigma), mouse monoclonal V5 antibody and β-actin antibody (Abcam), Phospho-TBK1 (Ser172) antibody, Phospho-IRF3 (Ser396) antibody and cGAS (D1D3G) antibody (Cell signaling), TBK1 antibody (Bethyl), His-probe antibody (H-3) and IRF3 antibody (FL-425) (Santa cruz), APC rat anti-mouse CD8a and PE hamster anti-mouse CD3ε (BD Biosciences).

Major histocompatibility complex (MHC)/peptide tetramers for HSV-1 gB 498-505/Kb (SSIEFARL (SEQ ID NO: 27)) conjugated to PE were obtained from the NIH Tetramer Core Facility (Emory University, Atlanta, Ga.).

HSV-1 UL37 and VHS polyclonal antibodies were generated by repeatedly immunizing rabbit with purified proteins.

HT-DNA and LPS (Sigma-Aldrich), 2', 3'-cGAMP (InvivoGen), streptavidin agarose (Thermo Fisher), Amylose Resin (New England Biolabs), Ni-NTA His-Bind Resin (Novagen), TEV protease (Invitrogen).

Biotin labeled ISD-45 DNA was ordered from IDT. [α-P32]-ATP was ordered from Perkin Elmer. Lipofectamine 2000 was purchased from Invitrogen.

Cells, Viruses, Mice and Viral Infections

THP1-Lucia ISG reporter cells (InvivoGen) was kindly provided by Dr. Fanxiu Zhu (Florida State University). L929 and L929 cGAS knockout cells were provided by Dr. Fanxiu Zhu.

MHV68 virus was propagated in BHK21 cells as previously described. HSV-1 WT and UL37 C819S recombinant viruses were propagated using VERO cells. cGAS knockout mice and BALB/c mice were purchased from the Jackson laboratory. STING knockout mice were provided by Dr. Jae Jung (the University of California). Six to eight-week old, gender-matched mice were used for all experiments. All animal work was performed under strict accordance with the recommendations in the Guide for the Care and Use of Laboratory Animals of the National Institutes of Health. The protocol was approved by the Institutional Animal Care and Use Committee (IACUC) of the University of Southern California.

For HSV-1 infection, BL/6, cGAS KO or STING KO mice were infected with $5 \times 10^7$ PFU of virus via intraperitoneal injection for survival curve analysis. For tetramer staining and antibody measurement, HSV-1 was reduced to $10^6$ PFU per mouse.

For BALB/c mice, the mice were immunized with HSV-1 UL37 C819S virus ($10^6$) twice with an interval of two weeks and then challenged with HSV-1 ($5 \times 10^6$) via intraperitoneal infection.

RNA Extraction and qRT-PCR

THP-1 or L929 cells were infected with HSV-1 (MOI=5) or stimulated with HT-DNA (2 μg/ml) or cGAMP (2 μg/ml) for 6 h unless specifically indicated otherwise. Cells were washed with cold PBS, and total RNA was extracted by using TRIzol Reagent (Invitrogen). RNA was digested with DNase I (New England Biolabs) to remove genomic DNA. One microgram of total RNA was used for reverse transcription with PrimeScript Reverse Transcriptase (Clontech) according to the manufacturer's instruction. Approximately 0.5% of the cDNA was used as template in each quantitative real-time PCR (qRT-PCR) reaction with SYBR master mix (Applied biosystems).

Q-PCR Primers Used in the Study:

| Q-PCR primers for human genes | | |
|---|---|---|
| IFNB1 | CTTTCGAAGCCTTTGCTCTG (SEQ ID NO: 28) | CAGGAGAGCAATTTGGAGGA (SEQ ID NO: 39) |
| ISG56 | TCTCAGAGGAGCCTGGCTAA (SEQ ID NO: 10) | TGACATCTCAATTGCTCCAG (SEQ ID NO: 11) |
| CXCL10 | CACCATGAATCAAACTGCGA (SEQ ID NO: 29) | GCTGATGCAGGTACAGCGT (SEQ ID NO: 40) |
| IL6 | AGTGAGGAACAAGCAGCCAG (SEQ ID NO: 30) | GTCAGGGGTGGTTATTGCAT (SEQ ID NO: 41) |
| IL8 | TCCTGATTTCTGCAGCTCTGT (SEQ ID NO: 31) | AAATTTGGGGTGGAAAGGTT (SEQ ID NO: 42) |
| MX1 | AGCTCGGCAACAGACTCTTC (SEQ ID NO: 32) | GATGATCAAAGGGATGTGGC (SEQ ID NO: 43) |
| IFIT3 | TCGGAACAGCAGAGACACAG (SEQ ID NO: 33) | AAGTTCCAGGTGAAATGGCA (SEQ ID NO: 44) |
| ACTB (β-actin) | GTTGTCGACGACGAGCG (SEQ ID NO: 34) | GCACAGAGCCTCGCCTT (SEQ ID NO: 45) |
| Q-PCR primers for mouse genes | | |
| Ifnb1 | CCCTATGGAGATGACGGAGA (SEQ ID NO: 35) | CCCAGTGCTGGAGAAATTGT (SEQ ID NO: 46) |
| Isg56 | CAAGGCAGGTTTCTGAGGAG (SEQ ID NO: 36) | GACCTGGTCACCATCAGCAT (SEQ ID NO: 47) |

| | | |
|---|---|---|
| Cxcl10 | CTCATCCTGCTGGGTC TGAG (SEQ ID NO: 37) | CCTATGGCCCTCATTCT CAC (SEQ ID NO: 48) |
| Actb (β-actin) | TCTACGAGGGCTATGCTC TCC (SEQ ID NO: 38) | TCTTTGATGTCACGCAC GATTTC (SEQ ID NO: 49) |

Luciferase Reporter Assay

HEK293T cells in 24-well plates were transfected with a reporter plasmid mixture that contained 50 ng of the plasmid expressing IFN-β or NF-κB firefly luciferase reporter and 20 ng of the plasmid expressing TK-renilla luciferase reporter. At 30 h post-transfection, cells were harvested and cell lysates were prepared. Cell lysates were used for dual luciferase assay according to the manufacturer's instruction (Promega).

Immunoprecipitation

Immunoprecipitation was carried out as described previously. Briefly, THP-1 cells were infected with HSV-1 FLAG-UL37 recombinant virus (MOI=0.5) for 16 h. The cells were harvested and lysed with NP40 buffer (50 mM Tris-HCl [pH 7.4], 150 mM NaCl, 1% NP-40, 1 mM EDTA, 5% glycerol) supplemented with a protease inhibitor cocktail (Roche). Centrifuged cell lysates were pre-cleared with Sepharose 4B beads and incubated with FLAG-agarose at 4° C. for 4 h. The agarose beads were washed three times with lysis buffer and precipitated proteins were released by boiling with 1×SDS sample buffer at 95° C. for 5 min. The resolved samples were applied to immunoblot analysis.

Protein Purification

Mouse MBP-cGAS fusion protein (151-522) was expressed in BL21 (DE3) and the bacteria were grown at 37° C. to an OD600 of 0.6. Then the cultures were cooled to 18° C. and protein expression was induced by adding 0.1 mM Isopropyl b-D-1-thiogalactopyranoside (IPTG) for 16 h. Cells were collected by centrifugation and lysed with lysis buffer (20 mM Tris-HCl [pH 7.4], 200 mM NaCl, 10% glycerol, 0.5% Triton X-100, 0.2 mg/ml lysozyme supplemented with protease inhibitor cocktail). Clarified lysates were mixed with amylose resin and incubated for 2 h at 4° C. The resin was washed extensively with lysis buffer and the recombinant proteins were eluted by 10 mM maltose.

For Mass spectrometry analysis, purified MBP-mcGAS was digested with TEV protease overnight at 4° C. and MBP proteins were depleted by incubation with Ni-NTA agarose.

UL37 or UL37C819S were purified as previously described. Briefly, HEK293T cells were transiently transfected with a plasmid containing UL37 or UL37C819S, harvested and lysed with lysis buffer (20 mM Tris (pH 7.4), 150 mM NaCl, 10% (vol/vol) glycerol, 0.5% Triton X-100, and 0.5 mM DTT) supplemented with a protease inhibitor cocktail (Roche), and lysates were precipitated with 20 μL of FLAG M2-conjugated agarose (Sigma). After extensive washing with lysis buffer, precipitated proteins was eluted with FLAG peptide (100 μg/ml) and used for in vitro deamidation assay.

Two-Dimensional Gel Electrophoresis

Cells or in vitro deamidation samples were resolved in 150 μl rehydration buffer (8 M urea, 2% CHAPS, 0.5% IPG buffer, and 0.002% bromophenol blue), and then the lysates were centrifuged at 20,000 g for 10 min. Supernatants were loaded to IEF strips with a program comprising 20 V, 10 hr; 100 V, 1 hr; 500 V, 1 hr; 1,000 V, 1 hr; 2,000 V, 1 hr; 4,000 V, 1 hr; and 8,000 V, 4 hr. Then strips were incubated with SDS equilibration buffer (50 mM Tris-HCl [pH 8.8], 6M urea, 30% glycerol, 2% SDS, 0.001% bromophenol blue) containing 10 mg/ml DTT for 15 min and SDS equilibration buffer containing 2-iodoacetamide for 15 min. Strips were washed with SDS-PAGE buffer, resolved by SDS-PAGE, and analyzed by immunoblotting.

In Vitro Deamidation Assay

The in vitro deamidation assay was performed as previously described. Briefly, 5 μg of purified MBP-mcGAS or MBP-mcGAS-DDEE mutant on amylose resin was incubated with 0.5 gig of purified FLAG-UL37 or FLAG-UL37C819S at 30° C. for 45 min in deamidation buffer (50 mM Tris-HCl [pH 7.5], 100 mM NaCl, and 5 mM MgCl$_2$). Then the reaction was stopped by adding rehydration buffer and the eluted proteins were analyzed by two-dimensional gel electrophoresis.

cGAMP Reporter Assay

THP-1 Cells were transfected with HT-DNA (2 μg/ml) or infected with HSV-1 virus for 6 h. Cell extracts were prepared by heating at 95° C. for 5 min to denature most proteins, and then the precipitated proteins were removed by centrifugation. The supernatant containing cGAMP was delivered to digitonin-permeabilized (2.5 μg/ml for 30 min) THP1-Lucia cells at 37° C. for 30 min. The cells were cultured for another 20 h before Lucia reporter activity was measured according to the manufacturer's instruction (InvivoGen). Pure cGAMP was diluted and used as standard for the assay.

In Vitro cGAMP Activity Assay

1 μM of MBP-cGAS or mutant proteins was mixed with 100 μM ATP and 100 μM GTP and 10 μCi [α-P32]-ATP in reaction buffer (20 mM Tris-Cl [pH 7.5], 150 mM NaCl, 5 mM MgCl$_2$, 1 mM dithiothreitol [DTT]). After 2 h of incubation at 37° C., 2 μl of reaction solution was spotted onto PEI-Cellulose thin layer chromatography plate (Sigma). Reaction products were resolved with running buffer (1 M (NH4)$_2$SO4, 1.5 M KH$_2$PO4, pH 3.8). The TLC plates were dried and scanned with Phosphoimager (Fuji).

Stable Cell Line Generation

Lentivirus production was carried out in 293T cells as described previously. THP-1 or L929 cells were infected with lentivirus containing UL37 or UL37 C819S mutant. After 36 h, THP-1 cells were selected with puromycin at 1 μg/ml and L929 cells were selected with puromycin at 5 μg/ml.

Deamidation Sites Analysis by LC/MS/MS

Purified mcGAS(141-507) was deamidated by purified FLAG-UL37 in vitro. Then the samples were resolved with SDS-PAGE and the mcGAS bands were excised and applied to LC/MS/MS analysis. The analysis of samples was carried out using a Thermo Scientific Q-Exactive hybrid Quadrupole-Orbitrap Mass Spectrometer and a Thermo Dionex UltiMate 3000 RSLCnano System. Peptide mixtures from each sample were loaded onto a peptide trap cartridge at a flow rate of 5 μL/min. The trapped peptides were eluted onto a reversed-phase PicoFrit column (New Objective, Woburn, Mass.) using a linear gradient of acetonitrile (3-36%) in 0.1% formic acid. The elution duration was 120 min at a flow rate of 0.3 μl/min. Eluted peptides from the PicoFrit column were ionized and sprayed into the mass spectrometer, using a Nanospray Flex Ion Source ES071 (Thermo) under the following settings: spray voltage, 2.0 kV, Capillary temperature, 250° C. Other settings were empirically determined. Raw data files were searched against mouse protein sequence database obtained from NCBI website using the Proteome Discoverer 1.4 software (Thermo, San Jose, Calif.) based on the SEQUEST algorithm. Carbamidomethylation (+57.021 Da) of cysteines was fixed modification, and Oxidation and Deamidation Q/N-deamidated (+0.98402 Da) were set as dynamic modifications. The minimum peptide length was specified to be five amino acids. The precursor mass tolerance was set to 15 ppm, whereas fragment mass tolerance was set to 0.05 Da. The maximum false peptide discovery rate was specified as 0.01. The resulting Proteome Discoverer Report contains all assembled proteins with peptides sequences and matched spectrum counts and peak area.

Tetramer Staining

HSV-1-infected mice were sacrificed at 4, 6, 8 days post-infection (dpi) and spleen were collected. Single cell suspension was generated by passing through 40 μM strainer on ice. Red blood cells were removed by adding 5 ml of Pharm Lysis buffer (BD Biosciences). Cells were washed once with cold PBS plus 1% FBS and subjected to tetramer staining.

Tetramer staining was carried out as previously described. Briefly, cells were incubated with anti-CD16/32 antibody for 10 min on ice, followed by staining for 1 h in the dark with tetramers (1:100). Then the cells were stained with anti-CD8 antibody for 20 min on ice. Samples were analyzed by flow cytometry using FACSCalibur and data were analyzed with FlowJo software.

H&E and Immunohistochemistry Staining

Mouse tissue samples were fixed in 10% (vol/vol) formalin solution (Sigma) overnight. Tissue specimens were dehydrated, embedded in paraffin, and cut into 8-μm sections. Tissue sections were analyzed by H&E and Images were collected with Keyence BZ-X700 microscope.

For immunohistochemistry staining, mouse tissue samples were fixed with 10% formalin solution overnight. Tissue specimens were dehydrated, embedded in paraffin, and cut into 8-μm sections. Tissue sections were analyzed by immunohistochemistry staining with antibodies against UL37, VHS and DAB substrate kit (Vector Laboratories). Images were visualized with Keyence BZ-X700 microscope.

Determining HSV-1-Specific Antibody

HSV-1-specific antibody detection was carried out as previously described. HSV-1 was purified by ultracentrifuge at 32,000 rpm for 2.5 h and concentrated viral particles were coated to ELISA plates at 4° C. overnight. Plates were then washed five times with PBS-Tween (0.05%) (PBST) and blocked with 1% BSA for 2 h at room temperature. Two-fold dilutions of sera, starting with an initial dilution of 1:10 in PBST were added to the wells and the plates were incubated at RT for 2 h. After washing, rabbit anti-mouse immunoglobulin conjugated to horseradish peroxidase (HRP) diluted at 1:5,000 was added and the plates were incubated for 1 h at room temperature. HSV-1-specific antibody was detected by adding TMB substrate (BD biosciences) and the absorbance was measured at 450 nm. Standard curve was generated by using mouse anti-HSV-1 antiserum. Antibody levels were expressed as arbitrary units against the standard.

Cytokine Measurement

THP-1 cells were stimulated with HT-DNA (2 μg/ml) or cGAMP (2 μg/ml) for 16 h or cells were infected with HSV-1 for 16 h. The medium were collected and applied to cytokine measurement. Mice were infected with HSV-1 or HSV-1 UL37 C819S virus ($5\times10^7$) and the sera were collected 8 hours post-infection.

ELISA kit for human interferon-β (PBL assay science) was used to determine the concentration of human interferon-β. ELISA kits for murine interferon-α (PBL assay science), interferon-β (PBL assay science), CCL5 (R&D systems) and IL-6 (BD Biosciences) were used to determine the concentration of cytokines in the mouse serum according to the manufacturer's instructions.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scoped of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

---

Sequence Listing

Sequence ID NO.: 1
UL37 Wild-type
ATGGCAGACCGCGGTCTCCCGTCCGAGGCCCCCGTCGTCACGACCTCACCCGCCGGTCCGCCCT
CGGACGGACCTATGCAGCGCCTATTGGCGAGCCTAGCCGGCCTTCGCCAACCGCCAACCCCCAC

| Sequence Listing |
|---|
| GGCCGAGACGGCAAACGGGGCGGACGACCCGGCGTTTCTGGCCACGGCCAAGCTGCGCGCCGCC |
| ATGGCGGCGTTTCTGTTGTCGGGAACGGCCATCGCCCCGGCAGACGCGCGGGACTGCTGGCGGC |
| CGCTGCTGGAACACCTGTGCGCGCTCCACCGGGCCCACGGGCTTCCGGAGACGGCGCTCTTGGC |
| CGAGAACCTCCCCGGGTTGCTCGTACACCGCTTGGTGGTGGCTCTCCCCGAGGCCCCCGACCAG |
| GCCTTCCGGGAGATGGAGGTCATCAAGGACACCATCCTCGCGGTCACCGGCTCCGACACGTCCC |
| ATGCGCTGGATTCCGCCGGCCTGCGCACCGCGGCGGCCCTGGGGCGGTCCGCGTCCGCCAGTG |
| CGCCGTGGAGTGGATAGACCGCTGGCAAACGTCACCAAGAGCTGCTTGGCCATGAGCCCGCGG |
| ACCTCCATCGAGGCCCTTGGGGAGACGTCGCTCAAGATGGCGCCGGTCCCGTTGGGGCAGCCCA |
| GCGCGAACCTTACCACCCCGGCGTACAGCCTGCTCTTCCCCGCCCCGTTCGTGCAAGAGGGCCT |
| CCGGTTCTTGGCCCTGGTGAGTAATCGGGTGACGCTGTTCTCGGCGCACCTCCAGCGCATAGAC |
| GACGCGACCCTCACTCCCCTCACACGGGCCCTCTTTACGTTGGCCCTGGTGGACGAGTACCTGA |
| CGACCCCCGAGCGGGGGGCTGTGGTCCCGCCGCCCCTGTTGGCGCAGTTTCAGCACACCGTGCG |
| GGAGATCGACCCGGCCATAATGATTCCGCCGCTCGAGGCCAACAAGATGGTTCGCAGCCGCGAG |
| GAGGTGCGCGTGTCGACGGCCCTCAGCCGCGTCAGCCCGCGCTCGGCCTGTGCGCCCCCGGGA |
| CGCTAATGGCGCGTGCGGACGGACGTGGCCGTGTTTGATCCCGACGTGCCCGTTCCTGAGTTC |
| GTCGGCACTGGCAGTCTTCCAGCCTGCCGTCTCCAGCCTGCTGCAGCTCGGGGAGCAGCCCTCC |
| GCCGGCGCCCAGCAGCGGCTGCTGGCTCTGCTGCAGCAGACGTGGACGTTGATCCAGAATACCA |
| ATTCGCCCTCCGTGGTGATCAACACCCTGATCGACGCTGGGTTCACGCCCTCGCACTGCACGCA |
| CTACCTTTCGGCCCTGGAGGGGTTTCTGGCGGCGGGCGTCCCCGCGCGGACGCCCACCGGCCAC |
| GGACTCGGCGAAGTCCAGCAGCTCTTTGGGTGCATTGCCCTCGCGGGGTCGAACGTGTTTGGGT |
| TGGCGCGGGAATACGGGTACTATGCCAACTACGTAAAAACTTTCAGGCGGGTCCAGGGCGCCAG |
| CGAGCACACGCACGGGCGGCTCTGCGAGGCGGTCGGCCTGTCGGGGGGCGTTCTAAGCCAGACG |
| CTGGCGCGTATCATGGGTCCGGCCGTGCCGACGGAACATCTGGCGAGCCTGCGGCGGGCGCTCG |
| TGGGGGAGTTTGAGACGGCCGAGCGCCGCTTTAGTTCCGGTCAACCCAGCCTTCTCCGCGAGAC |
| GGCGCTCATCTGGATCGACGTGTATGGTCAGACCCACTGGGACATCACCCCCACCACCCCGGCC |
| ACGCCGCTGTCCGCGCTTCTCCCCGTCGGGCAGCCCAGCCACGCCCCTCTGTCCACCTGGCCG |
| CGGCGACCCAGATCCGCTTCCCCGCCCTCGAGGGCATTCACCCCAACGTCCTCGCCGACCCGGG |
| CTTCGTCCCCTACGTTCTGGCCCTGGTGGTCGGGGACGCGCTGAGGGCCCACGTGTAGCGCGCC |
| TACCTTCCCCGCCCGGTCGAGTTCGCCCTGCGTGTGTTGGCCTGGGCCCGGGACTTTGGGCTGG |
| GCTATCTCCCCACGGTTGAGGGCCATCGCACCAAACTGGGCGCGCTGATCACCCTCCTCGAACC |
| GGCCGCCCGGGGCGGCCTCGGCCCCACTATGCAGATGGCCGACAACATAGAGCAGCTGCTCCGG |
| GAGCTGTACGTGATCTCCAGGGGTGCCGTCGAGCAGCTGCGCCCCGTGGTCCAGCTGCAGCCCC |
| CCCCGCCCCCGAGGTGGGCACCAGCCTCCTGTTGATTAGCATGTACGCCCTGGCCGCCCGGGG |
| GGTGCTGCAGGACCTCGCCGAGCGCGCAGACCCCCTGATTCGCCAACTGGAGGACGCCATCGTG |
| CTGCTGCGGCTGCACATGCGCACGCTCTCCGCCTTTTTCGAGTGTCGGTTCGAGAGCGACGGGC |
| GCCGCCTGTATGCGGTGGTCGGGGACACGCCCGACCGCCTGGGGCCCTGGCCCCCCGAGGCCAT |
| GGGGGACGCGGTGAGTCAGTACTGCAGCATGTATCACGACGCCAAGCGCGCGCTGGTCGCGTCC |
| CTCGCGAGCCTGCGTTCCGTCATCACCGAAACCACGGCGCACCTGGGGGTGTGCGACGAGCTGG |
| CGGCCCAGGTGTCGCACGAGGACAACGTGCTGGCCGTGGTCCGGCGCGAAATTCACGGGTTTCT |
| GTCCGTCGTGTCCGGCATTCACGCCCGGGCGTCGAAGCTGCTGTCGGGAGACCAGGTCCCCGGG |
| TTTTGCTTCATGGGTCAGTTTCTAGCGCGCTGGCGGCGTCTGTCGGCCTGCTATCAAGCCGCGC |
| GCGCGGCCGCGGGACCCGAGCCCGTGGCCGAGTTTGTCCAGGAACTCCACGACACGTGGAAGGG |
| CCTGCAGACGGAGCGCGCCGTGGTCGTGGCGCCCTTGGTCAGCTCGGCCGACCAGCGCGCCGCG |
| GCCATCCGAGAGGTAATGGCGCATGCGCCCGAGGACGCCCCCCGCAAAGCCCCGCGGCCGACC |
| GGTCGTGCTTACGAGCCGTCGCGACCTAGGGGCCTGGGGGGACTACAGCCTCGGCCCCCTGGG |
| CCAGACGACCGCGGTTCCGGACTCCGTGGATCTGTCTCGCCAGGGGCTGGCCGTTACGCTGAGT |
| ATGGATTGGTTACTGATGAACGAGCTCCTGCGGGTCACCGACGGCGTGTTTCGCGCTTCCGCGT |
| TTCGTCCGTTAGCCGGACCGGAGTCTCCCAGGGACCTGGAGGTCCGCGACGCCGGAAACAGTCT |
| CCCCGCGCCTATGCCCATGGACGCACAGAAGCCGGAGGCCTATGGGCACGGCCCCACGCCAGGCG |
| GACCGCGAGGGGGCGCCTCATTCCAACACCCCCGTCGAGGACGACGAGATGATCCCGGAGGACA |
| CCGTCGCGCCACCCACGGACTTGCCGTTAACTAGTTACCAATAA |
| Sequence ID NO.: 2 |
| UL37 C819S |
| ATGGCAGACCGCGGTCTCCCGTCCGAGGCCCCCGTCGTCACGACCTCACCCGCCGGTCCGCCCT |
| CGGACGGACCTATGCAGCGCCTATTGGCGAGCCTAGCCGGCCTTCGCCAACCGCCAACCCCCAC |
| GGCCGAGACGGCAAACGGGGCGGACGACCCGGCGTTTCTGGCCACGGCCAAGCTGCGCGCCGCC |
| ATGGCGGCGTTTCTGTTGTCGGGAACGGCCATCGCCCCGGCAGACGCGCGGGACTGCTGGCGGC |
| CGCTGCTGGAACACCTGTGCGCGCTCCACCGGGCCCACGGGCTTCCGGAGACGGCGCTCTTGGC |
| CGAGAACCTCCCCGGGTTGCTCGTACACCGCTTGGTGGTGGCTCTCCCCGAGGCCCCCGACCAG |
| GCCTTCCGGGAGATGGAGGTCATCAAGGACACCATCCTCGCGGTCACCGGCTCCGACACGTCCC |
| ATGCGCTGGATTCCGCCGGCCTGCGCACCGCGGCGGCCCTGGGGCGGTCCGCGTCCGCCAGTG |
| CGCCGTGGAGTGGATAGACCGCTGGCAAACGTCACCAAGAGCTGCTTGGCCATGAGCCCGCGG |
| ACCTCCATCGAGGCCCTTGGGGAGACGTCGCTCAAGATGGCGCCGGTCCCGTTGGGGCAGCCCA |
| GCGCGAACCTTACCACCCCGGCGTACAGCCTGCTCTTCCCCGCCCCGTTCGTGCAAGAGGGCCT |
| CCGGTTCTTGGCCCTGGTGAGTAATCGGGTGACGCTGTTCTCGGCGCACCTCCAGCGCATAGAC |
| GACGCGACCCTCACTCCCCTCACACGGGCCCTCTTTACGTTGGCCCTGGTGGACGAGTACCTGA |
| CGACCCCCGAGCGGGGGGCTGTGGTCCCGCCGCCCCTGTTGGCGCAGTTTCAGCACACCGTGCG |
| GGAGATCGACCCGGCCATAATGATTCCGCCGCTCGAGGCCAACAAGATGGTTCGCAGCCGCGAG |
| GAGGTGCGCGTGTCGACGGCCCTCAGCCGCGTCAGCCCGCGCTCGGCCTGTGCGCCCCCGGGA |
| CGCTAATGGCGCGTGCGGACGGACGTGGCCGTGTTTGATCCCGACGTGCCCGTTCCTGAGTTC |
| GTCGGCACTGGCAGTCTTCCAGCCTGCCGTCTCCAGCCTGCTGCAGCTCGGGGAGCAGCCCTCC |
| GCCGGCGCCCAGCAGCGGCTGCTGGCTCTGCTGCAGCAGACGTGGACGTTGATCCAGAATACCA |
| ATTCGCCCTCCGTGGTGATCAACACCCTGATCGACGCTGGGTTCACGCCCTCGCACTGCACGCA |
| CTACCTTTCGGCCCTGGAGGGGTTTCTGGCGGCGGGCGTCCCCGCGCGGACGCCCACCGGCCAC |
| GGACTCGGCGAAGTCCAGCAGCTCTTTGGGTGCATTGCCCTCGCGGGGTCGAACGTGTTTGGGT |
| TGGCGCGGGAATACGGGTACTATGCCAACTACGTAAAAACTTTCAGGCGGGTCCAGGGCGCCAG |

Sequence Listing

```
CGAGCACACGCACGGGCGGCTCTGCGAGGCGGTCGGCCTGTCGGGGGCGTTCTAAGCCAGACG
CTGGCGCGTATCATGGGTCCGGCCGTGCCGACGGAACATCTGGCGAGCCTGCGGCGGGCGCTCG
TGGGGGAGTTTGAGACGGCCGAGCGCCGCTTTAGTTCCGGTCAACCCAGCCTTCTCCGCGAGAC
GGCGCTCATCTGGATCGACGTGTATGGTCAGACCCACTGGGACATCACCCCCACCACCCCGGCC
ACGCCGCTGTCCGCGCTTCTCCCCGTCGGGCAGCCCAGCCACGCCCCCTCTGTCCACCTGGCCG
CGGCGACCCAGATCCGCTTCCCCGCCCTCGAGGGCATTCACCCCAACGTCCTCGCCGACCCGGG
CTTCGTCCCCTACGTTCTGGCCCTGGTGGTCGGGGACGCGCTGAGGGCCACGTGTAGCGCCGGT
TACCTTCCCCGCCCGGTCGAGTTCGCCCTGCGTGTGTTGGCCTGGGCCCGGGACTTTGGGCTGG
GCTATCTCCCCACGGTTGAGGGCCATCGCACCCAAACTGGGCGCGCTGATCACCCTCCTCGAACC
GGCCGCCCGGGCGGCCTCGGCCCCACTATGCAGATGGCCGACAACATAGAGCAGCTGCTCCGG
GAGCTGTACGTGATCTCCAGGGGTGCCGTCGAGCAGCTGCGCCCCTGGTCCAGCTGCAGCCCC
CCCCGCCCCCCGAGGTGGGCACCAGCCTCCTGTTGATTAGCATGTACGCCCTGGCCGCCCGGGG
GGTGCTGCAGGACCTCGCCGAGCGCGCAGACCCCCTGATTCGCCAACTGGAGGACGCCATCGTG
CTGCTGCGGCTGCACATGCGCACGCTCTCCGCCTTTTTCGAGTGTCGGTTCGAGAGCGACGGGC
GCCGCCTGTATGCGGTGGTCGGGGACACGCCCGACCGCCTGGGGCCCTGGGCCCCCCGAGGCCAT
GGGGGACGCGGTGAGTCAGTAC[[A]]GCAGCATGTATCACGACGCCAAGCGCGCGCTGGTCGC
GTCCCTCGCGAGCCTGCGTTCCGTCATCACCGAAACCACGGCGCACCTGGGGGTGTGCGACGAG
CTGGCGGCCCAGGTGTCGCACGAGGACAACGTGCTGGCCGTGGTCCGGCGCGAAATTCACGGGT
TTCTGTCCGTCGTGTCCGGCATTCACGCCCGGGCGTCGAAGCTGCTGTCGGGAGACCAGGTCCC
CGGGTTTTGCTTCATGGGTCAGTTTCTAGCGCGCTGGCGGCGCTGTCGGCCTGCTATCAAGCC
GCGCGCGCGGCCGCGGGACCCGAGCCCGTGGCCGAGTTTGTCCAGGAACTCCACGACACGTGGA
AGGGCCTGCAGACGGAGCGCGCCGTGGTCGTGGCGCCCTTGGTCAGCTCGGCCGACCAGCGCGC
CGCGGCCATCCGAGAGGTAATGGCGCATGCGCCCGAGGACGCCCCCCGCAAAGCCCCGCGGCC
GACCGCGTCGTGCTTACGAGCCGTCGCGACCTAGGGGCCTGGGGGGACTACAGCCTCGGCCCCC
TGGGCCAGACGACCGCGGTTCCGGACTCCGTGGATCTGTCTCGCCAGGGGCTGGCCGTTACGCT
GAGTATGGATTGGTTACTGATGAACGAGCTCCTGCGGGTCACCGACGGCGTGTTTCGCGCTTCC
GCGTTTCGTCCGTTAGCCGGACCGGAGTCTCCCAGGGACCTGGAGGTCCGCGACGCCGGAAACA
GTCTCCCGCGCCTATGCCCATGGACGCACAGAAGCCGGAGGCCTATGGGCACGGCCCACGCCA
GGCGGACCGCGAGGGGGCGCCTCATTCCAACACCCCCGTCGAGGACGACGAGATGATCCCGGAG
GACACCGTCGCGCCACCCACGGACTTGCCGTTAACTAGTTACCAATAA

Sequence ID NO.: 3
RIG-I Wild-type
MTTEQRRSLQAFQDYIRKTLDPTYILSYMAPWFREEEVQYIQAEKNNKGPMEAATLFLK
FLLELQEEGWERGELDALDHAGYSGLYEAIESWDEKKIEKLEEYRLLLKRLQPEFKTRIIP
TDIISDLSECLINQECEEILQICSTKGMMAGAEKLVECLLRSDKENWPKTLKLALEKERN
KFSELWIVEKGTKDVETEDLEDKMETSDIQIFYQEDPECQNLSENSCPPSEVSDTNLYSPF
KPRNYQLELALPAMKGKNTIICAPTGCGKTFVSLLICEHHLKKFPQGQKGKVVFFANQIP
VYEQQKSVFSKYFERHGYRVTGTSGATAENVPVEQIVENNDIIILTPQILVNNLKKGTIPSL
SIFTLMIFDECHNTSKQHPYNMIMFNYLDQKLGGSSGPLPQVIGLTASVGVGDAKNTDE
ALDYICKLCASLDASVIATVKHNLEELEQVVYKPQKFFRKVESRISDKFKYIIAQLMRDT
ESLAKRICKDLENLSQIQNREFGTQKYEQWIVTVQKACMVFQMPDKDEESRICKALFLY
TSHLRKYNDALITSEHARMKDALDYLKDFFSNVRAAGFEEIEQDLTQRFEEKLQELESVS
RDPSNENPKLEDLCFILQEEYHLNPETITILFVKTRALVDALKNWIEGNPKLSFLKPGTLTG
RGKTNQNTGMTLPAQKCTLDAFKASGDHNILIATSVADEGTDIAQCNLVILYEYVGNVIK
MIQTRGRGRARGSKCFLLTSNAGVIEKEQINMYKEKMMNDSILRLQTWDEAVFREKILH
IQTHEKFIRDSQEKPKPVPDKENKKLLCRKCKALACYTADVRVIEECHYTVLGDAFKEC
FVSRPHPKPKQFSSFEKRAKIFCARQNCSHDWGTHVKYKTFEIPVIKIESFVVEDIATGVQ
TLYSKWKDFHFEKIPFDPAEMSK Sequence ID NO.: 4
RIG-I-QQ
MTTEQRRSLQAFQDYIRKTLDPTYILSYMAPWFREEEVQYIQAEKNNKGPMEAATLFLK
FLLELQEEGWERGELDALDHAGYSGLYEAIESWDEKKIEKLEEYRLLLKRLQPEFKTRIIP
TDIISDLSECLINQECEEILQICSTKGMMAGAEKLVECLLRSDKENWPKTLKLALEKERN
KFSELWIVEKGTKDVETEDLEDKMETSDIQIFYQEDPECQNLSENSCPPSEVSDTNLYSPF
KPRNYQLELALPAMKGKNTIICAPTGCGKTFVSLLICEHHLKKFPQGQKGKVVFFANQIP
VYEQQKSVFSKYFERHGYRVTGTSGATAENVPVEQIVENNDIIILTPQILVNNLKKGTIPSL
SIFTLMIFDECHNTSKQHPYNMIMFNYLDQKLGGSSGPLPQVIGLTASVGVGDAKNTDE
ALDYICKLCASLDASVIATVKHNLEELEQVVYKPQKFFRKVESRISDKFKYIIAQLMRDT
ESLAKRICKDLE[[Q]]LSQIQNREFGTQKYEQWIVTVQKACMVFQMPDKDEESRICKALF
LYTSHLRKY[[Q]]DALITSEHARMKDALDYLKDFFSNVRAAGFEEIEQDLTQRFEEKLQEL
ESVSRDPSNENPKLEDLCFILQEEYHLNPETITILFVKTRALVDALKNWIEGNPKLSFLKP
GTLTGRGKTNQNTGMTLPAQKCTLDAFKASGDHNILIATSVADEGTDIAQCNLVILYEYV
GNVIKMIQTRGRGRARGSKCFLLTSNAGVIEKEQINMYKEKMMNDSILRLQTWDEAVF
REKILHIQTHEKFIRDSQEKPKPVPDKENKKLLCRKCKALACYTADVRVIEECHYTVLGD
AFKECFVSRPHPKPKQFSSFEKRAKIFCARQNCSHDWGTHVKYKTFEIPVIKIESFVVEDI
ATGVQTLYSKWKDFHFEKIPFDPAEMSK Sequence ID NO.: 5
C819S KOS genome
81548 a→t
          gcagcccggg ccccccgcgg gcgcgcgcgc gcgcaaaaaa ggcgggcggc ggtccgggcg
      61  gcgtgcgcgc gcgcggcggg cgtggggggc ggggccgcgg gagcggggga ggagcggggg
     121  aggagcgggg ggaggagcgg ggggaggagc ggggggagga gcggggggag gagcgggggg
     181  aggagcgggg ggaggagcgg ggggaggagc ggggggagga gcggggggag gagcgggggg
     241  aggagcgggg ggaggagcgg ggggaggagc ggggggagga gcggggggag gagcgggggg
```

-continued

Sequence Listing

```
 301 aggagcgggg gaggagcggc cagaccccgg aaacgggccc ccccaaaac acaccccccg
 361 ggggtcgcgc gcggcccttt aaaggcgggc ggcgggcagc ccgggccccc cgcggccgag
 421 actagcgagt tagacaggca agcactactc gcctctgcac gcacatgctt gcctgtcaaa
 481 ctctaccacc ccggcacgct ctctgtctcc atgcccgcc gccgccatcg cggccccgc
 541 cgcccccggc cgcccggcc cacgggcgcg gtcccaaccg cacagtccca ggtaacctcc
 601 acgcccaact cggaacccgt ggtcaggagc gcgcccgcgg ccgcccgcc gccgccccc
 661 gccagtgggc ccccgccttc ttgttcgctg ctgctgcgcc agtggctcca cgttcccgag
 721 tccgcgtccg acgacgacga cgacgactgg ccggacagcc ccccgcccga gccggcgcca
 781 gaggcccggc ccaccgccgc cgcccccgc ccccggtccc caccgccggg cgcgggcccg
 841 gggggcgggg ctaacccctc ccacccccc tcacgcccct tccgccttcc gccgcgcctc
 901 gccctccgcc tgcgcgtcac cgcagagcac ctggcgcgcc tgcgcctgcg acgcgcgggc
 961 gggggagggg cgccgaagcc ccccgcgacc ccgcgaccc cgcgaccccc cacgcgggtg
1021 cgcttctcgc cccacgtccg ggtgcgccac ctggtggtct gggcctcggc cgcccgcctg
1081 gcgcgccgcg gctcgtgggc ccgcgagcgg gccgaccggg ctcggttccg gcgccgggtg
1141 gcggaggccg aggcggtcat cgggccgtgc ctggggcccg aggcccgtgc ccgggccctg
1201 gcccgcggag ccggcccggc gaactcggtc taacgttaca cccgaggcgg cctgggtctt
1261 ccgcgagct cccgggagct ccgcaccaag ccgctctccg gagagacgat ggcaggagcc
1321 gcgcatatat acgcttggag ccggcccgcc cccgaggcgg gcccgccctc ggagggcggg
1381 actggccaat cggcggccgc cagcgcggcg gggcccggcc aaccagcgtc cgccgagtcg
1441 tcggggcccg gcccactggg cggtaactcc cgcccagtgg gccgggccgc ccacttcccg
1501 gtatggtaat taaaaacttg cagaggcctt gttccgcttc ccggtatggt aattagaaac
1561 tcattaatgg gcggcccgg ccgcccttcc cgcttccggc aattcccgcg gcccttaatg
1621 ggcaacccg gtattcccg cctcccgcgc cgcgcgtaac cactccctg gggttccggg
1681 ttatgttaat tgcttttttg gcggaacaca cggccccttcg cgcattggcc cgcgggtcgc
1741 tcaatgaacc cgcattggtc ccctgggggtt ccgggtatgg taatgagttt cttcgggaag
1801 gcgggaagcc ccggggcacc gacgcaggcc aagcccctgt tgcgtcggcg ggaggggcat
1861 gctaatgggg ttctttgggg gacaccgggt tggtccccca aatcggggggc cgggccgtgc
1921 atgctaatga tattctttgg gggcgcgggg ttggtccccg gggacggggc cgcccgcgg
1981 tgggcctgcc tcccctggga cgcgcggcca ttggggaat cgtcactgcc gccccttgg
2041 ggagggaaa ggcgtggggt ataagttagc cctggcccga cggtctggtc gcatttgcac
2101 ctcggcactc ggagcgagac gcagcagcca ggcagactcg ggccgccccc tctccgcatc
2161 accacagaag ccccgcctac cgttgcgacc ccagggaccc tccgtcagcg accctccagc
2221 cgcatacgac cccatggag ccccgcccg gagcgagtac ccgccggcct gagggccgcc
2281 cccagcgcga ggtgaggggc cgggcgccat gtctgggcg ccatgttggg gggcgccatg
2341 ttggggggcg ccatgttggg ggaccccga cccttacact ggaaccggcc gccatgttgg
2401 gggaccccca ctcatacacg ggagccgggc gccatgttgg ggcgccatgt taggggggcgt
2461 ggaacccgt gacactatat atacagggac cggggcgcc atgttagggg gcgcggaacg
2521 ccctgaccct atatatacag ggaccgggt cgccctgtta ggggtcgcca tgtgaccccc
2581 tgactttata tatacagacc cccaacacct acacatggcc cctttgactc agacgcaggg
2641 cccggggtcg ccgtgggacc ccctgactc atacacagag acacgccccc acaacaaaca
2701 cacagggacc ggggtcgccg tgttagggg cgtggtcccc actgactcat acgcagggcc
2761 cccttactca cacgcatcta gggggtggg gaggagccgc cgccatatt tggggggacgc
2821 cgtgggaccc ccgactccgg tgcgtctgga gggcgggaga agaggaaga agagggtcg
2881 ggatccaaag gacggaccca gaccacctt ggttgcagac ccctttctcc ccctcttcc
2941 gaggccagca ggggggcagg acttttgtgag gcgggggggg aaggggaact cgtgggcgct
3001 gattgacgcg ggaaatcccc ccattcttac ccgccccccc tttttttccc tcagcccgcc
3061 ccggatgtct gggtgttcc ctgcgaccga gacctgccgg acagcagcga ctcggaggcg
3121 gagaccgaag tgggggggcg ggggacgcc gaccaccatg acgacgactc cgcctccgag
3181 gcggacagca cggacacgga actgttcgag acggggctgc tggggccgca gggcgtggat
3241 ggggggggcgg tctcggggg gagccccccc cgcgaggaag acccggcag ttgcggggc
3301 gcccccctc gagaggacgg gggagcgac gagggcgacg tgtgcgccgt gtgcacggat
3361 gagatcgcgc cccacctgcg ctgcgacacc ttccgtgca tgcaccgctt ctgcatcccg
3421 tgcatgaaaa cctggatgca attgcgcaac acctgccgtc tgtgcaacgc caagctggtg
3481 tacctgatag tgggcgtgac gcccagcggg tcgttcagca ccatcccgat cgtgaacgac
3541 ccccagaccc gcatggaggc cgaggaggcc gtcagggcgg gcacggccgt ggacttatc
3601 tggacgggca atcagcggtt cgccccgcgg tacctgaccc tggggggggca cacggtgagg
3661 gccctgtcgc ccaccaccc tgagcccacc acggacgagg atgacgacga cctggacgac
3721 ggtgaggcgg gggggggcgg aggacccctgg ggaggaggga ggaggggggg gggaggggag
3781 aataggcggg cggggcgggcg aggaaagggc gggccgggga gggggcgtaa cctgatcgcg
3841 ccccccgttg tctcttgcag cagactacgt accgcccgcc ccccgccgga cgcccccgcg
3901 ccccccacgc agaggcgccg ccgcgccccc cgtgacgggc ggggcgtctc acgcagcccc
3961 ccagccggcc gcggctcgga cagcgcccc ctcggccgcc atcgggccac acggcagcag
4021 taacactaac accaccacca acagcagcgc cggcggcggc tcccgccagt cgcgagccgc
4081 ggtgccgcgg ggggcgtctg gcccctccgg ggggggttggg gttgttgaag cggaggcggg
4141 gcggccgagg ggccggacgg gccccccttgt caacagaccc gcccccttg caaacaacag
4201 agacccccata gtgatcagcg actcccccctc ggcctctccc cacaggcccc ccgcggcgcc
4261 catgccaggc tccgccccc gcccggtcc cccgcctcct gcgcccggt cgggccccg
4321 gcgccccgc gcggccgtgg cccgtgtgt gcgggcgccg cctccggggc ccggcccccg
4381 cgcccggcc cccggggcgg agccggccgc ccgcccgcg gacgcgccc gtgtgcccca
4441 gtcgcactcg tccctggctc aggccgcgaa ccaagaacag agtctgtgcc gggcgcgtgc
4501 gacggtggcg cgcggtcgg gggggccggg cgtggagggt ggacacgggc cctcccgcgg
4561 cgccgcccc tccggccgcc cctcccccg ccgcctctgt
4621 cgagcaggag gcggcggtgc gtccgaggaa gaggcgcggg tcgggccagg aaaacccctc
4681 cccccagtcc acgcgtcccc cctcgcgcc ggcagggcc aagagggcgg cgacgcaccc
4741 cccctccgac tcaggccgg ggggcgcgg ccaggagggg cccgggaccc ccctgacgtc
4801 ctcggcggcc tccgcctctt cctcctccg ctcttcctcc tcggcccga ctcccgcggg
4861 ggccacctct tccgccaccg gggccgcgtc ctcctccgct tccgcctcct cgggcgggc
```

Sequence Listing

```
4921  cgtcggtgcc ctgggaggga gacaagagga aacctccctc ggccccgcg ctgcttctgg
4981  gccgcggggg ccgaggaagt gtgcccggaa gacgcgccac gcggagactt ccggggccgt
5041  ccccgcgggc ggcctcacgc gctacctgcc catctcgggg gtctctagcg tggtcgccct
5101  gtcgccttac gtgaacaaga cgatcacggg ggactgcctg cccatcctgg acatggagac
5161  ggggaacatc ggggcgtacg tggtcctggt ggaccagacg ggaaacatgg cgacccggct
5221  gcgggccgcg gtccccggct ggagccgccg caccctgctc cccgagaccg cgggtaacca
5281  cgtgacgccc cccgagtacc cgacggcccc cgcgtcggag tggaacgacc tctggatgac
5341  ccccgtgggg aacatgctgt tcgaccaggg caccctagtg ggcgcctgg acttccgcag
5401  cctgccggtct cggcaccgt ggtccgggga gcaggggcg tcgacccggg acgagggaaa
5461  acaataaggg acgccccgt gtttgtgggg aggggggggt cgggcgctgg tggtctctg
5521  gccgcgccca ctacaccagc caatccgtgt cggggaggtg gaaagtgaaa gacacgggca
5581  ccacacacca gcgggtcttt tgtgttggcc ctaataaaaa aaactcaggg gattttttgct
5641  gtctgttggg aaataaaggt ttactttttgt atcttttccc tgtctgtgtt ggatgtatcg
5701  cggggggtgcg tgggagtggg ggtgcgtggg agtgggggtg cgtgggagtg ggggtgcgtg
5761  ggagtggggg tgcgtgggag tgggggtgcg tgggagtggg ggtgcgtggg agtgggggtg
5821  cgtgggagtg ggggtgcgtg ggagtggggg tgccatgttg ggcaggctct ggtgttaacc
5881  acagagccgc ggcccgggct gcctgaccac cgatcccga aagcatcctg ccactggcat
5941  ggagccagaa ccacagtggg ttgggtgtgg gtgttaagtt tccgcgagcg cctgcccgcc
6001  cggactgacc tggcctctgg ccgccacaaa gggcgggggg gggggttaac tacactatag
6061  ggcaacaaag gatgggaggg gtagcggggc gggacggggc gcccaaaagg gggtcggcca
6121  caccacagac gtgggtgttg ggggggtggg cggagggggtg ggggggggaga cagaaacagg
6181  aacatagtta gaaaacaaga atgcggtgca gccagagaat cacaggagac gaggggatgg
6241  gcgtgttggt taccaaccca cacccaggca tgctcggtgg tatgaaggag gggggggcggt
6301  gttttcttaga gaccgccggg ggacgtgggg ttggtgtgca aaggcacgcg caccccgcgcc
6361  ggccaggtgg gccggtaccc catcccccc tccccgacc cttccaccc ccgcgtgcca
6421  gagatcaccc cggtcccccg gcacccgcca ctcctccata tcctcgcttt aggaacaact
6481  ttagggggg gtacacacgc gccgtgcatt tccttccaca ccccccccct ccccgcact
6541  ccccccccc aggcagtaag acccaagcat agagagccag gcacaaaaac acaggcgggg
6601  tgggacacat gccttcttgg agtacgtggg tcattggcgt gggggggtac agcgacaccg
6661  gccgacccc tggcggtctt ccagccggcc cttagataag ggggcagttg gtggtcggac
6721  gggtaagtaa cagagtctaa ctaagggtgg gagggggga aaataacggg ctggtgtgct
6781  gtaacgacgag cccacccgcg agtggcgtgg ccgaccttag cctctggggc gcccctgtc
6841  gtttgggtcc ccccctct attgggaga agcaggtgtc taacctacct ggaaacgcgg
6901  cgtctttgtt gaacgacacc ggggcgccct cgacgagtgg gataacgggg gaggaaggga
6961  gggaggaggg tactgggggt gaaggggggg ggggagaagc gagaacagga aaggcgacgg
7021  agcccggcag aacaccgagg aaaaaaaaac cacagcgcat gcgccgggcc gttgtggggc
7081  cccgggccgg ggcccccttgg gtccgccggg gccccgggcc gggccgccac ggggggccggc
7141  cgttggcggt aaccccgagt gttcatctca ggccccgggc cgggaacccg gaaaagcctc
7201  cgggggggcct ttttcgcgtc gcgtgccggc gagcgggtcc ggacggggcc cggaccgccg
7261  cggtcggggg cccctcgtcc cgggccgtac gcggccttcg cccgtgagg ggacagacga
7321  acgaaacatt ccggcgacgg aacgaaaaac accccagacg ggttaaagaa acagaaaccg
7381  caaccccac cacccccgaa acgggggaaaa cgaaaaaaca gaccagcggc cggccggcgc
7441  ttagggggag gatgtcgccg acgcccttg gccgccccgg ctgcagggg gcccggagag
7501  ccgcggcacc cggacgcgcc cggaaagtct ttcgcaccac cggcgatcgg cacggccgcg
7561  cccccgcttt tataaagct cagatgacgc agcaaaaaca ggccacagca ccacatgagt
7621  aggtgatgta attttatttt cctcgtctgc ggcctaatgg atttccgggc gcggtgcccc
7681  tgtctgcaga gcacttaacg gattgatatc tcgcgggcac gcgcgcccctt aatggaccgg
7741  cgcggggcgg ggggccggat acccacacgg gcggggggggg gtgtcgcggg ccgtctgctg
7801  gcccgcgggcc acataaacaa tgactcgggg ccttcctgcc tctgccgctt gtgtgtgcgc
7861  gcgccggctc tgcggtgtcg gcgcgcggcg cggcggtggc cgccgtgttc ggtctcggta
7921  gccggccggc gggtggactc gcggggggcc ggaggtggaa aggcagggggg gtgtaggatg
7981  ggtatcagga cttccacttc ccgtccttcc atccccgtt ccctcggtt gttcctcgcc
8041  tccccaaca ccccgccgct ttccgttggg gttgttattg ttgtcgggat cgtgcgggcc
8101  gggggtcgcc ggggcagggg cggggcgtg ggcggggggg ctcgtcgatc gacccgggctc
8161  agtggggggcg tgggggtgggt gggagaaggc gaggagactg gggtgggggt gtcggtgggt
8221  ggttgttttt tgtggttgtt ttttgtgtct gttccgtcc cccgtcaccc ccctccctcc
8281  gtccctccg tccccccgtc gcgggtgttt gtgtttgttt attccgacat cggttttattt
8341  aaaataaaca cagccggttct gcgtgtctgt tcttgcgtgt ggctgggggc ttatatgtgg
8401  ggtcccgggg gcgggatggg gtttagcggc gggggggcggc gcgcggacg gggcgctgga
8461  gataacggcc cccgggggaac ggggggaccgg ggctgggttat cccgaggtgg gtgggtgggc
8521  ggcggtggcc gggccgggcc gggccgggcc gggtgggcgg ggtttggaaa aacgaggagg
8581  aggaggagaa ggcggggggg gacgggggg gaaagcaagg acacggccg ggggggtggga
8641  gcgcgggccg ggccgctcgt aagagccgcg accccgccgc cggggagcgt tgtcgccgtc
8701  ggtctgccgg ccccccgtcc tccctttttt gaccaaccag cgccctcccc ccaccacca
8761  ttcctactac caccaccacc accacccca ccaccgacac ctcccgcgca ccccccgccca
8821  catcccccca ccccgcacca cgagcacggg gtgggggtag cagggggatca aaggggggca
8881  aagccggcgg ggcggttcgg ggggggcggga gaccgagtag gccccgccat acgccgcccc
8941  tcccgcagc cacgcccccc agcgtcggggt gtcacggga aaagagcaggg gagagggggg
9001  gagaggggag agggggggag agggggagggg gggggggggg ggagggggg ggagaggga
9061  gaggggggga gagggggagag ggggggagag gggagagggg gggagagggg agaggggggg
9121  agagggggga ggggggggaga gggagagggg gggagagggg ggtatataaa ccaacgaaaa
9181  gcgcgggaac ggggatacgg ggcttgtgtg gcacgacgtc gtggttgtgt tactgggcaa
9241  acacttgggg actgtaggtt tctgtggggtg ccgacccctag gcgctatggg gattttgggt
9301  tgggtcgggc ttattgccgt tggggttttg tgtgtgcggg gggcttgtc ttcaaccgaa
9361  tatgttattc ggagtcgggt ggctcgagag gtgggggata tattaaaggt gccttgtgtg
9421  ccgctcccgt ctgacgatct tgattggcgt tacgagaccc cctcggctat aaactatgct
9481  ttgatagacg gtatattttt gcgttatcac tgtcccggat tggacacggt cttgtgggat
```

-continued

Sequence Listing

```
 9541  aggcatgccc agaaggcata ttgggttaac cccttttat ttgtggcggg ttttctggag
 9601  gacttgagtc accccgcgtt tcctgccaac acccaggaaa cagaaacgcg cttggcccctt
 9661  tataaagaga tacgccaggc gctggacagt cgcaagcagg cgccagcca cacacctgtg
 9721  aaggctgggt gtgtgaactt tgactattcg cgcacccgcc gctgtgtagg cgacaggat
 9781  ttgggaccta ccaacggaac gtctggacgg accccggttc tgccgccgga cgatgaagcg
 9841  ggcctgcaac cgaagcccct caccacgccg ccgcccatca tcgccacgtc ggaccccacc
 9901  ccgcgacggg acgccgccac aaaaagcaga cgccgacgac cccactcccg gcgcctctaa
 9961  cgatgcctcg acggaaaccc gtccggggttc gggggggcgaa ccggccgcct gtcgctcgtc
10021  agggccggcg ggcgctcctc gccgccctag aggctgtccc gctggtgtga cgttttcctc
10081  gtccgcgccc cccgaccctc ccatggattt aacaaacggg ggggtgtcgc ctgcggcgac
10141  ctcggcgcct ctggactgga ccacgtttcg gcgtgtgttt ctgatcgacg acgcgtggcg
10201  gcccctgatg gagcctgagc tggcgaaccc cttaaccgcc cacctcctgg ccgaatataa
10261  tcgtcggtgc cagaccgaag aggtgctgcc gccgcgggag gatgtgtttt cgtggactcg
10321  ttattgcacc cccgacgagg tgcgcgtggt tatcatcggc caggacccat atcaccaccc
10381  cggccaggcg cacggacttg cgtttagcgt gcgcgcgaac gtgccgcctc ccccgagtct
10441  tcggaatgtc ttggtggccg tcaagaactg ttatcccgag gcacggatga gcggccacgg
10501  ttgcctggaa aagtgggcgc gggacggcgt cctgttacta aacacgaccc tgaccgtcaa
10561  gcgcggggcg gcggcgtccc actctagaat cggttgggac cgcttcgtgg gcggagttat
10621  ccgccggttg gccgcgcgcc gccccggcct ggtgtttatg ctctggggcg cacacgccca
10681  gaatgccatc aggccggacc ctcggtcca ttgcgtcctc aagttttcgc acccgtcgcc
10741  cctctccaag gttccgttcg gaacctgcca gcatttcctc gtggcgaacc gatacctcga
10801  gacccggtcg atttcaccca tcgactggtc ggtttgaaag gcatcgacgt ccggggttt
10861  tgtcggtggg ggcttttggg tatttccgat gaataaagac ggttaatggt taaacctctg
10921  gtctcatacg ggtcggtgat gtcgggcgtc ggggggagag gagttccctc tgcgcttgcg
10981  attctagcct cgtggggctg gacgttcgac acgccaaacc acgagtcggg gatatcgcca
11041  gatacgactc ccgcagattc cattcggggg gccgctgtgg cctcacctaa ccaaccttta
11101  cacgggggcc cggaacggga ggccacagcg ccgtctttct ccccaacgcg cgcggatgac
11161  ggcccgccct gtaccgacgg gccctacgtg acgtttgata cccctgttat ggtgtcgtcg
11221  atcgacgaat tagggcgtcg ccagctcacg gacaccatcc gcaaggacct gcggttgtcg
11281  ctggccaagt ttagcattgc gtgcaccaag acctcctcgt tttcgggaaa cgccccgcgc
11341  caccacagac gcggggcgtt ccagcgcggc acgcgggcgc cgcgcagcaa caaaagcctc
11401  cagatgtttg tgttgtgcaa acgcgcccac gccgctcgag tgcgagagca gcttcgggtc
11461  gttattcagt cccgcaagcc gcgcaagtat tacacgcgat cttcggacgg gcggctctgc
11521  cccgccgtcc ccgtgttcgt ccacgagttc gtctcgtccg agccaatgcg cctccaccga
11581  gataacgtca tgctggcctc gggggccgag taaccgcccc cccccatgc caccctcact
11641  gcccgtcgcg cgtgtttgat gttaataaat aacacataaa tttggctggt tgtttgttgt
11701  ctttaatgga ccgccgcaa ggggggggg gcgtttcagt gtcgggtgac gagcgcgatc
11761  cggccgggat cctaggaccc caaaagtttg tctgctgatt ccagggtggg gctcagttga
11821  atctcccgca gcacctctac cagcaggtcc gcggtgggct ggagaaactc ggccgtcccg
11881  gggcaggcgg ttgtcgggg tggaggcgcg gcgcccaccc cgtgtgccgg gcctggcgtc
11941  tcctctgggg gcgacccgta aatggttgca gtgatgtaaa tggtgtccgc ggtccagacc
12001  acggtcaaaa tgccggccgt ggcgctccgg gcgctttcgc cgcgcgagga gctgacccag
12061  gagtcgaacg gatacgcgta catatgggcg tcccaccccgc gttcgagctt ctggttgctg
12121  tcccggccta taaagcgta ggcacaaaat tcgcgcgac agtcgataat caccaacagc
12181  ccaatggggg tgtgctggat aacaacgcct ccgcgcgcga ggcggtcctg gcgctcccgg
12241  ccccgtacca tgatcgcgcg ggtgccgtac tcaaaaacat gcaccacctg cgcggcgtcg
12301  ggcagtgcgc tggtcagcga ggccctggcg tggcataggc tatacgcgat ggtcgtctgt
12361  ggattggaca tctcgcggtg ggtagtgagt ccccgggcc gggttcggtg gaactgtaag
12421  gggacggcgg gttaatagac aatgaccacg ttcggatcgc gcagagccga tagtatgtgc
12481  tcactaatga cgtcatcgcg ctcgtggcgc tcccggagcg gatttaagtt catgcgaagg
12541  aattcggagg aggtggtgcg ggacatggcc acgtacgcgc tgttgaggcg caggttgccg
12601  ggcgtaaagc agatggcgac cttgtccagg ctaaggccct gggagcgcgt gatggtcatg
12661  gcaagcttgg agctgatgcc gtagtcggcg tttatgccga tggccagctc cgtagagtca
12721  atggactcga caaactcgct gatgttggtg ttgacgacgg acatgaagcc gtgttggtcc
12781  cgcaagacca cgtaaggcag ggggcctct tccagtaact cggccacgtt ggccgtcgcg
12841  tgccgcctcc gcagctcgtc cgcaaaggca acaccgtg tgtacgtgta tcccatgagc
12901  gtataattgt ccgtctgcag ggcgacggac atcagccccc cgcgcggcga gccggtcagc
12961  atctcgcagc cccggaagat aacgttgtcc acgtacgtgc taaaggggc gacttcaaat
13021  gcctccccga agagctcttg gaggattcgg aatctcccga ggaaggcccg cttcagcagc
13081  gcaaactggg tgtgaacggc ggcggtggtc tccggttccc cggggggtgta gtggcagtaa
13141  aaacgtcga gctgttgttc gtccagcccc gcgaaataa cgtcgaggtc gtcgtcggga
13201  aaatcgtccg ggccccgtc ccgcggcccc agttgcttaa aatcaaacgc acgctcgccg
13261  ggggcgcctg cgtcggccat taccgacgcc tgcgtggca ccccgaaga tttggggcgc
13321  agagacagaa tctccgccgt tagttctccc atgcgggcgt acgcgagggt cctctgggtc
13381  gcatccaggc ccgggcgctg cagaaagttg taaaggaga taagcccgct aaatatgagc
13441  cgcgacagga acctgtaggc aaactccacc gaagtctccc cctgagtctt tacaaagctg
13501  tcgtcacgca acactgcctc gaaggcccga aacgtcccac taaacccaaa aaccagtttt
13561  cgcaggcgcg cggtcaccgc gatctggctg ttgaggacgg aagtgacgtc gttgcgggcc
13621  acgaccagct gctgtttgct gtgcacctcg cagcgcatgt gccccgcgtc ctggtcctgg
13681  ctctgcgagt agttggtgat gcggctggcg ttggccgtga ccactttc aatagtcagg
13741  ccgggctggt gtgtcagccg tcggtattcg tcaaactcct tgaccgacac gaacgtaagc
13801  acggggaggg tgaacacgac gaactccccc tcggccgtca ccttcaggta ggcgtggagc
13861  ttggccatgt acgcgctcac ctctttgtgg gaggagaaca gccgcgtcca gccggggagg
13921  ttggcggggt tggtgatgta gttttccggg acgacgaagc gatccacgaa ctgcatgtgc
13981  tcctcggtga tgggcaggcc gtactccagc accttcatga ggttaccgaa ctcgtgctcg
14041  acgcaccgtt tgttgttaat aaaaatggcc cagctatacg agaggcgggc gtactcgcgc
14101  agcgtgcggt tgcagatgag gtacgtgagc acgttctcgc tctggcggac ggaacaccgc
```

```
                         Sequence Listing
14161   agtttctggt gctcgaaggt cgactccagg gacgccgtct gcgtcggcga gcccacacac
14221   accaacacgg gccgcaggcg ggccgcgtac tgggggggtgt ggtacagggc gttaatcatc
14281   caccagcaat acaccacggc cgtgaggagg tgacgcccaa ggagcccggc ctcgtcgatg
14341   acgatcacgt tgctgcgggt aaaggccggc agcgcccccgt gggtggccgg ggccaaccgc
14401   gtcagggcgc cctcggccaa ccccagggtc cgttccaggg cggccagggc gcgaaactcg
14461   ttccgcaact cctcgccccc ggaggcggcc agggcgcgct tcgtgaggtc caaaatcacc
14521   tcccagtagt acgtcagatc tcgtcgctgc aggtcctcca gcgaggcggg gttgctggtc
14581   agggtgtacg ggtactgtcc cagttgggcc tggacgtgat tcccgcgaaa cccaaattca
14641   tgaaagatgg tgttgatggg tcggctgaga aaggcgcccg agagtttggc gtacatgttt
14701   tgggccgcaa tgcgcgtggc gcccgtcacc acacagtcca agacctcgtt gattgtctgc
14761   acgcacgtgc tctttccgga gccagcgttg ccggtgataa gatacaccgc gaacggaaac
14821   tccctgaggg gcaggcctgc gggggactct aaggccgcca cgtcccggaa ccactgcaga
14881   cggggcactt gcgctccgtc gagctgttgt tgcgagagct ctcggatgcg cttaaggatt
14941   ggctgcaccc cgtgcataga cgtaaaattt aaaaaggcct cggccctccc tggaacggct
15001   ggtcggtccc cgggttgctg aaggtgcggc gggccgggtt tctgtccgtc tagctggcgc
15061   tccccgccgg ccgccgccat gaccgcacca cgctcgtggg ccccactac gcgtgcgcgg
15121   ggggacacgg aagcgctgtg ctcccccgag gacggctggg taaaggttca ccccaccccc
15181   ggtacgatgc tgttccgtga gattctccac gggcagctgg ggtataccga gggccagggg
15241   gtgtacaacg tcgtccggtc cagcgaggcg accacccggc agctgcaggc ggcgatcttt
15301   cacgcgctcc tcaacgccac cacttaccgg gacctcgagg cggactggct cggccacgtg
15361   gcggccccgcg gtctgcagcc ccaacggctg gttcgccggt acaggaacgc ccgggaggcg
15421   gatatcgccg gggtggccga gcgggtgttc gacacgtggc ggaacacgct taggacgacg
15481   ctgctggact ttgcccacgg gttggtcgcc tgctttgcgc cgggcgggcc gagcggcccg
15541   tcaagcttcc ccaaatatat cgactggctg acgtgcctgg ggctggtccc catattacgc
15601   aagcgacaag aagggggtgt gacgcagggt ctgagggcgt ttctcaagca gcacccgctg
15661   acccgccagc tggccacggt cgcggaggcc gcggagcgcg ccggccccgg gttttttgag
15721   ctggcgctgg ccttcgactc cacgcgcgtg gcggactacg accgcgtgta tatctactac
15781   aaccaccgcc ggggcgactg gctcgtgcga gaccccactg gcgggcagcg cggagaatgt
15841   ctggtgctgt ggccccccctt gtggaccggg gaccgtctgg tcttcgattc gcccgtccag
15901   cggctgtttc ccgagatcgt cgcgtgtcac tccctccggg aacacgcgca cgtctgccgg
15961   ctgcgcaata ccgcgtccgt caaggtgctg ctggggcgca agagcgacag cgagcgcggg
16021   gtggccggtg ccgcgcgggt cgttaacaag gtgttggggg aggacgacga gaccaaggcc
16081   gggtcggccg cctcgcgcct cgtgcggctt atcatcaaca tgaagggcat gcgccacgta
16141   ggcgacatta acgacaccgt gcgtgcctac ctcgacgagg ccgggggggca cctgatagac
16201   gccccggccg tcgacggtac cctccctgga ttcggcaagg gcggaaacag ccgcgggtct
16261   gcgggccagg accaggggg gcgggcgccg cagcttcgcc aggccttccg cacggccgtg
16321   gttaacaaca tcaacgcgt gttggagggc tatataaata acctgtttgg aaccatcgag
16381   cgcctgcgcg agaccaacgc gggcctggcg acccaattgc aggagcgcga ccgcgagctc
16441   cggcgcgcaa cagcgggggc cctgagcgc cagcagcgcg cggccgacct ggcggccgag
16501   tccgtgaccg gtggatgcgg cagccgccct gcggggcgg acctgctccg ggccgactat
16561   gacattatcg acgtcagcaa gtccatggac gacgacagt acgtcgccaa cagctttcag
16621   cacccgtaca tcccttcgta cgccaggac ctggagcgcc tgtcgcgcct ctgggagcac
16681   gagctggtgc gctgttttaa aattctgtgt caccgcaaca accagggcca agagacgtcg
16741   atctcgtact ccagcggggc gatcgccgca ttcgtcgccc cctactttga gtcagtgctt
16801   cgggccccccc gggtaggcgc gcccatcacg ggctccgatg tcatcctggg ggaggaggag
16861   ttatgggatg cggtgtttaa gaaaacccgc ctgcaaacgt acctgacaga catcgcggcc
16921   ctgttcgtcg cggacgtcca gcacgcagcg ctgcccccgc cccctcccc ggtcggcgcc
16981   gatttccggc ccggcgcgtc cccgcggggc cggtccagat cgcggtcgcc cggaagaact
17041   gcgccaggcg cgccggacca gggcgggggc atcgggcacc gggatggccg ccgcgacggc
17101   cgacgatgag gggtcggccg ccaccatcct caagcaggcc atcgccgggg accgcagcct
17161   ggtcgaggcg gccgaggcga ttagccagca gacgctgctc cgcctggcct gcgaggtgcg
17221   ccaggtcggc gaccgccagc cgcggtttac cgccaccagc atcgcgcgcg tcgacgtcgc
17281   gcctgggtgc cggttgcggt tcgttctgga gggagtccc gaggacgcct atgtgacgtc
17341   ggaggattac tttaagcgct gctgcggcca gtccagttat cgcggcttcg cggtggcggt
17401   cctgacggcc aacgaggacc acgtgcacag cctggccgtg cccccccctcg ttctgctgca
17461   ccggttctcc ctgttcaacc caggggacct cctggacttt gagcttgcct gtctgctgat
17521   gtacctggag aactgccccc gaagccacgc caccccgtcg acctttgcca aggttctggc
17581   gtggctcggg gtcgcgggtc gccgcacgtc cccattcgaa cgcgttcgct gccttttcct
17641   ccgcagttgc cactgggtcc taaacacact catgttcatg gtgcacgtaa aaccgttcga
17701   cgacgagttc gtcctgcccc actggtacat ggcccggtac ctgctggcca caacccgcc
17761   ccccgttctc tcggcccgt tctgtgccac cccgacgagc tcctcattcc ggctgccggg
17821   gccgcccccc cgctccgact gcgtggccta taacccggcg gggatcatgg ggagctgcgg
17881   ggcgtcggag gaggtgcgcg cgcctctggt ctattggtgg ctttcggaga ccccaaaacg
17941   acagacgtcg tcgctgtttt atcagttttg ttgaatttta ggaaataaac ccggttttgt
18001   ttctgtggcc tcccgacgga tgcgcgtgtc cttcctccgt cttggtgggt gggtgtctgt
18061   gtatcgcgtc ccatctgtgc ggagaggggg ggcatgtcgg cacgtattcg gacagactca
18121   agcacacacg ggggagcgct cttgtctcag ggcaatgttt ttattggtca aactcaggca
18181   aacagaaacg acatcttgtc gtcaaaggga tacacaaact tccccccctc tccccatact
18241   cccgccagca ccccgtaa caccaactca atctcgcgca ggatttcgcg caggtgatga
18301   gcgcagtcca cgggggggag cacaaggggc cgcgggtata gatcgacggg gacgccgacc
18361   gactccccgc ctcgggaca gacacgcacg acgcgccgcc agtagtgctc tgcgtccagc
18421   aaggcgccgc cgcggaaggc agtgggggggc aagggggtgc tagcctcaaa gggggacacc
18481   cgaacgctcc agtactccgc gtccaaccgt ttattaaacg cgtccacgat aaggcggtcg
18541   caggcgtcct ccataaggcc ccgggccgtg agtgcgtcct cctccggcac gctgccgtt
18601   gtcaggccca ggaccccgtcg cagcgtgtcg cgtacgaccc cggccgccgt ggtgtacgcg
18661   ggcccgcgga gaggaaatcc cccaagatgg tcagtgttgt cgcggagtt ccagaaccac
18721   actcccgcct ggttccaggc gactgcgtgg gtgtagacgc cctcgagggc caggcacagt
```

Sequence Listing

```
18781  gggtgccgca gccggaggcc gttggcccta agcacggctc ccacggccgt ctcgatggcc
18841  cgccgggcgt cctcgatcac cccggaagcc gcatccgcgt cttggggtc cacgttaaag
18901  acaccccaga acgcacccc atcgccccg cagaccgcga acttcaccga gctggccgtc
18961  tcctcgatct gcaggcagac ggcggccatt accccaccca ggagctgccg cagcgcaggg
19021  caggcgtcgc acgtgtccgg gaccaggcgc tccaagacgg ccccggccca gggctctgag
19081  ggagcggcca ccaccagcgc gtccagtctt gctaggcccg tccggccgtg ggggtccgcc
19141  agcccgctcc ccccgaggtc ggccagggcc gccaggagct gggcgcgaag tccggggaag
19201  caaaaccgcg ccgtccagac gggcccgacg gccgcgggcg ggtctaacag ttggatgatt
19261  ttagtggcgg gatgccaccg cgccaccgcc tcccgcaccg cgggcaggag gcatccggct
19321  gccgccgagg ccacgccggg ccaggctcgc ggggggagga cgaccctggc ccccaccgcg
19381  ggccaggccc ccaggagcgc ggcgtaagcg gccgcggccc cgcgcaccag gtcccgtgcc
19441  gactcggccg tggccggcac ggtgaacgtg ggccaaccg gaaaccccag gacggcaaag
19501  tacgggacgg gtcccccccg gacctcaaac tcgggcccca gaaaggcaaa gacgggggcc
19561  agggccccgg gggcggcgtg gaccgtggta tgccactgcc ggaaaagggc gacgagcgcc
19621  ggcgcggaga acttctcgcc ggcgcttaca aagtagtcgt aatcgcgggg cagcagcacc
19681  cgtgccgtga ctcgttgcgg gtgcccgcgt gcgccaggc ccacctcgca cacctcgacc
19741  aggtccccga acgcgccctc cttcttgatc ggcggaaacg caagagtctg gtattcgcgc
19801  gcaaatagcg cggttccggt ggtgatgtta acgtcagcg aagcggcgga cgcgcactgg
19861  ggggtgtcgc gaatggccgc caggcgcgcc cacgccagcc gcgcgtcggg atgctcggca
19921  acgcgcgccg ccagggccat agggtcgatg tcaatgttgg cctccgcgac caggagagcg
19981  gcgcgagggg cggcgggcgg gccccacgac gctctctcaa ctttcaccac cagtcccgtg
20041  cgtgggtccg agccgatacg cagcggggcg aacagggcca ccggccggt ctggcgctcc
20101  agggccgcca ggacgcacgc gtacagcgcc cgccacagag tcgggttctc caggggctcc
20161  agcggggagg cggccggcgt cgtcgcggcg ccacgacggc ctggacggag
20221  acgtccgcgg agccgtagaa atcccgcagc tccgtcgcgg tgacggagac ctccgcaaag
20281  cgcgcgcgac cctcccctgc ggcgttgcga catacaaaat acaccagggc gtggaagtac
20341  tcgcgagcgc ggggggggcag ccataccgcg taaagggtaa tggcgctgac gctctcctcc
20401  acccacacga tatctgcggt gtccatcgca cggcccctaa ggatcacgag cggtctgtgg
20461  gtcccatgct gccgtgcctg gccgggcccg gtgggtcgcg gaaaccggtg acgggggggg
20521  ggcggttttt ggggttgggg tgggggtggg aaacggcccg ggtccggggg ccaacttggc
20581  ccctcggtgc gttccggcaa cagcgccgcc ggtccgcgga cgaccacgta ccgaacgagt
20641  gcggtcccga gacttatagg gtgctaaagt tcaccgcccc ctgcatcatg ggccaggcct
20701  cggtggggag ctccgacagc gccgcctcca ggatgatgtc agcgttgggg ttggcgctgg
20761  atgagtgcgt gcgcaaacag cgccccacg caggcacgcg tagcttgaag cgcgcgcccg
20821  caaactcccg cttgtgggcc ataagcaggg cgtacagctg cctgtgggtc cggcaggcgc
20881  tgtggtcgat gtggtgggcg tccaacaacc ccacgattgt ctgtttggtg aggtttttaa
20941  cgcgcccgc cccggaaac gtctgcgtgc ttttggccat ctgcacgcca aacagttcgc
21001  cccagattat cttgaacagc gccaccgcgt ggtccgctc gctaacggac ccgcgcgggg
21061  gacagccgct tagggcgtcg gcgacgcgct tgacggcttc ctccgagagc agaagtccgt
21121  cggttacgtt acagtggccc agttcgaaca ccagctgcat gtagcggtcg tagtgggggg
21181  tcagtaggtc cagcacgtca tcggggccga aggtcctccc agatcccccg gccgccgagt
21241  cccaatgcag gcgcgcggcc atggtgctgc acaggcacaa cagctcccag acggggggtta
21301  cgttcagggt gggggggcagg gccacgagct ccagctctcc ggtgacgttg atcgtgggga
21361  tgacgcccgt ggcgtagtgg tcatagatcc gccgaaatat ggcgctgctg cgggtggcca
21421  tgggaacgcg gagacaggcc tccagcaacg ccaggtaaat aaaccgcgtg cgtcccatca
21481  ggctgttgag gttgcgcatg agcgcgacaa tttccgccgg cgcgacatcg gaccggaggt
21541  attttttcgac gaaaagaccc acctcctccg tctcggcggc ctgggccggc agcgacgcct
21601  cgggatcccg gcaccgcagc tcccgtagat cgcgctgggc cctgagggcg tcgaaatgta
21661  cgccccgcaa aaacagacag aagtcctttg gggtcagggt atcgtcgtgt ccccagaagc
21721  gcacgcgtat gcagtttagg gtcagcagca tgtgaaggat gttaaggctg tccgagagac
21781  acgccagcgt gcatctctca aagtagtgtt tgtaacgaaa tttgttgtag atgcgcgacc
21841  cccgccccag cgacgtgtcg catgccgacg cgtcacagcg ccccttgaac cggcgacaca
21901  gcaggtttgt gacctgggag aactgcgcgg gccactggcc gcaggaactg accacgtgat
21961  taaggagcat gggcgtaaag acgggctccg agcgcgcccc ggagccgtcc atgtaaatca
22021  gtagctcccc cttgcggagg gtcgcaccc gtcccaggga ctggtacacg gacaccatgt
22081  ccggtccgta gttcatgggt tttacgtagg cgaacatgcc atcaaagtgc aggggatcga
22141  agctgaggcc cacggttacg accgtcgtgt atataaccac gcggtattgg ccccacgtgg
22201  tcacgtcccc gagggggggtg agcgagtgaa gcaacagcac gcggtccgta aactgacggc
22261  agaaccgggc cacgatctcc gcgaaggaga ccgtcgacga aaaaatgcag atgttatcgc
22321  ccccgccaag gcgcgcttcc agctccccaa agaacgtggc ccccgggcg tccggagagg
22381  cgtccggaga cgggccgctc ggcggcccgg gcgggcgcag ggcagcctgc aggagctcgg
22441  tccccagacg cgggagaaac aggcaccggc ggccccattc ggcaaatcc gctactcgt
22501  cgaccaccac atgcacgttt ttttcgcccc ggagaccgca caggaagtcc accaactgcg
22561  cgttggcggt tgcgtccatg gcgatgatcc ggagcaggt gcgcagcagg cgtagcatta
22621  acgcatccac gcggcccagt tgctgcatcg ttggcgaata gagctggccc agcgtcgaca
22681  taacctcgtc cagaacgagg acgtcgtagt tgttcagaag gttggggccc acgcgatgaa
22741  ggcttttccac ctggacgata agtcggtgga agggggcgtc gttcataatg taattggtgg
22801  atgagaagta ggtgacaaag tcgaccaggc ctgactcagc gaaccgcgtc gccagggtct
22861  gggtaaaact ccgacgacag gagacgacga gcacactcgt gtccggagag tggatcgctt
22921  cccgcagcca gcggatcagc gcggtagttt ttcccgaccc cattggcgcg ggaccacag
22981  tcacgcacct ggccgtcggg gcgctcgcgt tggggaaggt gacgggtccg tgctgctgcc
23041  gctcgatcgt tgttttcggg tgaaccccgg gcacccattc ggcaaatcc ccccgtaca
23101  acatccgcgc tagcgatacg ctcgacgtgt actgttcgca ctcgtcgtcc ccaatgggac
23161  gccggccccc cagaggatct cccgactccg cgccccccac gaaaggcatg accggggcgc
23221  ggacgcgtg gtgggtctgg tgtgtgcagg tggcgacgtt tgtggtctct gcggtctgcg
23281  tcacggggct cctcgtcctg gcctctgtgt tccgggcacg gtttcctgc tttacgcca
23341  cggcgagctc ttatgccggg gtgaactcca cggccgaggt gcgcggggt gtagccgtgc
```

Sequence Listing

```
23401  ccctcaggtt ggacacgcag agccttgtgg gcacttatgt aatcacggcc gtgttgttgt
23461  tggccgcggc cgtgtatgcc gtggtcggcg ccgtgacctc ccgctacgac cgcgccctgg
23521  acgcggggcg ccgtctggct gcggcccgca tggccatgcc gcacgccacg ctgatcgccg
23581  gaaacgtctg ctcttggttg ctgcagatca ccgtcctgtt gctggccat cgcaccagcc
23641  agctggccca cctggtttac gtcctgcact ttgcgtgtct ggtgtatttt gcggcccatt
23701  tttgcaccag gggggtcctg agcgggacgt atctgcgtca ggtgcacggc ctgatggagc
23761  cggccccgac tcatcatcgc cgtcgttggcc cggctcgagc cgtgctgaca aacgccttgc
23821  tgttgggcgt cttcctgtgc acggccgacg ccgcggtatc cctgaatacc atcgccgcgt
23881  tcaactttaa ttttttcggcc ccgggcatgc tcatatgcct gaccgtgctg ttcgcccttc
23941  tcgtcgtatc gctgttgttg gtggtcgagg gggtgttgtg tcactacgtg cgcgtgttgg
24001  tgggccccca cctgggggcc gtggccgcca cgggcatcgt cggcctggca tgcgagcact
24061  attacaccaa cggctactac gttgtggaga cgcagtggcc ggggcccag acgggagtcc
24121  gcgtcgccct cgccctggtc gccgcctttg ccctcggcat ggccgtgctc cgctgcaccc
24181  gcgcctatct gtatcacagg cggcaccaca ccaaattttt tatgcgcatg cgcgacacgc
24241  gacaccgcgc acattccgcc ctcaagcgcg tacgcagttc catgcgcgga tcgcgagacg
24301  gccgccacag gcccgcaccc ggcagcccgc ccgggattcc cgaatatgcg gaagaccccct
24361  acgcgatctc atacggcggc cagctcgacc ggtacggaga ttccgacggg gagccgattt
24421  acgacgaggt ggcggacgac caaaccgacg tattgtacgc caagatacaa caccegcggc
24481  acctgcccga cgacgagccc atctatgaca ccgttggggg gtacgacccc gagcccgccg
24541  aggaccccgt gtacagccga gtccgccgtc ggtagctgtt tggttccgtt ttaataaacc
24601  gtttgtgttt aacccgaccg tggtgtatgt ctggtgtgtg gcgtccgatc ccgttactat
24661  caccgttccc cccaaacccc ggcgattgtg ggttttttta aaacgcacac gcgtgcgacc
24721  gtatacagaa cattgttgtt ttttattcgc tatcggacat gggggtggaa aactgggtgg
24781  cggggcaggc gcctccgggg gttcgccggt gagtgtggcc cgagggggga tccgacgaac
24841  gcaggcgctg tctccccggg gcccgcgtaa ccccgcgcat atccggggc acgtagaaat
24901  taccttcctc ttcggactcg atatccacga cgtcaaagtc gtgggcggtc agcgagacga
24961  cctccccgtc gtcggtgatg aggacgttgt tcggcagca gcagggccgg gtcccggaga
25021  acgagaggcc catagctcgg cgagcgtgtc gtcgaacgcc aggccgctgc ttcgctgtat
25081  ggccttatag atctccggat cgatgcggac gggggtaatg atcagggcga tcggaacggc
25141  ctggttcggg agaatggacg ccttgctggg tcctgcggcc ccgagagccc cggcgccgtc
25201  ctccaggcgg aacgttacgc cctcctccgc gctagtgcgg tgcctgccga taaacgtcac
25261  cagatgcggg tggggggggc agtcggggaa gtggctgtcg agcacgtagc cctgcaccaa
25321  gatctgctta aagttcgggt gacggggggtt cgcgaagacg ggctcggcgc gtaccagatc
25381  cccggagctc caggacacgg gggagatggt gtggcgtccg aggtcggggg cgccaaacag
25441  aagcacctcc gagacaacgc cgctatttaa ctccaccaag gcccgatccg cggcggagca
25501  ccgccttttt tcgcccgagg cgtgggcctc tgaccaggcc tggtcttgcg tgacgagagc
25561  ctcctccggg ccggggacgc gcccgggcgc gaagtatccgc acgctgggct tcgggatcga
25621  ccggataaat gcccggaacg cctccgggga ccgtgtgcc atcaagtcct cgtacgcgga
25681  ggccgtgggg tcgctggggt ccatgggtc gaaagcgtac ttggcccggc atttgacctc
25741  gtaaaaggcc aggggggtct tggggactgg ggcaagtag ccgtgaatgt cccgaggaca
25801  gacgagaata tccagggacg ccccgaccat ccccgtcctga cctccatga ggacccaca
25861  cgtatgcacg ttctcttcgg cgaggtcgcc gggttcgtga aagataaagc gccgcgtgtc
25921  ggcgccggcc tcgccgcgt cgtccgcgcg gcccacgcag tagcgaaaca gcaggcttcg
25981  ggccgtcggc tcgttcaccc gcccgaacat caccgccgaa gactgtacat ccggccgcag
26041  gctggcgttg tgcttcagcc actgggggcga gaaacacgga cccctgggggc cccagcggag
26101  ggtggatgcg gtcgtgaggc cccgccggag cagggcccat agctggcagt cggcctggtt
26161  ttgcgtggcc gcctcgtaaa acccatgag ggcccgggc gccacgcgt ccgcggcggc
26221  cgggggcccg cggcgcgtca ggcgccatag tgccggccg agtccgcggt ccaccatacc
26281  cgcctcctcg aggaccacgg ccagggaaca cagataatcc aggcgggccc agaggggacc
26341  gatggccaga gggcgcggac gccgcgcaca caacccgcgc aggtgggcgct cgaacgtctc
26401  ggctagtata tgggagggca gcgcgttggg gatcaccgac gccgaccaca tagagtcaag
26461  gtccggggag tcgggatcgg cgtccgggtc gcgggcgtgg gtgccccag gagatagcgg
26521  aatgtctggg gtcggaggcc ctgaggcgtc agaaagtgcc ggcgacgcgg cccgggggctt
26581  ttcgtctgcg gtgtcggtgg cgtgctgatc acgtggggggg ttaacgggcg aatgggagct
26641  cgggtccaca gctgacgtcg tctggggtgg gggggcagg ggacggaagg tggttgttag
26701  cggaagactg ttagggcggg ggcgcttggg ggggctgtcg gggccacgag gggtgtcctc
26761  ggccagggcc caggaacgct tagtcacggt gcgtcccggc ggacatgctg ggcctcccgt
26821  ggactccatt tccgagacga cgtggggggga cggtggttg agcgcgccgc cgggtgaacg
26881  ctgattctca cgacagcgcg tgccgcgcgc acgggttggt gtgacacagg cgggacacca
26941  gcaccaggag aggcttaagc tcggaggca cgccaccga cgacagtatc gccttgtgtg
27001  tgtgctggta atttatacac cgatccgtaa acgcgcgccg aatcttggga ttgcggaggt
27061  ggcgccggat gccctctggg acgtcatacg ccaggccgtg cgtgtcctgc tccgccgagt
27121  tgacaaacag ggctgggtgc agcacgcggc gataggcgag cagggccagg gcgaagtcca
27181  gcgacagctg gttgttgaaa tactggtaac cggggaaccg ggtcacgggt acgcccaggc
27241  tcggggcgac gtacacgcta accaccaact ccagcagcgt ctggccaagg gcgtacaggt
27301  caaccgctaa cccgacgtcg tgcttcaggc ggtggttggt aaattcggcc cgttcgttgt
27361  taaggtattt caccaacagc tccgggggct ggttatacc gtgacccacc agggtgtgaa
27421  agttggctgt ggttagggcg gtgggcatgc caaacatccg ggggacttg aggtccggct
27481  cctggaggca aaactgcccc cgggcgatcg tggagttgga gttgagggtg acgaggctaa
27541  agtcggcgag gacggccgc cggagcgaga cggcgtccga ccgcagcatg acgaggatgt
27601  tggcgcactt gatatccagg tggctgatcc cgcaggtggt gtttaaaaac acaacggcgc
27661  ggccagctc cgtgaagcac tggtggaggg ccgagggttt gttgtgcgca
27721  gggacgccag ttggccgata tacttaccga ggtccatgtc gtacgcgggg aacactatct
27781  gtcgttgttg cagcgagaac ccgaggggcg cgatgaagcc gcggatgttg gggtgcggc
27841  cggcgcgtag agcgcactcc ccgaccaaca gggtcgcgat gagctcaacg gcaaaccact
27901  ccttttcctt tatggtctta acggcaagct tatgttcgcg aatcagttgg acgtcgccgt
27961  atccccagaa cccccgaag cttcgggccc cggggatctc gagggtcgtg tagtgtaggg
```

-continued

Sequence Listing

```
28021  cggggttgat ggcgaacacg gggctgcata gcttgcggat gcgcgtgagg gtaaggatgt
28081  gcgaggggga cgagggggt gcggttaacg ccgcctggga tctgcgcagg ggcgggcggt
28141  tcagtttggc cgccgtaccg ggcgtctcgg gggacgcgg gcgatgagac gagcggctca
28201  ttcgccatcg ggatagtccc gcgcgaagcc gctcgcggag gccggatcgg tggcgggacc
28261  cgtgggagga gcgggagccg gcggcgtcct ggagagaggg gccgctgggg cgcccggagg
28321  ccccgtgtgg gttggagtgt atgtaggatg cgagccaatc cttgaaggac tgttggcgtg
28381  caccttgggg gctgaggtta gctgccacat gaccagcagg tcgctgtctg cgggactcat
28441  ccatccttcg gccaggtcgc cgtcttccca cagagaagcg ttggtcgctg cttcctcgag
28501  ttgctcctcc tggtccgcaa gacgatcgtc cacggcgtcc aggcgctcac caagcgccgg
28561  atcgaggtac cgtcggtgtg cggttagaaa gtcacgacgc gccgcttgct cctccacgcg
28621  aattttaaca caggtcgcgc gctgtcgcat catctctaag cgcgcgcggg actttagccg
28681  cgcctccaat tccaagtggg ccgcctttgc agccataaag gcgccaacaa accgaggatc
28741  ttgggtgctg acgccctccc ggtgcagctg cagggtctgg tccttgtaaa tctcggctcg
28801  gaggtgcgtc tcggccaggc gtcggcgcag ggccgcgtgg gcggcatctc ggtccattcc
28861  gccaccctgc gggcgacccg ggggtgctc tgatagtctc gcgtgcccaa ggcccgtgat
28921  cggggtactt cgccgccgcg acccgccacc cggtgtgcgc gatgtttggt cagcagctgg
28981  cgtccgacgt ccagcagtac ctggagcgcc tcgagaaaca gaggcaactt aaggtgggcg
29041  cggacgaggc gtcggcgggc ctcacaatgg gcggcgatgc cctacgagtg ccctttttag
29101  atttcgcgac cgcgacccc aagcgccacc agaccgtggt cccgggcgtc gggacgctcc
29161  acgactgctg cgagcactcg ccgctcttct gcggggctgc ctgtttaata
29221  gcctggtgcc ggcgcaacta aaggggcgtg atttcggggg cgaccacacg gccaagctgg
29281  aattcctggc ccccgagttg gtacgggcgg tggcgcgact gcggtttaag gagtgcgcgc
29341  cggcggacgt ggtgcctcag cgtaacgcct actatagcgt tctgaacacg tttcaggccc
29401  tccaccgctc cgaagccttt cgccagctgg tgcactttgt gcgggacttt gcccagctgc
29461  ttaaaacctc cttccggggcc tccagcctca cggagaccac gggccccca aaaaaacggg
29521  ccaaggtgga cgtggccacc cacggccgga cgtacggcac gctggagctg ttccaaaaaa
29581  tgatccttat gcacgccacc tactttctgg ccgccgtgct cctcggggac cacgcggagc
29641  aggtcaacac gttcctgcgt ctcgtgtttg agatccccct gtttagcgac gcggccgtgc
29701  gccacttccg ccagcgcgcc accgtgtttc tcgtccccg gcgccacggc aagacctggt
29761  ttctagtgcc cctcatcgcg ctgtcgctgg cctcctttcg ggggatcaag atcggctaca
29821  cggcgcacat ccgcaaggcg accgagccgg tgtttgagga gatcgacgcc tgcctgcggg
29881  gctggttcgg ttcggcccga gtggaccacg ttaaagggga aaccatctcc ttctcgtttc
29941  cggacgggtc gcgcagtacc atcgtgtttg cctccagcca caacacaaac gtaagtcctc
30001  tttctttcg catggctctc caaggggcc ccgggtcgac ccgacccaca cccacccacc
30061  cacccacata cacacacaac cagacgcggg aggaaagtct gccccgtggg cactgatttt
30121  tattcgggat cgcttgagga ggcccgggca acgcccggg caacggtggg gcaactcgta
30181  gcaaataggc gactgatgta cgaagagaag acacacaggc gccacccggc gctggtcggg
30241  gggatgttgt ccgcgccgca ccgtccccg acgaccttct ccagacggtc cgtgatgcaa
30301  ggacggcggg gggcctgcag cagggtgacc gtatccacgg gatgccaaa gagaagcgga
30361  cacaggctag catccccctg gaccgccagg gtacactggg ccatcttggc ccacagacac
30421  ggggcgacgc agggacagga ctccgttacg acggaggaga gccacagtgc gttggcgaa
30481  tcgatgtggg gcggcggggc gcaggactcg cagccccccg ggtggttggt gatcctggcc
30541  aggagccatc ccagatgcgg ggccctgctt cccggtggac agagcgaccc caggtcgctg
30601  tccatggccc agcagtagat ctggccgctg ggaggtgcc accaggcccc cgggcccaag
30661  gcgcaacacg cgcccggctc cgggggggtc ttcgcgggga ccagatacgc gccatccagc
30721  tcgccgacca ctggctcctc cgcgagctgt tcgtggttg ggtcgggggt ttcctccggg
30781  ggggtggccg cccgtatgcg ggcgaacgtg agggtgcaca ggagcgggt caggggtgc
30841  gtcacgctcc ggaggtggac gatcgcgcag tagcggcgct cgcggttaaa gaaaaagagg
30901  gcaaagaagg tgttcggggg caaccgcagc gccttgggc gcgtcagata cagaaaaatc
30961  tcgcagaaga gggcgcgccc ggggtctggg ttaggaaggg ccacctgaca cagaggctcg
31021  gtgaggaccg ttagacaccg aaagatcttg agccgctcgt ccgcccgaac gacgcgccac
31081  acaaagacgg agttgacaat gcgcgcgata gagtcgacgt ccgtccccag gtcgtcgact
31141  ctgtcgcgcg tgccgcgagc tccggcccgg gaatccggcc ggggcaaggt ccccggggga
31201  ccaggcggcg ccaggggccg ccggggtccc agctgcgcca tgccggggc gggggaggg
31261  caaacccccag aggcgggggc caacggcgcg gggaggagtg ggtgggcgag gtggccgggg
31321  gaaggcgccc gctagcgaga acggccgttc ccggacgaca ccttgcgaca aaacctaagg
31381  acagcggccc gcgcgacggg gtccgagagg ctaaggtagg ccgcgatgtt aatggtgaac
31441  gcaaagccgc cgggaaagac aactatgcca cagaggcggc gattaaaccc caggcagagg
31501  taggcgtagc ttttccccgg caggtattgc tcgcagaccc tgcgtgggc tgtggagggg
31561  acggcctcca tgaagcgaca tttactctgc tcgcgtttac tgacgtcacc atccatcgcc
31621  acggcgattg gacgattgtt aagccgcagc gtgtctccgc ttgtgctgta gtagtcaaaa
31681  acgtaatggc cgtcggagtc ggcaaagcgg gccgggaggt cgtgccgag cgggacgacc
31741  cgccgccccc gaccgcccg tcccccagg tgtgccagga cggcagggc atacgcggtg
31801  tgaaaaaagg cgtcggggc ggtccctcg acggcgcgca tcaggttctc gaggagaatg
31861  gggaagcgcc tggtcacctc ccccagccac gcgcgttggt cggggccaaa gtcatagcgc
31921  aggcgctgtg agattcgagg gccgccctga agcgcggccc ggatggcctg gcccagggcc
31981  cggaggcacg ccagatgtat gcgcgcagta aaggcgacct cggcgggcgat gtcaaagggc
32041  gcaggacgg ggcgcgggtg gcgcagggc acctcgaccg cgggaaagcg gagcagcagc
32101  tccgcctgcc cagcgggaga cagctggtgg gggcgcacga cgcgttctgc ggcgcaggcc
32161  tcggtcaggg ccgtggccag cgccgaggac agcagcggag ggcgggcgcg tcgcccgccc
32221  cacgccacgg agttctcgta ggagacgacg acgaagcgct gcttggttcc gtagtggtgg
32281  cgcaggacca cggagataga ggcgcggctc caaccccagt cgtccgggc gccgccgtcc
32341  agggcttccc atccgcgatc caaccactcg accagcgacc gcggctttgc ggtaccaggg
32401  gtcagggtta gaacgtcgtt caggatgtcc tcgccccggg gcccgtgggg cactgggccc
32461  acaaagcggc cccgcctgg gggctccaga cccgccaaca ccgcatctgc gtcagccgcc
32521  cccatggcgc ccccgctgac ggcctggtga accagggcgc cctggcgag ccccgatgca
32581  acgccacagg ccgcacgccc ggtccgagcg cggaccgggt ggcggcgggt gacgtcctgc
```

-continued

Sequence Listing

```
32641  actgcccgct gaaccaacgc gaggatctcc tcgttctcct gcgcgatgga cacgtcctgg
32701  gccgcggtcg tgtcgccgcc gggggccgtc agctgctcct ccggggagat ggggggggtcg
32761  gacgcccga cgatgggcgg gtctgcgggc gcccccgcag ggggccggc caagggctgc
32821  ggacgcgggg acgcgctttc ccccagaccc atggacaggt gggccgcagc ctccttcgcg
32881  gccggcgggg cggcggcgcc aagcagagcg acgtagcggc acaaatgccg acagacgcgc
32941  atgatgcgcg tgctgtcggc cgcgtagcgc gtgttggggg ggacgagctc gtcgtaacta
33001  aacagaatca cgcgggcaca gctcgccccc gagcccacg caaggcgcag cgccgccacg
33061  gcgtacgggt catagacgcc ctgtgcgtca cacaccacgg gcaaggagac gaacaacccc
33121  ccggcgctgg acgcacgcgg aaggaggcca gggtgtgccg gcacgacggg ggccagaagc
33181  tcccccaccg catccgcggg cacgtaggcg gcaaacgccg tgcaccacgg ggtacagtcg
33241  ccggtggcat gagcccgagt ctggatttcg acctggaagt ttgcggccgt cccgagtccg
33301  gggcggccgc gcatcagggc ggccagaggg attcccgcgg ccgccaggca ctcgctggat
33361  atgatgacgt gaaccaaaga cgagggccga cccgggacgg ggccgagatc gtactggacc
33421  tcgttggcca agtgcgcgtt catggttcgg gggtgggtgt gggtgtgtag gcgatgcggg
33481  tcccccgagt ccgcgggaag ggcgcggggtt tggcgcgcgt atgcgtattc gccaacggag
33541  gcgtgcgtgc ttatgccgag cgcgtttctt ctgtctccag ggaatccgag gccaggactt
33601  taacctgctc tttgtcgacg aggccaactt tattcgcccg gatgcggtcc agacgattat
33661  gggctttctc aaccaggcca actgcaagat tatcttcgtg tcgtccacca acaccgggaa
33721  ggccagtacg agcttttttgt acaacctccg cggggccgcc gacgagcttc tcaacgtggt
33781  gacctatata tgcgatgatc acatgccgcg ggtggtgacg cacacaaacg ccacggcctg
33841  ttcttgttat atcctcaaca agcccgttttt catcacgatg gacggggcgg ttcgccggac
33901  cgccgatttg ttttctggccg attccttcat gcaggagatc atcggggggcc aggccaggga
33961  gaccggcgac gaccggcccg ttctgaccaa gtctgcgggg gagcggtttc tgttgtaccg
34021  cccctcgacc accaccaaca gcggcctcat ggccccccgt ttgtacgtgt agcgtggatcc
34081  cgccgttcacg gccaacaccc gagcctccgg gaccgccgtc gctgtcgtcg ggcggtaccg
34141  cgacgattat atcatcttcg ccctggagca ctttttttctc cgcgcgctca cgggctcggc
34201  ccccgccgac atcgcccgct gcgtcgtcca cagtctgacg caggtcctgg ccctgcatcc
34261  cggggcgttt cgcggcgtcc gggtggcggt cgagggaaat agcagccagg actcggccgt
34321  cgccatcgcc acgcacgtgc acacagagat gcaccgccta ctggcctcgg aggggggccga
34381  cgcgggctcg ggcccgagc ttctcttcta ccactgcgag cctcccggga gcgcggtgct
34441  gtaccccttt ttcctgctca acaaacagaa gacgcccgcc tttgaacact ttattaaaaa
34501  gttttaactcc ggggggcgtca tggcctccca ggagatcgtt tccgcgacgg tgcgcctgca
34561  gaccgacccg gtcgagtatc tgctcgagca gctgaataac ctcaccgaaa ccgtctcccc
34621  caacacggac gtccgtacgt attccgaaaa acggaacggc gcctcggatg accttatggt
34681  cgccgtcatt atggccatct accttgcggc ccaggccgga cctccgcaca cattcgctcc
34741  catcacacgc gtttcgtgag cgcccaataa acacacccag gtatgctacg cacgaccacg
34801  gtgtcgcctg ttaagggggg gggaaggggg tgttggcggg aagcgtggga acacggggga
34861  ttctctcacg accggcacca gtaccacccc cctgtgaaca cagaaacccc aacccaaatc
34921  ccataaacat acgacacaca ggcatatttt ggaatttctt aggttttttat ttattaggt
34981  atgctgggggt ttctccctgg atgcccaccc ccaccccccc ccgtgggtct agccggggcct
35041  tagggatagc gtataacggg ggccatgtct ccggaccgca caacggccgc gccgtcaaag
35101  gtgcacaccc gaaccacggg agccagggcc aaggtgtctc ctagttggcc cgcgtgggtc
35161  agccaggcga cgagcgcctc gtagagcggc agccttcgct ctccatcctg catcagggcc
35221  ggggcttcgg ggtgaatgag ctgggcggcc tcccgcgtga cactctgcat ctgcaggaga
35281  gcgttcacgt acccgtcctg ggcacttagc gcaaagagcc ggggggattag cgtaaggatg
35341  atggtggttc cctccgtgat cgagtaaacc atgttaagga ccagcgatcg cagctcggcg
35401  tttacgggggc cgagttgttg gacgtccgcc agcagcgaga ggcgactccc gttgtagtac
35461  agcacgttga ggtctggcag ccctccgggg tttctgggggc tgggggttcag gtcccggatg
35521  ccccctggcca cgagccgcgc cacgatttcg cgcgccaggc gcgatggaag cggaacggga
35581  aaccgcaacg tgaggtccag cgaatccagg cgcacgtccg tcgcttggcc ctcgaacacg
35641  ggcgggacga ggctgatggg gtccccgtta cagagatcta cgggggggaggt gttgcgaagg
35701  ttaacggtgc cggcgtgggt gaggcccacg tccaggggggc aggcgacgat tcgcgtggga
35761  agcaccgggg tgatgaccgc ggggaagcgc cttcggtacg ccagcaacag ccccaaacgtg
35821  tcgggactga cgcctccgga gacgaaggat tcgtgcgcca cgtcggccag cgtcagttgc
35881  cggcgatgg tcggcaggaa taccacccgc ccttcgcagc gctgcagcgc cgccgcatcg
35941  gggcgcgaga tgcccgaggg tatcgcgatg tcagtttcaa agccgtccgc cagcatggcg
36001  ccgatccacg cggcagggag tgcagtggtg gttcgggtgg cgggaggagc gcggtggggg
36061  tcagcggcgt agcagacacg ggcgaccaac ctcgcataggg acggggggtg ggtcttaggg
36121  ggttgggagg cgacagggac cccagagcat gcgcggggag gtctgtcggg cccagacgca
36181  ccgagagcga atccgtccat ggagtcccgg cctgggtttt atgggggcccg gccctcggaa
36241  tcgcggcttg tcggcgggga caaaggggggc ggggctaggg ggcttgcgga aacagaagac
36301  gtgtgggata aaagaatcga actacccccaa ggaagggcgg ggcgttttat tacagacgca
36361  gtcccttgag cggggatgcg tcatagacga gatactcgcg gaagtgggtc tcccgcgcgt
36421  gggcttcccc gttgcggcg ctgcggagga gggcgggtc gctggcgcag gtgagcgggt
36481  aggcctcctg aaacaggcca cacgggtcct ccacgagttc gcggcacccc gggggggcgct
36541  taaactgtac gtcgctcggc gcggtggccg tggacaccgc cgaaccgtc tccacgatca
36601  ggcgctccag gcagcgatgt ttggcggcga tgtccggcca cgtaaagaac ttaaagcagg
36661  ggctgagcac cggcgaggcc ccgttgaggt ggtaggcccc gttatagagc aggtccccgt
36721  acgaaaatcg ctgcgacgcc cacgggttgg ccgtgccgc gaaggccgg gacgggtcgc
36781  tctggccgtg gtcgtacatg agggcggtga catccccctc cttgtccccc gcgtaaacgc
36841  cccccggcggc gcgtcccccgg gggttgcagg gccggcggaa gtagttgacg tcggtcgaca
36901  cggggggtggc gataaactca cacacggcgt cctggccgtg ctcatccct gcgcgccgcg
36961  gcacctgggc gcacccgaac acgggggacgg gctgggccgg cccaggcgg ttcccgcca
37021  cgaccgcgtt ccgcaggtac acggctgccg cgttgtccag tagaggggga gccccgcggc
37081  ccaggtaaaa gttttgggga aggttcccca tgtcggtgac gggggttgcgg acggttgccg
37141  tggccacgac ggcggtgtag cccacgccca ggtccacgtt cccgcggggc tgggtgagcg
37201  tgaagtttac ccccccgcca gtttcatgcc gggccacctg gagctggccc aggaagtacg
```

```
37261  cctccgacgc gcgctccgag aacagcacgt tctcagtcac aaagcggtcc tgtcggacga
37321  cggtgaaccc aaacccggga tggaggcccg tcttgagctg atgatgcaag gccacgggac
37381  tgatcttgaa gtaccccgcc atgagcgcgt aggtcacgc gttctccccg gccgcgctct
37441  cgcggacgtg ctgcacgacg ggctgtcgga tcgacgaaaa gtagttggcc cccagagccg
37501  gggggaccag ggggacctgc cgcgacaggt cgcgcagggc cgggggggaaa ttgggcgcgt
37561  tcgccacgtg gtcggccccg gcgaacagcg cgtggacggg gaggggggtaa aaatagtcgc
37621  cattttggat ggtatggtcc agatgctggg gggccatcag caggattccg gcgtgcaacg
37681  ccccgtcgaa tatgcgcatg ttggtggtgg acgcggtgtt ggcgcccgcg tcgggcgccg
37741  ccgagcagag cagcgccgtt gtgcgttcgg ccatgttgtg ggccagcacc tgcagcgtga
37801  gcatggcggg cccgtccact accacgcgcc cgttgtgaaa catgcgcttg accgtgttgg
37861  ccaccagatt ggccgggtgc aggggggtgcg cggggtccgt cacggggtcg ctggggcaat
37921  cctcgccggg ggtgatctcc gggaccacca tgttctgcag ggtggcgtat acgcggtcga
37981  agcgaacccc cgcggtgcag cagcggcccc gcgagaaggc gggcaccatc acgtagtagt
38041  aaatcttgtg gtgcacggtc cagtccgccc cccggtgcgg ccggtcgtcc gcggcgtccg
38101  cggctcgggc ctgggtgttg tgcagcagct ggccgtcgtt gcggttgaag tccgcggtcg
38161  ccacgttaca cgccgctgcg tacacggggt cgtggccccc cgcgctaacc cggcagtcgc
38221  gatggcggtc cagggccgcg cgccgcatca gggcgtcgca gtcccacacg aggggtggca
38281  gcagcgccgg gtctcgcatt aggtgattca gttcggcttg cgcctgcccg cccagttccg
38341  ggccggtcag ggtaaagtca tcaaccagct gggccagggc ctcgacgtgc gccaccaggt
38401  cccggtacac ggccatgcac tcctcgggaa ggtctccccc gaggtaggtc acgacgtacg
38461  agaccagcga gtagtcgttc acgaacgccg cgcaccgcgt gttgttccag tagctggtga
38521  tgcactggac cacgagccgg gccaggcgc agaagacgtg ctcgctgccg tgtatggcgg
38581  cctgcagcag gtaaaacacc gccgggtagt tgcggtcttc gaacgccccg cgaacggcgg
38641  cgatggtggc gggggccatg gcgtggcgtc ccacccccag ctccaggccc cggggcgtccc
38701  ggaacgccgc cggacatagc gccaggggca agttgccgtt caccacgcgc caggtggcct
38761  ggatctcccc cgggccggcc gggggaacgt ccccccccgg cagctccacg tcggccaccc
38821  ccacgaagaa gtcgaacgcg gggtgcagct caagagccag gttggcgttg tcgggctgca
38881  taaactgctc cggggtcatc tggccttccg cgacccatcg gacccgcccg tgggccaggc
38941  gctgccccca ggcgttcaaa aacagctgct gcatgtctgc ggcggggccg gccggggccg
39001  ccacgtacgc cccgtacgga ttggcggctt cgacggggtc gcggttaagg cccccgaccg
39061  ccgcgtcaac gttcatcagc gaagggtggc acacggtccc gatcgcgtgt tccagagaca
39121  ggcgcagcac ctggcggtcc ttcccccaaa aaaacagctg gcgggcggg aaggcgcggg
39181  gatccgggtg gccgggggcg gggactaggt ccccggcgtg cgcggcaaac cgttccatga
39241  ccggattgaa caggcccagg ggcaggacga acgtcaggtc catggcgccc accaggggggt
39301  agggaacgtt ggtggcgcg tagatgcgct tctccagggc ctccaaaaag atcagcttct
39361  cgccgatgga caccagatcc gcgcgcacgc gcgtcgtctg gggggcgctc tcgagctcgt
39421  ccagcgtctg ccggttcagg tcgagctgct cctcctgcat ctccagcagg tggcggccca
39481  cgtcgtccag acttcgcacg gccttgccca tcacgagccc cgtgaccagg ttggccccgt
39541  tcaggaccat ctcgccgtac gtcaccggca cgtcggcttc ggtgtcctcc actttcagga
39601  aggactgcag gaggcgctgt ttgatcgggg cggtggtgac gagcaccccg tcgaccggac
39661  gcccgcgcgt gtcggcatgc gtcagacggg gcacggccac ggagggctgg gtggccgtgg
39721  tgaggtccac gagccaggcc tcgacggcct cccggcggtg gcccgccttg cccaggaaaa
39781  agctcgtctc gcagaagctt cgctttagct cggcgaccag ggtcgcccgg gccaccctgg
39841  tggccaggcg gccgttgtcc aggtatcgtt gcatcggcaa caacaaagcc aggggcggcg
39901  ccttttccag cagcacgtgc agcatctggt cggccgtgcc gcgctcaaac gccccgagga
39961  cggcctggac gttgcgagcg agctgttgga tggcgcgcaa ctggcgatgc gcgctgatac
40021  ccgtcccgtc cagggcctcc ccgtgagca gggcgatggc ctcggtggcc aggctgaagg
40081  cggcgttcag ggcccggcgg tcgataatct tggtcatgta attgtgtgtg ggttgctcga
40141  tggggtgcgg gccgtcgcgg gcaatcagcg gctggtggac ctcgaactgt acgcgcccct
40201  cgttcatgta ggccagctcc ggaaacttgg tacacacgca cgccaccgac aacccgagct
40261  ccagaaagcg cacgagcgac agggtgttgc aatacgaccc caacagggcg tcgaactcga
40321  cgtcatacag gctgtttgca tcggagcgca cgcgggaaaa aaaatcgaac aggcgtcgat
40381  gcgacgccac ctcgatcgtg ctaaggaggg acccggtcgg caccatggcc gcggcatacc
40441  ggtatcccgg agggtcgcgg ttgggagcgg ccatggggcc gcgtggagat cggctgtctc
40501  tagcgatatt ggcccgggga ggctaagatc caccccaacg cccggccacc cgtgtacgtg
40561  cccgacggcc caaggtccac cgaaagacac gacgggcccg gacccaaaaa ggcgggggat
40621  gctgtgtgag aggccgggtg tcggtcgggg gggaaaggca ccgggagaag gctgcggcct
40681  cgttccagga gaaccagtg tccccaacag acccgggggac gtgggatcc aggccttata
40741  taccccccccc gccccacccc cgttagaacg cgacgggtgc attcaagatg gccctggtcc
40801  aaaagcgtgc caggaagaaa ttggcagagg cggcaaagct gtccgccgcc gccacccaca
40861  tcgaggcccc ggccgcgcag gctatcccca gggcccgtgt gcgcagggga tcggtgggcg
40921  gcagcatttg gttggtgggcg ataaagtgga aaagcccgtc gggactgaag gtctcgtggg
40981  cggcggcgaa caaggcacac agggccgtgc ctcccaaaaa cacggacatc cccaaaaaca
41041  cgggcgccga caacggcaga cgatccctct tgatgttaac gtacaggagg agcgcccgca
41101  ccgcccacgt aacgtagtag ccgacgatgg cggccaggat acaggccggc gccaccaccc
41161  ttccggtcag cccgtaatac atgcccgctg ccaccatctc caacggcttc aggaccaaaa
41221  acgaccaaag gaacagaatc acgcgctttg aaaagaccgg ctggctatgg ggcggaagac
41281  gcgagtatgc cgaactgaca aaaaagtcag aggtgccgta cgaggacaat gaaaactgtt
41341  cctccagtgg cagttctccc tcctccccc caaaggcggc ctcgtcgacc agatctcgat
41401  ccaccagagg aaggtcatcc cgcatggtca tggggtgtgc ggtggaggtg gggagaccga
41461  aaccgcaaag ggtcgcttac gtcagcagga tcccgagatc aaagacaccc gggttcttgc
41521  acaaaccacca cccggggttc atccgcggag gcgagtgttt tgataaggcc gttccgccgc
41581  ttgatataac cttttgatgtt gaccacaaaa cccggaattt acgcctacgc cccaatgccc
41641  acgcaagatg aggtaggtaa ccccccccccc gtgggtgtga cgttgcgttt agttcattgg
41701  aggccaaggg gaaatgggg tgggaggaa acggaaaacc cagtaggccg tgttgggaac
41761  acgcccgggg ttgtcctcaa aaggcagggt ccatactacg gaagccgtcg ttgtattcga
41821  gacctgcctg tgcgacgcac gtcggggttg cctgtgtccg gttcggcccc accgcgtgcg
```

```
41881  gcacgcacga ggacgagtcc gcgtgcttta ttggcgttcc aagcgttgcc ctccagtttc
41941  tgttgtcggt gttcccccat acccacgccc acatccaccg tagggggcct ctgggccgtg
42001  tcacgtcgcc gcccgcgatg gagcttagct acgccaccac catgcactac cgggacgttg
42061  tgttttacgt cacaacggac cgaaaccggg cctactttgt gtgcgggggg tgtgtttatt
42121  ccgtggggcg gccgtgtgcc tcgcagcccg gggagattgc caagtttggt ctggtcgttc
42181  gagggacagg cccagacgac cgcgtggtcg ccaactatgt acgaagcgag ctccgacaac
42241  gcggcctgca ggacgtgcgt cccattgggg aggacgaggt gtttctggac agcgtgtgtc
42301  ttctaaaccc gaacgtgagc tccgagctgg atgtgattaa cacgaacgac gtggaagtgc
42361  tggacgaatg tctgccgagc tactgcacct cgctgcgaac cagcccgggt gtgctaatat
42421  ccgggctgcg cgtcgggcg caggacagaa tcatcgagtt gtttgaacac caacgatag
42481  tcaacgtttc ctcgcacttt gtgtatacc cgtccccata cgtgttcgcc ctggcccagg
42541  cgcacctccc ccggctcccg agctcgctgg aggccctggt gagcggcctg tttgacggca
42601  tccccgcccc acgccagcca cttgacgccc acaacccgcg cacggatgtg gttatcacgg
42661  gccgccgcgc cccacgaccc atcgccgggt cggggggcggg gtcggggggc gcgggcgcca
42721  agcgggccac cgtcagcgag ttcgtgcaag tcaaacacat tgaccgcgtg ggccccgctg
42781  gcgtttcgcc ggcgcctccg ccaaacaaca ccgactcaag ttccctgctg cccggggccc
42841  aggattccgc cccgcccggc cccacgctaa gggagctgtg gtgggtgttt tatgccgcag
42901  accgggcgct ggaggagccc ccgcgccgact ctggcctcac ccgcgaggag gtacgtgccg
42961  tacgtgggtt ccgggagcag gcgtggaaac tgtttggctc cgcggggcc ccgcgggcgt
43021  ttatcgggc cgcgttgggc ctgagcccc tccaaaagct agccgtttac tactatatca
43081  tccaccgaga gaggcgcctg tccccttcc ccgcgctagt ccggctcgta ggccggtaca
43141  cacagcgcca cggcctgtac gtccctcggc ccgacgaccc agtcttggcc gatgccatca
43201  acgggctgtt tcgcgacgcg ctggcggccg aaccacagc cgagcagctc ctcatgttcg
43261  accttctccc ccaaaggac gtgccggtgg gaagcgacgt gcaggccgac agcaccgctc
43321  tgctgcgctt tatagaatcg caacgtctcg ccgtccccgg ggggtgatc tccccgagc
43381  acgtcgcgta ccttggtgcg ttcctgagcg tgctgtacgc tggccgcggg cgcatgtccg
43441  cagccacgca caccgcgcgg ctgacagggg tgacctccct ggtgctagcg gtgggtgacg
43501  tggaccgtct ttccgcgttt gaccgcggag cggcgggcgc ggccggccgc acgcgggccg
43561  ccgggtacct ggatgtgctt cttaccgttc gtctcgctcg ctcccaaac ggacagtctg
43621  tgtaacagac cccaataaac gtatgtcgct accacaccct tgtgtgtcaa tggacgcctc
43681  tccgggggg aagggaaaac aaagagggc tgggggagcg gcaccaccgg ggcctgaaca
43741  aacaaaccac agacacggtt acagttttatt cggtcgggcg gagaaacggc cgaagccacg
43801  ccccctttat tcgcgtctcc aaaaaaacgg gacacttgtc cggagaacct ttaggatgcc
43861  agcctgggcg gcggtaatca taaccacgcc cagcgcagag gcggccagaa acccgggcgc
43921  aattgcggcc acgggctgcg tgtcaaaggc tagcaaatga atgacggttc cgtttggaaa
43981  tagcaacaag gccgtggacg gcacgtcgct cgaaaacacg cttggggcgc cctccgtcgg
44041  ccggccgcg atttgctgct gtgtgttgtc cgtatccacc agcaacacag acatgacctc
44101  cccggccggg gtgtagcgca taaacacgg ccccacgagc cccaggtcgc gctggttttg
44161  ggtgcgcacc agccgcttgg actcgatatc ccgggtggag ccttcgcatg tcgcggtgag
44221  gtaggttagg aacagtgggc gtcggacgtc gacgccggtg agcttgtagc cgatccccg
44281  gggcagaggg gagtggtga cgacgtagct ggcgttgtgg gtgatgggta ccaggatccg
44341  tggctcgacg ttggcagact gccccccgca ccgatgtgag ggctcaggga cgaaggcgcg
44401  gatcagggcg ttgtagtgtg cccagcgcgt cagggtcgag gcgaggccgt gggtctgctg
44461  ggccaggact tcgaccgggg tctcggatcg ggtggcttga gccagcgcgt ccaggataaa
44521  cacgctctcg tctagatcaa agcgcaggga gccgcgcat ggcgaaaagt ggtccggaag
44581  ccaaaagagg gttttctggt ggtcggcccg ggccagcgcg gtccggaggt cggcgttggt
44641  cgctgcggcg acgtcggacg tacacagggc cgaggctatc agaaggctcc ggcgggcgcg
44701  ttcccgctgc accgccgagg ggacgcccg caagaacggc tgccggagga cagccgaggc
44761  gtaaaatagc gcccggtgga cgaccggggt ggtcagcacg cggcccccta gaaactcggc
44821  atacagggcg tcgatgagat gggctgcgct gggcgccact gcgtcgtacg ccgagggct
44881  atccagcacg aaggccagct gatagcccag cgcgtgtaat gccaagctct gttcgcgctc
44941  cagaatctcg gccaccaggt gctggagccg agcctctagc tgcaggcggg ccgtgggatc
45001  caagactgac acattaaaaa acacagaatc gcggcacag ccgcggccc cgcgggcggc
45061  caacccggca agcgcgcgcg agtgggccaa aaagctagc aggtcggaga ggcagaccgc
45121  gccgtttgcg tggcggcgt tcacgaaagc aaaacccgac gtcgcggagca gccccgttag
45181  gcgccagaag agaggggac gcgggccctg ctcggcgccc gcgtccccg agaaaaactc
45241  cgcgtatgcc cgcgacagga actgggcgta gttcgtgcc tcctcccggt agccgcccac
45301  gcggcggagg gcgtccagcg cggagccgtt gtcggcccgc gtcaggacc ctaggacaaa
45361  gacccgatac cggggccgc ccggggccc gggaagagcc ccgggggt tttcgtccgc
45421  ggggtccccg acccgatcta gcgtctggcc cgcggggacc accatcactt ccaccggagg
45481  gctgtcgtgc atggatatca cgagcccat gaattcccgc ccgtagcgcg cgcgcaccag
45541  cgcggcatcg cacccgaga ccagctcccc cgtcgtccag atgcccacgg gccacgtcga
45601  ggccgacggg gagaaataca cgtacctacc tggggatctc aacaggcccc gggtggccaa
45661  ccaggtcgtg gacgcgttgt gcaggtcgct gatgtccagc tccgtcgtcg ggtgccgccg
45721  ggccccaacc ggcggtcggg gggcggtgt atcacgcggc ccgctcgggt ggctcgccgt
45781  cgccacgttg tctcccccgcg ggaacgtcag ggcctcgggg tcagggacgg ccgaaaacgt
45841  tacccaggcc cgggaacgca gcaacacgga ggcggttgga ttgtgcaaga gacccttaag
45901  ggggcgacc gcggggggag gctgggcggt cggctcgacc gtgatggggg cgggcaggct
45961  cgcgttcggg ggccggccga gcaggtaggt cttcgagatg taaagcagct ggccggggtc
46021  ccgcggaaac tcggccgtgg tgaccaatac aaaacaaaag cgctcctcgt accagcgaag
46081  aagggggcaga gatgccgtag tcaggtttag ttcgtccggc gggcgccgaa atccgcgcgg
46141  tggttttgg gggtcggggg tgtttggcag ccacagacgc ccggtgttcg tgtcgcgcca
46201  gtacatgcgg tccatgccca ggccatccaa aaaccatggg tctgtctgct cagtccagtc
46261  gtggacctga ccccacgcaa cgcccaaaag aataaccccc acgaaccata aaccattccc
46321  catgggggac cccgtcccta acccacgggg cccgtggcta tgcagggct tgccgccccg
46381  acgttggctg cgagccctgg gccttcaccc gaacttgggg gttggggtgg ggaaaaggaa
46441  gaaacgcggg cgtattggcc ccaatggggt ctcggtgggg tatcgacaga gtgccagccc
```

```
46501  tgggaccgaa ccccgcgttt atgaacaaac gacccaacac ccgtgcgttt tattctgtct
46561  ttttatttcc gtcatagcgc gggttccttc cggtattgtc tccttccgtg tttcagttag
46621  cctcccccat ctcccgggca aacgtgcgcg ccaggtcgca gatcgtcggt atggagcctg
46681  gggtggtgac gtgggtctgg accatcccgg aggtaagttg cagcagggcg tcccggcagc
46741  cggcgggcga ttggtcgtaa tccaggataa agacgtgcat gggacggagg cgtttggcca
46801  agacgtccaa ggcccaggca aacacgttat acaggtcgcc gttgggggcc agcaactcgg
46861  gggcccgaaa cagggtaaat aacgtgtccc cgatatgggg tcgtgggcgc gcgttgctct
46921  ggggctcggc accctgggc ggcacggccg tccccgaaag ctgtccccaa tcctcccgcc
46981  acgacccgcc gccctgcaga taccgcaccg tattggcaag cagcccgtaa acgcggcgaa
47041  tcgcgccaa catagccagg tcaagccgct cgccggggcg ctggcgtttg gccaggcggt
47101  cgatgtgtct gtcctccgga agggccccca acacgatgtt tgtgccgggc aaggtcggcg
47161  ggatgagggc cacgaacgcc agcacgcct ggggggtcat gctgcccata aggtatcgcg
47221  cggccgggta gcacaggagg gcgcgatgg gatggcggtc gaagatgagg gtgagggccg
47281  ggggcggggc atgtgagctc ccagcctccc ccccgatatg aggagccaga acggcgtcgg
47341  tcacggcata aggcatgccc attgttatct gggcgcttgt cattaccacc gccgcgtccc
47401  cggccgatat ctcaccctgg tcgaggcggt gttgtgtggt gtagatgttc gcgattgtct
47461  cggaagcccc cagcacctgc cagtaagtca tcggctcggg tacgtagacg atatcgtcgc
47521  gcgaacccag ggccaccagc agttgcgtgg tggtggtttt ccccatcccg tgaggaccgt
47581  ctatataaac ccgcagtagc gtgggcattt tctgctccag gcggacttcc gtggcttctt
47641  gctgccggcg agggcgcaac gccgtacgtc ggttgctatg gccgcgagaa ccgcagcct
47701  ggtcgaacgc agacgcgtgt tgatggcagg ggtacgaagc catacgcgct tctacaaggc
47761  gcttgccaaa gaggtgcggg agtttcacgc caccaagatc tgcggcacgc tgtttgacgct
47821  gttaagcggg tcgctgcagg gtcgctcggt gttcgaggcc acacgcgtca ccttaatatg
47881  cgaagtggac ctgggaccgc gccgcccga ctgcatctgc gtgttcgaat tcgccaatga
47941  caagacgctg ggcggggttt gtgtcatcat agaactaaag acatgcaaat atatttcttc
48001  cggggacacc gccagcaaac gcgagcaacg ggccacgggg atgaagcagc tgcgccactc
48061  cctgaagctc ctgcagtccc tcgcgcctcc gggtgacaag atagtgtacc tgtgccccgt
48121  cctggtgttt gtcgcccaac ggacgctccg cgtcagccgg ctgaccggc tcgtcccgca
48181  gaaggtctcc ggtaatatca ccgcagtcgt gcggatgctc cagagcctgt ccacgtatac
48241  ggtccccatg gagcctagga cccagcgagc ccgtcgccgc cgcggcggcg ctgcccgggg
48301  gtctgcgagc agaccgaaaa ggtcacactc tggggcgcgc gacccgcccg agccagcggc
48361  ccgccaggta ccaccgccg accaaacccc cgcctccacg gagggcgggg gggtgcttaa
48421  gaggatcgcg gcgctcttct gcgtgcccgt ggccaccaag accaaacccc gagctgcctc
48481  cgaatgagag tgtttcgttc cttccccctc ccccgcgtc agacaaaccc taaccaccgc
48541  ttaagcggcc cccgcgaggt ccgaagactc atttggatcc ggcgggagcc acctgacaac
48601  agccccgggg tttccccacg ccagacgccg gtccgctgtg ccatcgctcc ccttcatccc
48661  accccatct tgtccccaaa taaaacaagg tctggtagtt aggacaacga ccgcagttct
48721  cgtgtgttat tgtcgctctc cgcctctcgc agatgaccc gtattgccca tttgacgctc
48781  tggacgtctg ggaacacagg cgcttcatag tcgccgattc ccgaaacttc atcaccccg
48841  agttcccccg ggactttgg atgtcgcccg tctttaacct cccccgggag acggcggcgg
48901  agcaggtggt cgtcctgcag gccagcgca cagcggctgc cgctgccctg gagaacgccg
48961  ccatgcaggc ggccgagctc cccgtcgata tcgagcgccg gttacgcccg atcgaacgga
49021  acgtgcacga gatcgcaggc gccctggagg cgctggagac ggcggcggcc gccgccgaag
49081  aggcggatgc cgcgcgcggg gatgagccgg cgggtggggg cgacgggggg gcgcccccgg
49141  gtctggccgt cgcggagatg gaggtccgaa tcgtgcgcaa cgaccgccg ctacgatacg
49201  acaccaacct ccccgtggat ctgctacata tggtgtaccg ggcccgcggg gcgaccggct
49261  cgtcgggggt ggtgttcggg acctggtacc gcactatcca ggaccgcacc atcacggact
49321  ttccccctgac cacccgcagt gccgactttc gggacggccg gatgtccaag accttcatga
49381  cggcgctggt cctgtccctg cagtcgtgcg gccggctgta tgtgggccag cgccactatt
49441  ccgccttcga gtgcgccgtg ttgtgtctct acctgctgta ccgaaacacg cacggggccg
49501  ccgacgatag cgaccgcgct ccggtcacgt tcggggatct gctgggccgg ctgccccgct
49561  acctggcgtg cctggccgcg gtgatcggga ccgagggcgg ccggccacag taccgctacc
49621  gcgacgacaa gctccccaag acgcagttcg cggccgggcg gggccgctac gaacacggag
49681  cgctggcgtc gcacatcgtg atcgccacgc tgatgcacca cggggtgctc ccggcggccc
49741  cggggacgt ccccgggac gcgagcaccc acgttaaccc cgacgcgtg gcgcaccacg
49801  acgacataaa ccgcgccgcc gccgcgttcc tcagccgggg ccacaaccta ttcctgtggg
49861  aggaccagac tctgctgcgg gcaaccgcga acaccataac ggccctgggc gttatccagc
49921  ggctcctcgc gaacggcaac gtgtacgcgg accgcctcaa caaccgcctg cagctgggca
49981  tgctgatccc cggagccgtc ccttcggagg ccatcgcccg tggggcctcc gggtccgact
50041  cggggggccat caagagcgga gacaacaatc tggaggcgct atgtgccaat tacgtgcttc
50101  cgctgtaccg ggccgacccg gcggtcgagc tgacccagct gtttcccggc ctggccgccc
50161  tgtgtcttga cgcccaggcg gggcggccgg tcgggtcgac gggcgggtg gtggatatgt
50221  catcggggc ccgccaggcg gcgctggtcg gcctcaccgg cctggaactc atcaaccgca
50281  cccgcacaaa cccaccccc gtgggggagg ttatccacgc ccacgacgcc ctggcgatcc
50341  aatacgaaca ggggcttggc ctgctgcgc agcaggcacg cattggcttg ggctccaaca
50401  ccaagcgttt ctccgcgttc aacgttagca gcgactacga catgttgtac tttttatgtc
50461  tggggttcat tccacagtac ctgtcggcgg tttagtgggt ggtgggcgag ggggagggg
50521  gcattaggga gaaagaacaa gagcctccgt tgggttttct ttgtgcctgt actcaaaagg
50581  tcatacccg taaacggcgg gctccagtcc cggcccggcg gttggcgtga acgcaacggc
50641  gggagctggg ttagcgttta gtttagcatt cgctctcgcc tttccgcccg ccccgaccg
50701  ttgagccttt tttttttcg tccaccaaag tctctgtggg tgcgcgcatg gcagccgatg
50761  ccccgggaga ccgcgatgga gagcccgttc cagacagggc cgtgccatt tacgtggctg
50821  ggttttttggc cctgtatgac agcggggact cgggcgagtt ggcattggat ccggatacgg
50881  tgcggcggc cctgcctccg gataacccac tcccgattaa cgtgaccac cgcgctggct
50941  gcgaggtggg gcgggtgctg ccgtggtcg acgaccccg cgggccgttt tttgtgggac
51001  tgatcgcctg cgtgcaactg gagcgcgtcc tcgagacggc cgccagcgct gcgattttcg
51061  agcgccgcgg gccgccgctc tcccgggagg agcgcctgtt gtacctgatc accaactacc
```

Sequence Listing

```
51121  tgccctcggt ctccctggcc acaaaacgcc tgggggggcga ggcgcacccc gatcgcacgc
51181  tgttcgcgca cgtagcgctg tgcgcgatcg ggcggcgcct tggcactatc gtcacctacg
51241  acaccggtct cgacgccgcc atcgcgccct ttcgccacct gtcgccggcg tctcgcgagg
51301  gggcgcggcg actggccgcc gaggccgagc tcgcgctatc cggacgcacc tgggcgcccg
51361  gcgtggaggc gctgacccac acgctgcttt ccaccgccgt taacaacatg atgctgcggg
51421  accgctggag cctggtggcc gagcggcgg ggcaggccgg gatcgccgga cacacctacc
51481  tccaggcgag cgaaaaattc aaaatgtggg gggcggagcc tgtttccgcg ccggcgcgcg
51541  ggtataagaa cggggccccg gagtccacgg acataccgcc cggctcgatc gctgccgcgc
51601  cgcagggtga ccggtgccca atcgtccgtc agcgcggggt cgcctcgccc ccggtactgc
51661  cccccatgaa ccccgttcca acatcgggca ccccggcccc cgcgccgccc ggcgacggga
51721  gctacctgtg gatcccggcc tcccattaca accagctcgt cgccggccac gccgcgcccc
51781  aaccccagcc gcattccgcg tttggttttcc cggctgcggc ggcgggaaccc gcctatgggc
51841  ctcacggcgc gggtctttcc cagcattacc ctccccacgt cgcccatcag tatcccgggg
51901  tgctgttctc gggacccagc ccactcgagg cgcagatagc cgcgttggtg ggggccatag
51961  ccgcggaccg ccaggcgggc ggtcagccgg ccgcgggaga ccctgggggtc cgggggtcgg
52021  gaaagcgtcg ccggtacgag gcgggggcgt cggagtccta ctgcgaccag gacgaaccgg
52081  acgcggacta cccgtactac cccggggagg ctcgaggcgg gccgcgcggg gtcgactctc
52141  ggcgcgcggc ccgccagtct cccgggacca acgagaccat cacggcgctg atggggggcgg
52201  tgacgtctct gcagcaggaa ctggcgcaca tgcgggctcg gaccagcgcc ccctatggaa
52261  tgtacacgcc ggtggcgcac tatcgccctc aggtgggggga gccggaacca acaacgaccc
52321  acccggccct ttgtccccg gaggccgtgt atcgcccccc accacacagc gccccctacg
52381  gtcctccca gggtccggcg tcccatgccc ccactcccc gtatgcccca gctgcctgcc
52441  cgccaggccc gccaccgccc ccatgtcctt ccaccagac gcgcgcccct ctaccgacgg
52501  agcccgcgtt ccccccgcc gccaccggat cccaaccgga ggcatccaac gcggaggccg
52561  gggcccttgt caacgccagc agcgcagcac acgtggacgt tgacacggcc cgcgccgcg
52621  atttgttcgt ctctcagatg atggggggccc gctgattcgc cccggtctt ggtaccatgg
52681  gatgtcttac tgtatatctt tttaaataaa ccaggtaata ccaaataaga cccattggtg
52741  tatgttcttt tttttattggg aggggggcggt aggcgggtag cttacaatg caaaagcctt
52801  tgacgtggag gaaggcgtgg ggggaggaa atcggcactg accaagggg tccgttttgt
52861  cacgggaaag gaaagaggaa acaggccgcg gacacccggg ggagtttatg tgttccttt
52921  tctttcttcc cacacacaca caaaaggcgt accaaacaaa aaaaccaaaa gatgcgcatg
52981  cggtttaaca cccgtcggtttt ttatttacaa caaccccccc gtcacaggtc gtcctcgtcg
53041  gcgtcaccgt ctttgttggg aacttgggtg tagttggtgg tgcggcgctt gcgcatgacc
53101  atgtcggtga ccttggcgct gagcagcgcg ctcgtgccct tcttcttggc cttgtgttcc
53161  gtgcgctcca tggccgacac cagggccatg taccgtatca tctccctggc ctcggctagc
53221  ttggcctcgt caaagtcgcc gccctcctcg ccctcccgg acgcgtccgg gttggtgggg
53281  ttcttgagct ccttggtggt tagagggtac agggccttca tggggttgct ctgcagccgc
53341  atgacgtaac gaaaggcgaa gaaggccgcc gccaggccgg ccaggaccaa cagacccacg
53401  gccagcgccc caaagggggtt ggacatgaag gaggacacgc ccgacacggc cgataccacg
53461  ccgcccacga tgcccatcac caccttgccg accgcgcgcc caggtcgcc catcccctcg
53521  aagaacgcgc ccaggcccgc gaacatggcc ggcgttggcgt cggcgtggat gaccgtgtcg
53581  atgtcggcga agcgcaggtc gtgcagctgg ttgcgggcgct ggacctccgt gtagtccagc
53641  aggccgctgt ccttgatctc gtggcgggtg tacacctcca gggggacaaa ctcgtgatcc
53701  tccagcatgg tgatgttgag gtcgatgaag gtgctgacgg tggtgatgtc ggcgcggctc
53761  agctggtggg agtacgcgta ctcctcgaag tacacgtagc ccccaccgaa ggtgaagtag
53821  cgccggtgtc ccacggtgca cggctcgatc gcatcgcgcg tcagccgcag ctcgttgttc
53881  tccccccagct gcccctcgac caacgggccc tggtcttcgt accgaaagct gaccagggg
53941  cggctgtagc aggcccccggg ccgcgagctg atgcgcatcg agttttggac gatcacgttg
54001  tccgcggcga ccggccacgca cgtggaacg gccatccagt gccgagcat ccgcgcgct
54061  acccgccggc ccacggtgac cgaggcgatg gcgttggggt tcagcttgcg ggcctcgttc
54121  cacagggtca gctcgtgatt ctgtagctcg caccacgcga tgcaacgcg gcccaacata
54181  tcgttgacat ggcgctgtat gtggttgtac gtaaactgca gccgggcgaa ctcgatggag
54241  gaggtggtct tgatgcgctc cacggacgcg ttggcgctgg ccccggggcg cggggcgtag
54301  gggtttgggg gcttgcggct ctgctctcgg aggtgttccc gcacgtacag ctccgcgagc
54361  gtgttgctga aaggggggctg gtacgcgatc agaaagcccc cattggccag gtagtactgc
54421  ggctggccca ccttgatgtg cgtcgcgttg tacctgcggg cgaagatgcg gtccatggcg
54481  tcgcgggcgt ccttgccgat gcagtccccc aggtccacgc ggagagccgg gtactcggtc
54541  aggttggtgg tgaaggtggt ggatatggcg tcggaggaga atcggaagga gccgccgtac
54601  tcggagcgca gcatctcgtc cacttcctgc cacttggtca tggtgcagac cgacgggcgc
54661  tttggcaccc agtcccaggc cacggtgaac ttgggggtcg tgagcaggtt ccgggtggtc
54721  ggcgccgtgg cccgggggctt ggtggtgagg tcgcgcgcgt agaagccgtc gacctgcttg
54781  aagcggtcgg cggcgtagct ggtgtgttcg gtgtgcgccc cctcccggta gccgtaaaac
54841  ggggacatgt acacaaagtc gccagtcgcg agcacaaact cgtcgtacgg gtacaccgag
54901  cgcgcgtcca cctcctcgac gatgcagttt accgtcgtcc cgtaccggtg aacgcctcc
54961  acccgcgagg ggttgtactt gaggtcggtg gtgtgccagc cccggctcgt gcgggtcgcg
55021  gcgttggccg gtttcagctc catgtcggtc tcgtcggtcgt cccggtgaaa cgcggtggtc
55081  tccaggttgt tgcgcacgta cttggccgtg gaccgacgaa cccccttggc gttgatcttg
55141  tcgatcacct cctcgaaggg gacgggggcg cggtcctcaa agatccccat aaactgggag
55201  tagcggtggc cgaaccacac ctgcgaaacg gtgacgtctt tgtagtacat ggtggccttg
55261  aacttgtacg gggcgatgtt ctccttgaag accaccgcga tgccctccgt gtagttctga
55321  ccctcgggcc gggtcgggca gcggcgcggc tgctcgaact gcaccaccgt ggcgcccgtg
55381  ggggggtgggc acacgtaaaa gtttgcatcg gtgttctccg ccttgatgtc ccgcaggtgc
55441  tcgcgcaggg tggcgtggcc cgcggcgacg gtccgcgttgt cgccgcgggg gcgtggtggc
55501  gttgggtttt tcggtttttt gttcttcttc ggtttcgggt ccccccgttgg ggcggcgcca
55561  agggcgggcg gcgccggagt ggcagggccc ccgttcgccg cctggtcgc ggccgcgacc
55621  ccaggcgtgc cggggggaact cggagcgcgc gacgccacca ggaccccag cgtcaacccc
55681  aagagcgccc atacgacgaa ccaccggcgc ccccacgagg gggcgccctg gtgcatggcg
```

Sequence Listing

```
55741  ggactacggg ggcccgtcgt gcccccgtc  aggtagcctg ggggcgaggt gctggaggac
55801  cgagtagagg atcgagaaaa cgtcgcggtc gtagaccacg accgaccggg ggccgataca
55861  gccgtcgggg gcgctctcga cgatggccac cagcggacag tcggagtcgt acgtgagata
55921  tacgccgggc gggtaacggt aacgaccttc ggaggtcggg cggctgcagt ccgggcggcg
55981  caactcgagc tccccgcacc ggtagaccga ggcaaagagt gtggtggcga taatcagctc
56041  gcgaatatat cgccaggcgg cgcgctgagt gggcgttatt ccggaaatgc cgtcaaaaca
56101  gtaaaacctc tgaaattcgc tgacggccca atcagcaccc gagcccccg  cccccatgat
56161  gaaccgggcg agctcctcct tcaggtgcgg caggagcccc acgttctcga cgctgtaata
56221  cagcgcggtg ttgggggct  gggcgaagct gtgggtggag tgatcaaaga ggggcccgtt
56281  gacgagctcg aagaagcgat gggtgatgct ggggagcagg gccgggtcca cctggtgtcg
56341  caggagagac gctcgcatga accggtgcgc gtcgaacacg cccggcgccg agcggttgtc
56401  gatgaccgtg cccgcgcccg ccgtcagggc gcagaagcgc gcgcgcgccg caaagccgtt
56461  ggcgaccgcg gcgaacgtcg cgggcagcac ctcgccgtgg acgctgaccc gcagcatctt
56521  ctcgagctcc ccgcgctgct cgcggacgca gcgccccagg ctggccaacg accgcttcgt
56581  caggcggtcc gcgtacagcc gccgtcgctc ccgtacgtcc gcggccgctt gcgtggcgat
56641  gtcccccac  gtctcggggc cctgccccc  ggcccgccgg cgacggtctt cgtcctcgcc
56701  cccgccccg  ggagctccca accccgtgc  cccttcctct acggcgacac ggtccccgtc
56761  gtcgtcgggg cccgcgcgc  ccttgggcgc gtccgccgcg ccccccgccc ccatgcgcgc
56821  cagcacgcga cgcagcgcct cctcgtcgca ctgttcgggg ctgacgagcg gccgcaagag
56881  cggcgtcgtc aggtggtggt cgtagcacgc gcggatgagc gccgatctga tcgtcggg
56941  tgacgtggcc tgaccgccga ttattagggc gtccaccata tccagcgccg ccaggtggct
57001  cccgaacgcg cgatcgaaat gctccgcccg ccgcccgaac agcgccagtt ccacggccac
57061  cgcggcggtc tcctgctgca actcgcgccg cgccagcgcg gtcaggttgc tggcaaacgc
57121  gtccatggtg gtctggccgg cgccgtcgcc ggacgcggac cagaatccga attcgctgat
57181  ggcgtacagg ccgggcgtgg tggcctgaaa cacgtcgtgc gcctccagca gggcgtcggc
57241  ctccttgcgg accgagtcgt tctcggggcga cgggtggggc tgcccgtcgc ccccgcggt
57301  ccgggccagc gcatggtcca acacggagag cgcccgcgcg cggtcggcgt ccgacagccc
57361  ggccgcgtgg ggcaggtacc gccgcagctc gttggcgtcc agccgcacct gcgcctgctg
57421  ggtgacgtgg ttacagatac ggtccgccag gcggcgggcg atcgtcgccc cctggttcgc
57481  cgtcacacac agttcctcga aacagaccgc gcagggtgg  gacgggtcgc taagctccgg
57541  ggggacgata aggcccgacc ccaccgcccc caccataaac tcccgaacgc gctccagcgc
57601  ggcggtggcg ccgcgcgagg gggtgatgag gtggcagtag tttagctgct ttagaaagtt
57661  ctcgacgtcg tgcaggaaac acagctccat atggacggtc ccgccatacg tatccagcct
57721  gacccgttgg tgatacggac agggtcgggc caggcccatg gtctcggtga aaaacgccgc
57781  gacgtctccc gcggtcgcga acgtctccag gctgcccagg agccgctcgc cctcgcgcca
57841  cgcgtactct agcagcaact ccagggtgac cgacagcggg gtgagaaagg ccccggcctg
57901  ggcctccagg cccggcctca gacgacgccg cagcgcccgc acctgaagcg cgttcagctt
57961  cagttggggg agcttccccc gtccgatgtg ggggtcgcac cgccggagca gctctatctg
58021  aaacacatag gtctgcacct gcccgagcag ggctaacaac ttttgacggg ccacgtgggg
58081  ctcggacacc ggggcggcca tctcgcggcg ccgatctgta ccgcggccgg agtatgcggt
58141  ggaccgaggc ggtccgtacg ctacccggtg tctggctgga cccggggtc  ccctcttcg
58201  gggcggcctc ccgcggggc  gccgaccggc aagccgggag tcggcggcgc gtgcgtttct
58261  gttctattcc cagacaccgc ggagaggaat cacggcccgc ccagagatat agacacggaa
58321  cacaaacaag cacggatgtc gtagcaataa tttattttac acacattccc cgcccccgcc
58381  taggttcccc caccccccaa cccctcacag catatccaac gtcaggtctc ccttttttgc
58441  ggggggcccc tccccaaacg ggtcatcccc gtggaacgcc cgtttgcggc cggcaaatgc
58501  cggtcccggg gcccccgggc cgccaacgg  cgtcgcgttg tcgtcctcgc agccaaaatc
58561  cccaaagtta aacacctccc cggcgttgcc gagttggctg actagggcct cggcctcgtg
58621  cgccacctcc agggccgcgt ccgtcgacca ctcgccgttg cgcgcgctcca gggcacgcgc
58681  ggtcagctcc atcatctcct cgcttaggta ctcgtcctcc aggacgcca  gccagtcctc
58741  gatctgcagc tgctgggtgc ggggccccag gcttttcacg gtcgccacga acacgctact
58801  ggcgacggcc gccccgccct cggagataat gccccggagc tgctcgcaca gcgagctttc
58861  gtgcgctccg ccgccgaggt tcgaggccgc gcacacaaac ccggcccggg gacaggccag
58921  gacgaacttg cgggtgcggt caaaaataag gagcgggcac gcgttttgc  cgcccatcag
58981  gctggcccag ttccggcct  gaaacacacg gtcgttgccg gccatgccgt agtatttgct
59041  gatgctcaac cccaacacga ccatggggcg cgccgccatg acgggccgca gcaggttgca
59101  gctggcgaac atggacgtcc acgcgcccgg atgcgcgtcc acggcgtcca tcagcgcgcg
59161  ggccccgcc  tccaggcccg ccccgcctg  cgcggaccac gcggccgccg cctgcacgct
59221  gggggacgg  cgggacccg  ccgatgatgc cgtgagggtg ttgatgaagt atgtcgagtg
59281  atcgcagtac cgcagaatct ggtttgccat gtagtacatc gccagctcgc tcacgttgtt
59341  ggggccagg  ttaataaagt ttatcgcgcc gtagtccagg gaaaactttt taatgaacgc
59401  gatggtctcg atgtcctcgc gcgacaggag ccgggcggga agctggttgc gttggagggc
59461  cgtccagaac cactgcgggt tcggctggtt ggaccccggg ggcttgccgt tggggaagat
59521  ggccgcgtgg aactgcttca gcagaaagcc cagcggtccg aggaggatgt ccacgcgctt
59581  gtcgggcttc tggtaggcgc tctggaggct ggcgacccgc gccttggcgg cctcggacgc
59641  gttggcgctc gcgcccgcga acaacacgcg gctcttgacg cgcagctcct gggaaaccc
59701  cagggtcacg cggcaacgt  cgccctcgaa gctgctctcg gcggggggcg tctggccgac
59761  cgttaggctg ggggcgcaga tagccgcccc ctccgagagc gcgaccgtca gcgttttggc
59821  cgacagaaac ccgttgttaa acatgtccat cacgcgccgc cgcagcaccg gttggaattg
59881  attgcgaaag ttgcgcccct cgaccgactg cccggcgaac accccgtggc actggctcag
59941  ggcaggtcc  tgatacacgg cgaggttgga tcgccgcccg agaagctgaa gcagggggca
60001  tggcccgcac gcgtacgggt ccagcgtcag gacatgtcg  tggttgacct cgcccagacc
60061  gtcgcgaaac ttgaagttcc tcccctccac caggttgcgc atcgctgct  ccacctcgcg
60121  gtccacgacc tgcctgacgt tgttcaccac cgtatgcagg gcctcgcggt tggtgatgat
60181  ggtctccagc cgcccatgg  ccgtggggac cgcctggtcc acgtactgca gggtctcgag
60241  ttcggccatg acgcgctcgg tcgccgcgcg gtacgtctcc tgcatgatgg tccgggcggt
60301  ctcggatccg tccgcgcgct tcagggccga gaaggcggcg tagttcccca gcacgtcgca
```

Sequence Listing

```
60361 gtcgctgtac atgctgttca tggtcccgaa gacgccgatg gctccgcggg cggcgctggc
60421 gaacttggga tggcgcgccc ggaggcgcat gagcgtcgtg tgtacgcagg cgtggcgcgt
60481 gtcgaaggtg cacaggttgc agggcacgtc ggtctggttg gagtccgcga cgtatcgaaa
60541 cacgtccatc tcctggcgcc cgacgatcac gccgccgtcg cagcgctcca ggtaaaacag
60601 catcttggcc agcagcgccg gggaaaaccc acacagcatg gccaggtgct cgccggcaaa
60661 ttcctgggtt ccgccgacga ggggcgcggt gggccgaccc tcgaacccgg gcaccacgtg
60721 tccctcgcgg tccacctgtg ggttggccgc cggctgggtc ccgggcacga ggaagaagcg
60781 gtaaaaggag ggtttgctgt ggtcctttgg gtccgccgga ccgcgtcgt ccacctcggt
60841 gagatggagg gccgagttgg tgctaaatac catggcccccc acgagtcccg cggcgcgcgc
60901 caggtacgcc ccgacggcgt tggcgcgggc cgcggccgtg tcctggccct cgcacagcgg
60961 ccacgcggag atgtcggtgg gcggctcgtc gaagacggcc atcgacacga tagactcgag
61021 ggccagggcg gcgtctccgg ccatgacgga ggccaggcgc tgttcgaacc cgcccgccgg
61081 gcccttgccg ccgccgtcgc gcccaccccg cggggtctta ccctggctgg cttcgaaggc
61141 cgtgaacgta atgtcggcgg ggagggcggc gccctcgtgg ttttcgtcaa acgccaggtg
61201 ggcggccgcg cgggccacgg cgtccacgtt tcggcatcgc agtgccacgg cggcgggtcc
61261 cacgaccgcc tcgaacagga ggcggttgag ggggcggtta aaaacggaa gcgggtaggt
61321 aaaattctcc ccgatcgatc ggtggttggg gttgaacggc tcggcgatga cccggctaaa
61381 atccggcatg aacagctgca acggatacac gggtatgcgg tgcacctccg ccccgcctat
61441 ggttaccttg tccgagcctc ccaggtgcag aaaggtgttg ttgatgcaca cggcctcctt
61501 gaagccctcg gtaacgacca gatacaggag ggcgtccagg cggtccagcc cgaggcgctc
61561 acacagcgcc tccccgtcg tctcgtgttt gaggtcgccg ggccgggggg tgtagtccga
61621 aaagccaaaa tggcggcgtg cccgctcgca gagtcgcgtc aggtttgggg cctgggtgct
61681 ggggtccagg tgccggccgc cgtgaaagac gtacacggac gagctgtagt gcgatggcgt
61741 cagtttcagg gacaccggca tacccccgag cccgtcgtg cgagaaccca cgaccacggc
61801 tacgttggcc tcaaagccgc tctccacggt caggcccacg accaggggcc ccacggcgac
61861 gtcggcatcg ccgctgcgcg ccgacagtaa cgccagaagc tcgatgcctt cggacggaca
61921 cgcgcgagcg tacacgtatc ccaggggccc ggggggggacc ttgatggtgg ttgccgtctt
61981 gggctttgtc tccatgtcct cctggcaatc ggtccgcaaa cggaggtaat cccggccaga
62041 cgacggacgc ccgacgaggt atgtctcccg agcgtcaaaa tccgggggg ggggcggcga
62101 cggtcaaggg gagggtggga gaccgggggtt ggggaatgaa tccctaccct tcacagacaa
62161 cccccgggta accacggggt gccgatgaac cccggcggct ggcaacgcgg ggtccctgcg
62221 agaggcacag atgcttacgg tcaggtgctc cgggccgggt gcgtctgata tgcggttggt
62281 atatgtacac tttacctggg ggcgtgccgg accgcccaq ccctcccac acccgccg
62341 tcatcagccg gtgggcgtgg ccgctattat aaaaaaagtg agaaccgaa gcgttcgcac
62401 tttgtcctaa taatatatat attattagga caaagtgcga acgcttcgcg ttctcacttt
62461 ttttataata gcggccacgc ccaccggcta cgtcacgctc ctgtcggccg ccggcggtcc
62521 ataagccggg ccggccgggc cgacgcgaat aaaccgggcc gccggccgg gcgccgcga
62581 gcagctcgcc gcccggatcc gccagacaaa caaggccctt gcacatgccg gcccgggcga
62641 gcctgggggt ccggtaattt tgccatccca cccaagcggc ttttgggggtt tttcctcttc
62701 ccccctcccc acatcccccc tctttagggg ttcgggtggg aacaaccgcg atgttttccg
62761 gtggcggcgg cccgctgctc cccggaggaa agtcggccgg cagggcggg tccggtttt
62821 ttgcgcccgc cggccctcgc ggagccggcc ggggaccccc gccttgtttg aggcaaaact
62881 tttacaaccc ctacctcgcc ccagtcggga cgcaacagaa gccgaccggg ccaacccagc
62941 gccatacgta ctatagcgaa tgcgatgaat ttcgattcat cgccccgcgg gtgctggacg
63001 aggatgcccc cccggagaag cgcgccgggg tgcacgacgg tcacctcaag cgcgccccca
63061 aggtgtactg cggggggggac gagcgcgacg tcctccgcgt cgggtcgggc ggcttctggc
63121 cgcggcgctc gcgcctgtgg ggcggcgtgg accacgcccc ggcggggttc aaccccaccg
63181 tcaccgtctt tcacgtgtac gacatcctga gaacgtgga gcacgcgtac ggcatgcgcg
63241 cggcccagtt ccacgcgcgg tttatgacg ccatcacacc caggccagcc gtcatcacgc
63301 tcctgggcct gactccggaa ggccaccggg tggccgttca cgtttacggc acgcggcagt
63361 acttttacat gaacaaggag gaggttgaca ggcacctaca atgccgcgcc ccacgagatc
63421 tctgcgagcg catggccgcg gccctgcgcg agtccccggg cgcgtcgttc cgcggcatct
63481 ccgcggacca cttcgaggcg gaggtggtgg agcgcaccgg cgtgtactac tacgagacgc
63541 gccccgctct gtttaccgc gtctacgtcc gaagcgggcg cgtgctgtcg tacctgtgcg
63601 acaacttctg cccggccatc aagaagtacg agggtgggt cgacgccacc acccggttca
63661 tcctggacaa ccccgggttc gtcaccttcg gctggtaccg tctcaaaccg ggccggaaca
63721 acacgctagc ccagccgcgg gccccgatgg ccttcgggac atccagcgac gtcgagttta
63781 actgtacggc ggacaacctg gccatcgagg cgacctaccg gcatacaagc
63841 tcatgtgctt cgatatcgaa tgcaaggcgg gggggagga cgagctggcc tttccggtgg
63901 ccgggcaccc ggaggacctg gttattcaga tatcctgtct gctctacgac cgtccacca
63961 ccgccctgga gcacgtcctc ctgttttcgc tcggttcctg cgacctcccc gaatcccacc
64021 tgaacgagct ggcggccagg ggctgccca ccccgtggg tctggaattc gacagcgaat
64081 tcgagatgct gttggccttc atgaccctttg tgaaacagta cggccccgag ttcgtgaccg
64141 ggtacaacat catcaacttc gactggccct tcttgctggc caagctgacg gacatttaca
64201 aggtccccct ggacgggtac ggccgcatga acgccggggg cgtgtttcgc gtgtgggaca
64261 taggccagag ccacttccag aagcgcagca agataaaggt gaaccgcatg gtgaacatcg
64321 acatgtacgg gatcataacc gacaagatca agctctcgag ctacaagctc aaccgcgtgg
64381 ccgaagccgt cctgaaggac aagaagaagg acctgagcta tcgcgacatc cccgcctact
64441 acgccaccgg gcccgcgcaa cgcgggggtga tcggcgagta ctgcatacag gattccctgc
64501 tggtgggcca gctgtttttt aagttttttgc cccatctgga gctctcggcc gtcgcgcgct
64561 tggcgggtat taacatcacc cgcaccatct acgacggcca gcagatccgc gtcttttacgt
64621 gcctgctgcg cctggccgac cagaagggct ttattctgcc ggacaccag gggcgattta
64681 gggggcgccgg ggggaggcg cccaagcgtc cggccgcagc cgggaggac gaggagcggc
64741 cagaggagga gggggaggac gggacgaac gcgaggaggg cggggaggag cgggagccgg
64801 agggcgcgcg ggagaccgcc ggccggcacg tgggggtacca gggggccagg gtccttgacc
64861 ccacttccgg gtttcacgtg aaccccgtgg tggtgttcga ctttgccagc ctgtacccca
64921 gcatcatcca ggcccacaac ctgtgcttca gcacgctctc cctgagggcc gacgcagtgg
```

Sequence Listing

```
64981  cgcacctgga ggcgggcaag gactacctgg agatcgaggt ggggggggcga cggctgttct
65041  tcgtcaaggc tcacgtgcga gagagcctcc tcagcatcct cctgcgggac tggctcgcca
65101  tgcgaaagca gatccgctcg cggattcccc agagcagccc gcaggaggcc gtgctcctgg
65161  acaagcagca ggccgccatc aaggtcgtgt gtaactcggt gtacgggttc acgggagtgc
65221  agcacggact cctgccgtgc ctgcacgttg ccgcgacggt gacgaccatc ggccgcgaga
65281  tgctgctcgc gacccgcgag tacgtccacg cgcgctgggc ggccttcgaa cagctcctgg
65341  ccgatttccc ggaggcggcc gacatgcgcg ccccgggcc ctattccatg cgcatcatct
65401  acggggacac ggactccata tttgtgctgt gccgcggcct caccggccgcc gggctgacgg
65461  ccatgggcga caagatggcg agccacatct cgcgcgcgct gtttctgccc cccatcaaac
65521  tcgagtgcga aaagacgttc accaagctgc tgctgatcgc caagaaaaag tacatcggcg
65581  tcatctacgg gggtaagatg ctcatcaagg gcgtggatct ggtgcgcaaa acaactgcg
65641  cgtttatcaa ccgcacctcc agggccctgg tcgacctgct gttttacgac gataccgtat
65701  ccggagcggc cgccgcgtta gccgagcgcc ccgcagagga gtggctggcg cgacccctgc
65761  ccgagggact gcaggcgttc ggggccgtcc tcgtagacgc ccatcggcgc atcaccgacc
65821  cggagaggga catccaggac tttgtcctca ccgccgaact gagcagacac ccgcgcgcgt
65881  acaccaacaa gcgcctggcc cacctgacgg tgtattacaa gctcatggcc cgccgcgcgc
65941  aggtcccgtc catcaaggac cggatcccgt acgtgatcgt ggcccagacc cgcgaggtag
66001  aggagacggt cgcgcggctg gccgcccctcc gcgagctaga cgccgccgcc caggggacg
66061  agcccgcccc ccccgcgcc ctgccctccc cggccaagcg cccccgggag acgccgtcgc
66121  atgccgaccc cccggaggc gcgtccaagc cccgcaagct gctggtgtcc gagctggccg
66181  aggatcccgc atacgccatt gcccacggcg tcgccctgaa cacggactat tacttctccc
66241  acctgttggg ggcggcgtgc gtgacattca aggccctgtt tgggaataac gccaagatca
66301  ccgagagtct gttaaaaagg tttattcccg aagtgtggca ccccccggac gacgtggccg
66361  cgcggctccg ggccgcaggg ttcggggcgg tgggtgccgg cgctacggcg gaggaaactc
66421  gtcgaatgtt gcatagagcc tttgatactc tagcatgagc ccccccgtcga agctgatgtc
66481  cctcattta caataaatgt ctgcggccga cacggtcgga atctccgcgt ccgtgggttt
66541  ctctgcgttg cgccggacca cgagcacaaa cgtgctctgc cacacgtggg cgacgaaccg
66601  gtaccccggg cacgcggtga gcatccggtc tatgagcgg tagtgcaggt gggcggacgt
66661  gccgggaaag atgacgtaca gcatgtggcc cccgtaagtg gggtccgggt aaaacaacag
66721  ccgcgggtcg cacgccccgc ctccgcgcag gatcgtgtgg acgaaaaaaa gctcggggttg
66781  gccaagaatc ccggccaaga ggtcctggag gggggcgttg tggcggtcgg ccaacacgac
66841  caaggaggcc aggaaggccgc gatgctcgaa tatcgtgttg atctgctgca cgaaggccag
66901  gattagggcc tcgcggctgg tggcggcgaa ccgccgcgtct cccgcgttgc acgcgggaca
66961  gcaaccccg atgcctaggt agtagcccat cccggagagg gtcaggcagt tgtcggccac
67021  ggtctggtcc agacagaagg gcagcgacac gggagtggtc ttcaccaggg gcaccgagaa
67081  cgagcgcacg atggcgatct cctcggaggg cgtctgggcg agggcggcga aaaggccccg
67141  atagcgctgg cgctcgtgta aacacagctc ctgttttgcg gcgtgaggcg gcaggctctt
67201  ccgggaggcc cgacgcacca cgcccagagt cccgccggcc gcagaggagc acgaccgccg
67261  gcgctccttg ccgtgatagg gcccgggccg ggagccgcgg cgatgggggt cggtatcata
67321  cataggtaca cagggtgtgc tccagggaca ggagcgagat cgagtggcgt ctaagcagcg
67381  cgcccgcctc acggacaaat gtggcgacg cggtgggctt tggtacaaat acctgatacg
67441  tcttgaaggt gtagatgagg gcacgcaacg ctatgcagac acgcccctcg aactcgttcc
67501  cgcaggccag cttggccttg tggagcagca gctcgtcggg atgggtggcg gggggatggc
67561  cgaacagaac ccaggggtca acctccatct ccgtgatggc gcacatgggt tcacagaaca
67621  tgtgcttaaa gatggcctcg ggccccgcgg cccgcgcag gctcacaaac cggccccgt
67681  ccccgggctg cgtctcgggg tccgcctcga gctggtcgac gacgggtacg atacagtcga
67741  agaggctcgt gttgttttcc gagtagcgga ccacggaggc ccggagtctg cgcagggcca
67801  gccagtaagc ccgcaccagt aacaggttac acagcaggca ttctccgccg gtgcgcccgc
67861  gcccccggcc gtgtttcagc acggtggcca tcagagggca caggtcaggt tcgggctgga
67921  catcgggttc ggtaaactgc gcaaagcgcg gagccacgtc gcgcgtgcgt gccccgcgat
67981  gcgcttccca ggactggcgg accgtggcgc gacgggcctc cgcggcagcg cgcagctggg
68041  gccccgactc ccagacgcg ggggtgccgg cgaggagcag caggaccaga tccgcgtacg
68101  cccacgtatc cggcgactcc tccggctcgc ggtccccgge gaccgtctcg aattcccgt
68161  tgcgagcggc ggcgcgcgta cagcagctgt ccccgccccc gcgccgacce tccgtgcagt
68221  ccaggagacg ggcgcaatcc ttccagttca tcagcgcggt ggtgagcgac ggctgcgtgc
68281  cggatcccgc cgccgacccc gccccctcct cgccccggga ggccaaggtt ccgatgaggg
68341  ccccgggtgg cagactgcgcc aggaacgagt agttggagta ctgcaccttg gcggctcccg
68401  gggagggcga gggcttgggt tgcttctggg catgccgccc gggcaccccg ccgtcggtac
68461  ggaagcagca gtggagaaaa aagtgccggt ggatgtcgtt tatggtgagg gcaaagcgtg
68521  cgaaggagcc gaccagggtc gccttcttgg tgcgcagaaa gtggcggtcc atgacgtaca
68581  caaactcgaa cgcggccacg aagatgctag cggcgcagtg gggcgccccc aggcatttgg
68641  cacagagaaa cgcgtaatcg gccacccact ggggcgagg gcggtaggtt tgcttgtaca
68701  gctcgatggt gcggcagacc agacagggcc ggtccagcgc gaaggtgtcg atgccgccg
68761  cggaaaaggg cccggtgtcc aaaagcccct cccacacggg atccggggc gggttgcggg
68821  gtcctccgcg cccgcccgaa cccctccgt cgcccgcccc ccgcgggcc cttgaggggg
68881  cggtgaccac gtcggcggcg acgtcctcgt cgagcgtacc gacgggcggc acacctatca
68941  cgtgactggc cgccaggagc tcggcgcaga gagcctgctt aagagccagg aggctgggat
69001  cgaaggccac atacgcgcgc tcgaacgccc ccgccttcca gctgctgccg ggggactctt
69061  cgcacaccgc gacgctcgcc aggacccccgg ggggcgaagt tgccatggct gggcggagg
69121  ggcgcacgcg ccagcgaact ttacgggaca caatccccga ctgcgcgctg cggtcccaga
69181  ccctggagag tctagacgcg cgctacgtct cgcgagacgg cgcgcatgac gcggccgtct
69241  ggttcgagga tatgacccccc gccgagctgg aggttgtctt cccgactacg gacgccaagc
69301  tgaactacct gtcgcggacg cagcggctgg cctccctcct gacgtacgcc gggcctataa
69361  aagcgcccga cgacgccgcc gccccgcaga ccccggacac cgcgtgtgtg cacgcgcagc
69421  tgctcgcccg caagcgggaa agattcgcgg cggtcattaa ccggttcctg gacctgcacc
69481  agattctgcg gggctgacgc gcgcgctgtt gggcgggacg gttcgcgaac cctttggtgg
69541  gtttacgcgg gcacgcacgc tcccatcgcg ggcgccatgg cgggactggg caagccctac
```

Sequence Listing

```
69601  cccggccacc caggtgacgc cttcgagggt ctcgttcagc gaattcggct tatcgtccca
69661  tctacgttgc ggggcgggga cgggaggcg ggccctact ctccctccag cctccctcc
69721  aggtgcgcct ttcagtttca tggccatgac gggtccgacg agtcgtttcc catcgagtat
69781  gtactgcggc ttatgaacga ctgggccgag gtcccgtgca acccttacct gcgcatacag
69841  aacaccggcg tgtcggtgct gtttcagggg tttttcatc gcccacacaa cgccccggg
69901  ggcgcgatta cgccagagcg gaccaatgtg atcctgggct ccaccgagac gacggggctg
69961  tccctcggcg acctggacac catcaagggg cggctcggcc tggatgcccg gccgatgatg
70021  gccagcatgt ggatcagctg ctttgtgcgc atgcccgcg tgcagctcgc gtttcggttc
70081  atgggccccg aagatgccgg acggacgaga cggatcctgt gccgcgccgc cgagcaggct
70141  attacccgtc gccgccgaac ccggcggtcc cggaggcgt acggggccga ggccgggctg
70201  ggggtggctg aacgggttt ccgggccagg ggggacggtt ttggcccgct ccccttgtta
70261  acccaagggc cctcccgccc gtggcaccag gccctgccgg gtcttaagca cctacggatt
70321  ggcccccccg cgctcgtttt ggcggcggga ctcgtcctgg ggccgctat ttggtgggtg
70381  gttggtgctg gcgcgcgcct ataaaaaagg acgcaccgcc gcctaatcg ccagtgcgtt
70441  ccggacgcct tcgccccaca cagccctccc gtccgacacc cccatatcgc ttcccgacct
70501  ccggtcccga tggcctcc gcaatttcac cgccccagca ccgttaccac cgatagcgtc
70561  cgggcgcttg gcatgcgcgg gctcgtcttg gccaccaata actctcagtt tatcatggat
70621  aacaaccacc cgcacccca gggcacccaa ggggccgtgc gggagtttct ccgcggtcag
70681  gcggcggcgc tgacggacct tggtctggcc cacgcaaaca acacgtttac cccgcagcct
70741  atgttcgcgg gcgacgcccc ggccgcctgg ttgcggcccg cgtttggcct gcggcgcacc
70801  tattcaccgt ttgtcgtccg agaaccttcg acgcccggga ccccgtgagg cccggggagt
70861  tccttctggg gtgtttaat caataaaaga ccacccaac gcacgagcct tgcgtttaat
70921  gtcgtgttta ttcaaggag tgggataggg ttcgacggtt cgaaacttaa cacacaaaat
70981  aatcgagcgc gtctagccca gtaacatgcg cacgtgttca aggctggtca gcacggcgtc
71041  gctgtgatga agcagcgccc ggcgggtccg ctgtaactgc tgttgtaggc ggtaacaggc
71101  gcggatcagc accgccaggg cgctacgacc ggtgcgttgc acgtagcgtc gcgacagaac
71161  tgcgttttgcc gatacgggcg ggggggccgaa ttgtaagcgc gtcacctctt gggagtcatc
71221  ggcggataac gcactgaatg gttcgttggt tatgggggga tgtggttccc gagggagtgg
71281  gtcgagcgcc tcggcctcgg aatccgagag gaacaacgag gtggtgtcgg agtcttcgtc
71341  gtcagagaca tacagggtct gaagcagcga cacgggcggg ggggtagcgt caatgtgtag
71401  cgcgagggag gatgcccacg aagacccc agacaaggag ctgcccgtgc gtggatttgt
71461  ggacgacgcg gaagccggga cggatggggcg gttttgcggt gcccggaacc gaaccgccgg
71521  atactccccg ggtgctacat gcccgttttg gggctgggt tggggctggg gctgggggttg
71581  gggttggggc tggggttggg gctggggttg gggctggggt tggggttggg gttggggctg
71641  gggttggggt tggggctggg gctggggctg gggctgggggc tggggctggg gctggggctg
71701  gggctggggc tggggctggg gctggggctg gggctgggt tggggctggg gttggggctg
71761  gggcgcggac aggcgggtga cggtcaaatg ccccccgggg cgcgcagatg tggtgggcgt
71821  ggccaccggc tgccgtgtag tggggcggcg ggaaccggg cctccggcg taacaccgcc
71881  ctccagcgtc aagtatgtgg ggggcgggcc tgacgtcggg ggcggggtga cgggttggac
71941  cgcgggaggc gggggagagg gacctgcggg agaggatgag gtcggctcgg ccggggttgcg
72001  gcctaaaaca gggccgtcgg ggtcggcggg gtcccagggt gaaggaggg attcccgcga
72061  ttcggacagc gacgcgacag cggggcgcgt aaggcgccgc tgcggcccgc ctacgggaac
72121  cctgggggg gttggcgcgg gacccgaggt tagcgggggg cggcggtttt cgcccccggg
72181  caaaaccgtg ccggttgcga ccgggggcgg aacgggatcg ataggagag cgggagaagc
72241  ctggccggcg aactggggac cgagcgggag gggcacacca gacaccaaag cgtggagcgc
72301  tggctctggg ggtttgggag gggccggggg gcgcgcgaaa tcggtaaccg gggcgaccgt
72361  gtcggggagg gcaggcgcc gccaaccctg ggtggtcgcg gaagcctggg tggcgcgcgc
72421  caggagcgt gcccggcggt gtcggcgcgc gcgcgacccg gacgaagaag cggcagaagc
72481  gcgggaggag gcgggggggc ggggggcggt ggcatcgggg ggcgccgggg aactttggg
72541  ggacggcaag cgccggaagt cgtcgcgggg gcccacgggc gccggccgcg tgctttcggc
72601  cgggacgccc ggtcgtgctt cgcgagccgt gactgccggc ccaggggcc gcggtgcaca
72661  ctgggacgtg gggacggact gatcggcggt gggcgaaagg gggtccgggg caaggagggg
72721  cgcggggccg cccggagtcgt cagacgcgag ctcctccagg ccgtgaatcc atgcccacat
72781  gcgagggggg acgggctcgc cggggggtggc gtcggtgaat agcgtgggg ccaggcttcc
72841  gggccccaac gagccctccg tcccaacaag gtccgccggg ccgggggtcg ggttcgggac
72901  cgaggggctc tggtcgtcgg gggcgcgctg gtacaccgga tgccccggga atagctcccc
72961  cgacaggagg gaggcgtcga acggcccgccc gaggatagct cgcgcgagga agggtgcctc
73021  gtcggtgcg ctggcggcga ggacgtcctc gccgcccgcc acaaacggga gctcctccgt
73081  ggcctcgctg ccaacaaacc gcacgtcggg ggggccgggg gggtccgggt tttcccacaa
73141  caccgcgacc gggggtcatgg agatgtccac gagcaccaga cacggcgggc cccgggcgag
73201  gggccgctcg gcgatgagcg cggacaggcg cgggagctgt gccgccagac acgcgttttc
73261  aatcgggttc aggtcggcgt gcaggaggcg ggcgcccac gtctcgattg cggacgacac
73321  ggcatcgcgc aaggcggcgt ccggcccgcg agcgcgtgag tcaaacagcg tgagacacag
73381  ctccagctcc gactcgcggg aaaaggccgt ggtgttgcgg agcgccacga cgacgggcgc
73441  gcccaggagc actgccgcca gcaccaggtc catggccgta acgcgcgccg cgggggtgcg
73501  gtgggtggcg gcggccggca cggcgacgtg ctggcccgtg ggccggtaga gggcgttggg
73561  gggagcgggg ggtgacgcct cgcgccccc cgagggggtc agcgtctgcc cagattccag
73621  acgcgcggtc agaagggcgt cgaaactgtc atactctgtg tagtcgtccg gaaacatgca
73681  ggtccaaaga gcggccagag cggtgcttgg gagacacatg cgcccgagga cgctcaccgc
73741  cgccagcgcc tgggcgggac tcagcttttcc cagcgcggcg ccgcgctcgg ttcccagctc
73801  ggggaccgag cgccaggggcg ccaggggggtc ggtttcggac aacttgccgc ggcgccagtc
73861  tgccagccgc gtgccgaaca taggccccg ggtcggaggg ctccggtcg aaaacactgg
73921  cagcacgcgg atgcgggcgt ctggatgcgg ggtcaggcgc tgcacgaata gcatgaatc
73981  tgctgcgttc tgaaacgcac ggggggagggt gagatgcatg tactcgtgtt ggcggaccag
74041  atccaggcgc caaaaggtgt aaatgtgttc cggggagctg gccaccagcg ccaccagcac
74101  gtcgttctcg ttaaaggaaa cgcggtgcct agtggagctg tggggcccga gcggcggtcc
74161  cggggccgcc gcgtcacccc cccattccag ctgggcccag cgacacccaa actcgcgcgt
```

| | | | | | |
|---|---|---|---|---|---|
| 74221 | gagagtggtc | gcgacgaggg | cgacgtagag | ctcggccgcc | gcatccatcg aggcccccca |
| 74281 | tctcgcctgg | cggtggcgca | caaagcgtcc | gaaagctgaa | aagttggcgg cctgggcgtc |
| 74341 | gctgagggcc | agctgaagcc | ggttgatgac | ggtgatgacg | tacatggccg tgacggtcga |
| 74401 | ggccgactcc | agggtgtccg | tcggaagcgg | ggggcgaatg | catgccgcct cgggacacat |
| 74461 | cagcagcgcg | ccgagcttgt | cggtcacggc | cgggaagcag | agcgcgtact gcagtggcgt |
| 74521 | tccatccggg | accaaaaagc | tgggggcgaa | cggccgatcc | agcgtactgg tggcctcgcg |
| 74581 | cagcaccagg | ggcccgggc  | ctccgctcac | tcgcaggtac | gcctcgcccc ggcggcgcag |
| 74641 | catctgcggg | tcggcctctt | ggccgggtgg | ggcggacgcc | cgggcgcggg cgtctagggc |
| 74701 | gcgaagatcc | acgagcaggg | gcgcgggcgc | ggcggccgcg | cccgcgcccg tctggcctgt |
| 74761 | ggccttggcg | tacgcgctat | ataagcccat | gcggcgttgg | atgagctccc gcgcgccccg |
| 74821 | gaactcctcc | accgcccatg | gggccaggtc | cccggccacc | gcgtcgaatt ccgccaacag |
| 74881 | gccccccagg | gtgtcaaagt | tcatctccca | ggccaccctt | ggcaccacct cgtcccgcag |
| 74941 | ccgggcgctc | aggtcggcgt | gttgggccac | gcgcccccg  | agctcctcca cggccccggc |
| 75001 | ccgctcggcg | ctcttggcgc | ccaggacgcc | ctggtacttg | gcgggaaggc gctcgtagtc |
| 75061 | ccgctgggct | cgcagccccg | acacagtgtt | ggtggtgtcc | tgcagggcgc gaagctgctc |
| 75121 | gcatgccgcg | cgaaatccct | cgggccccc  | ccgcgaaccgc ggccgaagcg |
| 75181 | accccatacc | tcgtcccact | ccgcctcggc | ctcctcgaga | gacctccgca gggcctcgac |
| 75241 | gcggcgacgg | tgtcgaaga  | gcgcctgcag | gcgcgcgccc | tgtcgcgtca ggaggcccgg |
| 75301 | gccgtcgccg | ctggccgcgt | ttagcgggtg | cgtctcaaag | gtacgctggg catgttccaa |
| 75361 | ccaggcgacc | gcctgcacgc | cgagctcgcg | cgccttctcc | gtctggtcca acagaatttc |
| 75421 | gacctgatcc | gcgatctcct | ccgccgagcg | cgcctggtcc | agcgtcttgg ccacggtcgc |
| 75481 | cgggacggcg | accaccttca | gcagggtctt | cagattggcc | agaccctcgg cctcgagctg |
| 75541 | ggcccggcgc | tcgcgcgcgg | ccagcacctc | ccgcagcccc | gccgtgaccc gctcggtggc |
| 75601 | ttcgggcgc  | tgctgttttgg | cgcgcaccac | ggcgtcgttg | gtatcggcca ggtcctgtcg |
| 75661 | ggtcacgaat | gcgacgtagt | cggcgtacgc | cgtgtccttc | acggggctct ggtccacgcg |
| 75721 | ctccagcgcc | gccacgcacg | ccaccagccg | gtcctcgctc | gggcagggca gggtgacccc |
| 75781 | tgcccggaca | agctcggcgg | ccgccgccgg | gtcgttgcgc | accgcggata tctcctccgc |
| 75841 | ggcgggcgcc | aggtccagcg | ccacgcttcc | gatcgcgcgc | cgcgcgtcgg cccggagggc |
| 75901 | gtccaggcga | tcgcggatat | ccacgtactc | ggcgtagccc | ttttgaaaaa acggcacgta |
| 75961 | ctggcgcagg | gccggcacgc | ccccaagtc  | ttccgacagg | tgtaggacgg cctcgtggta |
| 76021 | gtcgataaac | ccgtcgttcg | cctgggcccg | ctccagcagc | cccccgcca  gccgcagaag |
| 76081 | ccgcgccagg | ggctcggtgt | ccacccgaaa | catgtcggcg | tacgtgtccg ccgcggcccc |
| 76141 | gaaggccgcg | ctccagtcga | tgcggtgaat | ggctgcgagc | ggggggagca tggggtggcg |
| 76201 | ctggttctcg | ggggtgtatg | ggttaaacgc | aagggccgtc | tccagggcaa gggtcaccgc |
| 76261 | cttggcgttg | gttcccagcg | cctgttcggc | ccgctttcgg | aagtcccggg ggttgtagcc |
| 76321 | gtgcgtgccc | gccagcgcct | gcaggcgacg | gagctcgacc | acgtcaaact cggcaccgct |
| 76381 | ttccacgcgg | tccagcacgg | cctccacgtc | ggcggcccaa | cgctcgtgc  tactgcgggc |
| 76441 | gcgctgggcc | gccatcttct | ctctcaggtc | ggcggatgcg | gcctcaagtt cgtcggcgcg |
| 76501 | gcgtcgcgtg | gcgccgatga | cctttcccag | ctcctgcagg | gcgcgcccgc tgggggagtg |
| 76561 | gtccccggcc | gtcccttcgg | cgtgcaacag | gcccccgaac | ctgccctcgt ggcccgcgag |
| 76621 | gctttcccgc | gcgccggtgg | tcgcgcgcgt | cgcggccgtg | atcagggagg catgctctcc |
| 76681 | ctccggttgg | ttggcggccc | ggcgcacctg | gacgacaagg | tcggctgccg ccgaccctaa |
| 76741 | ggtcgtgagc | tggcgatgg  | ccccccgcgc | gtccagggcc | aaccgagtcg ccttgacgta |
| 76801 | tcccgcggcg | ctgtcggcca | tggccgctag | gaaggccagg | ggggaggccg ggtcgctggc |
| 76861 | ggccgcgccc | agggccgtca | ccgcgtcgac | caggacgccg | tgcgcccgca cggccgcatc |
| 76921 | caccgtcgac | gcggggtctg | ccgtcgcgac | ggcggcgctg | ccggcgttga tggcgttcga |
| 76981 | gacggcgtgg | gctatgatcg | gggcgtgatc | ggcgaagaac | tgcaagagaa acggagtctc |
| 77041 | tggggcgtcg | gcgaacaggt | tcttcagcac | caccacgaag | ctgggatgca agccagacag |
| 77101 | agccgtcgcc | gtgtccggag | tcgggtgctc | cagggcatct | cggtactgcc ccagcagccc |
| 77161 | ccacatgtcc | gcccgcagcg | ccgcctaac  | ctcaggggc  | gcccccgaa  cggcctcggg |
| 77221 | gaggtccgac | cagcccgccc | gcagggaggc | ccgcagggtc | gccaggacgg ccggacaggc |
| 77281 | ctttagcccc | acaaagtcag | ggagggggcg | caggacccccc | tggagtttgt gcaagaactt |
| 77341 | ctcccgggcg | tcgcgggcca | ccttcgcccg | ctcccgcgct | ccctcgagca ttgcctccag |
| 77401 | ggagcgcgcg | cgctcccgca | aacgggcacg | cgcatcgggg | gcgagctctg ccgtcagctt |
| 77461 | ggcggcatcc | atggcccgcg | cctgccgcag | cgcttcctcg | gccatgcgcg tggcctctgg |
| 77521 | cgacagcccg | ccgtcgtcgg | ggtagggcga | cgcgccgggc | gcaggaacaa aggccgcgtc |
| 77581 | gctgtccagc | tgctggccca | gggccgcatc | tggcgtcg   | aagcgccgca gctcggccag |
| 77641 | acccgagctg | cggcgcgcct | gctggtcgtt | aatgtcgcgg | atgctgcgcg ccagctcgtc |
| 77701 | cagcggcttg | cgttctatca | gcccttggtt | ggcggcgtcc | gtcaggacgg agagccaggc |
| 77761 | cgccaggtcc | tcgggggcgt | ccagcgtctg | gccccgctgg | atcagatccc gcaacaggat |
| 77821 | ggccgtgggg | ctggtcgcga | tcggggggcgg | ggcgggaatg | gcggcgcgct gcgcgatgtc |
| 77881 | ccgcgtgtgc | tggtcgaaga | caggcaggga | ctcgagcagc | tggaccacgg gcacgacggc |
| 77941 | ggccgaagcc | acgtgaaacc | ggcggtcgtt | gttgtcgctg | gcctgtagag ccttggcgct |
| 78001 | gtatacggcc | ccccggtaaa | agtactcctt | aaccgcgccc | tcgatcgccc gacgggcctg |
| 78061 | ggtccgcacc | tcctccagcc | gaacctgaac | ggcctcgggg | cccagggggg gtgggcgcgg |
| 78121 | agccccctgc | ggggccgcc  | ccgccggggc | gggcattacg | ccgagggggcc cggcgtgctg |
| 78181 | tgagaccgcg | tcgacccccgc | gagcgagggc | gtcgagggcc | tcgcgcatct ggcgatcctc |
| 78241 | cgcctccacc | ctaatctctt | cgccacgggc | aaatttggcc | agagcctgga ctctatacag |
| 78301 | aagcggttct | gggtgcgtcg | gggtggcggg | ggcaaaaagg | gtgtccgggt gggcctgcga |
| 78361 | gcgctccaga | agccactcgc | cgaggcgtgt | atacagattg | gccggcgggg ccgcgcgaag |
| 78421 | ctgcagctcc | aggtccgcga | gttcccgta  | aaaggcgtcc | gtctcccgaa tgacatccct |
| 78481 | agccacaagg | atcagcttcg | ccagcgccga | agagagtttt | cgtccagcac |
| 78541 | gtgctggacg | aggggcagat | gggcggccac | gtcggccagg | ctcaggcgcg tggaggccag |
| 78601 | aaagtccccc | acggccgttt | tccggggcag | catgctcagg | gtaaactcca gcagggcggc |
| 78661 | ggcggggccg | gccacccccgg | cctgggtgtg | cgtccgggcc | ccgttctcga tgagaaaggc |
| 78721 | gaggacgcgt | tcaaagaaaa | aaataacaca | gagctccagc | agcccggag  aagccggata |
| 78781 | cggcgaccgt | aaggcgctga | tggtgagccg | cgaacacgcg | gcgacctcgc gggccagggt |

Sequence Listing

```
78841  ggcggagcac gcggtgaact taaccgccgt ggcggccacg tttgggtggg cctcgaacag
78901  ctgggcgagg tctgcgcccg ggggctcggg tgagcggcga gtcttcagcg cctcgagggc
78961  ctgtgaggac gccggaacca tgggcccgtc gtcctcgccg gcctcggcga ccggcggccc
79021  ggccgggtcg ggggtgccg aggcgaggac aggctccgga acggaggcgg ggaccggcgg c
79081  cccgacgggg gttttgcctt tgggggtgga tttcttcttg gttttggcag gggggggccga
79141  gcgtttcgtt ttctccccg aagtcaggtc ttcgacgctg gaaggcggag tccaggtggg
79201  tcggcggcgc ttgggaaggc cggccgagta gcgtgcccgg tgccgaccaa cgggacgac
79261  gcccatctcc aggacccgca tgtcgtcgtc atcttcttcg gccgcctctg cggcggggt
79321  cttggggggcg gagggaggcg gtggtgggat cgcggagggt gggtcggcgg agggggggatc
79381  cgtgggtggg gtacccttta gggccaccgc ccatacatcg tcgggcgccc gattcgggcg
79441  cttggcctct ggttttgccg acggaccggc cgtccccgg gatgtctcgg aggccctgtc
79501  gtcgcgacgg gcccgggtcg gtggcggca ctgggcggct gtgggcgggt gtggccccgg
79561  ccccccctccc ccctccgggg ggcccacgcg gacgcaggcg tccccaggcc cgcgatctc
79621  gccccgcagg gggtgcgtga tggcacgcg ccgttcgctg aacgcttcgt cctgcatgta
79681  agtctcgctg gccccgtaaa gatgcagagc cgcggccgtc aagtccgcag gagccgcggg
79741  ttccggggccc gacggcacga aaaacaccat ggctcccgcc caccgtacgt ccgggcgatc
79801  gcgggtgtaa tacgtcaggt atggatacat gtccccgcc cgcactttgg cgatgaacgc
79861  ggggggtgccc tccggaaggc catgcgggtc aaaaaaggtat gcggtgtcgc cgtccctgaa
79921  cagccccatc cctaggggggc caatggttag gagcgtgtac gacagggggc gcagggccca
79981  cgggccggcg aagaacgtgt gtgcggggca ttgtgtctcc agcaggcctg ccgcgggctc
80041  cccgaagaag cccacctcgc cgtatacgcg cgagaagaca cagcgcagtc cgccgcgcgc
80101  ccctgggtac tcgaggaagt tggggagctc gacgatcgaa cacatgcgcg cggggcccagg
80161  gcccgcagtc gcgcgcgtcc actcgcccc ctcgaccaaa catccctcga tggcctccgc
80221  ggacagaacg tcgcgagggc ccacatcaaa tatgaggctg agaaaggaca gcgacgagcg
80281  catgcacgat accgaccccc ccggctccag gtcgggcgcg aactggttcc gagcaccggt
80341  gaccacgatg tcgcgatccc ccccgcgttc catcgtgag tgcggtgggg tgcccgcgat
80401  catatgtgcc ctgcgggcca gagacccggc ctgtttatgg accggacccc cggggttagt
80461  gttgtttccg ccacccacgc ccccgtacca tggcccccggt tccctgatt aggctacgag
80521  tcgcggtgat cgcttcccaa aaaccgagct gcgtttgtct gtcttggtct tcccccccc
80581  cagcccgcac accataacac cgagaacaac acacggggt gggcggaaca taataaagct
80641  ttattggtaa ctagttaacg gcaagtccgt gggtggcgcg acggtgtcct ccgggatcat
80701  ctcgtcgtcc tcgacggggg tgttggaatg aggcgcctcc tcgcggtcca cctggcgtgg
80761  gccgtgccca taggcctccg gcttctgtgc gtccatgggc gtaggcgcgg ggagactgtt
80821  tccggcgtcg cggacctcca ggtccctggg agcctccggt ccggctaacg gacgaaacgc
80881  ggaagcgcga aacacgccgt cggtgacccg caggagctcg ttcatcagta accaatccat
80941  actcagcgta acggccagcc cctggcgaga cagatccacg gagtccggaa ccgcggtcgt
81001  ctggcccagg gggccgaggc tgtagtcccc ccaggcccct aggtcgcgac ggctcgtaag
81061  cacgacgcgg tcggccgcgg ggctttgcgg gggggcgtcc tcgggcgcat gcgccattac
81121  ctctcggatg gccgcggcgc gctggtcggc cgagctgacc aagggcgcca cgaccacggc
81181  gcgctccgtc tgcaggccct tccacgtgtc gtggagttcc tggacaaact cggccacggg
81241  ctcgggtccc gcggccgcgc gcgcggcttg atagcaggcc gacgacgcc gccagcgcgc
81301  tagaaactga cccatgaaac aaaaccccggg gacctggtct cccgacagca gcttcgacgc
81361  ccgggcgtga atgccggaca cgacggacga aaaccgtga atttcgcgcc ggaccacggc
81421  cagcacgttg tcctcgtgcg cacctgggc cgccagctcg tcgcacaccc ccaggtgcgc
81481  cgtggttcg gtgatgacgg aacgcaggct cgcgagggac gcgaccaggc cgcgcttgcc
81541  gtcgtgatac atgctgctgt actgactcac cgcgtccccc atggcctcgg ggggccaggg
81601  ccccaggcgg tcgggcgtgt ccccgaccac cgcatacagg cggcgcccgt cgctctcgaa
81661  ccgacactcg aaaaaggcgg agagcgtgcg catgtgcagc cgcagcagca cgatggcgtc
81721  ctccagttgg cgaatcaggg ggtcggcgcg ctcggcgagg tcctgcagca ccccccgagc
81781  agccagggcg tacatgctaa tcaacaggag gctggtgccc acctcggggg gcgggggggg
81841  ctgcagttgg accaggggcc gcagctgctc gacggcaccc ctggagatca cgtacagctc
81901  ccggagcagc tgctctatgt tgtcggccat ctgcatagtg gggccgaggc cgccccgggc
81961  ggccggttcg aggagagtga tcagcgcgcc cagtttggtg cgatggccct cgaccgtggg
82021  gagatagccc agcccaaagt cccgggccca ggccaacaca cgcagggcga actcgaccgg
82081  gcgggaagg taggccgcgc tacacgtggc cctcagcgcg tccccaacca ccagggccag
82141  aacgtagggg acgaagcccg ggtcggcgag gacgttgggg tgaatgccct cgagggcggg
82201  gaagcggatc tgggtcgccg cggccaggtg gacagagggg gcatggctgg gctgcccgac
82261  ggggagaagc gcggacagcg gcgtggcccg ggtggtgggg gtgatgtccc agtgggtctg
82321  accatacacg tcgatccaga tgagcgccgt ctcgcggaga aggctggggtt gaccggaact
82381  aaagcggcgc tcggccgtct caaactccccc cacgagcgcc cgccgcaggc tcgccagatg
82441  ttccgtcggc acggccggcc ccatgatacg cgccagcgtc tggctcagaa cgccccccga
82501  caggccgacc gcctcacaga gccgcccgtg cgtgtgctcg ctggcgccct ggaccgcct
82561  gaaagttttt acgtagttgg catagtaccc gtattcccgc gccagaccaa acacgttcga
82621  ccccgcgagg gcaatgcacc caaagagctg ctggacttcg ccgagtccgt ggccggcggg
82681  cgtccgcgcg gggacgcccg ccgcagaaa ccctccagg gccgaaaggt agtgcgtgca
82741  gtgcgagggc gtgaaccccag cgtcgatcag ggtgttgatc accacggagg gcgaattggt
82801  attctggatc aacgtccacg tctgctgcag cagagccagc agccgctgt gggcgccgc
82861  ggagggctgc tccccgagct gcagcaggct gggacggca ggctggaaga ctgccagtgc
82921  cgacgaactc aggaacggca cgtcgggatc aaaacacgcc acgtccgtcc gcacgcgcgc
82981  cattagcgtc ccggggggcg cacaggccga gcgcgggctg acgcggctga gggccgtcga
83041  cacgcgcacc tcctcgcggc tgcgaaccat cttgttggcc tccagtggcg gaatcattat
83101  ggccgggtcg atctcccgca cggtgtgctg aacaggggcg gcgggaccac
83161  agccccccgc tcgggggtcg tcaggtactc gtccaccagg gccaacgtaa agagggcccg
83221  tgtgagggga gtgagggtcg cgtcgtctat gcgctggagg tgcgccgaga acagcgtcac
83281  ccgattactc accagggcca agaaccggag gccctcttgc acgaacgggg cggggaagag
83341  caggctgtac gccggggtgg taaggttcgc gctgggctgc cccaacggga ccggcgccag
83401  cttgagcgac gtctccccaa gggcctcgat ggaggtccgc gggctcatgg ccaagcagct
```

```
83461  cttggtgacg gtttgccagc ggtctatcca ctccacggcg cactggcgga cgcggaccgg
83521  ccccagggcc gccgcggtgc gcaggccggc ggactccagc gcatgggacg tgtcggagcc
83581  ggtgaccgcg aggatggtgt ccttgatgac ctccatctcc cggaaggcct ggtcggggc
83641  ctcggggaga gccaccacca agcggtgtac gagcaacccg gggaggttct cggccaagag
83701  cgccgtctcc ggaagccgt gggcccggtg gagcgcgcac aggtgttcca gcagcggccg
83761  ccagcatgcc cgcgcgtctg ccggggcgat ggccgttccc gacaacagaa acgccgccat
83821  ggcggcgcgc agcttggccg tggccagaaa cgccgggtcg tccgccccgt ttgccgtctc
83881  ggccgtgggg gttggcggtt ggcgaaggcc ggctaggctc gccaataggc gctgcatagg
83941  tccgtccgag ggcggaccgg cgggtgaggt cgtgacgacg ggggcctcgg acgggagacc
84001  gcggtctgcc atgacgcccg gctcgcgtgg gtgggggaca gcgtagacca acgacgagac
84061  cgggcgggaa tgactgtcgt gcgctgtagg gagcggcgaa ttatcgatcc cccgcggccc
84121  tccaggaacc ccgcaggcgt tgcgagtacc ccgcgtcttc gcggggtgtt atacggccac
84181  ttaagtcccg gcatcccgtt cgcggaccca ggccggggg attgtccgga tgtgcgggca
84241  gcccggacgg cgtgggttgc ggactttcgg cggggcggcc caaatggccc tttaaacgtg
84301  tgtatacgga cgcgccgggc cagtcggcca acacaaccca ccggaggcgg tagccgcgtt
84361  tggctgtggg gtgggtggtt ccgccttgcg tgagtgtcct ttcgaccccc cccctccccc
84421  gggtcttgct aggtcgcgat ctgtggtcgc aatgaagacc aatccgctac ccgcaaccc
84481  ttccgtgtgg ggcgggagta ccgtggaact cccccccacc acacgcgata ccgcggggca
84541  gggcctgctt cggcgcgtcc tgcgccccc gatctctcgc cgcgacggcc cagtgctccc
84601  caggggtcg ggaccccgga gggcggccag cacgcgtgtg ttgcttggcc tggacggcac
84661  agacgcgccc cctggggcgc tgaccccaa cgacgatacc gaacaggccc tggacaagat
84721  cctgcgggc accatgcgcg gggggcggc cctgatcggc tccccgcgcc atcatctaac
84781  ccgccaagtg atcctgacgg atctgtgcca acccaacgcg gatcgtgccg ggacgctgct
84841  tctgcgctg cggcaccccg ccgacctgcc tcacctggcc caccagccgc cccccgccagg
84901  ccggcagacc gagcggctgg gcgaggcctg gggccagctg atggaggcga ccgccctggg
84961  gtcggggcga gccgagagcg ggtgcacgcg cgcgggcctc gtgtcgttta acttcctggt
85021  ggcggcgtgt gccgcctcgt acgacgcgcg cgacgcgcc gatgcggtac gggcccacgt
85081  cacggccaac taccgcggga cgcgggtggg gcgcgtcg gatcgttttt ccgagtgtct
85141  gcgcgccatg gttcacacgc acgtcttccc ccacgaggtc atgcggtttt tcgggggct
85201  ggtgtcgtgg gtcacccagg acgagctagc gagcgtcacc gccgtgtgcg ccggggccca
85261  ggaggcggcg cacaccgcc acccgggccg gccccgctcg gccgtgatcc tcccggcgtg
85321  tgcgttcgtg gacctggacg ccgactgggg gctgggggc cgggcgcgg cgtttctgta
85381  cctggtattc acttaccgcc agcgccggga ccaggagctg tgttgtgt acgtgatcaa
85441  gagccagctc ccccgcgcg ggttggagcc ggccctggag cggctgtttg ggcgcctccg
85501  gatcaccaac acgattcacg gcaccgagga catgacgccc ccggcccaa accgaaaccc
85561  cgacttcccc ctcgcgggcc tggccgccaa tccccaaacc ccgcgttgct ctgctggcca
85621  ggtcacgaac ccccagttcg ccgacaggct gtaccgctgg cagccggacc tgcggggcg
85681  ccccaccgca cgcacctgta cgtacgccgc ctttgcagag ctcggcatga tgcccgagga
85741  tagtccccgc tgcctgcacc gcaccgagcg ctttggggcg gtcagcgtcc ccgttgtcat
85801  cctggaaggc gtggtgtggc gccccggcga gtggcgggcc tgcgcgtgag cgtagcaaac
85861  gccccgccca cacaacgctc cgcccccaac cccttcccg ctgtcactcg ttgttcgttg
85921  acccggacgt ccgccaaata aagccactga aacccgaaac gcgagtgttg taacgtcctt
85981  tgggcgggag gaagccacaa aatgcaaatg ggatacatgg aaggaacaca ccccgtgac
86041  tcaggacatc ggcgtgtcct tttgggttc actgaaactg gccgcgcgcc caccctgcg
86101  cgatgtggat aaaaagccag cgcgggtggt ttagggtacc acaggtgggt gcttggaaa
86161  cttgtcggtc gccgtgctcc tgtgagcttg cgtccctccc cggtttcctt tgcgctcccg
86221  ccttccggac ctgctctcgc ctatcttctt tggctctcgg tgcgattcgt caggcagtgg
86281  ccttgtcgaa tctcgacccc accactcgcc ggaccgccg acgtcccctc tcgagcccgc
86341  cgaaacccgc cgcgtctgtt gaaatggcca gccgcccgc tgcatcctct ccgtcgaag
86401  cgcgggcccc ggttgggga caggaggccg gcggcccag cgcagccacc caggggagg
86461  ccgccgggc ccctctcgcc cgcggccacc acgtgtactg ccagccagtc aatggcgtga
86521  tggtgctttc cgacaagacg cccgggtccg cgtcctaccg catcagcgat agcaactttg
86581  tccaatgtgg ttccaactgc accatgatca tagacggaga cgtggtgcgc gggcgcccc
86641  aggacccggg ggccgcggca tccccgctc ccttcgttgc ggtgacaaac atcggagccg
86701  gcagcgacgg cgggaccgcc gtcgtggcat tcgggggaac cccacgtcgc tcggcgggga
86761  cgtctaccgg tacccagacg accgacgtcc ccaccgaggc ccttgggggc cccctcctc
86821  ctccccgctt caccctgggt ggcggctgtt gttcctgtcg cgacacacgg cgccgctctg
86881  cggtattcgg gggggagggg gatcccgtcg gccccgcgga gttcgtctcg gacgaccggt
86941  cgtccgattc cgactcggat gactcggagg acaccgactc ggagacgctg tcacacgcct
87001  cctcggacgt gtccggcggg gccacgtacg acgacgccct tgactccgat tcgtcatcgg
87061  atgactccct gcagatagat ggccccgtgt gtcgcccgtg gagcaatgac accgcgcccc
87121  tggatgtttg ccccgggacc cccggcccgg gcgccgaccgc cggtggtccc tcagcggtag
87181  acccacacgc accgacgcca ggggccggcg ctggtcttgc ggccgatccc gccgtggccc
87241  gggacgacgc ggaggggctt tcggacccc ggccacgtct gggaacggc acggcctacc
87301  ccgtcccct ggaactcacg cccgagaacg cggaggccgt ggcgcgcttt ctgggagatg
87361  ccgtgaaccg cgaaccccgcg ctcatgctgg agtactttg ccggtgcgcc cgcgaggaaa
87421  ccaagcgtgt cccccccagg acattctgca gccccctcg cctcacggag gacgactttg
87481  ggcttctcaa ctacgcgctc gtggagatgc agcgcctgtg tctgacgtt cctccggtcc
87541  tgccgaacgc atacatgccc tattatctca gggagtatgt gacgcggctg gtcaacgggt
87601  tcaagccgct ggtgagccgg tccgctcgcc tttaccgcat cctgggggtt ctggtgcacc
87661  tgcggatccg gacccgggag gcctcctttg aggagtggct gcgatccaag gaagtggccc
87721  tggacttggg cctgacggaa aggcttcgcg agcacgaagc ccagtggtg atcctgaccc
87781  aggctctgga ccattacgac tgtctgatcc acagcacacc gcacacgctg tcgagcggg
87841  ggctgcaatc ggccctgaag tatgaggagt tttacctaaa gcgctttggc gggcactaca
87901  tggagtccgt cttccagatg tacacccgca tcgccggctt tttggcctgc cgggccacgc
87961  gcggcatgcg ccacatcgcc ctggggcgag agggggtcgtg gtgggaaatg ttcaagttct
88021  ttttccaccg cctctacgac caccagatcg taccgtcgac ccccgccatg ctgaacctgg
```

Sequence Listing

```
88081  ggacccgcaa ctactacacc tccagctgct acctggtaaa cccccaggcc accacaaaca
88141  aggcgaccct gcgggccatc accagcaacg tcagcgccat cctcgcccgc aacgggggca
88201  tcgggctatg cgtgcaggcg tttaacgact ccggcccggg gaccgctagc gtcatacccg
88261  ccctcaaggt cctcgactcg ctggtggcgg cgcacaacaa agagagcgcg cgtccaaccg
88321  gcgcgtgcgt gtacctggag ccgtggcaca ccgacgtgcg ggccgtgctc cggatgaagg
88381  gggtcctcgc cggcgaagag gcccagcgct gcgacaatat cttcagcgcc ctctggatgc
88441  cagacctgtt tttcaagcgc ctgattcgcc acctggacgg cgagaagaac gtcacatgga
88501  ccctgttcga ccgggacacc agcatgtcgc tcgccgactt tcacggggag gagttcgaga
88561  agctctacca gcacctcgag gtcatggggt tcggcgagca gatacccatc caggagctgg
88621  cctatggcat tgtgcgcagt gcggccacga ccgggagccc cttcgtcatg ttcaaagacg
88681  cggtgaaccg ccactacatc tacgacaccc aggggggcggc catcgccggc tccaacctct
88741  gcaccgagat cgtccatccg gcctccaagc gatccagtgg ggtctgcaat ctgggaagcg
88801  tgaatctggc ccgatgcgtc tccaggcaga cgtttgactt tgggcggctc cgcgacgccg
88861  tgcaggcgtg cgtgctgatg gtgaacatca tgatcgacag cacgctacaa cccacgcccc
88921  agtgcacccg cggcaacgac aacctgcggt ccatgggaat cggcatgcag ggcctgcaca
88981  cggcctgcct gaagctgggg ctggatctgg agtctgtcga atttcaggac ctgaacaaac
89041  acatcgccga ggtgatgctg ctgtcggcga tgaagaccag caacgcgctg tgcgttcgcg
89101  gggcccgtcc cttcaaccac tttaagcgca gcatgtatcg cgccggccgc tttcactggg
89161  agcgctttcc ggacgcccgg ccgcggtacg agggcgagtg ggagatgcta cgccagagca
89221  tgatgaaaca cggcctgcgc aacagccagt ttgtcgcgct gatgcccacc gccgcctcgg
89281  cgcagatctc ggacgtcagc gagggctttg cccccctgtt caccaacctg ttcagcaagg
89341  tgacccggga cggcgagacg ctgcgcccca acacgctcct gctaaaggaa ctgaacgca
89401  cgtttagcgg gaagcgcctc ctggaggtga tggacagtct cgacgccaag cagtggtccg
89461  tggcgcaggc gctcccgtgc ctggagccca cccaccccct ccggcgattc aagaccgcgt
89521  ttgactacga ccagaagttg ctgatcgacc tgtgtgcgga ccgcgccccc tacgtcgacc
89581  atagccaatc catgacctg tatgtcacgg agaaggcgga cgggaccctc ccagcctcca
89641  ccctggtccg ccttctggtc cacgcatata agcgcggact aaaaacaggg atgtactact
89701  gcaaggttcg caaggcgacc aacagcgggg tcttgggcg cgacgacaac attgtctgca
89761  cgagctgcgc gctgtgaccg acaaacccc tccgcccag gcccgccgcc actgtcgtcg
89821  ccgtcccacg cgctccccg ctgccatgga ttccgcggcc ccagccctct ccccgctct
89881  gacggcccat acgggccaga gcgcgccggc ggacctggcg atccagattc caaagtgccc
89941  cgaccccgag aggtacttct acacctccca gtgtcccgac attaaccacc tgcgctccct
90001  cagcatcctt aaccgctggc tggaaaccga gcttgtttc gtgggggacg aggaggacgt
90061  ctccaagctt tccgagggcg agctcagctt ttaccgcttc ctcttcgctt tcctgctcggc
90121  cgccgacgac ctggttacgg aaaacctggg cggcctctcc ggcctgtttg agcagaagga
90181  cattctccac tactacgtgg agcaggaatg catcgaagtc gtacactcgc gcgtgtacaa
90241  catcatccag ctggtgcttt ttcacaacaa cgaccaggcg cccgcgagt acgtggccgg
90301  caccatcaac cacccggcca tccgcgccaa ggtggactgg ctggaagcgc gggtgcggga
90361  atgcgcctcc gttccggaaa agttcatcct catgatcctc atcgagggca tctttttttgc
90421  cgcctcgttt gccgccatcg cctaccttcg caccaacaac cttctgcggg tcacctgcca
90481  gtcaaacgac ctcatcagcc gggacgaggc cgtgcacacg aaggcctcgt gttacatcta
90541  caacaactac ctcggcgggc acgccaagcc cccgcccgac cgcgtgtacg ggctgttccg
90601  ccaggcggtc gagatcgaga tcggatttat ccgatcccag gcgccgacgg acagccatat
90661  cctgagcccg gcggcgctgg cggccatcga aaactacgtg cgattcagcg cggatcgcct
90721  gttgggcctt atccacatga agccactgtt ttccgcccca cccccgacg ccagctttcc
90781  gctgagcctc atgtccaccg acaaacacac caatttttt gagtgtcgca gcacctccta
90841  cgccggggcg gtcgtcaacg atctgtgagg gtcgcggcgc gcttctaccc gtgtttgccc
90901  ataataaacc tctgaaccaa actttgggtc tcattgtgat tcttgtcagg acgcgggggg
90961  tgggagagga taaaaggcgg cgcaaaaagc agtaaccagg tccgtccaga ttctgagggc
91021  ataggatacc ataattttat tggtgggtcg tttgttcggg gacaagcgcg ctcgtctgac
91081  gtttgggcta ctcgtcccag aatttggcca ggacgtcctt gtagaacgcg ggtgggggggg
91141  cctgggtccg cagctgctcc agaaacctgt cggcgatatc aggggccgtg atatgccggg
91201  tcacaataga tcgcgccagg ttttcgtcgc gggatgtcctg gtagataggc aggcgtttca
91261  gaagagtcca cggccccgc tccttgggcc cgataagcga tatgacgtac ttaatgtagc
91321  ggtgttccac cagctcgtg atggtcatgg gatcggggag ccagtccagg gactctgggg
91381  cgtcgtggat gacgtggcgt cgccggctgg ccacataact gcggtgctct tccagcagct
91441  gcgcgttcgg gacctggacg agctcggggcg gggtgagtat ctccgaggag gacgacctgg
91501  ggccgggggtg gcccccggta acgtcccggg gatccagggg gaggtcctcg tcgtcttcgt
91561  atccgccggc gatctgttgg gttagaattt cggtccacga gacgcgcatc tcggtgccgc
91621  cggcggccgg cggcaaaggg ggcctggttt ccgtggagcg cgagctggtg tgttcccggc
91681  ggatggcccg ccgggtctga gagcgactcg gggggggtcca gtgacattcg cgcagcacat
91741  cctccacgga ggcgtaggtg ttattgggat ggaggtcggt gtggcagcgg acaaagaggg
91801  ccaggaactg ggggtagctc atcttaaagt actttagtat atcgcgacag ttgatcgtgg
91861  gaatgtagca ggcgctaata tccaacacaa tatcacagcc catcaacagg aggtcagtgt
91921  ctgtggtgta cacgtacgcg accgtgttgg tgtgatagag gttggcgcag gcatcgtccg
91981  cctccagctg acccgagtta atgtaggcgt accccagggc ccggagaacg cgaatacaga
92041  acagatgcgc cagacgcagg gccggcttcg agggcgggcc ggacggcagc gcggctccgg
92101  acccggccgt cccccgggtc cccgaggcca gagaggtgcc gcgccggcgc atgttggaaa
92161  aggcagagct gggtctggag tcggtgatgg gggaaggcgg tggagaggcg tccacgtcac
92221  tggcctcctc gtccgtccgg cattgggccg tcgtgcgggc caggatgcc ttggctccaa
92281  acacaaccgg ctccatacaa ttgacccgc gatcggtaac gaagatgggg aaaagggact
92341  tttgggtaaa cacctttaat aagcgacaga ggcagtgtag cgtaatgcc tcgccggtcgt
92401  aactggggta tcggcgctga tatttgacca ccaacgtgta catgacgttc cacaggtcca
92461  cggcgatggg ggtgaagtac ccggccgggg ccccaaggcc ctggcgcttg accagatggt
92521  gtgtgtgggc aaacttcatc atcccgaaca aacccatgtc aggtcgattg taactgcgga
92581  tcggcctaac taaggcgtgg ttggtgcgac ggtccgggac acccgagcct gtctctctgt
92641  gtatggtgac ccagacaaca acaccgacac aagaggacaa taatccgtta ggggacgctc
```

```
                          Sequence Listing
92701  tttataattt cgatggccca actccacgcg gattggtgca gcaccctgca tgcgccggtg
92761  tgggccaaac ttcccccgc  tcattgcctc ttccaaaagg gtgtggccta acgagctggg
92821  ggcgtattta atcaggctag cgcggcgggc ctgccgtagt ttctggctcg gtgagcgacg
92881  gtccggttgc ttgggtcccc tggctgccag caaaacccca ccctcgcagc ggcatacgcc
92941  ccctccgcgt cccgcacccg agacccggc  ccggctgccc tcaccaccga agcccacctc
93001  gtcactgtgg ggtgttccca gcccgcattg ggatgacgga ttccctggc  ggtgtggccc
93061  ccgcctcccc cgtggaggac gcgtcggacg cgtccctcgg gcagccggag gagggggcgc
93121  cctgccaggt ggtcctgcag ggcgccgaac ttaatggaat cctacaggcg tttgccccgc
93181  tgcgcacgag ccttctggac tcgcttctgg ttatgggcga ccggggcatc cttatccata
93241  acacgatctt tggggagcag gtgttcctgc ccctggaaca ctcgcaattc agtcggtatc
93301  gctggcgcgg acccacgcg  gcgttcctgt ctctcgtgga ccagaagcgc tccctcctga
93361  gcgtgtttcg cgccaaccag tacccggacc tacgtccggt ggagttggcg atcacgggcc
93421  aggccccgtt tcgcacgctg gttcagcgca tatggacgac gacgtccgac ggcgaggccg
93481  ttgagctagc cagcgagacg ctgatgaagc gcgaactgac gagctttgtg gtgctggttc
93541  cccagggaac ccccgacgtt cagttgcgcc tgacgaggcc gcagctcacc aaggtcctta
93601  acgcgaccgg ggccgatagt gccacgccca ccacgttcga gctcgggcgt aacggcaaat
93661  tttccgtgtt caccacgagt acctgcgtca catttgctgc ccgcgaggag ggcgtgtcgt
93721  ccagcaccag cacccaggtc cagatcctgt ccaacgcgct caccaaggcg ggccaggcgg
93781  ccgccaacgc caagacggtg tacggggaaa atacccatcg caccttctct gtggtcgtcg
93841  acgattgcag catgcgggcg gtgctccggc gactgcaggt cgccggggc  accctcaagt
93901  tcttcctcac gaccccgtc  cccagtctgt gcgtcaccgc caccggtccc aacgcggtat
93961  cggcggtatt tctcctgaaa ccccagaaga tttgcctgga ctggctgggt catagccagg
94021  ggtctccttc agccgggagc tcggcctccc gggcctctgg gagcgagcca acagacagcc
94081  aggactccgc gtcggacgcg gtcagccacg gcgatccgga agactctgat ggcgctgccc
94141  gggcgggaga ggcggggccc tcgcacgcct gtccgatgcc gtcgtcgacc acgcgggtca
94201  ctcccacgac caagcggggg cgctcggggg gcgaggatgc gcgcgcggac acggccctaa
94261  agaaacctaa gacggggtcg cccaccgcac ccccgcccac agatccagtc ccctggaca
94321  cggaggacga ctccgatgcg gcggacggga cggcggcccg tcccgccgct ccagacgccc
94381  ggagcggaag ccgttacgcg tgttactttc gcgacctccc gaccggagaa gcaagccccg
94441  gcgccttctc cgccttccgg gggggcccc  aaaccccgta tggttttgga ttccctgac
94501  ggggcggggc cttggcgccc gcccaactct cgcaccatcc cggttaatg  taaataaact
94561  tggtattgcc caacactctc ccgcgtgtcg cgtgtggttc atgtgtgtgc ctggcgtccc
94621  ccaccctcgg gttcgtgtat ttcctttccc tgtccttata aaagccgtat gtggggcgct
94681  gacggaacca ccccgcgtgc catcacggcc aaggcgcggg atgctccgca acgacagcca
94741  ccggggccgcg tccccggagg acggccaggg acgggtcgac gacggacggc cacacctcgc
94801  gtgcgtgggg gccctggcgc ggggggttcat gcatatctgg cttcaggccg ccacgctggg
94861  ttttgcggga tcggtcgtta tgtcgccgg  gccgtacgg  aatgccgcgt ctggggcgtt
94921  cgccgtcggg tgcgccgtgc tgggctttat gcgcgcaccc cctccctcg  cgcggcccac
94981  cgcgcggata tacgcctggc tcaaactggc ggccggtgga gcggcccttg ttctgtggag
95041  tctcggggag cccggaacgc agccgggggc cccgggcccg gccacccagt gcctggcgct
95101  gggcgccgcc tatgccgcc  tcctggtgct cgccgatgac gtctatccgc tcttttctcct
95161  cgcccccggg ccctgttccg tcggcaccct gggggatggtc tcggcgggc  tgacgatcgg
95221  aggcagcgcg cgctactggt ggatcggtgg gcccgccgcg gccgccttgg ccgcggcggt
95281  gttggcgggc ccgggggcga ccaccgccag ggactgcttc tccagggcgt gccccgacca
95341  ccgccgcgtc tgcgtcatcg tcgcaggcga gtctgtttcc cgccgcccc  cggaggaccc
95401  agagcgaccc ggggaccccg ggccaccgtc ccccccgaca ccccaacgat cccaggggcc
95461  gccggccgat gaggtcgcac cggccgggt  agcgcggccc gaaaacgtct gggtgcccgt
95521  ggtcaccttt ctggggcgg  gcgcgctcgc cgtcaagacg gtgcgagaac atgcccggga
95581  aacgccgggc ccgggcctgc cgctgtggcc ccaggtgttt ctcggaggcc atgtggcggt
95641  ggccctgacg gagctgtgtc aggcgcttat gccctgggac cttacggacc cgctgctgtt
95701  tgttcacgcc ggactgcagg tcatcaacct cgggttggtg tttcggtttt ccgaggttgt
95761  cgtgtatgcg gcgctagggg gtgccgtgtg gatttcgttg gcgcaggtgc tggggctccg
95821  gcgtcgcctg cacaggaagg accccgggga ttgggcccgg ttggccgcga cgcttcgaggg
95881  cctcttcttc tccgtgtacg cgctgggggtt tggggtgggg gcgctgctgt gccctccggg
95941  gtcaacggc  gggtggtcgg gcgattgata tattttttcaa taaaaggcat tagtcccgaa
96001  gaccgccggt gtgtgatgat ttcgccataa cacccaaacc ccggatgggg cccgggtata
96061  aattccgaa  ggggacacgg gctaccctca ctaccgaggg cgcttggtcg ggaggccgca
96121  tcgaacgcac accccccatcc ggtggtccgt gtggaggtcg tttttcagtg cccggtctcg
96181  ctttgccggg aacgctagcc gatccctcgc gaggggagg  cgtcgggcat ggccccggg
96241  cgggtgggcc ttgccgtggt cctgtgagc  ctgttgtggc tcgggcggg  ggtggccggg
96301  ggctcggaaa ctgcctccac cgggccacg  atcaccgcgg gagcggtgac gaacgcgagc
96361  gaggccccca catcggggtc cccggggtca gccgccacga tacggggcgt gggtgcgcgt ccgcatgttc
96421  accccaaacc ccaacaatgt cacacaaaac aaaaccaccc ccaccgagcc ggccagcccc
96481  ccaacaaccc caagcccac  ctccacgccc aaaagccccc ccacgtccac ccccgacccc
96541  aaacccaaga acaacaccac ccccgccaag tcgggccgcc ccactaaacc cccccgggccc
96601  gtgtggtgcg accgccgcga cccattggcc cggtacgcct cgcgggtgca gatccgatgc
96661  cggtttcgga attccacccg catggagttc cgcctccaga tatggcgtta ctccatgggt
96721  ccgtcccccc caatcgctcc ggctcccgac ctagaggagg tcctgacgaa catccaccgcc
96781  ccacccgggg gactcctggt gtacgacagc gcccccaacc tgacggaccc ccacgtgctc
96841  tgggcggagg gggccggccc gggcgccgac cctccgttgt attctgtcac cgggccgctg
96901  ccgacccagc ggctgattat cggcgaggtg acgcccgcga cccagggaat gtattacttg
96961  gcctggggc  ggatgacag  ccgcacgag  tacggcgcgt gggtgcgcgt ccgcatgttc
97021  cgcccccgt  ctctgaccct ccagcccac  gcggtgatgg aggtgcagcc gttcaaggcg
97081  acgtgcacgg ccgccgccta ctacccgcgt aacccccgtgg agtttgtctg gttcgaggac
97141  gaccgccagg tgtttaaccc gggccagatc gacacgcaga cgcacgagca ccccgacggg
97201  ttcaccacag tctctaccgt gacctccgag gctgtcggcg gccaggtccc ccgcgggacc
97261  ttcacctgcc agatgacgtg gcaccgcgac tccgtgatgt tctcgcgacg caatgccacc
```

Sequence Listing

```
 97321 gggctggccc tggtgctgcc gcggccaacc atcaccatgg aatttggggt ccggcatgtg
 97381 gtctgcacgg ccggctgcgt ccccgagggc gtgacgtttg cctggttcct ggggacgac
 97441 ccctcaccgg cggctaagtc ggccgttacg gcccaggagt cgtgcgacca ccccgggctg
 97501 gctacggtcc ggtccaccct gcccatttcg tacgactaca gcgagtacat ctgtcggttg
 97561 accggatatc cggccgggat tcccgttcta gagcaccacg gcagtcacca gcccccaccc
 97621 agggacccca ccgagcggca ggtgatcgag gcgatcgagt gggtggggat tggaatcggg
 97681 gttctcgcgg cgggggtcct ggtcgtaacg gcaatcgtgt acgtcgtccg cacatcacag
 97741 tcgcggcagc gtcatcggcg gtaacgcgag accccccgt tacctttta atatctatat
 97801 agtttggtcc ccctctatcc cgcccaccgc tgggcgctat aaagccgcca ccctctcttc
 97861 cctcaggtca tccttggtcg atcccgaacg cacacgcg tggagcaaaa cgcctccccc
 97921 tgagccgctt tcctaccaac acaacggcat gcctctgcgg gcatcggaac acgcctaccg
 97981 gccctgggc cccgggacac ccccatgcg ggctcggctc cccgccgcgg cctgggttgg
 98041 cgtcgggacc atcatcgggg gagttgtgat cattgccgcg ttggtcctcg tgccctcgcg
 98101 ggcctcgtgg gcactttccc catgcgacag cggatggcac gagttcaacc tcgggtgcat
 98161 atcctgggat ccgaccccca tggagcacga gcaggcggtc ggcggctgta gcgccccggc
 98221 gaccctgatc ccccgcgcgg ctgccaaaca gctggccgcc gtcgcacgcg tccagtcggc
 98281 aagatcctcg ggctactggt gggtgagcgg agacggcatt cgggcctgcc tgcggctcgt
 98341 cgacggcgtc ggcggtattg accagttttg cgaggagccc gcccttcgca tatgctacta
 98401 tccccgcagt cccgggggct ttgttcagtt tgtaacttcg acccgcaacg cgctggggct
 98461 gccgtgaggc gcgtgtactg cggtctgtct cgtctcctct tctccccttc cctccccctc
 98521 cgcatcccag gatcacaccg gccaacgagg gttggggggg tccggcacgg acccaaaata
 98581 ataaacacac aatcacgtgc gataaaaaga acacgcggtc ccctgtggtg ttttggtta
 98641 tttttattaa atctcgtcga caaacaggg gaaaggggcg tggtctagcg acggcagcac
 98701 gggcggaggc gttcaccggc tccggcgtcc ttcgcgttta agcttggtca ggaggggcgt
 98761 cagggcggcg acgttggtcg ggccgtcgtt ggtcagggcg ttggctcgat ggcgggcgag
 98821 gacgggcgag gggctcaacg gcgggggcgg gggtccggtg cggcccgggg ggaaaatag
 98881 ggcggatccc ccccagtcgt acaggggatt ttccgcctca atgtacgggg aggccggcgc
 98941 tgcattcgcc gtgttcacgc agacgttttc gtagacccgc atccatggta tttcctcgta
 99001 gacacgcccc ccgtcctcgc tcacggtctc gtatattgac tcgtcgtcct cgtaggggc
 99061 gtgccgttcg cgggccgagg cggcgtgggt ggcttttgcgg cgggcgtcgt cgtcgtcgtc
 99121 gtcggccgtc agatacgtgg cttccatctg gtcgggttct ccctccgggg cgggtcccca
 99181 cacccgtggc cgatcgaggc tccccagaga cgcgcgccgg acaagaaggg ggcacgtcgc
 99241 cgccggcggt cgcctgtcgg gtcccgcgac gttacgggcc gggaggcgcg gggcacctc
 99301 ccccatgtgc gtgtaatacg tggccggctg tgcggccgca gcggggggct cggcgaccgg
 99361 gtcgtccgca tccggaagcg ggggccccgc gccgtccgca cggcgcctcc ggaaccgccg
 99421 ggtggacggc gcggggtcg agtgtaggcg aggtcggggg aggggcgggg gctcgttgtc
 99481 gcgccgcgcc cgctgaatct tttcccgaca ggtcccaccc ccgcgcgcat gcccccccgg
 99541 gccgcgggcc atgtcgtccg ggggaggccc cgcggaccac gtcgtccggc gagacgccac
 99601 gagccgcagg atggactcgt agtggagcga cggcgccccg ctgcggagca gatccgcggc
 99661 cagggcggcc ccgaaccaag ccttgatgct caactccatc cgggcccagc tggggcggt
 99721 catcgtgggg aacaggggg cggtggtccg acagaaacgc tcctggctgt ccaccgcggc
 99781 ccgcagatac tcgttgttca ggctgtcggt ggcccagacg ccgtaccggg tgagggtcgc
 99841 gttgatgata tactgggcgt ggtgatggac gatcgacaga acctccaccg tggataccac
 99901 ggtatccacg gtcccgtacg taccgccgct ccgcttgccg gtctgccaca ggttggctag
 99961 gcacgtcagg tggcccagga cgtcgctgac cgccgccgtg agcgccatgc actgcatgga
100021 gccggtcgtg ccgctgggac cccggtccag atggcgcgcg aacgtttccg cgggcgcctc
100081 cgggctgccg ccgagcggga ggaaccggcg attggaggga ctcagccggt gacatacgtg
100141 cttgtccgtc gtccacagca tccaggacgc ccaccggtac agcacggaga cgtaggccag
100201 gagctcgtttg agccgcagtg cggtgtcggt gctggggcgg cttggtccg ccgggcgcat
100261 aaagaacatg tactgctgaa tccgatggag ggcgtcgcgc aggccggcca cggtggcggc
100321 gtacttggcc gccgcggccc cgctcttgaa cggggtgcgc gccagcagct ttggcgccag
100381 ggtgggccgc agcagcacgt gaaggctggg gtcgcagtcg cccacggggt cctcggggac
100441 gtccaggccg ctgggcacca ccgtctgcag gtacttccag tactgcgtga ggatgggcgg
100501 gctcaactgg ccgccgggca gctccacctc gcccagcgcc tgggtgcgg ccgaagcgta
100561 gtgccggatg tactcgtagt gcgggtcgct ggcgagcccg tccacgatca aactctcggg
100621 aaccgtgttg tgttgccgcg cggccaaccg gacgctgcga tcggtgcagg tcagaaacgc
100681 cggctgcgcg tcgtcggagc gctgccgcaa ggcgccacg gccgcgctaa ggagccccctc
100741 cggggtgggg agcagacacc cgccgaagat gcgccgctcg ggaacgcccg cgttgtcgcc
100801 gcggatcagg ttggcaggcg tcaggcaccg cgccagccgc agggagctcg cgccgcgcgt
100861 ccggcgctgc atggtgacgc ccgttcggtc gggacccgcc ggtcggagtt atgccgcgtc
100921 cagggccatc ggggcgcttt ttatcggag gagcttatgg gcgtggcggg cctcccagcc
100981 cggtcgcgcg cctccccgac acgtgcgccc ggccccctcg tctcccatca
101041 gcagtttcct aaactgggac atgatgtcca ccacgcggac ccgcgggccc aacacggacc
101101 cgccgcttac ggggcgggg gggaagggct ccaggtccttt gagcagaaag gcggggtctg
101161 ccgtcccgga cacggggcc cggggcgcgg aggaggcggg gcgcagatcc acgtgctccg
101221 cggccgcgcg gacgtccgcc cagaacttgg cggggtggt gcgcgcgtac aggggctggg
101281 tcgctcggag gacacacgcg tagcgcaggg gggtgtcagt gcccacctcg gggccgtga
101341 atccccgtc aaacgcggcc agtgtcacgc acgccaccac ggtgtccggca aagcccagca
101401 gccgctgcag gacgagcccg gcggccagaa tggcgccgt ggtcgcagcg tcgtcccggc
101461 gccggtgcgc gtcccgcac gcccgggcgt actttaaggt cactgtcgcc aggggccgtgt
101521 gcagcgcgta caccgcagcg cccagcacgg cgttgagccc gctgttggcg agcagccggc
101581 gcgctgcggt gtcgcccaac gctcgtgct cccccaccc cttcccaggg
101641 gcagggcgcg aaacagctcc tcccgcgcca cgtccgcaaa ggcggggtgg tgcacgtgcg
101701 ggtgcaggcg cgccccacg accaccgaga gccactggac cgtctgctcc gccatcaccg
101761 ccaacacatc cagcacgcgc cccaggaagg cggcctcccg cgtcaaaacg caccggacgg
101821 cgtcggatt gaagcggggcg agcagggccc cggtggccag gtacgtcatg cggccggcat
101881 agcgggcggc cacgcgacag tcgcggtcca gcagcgcgcg caccccgggc cagtacagca
```

```
101941  gggacccag  cgagctgcga  aacaccgcgg  cgtcgggcc   ggattggggg  gacactaacc
102001  ccccgcgct   cagtaacggc  acggccgcgg  ccccgacggg  acgcaacgcc  gtgaggctcg
102061  cgaactgccg  cctcagctcg  gcagccctgt  cgtccagtc   cgaccgcgc   gcctctgcgt
102121  gaaggcgcgt  cccgcacacc  caccgttga   tggccagcc   cacgacggca  tccgccaaaa
102181  agctcatcgc  ctgggcgggg  ctggttttg   ttcgacgatc  cgtcaggtca  agaatcccat
102241  cgcccgtgat  ataccaggcc  aacgcctcgc  cctgctgcag  ggtttggcgg  aaaaacaccg
102301  cggggttgtc  gggggaggcg  aagtgcatga  ccccacgcg   cgataacccg  aacgcgctat
102361  ccggacacgg  gtaaaacccg  gccggatgcc  ccagggctag  ggcggagcgc  acggactcgt
102421  cccacacggc  aacctgaggg  gccagtcgat  ccaacgggaa  tgccgccgg   agctccgggc
102481  ccggcacgcg  tccctccaga  acctccacct  tgggcgggga  acgggcccg   ccgccgtcct
102541  ccggcccgac  gtcttccggg  tagtcgtcct  cctcgtactg  cagttcctct  aggaacagcg
102601  gcgacggcgc  caccccgcgaa ccgccgaccc  gccccaaaat  agcccgccg   tcgacgggac
102661  ccaggtatcc  cccctgccg   gcctgcggag  gaccgcgggg  aacctcatca  tcatcgtcca
102721  ggcgaccgcg  caccgactgg  ctacggcc    catcgggcc   ggggcgctgc  cgggacgctc
102781  ggcgatggga  tgagggcggg  gcttccgacg  cgcgccgtcg  tcgggctcgc  gggccttccc
102841  gtcgacggcg  cacgggcggc  tcgtcgcccg  ccatctcctc  cagagcctct  agctcgctgt
102901  cgtcatcccc  gcggaacacc  gcacgcaggt  accccatgaa  ccccacccca  tcgcccgctg
102961  gctcgtccgc  cacgggcgag  gcgcgggggc  gggtggatgc  gcgcctcctg  cgccccgcgg
103021  gttcgcgagc  cgacatggtg  gcgatagacg  cgggttatcg  gatgtccgct  accccccaaa
103081  aaagaaaaag  accccacagc  gcggatggag  gtcggggtag  gtgccgccgg  accccctcgc
103141  gatgggaatg  gacgggagcg  acggggccgg  cgcaaaaaac  gcagtatctc  ccgcgaaggc
103201  tacccgccgc  cccagccccc  ggccaaatgc  ggaaacggtc  ccgcgctctc  gcctttatac
103261  gcgggccgcc  ctgcgacaca  atcaccgtc   cgtggtttcg  aatctacacg  acaggcccgc
103321  agacgcgggct aacacacacg  ccggcaaccc  agacccagt   gggttggttg  cgcggtcccg
103381  tctcctggct  agttctttcc  ccaccacca   aataatcaga  cgacaaccgc  aggttttgt
103441  aatgtatgtg  ctcgtgttta  ttgtggatac  gaaccgggga  cgggagggga  aaacccagac
103501  gggggatgcg  ggtccggtcg  cgccccctac  ccaccgtact  cgtcaattcc  aagggcatcg
103561  gtaaacatct  gctcaaactc  gaagtcggcc  atatccagag  cgccgtaggg  ggcggagtcg
103621  tggggggtaa  atcccggacc  cggggaatcc  ccgtcccca   acatgtccag  atcgaaatcg
103681  tctagcgcgt  cggcatgcgc  catcgccacg  tcctcgccgt  ctaagtggag  ctcgtcccc
103741  aggctgacat  cggtcggggg  ggccgtcgac  agtctgcgcg  tgtgtcccgc  ggggagaaag
103801  gacaggccgcg gagccgccaa  ccccgcctct  tcggggggcgt  cgtcgtccgg  gagatcgagc
103861  aggccctcga  tggtagaccc  gtaattgttt  ttcgtacgcg  cgcggctgta  cgcgtgttcc
103921  cgcatgaccg  cctcggaggg  cgaggtcgtg  aagctggaat  acgagtccaa  cttcgcccga
103981  atcaacacca  taaagtaccc  agaggcgcgg  gcctggttgc  catgcagggt  gggaggggtc
104041  gtcaacggcg  cccctggctc  ctccgtagcc  gcgctgcgca  ccagcgggag  gttaaggtgc
104101  tcgcgaatgt  ggtttagctc  ccgcagccgg  cgggcctgga  ttggcactcc  ccggacggtg
104161  agcgctccgt  tgacgaacat  gaagggctgg  aacagacccg  ccaactgacg  ccagctctcc
104221  aggtcgcaac  agaggcagtc  aaacaggtcg  ggccgcatca  tctgctcggc  gtacgcggcc
104281  cataggatct  cgcgggtcaa  aaatagatac  aaatgcaaaa  acagaacacg  cgccagacga
104341  gcggtctctc  ggtagtacct  gtccgcgatc  gtggcgcgca  gcatttctcc  caggtcgcga
104401  tcgcgtccgc  gcatgtgcgc  ctgcggtgc   agctgccga   cgctggcgcg  caggtaccgg
104461  tacagggccg  agcagaagtt  ggccaacacg  gttcgatagc  tctcctcccg  cgcccgtagc
104521  tcggcgtgga  agaaacgaga  gagcgcttcg  tagtagagcc  cgaggccgtc  gcgggtggcc
104581  ggaagcgtcg  ggaaggccac  gtcgccgtgg  gcgcgaaatgt cgatttgggc  gcgttcgggg
104641  acgtacgcgt  ccccccattc  caccacatcg  ctgggcagcg  ttgataggaa  tttacactcc
104701  cggtacaggt  cggcgttggt  cggtaacgcc  gaaaacaaat  cctcgttcca  ggtatcgagc
104761  atggtacata  gcgcgggcc   cgcgctaaag  cccaagtcgt  cgaggagacg  gttaagagg
104821  gcggcggggg  ggacgggcat  gggcggggag  ggcatgagct  gggcctggct  caggcgcccc
104881  gttgcgtaca  gcggaggggc  cgccggggtg  tttttgggac  ccccggccgg  gcgggggggt
104941  ggtggcgaag  cgccgtccgc  gtccatgtcg  gcaaacagct  cgtcgaccaa  gaggtccatt
105001  gggtggggtt  gatacgggaa  agacgatatc  gggcttttga  tgcgatcgtc  cccgcccgcc
105061  cagagagtgt  gggacgcccg  acggccgcgg  aagagaaaaa  ccccaaacg   cgttagagga
105121  ccggacggac  cttatggggg  gaagtgggca  gcgggaaccc  cgtccgttcc  cgaggaatga
105181  cagcccgtgg  tcgccacccc  gcatttaagc  aacccgcacg  ggccgccccg  tacctcgtga
105241  cttcccccca  cattggctcc  tgtcacgtga  aggcaaaccg  agggcggctg  tccaacccac
105301  cccccgccac  ccagtcacgg  tccccgtcgg  atgggaaac   aaaggcacgc  aacgccaaca
105361  ccgaatgaac  ccctgttgt   gctttattgt  ctgggtacgg  aagttttca   ctcgacgggc
105421  cgtctgggc   gagaagcgga  gcgggctggg  gctcgaggtc  gctcggtggg  gcgcgacgcc
105481  gcagaacgcc  ctcgagtcgc  cgtggccgcg  tcgacgtcct  gcaccacgtc  tggattcacc
105541  aactcgttgg  cgcgctgaat  caggttttg   ccctcgcaga  ccgtcacgcg  gatggtggtg
105601  atgccaagga  gttcgttgag  gtcttcgtct  gtgcgccgga  gcgacatgtc  ccagagctgg
105661  accgccgcca  tccgggcatg  catggccgac  aggcgcccaa  ccgcgcgca   gaagacgcgc
105721  ttgttaaagc  cggccacccg  ggggtccat   ggcgcgtcgg  ggtttggggg  ggcggtgcta
105781  aagtgcagct  ttctggccag  ccctgcgcg   ggtgtcttgg  atcggttgg   cgccgtcgac
105841  gcggggggcgt ctgggagtgc  ggcggattct  ggctgggccg  atttcctgcc  gcgggtggtc
105901  tccgccgccg  gggccgggg   ggccttagtc  gccaccgct   gggtcgggg   ggccgggggg
105961  gcggtggtgg  gtgtgcgtcc  ggccctccg   gacccagcgg  gcggggagg   cgcccgcgca
106021  ggccccgggg  cggacaaaac  cgccccggaa  acgggacgcc  gcgtccgggg  gacctccggg
106081  tgttcgtcgt  cttcggatga  cgagcccccc  tagagggcat  aatccgactc  gtcgtactgg
106141  acgaaacgga  cctcgcccct  tgggcgcgcg  cgtgtctgta  gggcgccacg  gcgggaggtg
106201  tcaggcggac  tatcgggact  cgcatacat   gaagacgggg  tgtagtacag  atcctcgtac
106261  tcatcgcgcg  gaacctcccg  cggaccgac   ttcacggagc  ggcgagaggt  catggttcca
106321  cgaacacgct  aggtcggat   gcgcggacaa  ttaggcctgg  gttcggacgg  cgggggtggt
106381  gcaggtgtgg  agaggtcgag  cgataggggc  ggcccgggag  agaagagagg  gtccgcaaaa
106441  cccactgggg  atgcgtgagt  ggccctctgt  gggcggtggg  ggagagtctt  ataggaagtg
106501  catataacca  caacccatgg  gtctaaccaa  tccccagggg  ccaagaaaca  gacacgcccc
```

```
106561  aaacggtctc ggtttccgcg aggaagggga agtcctggga caccctccac ccccacccct
106621  caccccacac agggcgggtt caggcgtgcc cggcagccag tagcctctgg cagatctgac
106681  agacgtgtgc gataatacac acgcccatcg aggccatgcc tacataaaag ggcaccaggg
106741  cccccggggc agacatttgg ccagcgtttt gggtctcgca ccgcgcgccc ccgatcccat
106801  cgcgcccgcc ctcctcgccg ggcggctccc cgtgcgggcc cgcgtctccc gccgctaagg
106861  cgacgagcaa gacaaacaac aggcccgccc gacagaccct tctgggggg cccatcgtcc
106921  ctaacaggaa gatgagtcag tggggatccg gggcgatcct tgtccagccg gacagcttgg
106981  gtcggggta cgatggcgac tggcacacgg ccgtcgctac tcgcggggc ggagtcgtgc
107041  aactgaacct ggtcaacagg cgcgcggtgg cttttatgcc gaaggtcagc ggggactccg
107101  gatgggccgt cgggcgcgtc tctctggacc tgcgaatggc tatgccggct gactttgtgt
107161  cgattattca cgccccgcg ctatccagcc cagggcacca cgtaatactg ggtcttatcg
107221  actcgggta ccgcggaacc gttatggccg tggtcgtagc gcctaaaagg acgcgggaat
107281  ttgcccccgg gaccctgcgg gtcgacgtga cgttcctgga catcctggcg accccccgg
107341  ccctcaccga gccgatttcc ctgcggcagt tcccgcaact ggcgccccc cctccaaccg
107401  gggccgggat acgcgcagat ccttggttgg aggggggcgct cggggaccca agcgtgactc
107461  ctgccctacc ggcgcgaccc gcgagggcggt ccctcgtcta tgccggcgag ctgacgccgg
107521  ttcagacgga acacggggac ggcgtacgag aagccatcgc cttccttcca aaacgcgagg
107581  aggatgccgg tttcgacatt gtcgtccgtc gcccggtcac cgtcccggca aacggcacca
107641  cggtcgtgca gccatccctc cgcatgctcc acgcggacgc cgggcccgcg gcctgctatg
107701  tgctggggcg gtcgtcgctc aacgcccgcg gcctcctggt cgttcctacg cgctggctcc
107761  ccgggcacgt atgtgcgttt gttgtttaca accttacggg ggttcctgtg accctcgagg
107821  ccggcgccaa ggtcgcccag ctcctggttg cggggggcgga cgctcttcct tggatccccc
107881  cggacaactt tcacgggacc aaagcgcttc gaaactaccc cagggggtgtt ccggactcaa
107941  ccgccgaacc caggaacccg ccgctcctgg tgtttacgaa cgagtttgac gcggaggccc
108001  ccccgagcga gcgcgggacc gggggttttg gctctaccgg tatttagccc atagcttggg
108061  gttcgttccg ggcaataaaa aacgtttgta tctcatcttt cctgtgtgta gttgtttctg
108121  ttggatgcct gtgggtctat cacaccgcc cctccatccc acaaacacag aacacacggg
108181  ttggatgaaa acacgcattt attgacccaa aacacaggga gctgctcgag atggggccagg
108241  gcgaggtgcg gttgggagg ctgtaggtct gggaacggac acgcgggggac acgattccgg
108301  tttggggtcc gggagggcgt cgccgtttcg ggcggcaggc gccagcgtaa cctccggggg
108361  cggcgtgtgg gggtgcccca aggaggggcgc ctcggtcacc ccaagccccc ccgagcgggt
108421  tcccccggca accccgaagg cggagaggcc aagggcccgt tcggcgatgg ccacatcctc
108481  catgaccacg tcgctctcgg ccatgctccg aatagcctgg gagacgagca catccgcgga
108541  cttgtcagcc gccccacgg acatgtacat ctgcaggatg gtggccatac acgtgtccgc
108601  caggcgccgc atcttgtcct gatgggccgc cacggccccg tcgatcgtgg gggcctcgag
108661  cccgggggtgg tggcgcgcca gtcgttctag gttcaccatg caggcgtggt acgtgcgggc
108721  caaggcgcgg gccttcacga ggcgtcgggt gtcgtccagg gaccccaggg cgtcatcgag
108781  cgtgatgggg gcgggaagta gcgcgttaac gaccaccagg gcctcctgca gccgcggctc
108841  cgcctccgag ggcggaacgg ccgcgcggat catctcatat tgttcctcgg ggcgcgctcc
108901  ccagccacat atagcccccga gaagagaagc catcgcgggc gggtactggc cctttgggcgc
108961  gcggacgcaa tggggcagga agacggggaac cgcgggggaga ggcggggcgc cgggactccc
109021  gtggaggtga ccgcgcttta tgccgaccgac gggtgcgtta ttacctcttc gatcgccctc
109081  ctcacaaact ctctactggg ggccgagccg gtttatatat tcagctacga cgcatacacg
109141  cacgatggcc gtgccgacgg gcccacgggag caagacaggt tcgaagagag tcgggcgctc
109201  taccaagcgt cgggcgggcgt aaatgcgac tccttccgag taacctttttg tttattgggg
109261  acgaagtgg gtgggaccca ccaggccccgc gggcgaaccc gacccatgtt cgtctgtcgc
109321  ttcgagcgag cggacgacgt cgccgcgcta caggacgccc tggcgcacgg gacccccgcta
109381  caaccggacc acatcgccgc cacccctggac gcggaggcca cgttcgcgct gcatgcgaac
109441  atgatcctgg ctctcaccgt ggccgtcaac aacgccagcc cccgcaccgg acgcgacgcc
109501  gccgcggcgc agtatgatca gggcgcgtcc ctacgctcgc tcgtggggcg cacgtccctg
109561  ggacaacgcg gccttaccac gctatacgtc caccacgagg cgcgcgtgct ggccgcgtac
109621  cgcagggcgt attatggaag cgcgcagagt cccttctggt ttcttagcaa attcgggcct
109681  gacgaaaaaa gcctggtgct caccactcgg tactacctgg ttcaggccca gcgtctgggg
109741  ggcgcgggg ccacgtacga cctgcaggcc atcaaggaca tctgcgccac ctacgcgatt
109801  ccccacgccc cccgcccga caccgtcagc gccgcgtccc tgacctcgtt tgccgccatc
109861  acgcggttct gttgcacgag ccagtacgcc cgcggggccg cggcggccgg gtttccgctt
109921  tacgtggagc gccgtattgc ggccgacgtc cgcagaacca gtgcgctgga gaagttcata
109981  acccacgatc gcagttgcct gcgcgtgtcc gaccgtgaat tcattacgta catttacctg
110041  gcccattttg agtgtttcag ccccccgcgc ctagccacgc atcttgggc cgtgacgacc
110101  caggaccccca accccgcggc caacacggag cagccctcgc ccctgggcag ggaggccgtg
110161  gaacaatttt tttgccacgt gcgcgcccaa ctgaatatcg gggagtacgt caaacacaac
110221  gtgaccccc gggagaccgt cctggatggc gatacggcca aggcctacct gcgcgctcgc
110281  acgtacgcgc ccggggcccct gacgcccgcc cccgcgtatt gcgggggccgt ggactccgcc
110341  accaaaatga tggggcgttt ggcggacgcg gaaaagctcc tggtccccg cgggtggccc
110401  gcgtttgcgc ccgccagtcc cggggaggat acgcgggggcg gcacgccgcc cccacagacc
110461  tgcggaatcg tcaagcgcct cctgagactg gccgccacgg aacaacagga caccacgccc
110521  ccggcgatcg cggcgcttat ccgtaatgcg gggacaagca ctccctgcc cgtctaccgg
110581  atatccatgg tccccacggg acaggcattt gccgcgctgg cctgggacga ctgggcccgc
110641  ataacgcggg acgctcgcct ggccgaagcg gtcgtgtccg ccgaagcggc ggcgcacccc
110701  gaccacggcg cgctgggcag gcggctcacg gatcgcatcc gcgcccaggg ccccgtgatg
110761  ccccctggcg gcctggatgc cgggggggcag atgtacgtga atcgcaacga gatatttaac
110821  ggcgcgctgc caatcacaaa catcatcctg gatctcgaca tcgatcgaga ggagcccgtc
110881  ccctttcgcc ggctccacga ggccctgggc cacttaggc gcggggctct ggcggcggtt
110941  cagctcctgt ttcccgcggc ccgcgtggac cccgacgcat atccctgtta ttttttcaaa
111001  agcgcatgtc ggcccggcc ggcgtccgtg ggtccggca gcggactcgg caacgacgac
111061  gacggggact ggtttccctg ctacgacgac gccggtgatg aggagtgggc ggaggacccg
111121  ggcgccatgg acacatccca cgatccccg gacgacgagg ttgcctactt tgacctgtgc
```

-continued

Sequence Listing

```
111181 cacgaagtcg gccccacggc ggaacctcgc gaaacggatt cgcccgtgtg ttcctgcacc
111241 gacaagatcg gactgcgggt gtgcatgccc gtccccgccc cgtacgtcgt ccacggttct
111301 ctaacgatgc gggggtggc acgggtcatc cagcaggcgg tgctgttgga ccgagatttt
111361 gtggaggcca tcgggagcta cgtaaaaaac ttcctgttga tcgatacggg ggtgtacgcc
111421 cacggccaca gcctgcgttt gccgtatttt gccaaaatcg cccccgacgg gcctgcgtgc
111481 ggaaggctgc tgccagtgtt tgtgatcccc cccgcctgca aagacgttcc ggcgtttgtc
111541 gccgcgcacg ccgacccgcg gcgcttccat tttcacgccc cgcccaccta tctcgcttcc
111601 ccccgggaga tccgtgtcct gcacagcctg ggtggggact atgtgagctt ctttgaaagg
111661 aaggcgtccc gcaacgcgct ggaacacttt gggcgacgcg agaccctgac ggaggtcctg
111721 ggtcggtaca acgtacagcc ggatgcgggg gggaccgtcg aggggttcgc atcggaactg
111781 ctggggcgga tagtcgcgtg catcgaaacc cactttcccg aacacgccgg cgaatatcag
111841 gccgtatccg tccggcgggc cgtcagtaag gacgactggg tcctcctaca gctagtcccc
111901 gttcgcggta ccctgcagca aagcctgtcg tgtctgcgct ttaagcacgg ccgggcgagt
111961 cgcgccacgg cgcggacatt cgtcgcgctg agcgtcgggg ccaacaaccg cctgtgcgtg
112021 tccttgtgtc agcagtgctt tgccgccaaa tgcgacagca accgcctgca cacgctgttt
112081 accattgacg ccggcaccgc atgctcgccg tccgttcccc gcagcacctc tcaaccgtcg
112141 tcttgataac ggcgtacggc ctcgtgctcg tgtggtacac cgtcttcggt gccagtccgc
112201 tgcaccgatg tatttacgcg gtacgcccca ccggcaccaa caacgacacc gccctcgtgt
112261 ggatgaaaat gaaccagacc ctattgtttc tgggggcccc gacgcacccc ccaacggggg
112321 gctggcgcaa ccacgcccat atctgctacg ccaatcttat cgcgggtagg gtcgtgccct
112381 tccaggtccc acccgacgcc acgaatcgtc ggatcatgaa cgtccacgag gcagttaact
112441 gtctggagac cctatggtac acacgggtgc gtctggtggt cgtagggtgg ttcctgtatc
112501 tggcgttcgt cgccctccac caacgccgat gtatgtttgg tgtcgtgagt cccgcccaca
112561 agatggtggc cccggccaca tacctcttga actacgcagg ccgcatcgta tcgagcgtgt
112621 tcctgcagta cccctacacg aaaattaccc gcctgctctg cgagctgtcg gtccagccgc
112681 aaaacctggt tcagttgttt gagacggacc cggtcacctt cttgtaccac cgccccgcca
112741 tcggggtcat cgtaggctgc gagttgatgc tacgctttgt ggccgtgggt ctcatcgtcg
112801 gcaccgcttt catatccggg ggggcatgtg cgatcacata ccccctgttt ctgaccatca
112861 ccacctggtg ttttgtctcc accatcggcc tgacagagct gtattgtatt ctgcggcggg
112921 gcccggcccc caagaacgca gacaaggccg ccgccccggg gcgatccaag gggctgtcgg
112981 gcgtctgcgg gcgctgttgt tccatcatcc tgtcgggcat cgcaatgcga ttgtgttata
113041 tcgccgtggt ggccggggtg gtgctcgtgg cgcttcacta cgagcaggag atccagaggc
113101 gcctgtttga tgtatgacgt cacatccagg ccggcggaaa ccggaacggc atatgcaaac
113161 tggaaactgt cctgtcttgg ggcccaccca cccgacgcgt catatgtaaa tgaaaatcgt
113221 tcccccgagg ccatgtgtag cctggatccc aacgaccccg cccatgggtc ccaattggcc
113281 gtcccgttac caagaccaac ccagccagcg tatccacccc cgcccgggtc ccgcggaag
113341 cggaacggtg tatgtgatat gctaattaaa tacatgccac gtacttattg tgtctgattg
113401 gtccttgtct gtgccggagg tggggcgggg gccccgcccg ggggcggaa ctaggagggg
113461 tttgggagag ccggcccgg caccacgggt ataaggacat ccaccacccg gccggtggtg
113521 gtgtgcagcc gtgttccaac cacggtcacg cttcggtgcc tctcccgat cgggcccgg
113581 tcgcttgcta ccggtgcgcc accaccagag gccatatccg cccgacggca
113641 gccgacagcc cggtcatggc gactgacatt gatatgctaa ttgacctcgg cctggacctc
113701 tccgacagcg atctggacga ggaccccccc gagccggcgg agagccgccg cgacgacctg
113761 gaatcggaca gcaacgggga gtgttcctcg tcgacgagg acatggaaga cccccacgga
113821 gaggacggac cggagccgat actcgacgcc gctcccgcgg ccgtccgccc gtctcgtcca
113881 gaagaccccg gcgtacccag cacccagacg cctcgtccga cggagcggca gggccccaac
113941 gatcctcaac cagcgcccca cagtgtgtgg tcgcgcctcg ggcccggcg accgtcttgc
114001 tcccccgagc ggcacggggg caaggtggcc cgcctccaac ccccaccgac caaagcccag
114061 cctgccgcg gcggacgccg tgggcgtcgc agggggtcggg gtcgcggtgg tcccggggcc
114121 gccgatggtt tgtcggaccc ccgccgcgt gccccagaa ccaatcgcaa cccggggga
114181 ccccgcccg gggcggggtg gacggacggc cccggcgccc ccatggcga ggcgtggcgc
114241 ggaagtgagc agcccgaccc acccggaggc ccgcggacac ggagcgtgcg ccaagcaccc
114301 cccccgctaa tgacgctggc gattgccccc ccgcccgcgg acccccgcgc cccggcccg
114361 gagcgaaagg cgcccgccgc cgacaccatc gacgccacca cgcggttggt cctgcgctcc
114421 atctccgagc gcgcggcggt cgaccgcatc agcgagagct tcggccgcag cgcacaggtc
114481 atgcacgacc cctttggggg gcagccgttt cccgccgcga atagcccctg ggccccggtg
114541 ctggcgggcc aaggagggcc ctttgacgcc gagaccagac gggtctcctg ggaaaccttg
114601 gtcgcccacg gcccgagcct ctatcgcact tttgccggca atcctcggcc cgcatcgacc
114661 gccaaggcca tgcgcgactg cgtgctcgcg caagaaaatt tcatcgagc gctggcctcc
114721 gccgacgaga cgctggccgtg gtgcaagatg tgcatccacc acaacctgcc gctgcgcccc
114781 caggacccca ttatcgggac ggccgcggcc gtgctggata acctcgccac gcgcctgcgg
114841 cccttctcc agtgctacct gaaggcgcga ggcctgttgcg gcctggacga actgtgttcg
114901 cggcggcgtc tggcggacat taaggacatt gcatccttcg tgtttgtcat tctgccagg
114961 ctcgccaacc gcgtcgagcg tggcgtcgcg gagatcgact acgcgaccct tggtgtcggg
115021 gtcggagaga agatgcattt ctacctcccc ggggcctgca tggcgggcct gatcgaaatc
115081 ctagacacgc accgccagga gtgttcgagt cgtgtctgcg agttgacggc cagtcacatc
115141 gtcgcccccc cgtacgtcg cggcaaatat ttttattgca actccctgtt ttaggtacaa
115201 taaaaacaaa acatttcaaa caaatcgccc cacgtgttgt ccttctttgc tcatggccgg
115261 cggggcgtgg gtcacggcag atggcggggg tgggcccggc gtacggcctg ggtgggcgga
115321 gggaactaac ccaacgtata aatccgtccc cgctccaagg ccggtgtcat agtgccctta
115381 ggagcttccc gcccgggcgc atccccccctt ttgcactatg acagcgaccc ccctcaccaa
115441 cctgttctta cggggccccca acataaccca cgtggccccc ccttactgcc tcaacgccac
115501 ctggcaggcc gaaacggcca tgcacaccag caaaacggac tccgcttgcg tggccgtgcg
115561 gagttacctg gtccgcgcct cctgtgagac cagcggcaca atccactgct ttttctttgc
115621 ggtatacaag gacacccacc ataccctcc gctgattacc gagctccgca actttgcgga
115681 cctggttaac cacccgccgg tcctacgcga actggaggat aagcgcgggg tgcggctgcg
115741 gtgtgcgcgg ccgtttagcg tcgggacgat taggacgtc tctgggtccg gcgcgtcctc
```

Sequence Listing

```
115801  ggcgggagag  tacacgataa  acgggatcgt  gtaccactgc  cactgtcggt  atccgttctc
115861  aaaaacatgc  tggatggggg  cctccgcggc  cctacagcac  ctgcgctcca  tcagctccag
115921  cggcatggcc  gcccgcgcgg  cagagcatcg  acgcgtcaag  attaaaatta  aggcgtgatc
115981  tccaaccccc  catgaatgtg  tgtaaccccc  cccaaaaaaa  taaagagccg  taacccaacc
116041  aaaccaggcg  tggtgtgagt  ttgtggaccc  aaagccctca  gagacaatgc  gacaggccag
116101  tatggaccgt  gatactttta  tttattaact  cacaggggcg  cttaccgcca  caggaatacc
116161  agaataatga  ccaccacaat  cgcgaccacc  ccaaatacag  catggcgcca  caccacgcca
116221  caacagccct  gtcgccggta  tggggcatga  tcagacgagc  cgcgcgccgc  gcgttgggcc
116281  ctgtacagct  cgcgcgaatt  gaccctagga  ggccgccacg  cgcccgagtt  ttgcgttcgt
116341  cgctggtcgt  cgggcgccaa  agccccggac  ggctgttcgg  tcgaacgaac  ggccacgaca
116401  gtggcatagg  ttgggggggtg  gtccgacata  gcctcggcgt  acgtcgggag  gcccgacaag
116461  aggtcccttg  tgatgtcggg  tggggccaca  agcctggttt  ccggaagaaa  caggggggtt
116521  gccaataacc  cgccagggcc  aaaactccgg  cgctgcgcac  gtcgttcggc  gcggcgccgg
116581  gcgcgccgag  cggctcgctg  ggcggcttgg  cgtgagcggc  cccgctccga  cgcctcgccc
116641  tctccggagg  aggttggcgg  aattggcacg  gacgacaggg  gcccagcaga  gtacggtgga
116701  ggtgggtccg  tgggggtgtc  cagatcaata  acgacaaacg  gcccctcgtt  cctaccagac
116761  aagctatcgt  agggggggcgg  gggatcagca  aacgcgttcc  ccgcgctcca  tagacccgcg
116821  tcgggttgcg  ccgcctccga  agccatggat  gcgccccaaa  gccacgactc  ccgcgcgcta
116881  ggtccttggg  gtaagggaaa  aggccctact  ccccatccaa  gccagccaag  ttaacgggct
116941  acgcttcgg  ggatgggact  ggcaccccgg  cggattttgt  tgggctggta  cgcgtcgccc
117001  aaccgagggc  cgcgtccacg  ggacgcgcct  tttataaccc  cggggtcatt  cccaacgatc
117061  acatgcaatc  taactggctc  ccctctcccc  ccctctcccc  tctccccccc  tctccctct
117121  ccccccctct  ccctctccc  ccctctccc  ctctccccc  ctctccctc  tccccctc
117181  tccctctcc  ccctctcc  cctctccc  cctctccc  ctccccct  ctccctctc
117241  cccccctctc  ccctgctctt  tcccgtgac  accgacgct  gggggcgtg  gctgccggga
117301  ggggccgcgt  atgggcgggc  ctactcggtc  tcccgccccc  ccgaaccgcc  ccgccggctt
117361  tgccccccctt  tgatcccctg  ctaccccac  cccgtgctcg  tggtgcgggg  tgggggatg
117421  tgggcggggg  tgcgcgggag  gtgtcggtgg  tgggggtggt  ggtggtgtg  gtagtaggaa
117481  tggtggtggg  ggggagggcg  ctggttggtc  aaaaaaggga  gggacgggg  ccggcagacc
117541  gacggcgaca  acgctcccg  gcggccgggt  cgcggctctt  acgagcggcc  cggcccgcgc
117601  tcccaccccc  cgggccgtgt  ccttgctttc  ccccgtctc  cccccccgcc  ttctcctcct
117661  cctcctcgtt  tttccaaacc  ccgccacc  ggccggccc  ggccggccc  ggccaccgcc
117721  gcccaccac  ccacctcggg  ataccagcc  ccggtcccc  gttcccggg  ggccgttatc
117781  tccagcgccc  cgtccggcgc  gccgcccccc  gccgctaaac  cccatcccgc  cccgggacc
117841  ccacatataa  gccccagcc  acacgcaaga  acagacacgc  agaacggctg  tgtttatttt
117901  aaataaaccg  atgtcggaat  aaacaaacac  aaacacccgc  gacgggggga  cggaggggac
117961  ggagggaggg  gggtgacggg  ggacggaaac  agacacaaa  aacaaccaca  aaaaacaacc
118021  acccaccgac  acccccaccc  cagtctcctc  gccttctccc  acccaccca  cgccccact
118081  gagcccggtc  gatcgacgag  caccccccgcc  cacgccccg  ccctgcccc  ggcgacccc
118141  ggcccgcacg  atcccgacaa  caataacaac  cccaacggaa  agcggcgggg  tgttggggga
118201  ggcgaggaac  aaccgaggag  aacggggat  ggaaggacgg  gaagtggaag  tcctgatacc
118261  catcctacac  ccccctgcct  tccaccctcc  ggcccccgc  gagtccacc  gccggccggc
118321  taccgagacc  gaacacgcg  gccaccgccg  ccgccgccgc  cgacaccgca  gagccggcgc
118381  gcgcacacac  aagcggcaga  ggcagaaagg  ccccgagtca  ttgtttatgt  ggccgcgggc
118441  cagcagacgg  cccgcgacac  cccccccgc  ccgtgtgggt  atccggcccc  ccgccccgcg
118501  ccggtccatt  aagggcgcgc  gtgcccgcga  gatatcaatc  cgttaagtgc  tctgcagaca
118561  ggggcaccgc  gcccggaaat  ccattaggcc  gcagacgagg  aaaataaaat  tacatcacct
118621  acccatgtgg  tgctgtggcc  tgtttttgct  gcgtcatctg  agcctttata  aaagcgggg
118681  gcggccgtg  ccgatcgccg  gtggtgcgaa  agactttccg  ggcgcgtccg  ggtgccgcgg
118741  ctctccggcc  ccccctgcag  ccggggcggc  caagggggcgt  cggcgacatc  ctcccctaa
118801  gcgccggccg  gccgctgtc  tgttttttcg  ttttcccgt  ttcggggtg  tggggggttg
118861  cggtttctgt  ttctttaacc  cgtctgggt  gtttttcgtt  ccgtcgccgg  aatgtttcgt
118921  tcgtctgtcc  cctcacgggg  cgaaggccgc  gtacggcccg  ggacgagggg  cccccgaccg
118981  cggcggtccg  ggccccgtcc  ggaccgctc  gccggcacg  gacgcgaaaa  aggccccccg
119041  gaggcttttc  cgggttcccg  gcccggggcc  tgagatgaac  actcggggtt  accgccaacg
119101  gccggccccc  gtggcggccc  ggcccggggc  cccggcggac  ccaagggggcc  ccggccggg
119161  gccccacaac  ggcccggcgc  atgcgctgtg  gtttttttt  cctcggtgtt  ctgccgggct
119221  ccgtcgcctt  tcctgttctc  gcttctcccc  cccccccttc  acccccagta  ccctcctccc
119281  tcccttcctc  ccccgttatc  ccactcgtcg  agggcgcccc  ggtcgttc  aacaaagacg
119341  ccgcgtttcc  aggtaggtta  gacacctgct  tctccccaat  agaggggggg  ggacccaaac
119401  gacagggggc  gccccagagg  ctaaggtcgg  ccacgccact  cgcgggtggg  ctcgtgttac
119461  agcacaccag  cccgttattt  tccccccctc  ttagactctg  ttacttaccc
119521  gtccgaccac  caactgcccc  cttatctaag  ggccggctgg  aagaccgcca  gggggtcggc
119581  cggtgtcgct  gtaaccccc  acgccaatga  cccacgtact  ccaagaaggc  atgtgtccca
119641  ccccgcctgt  gttttgtgc  ctggctctct  atgcttgggt  cttactgcct  gggggggggg
119701  agtgcgggggg  agggggggggg  tgtggaagga  aatgcacggc  gcgtgtgtac  ccccccctaa
119761  agttgttcct  aaagcgagga  tatggaggag  tggcgggtgc  gggggacgg  gggtgatctc
119821  tggcacgcgg  gggtgggaag  ggtcggggga  gggggggatg  gggtaccggc  ccacctggcc
119881  ggcgcgggtg  cgcgtgcctt  tgcacaccaa  ccccacgtcc  ccggcggtc  tctaagaaac
119941  accgcccccc  ctccttcata  ccaccgagca  tgcctgggtg  tgggttggta  accaacacgc
120001  ccatccctc  gtctcctgtg  attctctggc  tgcaccgcat  tcttgttttc  taactatgtt
120061  cctgttttctg  tctccccccc  caccccccc  caaccccac  gtctgtggtg
120121  tggccgaccc  ccttttgggc  gcccgtccc  gcccgctac  ccctcccatc  ctttgttgcc
120181  ctatagtgta  gttaacccc  ccccccgccc  tttgtggcgg  ccagaggcca  ggtcagtccg
120241  ggcgggcagg  cgctcgcgga  aacttaacac  ccacacccaa  cccactgtgg  ttctggctcc
120301  atgccagtgg  caggatgctt  tcggggatcg  tgtgtcaggc  agcccgggcc  gcggctctgt
120361  ggttaacacc  agagcctgcc  caacatggca  cccccactcc  cacgcacccc  cactcccacg
```

Sequence Listing

```
120421  cacccccact cccacgcacc cccactccca cgcaccccca ctcccacgca cccccactcc
120481  cacgcacccc cactcccacg cacccccact cccacgcacc cccactccca cgcaccccg
120541  cgatacatcc aacacagaca gggaaaagat acaaaagtaa acctttattt cccaacagac
120601  agcaaaaatc ccctgagttt tttttattag ggccaacaca aaagacccgc tggtgtgtgg
120661  tgcccgtgtc tttcactttc cacctccccg acacggattg gctggtgtag tgggcgcggc
120721  cagagaccac ccagcgcccg accccccct ccccacaaac acgggggcgt cccttattgt
120781  tttccctcgt cccgggtcga cgccccctgc tccccggacc acgggtgccg agaccgcagg
120841  ctgcggaagt ccagggcgcc cactagggtg ccctggtcga acagcatgtt ccccacgggg
120901  gtcatccaga ggctgttcca ctccgacgcg ggggccgtcg ggtactcggg gggcgtcacg
120961  tggttacccg cggtctcggg gagcagggtg cggcggctcc agccggggac cgcggcccgc
121021  agccgggtcg ccatgtttcc cgtctggtcc accaggacca cgtacgcccc gatgttcccc
121081  gtctccatgt ccaggatggg caggcagtcc ccgtgatcg tcttgttcac gtaaggcgac
121141  agggcgacca cgctagagac ccccgatg ggcaggtagc gcgtgaggcc gcccgcgggg
121201  acggccccgg aagtctccgc gtggcgcgtc ttccgggcac acttcctcgg ccccgcggc
121261  ccagaagcag cgcgggggcc gagggaggtt cctcttgtc tccctcccag ggcaccgacg
121321  gccccgcccg aggaggcgga agcggaggag gacgcggccc cggtggcgga agaggtggcc
121381  cccgcgggag tcggggccga ggaggaagag gcggaggagg aagaggcgga ggccgccgag
121441  gacgtcaggg gggtcccggg ccctccctgg ccgcgcccc ccggccctga gtcggagggg
121501  gggtgcgtcg ccgccctctt ggccctgcc ggcgcgaggg ggggacgcgt ggactgggg
121561  gagggtttt cctggcccga cccgcgcctc ttcctcggac gcaccgccgc ctcctgctcg
121621  acagaggcgg cggaggggag cgggggggcg ccggagggg cggcgccgga ggggcggcg
121681  ccgcgggagg gcccgtgtcc accctccacg cccggccccc ccgagccgcg cgccaccgtc
121741  gcacgcgccc ggcacagact ctgttcttgg ttcgcggcct gagccaggga cgagtgcgac
121801  tggggcacac ggcgcgcgtc cgcgggggcg gcggccggct ccgccccggg ggccgggatc
121861  cggggccgg gcccggagg cggcgcccgc acacacgggg ccacggccgc gcggggcgc
121921  gcggggcccg acgcggccgc ggacgcgggg ggaccgggc gggggcgga gcctggcatg
121981  ggcgccgcgg ggggcctgtg gggagaggcc gggggggagt cgctgatcac tatgggtct
122041  ctgttgtttg caaggggggc gggtctgttg acaaggggca cggtccggcc cctcggccgc
122101  cccgcctccg cttcaacaac cccaaccccc ccggagggc cagacgcccc ccgcggcacc
122161  gcggctcgcg actggcggga gccgccgccg ccgctgctgt tggtggtggt gttagtgtta
122221  ctgctgccgt gtgcccgat gggcgccgag gggggcgctg tccgagccgc ggccggctgg
122281  ggggctgcgt gagacgcccc gcccgtcacg gggggcgcgg cggcgcctct gcgtgggggg
122341  gcgcggggcg tccgcgggg gcgggcggt acgtagtcgg ctgcaagaga caacggggg
122401  cgcgatcagg ttacgcccc tccccggccc gcccttcct cgcccgcccg cccgcctatt
122461  cctccctccc ccccctcc tcctcctccc ccagggtcct cgccgcccc ccgcctcacc
122521  gtcgtccagg tcgtcgtcat cctcgtccgt ggtgggctca gggtgggtgg gcgacagggc
122581  cctcaccgtg tgcccccca gggtcaggta ccgcgggcg aaccgctgat tgcccgtcca
122641  gataaagtcc acggccgtgc ccgccctgac ggcctcctcg gcctccatgc gggtctgggg
122701  gtcgttcacg atcgggatgg tgctgaacga cccgctgggc gtcacgccca ctatcaggta
122761  caccagcttg gcgttgcaca gcgggcaggt gttgcgcaat tgcatccagg ttttcatgca
122821  cgggatgcag aagcggtgca tgcacgggaa ggtgtccgga cgcaggtggg gcgcgatctc
122881  atccgtgcac acggcgcaca cgtcgcccc gtcgctcccc ccgtcctctc gaggggggc
122941  gcccccgcaa ctgccggggt cttcctcgcg ggggggggctc ccccccgaga ccgccccccc
123001  atccacgccc tgcggcccca gcagcccgt ctcgaacagt tccgtgtccg tgctgtccgc
123061  ctcggaggcg gagtcgtcgt catggtggtc ggcgtccccc cgccccccca cttcggtctc
123121  cgcctccgag tcgctgctgt ccggcaggtc tcggtcgcag ggaaacaccc agacatccgg
123181  ggcgggctga ggggaaaaaa gggggggcgg gtaagaatgg ggggatttcc cgcgtcaatc
123241  agcgcccacg agttccccct ccccccccg ctcacaaagt cctgccccc tgctggcctc
123301  ggaagagggg ggagaaaggg gtctgcaacc aaaggtgctc tgggtccgtc cttttggatcc
123361  cgaccctct tcttccctct tctcccgccc tccagacgca ccggagtcgg gggtcccacg
123421  gcgtcccca aatatggcgg cggctcctc cccaccccc tagatgcgtg tgagtaaggg
123481  ggccctgcgt atgagtcagt ggggaccacg cccctaaca cggcgacccc ggtccctgtg
123541  tgtttgttgt gggggcgtgt ctctgtgtat gagtcagggg ggtcccacgg cgaccccggg
123601  ccctgcgtct gagtcaaagg ggccatgtgt aggtgttggg ggtctgtata tataaagtca
123661  gggggtcaca tggcgacccc taacagggcg accccggtcc ctgtatat agggtcaggg
123721  ggttccgcgc cccctaacat ggcgcccccg gtcctgtat atatagtgtc acggggttcc
123781  acgcccccta acatggcgcc caacatggcc gcccggctcc cgtgtatgag tgggggtccc
123841  ccaacatggc ggccggttcc agtgtaaggg tcgggggtcc cccaacatgg cgccccccaa
123901  catggcgccc cccaacatgg cgccccagac atggcgcccg gcccctcacc tcgcgctggg
123961  ggcggccctc aggccggcgg gtactgctc cggggcgggg ctccatgggg gtcgtatgcg
124021  gctggagggt cgctgacgga gggtccctgg gggtcgcaac gtaggcgggg cttctgtggt
124081  gatgcggaga gggggccgcc cgagtctgcc tggctgctgc gtctcgctcc gagtgccgag
124141  gtgcaaatgc gaccagaccg tcgggcagg gctaacttat accccacgcc ttttccctcc
124201  ccaaagggc ggcagtgacg attcccccaa tggccgcgcg tcccagggga ggcaggccca
124261  ccgcggggcg gccccgtccc cggggaccaa cccggcgccc caaagaata tcattagcat
124321  gcacggcccg gccccgatt tgggggcagga acccggtgtc ccccaaagaa cccccattagc
124381  atgccccctcc cgccgacgca acaggggctt ggcctgcctc ggtgcccgg ggcttcccgc
124441  cttcccgaag aaactcatta ccataccgg aaccccaggg gaccaatgcg ggttcattga
124501  gcgacccgcg ggccaatgcg cgaggggccg tgtgttccgc caaaaaagca attaacataa
124561  cccggaaccc caggggagtg gttacgcgcg gcgcgggagg cggggaatac cggggttgcc
124621  cattaagggc cgcgggaatt gccggaagcg ggaagggcgg ccggggccgc ccattaatga
124681  gtttctaatt accataccgg gaagcggaac aaggcctctg caagttttta attaccatac
124741  cgggaagtgg cggcccggc ccactgggcg ggagttaccg cccagtgggc cgggccccga
124801  cgactcggcg gacgctgtt ggccggggcc cgccgcgctg gcggccgccg attggccagt
124861  cccgccctcc gagggcgggc ccgcctcggg ggcgggccgg ctccaagcgt atatatgcgc
124921  ggctcctgcc atcgtctctc cggagagcgc cttggtgcgg agctcccggg agctccgcgg
124981  aagacccagg ccgcctcggg tgtaacgtta gaccgagttc gccgggccgg ctccgcgggc
```

```
125041  cagggcccgg gcacgggcct cgggccccag gcacgcccg atgaccgcct cggcctccgc
125101  caccggcgc cggaaccgag cccggtcggc ccgctcgcgg gcccacgagc cgcggcgcgc
125161  caggcgggcg gccgaggccc agaccaccag gtggcgcacc cggacgtggg gcgagaagcg
125221  caccgcgtg ggggtcgcgg gggtcgcggg ggtcgcgggg ggcttcggcg ccccctcccc
125281  gcccgcgcgt cgcaggcgca ggcgcgccaa gtgctctgcg gtgacgcgca ggcggagggc
125341  gaggcgcggc ggaaggcgga aggggcgtga ggggggggtgg gagggggttag ccccgccccc
125401  cgggcccgcg ccgggcggtg gggaccgggg gcggggggcg gcggcggtgg gccgggcctc
125461  tggcgccggc tcgggcgggg ggctgtccgg ccagtcgtcg tcgtcgtcgt cggacgcgga
125521  ctcgggaacg tggagccact ggcgcagcag cagcgaacaa gaaggcgggg gcccactggc
125581  gggggcggc ggcggggcgg ccgcggggcgc gctcctgacc acgggttccg agttgggcgt
125641  ggaggttacc tgggactgtg cggttgggac cgcgcccgtg ggcccggggcg gccgggggcg
125701  gcgggggccg cgatggcggc ggcgggccat ggagacagag agcgtgccgg ggtggtagag
125761  tttgacaggc aagcatgtgc gtgcagaggc gagtagtgct tgcctgtcta actcgctagt
125821  ctcggccgcg ggggggccgg gctgccggcc gccgcctttt aaagggccgc gcgcgacccc
125881  cggggggtgt gttttgggggg gggcccgttt ccggggtctg gccgctcctc ccccgctcct
125941  cccccgctc ctccccccgc tcctccccc gctcctcccc ccgctcctcc ccccgctcct
126001  cccccgctc ctccccccgc tcctcccccc gctcctcccc ccgctcctcc ccccgctcct
126061  cccccgctc ctccccccgc tcctcccccc gctcctcccc ccgctcctcc ccccgctcct
126121  cccccgctcc tccccgctc ccgcggcccc gcccccacg cccgcgcgc gcgcgcacgc
126181  cgcccggacc gccgcccgcc tttttgcgc gcgcgcggc ccgcggggggg cccggggctgc
126241  cacaggtaaa acaacaccaa caaagcacgg cgcaatccgc acgtcacacg tcacgtcatc
126301  caccacacct gcccaacaac acaactcaca gcgacaactc accgcgcaac aactcctgtt
126361  cctcatccac acgtcaccgc gcacctcccg ctcctccaga cgtacccgg cgcaacacac
126421  cgctcctgct acacaccacc gccctccccc agccccgccc ctccccaacc ccagccctcc
126481  ccggcccag ccctcccgg ccccagccct ccccggcccc agccctcccc ggcccagcc
126541  ctccccggcc ccagccctcc ccagccccag ccctccccag ccgcgtcccg cgctccctcg
126601  gggggggttcg ggcatctcta cctcagtgcc gccaatctca ggtcagagat ccaaaccctc
126661  cggggggcgcc cgcgcaccac caccgcccct ccccctcc cgccccctcc ccctcccgc
126721  ccctcgcccc ctcccgcccc tcgcccctc ccgcccctcg cccctcccg ccctcgccc
126781  cctcccgccc ctcgcccct ccgcccct gccccctccc gcccctgcc ccctcccgcc
126841  cctcgcccccc tcccgcccct cgccccctcc cgccccctcgc ccctcccgc ccctcgcccc
126901  ctcccgcccc ctcgcccccc tcgccccctg cccctcccg ccctcccgc cctcccgcc
126961  ctcgcccct ccgccccctc gccccctccc gccctcgcc cctcccgc cctcgaataa
127021  acaacgctac tgcaaaactt aatcaggtcg ttgccgttta ttgcgtcttc gggtttcaca
127081  agcgccccgc cccgtccgg cccgttacag caccccgtcc cctcgaacg cgccgccgtc
127141  gtcttcgtcc caggcgctt ccagtccac aacgtccgt cgcgggggcg tggccaagcc
127201  cgcctccgcc cccagcacct ccacggcccc cgccgccgcc agcacggtgc cgctgcggcc
127261  cgtggccgag gcccagcgaa tccggggcg cgccggcggc agggccccg ggccgtcgtc
127321  gtcgtcgccg cgcagcacca gcggggggggc gtcgtcgtcg ggctccagca gggcgcgggc
127381  gcaaaagtcc ctccgcggcc cgcgccaccg ggccgggccg gcgcgcaccg cctcgcgccc
127441  cagcgccacg tacacgggcc gcagcggcgc gccaggccc cagcgcgcg aggcgcggtg
127501  cgagtgggcc tcctcctcgc agaagtccgg cgcgccgggc ggccatgcgt cggtggtccc
127561  cgaggccgcc gcccggccgt ccagcgccgg cagcacggcc cggcggtact cgcgcggggga
127621  catgggcacc ggcgtgtccg ggccgaagcg cgtgcgcacg cggtagcgca cgttgccgcc
127681  gcggcacagg gtcagcgggc gcgcgtcggg gtacaggccg gcgtgcgcgg cctccacgcg
127741  cgcgaagacc cccggggccga acacgcggcc cgaggccagc accgtgcggc gcaggtcccg
127801  cgccgccggc cagcgcacgg cgcactgcac ggcgggcagc aggtcgcacg ccaggtaggc
127861  gtgctgccgc gacaccgcgg gcccgtcggc gggccagtcg caggcgcgca cggtgttgac
127921  cacgatgagc cgccggtcgc cggcgctggc gagcagcgca agaaactcca cggccccggc
127981  gaaggccagg tcccgcgtgg acagcagcag cacgcccctgc gcgcccagcc ccgacacgtc
128041  ggggggcgccg gtccagttgc ccgcccaggc ggccgtgtcc ggcccgcaca gccggttggc
128101  cagggccgcc agcaggcagg acagcccgcc gcgctcggcg gaccactccg gcggccccc
128161  cgaggccccg ccgccggcca ggtcctcgcc cggcagcggc gagtacagca ccaccacgcg
128221  cacgtcctcg gggtcgggga tctggcgcat ccaggccgcc atgcggcgca gcgggcccga
128281  ggcgcgcagg gggccaaaga ggcggccccc ggcggcccg tggggggtggg ggttctcgtc
128341  gtcgtcgccg ccgcacgcgg cctgggcggc ggggggcggc ccggcgcacc gcgcggcgat
128401  cgaggccagg ggccgcgggt caaaacatgag ggccggcctc cagggggacgg ggaacagcgg
128461  gtggtccgtg agctcggcca cggcgcgcgg ggagcagtag gcctccaggg cggcggccgg
128521  gggcgccgcc gtgtggctgg gccccggg ctgccgccgc cagccgccca ggggggtcggg
128581  gccctcggcg gccggcgcg acagcgccac ggggcgcggg cgggcctgcg ccgcggcgcc
128641  ccggggccgcc gcgggctggg cggggtgggg ctcggggcccc gggggcgtgg aggggggcgc
128701  ggggagggggg gcgcgggcgt ccgagcgggg ggcgtcccgg ccgctcttct tcgtcttcgg
128761  gggtcgcggg ccgccgcctc cgggcggccg ggccgggccg ggactcttgc gcttgcgccc
128821  ctcccgcggc gcgcggagg cggcggcggc cgcgcagcgc tcggcggcgt ccggtgcgct
128881  ggccgccgcc gccagcaggg ggcggaggct ctggttctca aacagcaggt ccgcggcggc
128941  ggcggccggcg gagctcggca ggcgcgggtc ccgcggcagc gcggggccca gggccccggc
129001  gaccaggctc acggcgcgca cggcgcctcg ctgccgcccg ccacgcgcag
129061  gtccccgcgc aggcgcatga gcaccagcgc gtcgcgcacg aacccgcagct cgcgcagcca
129121  cgcgcgcagg cggggcgcgt cggcgtgcgg cggcgcgggg gaagcggggc ccgcgggtcc
129181  ctccggccgc ggggggctgg cgggccgggc cccggccagc ccgggacgg ccgccaggtc
129241  gccgtcgaag ccctcggcca gcgcctccag gatcccgcgg caggcggcca ggcactcgac
129301  ggccacgcgg cggcgctggg ccgcgccgcg ggcgtcggcg tcggcgtggc gggcggcgtc
129361  ggggtcgtcg cccccacgg gggaggcggg cgcggcggac agccgcccca gggggcgcgag
129421  gatccccgcg gcgccgtacc cggcgggcac cgcgcgctcg cccggtgcgg cggcggcgac
129481  ggcggcgacc ccctcgtcat ctgcgccggc gccgggggctc ccgcggcccc cgtcagcgc
129541  cgcgttctcg cgcgcaaaca ggggcgcgta ggcgcggcgc aggctggtca gcaggaagcc
129601  cttctgcgcg cggtcgtatc ggcggctcat ggccacggcg gccgccgcgt gcgccaggcc
```

Sequence Listing

```
129661 ccagccgaag cggccggccg ccatggcgta gcccaggtgg ggcacggccc gcgccacgct
129721 gccggtgatg aaggagctgc tgttgcgcgc ggcgcccgag atccggaagc aggcctggtc
129781 cagcgccacg tccccgggga ccacgcgcgg gttctggacg caccccatgg cctccgcgtc
129841 cggggtgtac agcagccgcg tgatcagggc gtactgctgc gcggcgtcgc ccagctcggg
129901 cgcccacacg gccgccgggg cgcccgaggc ctcgaaccgg cgtcgcgcct cctccgcctc
129961 gggcgccccc cagaggcccg ggcggctgtc gcccaggccg ccgtacagca cccgccccgg
130021 gggcggggc ccggcgccgg gccacggctc cccgctgacg tacccgtcgc gatagcgcgc
130081 gtagaaggcg ccggaggccg cgtcgcgtc cagctcgacc cgccggggct gcccggccgt
130141 gaagcggccc gtggcgtcgc ggccggccac cgccgcgcgg gcccggcggc gctcgatgcg
130201 gcccgcggag gccgcggggg tcctcgccgc cgcccgggc ttgggcgcgg cctcggagag
130261 ggggggtggc ccgggcgggg gcggcgtccg cccgggggct tccggcgccg cgctcgacgg
130321 accccgcccg acggccgcg cctcgcgtgc gtggtcggcc gcgtcgttgc cgtcgtcgtc
130381 ctcgtcctcg tcggacgacg aggacgaaga ggatgcggac gacgaggacg aggacccgga
130441 gtccgacgag gtcgatgacg ccgatgccg ccgccggccg tgacgacgtc tccgcggcgg
130501 ctgggccggc gggcgcggcg acaggcggtc cgtgggggtcc ggatacgcgc gcgtagcgg
130561 ggcctcccgt tcgcggcccc gggccgggc ccggtcgccg gcggcgtcgg ctgcgtcgtc
130621 gtactcgtcc ccgtcatcgt cgtcggctag aaaggcgggg gtccggggcg gcgaggccgc
130681 ggggtcgggc gtcgggatcg tccggacggg ctcctctacc atggaggcca gcagagccag
130741 ctgtcgcgac gagacggcgt ccccggcgtc ctcgccggcg tcggtgcccg ccgcgggggc
130801 cctcccgtcc cgccgggcgt cgtcgaggtc gtggggggtgg tcggggatcg ggtcggggtc
130861 gtcccccgccc tcctccgtct ccgcgcccca cccgaggggcc ccccgctcgt cgcggtctgg
130921 gctcggggtg ggcggcgcc cgtcggtggg gcccggggag ccggggcgct gcttgttctc
130981 cgacgccatc gccgatgcgg ggcgatcctc cggggatacg gctgcgacgg cggacgtagc
131041 acggtaggtc acctacggac tctcgatggg gagacccgac gacccgacg
131101 accccgccg tcgacgcgga actagcgcgg accggtcgat gcttgggtgg ggaaaaagga
131161 cagggacggc cgatccccct ccgcgcttc gtccgcgtat cggcgtcccg gcgcggcgag
131221 cgtctgacgg tctgtctctg gcggtcccgc gtcgggtcgt ggatccgtgt cggcagccgc
131281 gctccgtgtg gacgatcggg gcgtcctcgg gctcatatag tcccagggcg cggcgggaag
131341 gaggagcagc ggaggccgcc ggccccccgc ccccccggcgg gcccaccccg aacggaattc
131401 cattatgcac gaccccgccc cgacgccggc acgccggggg cccgtggccg cggcccgttg
131461 gtcgaacccc cggccccgcc catccgcgcc atctgccatg gacggggcgc gagggcgggt
131521 gggtccgcgc ccgccccgc atggcatctc attaccgccc gatccggccgg tttccgcttc
131581 cgttccgcat gctaacgagg aacgggcagg gggcgggccc cgggcccga cttcccggtt
131641 cggcggtaat gagatacgag ccccgcgcgc ccgttggccg tccccggccc cccggtcccg
131701 cccgccggac gccgggacca acgggacggg gggcggccct gggccgccc gccttgccgc
131761 cccccattg gccggcgggc gggaccgccc caagggggcg gggccgccgg gtaaaagaag
131821 tgagaacgcg aagcgttcgc acttcgtccc aatatatata tattattagg gcgaagtgcg
131881 agcactggcg ccgtgcccga ctccgcgccg gccccggggg cggaccgggg cggcgggggg
131941 cgggtctctc cggcgcacat aaaggcccgg cgcgaccgac gcccgcagac ggcgccagcc
132001 acgaacgacg ggagcggctg cggagcacgg ggaccgggag cgggagtcgc agagggccgt
132061 cggagcggac ggcgtcggca tcgcgacgcc ccggctcggg atcgggatcg catcggaaag
132121 ggacacgcgg acgcgggggg gaaagacccg cccacccccac ccacgaaaca caggggacgc
132181 accccggggg cctccgacga cagaaaccca ccggtccgcc tttttttgcac gggtaagcac
132241 cttgggtggg cagaggaggg gggacgcggg ggcggaggag gggggacgcg ggggcggagg
132301 aggggggacg cggggggcgga ggaggggggga ggagggggg gacgcggggg
132361 cggaggaggg ggctcacccg cgttcgtgcc ttcccgcagg aggaacgccc tcgtcgaggc
132421 gaccggcggc gaccgttgcg tggaccgctt cctgctcgtc ggggggggggg gagccactgt
132481 ggtcctccgg gacgttttct ggatggccga catttcccca ggcgcttttg tgccttgtgt
132541 aaaaagcgcgg cgtcccgctc tccgatcccc gccctgggc acgcgcaagc gcaagccgcc
132601 tgcccgcccc ctctcatcgg agtctgaggt cgaatccgag acagccttgg agtctgaggt
132661 cgaatccgag acagcatcgg attcgaccga gtctggggac caggaggaag ccccccgcat
132721 cggtggccgt agggccccc ggaggcttgg ggggcggttt ttctggaca tgtcggcgga
132781 atccaccacg gggacggaaa cggatgcgtc ggtgtcggac gaccccgacg acacgtccga
132841 ctggtcttgt gacgacattc ccccacgacc caagcggcc cgggtaaacc tgcggctcac
132901 tagctctccc gatcggcggg atggggttat tttcctaag atggggcggg tccggtctac
132961 ccgggaaacg cagccccggg ccccccccc gtcggcccca agcccaaatg caatgctccg
133021 gcgctcggtg cgccaggccc agaggcggag cagcgcacga tggaccccg acctgggcta
133081 catgcgccag tgtatcaatc agctgttcg ggtcctgcgg gtcgcccggg acccccacgg
133141 cagtgccaac cgcctgcgcc acctgatacg cgactgttac ctgatgggat actgccgagc
133201 ccgtctggcc ccgcgcacgt ggtgccgctt gctgcaggtg tccggcgaa cctggggcat
133261 gcacctgcgc aacaccatac gggaggtgga ggctcgattc gacgccaccg cagaacccgt
133321 gtgcaagctt ccttgtttgg aggcagacg gtacggcccg gagtgtgatc ttagtaatct
133381 cgagattcat ctcagcgcga caagcgatga tgaaatctcc gatgccaccg atctggaggc
133441 cgccggttcg gaccacacgc tcgcgtccca gtccgacacg gaggatgccc cctccccccgt
133501 tacgctggaa accccagaac cccgcgggtc cctcgctgtg cgtctggagg atgagtttgg
133561 ggagtttgac tggaccccc aggagggctc ccagccctgg ctgtctgcgg tcgtggccga
133621 taccagctcc gtggaacgcc cgggcccatc cgattctggc gcgggtcgcg cagcagaaga
133681 ccgcaagtgt ctggacggct gccggaaaat gcgcttctcc accgcctgcc cctatccgtg
133741 cagcgcacg tttctccggc cgtgagtccg gtcgcccga cccccttgta tgtcccccaaa
133801 ataaaagacc aaaatcaaag cgtttgtccc agcgtcttaa tggcgggaag ggcggagaga
133861 aacagaccac gcgtacatgg ggggtgttg ggggtttatt gacatcgggg ctacagggtg
133921 gtaaccggat agcagatgtg aggaagtctg gcagggcccg gccgaacggc gatcagaggg
133981 tccgtttctt gcggaccacg gcccggtgat gtgggttgct cgtcaaaat ctcgggcata
134041 cccatacacg cacaacacg acgccgcacc gaatgggacg tcgtaagggg gtgggaggta
134101 gctgggtggg gtttgtgcag agcaatcagg gaccgcagcc agcgcataca atcgcgctcc
134161 cgtccgttgg tcccgggcag gaccacgccg tactggtatt cgtaccggct gagcagggtc
134221 tccaggggggt ggttgggtgc cgcggggaac ggggtccacg ccacggtcca ctcgggcaaa
```

```
134281  aaccgagtcg gcacggccca cggttctccc acccacgcgt ctggggtctt gatggcgata
134341  aatcttaccc cgagccggat tttttgggcg tattcgagaa acggcacaca cagatccgcc
134401  gcgcctacca cccacaagtg gtagaggcga gggggcggg gttggtctcg gtgcaacagt
134461  cggaagcacg ccacggcgtc cacgacctcg gtgctctcca aggggctgtc ctccgcaaac
134521  aggcccgtgg tggtgtttgg ggggcagcga caggacctag tgcgcacgat cgggcgggtg
134581  ggtttgggta agtccatcag cggctcggcc aaccgtcgaa ggttggccgg gcgaacgacg
134641  accggggtac ccaggggttc tgatgccaaa atgcggcact gcctaagcag gaagctccac
134701  agggccgggc ttgcgtcgac ggaagtccgg ggcagggcgt tgttctggtc aaggagggtc
134761  attacgttga cgacaacaac gcccatgttg gtatattaca ggcccgtgtc cggtttgggg
134821  cacttgcaga tttgtaaggc cacgcacggc ggggagacag gccgacgcgg gggctgctct
134881  aaaaatttaa gggccctacg gtccacagac ccgccttccc gggggggccc ttggagcgac
134941  cggcagcgga ggcgtccggg ggaggggagg gttatttacg ggggggtagg tcaggggggtg
135001  ggtcgtcaaa ctgccgctcc ttaaaacccc ggggcccgtc gttcggggtg ctcgttggtt
135061  ggcactcacg gtgcggcgaa tggcctgtcg taagttttgt cgcgtttacg ggggacaggg
135121  caggaggaag gaggaggccg tcccgccgga gacaaagccg tcccgggtgt ttcctcatgg
135181  cccctttttat accccagccg aggacgcgtg cctggactcc ccgcccccgg agacccccaa
135241  accttcccac accacaccac ccggcgatgc cgagcgcctg tgtcatctgc aggagatcct
135301  ggcccagatg tacgaaacc aggactaccc catagaggac gaccccagcg cggatgccgc
135361  ggacgatgtc gacgaggacg ccccggacga cgtggcctat ccggaggaat acgcagagga
135421  gcttttttctg cccggggacg cgaccggtcc ccttatcggg ccaacgacc acatccctcc
135481  cccgcgtggc gcatctcccc ccggtatacg acgacgcagc cgggatgaga ttggggccac
135541  gggatttacc gcagaagagc tggacgccat ggacaggcag gcggctcgag ccatcagccg
135601  cggcggcaag ccccccctcga ccatggccaa gctggtgact ggcatgggct tacgatcca
135661  cggagcgctc accccaggat cggaggggtg tgtctttgac agcagccacc cagattaccc
135721  ccaacgggta atcgtgaagg cggggtggta cacgagcacg agccacgagg cgcgactgct
135781  gaggcgactg gaccaccccgg cgatcctgcc cctcctggac ctgcatgtcg tctccgggggt
135841  cacgtgtctg gtcctcccca gtaccaggc cgacctgtat acctatctga gtaggcgcct
135901  gaacccactg ggacgcccgc agatcgcagc ggtctcccgg cagctcctaa gcgccgttga
135961  ctacattcac cgccagggca ttatccaccg cgacattaag accgaaaata ttttttattaa
136021  cacccccgag gacatttgcc tgggggggactt tggtgccgcg tgcttcgtgc agggggttcccg
136081  atcaagcccc ttcccctacg gaatcgccgg aaccatcgac accaacgccc ccgaggtcct
136141  ggccggggat ccgtatacca cgccgtcga catttggagc gccggtctgg tgatcttcga
136201  gactgccgtc cacaacgcgt ccttgttctc ggccccccaaa gggggcccgtg
136261  cgacagtcag atcacccgca tcatccgaca ggcccaggtc cacgttgacg agttttcccc
136321  gcatccagaa tcgcgcctca cctcgcgcta ccgctcccgc gcggccggga caatcgccc
136381  gccttacacc cgaccggcct ggacccgcta ctacaagatg gacatagacg tcgaatatct
136441  ggttttgcaaa gccctcacct tcgacgggcg gcttcgcccc agcgccgcag agctgctttg
136501  tttgccgctg tttcaacaga aatgaccgcc ccggggggc ggtgctgttt gcgggttggc
136561  acaaaaagac cccgaccgcc gtctgtggtg ttttttggcat catgtcgccg ggcgccatgc
136621  gtgccgttgt tcccattatc ccattccttt tggttcttgt cggtgtatcg ggggttccca
136681  ccaacgtctc ctccaccacc caaccccaac tccagaccac cggtcgtccc tcgcatgaag
136741  cccccaacat gacccagacc ggcaccaccg actctcccac cgccatcagc cttaccacgc
136801  ccgaccacac accccccatg ccaagtatcg gactgagga ggaggaggaa gaggaggagg
136861  gggccgggga tggcgaacat cttaaggggg gagatgggac ccgtgacacc ctaccccagt
136921  ccccgggtcc agccgtcccg ttggccgggg atgacgagaa ggacaaaccc aaccgtcccg
136981  tagtcccacc ccccggtccc aacaactccc ccgcgcgccc cgagaccagt cgaccgaaga
137041  cacccccac cagtatcggg ccgctggcaa ctcgacccac gacccaactc ccctcaaagg
137101  ggcgacccctt ggttccgacg cctcaacata ccccgctgtt ctcgttcctc actgcctccc
137161  ccgccctgga caccctcttc gtcgtcagca ccgtcatcca cacctttatc tttgtgtgta
137221  ttgttgctat ggcgacacac ctgtgtggtg gttggtccag acgcgggcga cgcacacacc
137281  ctagcgtgcg ttacgtgtgc ctgccgcccg aacgcgggta gggtatgggg cggggatggg
137341  gagagcccac acgcggaaag caagaacaat aaaggcggcg ggatctagtt gatatgcgtc
137401  tctgggtgtt tttgggggtgt ggtgggcgcg gggcggtcat tggacgggggg tgcagttaaa
137461  tacatgcccg ggacccatga agcatgcgcg acttccgggc ctcgggaaccc acccgaaacg
137521  gccaacggac gtctgagcca ggcctggcta tccggagaaa cagcacacga cttggcgttc
137581  tgtgtgtcgc gatgtctctg cgcgcagtct ggcatctggg gcttttggga agcctcgtgg
137641  gggctgttct tgccgccacc catctggac ctgcggccaa cacaacgac cccttaacgc
137701  acgccccagt gtcccctcac cccagccccc tggggggcctt tgccgtcccc ctcgtagtcg
137761  gtgggctgtg tgccgtagtc ctgggggcgg cgtgtctgct tgagctcctg cgtcgtacgt
137821  gccgcgggtg gggcgttac catccctaca tggacccagt tgtcgtataa ttttttcccc
137881  cccccccttc tccgcatggg tgatgtcggg tccaaactcc cgacaccacc agctggcatg
137941  gtataaatca ccggtgcgcc cccaaaacca tgtccggcag gggggatgggg ggcgaatgcg
138001  gagggcaccc aacaacaccg ggctaaccag gaaatccgtg gccccgccc ccaacaaaga
138061  tcgcggtagc ccggccgtgt gacattatcg tccataccga ccacaccgac gaatccccta
138121  agggggaggg gccattttac gaggaggagg ggtataacaa agtctgtctt taaaaagcag
138181  gggttaggga gttgttcggt cataagcttc agtgcgaacg accaactacc ccgatcatca
138241  gttatccta aggtctcttt tgtgtggtgc gttccggtat gggggggggct gccgccaggt
138301  tgggggccgt gattttgttt gtcgtcatag tgggcctcca tggggtccgc ggcaaaatatg
138361  ccttggcgga tgcctctctc aagatggccg accccaatcg cttctcgcggc aaagaccttc
138421  cggtcctgga ccagctgacc gaccctccgg gggtccggcg cgtgtaccac atccaggcgg
138481  gcctaccgga cccgttccag ccccccagcc tcccgatcac ggtttactac gccgtgttgg
138541  agccgcgcctg ccgcagcgtg ctcctaaacg cacgtccag attgtccgcg
138601  gggcctccga agacgtccgg aaacaaccct acaacctgac catcgcttgg tttcggatgg
138661  gaggcaactg tgctatcccc atcacggtca tggagtacac cgaatgctcc tacaacaagt
138721  ctctgggggc ctgtcccatc cgaacgcagc cccgctggaa ctactatgac agcttcagcg
138781  ccgtcagcga ggataacctg gggttcctga tgcacgcccc cgcgtttgag accgccggca
138841  cgtacctgcg gctcgtgaag ataaacgact ggacggagat tacacagttt atcctggagc
```

-continued

Sequence Listing

```
138901  accgagccaa gggctcctgt aagtacgccc tcccgctgcg catcccccg tcagcctgcc
138961  tctccccca ggcctaccag caggggtga cggtggacag catcgggatg ctgccccgct
139021  tcatcccga gaaccagcgc accgtcgccg tatacagctt gaagatcgcc gggtggcacg
139081  ggcccaaggc cccatacacg agcaccctgc tgcccccgga gctgtccgag accccaacg
139141  ccacgcagcc agaactcgcc ccggaagacc ccgaggattc ggccctcttg gaggaccccg
139201  tggggacggt ggcgccgcaa atcccaccaa actggcacat cccgtcgatc caggacgccg
139261  cgacgcctta ccatccccg gccaccccga acaacatggg cctgatcgcc ggcgcggtgg
139321  gcggcagtct cctggcagcc ctggtcattt gcggaattgt gtactggatg caccgccgca
139381  ctcggaaagc cccaaagcgc atacgcctcc cccacatccg ggaagacgac cagccgtcct
139441  cgcaccagcc cttgttttac tagatacccc cccttaatgg gtgcggggg gtcaggtctg
139501  cggggttggg atgggacctt aactccatat aaagcgagtc tggaaggggg gaaaggcgga
139561  cagtcgataa gtcggtagcg ggggacgcgc acctgttccg cctgtcgcac ccacagcttt
139621  ttcgcgaacc gtcccgtttc gggatgccgt gccgcccgtt gcagggcctg gtgctcgtgg
139681  gcctctgggt ctgtgccacc agcctggttg tccgtggccc cacggtcagt ctggtatcaa
139741  actcatttgt ggacgccggg gccttggggc ccgacggcgt agtggaggaa gacctgctta
139801  ttctcgggga gcttcgcttt gtggggggacc aggtccccca caccacctac tacgatgggg
139861  tcgtagagct gtggcactac cccatgggac acaaatgccc acgggtcgtg catgtcgtca
139921  cggtgaccgc gtgcccacgt cgcccgccg tggcatttgc cctgtgtcgc gcgaccgaca
139981  gcactcacag ccccgcatat cccaccctgg agctgaatct ggcccaacag ccgcttttgc
140041  gggtccggag ggcgacgcgt gactatgccg gttacgcgta tgggtcgggg
140101  acgcaccaaa cgccagcctg tttgtcctgg ggatggccat agccgccgaa ggtactctgg
140161  cgtacaacgg ctcggcccat ggctcctgcg acccgaaact gcttccgtct tcggccccgc
140221  gtctggcccc ggcgagcgta taccaacccg cccctaaccc ggcctccacc ccctcgacca
140281  ccacctccac ccctcgacc accatccccg ctcccaagc atcgaccaca cccttcccca
140341  cgggagaccc aaaacccaa cctcacgggg tcaaccacga accccatcg aatgccacgc
140401  gagcgacccg cgactcgcga tatgcgctaa cggtgaccca gataatccag atagccatcc
140461  ccgcgtccat tatagccctg gtgtttctgg ggagctgtat ttgctttata cacagatgtc
140521  aacgccgcta ccgacgctcc cgccgcccga tttacagccc cagataccc acgggcatct
140581  catgcgcggt gaacgaagcg gccatggccc gcctcggagc cgagctcaaa tcgcatccga
140641  gcaccccccc caaatcccgg cgccggtcgt cacgcacgcc aatgccctcc ctgacggcca
140701  tcgccgaaga gtcggagccc cgggggcgg ctgggcttcc gacgccccc gtggacccca
140761  cgacatccac cccaacgcct ccctgttgg tataggtcca cggcactggg ccgggggcac
140821  cacataaccg accgcagtca ctgagttggg aataaaccgg tattatttac ctatatccgt
140881  gtatgtccat ttctttcttc ccccccccc ccggaaacca agaggaag caaagaatgg
140941  atgggaggag ttcaggaagc cggggagagg gcccgcggcg catttaaggc gttgttgtgt
141001  tgactttggc tcttctggcg ggttggtgcg gtgctgtttg ttgggctccc attttacccg
141061  aagatcggct gctatcccg ggacatggat cgcgggggcg tgggggggtt tcttctcggt
141121  gtttgtgttg tatcgtgctt ggcgggaacg cccaaaacgt cctggagacg ggtgagtgtc
141181  ggcgaggacg tttcgttgct tccagctccg gggcctacgg ggcgcggccc gacccagaaa
141241  ctactatggg ccgtggaacc cctgatggg tgcggcccct tacacccgtc gtgggtctcg
141301  ctgatgcccc ccaagcaggt gcccgagacg gtcgtggatg cggcgtcat gcgcgctccg
141361  gtcccgctgg cgatggcgta cgcccccccg gccccatctg cgaccggggg tctacgaacg
141421  gacttcgtgt ggcaggagcg cgcggccgtg gttaaccgga gtctggttat tcacggggtc
141481  cgagagacgg acagcggcct gtataccctg tccgtgggcg acataaagga cccggctcgc
141541  caagtggcct cggtggtcct ggtggtgcaa ccggccccag ttccgacccc acccccgacc
141601  ccagccgatt acgacgagga tgacaatgac gagggcgagg acgaaagtct cgccggcact
141661  cccgccagcg ggaccccccg gctcccgcct ccccccgccc cccgaggtc ttggcccagc
141721  gcccccgaag tctcacatgt gcgtggggtg accgtgcgta tggagactcc ggaagctatc
141781  ctgttttccc ccggggagac gttcagcacg aacgtctcca tccatgccat cgcccacgac
141841  gaccagacct actccatgga cgtcgtctgg ttgaggttcg acgtgccgac ctcgtgtgcc
141901  gagatgcgaa tatacgaatc gtgtctgtat cacccgcagc tcccagaatg tctgtccccg
141961  gccgacgcgc cgtgcgccgc gagtacgtgg acgtctcgcc tggccgtccg cagctacgcg
142021  gggtgttcca gaacaaaccc ccaccgcgc tgttcgggcg aggctcacat ggagcccgtc
142081  ccggggctgg cgtggcaggc ggcctccgtc aatctggagt tcgggacgc gtccccacaa
142141  cactccggcc tgtatctgtg tgtggtgtac gtcaacgacc atattcacgc ctggggccac
142201  attaccatca gcaccgcggc gcagtaccgg aacgcggtgg tggaacagcc cctcccacag
142261  cgcggcgcgg atttggccga gcccacccac ggcacgtcg gggccccctcc ccacgcgccc
142321  ccaacccacg gcgccctgcg gttaggggcg gtgatggggg ccgcctgct gctgtctgcg
142381  ctgggggttgt cggtgtgggc gtgtatgacc tgttggcgca ggcgtgcctg gcgggcggtt
142441  aaaagcaggg cctcgggtaa ggggcccacg tacattcgcg tggccgacag cgagctgtac
142501  gcggactgga gctcggacag cgagggagaa cgcgaccagg tcccgtggct ggccccccg
142561  gagagacccg actctccctc caccaatgga tccggcttgg agatcttatc accaacggct
142621  ccgtctgtat accccgtag cgacgggcat caatctcgcc gccagctcac aacctttgga
142681  tccggaaggc ccgatcgccg ttactcccag gcctccgatt cgtccgtctt ctggtaaggc
142741  gccccatccc gaggcccac gtcggtcgcc gaactgggcg accgccggcg aggtggacgt
142801  cggagacgag ctaatcgcga tttccgacga acgcggaccc cccgacatg accgcccgcc
142861  cctcgccacg tcgaccggca cctcgcaca ccccgaccc ccggcgtaca cggccgttgt
142921  ctccccgatg gccctccagg ctgtcgacgc cccctccctg tttgtcgcct ggctggccgc
142981  tcggtggctc cggggggctt ccggcctggg ggccgtcctg tgtgggattg cgtggtatgt
143041  gacgtcaatt gcccgaggcg cacaaaggggc cggtggtccg cctagccgca gcaaattaaa
143101  aatcgtgagt cacagcgacc gcaacttccc accggagct tcttccggc tcgatgacg
143161  tcccgctct ccgatcccaa ctcctcagcg gccgacgaca tgtccgtccg gcttttatccc
143221  acggcctcgc cagtttcggt cgaagcctac tactcggaaa gcgaagacga ggcggccaac
143281  gacttcctcg tacgcatggg ccgccaacag tcggtattaa ggcgttgacg cagacgcacc
143341  cgctgcgtcg gcatggtgat cgcctgtctc ctcgtggccg ttctgtcggg cggatttggg
143401  gcgctcctga tgtggctgct ccgctaaaag accgcatcga cacgcgtc cttcttgtcg
143461  tctctcttcc cccccatcac cccgcaattt gcaccagcc tttaactaca ttaaattggg
```

Sequence Listing

```
143521  ttcgattggc aatgttgtct cccggttgat ttttgggtgg gtggggagtg ggtgggtggg
143581  gagtgggtgg gtggggagtg ggtgggtggg gagtgggtgg gtggggagtg ggtgggtggg
143641  gagtgggtgg gtggggagtg ggtgggtggg gagtgggtgg gtggggagtg ggtgggtggg
143701  gagtggcaag gaagaaacaa gcccgaccac cagacagaaa atgtaaccat acccaaaccg
143761  actctggggg ctgtttgtgg ggtcggaacc ataggatgaa caaaccaccc cgtacctccc
143821  gcacccaagg gtgcgggtgg ctcatcggca tctgtccggt atgggttgtt ccccacccac
143881  tcgcgttcgg acgtcttaga atcatggcgg ttttctatgc cgacatcggt tttctccccc
143941  gcaataagac acgatgcgat aaaatctgtt tgtaaaattt attaagggta caaattgccc
144001  tagcacaggg gtgggggttag ggccgggtcc ccacacccaa acgcaccaaa cagatgcagg
144061  cagtgggtcg agtacagccc cgcgtacgaa cacgtcgatg cgtgtgtcag acagcaccag
144121  aaagcacagg ccatcaacag gtcgtgcatg tgtcggtggg tttggacgcg gggggccatg
144181  gtggtgataa agttaatggc cgccgtccgc caggggccaca gggcgacgt cttcttggttg
144241  gcccggagcc actgggtgtg gaccagccgc gcgtggcggc ccaacatggc ccctgtagcc
144301  gggggcgggg gatcgcgcac gtttgcagcg cacatgcgag acacctcgac cacggttcga
144361  aagaaggccc ggtggtccgc gggcaacatc accaggtgcg caagcgcccg ggcgtccaga
144421  gggtagagcc ctgagtcatc cgaggttggc tcatcgcccg ggtcttgccg caagtgcgtg
144481  tggggttggc ttccggtggg cgggacgcga accgcggtgt ggatcccgac gcgggcccga
144541  gcgtatgctc catcttgtgg ggagaagggg tctgggctcg ccagggggc atacttgccc
144601  gggctataca gacccgcgag ccgtacgtgg ttcgcggggg gtgcgtgggg tccggggctc
144661  cctgggagac cggggtttgtc gtggatccct ggtaccctgg ggtctctggg
144721  agctcgcggt actctgggtt ccctaggttc tcggggtggt cgcggaaccc ggggctcccg
144781  gggaacacgc ggtgtcctgg ggattgttgg cggtcggacg gcttcagatg gcttcgagat
144841  cgtagtgtcc gcaccgactc gtagtagacc cgaatctcca cattgccccg ccgcttgatc
144901  attatcaccc cgttgcgggg gtccggagat catgcgggtg tgtcctcgga gtgcgtgaac
144961  acctctgggg tgcatgccgg cggacggcac gccttttaag taaacatctg ggtcgcccgg
145021  cccaactggg gccggggggtt gggtctggct catctcgaga gacacggggg ggaaccaccc
145081  tccgcccaga gactcgggtg atggtcgtac ccgggactca acgggttacc ggattacggg
145141  gactgtcggt cacggtcccg ccggttcttc gatgtgccac acccaaggat gcgttggggg
145201  cgatttcggg cagcagcccg ggagagcgca gcaggggacg ctccgggtcg tgcacggcgg
145261  ttctggccgc ctcccggtcc tcacgccccc ttttattgat ctcatcgcgt acgtcggcgt
145321  acgtcctggg cccaacccgc atgttgtcca ggaaggtgtc cgccatttcc agggcccacg
145381  acatgctttt ccccccgacg agcaggaagc ggtccacgca acggtcgccg ccggtcgcct
145441  cgacgagggc gttcctcctg cgggaaggca cgaacgcggg tgagccccct cctccgcccc
145501  cgcgtccccc ctcctccgcc cccgcgtccc ccctcctccg ccccccgcgtc ccccctcctc
145561  cgccccccgcg tccccctcc tccgccccccg cgtccccccct cctctgccca cccaaggtgc
145621  ttaccccgtgc aaaaaaggcg gaccggtggg ttttctgtcgt cggaggcccc cggggtgcgt
145681  cccctgtgtt tcgtgggtgg ggtgggcggg tcttttccccc ccgcgtccgc gtgtcccttt
145741  ccgatgcgat cccgatcccg agcggggggc tcgcgatgcc gacgccgtcc gctccgacgg
145801  ccctctgcga ctcccgctcc cggtccgcgt gctccgcagc cgctcccgtc gttcgtggct
145861  ggcgccgtct gcgggcgtcg gtcgcgccgg gcctttatgt gcgccggaga gacccgcccc
145921  ccgccgcccg ggtccgcccc cggggccggc gcggagtcgg gcacggcgcc agtgctcgca
145981  cttcgcccta ataatatata tatattggga cgaagtgcga acgcttcgcg ttctcactc
146041  ttttacccgg cggccccgcc cccttgggggc ggtccccgccc gccggccaat gggggggcgg
146101  caaggcgggc ggcccaaggg ccgcccgccg tccccgttggt cccggcgtcc ggcgggcggg
146161  accggggggcc cggggacggc caacggccgc gcgggggtcg tatctcatta ccgccgaacc
146221  gggaagtcgg ggcccggggcc ccgcccccctg cccgttcctc gttagcatgc ggaacggaag
146281  cggaaaccgc cggatcgggc ggtaatgaga tgccatgcgg ggccggggcgc ggacccaccc
146341  gccctcgcgc cccgtccatg gcagatggcc cggatgggcg gggccggggg ttcgaccaac
146401  gggccggggc cacggggccc ccggcgtgcc gggtcgtgc ataatggaat
146461  tccgttcggg gtgggccgc cgggggggcg ggggccggcg gcctccgctg ctcctccttc
146521  ccgccggccc ctgggactat atgagcccga ggacgccccg atcgtccaca cggagcgcgg
146581  ctgccgacac ggatccacga cccgacgcgg gaccgccaga gacagaccgt cagacgctcg
146641  ccgcgccggg acgccgatac gcggacgaag ggatcggccg tccctgtcct
146701  ttttccccac ccaagcatcg accggtccgc gctagttccg cgtcgacgcc ggggggtcgtc
146761  ggggtccgtg ggtctcgccc cctcccccca tcgagagtcc gtaggtgacc taccgtgcta
146821  cgtccgccgt cgcagccgta tcccccggagg atcgcccccgc atcgcgatg gcgtcggaga
146881  acaagcagcg cccccgcctc ccgggcccca ccgacgggcc gccgccccac ccgagcccag
146941  accgcgacga gcggggggc ctcgggtggg gcgcggaggac ggaggagggc ggggacgacc
147001  ccgaccacga ccccgaccac ccccacgacc tcgacgacgc ccggcgggac gggagggccc
147061  ccgcggcggg caccgacgcc ggcgaggacg ccggggacgc cgtctcgtcg cgacagctgg
147121  ctctgctggc ctccatggta gaggaggccg tccggacgat cccgacgccc gaccccgcgg
147181  cctcgcctgcc ccggaccccc gcctttctag ccgacgacga tgacgggggac gagtacgacg
147241  acgcagccga cgccgccggc gaccgggccc cggccgggg ccgcgaacgg gaggccccgc
147301  tacgcggcgc gtatccggac cccacggacc gcctgtcgcc gcgcccgccg gcccagccgc
147361  cgcggagacg tcgtcacggc cggcggcggc catcggcgtc atcgacctcg tcggactccg
147421  ggtcctcgtc ctcgtcgtcc gcatcctctt cgtcctcgtc gtccgacgag gacgaggacg
147481  acgacggcaa cgacgcggcc gaccacgcac gcgaggcgcg gcgcgtcggg cggggtccgt
147541  cgagcgcggc gccggaagcc cccgggcgga cgccgccccc gcccgggcca ccccccctct
147601  ccgaggccgc gcccaagccc gggcgcgcgg cgaggacccc cgcggcctcc gcgggccgca
147661  tcgagcgccg ccgggcccgc gcggcggtgg ccggccgcga cgccacgggc cgcttcacgg
147721  ccgggcagcc ccggcgggtc gagctgacgg ccgacgcggc ctccggcgcc ttctacgcgc
147781  gctatcgcga cggtacgtc agcggggagc ccggccccg ccgccccccgg
147841  ggcgggtgct gtacggcggc ctgggcgaca gccgcccggg cctctgggggg gcgcccgagg
147901  cggaggaggc gcgacgcgg ttcgaggcct cggggcgcccc ggcggccgtg tgggcgcccg
147961  agctgggcga cgccgcgcag cagtacgccc tgatcacgcg gctgctgtac accccggacg
148021  cggaggccat ggggtggctc cagaacccgc gcgtggtccc cggggacgtg gcgctggacc
148081  aggcctgctt ccggatctcg ggcgccgcgc gcaacagcag ctccttcatc accggcagcg
```

```
148141  tggcgcgggc cgtgccccac ctgggctacg ccatggcggc cggccgcttc ggctggggcc
148201  tggcgcacgc ggcggccgcc gtggccatga gccgccgata cgaccgcgcg cagaagggct
148261  tcctgctgac cagcctgcgc cgcgcctacg cgcccctgtt ggcgcgcgag aacgcggcgc
148321  tgacggggc cgcggggagc cccggcgccg gcgcagatga cgaggggtc gccgccgtcg
148381  ccgccgccgc accgggcgag cgcgcggtgc ccgccgggta cggcgccgcg ggatcctcg
148441  ccgccctggg gcggctgtcc gccgcgcccg cctccccgt gggggcgac gaccccgacg
148501  ccgcccgcca cgccgacgcc gacgccgggc gccgcgccca ggccggccgc gtggccgtcg
148561  agtgcctggc cgcctgccgc gggatcctgg aggcgctggc cgagggcttc gacggcgacc
148621  tggcggccgt cccggggctg gccggggccc ggcccgccag cccccgcgg ccggagggac
148681  ccgcgggccc cgcttccccg ccgccgccgc acgccgacgc gccccgcctg cgcgcgtggc
148741  tgcgcgagct gcggttcgtg cgcgacgcgc tggtgctcat gcgcctgcgc ggggacctgc
148801  gcgtggccgg cggcagcgag gccgccgtgg ccgccgtgcg cgccgtgagc ctggtcgccg
148861  gggccctggg ccccgcgctg ccgcgggacc cgcgcctgcc gagctccgcg gccgccgccg
148921  ccgcggacct gctgtttgag aaccagagcc tccgcccct gctggcggcg gcggccagcg
148981  caccggacgc cgccgacgcg ctggccgccg ccgccgcctc cgccgccgcg cgggagggc
149041  gcaagcgcaa gagtcccggc ccggccggc cgcccggagg cggcggcccg cgaccccga
149101  agacgaagaa gagcggccgcg gacgcccccg gctcggacgc ccgcgcccc ctccccgcgc
149161  ccccctccac gccccgggg cccgagccca ccccgccca gcccgcggcg gcccggggcg
149221  ccgcggcgca ggcccgcccg cgccccgtgg cgctgtcgcg ccggcccgcc gagggcccg
149281  accccctggg cggctggcgg cggcagcccc gggggcccag ccacacggcg gcgcccgcgg
149341  ccgccgccct ggaggcctac tgctcccgc gcgccgtggc cgagctcacg gaccacccgc
149401  tgttccccgt ccctggcga ccggccctca tgtttgaccc gcgggccctg gcctcgatcg
149461  ccgcgcggtg cgccgggccc gccccgccg cccaggccgc gtgcggcggc gacgacgacg
149521  agaaccccca ccccacggg gccgccgggg ccgcctctt tggccccctg cgcgcctcgg
149581  gcccgctgcg ccgcatgcg gcctggatgc gccagatccc cgaccccgag gacgtgcgcg
149641  tggtggtgct gtactcgccg ctgccggggcg aggacctggc cggcggcggg gcctcggggg
149701  ggccgccgga gtggtccgcc gagcgcggcg ggctgtcctg cctgctggcg gccctggcca
149761  accggctgtg cgggccggac acggccgcct gggcgggcaa ctggaccggc gccccgacg
149821  tgtcgcgct gggcgcgcag ggcgtgctgc tgctgtccac gcgggacctg gccttcgccg
149881  gggccgtgga gtttctgggg ctgctcgcca gcgccggcga ccggcggctc atcgtggtca
149941  acaccgtgcg cgcctgcgac tggcccgccg acgggccccgc ggtgtcgcgg cagcacgcct
150001  acctggcgtg cgacctgctg cccgccgtgc agtgcgccgt gcgctggccg gcggcgcggg
150061  acctgcgccg cacggtgctg gcctcgggcc gcgtgttcgg cccgggggtc ttcgcgcgcg
150121  tggaggccgc gcacgcgcgc ctgtaccccg acgcgccgcc gctgcgcctg tgccgcggcg
150181  gcaacgtgcg ctaccgcgt cggcccgga cacgccggtg cccatgtccc
150241  cgcgcgagta ccgccggccc gtgctgccgg cgctggacgg ccgggcggcg gcctcgggga
150301  ccaccgacgc catggcgccc ggcgcgccgg acttctgcga ggaggaggcc cactcgcacc
150361  gcgcctgcgc gcgctgggc ctgggcgcgc cgctgcgcc cgtgtacgtg gcgctggggc
150421  gcgaggcggt gcgcgccggc ccggcccggt ggcgcgggcc gcggagggac ttttgcgccc
150481  gcgcccctgct ggagcccgac gacgacgccc cccgctggt gctgcgcggc gacgacgacg
150541  acgcccgggg ggccctgccg ccggcgccgc ccgggattcg ctgggcctcg gccacgggcc
150601  gcagcggcac cgtgctggcg gcggcggggg ccgtggaggt gctggggcg gaggcgggct
150661  tggccacgcc cccgcgacgg gacgttgtgg actgggaagg cgcctgggac gaagacgacg
150721  gcggcgcgtt cgaggggaac ggggtgctgt aacgggccgg gacgggcgg ggcgcttgtg
150781  aaacccgaag acgcaataaa cggcaacgac ctgattaagt tttgcagtag cgttgtttat
150841  tcgagggggcg ggaggggcg aggggcggga ggggcgagg gggcgaggg ggcgagggg
150901  gggaggggc gagggcggg aggggcgag gggcgagg gggcgaggg cggagggg
150961  cgagggcgg gaggggcga gggcggga gggcgaggg gcggaggggg gcgagggcg
151021  gaagggcg aggggcgga gggcgagg gcggagg ggcgagggc gggagggggc
151081  gagggcggg aggggcgag gggcggagg gggcgagg cggaggggg cgagggcgg
151141  gaggggcga gggcggag gggcgaggg gcgtggtgg tgcgcgggcg ccccccggagg
151201  gtttggatct ctgacctgag attggcggca ctgaggtaga gatgcccgaa ccccccccgag
151261  ggagcgcggg acgcggctgg ggagggctgg ggctggggag ggctggggcc ggggagggct
151321  ggggccgggg agggctgggg ccggggaggg ctggggccgg ggagggctgg ggccggggag
151381  ggctggggct ggggagggct ggggctgggg agggcggtg gtgtgtagca ggagcggtgt
151441  gttgcgccgg ggtacgtctg ggagcggg aggtgccgg tgacgtgtgg atgaggaaca
151501  ggagttgttg cgcggtgagt tgtcgctgtg agttgtgttg ttgggcaggt gtggtggatg
151561  acgtgacgtg tgacgtgcg attgcgccgt gctttgttgg tgttgtttta cctgtggcag
151621  cccgggcccc ccgcgggcgc gcgcgcgcgc aaaaaaggcg ggcggcggtc cgggcggcgt
151681  gcgcgcgcgc ggcgggcgtg ggggcgcggg ccgcgggagc gggggaggag cgggggagga
151741  gcggggggag gagcgggggg aggagcggg ggaggagcgg gggaggagc gggggagga
151801  gcggggggag gagcgggggg aggagcggg ggaggagcgg gggaggagc ggggggagga
151861  gcggggggag gagcgggggg aggagcggg ggaggagcgg gggaggagc ggggggagga
151921  gcggggagg agcggccaga ccccggaaac gggccccccc caaaacacac ccccgggggg
151981  tcgcgcgcgg cccttttaaag gcgggcggcg g
```

REFERENCES

1. Anchisi, S., Guerra, J., and Garcin, D. (2015). RIG-I ATPase activity and discrimination of self-RNA versus non-self-RNA. MBio 6, e02349.
2. Bhatt, D., and Ghosh, S. (2014). Regulation of the NF-kappaB-Mediated Transcription of Inflammatory Genes. Front Immunol 5, 71.
3. Bidinosti, M., Ran, I., Sanchez-Carbente, M. R., Martineau, Y., Gingras, A. C., Gkogkas, C., Raught, B., Bramham, C. R., Sossin, W. S., Costa-Mattioli, M., et al. (2010). Postnatal Deamidation of 4E-BP2 in Brain Enhances Its Association with Raptor and Alters Kinetics of Excitatory Synaptic Transmission. Molecular cell 37, 797-808.
4. Chan, Y. K., and Gack, M. U. (2015). RIG-I-like receptor regulation in virus infection and immunity. Curr Opin Virol 12, 7-14.
5. Chen, Z. J., Parent, L., and Maniatis, T. (1996). Site-specific phosphorylation of IkappaBalpha by a novel ubiquitination-dependent protein kinase activity. Cell 84, 853-862.
6. Cui, J., Yao, Q., Li, S., Ding, X., Lu, Q., Mao, H., Liu, L., Zheng, N., Chen, S., and Shao, F. (2010). Glutamine deamidation and dysfunction of ubiquitin/NEDD8 induced by a bacterial effector family. Science 329, 1215-1218.
7. da Silva, L. F., and Jones, C. (2013). Small non-coding RNAs encoded within the herpes simplex virus type 1 latency associated transcript (LAT) cooperate with the retinoic acid inducible gene I (RIG-I) to induce beta-interferon promoter activity and promote cell survival. Virus research 175, 101-109.
8. Desai, P., Sexton, G. L., McCaffery, J. M., and Person, S. (2001). A null mutation in the gene encoding the herpes simplex virus type 1 UL37 polypeptide abrogates virus maturation. J Virol 75, 10259-10271.
9. Deverman, B. E., Cook, B. L., Manson, S. R., Niederhoff, R. A., Langer, E. M., Rosova, I., Kulans, L. A., Fu, X., Weinberg, J. S., Heinecke, J. W., et al. (2002). Bcl-xL deamidation is a critical switch in the regulation of the response to DNA damage. Cell 111, 51-62.
10. Dho, S. H., Deverman, B. E., Lapid, C., Manson, S. R., Gan, L., Riehm, J. J., Aurora, R., Kwon, K. S., and Weintraub, S. J. (2013). Control of cellular Bcl-xL levels by deamidation-regulated degradation. PLoS Biol 11, e1001588.
11. Dong, X., Feng, H., Sun, Q., Li, H., Wu, T. T., Sun, R., Tibbetts, S. A., Chen, Z. J., and Feng, P. (2010). Murine gamma-herpesvirus 68 hijacks MAVS and IKKbeta to initiate lytic replication. PLoS pathogens 6, e1001001.
12. Dong, X., and Feng, P. (2011). Murine gamma herpesvirus 68 hijacks MAVS and IKKbeta to abrogate NFkappaB activation and antiviral cytokine production. PLoS pathogens 7, e1002336.
13. Dong, X., He, Z., Durakoglugil, D., Arneson, L., Shen, Y., and Feng, P. (2012). Murine gammaherpesvirus 68 evades host cytokine production via replication transactivator-induced RelA degradation. Journal of virology 86, 1930-1941.
14. Feng, P., Moses, A., and Fruh, K. (2013). Evasion of adaptive and innate immune response mechanisms by gamma-herpesviruses. Curr Opin Virol 3, 285-295.
15. Fitzgerald, K. A., McWhirter, S. M., Faia, K. L., Rowe, D. C., Latz, E., Golenbock, D. T., Coyle, A. J., Liao, S. M., and Maniatis, T. (2003). IKKepsilon and TBK1 are essential components of the IRF3 signaling pathway. Nature immunology 4, 491-496.
16. Flatau, G., Lemichez, E., Gauthier, M., Chardin, P., Paris, S., Fiorentini, C., and Boquet, P. (1997). Toxin-induced activation of the G protein p21 Rho by deamidation of glutamine. Nature 387, 729-733.
17. Full, F., Jungnickl, D., Reuter, N., Bogner, E., Brulois, K., Scholz, B., Sturzl, M., Myoung, J., Jung, J. U., Stamminger, T., et al. (2014). Kaposi's sarcoma associated herpesvirus tegument protein ORF75 is essential for viral lytic replication and plays a critical role in the antagonization of ND10-instituted intrinsic immunity. PLoS pathogens 10, e1003863.
18. Gaspar, M., Gill, M. B., Losing, J. B., May, J. S., and Stevenson, P. G. (2008). Multiple functions for ORF75c in murid herpesvirus-4 infection. PLoS One 3, e2781.
19. He, S., Zhao, J., Song, S., He, X., Minassian, A., Zhou, Y., Zhang, J., Brulois, K., Wang, Y., Cabo, J., et al. (2015). Viral pseudo-enzymes activate RIG-I via deamidation to evade cytokine production. Mol Cell 58, 134-146.
20. Jacquemont, B., and Roizman, B. (1975). Rna-Synthesis in Cells Infected with Herpes-Simplex Virus 0.10. Properties of Viral Symmetric Transcripts and of Double-Stranded-Rna Prepared from Them. Journal of virology 15, 707-713.
21. Kato, H., Takeuchi, O., Sato, S., Yoneyama, M., Yamamoto, M., Matsui, K., Uematsu, S., Jung, A., Kawai, T., Ishii, K. J., et al. (2006). Differential roles of MDA5 and RIG-I helicases in the recognition of RNA viruses. Nature 441, 101-105.
22. Kato, H., Sato, S., Yoneyama, M., Yamamoto, M., Uematsu, S., Matsui, K., Tsujimura, T., Takeda, K., Fujita, T., Takeuchi, O., et al. (2005). Cell type-specific involvement of RIG-I in antiviral response. Immunity 23, 19-28.
23. Kawai, T., Takahashi, K., Sato, S., Coban, C., Kumar, H., Kato, H., Ishii, K. J., Takeuchi, O., and Akira, S. (2005). IPS-1, an adaptor triggering RIG-I- and Mda5-mediated type I interferon induction. Nature immunology 6, 981-988.
24. Kerur, N., Veettil, M. V., Sharma-Walia, N., Bottero, V., Sadagopan, S., Otageri, P., and Chandran, B. (2011). IFI16 acts as a nuclear pathogen sensor to induce the inflammasome in response to Kaposi Sarcoma-associated herpesvirus infection. Cell Host Microbe 9, 363-375.
25. Kohlway, A., Luo, D., Rawling, D. C., Ding, S. C., and Pyle, A. M. (2013). Defining the functional determinants for RNA surveillance by RIG-I. EMBO Rep 14, 772-779.
26. Kolakofsky, D., and Garcin, D. (2015). gammaHV68 vGAT: a viral pseudoenzyme pimping for PAMPs. Mol Cell 58, 3-4.
27. Kowalinski, E., Lunardi, T., McCarthy, A. A., Louber, J., Brunel, J., Grigorov, B., Gerlier, D., and Cusack, S. (2011). Structural basis for the activation of innate immune pattern-recognition receptor RIG-I by viral RNA. Cell 147, 423-435.
28. Lassig, C., Matheisl, S., Sparrer, K. M., de Oliveira Mann, C. C., Moldt, M., Patel, J. R., Goldeck, M., Hartmann, G., Garcia-Sastre, A., Hornung, V., et al. (2015). ATP hydrolysis by the viral RNA sensor RIG-I prevents unintentional recognition of self-RNA. Elife 4.
29. Lieber, D., and Bailer, S. M. (2013). Determination of HSV-1 infectivity by plaque assay and a luciferase reporter cell line. Methods Mol Biol 1064, 171-181.
30. Liu, X., Fitzgerald, K., Kurt-Jones, E., Finberg, R., and Knipe, D. M. (2008). Herpesvirus tegument protein activates NF-kappaB signaling through the TRAF6 adaptor protein. Proc Natl Acad Sci USA 105, 11335-11339.

31. Luo, D., Ding, S. C., Vela, A., Kohlway, A., Lindenbach, B. D., and Pyle, A. M. (2011). Structural insights into RNA recognition by RIG-I. Cell 147, 409-422.
32. Luo, D., Kohlway, A., and Pyle, A. M. (2013). Duplex RNA activated ATPases (DRAs): platforms for RNA sensing, signaling and processing. RNA Biol 10, 111-120.
33. Medzhitov, R. (2007). Recognition of microorganisms and activation of the immune response. Nature 449, 819-826.
34. Meylan, E., Curran, J., Hofinann, K., Moradpour, D., Binder, M., Bartenschlager, R., and Tschopp, J. (2005). Cardif is an adaptor protein in the RIG-I antiviral pathway and is targeted by hepatitis C virus. Nature 437, 1167-1172.
35. Mycek, M. J., and Waelsch, H. (1960). The enzymatic deamidation of proteins. J Biol Chem 235, 3513-3517.
36. Pitts, J. D., Klabis, J., Richards, A. L., Smith, G. A., and Heldwein, E. E. (2014). Crystal structure of the herpesvirus inner tegument protein UL37 supports its essential role in control of viral trafficking. J Virol 88, 5462-5473.
37. Rasmussen, S. B., Jensen, S. B., Nielsen, C., Quartin, E., Kato, H., Chen, Z. J., Silverman, R. H., Akira, S., and Paludan, S. R. (2009). Herpes simplex virus infection is sensed by both Toll-like receptors and retinoic acid-inducible gene-like receptors, which synergize to induce type I interferon production. J Gen Virol 90, 74-78.
38. Robinson, N. E., and Robinson, A. B. (2001). Molecular clocks. Proceedings of the National Academy of Sciences of the United States of America 98, 944-949.
39. Sanada, T., Kim, M., Mimuro, H., Suzuki, M., Ogawa, M., Oyama, A., Ashida, H., Kobayashi, T., Koyama, T., Nagai, S., et al. (2012). The *Shigella flexneri* effector OspI deamidates UBC13 to dampen the inflammatory response. Nature 483, 623-U149.
40. Schmidt, G., Sehr, P., Wilm, M., Seizer, J., Mann, M., and Aktories, K. (1997). Gln 63 of Rho is deamidated by *Escherichia coli* cytotoxic necrotizing factor-1. Nature 387, 725-729.
41. Seth, R. B., Sun, L., Ea, C. K., and Chen, Z. J. (2005). Identification and characterization of MAVS, a mitochondrial antiviral signaling protein that activates NF-kappaB and IRF 3. Cell 122, 669-682.
42. Sharma, S., tenOever, B. R., Grandvaux, N., Zhou, G. P., Lin, R., and Hiscott, J. (2003). Triggering the interferon antiviral response through an IKK-related pathway. Science 300, 1148-1151.
43. Sen, J., Liu, X., Roller, R., and Knipe, D. M. (2013). Herpes simplex virus US3 tegument protein inhibits Toll-like receptor 2 signaling at or before TRAF6 ubiquitination. Virology 439, 65-73.
44. Sun, Q., Sun, L., Liu, H. H., Chen, X., Seth, R. B., Forman, J., and Chen, Z. J. (2006). The specific and essential role of MAVS in antiviral innate immune responses. Immunity 24, 633-642.
45. Takahasi, K., Yoneyama, M., Nishihori, T., Hirai, R., Kumeta, H., Narita, R., Gale, M., Jr., Inagaki, F., and Fujita, T. (2008). Nonself RNA-sensing mechanism of RIG-I helicase and activation of antiviral immune responses. Molecular cell 29, 428-440.
46. Takeuchi, O., and Akira, S. (2010). Pattern recognition receptors and inflammation. Cell 140, 805-820.
47. Ting, J. P., Duncan, J. A., and Lei, Y. (2010). How the noninflammasome NLRs function in the innate immune system. Science 327, 286-290.
48. Unterholzner, L., Keating, S. E., Baran, M., Horan, K. A., Jensen, S. B., Sharma, S., Sirois, C. M., Jin, T., Latz, E., Xiao, T. S., et al. (2010). IFI16 is an innate immune sensor for intracellular DNA. Nature immunology 11, 997-1004.
49. Wang, H., Piatkov, K. I., Brower, C. S., and Varshavsky, A. (2009). Glutamine-specific N-terminal amidase, a component of the N-end rule pathway. Mol Cell 34, 686-695.
50. Weber, F., Wagner, V., Rasmussen, S. B., Hartmann, R., and Paludan, S. R. (2006). Double-stranded RNA is produced by positive-strand RNA viruses and DNA viruses but not in detectable amounts by negative-strand RNA viruses. Journal of virology 80, 5059-5064.
51. Weerapana, E., Wang, C., Simon, G. M., Richter, F., Khare, S., Dillon, M. B., Bachovchin, D. A., Mowen, K., Baker, D., and Cravatt, B. F. (2010). Quantitative reactivity profiling predicts functional cysteines in proteomes. Nature 468, 790-795.
52. Weintraub, S. J., and Deverman, B. E. (2007). Chrono-regulation by asparagine deamidation. Science's STKE: signal transduction knowledge environment 2007, re7.
53. Xu, L. G., Wang, Y. Y., Han, K. J., Li, L. Y., Zhai, Z., and Shu, H. B. (2005). VISA is an adapter protein required for virus-triggered IFN-beta signaling. Molecular cell 19, 727-740.
54. Zandi, E., Rothwarf, D. M., Delhase, M., Hayakawa, M., and Karin, M. (1997). The IkappaB kinase complex (IKK) contains two kinase subunits, IKKalpha and IKKbeta, necessary for IkappaB phosphorylation and NF-kappaB activation. Cell 91, 243-252.
55. Zhao, J., Li, J., Xu, S., and Feng, P. (2016). Emerging roles of regulated protein deamidation in innate immune signaling. J Virol.

What is claimed is:

1. An isolated polynucleotide encoding a RIG-I-QQ mutant, complementary polynucleotides and equivalents of each thereof, wherein the encoded RIG-I-QQ mutant is a polypeptide that comprises the amino acid substitution(s) N495Q and/or N549Q according to SEQ ID NO:4.

2. An isolated polynucleotide encoding a RIG-I-QQ mutant polypeptide that has at least 90% sequence identity to SEQ ID NO: 4 while still comprising the amino acid substitution(s) N495Q and/or N549Q according to SEQ ID NO:4.

3. An isolated RIG-I-QQ mutant polypeptide that has at least 90% sequence identity to SEQ ID NO: 4 while still comprising the amino acid substitution(s) N495Q and/or N549Q according to SEQ ID NO:4.

4. The polynucleotide of claim 1 or 2, further comprising a vector or gene delivery vehicle.

5. An isolated host cell comprising the isolated polynucleotide of claim 1 or 2.

6. An isolated RIG-I-QQ mutant, wherein the RIG-I-QQ mutant comprises the amino acid substitution(s) N495O and/or N549Q according to SEQ ID NO:4.

7. An isolated host cell comprising the polypeptide of claim 6 or 3.

8. A composition comprising one or more of the polynucleotide of claim 1 or 2, and a carrier.

9. A composition comprising the host cell of claim 7 and a carrier.

10. An isolated polypeptide encoded by the isolated polynucleotide of claim 1 or 2.

11. An immunogenic composition comprising an effective amount of the isolated polypeptide of claim 6 or 3 and a pharmaceutically acceptable carrier.

12. The composition of claim 11, further comprising an adjuvant.

13. An immunogenic composition comprising an effective amount of the isolated polynucleotide of claim 1 or 2.

14. The composition of claim 13, further comprising a carrier.

15. The composition of claim 14, wherein the carrier is a pharmaceutically acceptable carrier and wherein the composition optionally further comprises an adjuvant.

16. A method comprising delivering an effective amount of the composition of claim 11 to a host, cell, or tissue.

17. The method of claim 16, wherein the delivery can result in one or more of the following:
   a) inhibiting viral replication;
   b) abolishing 5'-ppp-RNA-binding and ATP hydrolysis;
   c) switching off RIG-1;
   d) blocking RNA-induced activation;
   e) inhibiting the deamidation activity of herpes simplex virus (HSV) UL37;
   f) inducing an anti-viral immune response;
   g) inducing expression of anti-viral cytokine genes; or
   h) enhancing the adaptive immune response in a host.

18. The method of claim 16, wherein the delivery is in vivo or in vitro.

19. The method of claim 17, wherein the delivery is in vivo or in vitro.

20. The method of claim 16, wherein the host is a mammal or a human patient.

21. The method of claim 17, wherein the host is a mammal or a human patient.

22. The method of claim 16, wherein the delivery is in one or more doses.

23. The method of claim 17, wherein the delivery is in one or more doses.

24. An isolated host cell comprising the isolated polynucleotide of claim 4.

25. An immunogenic composition comprising an effective amount of the isolated polypeptide of claim 10, a pharmaceutically acceptable carrier, and optionally an adjuvant.

26. An immunogenic composition comprising an effective amount of the isolated polynucleotide of claim 4.

27. An isolated host cell comprising the polypeptide of claim 10.

28. A composition comprising one or more of the polynucleotide of claim 4 and a carrier.

29. A method comprising delivering an effective amount of the composition of claim 13 to a host, cell, or tissue.

30. The method of claim 29, wherein the delivery can result in one or more of the following:
   a) inhibiting viral replication;
   b) abolishing 5'-ppp-RNA-binding and ATP hydrolysis;
   c) switching off RIG-1;
   d) blocking RNA-induced activation;
   e) inhibiting the deamidation activity of herpes simplex virus (HSV) UL37;
   f) inducing an anti-viral immune response;
   g) inducing expression of anti-viral cytokine genes; or
   h) enhancing the adaptive immune response in a host.

31. The method of claim 29, wherein the delivery is in vivo or in vitro.

32. The method of claim 30, wherein the delivery is in vivo or in vitro.

33. The method of claim 29, wherein the host is a mammal or a human patient.

34. The method of claim 30, wherein the host is a mammal or a human patient.

35. The method of claim 29, wherein the delivery is in one or more doses.

36. The method of claim 30, wherein the delivery is in one or more doses.

* * * * *

SEQUENCE LISTING

```
<160> NUMBER OF SEQ ID NOS: 52

<210> SEQ ID NO 1
<211> LENGTH: 3372
<212> TYPE: DNA
<213> ORGANISM: Herpes simplex virus

<400> SEQUENCE: 1
atggcagacc gcggtctccc gtccgaggcc cccgtcgtca cgacctcacc cgccggtccg      60
ccctcggacg gacctatgca gcgcctattg gcgagcctag ccggccttcg ccaaccgcca     120 accccacgg ccgagacggc aaacggggcg gacgacccgc cgtttctggc cacggccaag     180
ctgcgcgccg ccatggcggc gtttctgttg tcgggaacgg ccatcgcccc ggcagacgcg     240
```

```
cgggactgct ggcggccgct gctggaacac ctgtgcgcgc tccaccgggc ccacgggctt    300
ccggagacgg cgctcttggc cgagaacctc cccgggttgc tcgtacaccg cttggtggtg    360
gctctccccg aggccccga ccaggccttc cgggagatgg aggtcatcaa ggacaccatc    420
ctcgcggtca ccggctccga cacgtccat gcgctggatt ccgccggcct gcgcaccgcg    480
gcggccctgg ggccggtccg cgtccgccag tgcgccgtgg agtggataga ccgctggcaa    540
accgtcacca agagctgctt ggccatgagc ccgcggacct ccatcgaggc ccttggggag    600
acgtcgctca agatggcgcc ggtcccgttg gggcagccca gcgcgaacct taccaccccg    660
gcgtacagcc tgctcttccc cgccccgttc gtgcaagagg gcctccggtt cttggccctg    720
gtgagtaatc gggtgacgct gttctcggcg cacctccagc gcatagacga cgcgaccctc    780
actcccctca cacgggccct ctttacgttg gccctggtgg acgagtacct gacgaccccc    840
gagcgggggg ctgtggtccc gccgccctg ttggcgcagt tcagcacac cgtgcgggag    900 atcgaccggg ccataatgat tccgccgctc gaggccaaca agatggttcg cagccgcgag    960
gaggtgcgcg tgtcgacggc cctcagccgc gtcagcccgc gctcggcctg tgcgccccg    1020 gggacgctaa tggcgcgcgt gcggacggac gtggccgtgt ttgatcccga cgtgccgttc    1080
ctgagttcgt cggcactggc agtcttccag cctgccgtct ccagcctgct gcagctcggg    1140
gagcagccct ccgccggcgc ccagcagcgg ctgctggctc tgctgcagca gacgtggacg    1200
ttgatccaga ataccaattc gccctccgtg gtgatcaaca ccctgatcga cgctgggttc    1260
acgccctcgc actgcacgca ctacctttcg gccctggagg ggtttctggc ggcgggcgtc    1320
cccgcgcgga cgcccaccgg ccacggactc ggcgaagtcc agcagctctt tgggtgcatt    1380
gccctcgcgg ggtcgaacgt gtttgggttg gcgcgggaat acgggtacta tgccaactac    1440
gtaaaaactt tcaggcgggt ccaggcgcc agcgagcaca cgcacgggcg gctctgcgag    1500
gcggtcggcc tgtcgggggg cgttctaagc cagacgctgg cgcgtatcat gggtccggcc    1560
gtgccgacgg aacatctggc gagcctgcgg cgggcgctcg tgggggagtt tgagacggcc    1620
gagcgccgct ttagttccgg tcaacccagc cttctccgcg agacggcgct catctggatc    1680
gacgtgtatg gtcagaccca ctgggacatc accccacca ccccggccac gccgctgtcc    1740
gcgcttctcc ccgtcgggca gcccagccac gcccctctg tccacctggc gcggcgacc    1800 cagatccgct tccccgccct cgagggcatt caccccaacg tcctcgccga cccgggcttc    1860
gtcccctacg ttctggccct ggtggtcggg gacgcgctga gggccacgtg tagcgcggcc    1920
taccttcccc gcccggtcga gttcgccctg cgtgtgttgg cctgggcccg ggactttggg    1980
ctgggctatc tccccacggt tgagggccat cgcaccaaac tgggcgcgct gatcaccctc    2040
ctcgaaccgg ccgccgggg cggcctcggc ccactatgc agatggccga caacatagag    2100
cagctgctcc gggagctgta cgtgatctcc agggtgccg tcgagcagct gcggccctg    2160 gtccagctga gccccccc gccccccgag gtgggcacca gcctcctgtt gattagcatg    2220
tacgccctgg ccgcccgggg ggtgctgcag gacctcgccg agcgcgcaga ccccctgatt    2280
cgccaactgg aggacgccat cgtgctgctg cggctgcaca tgcgcacgct ctccgccttt    2340
ttcgagtgtc ggttcgagag cgacgggcgc cgcctgtatg cggtggtcgg ggacacgccc    2400
gaccgcctgg ggccctggcc cccgaggcc atggggggacg cggtgagtca gtactgcagc    2460
atgtatcacg acgccaagcg cgcgctggtc gcgtccctcg cgagcctgcg ttccgtcatc    2520
accgaaacca cggcgcacct gggggtgtgc gacgagctgc cggcccaggt gtcgcacgag    2580
```

```
gacaacgtgc tggccgtggt ccggcgcgaa attcacgggt ttctgtccgt cgtgtccggc    2640
attcacgccc gggcgtcgaa gctgctgtcg ggagaccagg tccccgggtt ttgcttcatg    2700
ggtcagtttc tagcgcgctg gcggcgtctg tcggcctgct atcaagccgc gcgcgcggcc    2760 gcggacccg  agcccgtggc cgagtttgtc caggaactcc acgacacgtg aagggcctg     2820 cagacggagc gcgccgtggt cgtggcgccc ttggtcagct cggccgacca gcgcgccgcg    2880
gccatccgag aggtaatggc gcatgcgccc gaggacgccc ccccgcaaag ccccgcggcc    2940
gaccgcgtcg tgcttacgag ccgtcgcgac ctaggggcct gggggggacta cagcctcggc    3000 cccctgggcc agacgaccgc ggttccggac tccgtggatc tgtctcgcca ggggctggcc    3060
gttacgctga gtatggattg gttactgatg aacgagctcc tgcgggtcac cgacggcgtg    3120
tttcgcgctt ccgcgtttcg tccgttagcc ggaccggagt ctcccaggga cctggaggtc    3180
cgcgacgccg gaaacagtct ccccgcgcct atgcccatgg acgcacagaa gccggaggcc    3240
tatgggcacg gccacgcca  ggcggaccgc gaggggcgc ctcattccaa caccccgtc     3300 gaggacgacg agatgatccc ggaggacacc gtcgcgccac ccacggactt gccgttaact    3360
agttaccaat aa                                                        3372

<210> SEQ ID NO 2
<211> LENGTH: 3372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggcagacc gcggtctccc gtccgaggcc ccgtcgtca  cgacctcacc cgccggtccg      60
ccctcggacg gacctatgca gcgcctattg gcgagcctag ccggccttcg ccaaccgcca     120 accccacgg  ccgagacggc aaacggggc  gacgacccgg cgtttctggc cacgccaag     180 ctgcgcgccg ccatggcggc gtttctgttg tcgggaacgg ccatcgcccc ggcagacgcg    240
cgggactgct ggcggccgct gctgaacac  ctgtgcgcgc tccaccgggc ccacgggctt    300
ccggagacgg cgctcttggc cgagaacctc cccgggttgc tcgtacaccg cttggtggtg    360
gctctccccg aggcccccga ccaggccttc cgggagatgg aggtcatcaa ggacaccatc    420
ctcgcggtca ccgctccga  cacgtccat  gcgctggatt ccgccggcct gcgcaccgcg    480
gcggccctgg ggccggtccg cgtccgccag tgccgcgtgg agtggataga ccgctggcaa    540
accgtcacca agagctgctt ggccatgagc ccgcggacct ccatcgaggc ccttggggag    600
acgtcgctca agatggcgcc ggtccgttg  gggcagccca gcgcgaacct taccaccccg    660
gcgtacagcc tgctcttccc cgcccgttc  gtgcaagagg gctccggtt  cttggccctg    720 gtgagtaatc gggtgacgct gttctcggcg cacctccagc gcatagacga cgcgacccct    780
actcccctca cacgggccct cttacgttg  gccctggtgg acgagtacct gacgacccc     840 gagcgggggg ctgtggtccc gccgccctg  ttggcgcagt tcagcacac  cgtgcgggag    900 atcgaccccgg ccataatgat tccgccgctc gaggccaaca agatggttcg cagccgcgag    960
gaggtgcgcg tgtcgacggc cctcagccgc gtcagcccgc gctcggcctg tgcgcccccg    1020
gggacgctaa tggcgcgcgt gcggacggac gtggccgtgt tgatcccga  cgtgccgttc    1080 ctgagttcgt cggcactggc agtcttccag cctgccgtct ccagcctgct gcagctcggg    1140
gagcagccct ccgccggcgc ccagcagcgg ctgctggctc tgctgcagca gacgtggacg    1200
```

```
ttgatccaga ataccaattc gccctccgtg gtgatcaaca ccctgatcga cgctgggttc   1260
acgccctcgc actgcacgca ctacctttcg gccctggagg ggtttctggc ggcgggcgtc   1320
cccgcgcgga cgcccaccgg ccacggactc ggcgaagtcc agcagctctt tgggtgcatt   1380
gccctcgcgg ggtcgaacgt gtttggggtt gcgcgggaat acgggtacta tgccaactac   1440
gtaaaaactt tcaggcgggt ccaggcgcc agcgagcaca cgcacgggcg gctctgcgag    1500
gcggtcggcc tgtcgggggg cgttctaagc cagacgctgg cgcgtatcat gggtccggcc   1560
gtgccgacgg aacatctggc gagcctgcgg cgggcgctcg tgggggagtt tgagacggcc   1620
gagcgccgct ttagttccgg tcaacccagc cttctccgcg agacggcgct catctggatc   1680
gacgtgtatg gtcagaccca ctgggacatc accccccacca ccccggccac gccgctgtcc  1740
gcgcttctcc ccgtcgggca gcccagccac gcccccctctg tccacctggc cgcggcgacc  1800
cagatccgct tccccgccct cgagggcatt caccccaacg tcctcgccga cccgggcttc   1860
gtccccctacg ttctggccct ggtggtcggg gacgcgctga gggccacgtg tagcgcggcc  1920
taccttcccc gcccggtcga gttcgccctg cgtgtgttgg cctgggcccg ggactttggg   1980
ctgggctatc tccccacggt tgagggccat cgcaccaaac tgggcgcgct gatcaccctc   2040
ctcgaaccgg ccgcccgggg cggcctcggc cccactatgc agatggccga caacatagag   2100
cagctgctcc gggagctgta cgtgatctcc aggggtgccg tcgagcagct gcggcccctg   2160
gtccagctgc agccccccccc gccccccgag gtgggcacca gctcctgtt gattagcatg    2220
tacgccctgg ccgccggggg ggtgctgcag gacctcgccg agcgcgcaga cccccctgatt  2280
cgccaactgg aggacgccat cgtgctgctg cggctgcaca tgcgcacgct ctccgccttt   2340
ttcgagtgtc ggttcgagag cgacgggcgc cgcctgtatg cggtggtcgg ggacacgccc   2400
gaccgcctgg ggcctggcc ccccgaggcc atggggacg cggtgagtca gtacagcagc     2460
atgtatcacg acgccaagcg cgcgctggtc gcgtccctcg cgagcctgcg ttccgtcatc    2520
accgaaacca cggcgcacct gggggtgtgc gacgagctgg cggcccaggt gtcgcacgag   2580
gacaacgtgc tggccgtggt ccggcgcgaa attcacgggt ttctgtccgt cgtgtccggc   2640
attcacgccc gggcgtcgaa gctgctgtcg ggagaccagg tccccgggtt ttgcttcatg   2700
ggtcagtttc tagcgcgctg gcggcgtctg tcggcctgct atcaagccgc gcgcgcggcc   2760
gcgggacccg agcccgtggc cgagtttgtc caggaactcc acgacacgtg gaagggcctg   2820
cagacggagc gcgccgtggt cgtggcgccc ttggtcagct cggccgacca gcgcgccgcg   2880
gccatccgag aggtaatggc gcatgcgccc gaggacgccc cccgcaaag ccccgcggcc    2940
gaccgcgtcg tgcttacgag ccgtcgcgac ctaggggcct ggggggacta cagcctcggc   3000
ccctgggcc agacgaccgc ggttccggac tccgtggatc tgtctcgcca ggggctggcc   3060
gttacgctga gtatggattg gttactgatg aacgagctcc tgcgggtcac cgacggcgtg   3120
tttcgcgctt ccgcgtttcg tccgttagcc ggaccggagt ctcccaggga cctggaggtc   3180
cgcgacgccg gaaacagtct ccccgcgcct atgcccatgg acgcacagaa gccggaggcc   3240
tatgggcacg gcccacgcca ggcggaccgc gaggggcgc ctcattccaa cacccccgtc     3300
gaggacgacg agatgatccc ggaggacacc gtcgcgccac ccacggactt gccgttaact   3360
agttaccaat aa                                                         3372
```

<210> SEQ ID NO 3
<211> LENGTH: 925
<212> TYPE: PRT
<213> ORGANISM: Homo sapiens

<400> SEQUENCE: 3

```
Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65                  70                  75                  80

Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Lys Arg Leu Gln Pro
                100                 105                 110

Glu Phe Lys Thr Arg Ile Ile Pro Thr Asp Ile Ile Ser Asp Leu Ser
            115                 120                 125

Glu Cys Leu Ile Asn Gln Glu Cys Glu Glu Ile Leu Gln Ile Cys Ser
    130                 135                 140

Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Lys Gly Ile
            180                 185                 190

Lys Asp Val Glu Thr Glu Asp Leu Glu Asp Lys Met Glu Thr Ser Asp
            195                 200                 205

Ile Gln Ile Phe Tyr Gln Glu Asp Pro Glu Cys Gln Asn Leu Ser Glu
    210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
            245                 250                 255

Gly Lys Asn Thr Ile Ile Cys Ala Pro Thr Gly Cys Gly Lys Thr Phe
            260                 265                 270

Val Ser Leu Leu Ile Cys Glu His His Leu Lys Lys Phe Pro Gln Gly
            275                 280                 285

Gln Lys Gly Lys Val Val Phe Phe Ala Asn Gln Ile Pro Val Tyr Glu
            290                 295                 300

Gln Gln Lys Ser Val Phe Ser Lys Tyr Phe Glu Arg His Gly Tyr Arg
305                 310                 315                 320

Val Thr Gly Ile Ser Gly Ala Thr Ala Glu Asn Val Pro Val Glu Gln
                325                 330                 335

Ile Val Glu Asn Asn Asp Ile Ile Ile Leu Thr Pro Gln Ile Leu Val
            340                 345                 350

Asn Asn Leu Lys Lys Gly Thr Ile Pro Ser Leu Ser Ile Phe Thr Leu
            355                 360                 365

Met Ile Phe Asp Glu Cys His Asn Thr Ser Lys Gln His Pro Tyr Asn
    370                 375                 380

Met Ile Met Phe Asn Tyr Leu Asp Gln Lys Leu Gly Gly Ser Ser Gly
385                 390                 395                 400

Pro Leu Pro Gln Val Ile Gly Leu Thr Ala Ser Val Gly Val Gly Asp
```

```
                    405                 410                 415
Ala Lys Asn Thr Asp Glu Ala Leu Asp Tyr Ile Cys Lys Leu Cys Ala
                420                 425                 430

Ser Leu Asp Ala Ser Val Ile Ala Thr Val Lys His Asn Leu Glu Glu
                435                 440                 445

Leu Glu Gln Val Val Tyr Lys Pro Gln Lys Phe Phe Arg Lys Val Glu
                450                 455                 460

Ser Arg Ile Ser Asp Lys Phe Lys Tyr Ile Ile Ala Gln Leu Met Arg
465                 470                 475                 480

Asp Thr Glu Ser Leu Ala Lys Arg Ile Cys Lys Asp Leu Glu Asn Leu
                485                 490                 495

Ser Gln Ile Gln Asn Arg Glu Phe Gly Thr Gln Lys Tyr Glu Gln Trp
                500                 505                 510

Ile Val Thr Val Gln Lys Ala Cys Met Val Phe Gln Met Pro Asp Lys
                515                 520                 525

Asp Glu Glu Ser Arg Ile Cys Lys Ala Leu Phe Leu Tyr Thr Ser His
                530                 535                 540

Leu Arg Lys Tyr Asn Asp Ala Leu Ile Ile Ser Glu His Ala Arg Met
545                 550                 555                 560

Lys Asp Ala Leu Asp Tyr Leu Lys Asp Phe Phe Ser Asn Val Arg Ala
                565                 570                 575

Ala Gly Phe Glu Glu Ile Glu Gln Asp Leu Thr Gln Arg Phe Glu Glu
                580                 585                 590

Lys Leu Gln Glu Leu Glu Ser Val Ser Arg Asp Pro Ser Asn Glu Asn
                595                 600                 605

Pro Lys Leu Glu Asp Leu Cys Phe Ile Leu Gln Glu Tyr His Leu
                610                 615                 620

Asn Pro Glu Thr Ile Thr Ile Leu Phe Val Lys Thr Arg Ala Leu Val
625                 630                 635                 640

Asp Ala Leu Lys Asn Trp Ile Glu Gly Asn Pro Lys Leu Ser Phe Leu
                645                 650                 655

Lys Pro Gly Ile Leu Thr Gly Arg Gly Lys Thr Asn Gln Asn Thr Gly
                660                 665                 670

Met Thr Leu Pro Ala Gln Lys Cys Ile Leu Asp Ala Phe Lys Ala Ser
                675                 680                 685

Gly Asp His Asn Ile Leu Ile Ala Thr Ser Val Ala Asp Glu Gly Ile
                690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
                740                 745                 750

Ile Asn Met Tyr Lys Glu Lys Met Met Asn Asp Ser Ile Leu Arg Leu
                755                 760                 765

Gln Thr Trp Asp Glu Ala Val Phe Arg Glu Lys Ile Leu His Ile Gln
                770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
                820                 825                 830
```

```
Val Leu Gly Asp Ala Phe Lys Glu Cys Phe Val Ser Arg Pro His Pro
            835                 840                 845

Lys Pro Lys Gln Phe Ser Ser Phe Glu Lys Arg Ala Lys Ile Phe Cys
        850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
            885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
            915                 920                 925

<210> SEQ ID NO 4
<211> LENGTH: 925
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Thr Glu Gln Arg Arg Ser Leu Gln Ala Phe Gln Asp Tyr Ile
1               5                   10                  15

Arg Lys Thr Leu Asp Pro Thr Tyr Ile Leu Ser Tyr Met Ala Pro Trp
            20                  25                  30

Phe Arg Glu Glu Glu Val Gln Tyr Ile Gln Ala Glu Lys Asn Asn Lys
        35                  40                  45

Gly Pro Met Glu Ala Ala Thr Leu Phe Leu Lys Phe Leu Leu Glu Leu
    50                  55                  60

Gln Glu Glu Gly Trp Phe Arg Gly Phe Leu Asp Ala Leu Asp His Ala
65              70                  75                  80

Gly Tyr Ser Gly Leu Tyr Glu Ala Ile Glu Ser Trp Asp Phe Lys Lys
                85                  90                  95

Ile Glu Lys Leu Glu Glu Tyr Arg Leu Leu Leu Lys Arg Leu Gln Pro
            100                 105                 110

Glu Phe Lys Thr Arg Ile Ile Pro Thr Asp Ile Ile Ser Asp Leu Ser
        115                 120                 125

Glu Cys Leu Ile Asn Gln Glu Cys Glu Glu Ile Leu Gln Ile Cys Ser
    130                 135                 140

Thr Lys Gly Met Met Ala Gly Ala Glu Lys Leu Val Glu Cys Leu Leu
145                 150                 155                 160

Arg Ser Asp Lys Glu Asn Trp Pro Lys Thr Leu Lys Leu Ala Leu Glu
                165                 170                 175

Lys Glu Arg Asn Lys Phe Ser Glu Leu Trp Ile Val Glu Lys Gly Ile
            180                 185                 190

Lys Asp Val Glu Thr Glu Asp Leu Glu Asp Lys Met Glu Thr Ser Asp
        195                 200                 205

Ile Gln Ile Phe Tyr Gln Glu Asp Pro Glu Cys Gln Asn Leu Ser Glu
    210                 215                 220

Asn Ser Cys Pro Pro Ser Glu Val Ser Asp Thr Asn Leu Tyr Ser Pro
225                 230                 235                 240

Phe Lys Pro Arg Asn Tyr Gln Leu Glu Leu Ala Leu Pro Ala Met Lys
                245                 250                 255

Gly Lys Asn Thr Ile Ile Cys Ala Pro Thr Gly Cys Gly Lys Thr Phe
```

```
            260             265             270
Val Ser Leu Leu Ile Cys Glu His His Leu Lys Lys Phe Pro Gln Gly
        275             280             285
Gln Lys Gly Lys Val Val Phe Phe Ala Asn Gln Ile Pro Val Tyr Glu
    290             295             300
Gln Gln Lys Ser Val Phe Ser Lys Tyr Phe Glu Arg His Gly Tyr Arg
305             310             315             320
Val Thr Gly Ile Ser Gly Ala Thr Ala Glu Asn Val Pro Val Glu Gln
                325             330             335
Ile Val Glu Asn Asn Asp Ile Ile Leu Thr Pro Gln Ile Leu Val
        340             345             350
Asn Asn Leu Lys Lys Gly Thr Ile Pro Ser Leu Ser Ile Phe Thr Leu
        355             360             365
Met Ile Phe Asp Glu Cys His Asn Thr Ser Lys Gln His Pro Tyr Asn
        370             375             380
Met Ile Met Phe Asn Tyr Leu Asp Gln Lys Leu Gly Gly Ser Ser Gly
385             390             395             400
Pro Leu Pro Gln Val Ile Gly Leu Thr Ala Ser Val Gly Val Gly Asp
                405             410             415
Ala Lys Asn Thr Asp Glu Ala Leu Asp Tyr Ile Cys Lys Leu Cys Ala
                420             425             430
Ser Leu Asp Ala Ser Val Ile Ala Thr Val Lys His Asn Leu Glu Glu
        435             440             445
Leu Glu Gln Val Val Tyr Lys Pro Gln Lys Phe Phe Arg Lys Val Glu
    450             455             460
Ser Arg Ile Ser Asp Lys Phe Lys Tyr Ile Ile Ala Gln Leu Met Arg
465             470             475             480
Asp Thr Glu Ser Leu Ala Lys Arg Ile Cys Lys Asp Leu Glu Gln Leu
                485             490             495
Ser Gln Ile Gln Asn Arg Glu Phe Gly Thr Gln Lys Tyr Glu Gln Trp
        500             505             510
Ile Val Thr Val Gln Lys Ala Cys Met Val Phe Gln Met Pro Asp Lys
        515             520             525
Asp Glu Glu Ser Arg Ile Cys Lys Ala Leu Phe Leu Tyr Thr Ser His
        530             535             540
Leu Arg Lys Tyr Gln Asp Ala Leu Ile Ile Ser Glu His Ala Arg Met
545             550             555             560
Lys Asp Ala Leu Asp Tyr Leu Lys Asp Phe Phe Ser Asn Val Arg Ala
                565             570             575
Ala Gly Phe Glu Glu Ile Glu Gln Asp Leu Thr Gln Arg Phe Glu Glu
                580             585             590
Lys Leu Gln Glu Leu Glu Ser Val Ser Arg Asp Pro Ser Asn Glu Asn
        595             600             605
Pro Lys Leu Glu Asp Leu Cys Phe Ile Leu Gln Glu Glu Tyr His Leu
        610             615             620
Asn Pro Glu Thr Ile Thr Ile Leu Phe Val Lys Thr Arg Ala Leu Val
625             630             635             640
Asp Ala Leu Lys Asn Trp Ile Glu Gly Asn Pro Lys Leu Ser Phe Leu
                645             650             655
Lys Pro Gly Ile Leu Thr Gly Arg Gly Lys Thr Asn Gln Asn Thr Gly
                660             665             670
Met Thr Leu Pro Ala Gln Lys Cys Ile Leu Asp Ala Phe Lys Ala Ser
        675             680             685
```

```
Gly Asp His Asn Ile Leu Ile Ala Thr Ser Val Ala Asp Glu Gly Ile
        690                 695                 700

Asp Ile Ala Gln Cys Asn Leu Val Ile Leu Tyr Glu Tyr Val Gly Asn
705                 710                 715                 720

Val Ile Lys Met Ile Gln Thr Arg Gly Arg Gly Arg Ala Arg Gly Ser
                725                 730                 735

Lys Cys Phe Leu Leu Thr Ser Asn Ala Gly Val Ile Glu Lys Glu Gln
                740                 745                 750

Ile Asn Met Tyr Lys Glu Lys Met Met Asn Asp Ser Ile Leu Arg Leu
            755                 760                 765

Gln Thr Trp Asp Glu Ala Val Phe Arg Glu Lys Ile Leu His Ile Gln
        770                 775                 780

Thr His Glu Lys Phe Ile Arg Asp Ser Gln Glu Lys Pro Lys Pro Val
785                 790                 795                 800

Pro Asp Lys Glu Asn Lys Lys Leu Leu Cys Arg Lys Cys Lys Ala Leu
                805                 810                 815

Ala Cys Tyr Thr Ala Asp Val Arg Val Ile Glu Glu Cys His Tyr Thr
                820                 825                 830

Val Leu Gly Asp Ala Phe Lys Glu Cys Phe Val Ser Arg Pro His Pro
            835                 840                 845

Lys Pro Lys Gln Phe Ser Ser Phe Glu Lys Arg Ala Lys Ile Phe Cys
850                 855                 860

Ala Arg Gln Asn Cys Ser His Asp Trp Gly Ile His Val Lys Tyr Lys
865                 870                 875                 880

Thr Phe Glu Ile Pro Val Ile Lys Ile Glu Ser Phe Val Val Glu Asp
                885                 890                 895

Ile Ala Thr Gly Val Gln Thr Leu Tyr Ser Lys Trp Lys Asp Phe His
            900                 905                 910

Phe Glu Lys Ile Pro Phe Asp Pro Ala Glu Met Ser Lys
        915                 920                 925

<210> SEQ ID NO 5
<211> LENGTH: 152011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gcagcccggg ccccccgcgg gcgcgcgcgc gcgcaaaaaa ggcgggcggc ggtccgggcg        60
gcgtgcgcgc gcgcggcggg cgtggggggc ggggccgcgg gagcggggga ggagcggggg       120
aggagcgggg ggaggagcgg ggggaggagc ggggggagga gcggggggag gagcggggg        180 aggagcgggg ggaggagcgg ggggaggagc ggggggagga gcggggggag gagcggggg        240 aggagcgggg ggaggagcgg ggggaggagc ggggggagga gcggggggag gagcggggg        300 aggagcgggg gaggagcggc cagaccccgg aaacgggccc ccccaaaac acaccccccg        360 ggggtcgcgc gcggcccttt aaaggcgggc ggcgggcagc ccgggccccc cgcggccgag       420
actagcgagt tagacaggca agcactactc gcctctgcac gcacatgctt gcctgtcaaa       480
ctctaccacc ccggcacgct ctctgtctcc atggcccgcc gccgccatcg cggcccccgc       540 cgccccggc cgcccgggcc cacgggcgcg gtcccaaccg cacagtccca ggtaaacctcc       600 acgcccaact cggaacccgt ggtcaggagc gcgcccgcgg ccgccccgcc gccgccccc        660
```

```
gccagtgggc ccccgccttc ttgttcgctg ctgctgcgcc agtggctcca cgttcccgag   720
tccgcgtccg acgacgacga cgacgactgg ccggacagcc cccgcccga gccggcgcca    780 gaggcccggc ccaccgccgc cgccccccgc cccggtccc accgcccgg cgcgggcccg     840 gggggcgggg ctaacccctc ccaccccccc tcacgcccct tccgccttcc gccgcgcctc   900
gccctccgcc tgcgcgtcac cgcagagcac ctggcgcgcc tgcgcctgcg acgcgcgggc   960 ggggagggggg cgccgaagcc ccccgcgacc ccgcgaccc ccgcgacccc cacgcgggtg  1020
cgcttctcgc cccacgtccg ggtgcgccac ctggtggtct gggcctcggc cgcccgcctg  1080
gcgcgccgcg gctcgtgggc ccgcgagcgg gccgaccggg ctcggttccg cgcccggtg   1140 gcggaggccg aggcggtcat cgggccgtgc ctggggcccg aggcccgtgc ccgggccctg  1200
gcccgcggag ccggcccggc gaactcggtc taacgttaca cccgaggcgg cctgggtctt  1260
ccgcggagct cccgggagct ccgcaccaag ccgctctccg gagagacgat ggcaggagcc  1320
gcgcatatat acgcttggag ccggcccgcc cccgaggcgg gccgccctc ggagggcggg   1380 actggccaat cggcggccgc cagcgcggcg gggcccggcc aaccagcgtc cgccgagtcg   1440
tcggggcccg gcccactggg cggtaactcc cgcccagtgg gccgggccgc ccacttcccg   1500
gtatggtaat taaaaacttg cagaggcctt gttccgcttc ccggtatggt aattagaaac   1560
tcattaatgg gcggccccgg ccgcccttcc cgcttccggc aattcccgcg gcccttaatg   1620
ggcaaccccg gtattcccg cctcccgcgc gcgcgtaac cactcccctg gggttccggg     1680
ttatgttaat tgcttttttg gcggaacaca cggcccctcg cgcattggcc cgcgggtcgc   1740
tcaatgaacc cgcattggtc ccctgggggtt ccgggtatgg taatgagttt cttcgggaag  1800
gcgggaagcc ccggggcacc gacgcaggcc aagcccctgt tgcgtcggcg ggaggggcat   1860
gctaatgggg ttctttgggg gacaccgggt tggtccccca aatcggggc cgggccgtgc    1920 atgctaatga tattctttgg gggcgccggg ttggtccccg gggacggggc cgccccgcgg   1980
tgggcctgcc tccctggga cgcgcggcca ttggggggaat cgtcactgcc gccccttttgg  2040 ggaggggaaa ggcgtggggt ataagttagc cctggcccga cggtctggtc gcatttgcac   2100
ctcggcactc ggagcgagac gcagcagcca ggcagactcg ggccgccccc tctccgcatc   2160
accacagaag ccccgcctac gttgcgaccc ccagggaccc tccgtcagcg accctccagc   2220
cgcatacgac ccccatggag cccgccccg gagcgagtac ccgccggcct gagggccgcc    2280
cccagcgcga ggtgaggggc cgggcgccat gtctggggcg ccatgttggg gggcgccatg   2340 ttgggggggcg ccatgttggg ggaccccga cccttacact ggaaccggcc gccatgttgg   2400 gggacccca ctcatacacg ggagccgggc gccatgttgg ggcgccatgt tagggggcgt    2460
ggaaccccgt gacactatat atacagggac cggggggcgcc atgttagggg gcgcggaacc   2520
ccctgaccct atatatacag gaccggggt cgccctgtta ggggtcgcca tgtgaccccc   2580
tgactttata tatacagacc cccaacacct acacatggcc cctttgactc agacgcaggg   2640
cccggggtcg ccgtgggacc cccctgactc atacacagag acacgcccc acaacaaaca   2700 cacagggacc ggggtcgccg tgttaggggg cgtggtcccc actgactcat acgcagggcc   2760
cccttactca cacgcatcta gggggtggg gaggagccgc ccgccatatt tgggggacgc    2820
cgtgggaccc ccgactccgg tgcgtctgga gggcgggaga agagggaaga gagggggtcg   2880
ggatccaaag gacggaccca gaccacctttt ggttgcagac ccctttctcc ccctcttccc  2940
gaggccagca gggggggcagg actttgtgag gcgggggggg aggggggaact cgtgggcgct  3000 gattgacgcg ggaaatcccc ccattcttac ccgccccccc ttttttcccc tcagcccgcc   3060
```

```
ccggatgtct gggtgtttcc ctgcgaccga gacctgccgg acagcagcga ctcggaggcg   3120
gagaccgaag tgggggggcg gggggacgcc gaccaccatg acgacgactc cgcctccgag   3180
gcggacagca cggacacgga actgttcgag acggggctgc tggggccgca gggcgtggat   3240
gggggggcgg tctcgggggg gagccccccc cgcgaggaag accccggcag ttgcggggc   3300 gccccccctc gagaggacgg gggagcgac gagggcgacg tgtgcgccgt gtgcacggat   3360
gagatcgcgc cccacctgcg ctgcgacacc ttcccgtgca tgcaccgctt ctgcatcccg   3420
tgcatgaaaa cctggatgca attgcgcaac acctgcccgc tgtgcaacgc caagctggtg   3480
tacctgatag tgggcgtgac gcccagcggg tcgttcagca ccatcccgat cgtgaacgac   3540
ccccagaccc gcatggaggc cgaggaggcc gtcagggcgg gcacggccgt ggactttatc   3600
tggacgggca atcagcggtt cgcccgcgcg tacctgaccc tggggggggca cacggtgagg   3660 gccctgtcgc ccacccaccc tgagcccacc acggacgagg atgacgacga cctggacgac   3720
ggtgaggcgg gggggcggcg aggacccctgg gggaggagga ggagggggg gggagggagg   3780 aataggcggg cgggcgggcg aggaaagggc gggccgggga gggggcgtaa cctgatcgcg   3840 cccccgttg tctcttgcag cagactacgt accgcccgcc cccgccgga cgccccgcgc   3900 cccccacgc agaggcgccg ccgcgccccc cgtgacgggc ggggcgtctc acgcagcccc   3960
ccagccggcc gcggctcgga cagcgccccc ctcggcgccc atcgggccac acggcagcag   4020
taacactaac accaccacca acagcagcgg cggcggcggc tcccgccagt cgcgagccgc   4080
ggtgccgcgg ggggcgtctg gcccctccgg ggggttggg gttgttgaag cggaggcggg   4140
gcggccgagg ggccggacgg gccccccttgt caacagaccc gcccccccttg caaacaacag   4200 agacccata gtgatcagcg actccccccc ggcctctccc cacaggcccc ccgcggcgcc   4260
catgccaggc tccgccccccc gccccggtcc cccgcgtcc gcggccgcgt cgggccccgc   4320 gcgccccccgc gcggccgtgg cccccgtgtgt gcgggcgccg cctccggggc ccggccccccg   4380 cgccccggcc ccggggcgg agccggccgc ccgccccgcg gacgcgcgcc gtgtgcccca   4440
gtcgcactcg tccctggctc aggccgcgaa ccaagaacag agtctgtgcc gggcgcgtgc   4500
gacggtggcg cgcggctcgg ggggggccggg cgtggagggt ggacacgggc cctcccgcgg   4560
cgccgccccc tccggcgccg ccccctccgg cgccccccg ctccccctccg ccgcctctgt   4620 cgagcaggag gcggcggtgc gtccgaggaa gaggcgcggg tcgggccagg aaaacccctc   4680 ccccagtcc acgcgtcccc ccctcgcgcc ggcaggggcc aagagggcgg cgacgcaccc   4740
cccctccgac tcagggccgg gggggcgcgg ccagggaggg cccgggaccc ccctgacgtc   4800
ctcggcggcc tccgcctctt cctcctccgc ctcttcctcc tcggccccga ctcccgcggg   4860
ggccacctct tccgccaccg gggccgcgtc tcctccgct tccgcctcct cgggcggggc   4920
cgtcggtgcc ctgggaggga gacaagagga aacctccctc ggcccccgcg ctgcttctgg   4980
gccgcggggg ccgaggaagt gtgcccggaa gacgcgccac gcggagactt ccggggccgt   5040
ccccgcgggc ggcctcacgc gctacctgcc catctcgggg gtctctagcg tggtcgccct   5100
gtcgccttac gtgaacaaga cgatcacggg ggactgcctg cccatcctgg acatggagac   5160
ggggaacatc ggggcgtacg tggtcctggt ggaccagacg ggaaacatgg cgacccggct   5220
gcgggccgcg gtccccggct ggagccgccg caccctgctc cccgagaccg cgggtaacca   5280
cgtgacgccc cccgagtacc cgacggcccc cgcgtcggag tggaacagcc tctggatgac   5340
ccccgtgggg aacatgctgt tcgaccaggg caccctagtg ggcgccctgg acttccgcag   5400
```

-continued

```
cctgcggtct cggcacccgt ggtccgggga gcaggggggcg tcgacccggg acgagggaaa    5460
acaataaggg acgcccccgt gtttgtgggg agggggggggt cgggcgctgg gtggtctctg    5520
gccgcgccca ctacaccagc caatccgtgt cggggaggtg gaaagtgaaa gacacgggca    5580
ccacacacca gcgggtcttt tgtgttggcc ctaataaaaa aaactcaggg gattttttgct   5640
gtctgttggg aaataaaggt ttacttttgt atcttttccc tgtctgtgtt ggatgtatcg    5700
cggggggtgcg tgggagtggg ggtgcgtggg agtgggggtg cgtgggagtg ggggtgcgtg   5760
ggagtggggg tgcgtgggag tggggggtgcg tgggagtggg ggtgcgtggg agtgggggtg   5820
cgtgggagtg ggggtgcgtg ggagtggggg tgccatgttg ggcaggctct ggtgttaacc    5880
acagagccgc ggcccgggct gcctgaccac cgatccccga aagcatcctg ccactggcat    5940
ggagccagaa ccacagtggg ttgggtgtgg gtgttaagtt tccgcgagcg cctgcccgcc    6000
cggactgacc tggcctctgg ccgccacaaa gggcggggggg ggggggttaac tacactatag   6060
ggcaacaaag gatgggaggg gtagcggggc gggacggggc gcccaaaagg gggtcggcca    6120
caccacagac gtgggtgttg ggggggtgggg cggagggggtg gggggggaga cagaaacagg   6180
aacatagtta gaaaacaaga atgcggtgca gccagagaat cacaggagac gaggggatgg    6240
gcgtgttggt taccaaccca cacccaggca tgctcggtgg tatgaaggag gggggggcggt   6300
gtttcttaga gaccgccggg ggacgtgggg ttggtgtgca aaggcacgcg cacccgcgcc    6360
ggccaggtgg gccggtaccc catccccccc tcccccgacc cttcccaccc ccgcgtgcca    6420
gagatcaccc cggtccccccg gcacccgcca ctcctccata tcctcgcttt aggaacaact   6480
ttagggggggg gtacacacgc gccgtgcatt tccttccaca cccccccccct cccccgcact   6540
cccccccccc aggcagtaag acccaagcat agagagccag gcacaaaaac acaggcgggg    6600
tgggacacat gccttcttgg agtacgtggg tcattggcgt ggggggggttac agcgacaccg   6660
gccgaccccc tggcggtctt ccagccggcc cttagataag ggggcagttg gtggtcggac    6720
gggtaagtaa cagagtctaa ctaagggtgg gaggggggggga aaataacggg ctggtgtgct   6780
gtaacacgag cccacccgcg agtggcgtgg ccgaccttag cctctggggc gccccctgtc    6840
gtttgggtcc cccccccctct attggggaga agcaggtgtc taacctacct ggaaacgcgg    6900
cgtctttgtt gaacgacacc ggggcgccct cgacgagtgg gataacgggg gaggaaggga    6960
gggaggaggg tactgggggt gaaggggggggg gggagaagc gagaacagga aaggcgacgg   7020
agcccggcag aacaccgagg aaaaaaaaac cacagcgcat gcgccgggcc gttgtggggc    7080
cccgggccgg ggcccttgg gtccgccggg gccccgggcc gggccgccac ggggggccggc     7140
cgttggcggt aaccccgagt gttcatctca ggccccgggc cgggaacccg gaaaagcctc    7200
cgggggggcct ttttcgcgtc gcgtgccggc gagcgggtcc ggacggggcc cggaccgccg   7260
cggtcggggg cccctcgtcc cgggccgtac gcggccttcg ccccgtgagg ggacagacga    7320
acgaaacatt ccggcgacgg aacgaaaaac accccagacg ggttaaagaa acagaaaccg    7380
caaccccccac caccccccgaa acgggggaaaa cgaaaaaaaca gaccagcggc cggccggcgc   7440
ttaggggggag gatgtcgccg acgccccttg gccgcccccgg ctgcagggggg gcccggagag  7500
ccgcggcacc cggacgcgcc cggaaagtct ttcgcaccac cggcgatcgg cacggccgcg    7560
cccccgcttt tataaaggct cagatgacgc agcaaaaaca ggccacagca ccacatgggt    7620
aggtgatgta atttttatttt cctcgtctgc ggcctaatgg atttccgggc gcggtgcccc   7680
tgtctgcaga gcacttaacg gattgatatc tcgcgggcac gcgcgccctt aatgaccgcg    7740
cgcggggcgg ggggccggat acccacacgg gcggggggggg gtgtcgcggg ccgtctgctg   7800
```

```
gcccgcggcc acataaacaa tgactcgggg cctttctgcc tctgccgctt gtgtgtgcgc    7860
gcgccggctc tgcggtgtcg gcggcggcgg cggcggtggc cgccgtgttc ggtctcggta    7920
gccggccggc gggtggactc gcgggggggcc ggagggtgga aggcaggggg gtgtaggatg   7980
ggtatcagga cttccacttc ccgtccttcc atccccgtt cccctcggtt gttcctcgcc    8040
tcccccaaca ccccgccgct ttccgttggg gttgttattg ttgtcgggat cgtgcgggcc    8100
gggggtcgcc ggggcagggg cggggcgtg gcgggggtg ctcgtcgatc gaccgggctc    8160
agtgggggcg tggggtgggt gggagaaggc gaggagactg gggtgggggt gtcggtgggt    8220
ggttgttttt tgtggttgtt ttttgtgtct gtttccgtcc cccgtcaccc ccctccctcc    8280
gtcccctccg tccccccgtc gcgggtgttt gtgtttgttt attccgacat cggtttattt    8340
aaaataaaca cagccgttct gcgtgtctgt tcttgcgtgt ggctggggc ttatatgtgg    8400 ggtcccgggg gcgggatggg gtttagcggc ggggggcggc gcgccggacg gggcgctgga    8460
gataacggcc cccggggaac gggggaccgg ggctgggtat cccgaggtgg gtgggtgggc    8520
ggcggtggcc gggccgggcc gggccgggcc gggtgggcgg ggtttggaaa acgaggagg    8580 aggaggagaa ggcggggggg gagacggggg gaaagcaagg acacggcccg ggggggtggga   8640 gcgcgggccg ggccgctcgt aagagccgcg accggccgc cggggagcgt tgtcgccgtc    8700
ggtctgccgg ccccgtccc tccttttt gaccaaccag cgccctcccc ccaccacca    8760 ttcctactac caccaccacc accaccccca ccacgacac ctcccgcgca ccccgccca    8820 catcccccca ccccgcacca cgagcacggg gtgggggtag caggggatca aggggggca    8880 aagccggcgg ggcggttcgg gggggcggga gaccgagtag gcccgcccat acgcggcccc   8940
tcccggcagc cacgccccc agcgtcgggt gtcacgggga aagagcaggg gagaggggg   9000 gagaggggag agggggggag agggggagagg gggggagagg ggagagggg ggagagggga   9060 gaggggggga gaggggagag gggggagag gggagagggg gggagagggg agaggggggg    9120 agagggggaga gggggggaga gggggagggg ggggagaggg ggtatataaa ccaacgaaaa    9180
gcgcgggaac ggggatacgg ggcttgtgtg gcacgacgtc gtggttgtgt tactgggcaa    9240
acacttgggg actgtaggtt tctgtgggtg ccgaccctag gcgctatggg gattttgggt    9300
tgggtcgggc ttattgccgt tgggttttg tgtgtgcggg ggggcttgtc ttcaaccgaa    9360
tatgttattc ggagtcgggt ggctcgagag gtggggata tattaaaggt gccttgtgtg    9420
ccgctcccgt ctgacgatct tgattggcgt tacgagaccc cctcggctat aaactatgct    9480
ttgatagacg gtatattttt gcgttatcac tgtcccggat tggacacggt cttgtgggat    9540
aggcatgccc agaaggcata ttgggttaac ccctttttat ttgtggcggg ttttctggag    9600
gacttgagtc acccgcgtt tcctgccaac acccaggaaa cagaaacgcg cttggccctt    9660
tataaagaga tacgccaggc gctggacagt cgcaagcagg ccgccagcca cacacctgtg    9720
aaggctgggt gtgtgaactt tgactattcg cgcacccgcc gctgtgtagg gcgacaggat    9780
ttgggaccta ccaacggaac gtctggacgg accccggttc tgccgccgga cgatgaagcg    9840
ggcctgcaac cgaagcccct caccacgccg ccgcccatca tcgccacgtc ggaccccacc    9900
ccgcgacggg acgccgccac aaaaagcaga cgccgacgac cccactcccg cgcctctaa    9960 cgatgcctcg acggaaaccc gtccgggttc gggggggcgaa ccggccgcct gtcgctcgtc    10020
agggccggcg ggcgctcctc gccgccctag aggctgtccc gctggtgtga cgttttcctc    10080
gtccgcgccc cccgaccctc ccatggattt aacaaacggg ggggtgtcgc ctgcggcgac    10140
```

```
ctcggcgcct ctggactgga ccacgtttcg gcgtgtgttt ctgatcgacg acgcgtggcg    10200 gccctgatg gagcctgagc tggcgaaccc cttaaccgcc cacctcctgg ccgaatataa    10260
tcgtcggtgc cagaccgaag aggtgctgcc gccgcgggag gatgtgtttt cgtggactcg    10320
ttattgcacc cccgacgagg tgcgcgtggt tatcatcggc caggacccat atcaccaccc    10380
cggccaggcg cacggacttg cgtttagcgt gcgcgcgaac gtgccgcctc ccccgagtct    10440
tcggaatgtc ttggtggccg tcaagaactg ttatcccgag gcacggatga gcggccacgg    10500
ttgcctggaa aagtgggcgc gggacggcgt cctgttacta aacacgaccc tgaccgtcaa    10560
gcgcggggcg gcggcgtccc actctagaat cggttgggac cgcttcgtgg gcggagttat    10620
ccgccggttg gccgcgcgcc gccccggcct ggtgtttatg ctctggggcg cacacgccca    10680
gaatgccatc aggccggacc ctcgggtcca ttgcgtcctc aagttttcgc acccgtcgcc    10740
cctctccaag gttccgttcg gaacctgcca gcatttcctc gtggcgaacc gatacctcga    10800
gacccggtcg atttcaccca tcgactggtc ggtttgaaag gcatcgacgt ccggggtttt    10860
tgtcggtggg ggcttttggg tatttccgat gaataaagac ggttaatggt taaacctctg    10920
gtctcatacg ggtcggtgat gtcgggcgtc gggggagagg gagttccctc tgcgcttgcg    10980
attctagcct cgtggggctg gacgttcgac acgccaaacc acgagtcggg gatatcgcca    11040
gatacgactc ccgcagattc cattcggggg gccgctgtgg cctcacctaa ccaaccttta    11100 cacggggggcc cggaacggga ggccacagcg ccgtctttct ccccaacgcg cgcggatgac    11160
ggcccgccct gtaccgacgg gccctacgtg acgtttgata ccctgtttat ggtgtcgtcg    11220
atcgacgaat tagggcgtcg ccagctcacg gacaccatcc gcaaggacct gcggttgtcg    11280
ctggccaagt ttagcattgc gtgcaccaag acctcctcgt tttcgggaaa cgccccgcgc    11340
caccacagac gcggggcgtt ccagcgcggc acgcgggcgc cgcgcagcaa caaaagcctc    11400
cagatgtttg tgttgtgcaa acgcgcccac gccgctcgag tgcgagagca gcttcgggtc    11460
gttattcagt cccgcaagcc gcgcaagtat tacacgcgat cttcggacgg gcggctctgc    11520
cccgccgtcc ccgtgttcgt ccacgagttc gtctcgtccg agccaatgcg cctccaccga    11580
gataacgtca tgctggcctc gggggccgag taaccgcccc cccccatgc caccctcact    11640 gcccgtcgcg cgtgtttgat gttaataaat aacacataaa tttggctggt tgtttgttgt    11700
ctttaatgga ccgcccgcaa ggggggggggg gcgtttcagt gtcgggtgac gagcgcgatc    11760
cggccgggat cctaggaccc caaaagtttg tctgcgtatt ccagggtggg gctcagttga    11820
atctcccgca gcacctctac cagcaggtcc gcggtgggct ggagaaactc ggccgtcccg    11880
gggcaggcgg ttgtcggggg tggaggcgcg gcgcccaccc cgtgtgccgc gcctggcgtc    11940
tcctctgggg gcgacccgta aatggttgca gtgatgtaaa tggtgtccgc ggtccagacc    12000
acggtcaaaa tgccggccgt ggcgctccgg gcgctttcgc cgcgcgagga gctgacccag    12060
gagtcgaacg gatacgcgta catatggggcg tcccacccgc gttcgagctt ctggttgctg    12120
tcccggccta taaagcggta ggcacaaaat tcggcgcgac agtcgataat caccaacagc    12180
ccaatggggg tgtgctggat aacaacgcct ccgcgcggca ggcggtcctg gcgctcccgg    12240
ccccgtacca tgatcgcgcg ggtgccgtac tcaaaaacat gcaccacctg cgcggcgtcg    12300
ggcagtgcgc tggtcagcga ggccctggcg tggcataggc tatacgcgat ggtcgtctgt    12360
ggattggaca tctcgcggtg ggtagtgagt cccccgggcc gggttcggtg gaactgtaag    12420
gggacgcgcg gttaatagac aatgaccacg ttcggatcgc gcagagccga tagtatgtgc    12480
tcactaatga cgtcatcgcg ctcgtggcgc tcccggagcg gatttaagtt catgcgaagg    12540
```

```
aattcggagg aggtggtgcg ggacatggcc acgtacgcgc tgttgaggcg caggttgccg   12600
ggcgtaaagc agatggcgac cttgtccagg ctaaggccct gggagcgcgt gatggtcatg   12660
gcaagcttgg agctgatgcc gtagtcggcg tttatggcca tggccagctc cgtagagtca   12720
atggactcga caaactcgct gatgttggtg ttgacgacgg acatgaagcc gtgttggtcc   12780
cgcaagacca cgtaaggcag gggggcctct tccagtaact cggccacgtt ggccgtcgcg   12840
tgccgcctcc gcagctcgtc cgcaaaggca aacacccgtg tgtacgtgta tcccatgagc   12900
gtataattgt ccgtctgcag ggcgacggac atcagccccc gcgcggcga gccggtcagc    12960 atctcgcagc cccggaagat aacgttgtcc acgtacgtgc taaaggggc gacttcaaat    13020 gcctccccga agagctcttg gaggattcgg aatctcccga ggaaggcccg cttcagcagc   13080
gcaaactggg tgtgaacggc ggcggtggtc tccggttccc cggggtgta gtggcagtaa    13140 aacacgtcga gctgttgttc gtccagcccc gcgaaaataa cgtcgaggtc gtcgtcggga   13200
aaatcgtccg ggccccgtc ccgcggcccc agttgcttaa aatcaaacgc acgctcgccg    13260
ggggcgcctg cgtcggccat taccgacgcc tgcgtcggca cccccgaaga tttgggcgc    13320 agagacagaa tctccgccgt tagttctccc atgcgggcgt acgcgagggt cctctgggtc   13380
gcatccaggc ccgggcgctg cagaaagttg taaaaggaga taagcccgct aaatatgagc    13440
cgcgacagga acctgtaggc aaactccacc gaagtctccc cctgagtctt tacaaagctg   13500
tcgtcacgca acactgcctc gaaggcccgg aacgtccac taaacccaaa accagtttt     13560 cgcaggcgcg cggtcaccgc gatctggctg ttgaggacgt aagtgacgtc gttgcgggcc   13620
acgaccagct gctgtttgct gtgcacctcg cagcgcatgt gccccgcgtc ctggtcctgg   13680
ctctgcgagt agttggtgat gcggctggcg ttggccgtga ccactttc aatagtcagg     13740 ccgggctggt gtgtcagccg tcggtattcg tcaaactcct tgaccgacac gaacgtaagc   13800
acggggaggg tgaacacgac gaactccccc tcacgggtca ccttcaggta ggcgtggagc   13860
ttggccatgt acgcgctcac ctctttgtgg gaggagaaca gccgcgtcca gccggggagg   13920
ttggcggggt tggtgatgta gttttccggg acgacgaagc gatccacgaa ctgcatgtgc   13980
tcctcggtga tgggcaggcc gtactccagc accttcatga ggttaccgaa ctcgtgctcg   14040
acgcaccgtt tgttgttaat aaaaatggcc cagctatacg agaggcgggc gtactcgcgc   14100
agcgtgcggt tgcagatgag gtacgtgagc acgttctcgc tctggcggac ggaacaccgc   14160
agtttctggt gctcgaaggt cgactccagg acgccgtct gcgtcggcga gcccacacac    14220
accaacacgg gccgcaggcg ggccgcgtac tgggggtgt ggtacagggc gttaatcatc    14280
caccagcaat acaccacggc cgtgaggagg tgacgcccaa ggagcccggc ctcgtcgatg   14340
acgatcacgt tgctgcgggt aaaggccggc agcgccccgt gggtggccgg ggccaaccgc   14400
gtcagggcgc cctcggccaa ccccagggtc cgttccaggg cggccagggc gcgaaactcg   14460
ttccgcaact cctcgccccc ggaggcggcc agggcgcgct tcgtgaggtc caaaatcacc   14520
tcccagtagt acgtcagatc tcgtcgctgc aggtcctcca gcgaggcggg gttgctggtc   14580
agggtgtacg ggtactgtcc cagttgggcc tggacgtgat tccgcgaaa cccaaattca    14640 tgaaagatgg tgttgatggg tcggctgaga aaggcgcccg agagtttggc gtacatgttt   14700
tgggccgcaa tgcgcgtggc gcccgtcacc acacagtcca agacctcgtt gattgtctgc   14760
acgcacgtgc tctttccgga gccagcgttg ccggtgataa gatacaccgc gaacggaaac   14820
tccctgaggg gcaggcctgc gggggactct aaggccgcca cgtcccggaa ccactgcaga   14880
```

```
cggggcacttt gcgctccgtc gagctgttgt tgcgagagct ctcggatgcg cttaaggatt   14940
ggctgcaccc cgtgcataga cgtaaaattt aaaaaggcct cggccctccc tggaacggct   15000
ggtcggtccc cggggttgctg aaggtgcggc gggccgggtt tctgtccgtc tagctggcgc   15060
tccccgccgg ccgccgccat gaccgcacca cgctcgtggg ccccactac gcgtgcgcgg    15120 ggggacacgg aagcgctgtg ctcccccgag gacggctggg taaaggttca ccccaccccc   15180
ggtacgatgc tgttccgtga gattctccac gggcagctgg ggtataccga gggccagggg   15240
gtgtacaacg tcgtccggtc cagcgaggcg accacccggc agctgcaggc ggcgatcttt   15300
cacgcgctcc tcaacgccac cacttaccgg gacctcgagg cggactggct cggccacgtg   15360
gcggcccgcg gtctgcagcc ccaacggctg gttcgccggt acaggaacgc ccgggaggcg   15420
gatatcgccg gggtggccga gcgggtgttc gacacgtggc ggaacacgct taggacgacg   15480
ctgctggact ttgcccacgg gttggtcgcc tgctttgcgc cgggcggccc gagcggcccg   15540
tcaagcttcc ccaaatatat cgactggctg acgtgcctgg ggctggtccc catattacgc   15600
aagcgacaag aagggggtgt gacgcagggt ctgagggcgt ttctcaagca gcacccgctg   15660
acccgccagc tggccacggt cgcggaggcc gcggagcgcg ccggccccgg gttttttgag   15720
ctggcgctgg ccttcgactc cacgcgcgtg gcggactacg accgcgtgta tatctactac   15780
aaccaccgcc ggggcgactg gctcgtgcga gaccccatca gcgggcagcg cggagaatgt   15840
ctggtgctgt ggccccccctt gtggaccggg gaccgtctgg tcttcgattc gcccgtccag   15900
cggctgtttc ccgagatcgt cgcgtgtcac tccctccggg aacacgcgca cgtctgccgg   15960
ctgcgcaata ccgcgtccgt caaggtgctg ctggggcgca agagcgacag cgagcgcggg   16020
gtggccggtg ccgcgcgggt cgttaacaag gtgttggggg aggacgacga gaccaaggcc   16080
gggtcggccg cctcgcgcct cgtgcggctt atcatcaaca tgaagggcat gcgccacgta   16140
ggcgacatta acgacaccgt gcgtgcctac ctcgacgagg ccgggggggca cctgatagac   16200 gccccggccg tcgacggtac cctccctgga ttcggcaagg gcggaaacag ccgcgggtct   16260
gcgggccagg accagggggg gcgggcgccg cagcttcgcc aggccttccg cacggccgtg   16320
gttaacaaca tcaacggcgt gttggagggc tatataaata acctgtttgg aaccatcgag   16380
cgcctgcgcg agaccaacgc gggcctggcg acccaattgc aggagcgcga ccgcgagctc   16440
cggcgcgcaa cagcggggc cctggagcgc cagcagcgcg cggccgacct ggcggccgag   16500
tccgtgaccg gtggatgcgg cagccgccct gcggggggcgg acctgctccg ggccgactat   16560
gacattatcg acgtcagcaa gtccatggac gacgacacgt acgtcgccaa cagctttcag   16620
cacccgtaca tcccttcgta cgcccaggac ctggagcgcc tgtcgcgcct ctgggagcac   16680
gagctggtgc gctgttttaa aattctgtgt caccgcaaca accagggcca agagacgtcg   16740
atctcgtact ccagcggggc gatcgccgca ttcgtcgccc cctactttga gtcagtgctt   16800 cgggccccc gggtaggcgc gcccatcacg ggctccgatg tcatcctggg ggaggaggag   16860
ttatgggatg cggtgtttaa gaaaacccgc ctgcaaacgt acctgacaga catcgcggcc   16920
ctgttcgtcg cggacgtcca gcacgcagcg ctgcccccgc cccctcccc ggtcggcgcc   16980 gatttccggc ccgcgcgtc cccgcgggc cggtccagat cgcggtcgcc cggaagaact   17040
gcgccaggcg cgccggacca gggcgggggc atcgggcacc gggatggccg ccgcgacggc   17100
cgacgatgag gggtcggccg ccaccatcct caagcaggcc atcgccgggg accgcagcct   17160
ggtcgaggcg gccgaggcga ttagccagca gacgctgctc cgcctggcct gcgaggtgcg   17220
ccaggtcggc gaccgccagc cgcggtttac cgccaccagc atcgcgcgcg tcgacgtcgc   17280
```

```
gcctgggtgc cggttgcggt tcgttctgga cgggagtccc gaggacgcct atgtgacgtc   17340
ggaggattac tttaagcgct gctgcggcca gtccagttat cgcggcttcg cggtggcggt   17400
cctgacggcc aacgaggacc acgtgcacag cctggccgtg ccccccctcg ttctgctgca   17460
ccggttctcc ctgttcaacc ccagggacct cctggacttt gagcttgcct gtctgctgat   17520
gtacctggag aactgccccc gaagccacgc caccccgtcg acctttgcca aggttctggc   17580
gtggctcggg gtcgcgggtc gccgcacgtc cccattcgaa cgcgttcgct gccttttcct   17640
ccgcagttgc cactgggtcc taaacacact catgttcatg gtgcacgtaa aaccgttcga   17700
cgacgagttc gtcctgcccc actggtacat ggcccggtac ctgctggcca caacccgcc    17760
ccccgttctc tcggccctgt tctgtgccac cccgacgagc tcctcattcc ggctgccggg   17820
gccgccccc cgctccgact gcgtggccta aaccccgcc gggatcatgg ggagctgctg     17880
ggcgtcggag gaggtgcgcg cgcctctggt ctattggtgg ctttcggaga ccccaaaacg   17940
acagacgtcg tcgctgtttt atcagttttg ttgaattta ggaaataaac ccggttttgt    18000
ttctgtggcc tcccgacgga tgcgcgtgtc cttcctccgt cttggtgggt gggtgtctgt   18060
gtatcgcgtc ccatctgtgc ggagagggg ggcatgtcgg cacgtattcg acagactca     18120
agcacacacg ggggagcgct cttgtctcag ggcaatgttt ttattggtca aactcaggca   18180
aacagaaacg acatcttgtc gtcaaaggga tacacaaact tccccccctc tccccatact   18240
cccgccagca ccccggtaaa caccaactca atctcgcgca ggatttcgcg caggtgatga   18300
gcgcagtcca cggggggag cacaagggc gcgggtata gatcgacggg gacgccgacc      18360
gactccccgc ctccgggaca gacacgcacg acgcgccgcc agtagtgctc tgcgtccagc   18420
aaggcgccgc cgcggaaggc agtgggggc aaggggtcgc tagcctcaaa ggggacacc     18480
cgaacgctcc agtactccgc gtccaaccgt ttattaaacg cgtccacgat aaggcggtcg   18540
caggcgtcct ccataaggcc ccgggccgtg agtgcgtcct cctccggcac gcctgccgtt   18600
gtcaggccca ggacccgtcg cagcgtgtcg cgtacgaccc cggccgccgt ggtgtacgcg   18660
ggcccgcgga gaggaaatcc cccaagatgg tcagtgttgt cgcggagtt ccagaaccac    18720
actcccgcct ggttccaggc gactgcgtgg gtgtagacgc cctcgagggc caggcacagt   18780
gggtgccgca gccggaggcc gttggcccta agcacggctc ccacggccgt ctcgatggcc   18840
cgccgggcgt cctcgatcac cccggaagcc gcatccgcgt cttgggggtc cacgttaaag   18900
acacccagga acgcacccc atcgcccccg cagaccgcga acttcaccga gctggccgtc    18960
tcctcgatct gcaggcagac ggcggccatt accccaccca ggagctgccg cagcgcaggg   19020
caggcgtcgc acgtgtccgg gaccaggcgc tccaagacgg ccccggccca gggctctgag   19080
ggagcggcca ccaccagcgc gtccagtctt gctaggcccg tccggccgtg ggggtccgcc   19140
agcccgctcc ccccgaggtc ggccagggcc gccaggagct gggcgcgaag tccggggaag   19200
caaaaccgcg ccgtccagac gggcccgacg gccgcgggc ggtctaacag ttggatgatt    19260
ttagtggcgg gatgccaccg cgccaccgcc tcccgcaccg cgggcaggag gcatccggct   19320
gccgccgagg ccacgccggg ccaggctcgc ggggggagga cgaccctggc ccccaccgcg   19380
ggccaggccc ccaggagcgc ggcgtaagcg ccgcggccc cgcgcaccag gtcccgtgcc    19440
gactcggccg tggccggcac ggtgaacgtg ggccaacccg gaaacccag gacggcaaag    19500
tacgggacgg gtccccccg gacctcaaac tcgggcccca gaaaggcaaa gacggggggc    19560
agggccccgg gggcggcgtg gaccgtggta tgccactgcc ggaaaagggc gacagagcgcc  19620
```

```
ggcgcggaga acttctcgcc ggcgcttaca aagtagtcgt aatcgcgggg cagcagcacc    19680
cgtgccgtga ctcgttgcgg gtgcccgcgt ggccgcaggc ccacctcgca cacctcgacc    19740
aggtccccga acgcgccctc cttcttgatc ggcggaaacg caagagtctg gtattcgcgc    19800
gcaaatagcg cggttccggt ggtgatgtta acggtcagcg aagcggcgga cgcgcactgg    19860
ggggtgtcgc gaatggccgc caggcgcgcc cacgccagcc gcgcgtcggg atgctcggca    19920
acgcgcgccg ccagggccat agggtcgatg tcaatgttgg cctccgcgac caggagagcg    19980
gcgcgagggg cggcgggcgg gccccacgac gctctctcaa ctttcaccac cagtcccgtg    20040
cgtgggtccg agccgatacg cagcggggcg aacagggcca ccggcccggt ctggcgctcc    20100
agggccgcca ggacgcacgc gtacagcgcc cgccacagag tcgggttctc cagggctcc    20160 agcggggagg cggccggcgt cgtcgcggcg cgggcggccg ccacgacggc ctggacggag    20220
acgtccgcgg agccgtagaa atcccgcagc tccgtcgcgg tgacggagac ctccgcaaag    20280
cgcgcgcgac cctcccctgc ggcgttgcga catacaaaat acaccagggc gtggaagtac    20340
tcgcgagcgc ggggggggcag ccataccgcg taaagggtaa tggcgctgac gctctcctcc    20400
acccacacga tatctgcggt gtccatcgca cggcccctaa ggatcacggg cggtctgtgg    20460
gtcccatgct gccgtgcctg gccgggcccg gtgggtcgcg gaaaccggtg acggggggg    20520 ggcggttttt ggggttgggg tggggtggg aaacggcccg ggtccggggg ccaacttggc    20580
ccctcggtgc gttccggcaa cagccgccgc ggtccgcgga cgaccacgta ccgaacgagt    20640
gcggtcccga gacttatagg gtgctaaagt tcaccgcccc ctgcatcatg ggccaggcct    20700
cggtggggag ctccgacagc gccgcctcca ggatgatgtc agcgttgggg ttggcgctgg    20760
atgagtgcgt gcgcaaacag cgcccccacg caggcacgcg tagcttgaag cgcgcgcccg    20820
caaactcccg cttgtgggcc ataagcaggg cgtacagctg cctgtgggtc cggcaggcgc    20880
tgtggtcgat gtggtgggcg tccaacaacc ccacgattgt ctgtttggtg aggttttaa    20940 cgcgccccgc cccgggaaac gtctgcgtgc ttttggccat ctgcacgcca aacgttcgc    21000 cccagattat cttgaacagc gccaccgcgt ggtccgtctc gctaacggac ccgcgcgggg    21060
gacagccgct tagggcgtcg gcgacgcgct tgacggcttc ctccgagagc agaagtccgt    21120
cggttacgtt acagtggccc agttcgaaca ccagctgcat gtagcggtcg tagtgggggg    21180
tcagtaggtc cagcacgtca tcggggccga aggtcctccc agatccccg gccgccgagt    21240 cccaatgcag gcgcgcggcc atggtgctgc acaggcacaa cagctcccag acgggggtta    21300
cgttcagggt ggggggcagg gccacgagct ccagctctcc ggtgacgttg atcgtgggga    21360
tgacgcccgt ggcgtagtgg tcatagatcc gccgaaatat ggcgctgctg cgggtggcca    21420
tgggaacgcg gagacaggcc tccagcaacg ccaggtaaat aaaccgcgtg cgtcccatca    21480
ggctgttgag gttgcgcatg agcgcgacaa tttccgccgg cgcgacatcg gaccggaggt    21540
atttttcgac gaaagaccc acctcctccg tctcggcggc ctgggccggc agcgacgcct    21600
cgggatcccg gcaccgcagc tcccgtagat cgcgctgggc cctgagggcg tcgaaatgta    21660
cgccccgcaa aaacagacag aagtcctttg gggtcagggt atcgtcgtgt cccagaagc    21720 gcacgcgtat gcagtttagg gtcagcagca tgtgaaggat gttaaggctg tccgagagac    21780
acgccagcgt gcatctctca agtagtgtt tgtaacggaa tttgttgtag atgcgcgacc    21840
cccgccccag cgacgtgtcg catgccgacg cgtcacagcg ccccttgaac cggcgacaca    21900
gcaggtttgt gacctgggag aactgcgcgg gccactggcc gcaggaactg accacgtgat    21960
taaggagcat gggcgtaaag acgggctccg agcgcgcccc ggagccgtcc atgtaaatca    22020
```

```
gtagctcccc cttgcggagg gtgcgcaccc gtcccaggga ctggtacacg gacaccatgt    22080
ccggtccgta gttcatgggt tttacgtagg cgaacatgcc atcaaagtgc aggggatcga    22140
agctgaggcc cacggttacg accgtcgtgt atataaccac gcggtattgg ccccacgtgg    22200
tcacgtcccc gagggggggtg agcgagtgaa gcaacagcac gcggtccgta aactgacggc    22260
agaaccgggc cacgatctcc gcgaaggaga ccgtcgacga aaaaatgcag atgttatcgc    22320
ccccgccaag gcgcgcttcc agctccccaa gaaacgtggc cccccgggcg tccgagagg     22380 cgtccggaga cgggccgctc ggcggcccgg gcgggcgcag ggcagcctgc aggagctcgg    22440
tccccagacg cgggagaaac aggcaccggc gcgccgaaaa cccgggcatg gcgtactcgc    22500
cgaccaccac atgcacgttt ttttcgcccc ggagaccgca caggaagtcc accaactgcg    22560
cgttggcggt tgcgtccatg gcgatgatcc gaggacaggt gcgcagcagg cgtagcatta    22620
acgcatccac gcggcccagt tgctgcatcg ttggcgaata gagctggccc agcgtcgaca    22680
taacctcgtc cagaacgagg acgtcgtagt tgttcagaag gttggggccc acgcgatgaa    22740
ggctttccac ctggacgata agtcggtgga aggggcggtc gttcataatg taattggtgg    22800
atgagaagta ggtgacaaag tcgaccaggc ctgactcagc gaaccgcgtc gccagggtct    22860
gggtaaaact ccgacgacag gagacgacga gcacactcgt gtccggagag tggatcgctt    22920
cccgcagcca gcggatcagc gcggtagttt ttcccgaccc cattggcgcg cggaccacag    22980
tcacgcacct ggccgtcggg gcgctcgcgt tggggaaggt gacgggtccg tgctgctgcc    23040
gctcgatcgt tgttttcggg tgaacccggg gcacccattc ggccaaatcc ccccgtaca    23100 acatccgcgc tagcgatacg ctcgacgtgt actgttcgca ctcgtcgtcc ccaatgggac    23160
gcccggcccc cagaggatct cccgactccg cgccccccac gaaaggcatg accggggcgc    23220
ggacggcgtg gtgggtctgg tgtgtgcagg tggcgacgtt tgtggtctct gcggtctgcg    23280
tcacggggct cctcgtcctg gcctctgtgt tccgggcacg gtttccctgc ttttacgcca    23340
cggcgagctc ttatgccggg gtgaactcca cggccgaggt gcgcggggggt gtagccgtgc    23400 ccctcaggtt ggacacgcag agccttgtgg gcacttatgt aatcacggcc gtgttgttgt    23460
tggccgcggc cgtgtatgcc gtggtcggcg ccgtgacctc ccgctacgac cgcgccctgg    23520
acgcgggccg ccgtctggct gcggcccgca tggccatgcc gcacgccacg ctgatcgccg    23580
gaaacgtctg ctcttggttg ctgcagatca ccgtcctgtt gctggcccat cgcaccagcc    23640
agctggccca cctggtttac gtcctgcact ttgcgtgtct ggtgtatttt gcggcccatt    23700
tttgcaccag gggggtcctg agcgggacgt atctgcgtca ggtgcacggc ctgatggagc    23760
cggccccgac tcatcatcgc gtcgttggcc cggctcgagc cgtgctgaca aacgccttgc    23820
tgttgggcgt cttcctgtgc acggccgacg ccgcggtatc cctgaatacc atcgccgcgt    23880
tcaactttaa tttttcggcc ccgggcatgc tcatatgcct gaccgtgctg ttcgcccttc    23940
tcgtcgtatc gctgttgttg gtggtcgagg gggtgttgtg tcactacgtg cgcgtgttgg    24000
tgggccccca cctgggggcc gtggccgcca cgggcatcgt cggcctggca tgcgagcact    24060
attacaccaa cggctactac gttgtggaga cgcagtggcc gggggccccag acgggagtcc    24120 gcgtcgccct cgccctggtc gccgcctttg ccctcggcat ggccgtgctc cgctgcaccc    24180
gcgcctatct gtatcacagg cggcaccaca ccaaatttt tatgcgcatg cgcgacacgc    24240
gacaccgcgc acattccgcc ctcaagcgcg tacgcagttc catgcgcgga tcgcgagacg    24300
gccgccacag gcccgcaccc ggcagcccgc ccgggattcc cgaatatgcg gaagacccct    24360
```

```
acgcgatctc atacggcggc cagctcgacc ggtacggaga ttccgacggg gagccgattt    24420
acgacgaggt ggcggacgac caaaccgacg tattgtacgc caagatacaa cacccgcggc    24480
acctgcccga cgacgagccc atctatgaca ccgttggggg gtacgacccc gagcccgccg    24540 aggacccgt gtacagcacc gtccgccgtt ggtagctgtt tggttccgtt ttaataaacc     24600
gtttgtgttt aacccgaccg tggtgtatgt ctggtgtgtg gcgtccgatc ccgttactat    24660
caccgttccc cccaaacccc ggcgattgtg ggtttttta aaaacgacac gcgtgcgacc    24720
gtatacagaa cattgttgtt ttttattcgc tatcggacat gggggtgga aactgggtgg     24780 cggggcaggc gcctccgggg gttcgccggt gagtgtggcg cgagggggga tccgacgaac    24840
gcaggcgctg tctcccgggg gcccgcgtaa ccccgcgcat atccgggggc acgtagaaat    24900
taccttcctc ttcggactcg atatccacga cgtcaaagtc gtgggcggtc agcgagacga    24960
cctccccgtc gtcggtgatg aggacgttgt ttcggcagca gcagggccgg gtcccggaga   25020
acgagaggcc catagctcgg cgagcgtgtc gtcgaacgcc aggcggctgc ttcgctgtat    25080
ggccttatag atctccggat cgatgcggac ggggtaatg atcagggcga tcggaacggc     25140
ctggttcggg agaatggacg ccttgctggg tcctgcggcc ccgagagccc cggcgccgtc    25200
ctccaggcgg aacgttacgc cctcctccgc gctagtgcgg tgcctgccga taaacgtcac    25260
cagatgcggg tggggggggc agtcgggaa gtggctgtcg agcacgtagc cctgcaccaa     25320
gatctgctta aagttcgggt gacggggggtt cgcgaagacg ggctcgcggc gtaccagatc   25380
cccggagctc caggacacgg gggagatggt gtggcgtccg aggtcggggg cgccaaacag   25440
aagcacctcc gagacaacgc cgctatttaa ctccaccaag gcccgatccg cggcggagca    25500
ccgccttttt tcgcccgagg cgtgggcctc tgaccaggcc tggtcttgcg tgacgagagc    25560
ctcctccggg ccggggacgc gcccgggcgc gaagtatcgc acgctgggct tcgggatcga    25620
ccggataaat gcccggaacg cctccgggga ccggtgtgcc atcaagtcct cgtacgcgga    25680
ggccgtgggg tcgctggggt ccatgggggtc gaaagcgtac ttggcccggc atttgacctc   25740
gtaaaaggcc agggggggtct tggggactgg ggccaagtag ccgtgaatgt cccgaggaca    25800
gacgagaata tccagggacg ccccgaccat ccccgtgtga ccgtccatga ggaccccaca    25860
cgtatgcacg ttctcttcgg cgaggtcgcc gggttcgtgg aagataaagc gccgcgtgtc    25920
ggcgccggcc tcgccgccgt cgtccgcgcg gcccacgcag tagcgaaaca gcaggcttcg    25980
ggccgtcggc tcgttcaccc gcccgaacat caccgccgaa gactgtacat ccggccgcag    26040
gctggcgttg tgcttcagcc actggggcga gaaacacgga ccctgggggc cccagcggag    26100
ggtggatgcg gtcgtgaggc cccgccggag cagggcccat agctggcagt cggcctggtt    26160
ttgcgtggcc gcctcgtaaa acccccatgag ggggccgggggc gccacggcgt ccgcggcggc   26220
cgggggcccg cggcgcgtca ggcgccatag gtgccggccg agtccgcggt ccaccatacc    26280
cgcctcctcg aggaccacgg ccagggaaca cagataatcc aggcgggccc agaggggacc    26340 gatgccaga ggggcgcgga cgccgcgcag caacccgcgc aggtggcgct cgaacgtctc      26400
ggctagtata tgggagggca gcgcgttggg gatcaccgac gccgaccaca tagagtcaag    26460
gtccggggag tcgggatcgg cgtccgggtc gcggggcgtgg gtgccccccag gagatagcgg  26520 aatgtctggg gtcggaggcc ctgaggcgtc agaaagtgcc ggcgacgcgg cccggggctt    26580
ttcgtctgcg gtgtcggtgg cgtgctgatc acgtgggggg ttaacgggcg aatgggagct    26640
cgggtccaca gctgacgtcg tctgggggtgg gggggggcagg ggacgaaagg tggttgttag   26700
cggaagactg ttagggcggg ggcgcttggg ggggctgtcg gggccacgag gggtgtcctc    26760
```

```
ggccagggcc caggaacgct tagtcacggt gcgtcccggc ggacatgctg ggcctcccgt   26820
ggactccatt tccgagacga cgtggggga gcggtggttg agcgcgccgc cgggtgaacg    26880
ctgattctca cgacagcgcg tgccgcgcgc acgggttggt gtgacacagg cgggacacca   26940
gcaccaggag aggcttaagc tcgggaggca gcgccaccga cgacagtatc gccttgtgtg   27000
tgtgctggta atttatacac cgatccgtaa acgcgcgccg aatcttggga ttgcggaggt   27060
ggcgccggat gccctctggg acgtcatacg ccaggccgtg ggtgttggtc tcggccgagt   27120
tgacaaacag ggctgggtgc agcacgcggc gataggcgag cagggccagg gcgaagtcca   27180
gcgacacgctg gttgttgaaa tactggtaac cgggaaaccg ggtcacgggt acgcccaggc  27240
tcggggcgac gtacacgcta accaccaact ccagcagcgt ctggccaagg gcgtacaggt   27300
caaccgctaa cccgacgtcg tgcttcaggc ggtggttggt aaattcggcc cgttcgttgt   27360
taaggtattt caccaacagc tccgggggct ggttataccc gtgacccacc agggtgtgaa   27420
agttggctgt ggttagggcg gtgggcatgc caaacatccg gggggacttg aggtccggct   27480
cctggaggca aaactgcccc cgggcgatcg tggagttgga gttgagggtg acgaggctaa   27540
agtcggcgag gacggcccgc cggagcgaga cggcgtccga ccgcagcatg acgaggatgt   27600
tggcgcactt gatatccagg tggctgatcc cgcaggtggt gtttaaaaac acaacggcgc   27660
gggccagctc cgtgaagcac tggtggaggg ccgtcgagac cgaggggttt gttgtgcgca   27720
gggacgccag ttggccgata tacttaccga ggtccatgtc gtacgcgggg aacactatct   27780
gtcgttgttg cagcgagaac ccgaggggcg cgatgaagcc gcggatgttg tgggtgcggc   27840
cggcgcgtag agcgcactcc ccgaccaaca gggtcgcgat gagctcaacg gcaaaccact   27900
cctttcctt tatggtctta acggcaagct tatgttcgcg aatcagttgg acgtcgccgt    27960
atccccaga cccccgaag cttcgggccc cggggatctc gagggtcgtg tagtgtaggg     28020
cggggttgat ggcgaacacg gggctgcata gcttgcggat gcgcgtgagg gtaaggatgt   28080
gcgagggga cgaggggggt gcggttaacg ccgcctggga tctgcgcagg ggcgggcggt   28140
tcagtttggc cgccgtaccg ggcgtctcgg gggacgcgcg gcgatgagac gagcggctca   28200
ttcgccatcg ggatagtccc gcgcgaagcc gctcgcggag gccggatcgg tggcgggacc   28260
cgtgggagga gcgggagccg gcggcgtcct ggagagaggg gccgctgggg cgcccggagg   28320
ccccgtgtgg gttggagtgt atgtaggatg cgagccaatc cttgaaggac tgttggcgtg   28380
caccttgggg gctgaggtta gctgccacat gaccagcagg tcgctgtctg cgggactcat   28440
ccatccttcg gccaggtcgc cgtcttccca cagagaagcg ttggtcgctg cttcctcgag   28500
ttgctcctcc tggtccgcaa gacgatcgtc cacggcgtcc aggcgctcac caagcgccgg   28560
atcgaggtac cgtcggtgtg cggttagaaa gtcacgacgc gccgcttgct cctccacgcg   28620
aattttaaca caggtcgcgc gctgtcgcat catctctaag cgcgcgcggg actttagccg   28680
cgcctccaat tccaagtggg ccgcctttgc agccataaag gcgccaacaa accgaggatc   28740
ttgggtgctg acgccctccc ggtgcagctg cagggtctgg tccttgtaaa tctcggctcg   28800
gaggtgcgtc tcggccaggc gtcggcgcag ggccgcgtgg gcggcatctc ggtccattcc   28860
gccaccctgc gggcgacccg ggggtgctc tgatagtctc gcgtgcccaa ggcccgtgat    28920
cggggtactt cgccgccgcg acccgccacc cggtgtgcgc gatgtttggt cagcagctgg   28980
cgtccgacgt ccagcagtac ctggagcgcc tcgagaaaca gaggcaactt aaggtgggcg   29040
cggacgaggc gtcggcgggc ctcacaatgg gcggcgatgc cctacgagtg cccttttag    29100
```

```
atttcgcgac cgcgacccccc aagcgccacc agaccgtggt cccgggcgtc gggacgctcc    29160
acgactgctg cgagcactcg ccgctcttct cggccgtggc gcggcggctg ctgtttaata    29220
gcctggtgcc ggcgcaacta aagggggcgtg atttcggggg cgaccacacg gccaagctgg   29280
aattcctggc ccccgagttg gtacgggcgg tggcgcgact gcggtttaag gagtgcgcgc    29340
cggcggacgt ggtgcctcag cgtaacgcct actatagcgt tctgaacacg tttcaggccc    29400
tccaccgctc cgaagccttt cgccagctgg tgcactttgt gcgggacttt gcccagctgc    29460
ttaaaacctc cttccgggcc tccagcctca cggagaccac gggcccccca aaaaaacggg    29520
ccaaggtgga cgtggccacc cacggccgga cgtacggcac gctggagctg ttccaaaaaa    29580
tgatccttat gcacgccacc tactttctgg ccgccgtgct cctcggggac cacgcgggagc   29640
aggtcaacac gttcctgcgt ctcgtgtttg agatccccct gtttagcgac gcggccgtgc    29700
gccacttccg ccagcgcgcc accgtgtttc tcgtccccccg gcgccacggc aagacctggt   29760
ttctagtgcc cctcatcgcg ctgtcgctgg cctccttcg ggggatcaag atcggctaca    29820
cggcgcacat ccgcaaggcg accgagccgg tgtttgagga gatcgacgcc tgcctgcggg   29880
gctggttcgg ttcggcccga gtggaccacg ttaaagggga aaccatctcc ttctcgtttc    29940
cggacgggtc gcgcagtacc atcgtgtttg cctccagcca caacacaaac gtaagtcctc    30000
tttctttcg catggctctc ccaaggggcc ccgggtcgac ccgacccaca cccacccacc    30060
cacccacata cacacacaac cagacgcggg aggaaagtct gccccgtggg cactgatttt   30120
tattcgggat cgcttgagga ggcccgggca acggcccggg caacggtggg gcaactcgta    30180
gcaaataggc gactgatgta cgaagagaag acacacaggc gccacccggc gctggtcggg   30240
gggatgttgt ccgcgccgca ccgtcccccg acgacctctt gcagacggtc cgtgatgcaa    30300
ggacggcggg gggcctgcag cagggtgacc gtatccacgg gatggccaaa gagaagcgga   30360
cacaggctag catccccctg gaccgccagg gtacactggg ccatcttggc ccacagacac    30420
ggggcgacgg agggacagga ctccgttacg acggaggaga gccacagtgc gttggcggaa   30480
tcgatgtggg gcggcggggc gcaggactcg cagccccccg ggtggttggt gatcctggcc    30540
aggagccatc ccagatggcg ggccctgctt cccggtggac agagcgaccc caggtcgctg    30600
tccatggccc agcagtagat ctggccgctg gggaggtgcc accaggcccc cgggcccaag    30660
gcgcaacacg cgcccggctc cgggggggtc ttcgcgggga ccagatacgc gccatccagc   30720
tcgccgacca ctggctcctc cgcgagctgt tcggtggttg ggtcgggggt ttcctccggg    30780
ggggtggccg cccgtatgcg ggcgaacgtg agggtgcaca ggagcggggt caggggggtgc  30840
gtcacgctcc ggaggtggac gatcgcgcag tagcggcgct cgcggttaaa gaaaaagagg    30900
gcaaagaagg tgttcggggg caaccgcagc gccttgggc gcgtcagata cagaaaaatc     30960
tcgcagaaga gggcgcgccc ggggtctggg ttaggaaggg ccacctgaca cagaggctcg    31020
gtgaggaccg ttagacaccg aaagatcttg agccgctcgt ccgccgaac gacgcgccac     31080
acaaagacgg agttgacaat gcgcgcgata gagtcgacgt ccgtccccag gtcgtcgact    31140
ctgtcgcgcg tgccgcgagc tccggcccgg gaatccggcc ggggcaaggt ccccggggga   31200
ccaggcggcg ccaggggccg ccggggtccc agctgcgcca tgccggggggc gggggagggg  31260
caaacccccag aggcgggggc caacggcgcg gggaggagtg ggtgggcgag gtggccgggg  31320
gaaggcgccc gctagcgaga acggccgttc ccggacgaca ccttgcgaca aaacctaagg   31380
acagcggccc gcgcgacggg gtccgagagg ctaaggtagg ccgcgatgtt aatggtgaac   31440
gcaaagccgc cgggaaagac aactatgcca cagaggcggc gattaaaccc caggcagagg    31500
```

```
taggcgtagc tttccccggg caggtattgc tcgcagaccc tgcgtggggc tgtggagggg   31560
acggcctcca tgaagcgaca tttactctgc tcgcgtttac tgacgtcacc atccatcgcc   31620
acggcgattg gacgattgtt aagccgcagc gtgtctccgc ttgtgctgta gtagtcaaaa   31680
acgtaatggc cgtcggagtc ggcaaagcgg gccgggaggg cgtcgccgag cgggacgacc   31740
cgccgccccc gaccgccccg tcccccagg tgtgccagga cggccagggc atacgcggtg    31800
tgaaaaaagg cgtcggggc ggtcccctcg acggcgcgca tcaggttctc gaggagaatg    31860
gggaagcgcc tggtcacctc ccccagccac gcgcgttggt cggggccaaa gtcatagcgc   31920
aggcgctgtg agattcgagg gccgccctga agccgcgccc ggatggcctg cccagggcc    31980
cggaggcacg ccagatgtat gcgcgcagta aaggcgacct cggcggcgat gtcaaagggc   32040
ggcaggacgg ggcgcgggtg gcgcaggggc acctcgagcg cgggaaagcg gagcagcagc   32100
tccgcctgcc cagcgggaga cagctggtgg gggcgcacga cgcgttctgc ggcgcaggcc   32160
tcggtcaggg ccgtggccag cgccgaggac agcagcggag ggcgggcgcg tcgcccgccc   32220
cacgccacgg agttctcgta ggagacgacg acgaagcgct gcttggttcc gtagtggtgg   32280
cgcaggacca cggagataga acgacggctc cacagccagt ccggccggtc gccgccggcc   32340
agggcttccc atccgcgatc caaccactcg accagcgacc gcggctttgc ggtaccaggg   32400
gtcagggtta gaacgtcgtt caggatgtcc tcgcccccgg gcccgtgggg cactggggcc   32460
acaaagcggc cccgcctgg gggctccaga cccgccaaca ccgcatctgc gtcagccgcc   32520
cccatgcgc cccgctgac ggcctggtga accaggcgc cctggcggag ccccgatgca    32580
acgccacagg ccgcacgccc ggtccgagcg cggacccgggt ggcggcgggt gacgtcctgc   32640
actgcccgct gaaccaacgc gaggatctcc tcgttctcct gcgcgatgga cacgtcctgg   32700
gccgcggtcg tgtcgccgcc ggggggccgtc agctgctcct ccggggagat gggggggtcg   32760
gacgccccga cgatgggcgg gtctgcgggc gccccgcgt ggggccgggc caagggctgc    32820
ggacgcgggg acgcgctttc ccccagaccc atggacaggt gggccgcagc ctccttcgcg   32880
gccgcgggg cggcggcgcc aagcagagcg acgtagcggc acaaatgccg acagacgcgc    32940
atgatgcgcg tgctgtcggc cgcgtagcgc gtgttggggg ggacgagctc gtcgtaacta   33000
aacagaatca cgcgggcaca gctcgccccc gagcccacg caaggcgcag cgccgccacg    33060
gcgtacgggt catagacgcc ctgtgcgtca cacaccacgg gcaaggagac gaacaacccc   33120
ccggcgctgg acgcacgcgg aaggaggcca gggtgtgccg gcacgacggg ggccagaagc   33180
tcccccaccg catccgcggg cacgtaggcg gcaaacgccg tgcaccacgg ggtacagtcg   33240
ccggtggcat gagcccgagt ctggatttcg acctggaagt ttgcggccgt cccgagtccg   33300
gggcggccgc gcatcagggc ggccagaggg attcccgcgg ccgccaggca ctcgctggat   33360
atgatgacgt gaaccaaaga cgagggccga cccgggacgt ggccgagatc gtactggacc   33420
tcgttggcca agtgcgcgtt catggttcgg gggtgggtgt gggtgtgtag gcgatgcggg   33480
tcccccgagt ccgcgggaag ggcgcgggtt tggcgcgcgt atgcgtattc gccaacggag   33540
gcgtgcgtgc ttatgcgcgg cgcgtttctt ctgtctccag ggaatccgag gccaggactt   33600
taacctgctc tttgtcgacg aggccaactt tattcgcccg gatgcggtcc agacgattat   33660
gggctttctc aaccaggcca actgcaagat tatcttcgtg tcgtccacca acaccgggaa   33720
ggccagtacg agcttttttgt acaacctccg cggggccgcc gacagagcttc tcaacgtggt   33780
gacctatata tgcgatgatc acatgccgcg ggtggtgacg cacacaaacg ccacggcctg   33840
```

```
ttcttgttat atcctcaaca agcccgtttt catcacgatg gacggggcgg ttcgccggac    33900
cgccgatttg tttctggccg attccttcat gcaggagatc atcggggggcc aggccaggga    33960
gaccggcgac gaccggcccg ttctgaccaa gtctgcgggg gagcggtttc tgttgtaccg    34020
cccctcgacc accaccaaca gcggcctcat ggccccgat ttgtacgtgt acgtggatcc    34080
cgcgttcacg gccaacaccc gagcctccgg gaccggcgtc gctgtcgtcg ggcggtaccg    34140
cgacgattat atcatcttcg ccctggagca ctttttttctc cgcgcgctca cgggctcggc    34200
ccccgccgac atcgcccgct gcgtcgtcca cagtctgacg caggtcctgg ccctgcatcc    34260
cggggcgttt cgcggcgtcc gggtggcggt cgagggaaat agcagccagg actcggccgt    34320
cgccatcgcc acgcacgtgc acacagagat gcaccgccta ctggcctcgg aggggccga    34380
cgcgggctcg ggccccgagc ttctcttcta ccactgcgag cctccgggga gcgcggtgct    34440
gtaccccttt ttcctgctca acaaacagaa gacgcccgcc tttgaacact ttattaaaaa    34500
gtttaactcc gggggcgtca tggcctccca ggagatcgtt ccgcgacgg tgcgcctgca    34560
gaccgacccg gtcgagtatc tgctcgagca gctgaataac ctcaccgaaa ccgtctcccc    34620
caacacggac gtccgtacgt attccggaaa acggaacggc gcctcggatg accttatggt    34680
cgccgtcatt atggccatct accttgcggc ccaggccgga cctccgcaca cattcgctcc    34740
catcacacgc gtttcgtgag cgcccaataa acacacccag gtatgctacg cacgaccacg    34800
gtgtcgcctg ttaaggggggg gggaagggggg tgttggcggg aagcgtggga acacggggga    34860
ttctctcacg accggcacca gtaccacccc cctgtgaaca cagaaacccc aacccaaatc    34920
ccataaacat acgacacaca ggcatatttt ggaatttctt aggtttttat ttatttaggt    34980
atgctggggt ttctccctgg atgcccaccc ccaccccccc ccgtgggtct agccgggcct    35040
tagggatagc gtataacggg ggccatgtct ccggaccgca caacggccgc gccgtcaaag    35100
gtgcacaccc gaaccacggg agccagggcc aaggtgtctc ctagttggcc cgcgtgggtc    35160
agccaggcga cgagcgcctc gtagagcggc agccttcgct ctccatcctg catcagggcc    35220
ggggcttcgg ggtgaatgag ctgggcggcc tcccgcgtga cactctgcat ctgcaggaga    35280
gcgttcacgt acccgtcctg ggcacttagc gcaaagagcc gggggattag cgtaaggatg    35340
atggtggttc cctccgtgat cgagtaaacc atgttaagga ccagcgatcg cagctcggcg    35400
tttacggggc cgagttgttg gacgtccgcc agcagcgaga ggcgactccc gttgtagtac    35460
agcacgttga ggtctggcag ccctccgggg tttctggggc tggggttcag gtcccggatg    35520
cccctggcca cgagccgcgc cacgatttcg cgcgccaggg gcgatggaag cggaacggga    35580
aaccgcaacg tgaggtccag cgaatccagg cgcacgtccg tcgcttggcc ctcgaacacg    35640
ggcgggacga ggctgatggg gtccccgtta cagagatcta cggggaggt gttgcgaagg    35700
ttaacggtgc cggcgtgggt gaggcccacg tccaggggc aggcgacgat tcgcgtggga    35760
agcacccggg tgatgaccgc ggggaagcgc cttcggtacg ccagcaacag ccccaacgtg    35820
tcgggactga cgcctccgga gacgaaggat tcgtgcgcca cgtcggccag cgtcagttgc    35880
cggcggatgg tcggcaggaa taccacccgc ccttcgcagc gctgcagcgc cgccgcatcg    35940
gggcgcgaga tgcccgaggg tatcgcgatg tcagtttcaa agccgtccgc cagcatggcg    36000
ccgatccacg cggcagggag tgcagtggtg gttcgggtgg cggaggagc gcggtggggg    36060
tcagcggcgt agcagagacg ggcgaccaac ctcgcatagg acgggggtg ggtcttaggg    36120
ggttgggagg cgacagggac cccagagcat gcgcggggag gtctgtcggg cccagacgca    36180
ccgagagcga atccgtccat ggagtcccgg cctgggtttt atggggcccg gccctcggaa    36240
```

```
tcgcggcttg tcggcgggga caaagggggc ggggctaggg ggcttgcgga aacagaagac   36300
gtgtgggata aaagaatcgc actaccccaa ggaagggcgg ggcggtttat tacagagcca   36360
gtcccttgag cggggatgcg tcatagacga gatactgcgc gaagtgggtc tcccgcgcgt   36420
gggcttcccc gttgcgggcg ctgcggagga gggcggggtc gctggcgcag gtgagcgggt   36480
aggcctcctg aaacaggcca cacgggtcct ccacgagttc gcggcacccc gggggcgct   36540 taaactgtac gtcgctggcg gcggtggccg tggacaccgc cgaacccgtc tccacgatca   36600
ggcgctccag gcagcgatgt ttggcggcga tgtcggccga cgtaaagaac ttaaagcagg   36660
ggctgagcac cggcgaggcc ccgttgaggt ggtaggcccc gttatagagc aggtccccgt   36720
acgaaaatcg ctgcgacgcc cacgggttgg ccgtggccgc gaaggcccgg gacgggtcgc   36780
tctggccgtg gtcgtacatg agggcggtga catcccctc cttgtccccc gcgtaaacgc   36840
ccccggcggc gcgtccccgg gggttgcagg gccggcggaa gtagttgacg tcggtcgaca   36900
cggggggtgg gataaactca cacacggcgt cctggccgtg gtccatccct gcgcgccgcg   36960
gcacctgggc gcacccgaac acggggacgg gctgggccgg ccccaggcgg tttcccgcca   37020
cgaccgcgtt ccgcaggtac acggctgccg cgttgtccag tagaggggga gccccgcggc   37080
ccaggtaaaa gttttgggga aggttgccca tgtcggtgac ggggttgcgg acggttgccg   37140
tggccacgac ggcggtgtag cccacgccca ggtccacgtt cccgcgcggc tgggtgagcg   37200
tgaagtttac ccccccgcca gtttcatgcc gggccacctg gagctggccc aggaagtacg   37260
cctccgacgc gcgctccgag aacagcacgt tctcagtcac aaagcggtcc tgtcggacga   37320
cggtgaaccc aaacccggga tggaggcccg tcttgagctg atgatgcaag gccacgggac   37380
tgatcttgaa gtaccccgcc atgagcgcgt aggtcagcgc gttctccccg gccgcgctct   37440
cgcggacgtg ctgcacgacg ggctgtcgga tcgacgaaaa gtagttggcc cccagagccg   37500 ggggaccag ggggacctgc cgcgacaggt cgcgcagggc cggggggaaa ttggcgcgt   37560 tcgccacgtg gtcggccccg gcgaacagcg cgtggacggg gaggggggtaa aaatagtcgc   37620 cattttggat ggtatggtcc agatgctggg gggccatcag caggattccg gcgtgcaacg   37680
ccccgtcgaa tatgcgcatg ttggtggtgg acgcggtgtt ggcgcccgcg tcgggcgccg   37740
ccgagcagag cagcgccgtt gtgcgttcgg ccatgttgtg ggccagcacc tgcagcgtga   37800
gcatggcggg cccgtccact accacgcgcc cgttgtgaaa catggcgttg accgtgttgg   37860
ccaccagatt ggccgggtgc aggggggtgcg cggggtccgt cacggggtcg ctggggcaat   37920
cctcgccggg ggtgatctcc gggaccacca tgttctgcag ggtggcgtat acgcggtcga   37980 agcgaaccc cgcggtgcag cagcggcccc gcgagaaggc gggcaccatc acgtagtagt   38040
aaatcttgtg gtgcacggtc cagtccgccc cccggtgcgg ccgtcgtcc gcggcgtccg   38100 cggctcgggc ctgggtgttg tgcagcagct ggccgtcgtt gcggttgaag tccgcggtcg   38160
ccacgttaca cgccgctgcg tacacggggt cgtggccccc cgcgctaacc cggcagtcgc   38220
gatggcggtc cagggccgcg cgccgcatca gggcgtcgca gtcccacacg aggggtggca   38280
gcagcgccgg gtctcgcatt aggtgattca gttcggcttg cgcctgcccg cccagttccg   38340
ggccggtcag ggtaaagtca tcaaccagct gggccagggc ctcgacgtgc gccaccaggt   38400
cccggtacac ggccatgcac tcctcgggaa ggtctccccc gaggtaggtc acgacgtacg   38460
agaccagcga gtagtcgttc acgaacgccg cgcaccgcgt gttgttccag tagctggtga   38520
tgcactggac cacgagccgg gccagggcgc agaagacgtg ctcgctgccg tgtatggcgg   38580
```

```
cctgcagcag gtaaaacacc gccgggtagt tgcggtcttc gaacgccccg cgaacggcgg    38640
cgatggtggc gggggccatg gcgtggcgtc ccaccccag ctccaggccc cgggcgtccc     38700
ggaacgccgc cggacatagc gccaggggca agttgccgtt caccacgcgc caggtggcct    38760
ggatctcccc cgggccggcc gggggaacgt ccccccccgg cagctccacg tcggccaccc    38820
ccacgaagaa gtcgaacgcg gggtgcagct caagagccag gttggcgttg tcgggctgca    38880
taaactgctc cggggtcatc tggccttccg cgacccatcg gacccgcccg tgggccaggc    38940
gctgccccca ggcgttcaaa aacagctgct gcatgtctgc ggcggggccg gccggggccg    39000
ccacgtacgc cccgtacgga ttggcggctt cgacggggtc gcggttaagg cccccgaccg    39060
ccgcgtcaac gttcatcagc gaagggtggc acacggtccc gatcgcgtgt tccagagaca    39120
ggcgcagcac ctggcggtcc ttcccccaaa aaaacagctg gcggggcggg aaggcgcggg    39180
gatccgggtg gccgggggcg gggactaggt ccccggcgtg cgcggcaaac cgttccatga    39240
ccggattgaa caggcccagg ggcaggacga acgtcaggtc catggcgccc accaggtggt    39300
agggaacgtt ggtggcggcg tagatgcgct tctccagggc ctccaaaaag atcagcttct    39360
cgccgatgga caccagatcc gcgcgcacgc gcgtcgtctg gggggcgctc tcgagctcgt    39420
ccagcgtctg ccggttcagg tcgagctgct cctcctgcat ctccagcagg tggcggccca    39480
cgtcgtccag acttcgcacg gccttgccca tcacgagcgc cgtgaccagg ttggccccgt    39540
tcaggaccat ctcgccgtac gtcaccggca cgtcggcttc ggtgtcctcc actttcagga    39600
aggactgcag gaggcgctgt ttgatcgggg cggtggtgac gagcaccccg tcgaccggac    39660
gcccgcgcgt gtcggcatgc gtcagacggg cacggccac ggagggctgc gtggccgtgg     39720
tgaggtccac gagccaggcc tcgacggcct cccggcggtg gcccgccttg cccaggaaaa    39780
agctcgtctc gcagaagctt cgctttagct cggcgaccag ggtcgcccgg ccaccctgg    39840 tggccaggcg gccgttgtcc aggtatcgtt gcatcggcaa caacaaagcc aggggcggcg    39900
ccttttccag cagcacgtgc agcatctggt cggccgtgcc gcgctcaaac gccccgagga    39960
cggcctggac gttgcgagcg agctgttgga tggcgcgcaa ctggcgatgc gcgctgatac    40020
ccgtcccgtc cagggcctcc cccgtgagca gggcgatggc ctcggtggcc aggctgaagg    40080
cggcgttcag ggcccggcgg tcgataatct tggtcatgta attgtgtgtg ggttgctcga    40140
tggggtgcgg gccgtcgcgg gcaatcagcg gctggtggac ctcgaactgt acgcgcccct    40200
cgttcatgta ggccagctcc ggaaacttgg tacacacgca cgccaccgac aacccgagct    40260
ccagaaagcg cacgagcgac agggtgttgc aatacgaccc caacagggcg tcgaactcga    40320
cgtcatacag gctgtttgca tcggagcgca cgcgggaaaa aaaatcgaac aggcgtcgat    40380
gcgacgccac ctcgatcgtg ctaaggaggg accggtcgg caccatggcc gcggcatacc     40440
ggtatcccgg agggtcgcgg ttgggagcgg ccatggggtc gcgtggagat cggctgtctc    40500
tagcgatatt ggcccgggga ggctaagatc caccccaacg cccggccacc cgtgtacgtg    40560
cccgacggcc caaggtccac cgaaagacac gacgggcccg gacccaaaaa ggcggggat     40620 gctgtgtgag aggccgggtg tcggtcgggg gggaaaggca ccgggagaag gctgcggcct    40680
cgttccagga gaacccagtg tccccaacag acccggggac gtgggatccc aggccttata    40740
tacccccccc gccccacccc cgttagaacg cgacgggtgc attcaagatg gccctggtcc    40800
aaaagcgtgc caggaagaaa ttggcagagg cggcaaagct gtccgccgcc gccacccaca    40860
tcgaggcccc ggccgcgcag gctatcccca gggcccgtgt gcgcagggga tcggtgggcg    40920
gcagcatttg gttggtggcg ataaagtgga aaagcccgtc cggactgaag gtctcgtggg    40980
```

-continued

```
cggcggcgaa caaggcacac agggccgtgc ctcccaaaaa cacgacatc ccccaaaaca    41040
cgggcgccga caacggcaga cgatccctct tgatgttaac gtacaggagg agcgcccgca    41100
ccgcccacgt aacgtagtag ccgacgatgg cggccaggat acaggccggc gccaccaccc    41160
ttccggtcag cccgtaatac atgcccgctg ccaccatctc caacggcttc aggaccaaaa    41220
acgaccaaag gaacagaatc acgcgctttg aaaagaccgg ctgggtatgg ggcggaagac    41280
gcgagtatgc cgaactgaca aaaaagtcag aggtgccgta cgaggacaat gaaaactgtt    41340
cctccagtgg cagttctccc tcctcccccc caaaggcggc ctcgtcgacc agatctcgat    41400
ccaccagagg aaggtcatcc cgcatggtca tggggtgtgc ggtggaggtg gggagaccga    41460
aaccgcaaag ggtcgcttac gtcagcagga tcccgagatc aaagacaccc gggttcttgc    41520
acaaacacca cccggggttgc atccgcggag gcgagtgttt tgataaggcc gttccgcgcc    41580
ttgatataac ctttgatgtt gaccacaaaa cccggaattt acgcctacgc cccaatgccc    41640
acgcaagatg aggtaggtaa cccccccccc gtgggtgtga cgttgcgttt agttcattgg    41700
aggccaaggg gaaatggggt tggggaggaa acggaaaacc cagtaggccg tgttgggaac    41760
acgcccgggg ttgtcctcaa aaggcagggt ccatactacg gaagccgtcg ttgtattcga    41820
gacctgcctg tgcgacgcac gtcggggttg cctgtgtccg gttcggcccc accgcgtgcg    41880
gcacgcacga ggacgagtcc gcgtgcttta ttggcgttcc aagcgttgcc ctccagtttc    41940
tgttgtcggt gttcccccat acccacgccc acatccaccg taggggggcct ctgggccgtg    42000
tcacgtcgcc gcccgcgatg gagcttagct acgccaccac catgcactac cgggacgttg    42060
tgttttacgt cacaacggac cgaaaccggg cctactttgt gtgcgggggg tgtgtttatt    42120
ccgtggggcg gccgtgtgcc tcgcagcccg gggagattgc caagtttggt ctggtcgttc    42180
gagggacagg cccagacgac cgcgtggtcg ccaactatgt acgaagcgag ctccgacaac    42240
gcggcctgca ggacgtgcgt cccattgggg aggacgaggt gtttctggac agcgtgtgtc    42300
ttctaaaccc gaacgtgagc tccgagctgg atgtgattaa cacgaacgac gtggaagtgc    42360
tggacgaatg tctggccgag tactgcacct cgctgcgaac cagcccgggt gtgctaatat    42420
ccgggctgcg cgtgcgggcg caggacagaa tcatcgagtt gtttgaacac ccaacgatag    42480
tcaacgtttc ctcgcacttt gtgtataccc cgtccccata cgtgttcgcc ctggcccagg    42540
cgcacctccc ccgctccg agctcgctgg aggcctggt gagcggcctg tttgacggca    42600
tccccgcccc acgccagcca cttgacgccc acaacccgcg cacggatgtg gttatcacgg    42660
gccgccgcgc cccacgaccc atcgccggt cggggcggg gtcggggggc gcgggcgcca    42720
agcgggccac cgtcagcgag ttcgtgcaag tcaaacacat tgaccgcgtg ggccccgctg    42780
gcgtttcgcc ggcgcctccg ccaaacaaca ccgactcaag ttccctggtg cccggggccc    42840
aggattccgc ccgcccggc cccacgctaa gggagctgtg gtgggtgttt tatgccgcag    42900
accgggcgct ggaggagccc cgcgccgact ctggcctcac ccgcgaggag gtacgtgccg    42960
tacgtgggtt ccgggagcag gcgtggaaac tgtttggctc cgcggggggcc ccgcgggcgt    43020
ttatcgggc cgcgttgggc ctgagccccc tccaaaagct agccgtttac tactatatca    43080
tccaccgaga gaggcgcctg tccccttcc ccgcgctagt ccggctcgta ggccggtaca    43140
cacagcgcca cggcctgtac gtccctcggc ccgacgaccc agtcttggcc gatgccatca    43200
acgggctgtt tcgcgacgcg ctggcggccg gaaccacagc cgagcagctc ctcatgttcg    43260
accttctccc cccaaaggac gtgccggtgg gaagcgacgt gcaggccgac agcaccgctc    43320
```

```
tgctgcgctt tatagaatcg caacgtctcg ccgtccccgg ggggggtgatc tcccccgagc  43380
acgtcgcgta ccttggtgcg ttcctgagcg tgctgtacgc tggccgcggg cgcatgtccg  43440
cagccacgca caccgcgcgg ctgacagggg tgacctccct ggtgctagcg gtgggtgacg  43500
tggaccgtct ttccgcgttt gaccgcggag cggcggggcgc ggccagccgc acgcgggccg  43560
ccgggtacct ggatgtgctt cttaccgttc gtctcgctcg ctcccaacac ggacagtctg  43620
tgtaacagac cccaataaac gtatgtcgct accacaccct tgtgtgtcaa tggacgcctc  43680
tccgggggggg aagggaaaac aaagaggggc tgggggagcg gcaccaccgg ggcctgaaca  43740
aacaaaccac agacacggtt acagtttatt cggtcgggcg gagaaacggc cgaagccacg  43800
ccccctttat tcgcgtctcc aaaaaaacgg gacacttgtc cggagaacct ttaggatgcc  43860
agccagggcg gcggtaatca taaccacgcc cagcgcagag gcggccagaa acccgggcgc  43920
aattgcggcc acgggctgcg tgtcaaaggc tagcaaatga atgacggttc cgtttggaaa  43980
tagcaacaag gccgtggacg gcacgtcgct cgaaaacacg cttggggcgc cctccgtcgg  44040
cccgcggcg  atttgctgct gtgtgttgtc cgtatccacc agcaacacag acatgacctc  44100
cccggccggg gtgtagcgca taaacacggc ccccacgagc cccaggtcgc gctggttttg  44160
ggtgcgcacc agccgcttgg actcgatatc ccgggtggag ccttcgcatg tcgcggtgag  44220
gtaggttagg aacagtgggc gtcggacgtc gacgccggtg agcttgtagc cgatcccccg  44280
gggcagaggg gagtgggtga cgacgtagct ggcgttgtgg gtgatgggta ccaggatccg  44340
tggctcgacg ttggcagact gccccccgca ccgatgtgag gcctcaggga cgaaggcgcg  44400
gatcagggcg ttgtagtgtg cccagcgcgt cagggtcgag gcgaggccgt gggtctgctg  44460
ggccaggact tcgaccgggg tctcggatcg ggtggcttga ccagcgcgt ccaggataaa   44520
cacgctctcg tctagatcaa agcgcaggga ggccgcgcat ggcgaaaagt ggtccggaag  44580
ccaaaagagg gttttctggt ggtcggcccg ggccagcgcg gtccggaggt cggcgttggt  44640
cgctgcggcg acgtcggacg tacacagggc cgaggctatc agaaggctcc ggcgggcgcg  44700
ttcccgctgc accgccgagg ggacgcccgc caagaacggc tgccggagga cagccgaggc  44760
gtaaaatagc gcccgtggga cgaccggggt ggtcagcacg cggccccta  gaaactcggc   44820
atacagggcg tcgatgagat gggctgcgct gggcgccact gcgtcgtacg ccgaggggct  44880
atccagcacg aaggccagct gatagcccag cgcgtgtaat gccaagctct gttcgcgctc  44940
cagaatctcg gccaccaggt gctggagccg agcctctagc tgcaggcggg ccgtgggatc  45000
caagactgac acattaaaaa acacagaatc cgcggcacag cccgcggccc cgcgggcggc  45060
caacccggca agcgcgcgcg agtgggccaa aaagcctagc aggtcggaga ggcagaccgc  45120
gccgtttgcg tgggcggcgt tcacgaaagc aaaacccgac gtcgcgagca gcccgttag   45180
gcgccagaag agaggggggac gcgggccctg ctcggcgccc gcgtcccccg agaaaaactc  45240
cgcgtatgcc cgcgacagga actgggcgta gttcgtgccc tcctccgggt agccgcccac  45300
gcggcggagg gcgtccagcg cggagccgtt gtcggcccgc gtcagggacc ctaggacaaa  45360
gacccgatac cggggccgc ccggggggccc gggaagagcc cccggggggt tttcgtccgc   45420
ggggtccccg acccgatcta gcgtctggcc cgcggggacc accatcactt ccaccggagg  45480
gctgtcgtgc atggatatca cgagccccat gaattcccgc ccgtagcgcg cgcgcaccag  45540
cgcggcatcg cacccgagca ccagctcccc cgtcgtccag atgccacgg gccacgtcga   45600
ggccgacggg gagaaaataca cgtacctacc tggggatctc aacaggcccc gggtggccaa  45660
ccaggtcgtg gacgcgttgt gcaggtgcgt gatgtccagc tccgtcgtcg ggtgccgccg  45720
```

```
ggccccaacc ggcggtcggg ggggcggtgt atcacgcggc ccgctcgggt ggctcgccgt   45780
cgccacgttg tctccccgcg ggaacgtcag ggcctcgggg tcaggacgg ccgaaaacgt   45840 tacccaggcc cgggaacgca gcaacacgga ggcggttgga ttgtgcaaga gacccttaag   45900
gggggcgacc gcggggggag gctgggcggt cggctcgacc gtgatggggg cgggcaggct   45960
cgcgttcggg ggccggccga gcaggtaggt cttcgagatg taaagcagct ggccggggtc   46020
ccgcggaaac tcggccgtgg tgaccaatac aaaacaaaag cgctcctcgt accagcgaag   46080
aaggggcaga gatgccgtag tcaggtttag ttcgtccggc ggcgccagaa atccgcgcgg   46140 tggttttttgg gggtcggggg tgtttggcag ccacagacgc ccggtgttcg tgtcgcgcca   46200
gtacatgcgg tccatgccca ggccatccaa aaaccatggg tctgtctgct cagtccagtc   46260
gtggacctga ccccacgcaa cgcccaaaag aataaccccc acgaaccata aaccattccc   46320
catgggggac cccgtcccta acccacgggg cccgtggcta tggcagggct tgccgccccg   46380
acgttggctg cgagccctgg gccttcaccc gaacttgggg gttggggtgg ggaaaaggaa   46440
gaaacgcggg cgtattggcc ccaatggggt ctcggtgggg tatcgacaga gtgccagccc   46500
tgggaccgaa ccccgcgttt atgaacaaac gacccaacac ccgtgcgttt tattctgtct   46560
ttttatttcc gtcatagcgc gggttccttc cggtattgtc tccttccgtg tttcagttag   46620
cctcccccat ctcccgggca aacgtgcgcg ccaggtcgca gatcgtcggt atggagcctg   46680
gggtggtgac gtgggtctgg accatcccgg aggtaagttg cagcagggcg tcccggcagc   46740
cggcgggcga ttggtcgtaa tccaggataa agacgtgcat gggacggagg cgtttggcca   46800
agacgtccaa ggcccaggca aacacgttat acaggtcgcc gttgggggcc agcaactcgg   46860
gggcccgaaa cagggtaaat aacgtgtccc cgatatgggg tcgtgggccc gcgttgctct   46920
ggggctcggc accctggggc ggcacggccg tccccgaaag ctgtcccaa tcctcccgcc   46980 acgacccgcc gccctgcaga taccgcaccg tattggcaag cagcccgtaa acgcggcgaa   47040
tcgcggccaa catagccagg tcaagccgct cgccggggcg ctggcgtttg ccaggcggt   47100 cgatgtgtct gtcctccgga agggccccca acacgatgtt tgtgccgggc aaggtcggcg   47160
ggatgagggc cacgaacgcc agcacggcct gggggtgtcat gctgcccata aggtatcgcg   47220
cggccgggta gcacaggagg gcggcgatgg gatggcggtc gaagatgagg gtgagggccg   47280
ggggcggggc atgtgagctc ccagcctccc ccccgatatg aggagccaga acggcgtcgg   47340
tcacggcata aggcatgccc attgttatct gggcgcttgt cattaccacc gccgcgtccc   47400
cggccgatat ctcaccctgg tcgaggcggt gttgtgtggt gtagatgttc gcgattgtct   47460
cggaagcccc cagcacctgc cagtaagtca tcggctcggg tacgtagacg atatcgtcgc   47520
gcgaacccag ggcaccagc agttgcgtgg tggtggtttt ccccatcccg tgaggaccgt   47580
ctatataaac ccgcagtagc gtgggcattt tctgctccag gcggacttcc gtggcttctt   47640
gctgccggcg agggcgcaac gccgtacgtc ggttgctatg gccgcgagaa cgcgcagcct   47700
ggtcgaacgc agacgcgtgt tgatggcagg ggtacgaagc catacgcgct tctacaaggc   47760
gcttgccaaa gaggtgcggg agtttcacgc caccaagatc tgcggcacgc tgttgacgct   47820
gttaagcggg tcgctgcagg gtcgctcggt gttcgaggcc acacgcgtca ccttaatatg   47880
cgaagtggac ctgggaccgc gccgccccga ctgcatctgc gtgttcgaat cgccaatga   47940 caagacgctg ggcggggttt gtgtcatcat agaactaaag acatgcaaat atatttcttc   48000
cggggacacc gccagcaaac gcgagcaacg ggccacgggg atgaagcagc tgcgccactc   48060
```

```
cctgaagctc ctgcagtccc tcgcgcctcc gggtgacaag atagtgtacc tgtgccccgt    48120
cctggtgttt gtcgcccaac ggacgctccg cgtcagccgc gtgacccggc tcgtcccgca    48180
gaaggtctcc ggtaatatca ccgcagtcgt gcggatgctc cagagcctgt ccacgtatac    48240
ggtccccatg gagcctagga cccagcgagc ccgtcgccgc cgcggcggcg ctgcccgggg    48300
gtctgcgagc agaccgaaaa ggtcacactc tggggcgcgc gacccgcccg agccagcggc    48360
ccgccaggta ccacccgccg accaaacccc cgcctccacg gagggcgggg gggtgcttaa    48420
gaggatcgcg gcgctcttct gcgtgcccgt ggccaccaag accaaacccc gagctgcctc    48480
cgaatgagag tgtttcgttc cttccccctc ccccgcgtc agacaaaccc taaccaccgc     48540
ttaagcggcc cccgcgaggt ccgaagactc atttggatcc ggcgggagcc acctgacaac    48600
agcccccggg tttccccacg ccagacgccg gtccgctgtg ccatcgctcc ccttcatccc    48660 accccatct tgtcccaaa taaacaagg tctggtagtt aggacaacga ccgcagttct      48720
cgtgtgttat tgtcgctctc cgcctctcgc agatggaccc gtattgccca tttgacgctc    48780
tggacgtctg ggaacacagg cgcttcatag tcgccgattc ccgaaacttc atcaccccg     48840 agttccccg ggacttttgg atgtcgcccg tcttaacct ccccgggag acggcggcgg       48900 agcaggtggt cgtcctgcag gcccagcgca cagcggctgc cgctgccctg gagaacgccg    48960
ccatgcaggc ggccgagctc cccgtcgata tcgagcgccg gttacgcccg atcgaacgga    49020
acgtgcacga gatcgcaggc gccctggagg cgctggagac ggcggcggcc gccgccgaag    49080
aggcggatgc cgcgcgcggg gatgagccgg cgggtggggg cgacgggggg cgcccccgg     49140 gtctggccgt cgcggagatg gaggtccaga tcgtgcgcaa cgacccgccg ctacgatacg    49200
acaccaacct ccccgtggat ctgctacata tggtgtacgc gggccgcggg gcgaccggct    49260
cgtcgggggt ggtgttcggg acctggtacc gcactatcca ggaccgcacc atcacggact    49320
ttcccctgac cacccgcagt gccgactttc gggacggccg gatgtccaag accttcatga    49380
cggcgctggt cctgtccctg cagtcgtgcg gccggctgta tgtgggccag cgccactatt    49440
ccgccttcga gtgcgccgtg ttgtgtctct acctgctgta ccgaaacacg cacggggccg    49500
ccgacgatag cgaccgcgct ccggtcacgt tcggggatct gctgggccgg ctgccccgct    49560
acctggcgtg cctggccgcg gtgatcggga ccgagggcgg ccggccacag taccgctacc    49620
gcgacgacaa gctccccaag acgcagttcg cggccggcgg gggccgctac gaacacggag    49680
cgctggcgtc gcacatcgtg atcgccacgc tgatgcacca cggggtgctc ccggcggccc    49740
cgggggacgt ccccccggga cgcgagcacc cacgttaacc cgacggcgtg gcgcaccacg    49800
acgacataaa ccgcgccgcc gccgcgttcc tcagccgggg ccacaaccta ttcctgtggg    49860
aggaccagac tctgctgcgg gcaaccgcga acaccataac ggccctgggc gttatccagc    49920
ggctcctcgc gaacggcaac gtgtacgcgg accgcctcaa caaccgcctg cagctgggca    49980
tgctgatccc cggagccgtc ccttcggagg ccatcgcccg tggggcctcc gggtccgact    50040
cgggggccat caagagcgga gacaacaatc tggaggcgct atgtgccaat tacgtgcttc    50100
cgctgtaccg ggccgacccg gcggtcgagc tgacccagct gttttcccggc ctggccgccc    50160 tgtgtcttga cgcccaggcg gggcggccgg tcggtcgac gcggcgggtg gtggatatgt     50220
catcgggggc ccgccaggcg gcgctggtgc gcctcaccgc cctggaactc atcaaccgca    50280
cccgcacaaa ccccacccccc gtgggggagg ttatccacgc ccacgacgcc ctggcgatcc    50340
aatacgaaca ggggcttggc ctgctggcgc agcaggcacg cattggcttg ggctccaaca    50400
ccaagcgttt ctccgcgttc aacgttagca gcgactacga catgttgtac tttttatgtc    50460
```

```
tggggttcat tccacagtac ctgtcggcgg tttagtgggt ggtgggcgag ggggagggg    50520 gcattaggga gaaagaacaa gagcctccgt tgggttttct ttgtgcctgt actcaaaagg   50580 tcatacccg taaacggcgg gctccagtcc cggcccggcg gttggcgtga acgcaacggc    50640
gggagctggg ttagcgttta gtttagcatt cgctctcgcc tttccgcccg cccccgaccg   50700
ttgagccttt ttttttttcg tccaccaaag tctctgtggg tgcgcgcatg gcagccgatg   50760 cccgggaga ccggatggag gagccctgc cagacagggc cgtgcccatt tacgtggctg     50820 ggttttggc cctgtatgac agcggggact cgggcgagtt ggcattggat ccggatacgg    50880
tgcgggcggc cctgcctccg gataacccac tcccgattaa cgtggaccac cgcgctggct   50940
gcgaggtggg gcgggtgctg gccgtggtcg acaccccg cgggccgttt tttgtgggac     51000
tgatcgcctg cgtgcaactg gagcgcgtcc tcgagacggc cgccagcgct gcgattttcg   51060
agcgccgcgg gccgccgctc tcccgggagg agcgcctgtt gtacctgatc accaactacc   51120
tgccctcggt ctccctggcc acaaaacgcc tgggggcga ggcgcacccc gatcgcacgc    51180
tgttcgcgca cgtagcgctg tgcgcgatcg ggcggcgcct tggcactatc gtcacctacg   51240
acaccggtct cgacgccgcc atcgcgccct ttcgccacct gtcgccggcg tctcgcgagg   51300
gggcgcggcg actggccgcc gaggccgagc tcgcgctatc cggacgcacc tgggcgcccg   51360
gcgtggaggc gctgacccac acgctgcttt ccaccgccgt taacaacatg atgctgcggg   51420
accgctggag cctggtggcc gagcggcggc ggcaggccgg gatcgccgga cacacctacc   51480
tccaggcgag cgaaaaattc aaaatgtggg gggcggagcc tgtttccgcg ccggcgcgcg   51540
ggtataagaa cggggccccg gagtccacgg acataccgcc cggctcgatc gctgccgcgc   51600
cgcagggtga ccggtgccca atcgtccgtc agcgcgggt cgcctcgccc ccggtactgc    51660
cccccatgaa ccccgttcca acatcgggca ccccggcccc cgcgccgccc ggcgacggga   51720
gctacctgtg gatcccggcc tcccattaca accagctcgt cgccggccac gccgcgcccc   51780
aaccccagcc gcattccgcg tttggtttcc cggctgcggc gggggccgtg gcctatgggc   51840
ctcacggcgc gggtctttcc cagcattacc ctccccacgt cgcccatcag tatcccgggg   51900
tgctgttctc gggacccagc ccactcgagg cgcagatagc cgcgttggtg ggggccatag   51960
ccgcggaccg ccaggcgggc ggtcagccgg ccgcggaga ccctgggtc cggggtcgg     52020 gaaagcgtcg ccggtacgag gcggggccgt cggagtccta ctgcgaccag gacgaaccgg   52080
acgcggacta cccgtactac cccggggagg ctcgaggcgg gccgcgcggg gtcgactctc   52140
ggcgcgcggc ccgccagtct cccgggacca acgagaccat cacggcgctg atggggcgg    52200 tgacgtctct gcagcaggaa ctggcgcaca tgcgggctcg gaccagcgcc ccctatggaa   52260
tgtacacgcc ggtggcgcac tatcgccctc aggtggggga gccggaacca acaacgaccc   52320
acccggccct ttgtcccccg gaggccgtgt atcgcccccc accacacagc gcccctacg    52380 gtcctcccca gggtccggcg tcccatgccc ccactccccc gtatgcccca gctgcctgcc   52440
cgccaggccc gccaccgccc ccatgtcctt ccacccagac gcgcgccct ctaccgacgg    52500 agcccgcgtt cccccccgcc gccaccggat cccaaccgga ggcatccaac gcggaggccg   52560
gggcccttgt caacgccagc agcgcagcac acgtggacgt tgacacgcc cgcgccgccg    52620 atttgttcgt ctctcagatg atgggggccc gctgattcgc cccggtctt ggtaccatgg    52680 gatgtcttac tgtatatctt tttaaataaa ccaggtaata ccaaataaga cccattggtg   52740 tatgttctt ttttattggg aggggcgggt aggcgggtag ctttacaatg caaaagcctt    52800
```

```
tgacgtggag gaaggcgtgg gggggaggaa atcggcactg accaagggg tccgttttgt    52860
cacgggaaag gaaagaggaa acaggccgcg gacacccggg ggagtttatg tgttcctttt    52920
tctttcttcc cacacacaca caaaaggcgt accaaacaaa aaaaccaaaa gatgcgcatg    52980
cggtttaaca cccgtggttt ttatttacaa caaaccccc gtcacaggtc gtcctcgtcg    53040
gcgtcaccgt ctttgttggg aacttgggtg tagttggtgt tgcggcgctt gcgcatgacc    53100
atgtcggtga ccttggcgct gagcagcgcg ctcgtgccct tcttcttggc cttgtgttcc    53160
gtgcgctcca tggccgacac cagggccatg taccgtatca tctccctggc ctcggctagc    53220
ttggcctcgt caaagtcgcc gccctcctcg ccctccccgg acgcgtccgg gttggtgggg    53280
ttcttgagct ccttggtggt tagagggtac agggccttca tggggttgct ctgcagccgc    53340
atgacgtaac gaaaggcgaa gaaggccgcc gccaggccgg ccaggaccaa cagacccacg    53400
gccagcgccc caaagggtt ggacatgaag gaggacacgc ccgacacggc cgataccacg    53460
ccgcccacga tgcccatcac caccttgccg accgcgcgcc ccaggtcgcc catccctcg    53520
aagaacgcgc ccaggcccgc gaacatgcg gcgttggcgt cggcgtggat gaccgtgtcg    53580
atgtcggcga agcgcaggtc gtgcagctgg ttgcggcgct ggacctccgt gtagtccagc    53640
aggccgctgt ccttgatctc gtggcgggtg tacacctcca gggggacaaa ctcgtgatcc    53700
tccagcatgg tgatgttgag gtcgatgaag gtgctgacgg tggtgatgtc ggcgcggctc    53760
agctggtggg agtacgcgta ctcctcgaag tacacgtagc ccccaccgaa ggtgaagtag    53820
cgccggtgtc ccacggtgca cggctcgatc gcatcgcgcg tcagccgcag ctcgttgttc    53880
tcccccagct gccctcgac caacgggccc tggtcttcgt accgaaagct gaccaggggg    53940
cggctgtagc aggcccggg ccgcgagctg atgcgcatcg agttttggac gatcacgttg    54000
tccgcggcga ccggcacgca cgtggagacg gccatcacgt cgccgagcat ccgcgcgctc    54060
acccgccggc ccacggtgac cgaggcgatg gcgttgggt tcagcttgcg ggcctcgttc    54120
cacagggtca gctcgtgatt ctgtagctcg caccacgcga tggcaacgcg gcccaacata    54180
tcgttgacat ggcgctgtat gtggttgtac gtaaactgca gccgggcgaa ctcgatggag    54240
gaggtggtct tgatgcgctc cacggacgcg ttggcgctgg ccccgggcgg cggggcgtg    54300
gggtttgggg gcttgcggct ctgctctcgg aggtgttccc gcacgtacag ctccgcgagc    54360
gtgttgctga gaaggggctg gtacgcgatc agaaagcccc cattggccag gtagtactgc    54420
ggctggccca ccttgatgtg cgtcgcgttg tacctgcggg cgaagatgcg gtccatggcg    54480
tcgcgggcgt ccttgccgat gcagtccccc aggtccacgc gcgagagcgg gtactcggtc    54540
aggttggtgg tgaaggtggt ggatatggcg tcggaggaga atcggaagga gccgccgtac    54600
tcggagcgca gcatctcgtc cacttcctgc cacttggtca tggtgcagac cgacgggcgc    54660
tttggcaccc agtcccaggc cacggtgaac ttggggtcg tgagcaggtt ccgggtggtc    54720
ggcgccgtgg cccgggcctt ggtggtgagg tcgcgcgcgt agaagccgtc gacctgcttg    54780
aagcggtcgg cggcgtagct ggtgtgttcg gtgtgcgacc cctcccggta gccgtaaaac    54840
ggggacatgt acacaaagtc gccagtcgcc agcacaaact cgtcgtacgg gtacaccgag    54900
cgcgcgtcca cctcctcgac gatgcagttt accgtcgtcc cgtaccggtg gaacgcctcc    54960
acccgcgagg ggttgtactt gaggtcggtg gtgtgccagc cccggctcgt gcgggtcgcg    55020
gcgttggccg gtttcagctc catgtcggtc tcgtggtcgt cccggtgaaa cgcggtggtc    55080
tccaggttgt tgcgcacgta cttggccgtg gaccgacaga cccccttggc gttgatcttg    55140
tcgatcacct cctcgaaggg gacggggcg cggtcctcaa agatccccat aaactgggag    55200
```

```
tagcggtggc cgaaccacac ctgcgaaacg gtgacgtctt tgtagtacat ggtggccttg    55260
aacttgtacg gggcgatgtt ctccttgaag accaccgcga tgccctccgt gtagttctga    55320
ccctcgggcc gggtcgggca gcggcgcggc tgctcgaact gcaccaccgt ggcgcccgtg    55380
gggggtgggc acacgtaaaa gtttgcatcg gtgttctccg ccttgatgtc ccgcaggtgc    55440
tcgcgcaggg tggcgtggcc cgcggcgacg gtcgcgttgt cgccggcggg gcgtggtggc    55500
gttgggtttt tcggtttttt gttcttcttc ggtttcgggt ccccgttgg ggcggcgcca     55560
```

```
agggcgggcg gcgccggagt ggcagggccc ccgttcgccg cctgggtcgc ggccgcgacc    55620
ccaggcgtgc cggggaact  cggagccgcc gacgccacca ggaccccag cgtcaacccc     55680 aagagcgccc atacgacgaa ccaccggcgc ccccacgagg gggcgccctg gtgcatggcg    55740
ggactacggg ggcccgtcgt gccccccgtc aggtagcctg ggggcgaggt gctggaggac    55800
cgagtagagg atcgagaaaa cgtcgcggtc gtagaccacg accgaccggg ggccgataca    55860
gccgtcgggg gcgctctcga cgatggccac cagcggacag tcggagtcgt acgtgagata    55920
tacgccgggc gggtaacggt aacgaccttc ggaggtcggg cggctgcagt ccgggcggcg    55980
caactcgagc tccccgcacc ggtagaccga ggcaaagagt gtggtggcga taatcagctc    56040
gcgaatatat cgccaggcgg cgcgctgagt gggcgttatt ccggaaatgc cgtcaaaaca    56100
gtaaaacctc tgaaattcgc tgacggccca atcagcaccc gagcccccg ccccatgat     56160 gaaccgggcg agctcctcct tcaggtgcgg caggagcccc acgttctcga cgctgtaata    56220
cagcgcggtt ttgggggggct gggcgaagct gtgggtggag tgatcaaaga ggggcccgtt   56280
gacgagctcg aagaagcgat gggtgatgct ggggagcagg gccgggtcca cctggtgtcg    56340
caggagagac gctcgcatga accggtcgcg gtcgaacacg cccggcgccg agcggttgtc    56400
gatgaccgtg cccgcgcccg ccgtcagggc gcagaagcgc gcgcgcgccg caaagccgtt    56460
ggcgaccgcg gcgaacgtcg cgggcagcac ctcgccgtgg acgctgaccc gcagcatctt    56520
ctcgagctcc ccgcgctgct cgcggacgca gcgcccagg ctggccaacg accgcttcgt     56580
caggcggtcc gcgtacagcc gccgtcgctc ccgtacgtcc gcggccgctt gcgtggcgat    56640
gtccccccac gtctcgggcc cctgcccccc gggcccgcgg cgacggtctt cgtcctcgcc    56700 cccgccccg ggagctccca accccgtgc cccttcctct acggcgacac ggtccccgtc      56760
gtcgtcgggg cccgcgccgc ccttgggcgc gtccgccgcg ccccccgccc ccatgcgcgc    56820
cagcacgcga cgcagcgcct cctcgtcgca ctgttcgggg ctgacgaggc gccgcaagag    56880
cggcgtcgtc aggtggtggt cgtagcacgc gcggatgagc gcctcgatct gatcgtcggg    56940
tgacgtggcc tgaccgccga ttattagggc gtccaccata tccagcgccg ccaggtggct    57000
cccgaacgcg cgatcgaaat gctccgcccg ccgcccgaac agcgccagtt ccacggccac    57060
cgcggcggtc tcctgctgca actcgcgccg cgccagcgcg gtcaggttgc tggcaaacgc    57120
gtccatggtg gtctggccgg cgcggtcgcc ggacgcgagc cagaatcgca attcgctgat    57180
ggcgtacagg ccgggcgtgg tggcctgaaa cacgtcgtgc gcctccagca gggcgtcggc    57240
ctccttgcgg accagagtcgt tctcgggcga cgggtgggc tgcccgtcgc ccccgcggt    57300 ccgggccagc gcatggtcca acacggagag cgcccgcgcg cggtcggcgt ccgacagccc    57360
ggcggcgtgg ggcaggtacc gccgcagctc gttggcgtcc agccgcacct gcgcctgctg    57420
ggtgacgtgt tacagatac ggtccgccag gcggcgggcg atcgtcgccc cctggttcgc     57480
cgtcacacac agttcctcga aacagaccgc gcaggggtgg gacgggtcgc taagctccgg    57540
```

```
ggggacgata aggcccgacc ccaccgcccc caccataaac tcccgaacgc gctccagcgc    57600
ggcggtggcg ccgcgcgagg gggtgatgag gtggcagtag tttagctgct ttagaaagtt    57660
ctcgacgtcg tgcaggaaac acagctccat atggacggtc ccgccatacg tatccagcct    57720
gacccgttgg tgatacggac agggtcgggc caggcccatg gtctcggtga aaaacgccgc    57780
gacgtctccc gcggtcgcga acgtctccag gctgcccagg agccgctcgc cctcgcgcca    57840
cgcgtactct agcagcaact ccagggtgac cgacagcggg gtgagaaagg ccccggcctg    57900
ggcctccagg cccggcctca gacgacgccg cagcgcccgc acctgaagcg cgttcagctt    57960
cagttggggg agcttccccc gtccgatgtg gggtcgcac cgccggagca gctctatctg    58020
aaacacatag gtctgcacct gcccgagcag ggctaacaac ttttgacggg ccacggtggg    58080
ctcggacacc ggggcggcca tctcgcggcg ccgatctgta ccgcggccgg agtatgcggt    58140
ggaccgaggc ggtccgtacg ctacccggtg tctggctgag cccgggggtc cccctcttcg    58200
gggcggcctc ccgcgggccc gccgaccggc aagccgggag tcggcggcgc gtgcgtttct    58260
gttctattcc cagacaccgc ggagaggaat cacggcccgc ccagagatat agacacggaa    58320
cacaaacaag cacggatgtc gtagcaataa tttattttac acacattccc cgccccgccc    58380
taggttcccc cacccccccaa cccctcacag catatccaac gtcaggtctc ccttttttgtc    58440 gggggggcccc tccccaaacg ggtcatcccc gtggaacgcc cgtttgcggc cggcaaatgc    58500
cggtcccggg gccccccgggc cgccgaacgg cgtcgcgttg tcgtcctcgc agccaaaatc    58560
cccaaagtta aacacctccc cggcgttgcc gagttggctg actagggcct cggcctcgtg    58620
cgccacctcc agggccgcgt ccgtcgacca ctcgccgttg ccgcgctcca gggcacgcgc    58680
ggtcagctcc atcatctcct cgcttaggta ctcgtcctcc aggagcgcca gccagtcctc    58740
gatctgcagc tgctgggtgc ggggcccag gcttttcacg gtcgccacga acacgctact    58800
ggcgacggcc gccccgccct cggagataat gccccggagc tgctcgcaca gcgagctttc    58860
gtgcgctccg ccgccgaggt tcgaggccgc gcacacaaac ccggcccggg gacaggccag    58920
gacgaacttg cgggtgcggt caaaaataag gagcgggcac gcgttttttgc cgcccatcag    58980 gctggcccag ttcccggcct gaaacacacg gtcgttgccg gccatgccgt agtatttgct    59040
gatgctcaac cccaacacga ccatggggcg cgccgccatg acgggccgca gcaggttgca    59100
gctggcgaac atggacgtcc acgcgcccgg atgcgcgtcc acggcgtcca tcagcgcgcg    59160
ggccccggcc tccaggcccg ccccgccctg cgcggaccac gcggccgccg cctgcacgct    59220 gggggacgg cgggacccccg cgatgatggc cgtgagggtg ttgatgaagt atgtcgagtg    59280
atcgcagtac cgcagaatct ggtttgccat gtagtacatc gccagctcgc tcacgttgtt    59340
gggggccagg ttaataaagt ttatcgcgcc gtagtccagg gaaaacttttt taatgaacgc    59400 gatggtctcg atgtcctcgc gcgacaggag ccgggcggga agctggttgc gttggagggc    59460
cgtccagaac cactgcgggt tcggctggtt ggaccccggg ggcttgccgt tgggggaagat    59520 ggccgcgtgg aactgcttca gcagaaagcc cagcggtccg aggaggatgt ccacgcgctt    59580
gtcgggcttc tggtaggcgc tctggaggct ggcgacccgc gccttggcgg cctcggacgc    59640
gttggcgctc gcgcccgcga acaacacgcg gctcttgacg cgcagctcct tgggaaaccc    59700
cagggtcacg cgggcaacgt cgccctcgaa gctgctctcg gcgggggccg tctggccggc    59760
cgttaggctg ggggcgcaga tagccgcccc ctccgagagc gcgaccgtca gcgttttggc    59820
cgacagaaac ccgttgttaa acatgtccat cacgcgccgc cgcagcaccg gttggaattg    59880
attgcgaaag ttgcgcccct cgaccgactg cccggcgaac accccgtggc actggctcag    59940
```

```
ggccaggtcc tgatacacgg cgaggttgga tcgccgcccg agaagctgaa gcaggggca    60000
tggcccgcac gcgtacgggt ccagcgtcag ggacatggcg tggttggcct cgcccagacc    60060
gtcgcgaaac ttgaagttcc tccctccac caggttgcgc atcagctgct ccacctcgcg    60120
gtccacgacc tgcctgacgt tgttcaccac cgtatgcagg gcctcgcggt tggtgatgat    60180
ggtctccagc cgccccatgg ccgtggggac cgcctggtcc acgtactgca gggtctcgag    60240
ttcggccatg acgcgctcgg tcgccgcgcg gtacgtctcc tgcatgatgg tccgggcggt    60300
ctcggatccg tccgcgcgct tcagggccga gaaggcggcg tagtttccca gcacgtcgca    60360
gtcgctgtac atgctgttca tggtcccgaa gacgccgatg gctccgcggg cggcgctggc    60420
gaacttggga tggcgcgccc ggaggcgcat gagcgtcgtg tgtacgcagg cgtggcgcgt    60480
gtcgaaggtg cacaggttgc agggcacgtc ggtctggttg gagtccgcga cgtatcgaaa    60540
cacgtccatc tcctggcgcc cgacgatcac gccgccgtcg cagcgctcca ggtaaaacag    60600
catcttggcc agcagcgccg gggaaaaccc acacagcatg ccaggtgct cgccggcaaa    60660
ttcctgggtt ccgccgacga ggggcgcggt gggccgaccc tcgaacccgg gcaccacgtg    60720
tccctcgcgg tccacctgtg ggttggccgc cacgtgggtc ccgggcacga ggaagaagcg    60780
gtaaaaggag ggtttgctgt ggtcctttgg gtccgccgga ccggcgtcgt ccacctcggt    60840
gagatggagg gccgagttgg tgctaaatac catggccccc acgagtcccg cggcgcgcgc    60900
caggtacgcc ccgacggcgt tggcgcgggc gcgccgtg tcctggccct cgcacagcgg    60960
ccacgcggag atgtcggtgg gcggctcgtc gaagacggcc atcgacacga tagactcgag    61020
ggccagggcg gcgtctccgg ccatgacgga ggccaggcgc tgttcgaacc cgcccgccgg    61080
gccctttgccg ccgccgtcgc gcccaccccg cggggtctta ccctggctgg cttcgaaggc    61140
cgtgaacgta atgtcggcgg ggagggcggc gccctcgtgg ttttcgtcaa acgccaggtg    61200
ggcggccgcg cgggccacgg cgtccacgtt tcggcatcgc agtgccacgg cggcgggtcc    61260
cacgaccgcc tcgaacagga ggcggttgag ggggcggtta aaaacggaa gcgggtaggt    61320
aaaattctcc ccgatcgatc ggtggttggc gttgaacggc tcggcgatga cccggctaaa    61380
atccggcatg aacagctgca acggatacac gggtatgcgg tgcacctccg ccccgcctat    61440
ggttaccttg tccgagcctc ccaggtgcag aaaggtgttg ttgatgcaca cggcctcctt    61500
gaagccctcg gtaacgacca gatacaggag ggcgcggtcc gggtccaggc cgaggcgctc    61560
acacagcgcc tccccgtcg tctcgtgttt gaggtcgccg gccggggg tgtagtccga    61620
aaagccaaaa tggcggcgtg cccgctcgca gagtcgcgtc aggtttgggg cctggtgct    61680
ggggtccagg tgccggccgc cgtgaaagac gtacacggac gagctgtagt gcgatggcgt    61740
cagtttcagg gacaccgcgg taccccgag ccccgtcgtg cgagaaccca cgaccacggc    61800
tacgttggcc tcaaagccgc tctccacggt caggcccacg accaggggcg ccacggcgac    61860
gtcggcatcg ccgctgcgcg ccgacagtaa cgccagaagc tcgatgcctt cggacggaca    61920
cgcgcgagcg tacacgtatc ccaggggccc gggggggacc ttgatggtgg ttgccgtctt    61980
gggctttgtc tccatgtcct cctggcaatc ggtccgcaaa cggaggtaat cccggcacga    62040
cgacggacgc ccgacgaggt atgtctcccg agcgtcaaaa tccgggggg ggcgcggcga    62100
cggtcaaggg gagggtggga gaccggggtt ggggaatgaa tccctaccct tcacagacaa    62160
cccccgggta accacgggt gccgatgaac cccggcggct ggcaacgcgg ggtccctgcg    62220
agaggcacag atgcttacgg tcaggtgctc cgggccgggt gcgtctgata tgcggttggt    62280
```

```
atatgtacac tttacctggg ggcgtgccgg accgccccag cccctcccac accccgcgcg    62340
tcatcagccg gtgggcgtgg ccgctattat aaaaaaagtg agaacgcgaa gcgttcgcac    62400
tttgtcctaa taatatatat attattagga caaagtgcga acgcttcgcg ttctcacttt    62460
ttttataata gcggccacgc ccaccggcta cgtcacgctc ctgtcggccg ccggcggtcc    62520
ataagcccgg ccggccgggc cgacgcgaat aaaccgggcc gccggccggg gcgccgcgca    62580
gcagctcgcc gcccggatcc gccagacaaa caaggccctt gcacatgccg gcccgggcga    62640
gcctgggggt ccggtaattt tgccatccca cccaagcggc ttttggggtt tttcctcttc    62700 cccccctcccc acatccccccc tctttagggg ttcgggtggg aacaaccgcg atgttttccg    62760
gtggcggcgg cccgctgtcc cccggaggaa agtcggcggc cagggcggcg tccgggtttt    62820
ttgcgcccgc cggccctcgc ggagccggcc ggggaccccc gccttgtttg aggcaaaact    62880
tttacaaccc ctacctcgcc ccagtcggga cgcaacagaa gccgaccggg ccaacccagc    62940
gccatacgta ctatagcgaa tgcgatgaat ttcgattcat cgccccgcgg gtgctggacg    63000
aggatgcccc cccggagaag cgcgccgggg tgcacgacgg tcacctcaag cgcgccccca    63060
aggtgtactg cggggggggac gagcgcgacg tcctccgcgt cgggtcgggc ggcttctggc    63120
cgcggcgctc gcgcctgtgg ggcggcgtgg accacgcccc ggcggggttc aaccccaccg    63180
tcaccgtctt tcacgtgtac gacatcctgg agaacgtgga gcacgcgtac ggcatgcgcg    63240
cggcccagtt ccacgcgcgg tttatggacg ccatcacacc gacggggacc gtcatcacgc    63300
tcctgggcct gactccggaa ggccaccggg tggccgttca cgtttacggc acgcggcagt    63360
acttttacat gaacaaggag gaggttgaca ggcacctaca atgccgcgcc ccacgagatc    63420
tctgcgagcg catggccgcg gccctgcgcg agtccccggg cgcgtcgttc cgcggcatct    63480
ccgcggacca cttcgaggcg gaggtggtgg agcgcaccga cgtgtactac tacgagacgc    63540
gccccgctct gttttaccgc gtctacgtcc gaagcgggcg cgtgctgtcg tacctgtgcg    63600
acaacttctg cccggccatc aagaagtacg agggtggggt cgacgccacc acccggttca    63660
tcctggacaa ccccgggttc gtcaccttcg gctggtaccg tctcaaaccg ggccggaaca    63720
acacgctagc ccagccgcgg gccccgatgg ccttcgggac atccagcgac gtcgagttta    63780
actgtacggc ggacaacctg gccatcgagg ggggcatgag cgacctaccg gcatacaagc    63840
tcatgtgctt cgatatcgaa tgcaaggcgg gggggggagga cgagctggcc tttccggtgg    63900
ccgggcaccc ggaggacctg gttattcaga tatcctgtct gctctacgac ctgtccacca    63960
ccgccctgga gcacgtcctc ctgttttcgc tcggttcctg cgacctcccc gaatcccacc    64020
tgaacgagct ggcggccagg ggcctgccca cgcccgtggt tctggaattc gacagcgaat    64080
tcgagatgct gttggccttc atgacccttg tgaaacagta cggccccgag ttcgtgaccg    64140
ggtacaacat catcaacttc gactggccct tcttgctggc caagctgacg gacatttaca    64200
aggtccccct ggacgggtac ggccgcatga acgccggggg cgtgtttcgc gtgtgggaca    64260
taggccagag ccacttccag aagcgcagca agataaaggt gaacggcatg gtgaacatcg    64320
acatgtacgg gatcataacc gacaagatca agctctcgag ctacaagctc aacgccgtgg    64380
ccgaagccgt cctgaaggac aagaagaagg acctgagcta tcgcgacatc cccgcctact    64440
acgccaccgg gcccgcgcaa cgcggggtga tcggcgagta ctgcatacag gattccctgc    64500
tggtgggcca gctgtttttt aagttttttgc cccatctgga gctctcggcc gtcgcgcgct    64560
tggcgggtat taacatcacc cgcaccatct acgacggcca gcagatccgc gtctttacgt    64620
gcctgctgcg cctggccgac cagaagggct ttattctgcc ggacacccag gggcgattta    64680
```

```
ggggcgccgg gggggaggcg cccaagcgtc cggccgcagc ccgggaggac gaggagcggc    64740
cagaggagga gggggaggac gaggacgaac gcgaggaggg cggggggcgag cgggagccgg    64800 agggcgcgcg ggagaccgcc ggccggcacg tggggtacca gggggccagg gtccttgacc    64860
ccacttccgg gtttcacgtg aaccccgtgg tggtgttcga ctttgccagc ctgtacccca    64920
gcatcatcca ggcccacaac ctgtgcttca gcacgctctc cctgagggcc gacgcagtgg    64980
cgcacctgga ggcgggcaag gactacctgg agatcgaggt gggggggcga cggctgttct    65040
tcgtcaaggc tcacgtgcga gagagcctcc tcagcatcct cctgcgggac tggctcgcca    65100
tgcgaaagca gatccgctcg cggattcccc agagcagccc cgaggaggcc gtgctcctgg    65160
acaagcagca ggccgccatc aaggtcgtgt gtaactcggt gtacgggttc acgggagtgc    65220
agcacggact cctgccgtgc ctgcacgttg ccgcgacggt gacgaccatc ggccgcgaga    65280
tgctgctcgc gacccgcgag tacgtccacg cgcgctgggc ggccttcgaa cagctcctgg    65340
ccgatttccc ggaggcggcc gacatgcgcg ccccgggcc ctattccatg cgcatcatct    65400
acggggacac ggactccata tttgtgctgt gccgcggcct cacggccgcc gggctgacgg    65460
ccatgggcga caagatggcg agccacatct cgcgcgcgct gtttctgccc cccatcaaac    65520
tcgagtgcga aaagacgttc accaagctgc tgctgatcgc caagaaaaag tacatcggcg    65580
tcatctacgg gggtaagatg ctcatcaagg gcgtggatct ggtgcgcaaa acaactgcg    65640 cgtttatcaa ccgcacctcc agggccctgg tcgacctgct gttttacgac gataccgtat    65700
ccggagcggc cgccgcgtta gccgagcgcc ccgcagagga gtggctggcg cgaccccctgc    65760 ccgagggact gcaggcgttc ggggccgtcc tcgtagacgc ccatcggcgc atcaccgacc    65820
cggagaggga catccaggac tttgtcctca ccgccgaact gagcagacac ccgcgcgcgt    65880
acaccaacaa gcgcctggcc cacctgacgg tgtattacaa gctcatggcc cgccgcgcgc    65940
aggtcccgtc catcaaggac cggatcccgt acgtgatcgt ggcccagacc cgcgaggtag    66000
aggagacggt cgcgcggctg gccgcccccc gcgagctaga cgccgccgcc ccaggggacg    66060
agcccgcccc cccccgcggcc ctgccctccc cggccaagcg cccccgggag acgccgtcgc    66120
atgccgaccc ccgggaggc gcgtccaagc cccgcaagct gctggtgtcc gagctggccg    66180
aggatcccgc atacgccatt gcccacggcg tcgccctgaa cacggactat tacttctccc    66240
acctgttggg ggcggcgtgc gtgacattca aggccctgtt tgggaataac gccaagatca    66300
ccgagagtct gttaaaaagg tttattcccg aagtgtggca cccccccggac gacgtggccg    66360 cgcggctccg ggccgcaggg ttcggggcgg tgggtgccgg cgctacggcg gaggaaactc    66420
gtcgaatgtt gcatagagcc tttgatactc tagcatgagc cccccgtcga agctgatgtc    66480
cctcatttta caataaatgt ctgcggccga cacggtcgga atctccgcgt ccgtgggttt    66540
ctctgcgttg cgccggacca cgagcacaaa cgtgctctgc cacacgtggg cgacgaaccg    66600 gtacccggg cacgcggtga gcatccggtc tatgagccgg tagtgcaggt gggcggacgt    66660
gccgggaaag atgacgtaca gcatgtggcc cccgtaagtg gggtccgggt aaaacaacag    66720
ccgcgggtcg cacgccccgc ctccgcgcag gatcgtgtgg acgaaaaaaa gctcgggttg    66780
gccaagaatc ccgccaaga ggtcctggag gggggcgttg tggcggtcgg ccaacacgac    66840
caaggaggcc aggaaggcgc gatgctcgaa tatcgtgttg atctgctgca cgaaggccag    66900
gattagggcc tcgcggctgg tggcggcgaa ccgcccgtct cccgcgttgc acgcgggaca    66960
gcaacccccg atgcctaggt agtagcccat cccggagagg gtcaggcagt tgtcggccac    67020
```

```
ggtctggtcc agacagaagg gcagcgacac gggagtggtc ttcaccaggg gcaccgagaa    67080
cgagcgcacg atggcgatct cctcggaggg cgtctgggcg agggcggcga aaaggccccg    67140
atagcgctgg cgctcgtgta aacacagctc ctgtttgcgg gcgtgaggcg gcaggctctt    67200 ccggggaggcc cgacgcacca cgcccagagt cccgccggcc gcagaggagc acgaccgccg    67260
gcgctccttg ccgtgatagg gcccgggccg ggagccgcgg cgatgggggt cggtatcata    67320
cataggtaca cagggtgtgc tccagggaca ggagcgagat cgagtggcgt ctaagcagcg    67380
cgcccgcctc acggacaaat gtggcgagcg cggtgggctt tggtacaaat acctgatacg    67440
tcttgaaggt gtagatgagg gcacgcaacg ctatgcagac acgcccctcg aactcgttcc    67500
cgcaggccag cttggccttg tggagcagca gctcgtcggg atgggtggcg gggggatggc    67560
cgaacagaac ccaggggtca acctccatct ccgtgatggc gcacatgggg tcacagaaca    67620
tgtgcttaaa gatggcctcg ggccccgcgg cccgcagcag gctcacaaac cggcccccgt    67680
ccccgggctg cgtctcgggg tccgcctcga gctggtcgac gacgggtacg atacagtcga    67740
agaggctcgt gttgttttcc gagtagcgga ccacggaggc ccggagtctg cgcagggcca    67800
gccagtaagc ccgcaccagt aacaggttac acagcaggca ttctccgccg gtgcgcccgc    67860
gcccccggcc gtgtttcagc acggtggcca tcagagggcc caggtcgagg tcgggctggg    67920
catcgggttc ggtaaactgc gcaaagcgcg gagccacgtc gcgcgtgcgt gccccgcgat    67980
gcgcttccca ggactggcgg accgtggcgc gacgggcctc cgcggcagcg cgcagctggg    68040
gccccgactc ccagacggcg ggggtgccgg cgaggagcag caggaccaga tccgcgtacg    68100
cccacgtatc cggcgactcc tccggctcgc ggtccccggc gaccgtctcg aattccccgt    68160
tgcgagcggc ggcgcgcgta cagcagctgt ccccgccccc gcgccgaccc tccgtgcagt    68220
ccaggagacg ggcgcaatcc ttccagttca tcagcgcggt ggtgagcgac ggctgcgtgc    68280
cggatcccgc cgccgacccc gccccctcct cgcccccgga ggccaaggtt ccgatgaggg    68340
cccgggtggc agactgcgcc aggaacgagt agttggagta ctgcacctttg gcggctcccg    68400 gggagggcga gggcttgggt tgcttctggg catgccgccc gggcaccccg ccgtcggtac    68460
ggaagcagca gtggagaaaa aagtgccggt ggatgtcgtt tatggtgagg gcaaagcgtg    68520
cgaaggagcc gaccagggtc gccttcttgg tgcgcagaaa gtggcggtcc atgacgtaca    68580
caaactcgaa cgcggccacg aagatgctag cggcgcagtg gggcgccccc aggcatttgg    68640
cacagagaaa cgcgtaatcg gccacccact ggggcgagag gcggtaggtt tgcttgtaca    68700
gctcgatggt gcggcagacc agacagggcc ggtccagcgc gaaggtgtcg atggccgccg    68760
cggaaaaggg cccggtgtcc aaaagcccct ccccacaggg atccgggggc gggttgcggg    68820
gtcctccgcg cccgcccgaa cccctccgt cgcccgcccc ccgcgggcc cttgaggggg    68880 cggtgaccac gtcggcggcg acgtcctcgt cgagcgtacc gacgggcggc acacctatca    68940
cgtgactggc cgccaggagc tcggcgcaga gagcctcgtt aagagccagg aggctgggat    69000
cgaaggccac atacgcgcgc tcgaacgccc ccgccttcca gctgctgccg ggggactctt    69060
cgcacaccgc gacgctcgcc aggaccccgg ggggcgaagt tgccatggct gggcgggagg    69120
ggcgcacgcg ccagcgaact ttacgggaca caatccccga ctgcgcgctg cggtcccaga    69180
ccctggagag tctagacgcg cgctacgtct cgcgagacgg cgcgcatgac gcggccgtct    69240
ggttcgagga tatgaccccc gccgagctgg aggttgtctt cccgactacg gacgccaagc    69300
tgaactacct gtcgcggacg cagcggctgg cctccctcct gacgtacgcc gggcctataa    69360
aagcgcccga cgacgccgcc gccccgcaga cccccggaca cgcgcgtgtgtg cacggcgagc    69420
```

-continued

```
tgctcgcccg caagcgggaa agattcgcgg cggtcattaa ccggttcctg gacctgcacc    69480
agattctgcg gggctgacgc gcgcgctgtt gggcgggacg gttcgcgaac cctttggtgg    69540
gtttacgcgg gcacgcacgc tcccatcgcg ggcgccatgg cgggactggg caagccctac    69600
cccggccacc caggtgacgc cttcgagggt ctcgttcagc gaattcggct tatcgtccca    69660
tctacgttgc ggggcgggga cggggaggcg ggcccctact ctccctccag cctcccctcc    69720
aggtgcgcct ttcagtttca tggccatgac gggtccgacg agtcgtttcc catcgagtat    69780
gtactgcggc ttatgaacga ctgggccgag gtcccgtgca acccttacct gcgcatacag    69840
aacaccggcg tgtcggtgct gtttcagggg ttttttcatc gcccacacaa cgcccccggg    69900
ggcgcgatta cgccagagcg gaccaatgtg atcctgggct ccaccgagac gacggggctg    69960
tccctcggcg acctggacac catcaagggg cggctcggcc tggatgcccg gccgatgatg    70020
gccagcatgt ggatcagctg ctttgtgcgc atgcccgcg tgcagctcgc gtttcggttc     70080
atgggccccg aagatgccgg acggacgaga cggatcctgt gccgcgccgc cgagcaggct    70140
attacccgtc gccgccgaac ccggcggtcc cgggaggcgt acggggccga ggccgggctg    70200
ggggtggctg gaacgggttt ccgggccagg ggggacggtt ttggcccgct ccccttgtta    70260
acccaagggc cctcccgccc gtggcaccag gccctgcggg gtcttaagca cctacggatt    70320
ggccccccg cgctcgtttt ggcggcggga ctcgtcctgg gggccgctat ttggtgggtg     70380
gttggtgctg gcgcgcgcct ataaaaaagg acgcaccgcc gccctaatcg ccagtgcgtt    70440
ccggacgcct tcgccccaca cagccctccc gtccgacacc cccatatcgc ttcccgacct    70500
ccggtcccga tggccgtccc gcaatttcac cgccccagca ccgttaccac cgatagcgtc    70560
cgggcgcttg gcatgcgcgg gctcgtcttg gccaccaata actctcagtt tatcatggat    70620
aacaaccacc cgcacccca gggcacccaa ggggccgtgc gggagtttct ccgcggtcag    70680
gcggcggcgc tgacggacct tggtctggcc cacgcaaaca acacgtttac cccgcagcct    70740
atgttcgcgg gcgacgcccc ggccgcctgg ttgcggcccg cgtttggcct gcggcgcacc    70800
tattcaccgt ttgtcgttcg agaaccttcg acgcccggga ccccgtgagg cccggggagt    70860
tccttctggg gtgttttaat caataaaaga ccacaccaac gcacgagcct tgcgtttaat    70920
gtcgtgttta ttcaagggag tgggataggg ttcgacggtt cgaaacttaa cacacaaaat    70980
aatcgagcgc gtctagccca gtaacatgcg cacgtgatgt aggctggtca gcacggcgtc    71040
gctgtgatga agcagcgccc ggcgggtccg ctgtaactgc tgttgtaggc ggtaacaggc    71100
gcggatcagc accgccaggg cgctacgacc ggtgcgttgc acgtagcgtc gcgacagaac    71160
tgcgtttgcc gatacgggcg gggggccgaa ttgtaagcgc gtcacctctt gggagtcatc    71220
ggcggataac gcactgaatg gttcgttggt tatggggag tgtggttccc gagggagtgg     71280
gtcgagcgcc tcggcctcgg aatccgagag gaacaacgag gtggtgtcgg agtcttcgtc    71340
gtcagagaca tacagggtct gaagcagcga cacgggcggg ggggtagcgt caatgtgtag    71400
cgcgagggag gatgcccacg aagacacccc agacaaggag ctgcccgtgc gtggatttgt    71460
ggacgacgcg gaagccggga cggatgggcg gttttgcggt gccggaacc gaaccgccgg     71520
atactccccg ggtgctacat gcccgttttg gggctggggt tggggctggg gctgggggttg   71580
gggttgggc tggggttggg gctggggttg gggctgggt tggggttggg gttggggctg      71640
gggttgggt tggggctggg gctggggctg gggctggggc tggggctggg gctgggctg      71700
gggctggggc tggggctggg gctggggctg ggctggggt tggggctggg gttggggctg     71760
```

```
gggcgcggac aggcggttga cggtcaaatg cccccggggg cgcgcagatg tggtgggcgt    71820
ggccaccggc tgccgtgtag tggggcggcg ggaaaccggg cctccgggcg taacaccgcc    71880
ctccagcgtc aagtatgtgg ggggcgggcc tgacgtcggg ggcggggtga cgggttggac    71940
cgcgggaggc gggggagagg gacctgcggg agaggatgag gtcggctcgg ccgggttgcg    72000
gcctaaaaca ggggccgtgg ggtcggcggg gtcccagggt gaagggaggg attcccgcga    72060
ttcggacagc gacgcgacag cggggcgcgt aaggcgccgc tgcggcccgc ctacgggaac    72120
cctggggggg gttggcgcgg gacccgaggt tagcgggggg cggcggtttt cgcccccggg    72180
caaaaccgtg ccggttgcga ccggggggcg aacgggatcg ataggagag cgggagaagc    72240 ctggccggcg aactggggac cgagcgggag gggcacacca gacaccaaag cgtggagcgc    72300
tggctctggg ggtttgggag gggcggggg gcgcgcgaaa tcggtaaccg gggcgaccgt    72360
gtcggggagg gcaggcggcc gccaaccctg ggtggtcgcg gaagcctggg tggcgcgcgc    72420 caggagcgt gcccggcggt gtcggcgcgc gcgcgacccg gacgaagaag cggcagaagc    72480
gcgggaggag gcgggggggc gggggggcggt ggcatcgggg ggcgccgggg aactttgggg    72540
ggacggcaag cgccggaagt cgtcgcgggg gcccacgggc gccggccgcg tgctttcggc    72600
cgggacgccc ggtcgtgctt cgcgagccgt gactgccggc ccaggggcc gcggtgcaca    72660 ctggacgtg gggacggact gatcggcggt gggcgaaagg gggtccgggg caaggagggg    72720
cgcggggccg ccggagtcgt cagacgcgag ctcctccagg ccgtgaatcc atgcccacat    72780
gcgagggggg acgggctcgc cggggtggc gtcggtgaat agcgtggggg ccaggcttcc    72840 gggcccaac gagccctccg tcccaacaag gtccgccggg ccggggtcg ggttcgggac    72900 cgagggctc tggtcgtcgg gggcgcgctg gtacaccgga tgccccggga atagctcccc    72960
cgacaggagg gaggcgtcga acggccgccc gaggatagct cgcgcgagga aggggtcctc    73020
gtcggtggcg ctggcggcga ggacgtcctc gccgcccgcc acaaacggga gctcctcggt    73080
ggcctcgctg ccaacaaacc gcacgtcggg ggggccgggg gggtccgggt tttcccacaa    73140
caccgcgacc ggggtcatgg agatgtccac gagcaccaga cacggcgggc cccgggcgag    73200
gggccgctcg gcgatgagcg cggacaggcg cgggagctgt gccgcagac acgcgttttc    73260 aatcgggttc aggtcggcgt gcaggaggcg gacgcccac gtctcgatgt cggacgacac    73320
ggcatcgcgc aaggcggcgt ccggcccgcg agcgcgtgag tcaaacagcg tgagacacag    73380
ctccagctcc gactcgcggg aaaaggccgt ggtgttgcgg agcgccacga cgacgggcgc    73440
gcccaggagc actgccgcca gcaccaggtc catggccgta acgcgcgccg cggggtgcg    73500 gtgggtggcg gcggccggca cggcgacgtg ctggcccgtg ggccggtaga gggcgttggg    73560
gggagcgggg ggtgacgcct cgcgcccccc cgaggggctc agcgtctgcc cagattccag    73620
acgcgcggtc agaagggcgt cgaaactgtc atactctgtg tagtcgtccg gaaacatgca    73680
ggtccaaaga gcggccagag cggtgcttgg gagacacatg cgcccgagga cgctcaccgc    73740
cgccagcgcc tgggcgggac tcagctttcc cagcgcggcg ccgcgctcgg ttcccagctc    73800
ggggaccgag cgccagggcg ccaggggtc ggtttcggac aacttgccgc ggcgccagtc    73860
tgccagccgc gtgccgaaca tgaggccccg ggtcggaggg cctccggtcg aaaacactgg    73920
cagcacgcgg atgcgggcgt ctggatgcgg ggtcaggcgc tgcacgaata gcatggaatc    73980
tgctgcgttc tgaaacgcac gggggagggt gagatgcatg tactcgtgtt ggcggaccag    74040
atccaggcgc caaaaggtgt aaatgtgttc cgggagctg gccaccagcg ccaccagcac    74100
gtcgttctcg ttaaaggaaa cgcggtgcct agtggagctg tggggcccga gcggcggtcc    74160
```

```
cggggccgcc gcgtcacccc cccattccag ctgggcccag cgacacccaa actcgcgcgt    74220
gagagtggtc gcgacgaggg cgacgtagag ctcggccgcc gcatccatcg aggccccca    74280 tctcgcctgg cggtggcgca caaagcgtcc gaagagctga agttggcgg cctgggcgtc    74340 gctgagggcc agctgaagcc ggttgatgac ggtgatgacg tacatggccg tgacggtcga    74400
ggccgactcc agggtgtccg tcggaagcgg ggggcgaatg catgccgcct cgggacacat    74460
cagcagcgcg ccgagcttgt cggtcacggc cgggaagcag agcgcgtact gcagtggcgt    74520
tccatccggg accaaaaagc tggggggcgaa cggccgatcc agcgtactgg tggcctcgcg    74580
cagcaccagg ggcccgggc ctccgctcac tcgcaggtac gcctcgcccc ggcggcgcag    74640
catctgcggg tcggcctctt ggccgggtgg ggcggacgcc cgggcgcggg cgtctagggc    74700
gcgaagatcc acgagcaggg gcgcgggcgc ggcggccgcg cccgcgcccg tctggcctgt    74760
ggccttggcg tacgcgctat ataagcccat gcggcgttgg atgagctccc gcgcgccccg    74820
gaactcctcc accgcccatg gggccaggtc cccggccacc gcgtcgaatt ccgccaacag    74880
gccccccagg gtgtcaaagt tcatctccca ggccacccctt ggcaccacct cgtcccgcag    74940
ccgggcgctc aggtcggcgt gttgggccac gcgccccccg agctcctcca cggccccggc    75000
ccgctcggcg ctcttggcgc ccaggacgcc ctggtacttg gcgggaaggc gctcgtagtc    75060
ccgctgggct cgcagccccg acacagtgtt ggtggtgtcc tgcagggcgc gaagctgctc    75120
gcatgccgcg cgaaatccct cgggcgattt ccaggcccccc ccgcgaacgc ggccgaagcg    75180
accccatacc tcgtcccact ccgcctcggc ctcctcgaga gacctccgca gggcctcgac    75240
gcggcgacgg gtgtcgaaga gcgcctgcag gcgcgcgccc tgtcgcgtca ggaggcccgg    75300
gccgtcgccg ctggccgcgt ttagcgggtg cgtctcaaag gtacgctggg catgttccaa    75360
ccaggcgacc gcctgcacgt cgagctcgcg cgccttctcc gtctggtcca acagaatttc    75420
gacctgatcc gcgatctcct ccgccgagcg cgcctggtcc agcgtcttgg ccacggtcgc    75480
cgggacggcg accaccttca gcagggtctt cagattggcc agaccctcgg cctcgagctg    75540
ggcccggcgc tcgcgcgcgg ccagcacctc ccgcagcccc gccgtgaccc gctcggtggc    75600
ttcggcgcgc tgctgtttgg cgcgcaccac ggcgtccttg gtatcggcca ggtcctgtcg    75660
ggtcacgaat gcgacgtagt cggcgtacgc cgtgtccttc acgggctct ggtccacgcg    75720 ctccagcgcc gccacgcacg ccaccagcgc gtcctcgctc gggcagggca gggtgacccc    75780
tgcccggaca agctcggcgg ccgccgccgg gtcgttgcgc accgcggata tctcctccgc    75840
ggcggcggcc aggtccagcg ccacgcttcc gatcgcgcgc cgcgcgtcgg cccggagggc    75900
gtccaggcga tcgcggatat ccacgtactc ggcgtagccc ttttgaaaaa acggcacgta    75960
ctggcgcagg gccggcacgc ccccccaagtc ttccgacagg tgtaggacgg cctcgtggta    76020
gtcgataaac ccgtcgttcg cctgggcccg ctccagcagc cccccgccca gccgcagaag    76080
ccgcgccagg ggctcggtgt ccacccgaaa catgtcggcg tacgtgtcgg ccgcggcccc    76140
gaaggccgcg ctccagtcga tgcggtgaat ggctgcgagc gggggagca tggggtggcg    76200 ctggttctcg ggggtgtatg ggttaaacgc aagggccgtc tccagggcaa gggtcaccgc    76260
cttggcgttg gttcccagcg cctgttcggc ccgctttcgg aagtcccggg ggttgtagcc    76320
gtgcgtgccc gccagcgcct gcaggcgacg gagctcgacc acgtcaaact cggcaccgct    76380
ttccacgcgg tccagcacgg cctccacgtc ggcggcccag cgctcgtggc tactgcgggc    76440
gcgctgggcc gccatcttct ctctcaggtc ggcgatggcg gcctcaagtt cgtcggcgcg    76500
```

```
gcgtcgcgtg gcgccgatga cctttcccag ctcctgcagg gcgcgcccgc tgggggagtg   76560
gtccccggcc gtcccttcgg cgtgcaacag gcccccgaac ctgccctcgt ggcccgcgag   76620
gctttcccgc gcgccggtgg tcgcgcgcgt cgcggcctgg atcagggagg catgctctcc   76680
ctccggttgg ttggcggccc ggcgcacctg gacgacaagg tcggctgccg ccgaccctaa   76740
ggtcgtgagc tgggcgatgg ccccccgcgc gtccagggcc aaccgagtcg ccttgacgta   76800
tcccgcggcg ctgtcggcca tggccgctag gaaggccagg ggggaggccg ggtcgctggc   76860
ggccgcgccc agggccgtca ccgcgtcgac caggacgcgg tgcgcccgca cggccgcatc   76920
caccgtcgac gcggggtctg ccgtcgcgac ggcggcgctg ccggcgttga tggcgttcga   76980
gacggcgtgg gctatgatcg gggcgtgatc ggcgaagaac tgcaagagaa acggagtctc   77040
tggggcgtcg gcgaacaggt tcttcagcac caccacgaag ctgggatgca agccagacag   77100
agccgtcgcc gtgtccggag tcgggtgctc cagggcatct cggtactgcc ccagcagccc   77160
ccacatgtcc gcccgcagcg ccgccgtaac ctcagggggc gcccccgaa cggcctcggg    77220 gaggtccgac cagcccgccg gcaggaggcc ccgcagggtc gccaggacgg ccggacaggc   77280
ctttagcccc acaaagtcag ggaggggggcg caggaccccc tggagtttgt gcaagaactt   77340
ctcccgggcg tcgcgggcca ccttcgcccg ctcccgcgct ccctcgagca ttgcctccag   77400
ggagcgcgcg cgctcccgca aacgggcacg cgcatcgggg gcgagctctg ccgtcagctt   77460
ggcggcatcc atggcccgcg cctgccgcag cgcttcctcg gccatgcgcg tggcctctgg   77520
cgacagcccg ccgtcgtcgg ggtagggcga cgcgccgggc gcaggaacaa aggccgcgtc   77580
gctgtccagc tgctggccca gggccgcatc tagggcgtcg aagcgccgca gctcggccag   77640
acccgagctg cggcgcgcct gctggtcgtt aatgtcgcgg atgctgcgcg ccagctcgtc   77700
cagcggcttg cgttctatca gcccttggtt ggcggcgtcc gtcaggacgg agagccaggc   77760
cgccaggtcc tcggggggcgt ccagcgtctg gccccgctgg atcagatccc gcaacaggat   77820
ggccgtgggg ctggtcgcga tcgggggcgg ggcgggaatg gcggcgcgct gcgcgatgtc   77880
ccgcgtgtgc tggtcgaaga caggcaggga ctcgagcagc tggaccacgg gcacgacggc   77940
ggccgaagcc acgtgaaacc ggcggtcgtt gttgtcgctg gcctgtagag ccttggcgct   78000
gtatacggcc ccccggtaaa agtactcctt aaccgcgccc tcgatcgccc gacgggcctg   78060
ggtccgcacc tcctccagcc gaacctgaac ggctcgggg cccagggggg gtgggcgcgg    78120 agcccctgc ggggccgccc cggccggggc gggcattacg ccgaggggcc cggcgtgctg    78180
tgagaccgcg tcgaccccgc gagcgagggc gtcgagggcc tcgcgcatct ggcgatcctc   78240
cgcctccacc ctaatctctt cgccacgggc aaatttggcc agagcctgga ctctatacag   78300
aagcggttct gggtgcgtcg gggtggcggg ggcaaaaagg gtgtccgggt gggcctgcga   78360
gcgctccaga agccactcgc cgaggcgtgt atacagattg gccggcgggg ccgcgcgaag   78420
ctgcagctcc aggtccgcga gttccccgta aaaggcgtcc gtctcccgaa tgacatccct   78480
agccacaagg atcagcttcg ccagcgccag gcgaccgatc agagagttttt cgtccagcac   78540 gtgctggacg aggggcagat gggcggccac gtcggccagg ctcaggcgcg tggaggccag   78600
aaagtccccc acgccgtttt tccggggcag catgctcagg gtaaactcca gcagggcggc   78660
ggccgggccg gccaccccgg cctgggtgtg cgtccgggcc ccgttctcga tgagaaaggc   78720
gaggacgcgt tcaaagaaaa aaataacaca gagctccagc agccccggag aagccggata   78780
cggcgaccgt aagcgctga tggtgagccg cgaacacgcg gcgacctcgc gggccagggt   78840
ggcggagcac gcggtgaact taaccgccgt ggcggccacg tttgggtggg cctcgaacag   78900
```

```
ctgggcgagg tctgcgcccg ggggctcggg tgagcggcga gtcttcagcg cctcgagggc    78960
ctgtgaggac gccggaacca tgggcccgtc gtcctcgccc gcctcggcga ccggcggccc    79020
ggccgggtcg gggggtgccg aggcgaggac aggctccgga acggaggcgg ggaccgcggc    79080
cccgacgggg gttttgcctt tggggtgga tttcttcttg gttttggcag ggggggccga    79140
gcgtttcgtt ttctcccccg aagtcaggtc ttcgacgctg gaaggcggag tccaggtggg    79200
tcggcggcgc ttgggaaggc cggccgagta gcgtgcccgg tgccgaccaa ccgggacgac    79260
gcccatctcc aggacccgca tgtcgtcgtc atcttcttcg gccgcctctg cggcggggt     79320
cttgggggcg gagggaggcg gtggtgggat cgcggagggt gggtcggcgg agggggatc     79380
cgtgggtggg gtacccttta gggccaccgc ccatacatcg tcgggcgccc gattcgggcg    79440
cttgccctct ggttttgccg acggaccggc cgtcccccgg gatgtctcgg aggccctgtc    79500
gtcgcgacgg gcccgggtcg gtggcggcga ctgggcggct gtgggcgggt gtggcccgg     79560
cccccctccc ccctcccggg ggccacgcc gacgcagggc tccccaggc ccgcgatctc      79620
gccccgcagg gggtgcgtga tggccacgcg ccgttcgctg aacgcttcgt cctgcatgta    79680
agtctcgctg gccccgtaaa gatgcagagc cgcggccgtc aagtccgcag agccgcggg     79740
ttccgggccc gacggcacga aaaacaccat ggctcccgcc caccgtacgt ccgggcgatc    79800
gcgggtgtaa tacgtcaggt atggatacat gtccccgcc cgcactttgg cgatgaacgc     79860
ggggggtgccc tccggaaggc catgcgggtc aaaaaggtat gcggtgtcgc cgtccctgaa    79920
cagccccatc cctaggggc caatggttag gagcgtgtac gacaggggc gcagggccca      79980
cgggccggcg aagaacgtgt gtgcggggca ttgtgtctcc agcaggcctg ccgcgggctc    80040
cccgaagaag cccacctcgc cgtatacgcg cgagaagaca cagcgcagtc cgccgcgcgc    80100
ccctgggtac tcgaggaagt tggggagctc gacgatcgaa cacatgcgcg gcggcccagg    80160
gcccgcagtc gcgcgcgtcc actcgccccc ctcgaccaaa catccctcga tggcctccgc    80220
ggacagaacg tcgcgagggc ccacatcaaa tatgaggctg agaaaggaca gcgacgagcg    80280
catgcacgat accgaccccc ccggctccag gtcgggcgcg aactggttcc gagcaccggt    80340
gaccacgatg tcgcgatccc ccccgcgttc catcgtggag tgcggtgggg tgcccgcgat    80400
catatgtgcc ctgcgggcca gagacccggc ctgtttatgg accggacccc cggggttagt    80460
gttgtttccg ccacccacgc ccccgtacca tggcccccggt tcccctgatt aggctacgag    80520
tcgcggtgat cgcttcccaa aaaccgagct gcgtttgtct gtcttggtct tcccccccc     80580
cagcccgcac accataacac cgagaacaac acacgggggg gggcggaaca taataaagct    80640
ttattggtaa ctagttaacg gcaagtccgt gggtggcgcg acggtgtcct ccgggatcat    80700
ctcgtcgtcc tcgacggggg tgttggaatg aggcgcctcc tcgcggtcca cctggcgtgg    80760
gccgtgccca taggcctccg gcttctgtgc gtccatgggc gtaggcgcgg ggagactgtt    80820
tccggcgtcg cggacctcca ggtccctggg agcctccggt ccggctaacg gacgaaacgc    80880
ggaagcgcga aacacgccgt cggtgacccg caggagctcg ttcatcagta accaatccat    80940
actcagcgta acggccagcc cctggcgaga cagatccacg gagtccggaa ccgcggtcgt    81000
ctggcccagg gggccgaggc tgtagtcccc ccaggcccct aggtcgcgac ggctcgtaag    81060
cacgacgcgg tcggccgcgg ggctttgcgg ggggcgtcc tcgggcgcat gcgccattac     81120
ctctcggatg gccgcggcgc gctggtcggc cgagctgacc aagggcgcca cgaccacggc    81180
gcgctccgtc tgcaggccct tccacgtgtc gtggagttcc tggacaaact cggccacggg    81240
```

```
ctcgggtccc gcggccgcgc gcgcggcttg atagcaggcc gacagacgcc gccagcgcgc    81300
tagaaactga cccatgaaac aaaacccggg gacctggtct cccgacagca gcttcgacgc    81360
ccgggcgtga atgccggaca cgacggacag aaacccgtga atttcgcgcc ggaccacggc    81420
cagcacgttg tcctcgtgcg acacctgggc cgccagctcg tcgcacaccc ccaggtgcgc    81480
cgtggtttcg gtgatgacgg aacgcaggct cgcgagggac gcgaccagcg cgcgcttggc    81540
gtcgtgatac atgctgctgt actgactcac cgcgtccccc atggcctcgg ggggccaggg    81600
ccccaggcgg tcgggcgtgt ccccgaccac cgcatacagg cggcgcccgt cgctctcgaa    81660
ccgacactcg aaaaaggcgg agagcgtgcg catgtgcagc cgcagcagca cgatggcgtc    81720
ctccagttgg cgaatcaggg ggtcggcgcg ctcggcgagg tcctgcagca cccccccggc    81780 agccaggggcg tacatgctaa tcaacaggag gctggtgccc acctcgggggg gcggggggggg    81840 ctgcagttgg accaggggcc gcagctgctc gacggcaccc ctggagatca cgtacagctc    81900
ccggagcagc tgctctatgt tgtcggccat ctgcatagtg gggccgaggc cgccccgggc    81960
ggccggttcg aggagagtga tcagcgcgcc cagtttggtg cgatggccct cgaccgtggg    82020
gagatagccc agcccaaagt cccgggccca ggccaacaca cgcagggcga actcgaccgg    82080
gcggggaagg taggccgcgc tacacgtggc cctcagcgcg tccccaacca ccagggccag    82140
aacgtagggg acgaagcccg ggtcggcgag gacgttgggg tgaatgccct cgagggcggg    82200
gaagcggatc tgggtcgccg cggccaggtg gacagagggg gcatggctgg gctgcccgac    82260
ggggagaagc gcggacagcg gcgtggccgg ggtggtgggg gtgatgtccc agtgggtctg    82320
accatacacg tcgatccaga tgagcgccgt ctcgcggaga aggctgggtt gaccggaact    82380
aaagcggcgc tcggccgtct caaactcccc cacgagcgcc cgccgcaggc tcgccagatg    82440
ttccgtcggc acgccggcc ccatgatacg cgccagcgtc tggctcagaa cgccccccga    82500
caggccgacc gcctcacaga gccgcccgtg cgtgtgctcg ctggcgccct ggacccgcct    82560
gaaagttttt acgtagttgg catagtaccc gtattcccgc gccagaccaa acacgttcga    82620
ccccgcgagg gcaatgcacc caaagagctg ctggacttcg ccgagtccgt ggccggcggg    82680
cgtccgcgcg gggacgcccg ccgccagaaa cccctccagg gccgaaaggt agtgcgtgca    82740
gtgcgagggc gtgaacccag cgtcgatcag ggtgttgatc accacggagg gcgaattggt    82800
attctggatc aacgtccacg tctgctgcag cagagccagc agccgctgct gggcgccggc    82860
ggagggctgc tccccgagct gcagcaggct ggagacggca ggctggaaga ctgccagtgc    82920
cgacgaactc aggaacggca cgtcgggatc aaacacggcc acgtccgtcc gcacgcgcgc    82980
cattagcgtc cccgggggcg cacaggccga gcgcgggctg acgcggctga gggccgtcga    83040
cacgcgcacc tcctcgcggc tgcgaaccat cttgttggcc tccagtggcg gaatcattat    83100
ggccgggtcg atctcccgca cggtgtgctg aaactgcgcc aacaggggcg gcgggaccac    83160
agccccccgc tcggggggtcg tcaggtactc gtccaccagg gccaacgtaa agagggcccg    83220
tgtgagggga gtgagggtcg cgtcgtctat gcgctggagg tgcgccgaga acagcgtcac    83280
ccgattactc accagggcca agaaccggag gccctcttgc acgaacgggg cggggaagag    83340
caggctgtac gccggggtgg taaggttcgc gctgggctgc cccaacggga ccggcgcgag    83400
cttgagcgac gtctccccaa gggcctcgat ggaggtccgc gggctcatgg ccaagcagct    83460
cttggtgacg gtttgccagc ggtctatcca ctccacggcg cactggcgga cgcggaccgg    83520 ccccaggggcc gccgcggtgc gcaggccggc ggactccagc gcatgggacg tgtcggagcc    83580
ggtgaccgcg aggatggtgt ccttgatgac ctccatctcc cggaaggcct ggtcggggggc    83640
```

```
ctcggggaga gccaccacca agcggtgtac gagcaacccg gggaggttct cggccaagag   83700
cgccgtctcc ggaagcccgt gggcccggtg gagcgcgcac aggtgttcca gcagcggccg   83760
ccagcatgcc cgcgcgtctg ccggggcgat ggccgttccc gacaacagaa acgccgccat   83820
ggcggcgcgc agcttggccg tggccagaaa cgccgggtcg tccgcccgt ttgccgtctc    83880
ggccgtgggg gttggcggtt ggcgaaggcc ggctaggctc gccaataggc gctgcatagg   83940
tccgtccgag ggcggaccgg cgggtgaggt cgtgacgacg ggggcctcgg acgggagacc   84000
gcggtctgcc atgacgcccg gctcgcgtgg gtggggaca gcgtagacca acgacgagac    84060
cgggcgggaa tgactgtcgt gcgctgtagg gagcggcgaa ttatcgatcc cccgcggccc   84120
tccaggaacc ccgcaggcgt tgcgagtacc ccgcgtcttc gcggggtgtt atacggccac   84180
ttaagtcccg gcatcccgtt cgcggaccca ggcccggggg attgtccgga tgtgcgggca   84240
gccccggacgg cgtgggttgc ggactttcgg cggggcggcc caaatggccc tttaaacgtg  84300
tgtatacgga cgcgccgggc cagtcggcca acacaaccca ccggaggcgg tagccgcgtt   84360
tggctgtggg gtgggtggtt ccgccttgcg tgagtgtcct ttcgaccccc ccctccccc    84420
gggtcttgct aggtcgcgat ctgtggtcgc aatgaagacc aatccgctac ccgcaacccc   84480
ttccgtgtgg ggcgggagta ccgtggaact cccccccacc acacgcgata ccgcggggca   84540
gggcctgctt cggcgcgtcc tgcgcccccc gatctctcgc cgcgacggcc cagtgctccc   84600
caggggggtcg ggaccccgga gggcggccag cacgctgtgg ttgcttggcc tggacggcac  84660
agacgcgccc cctggggcgc tgaccccccaa cgacgatacc gaacaggccc tggacaagat  84720
cctgcggggc accatgcgcg ggggggcggc cctgatcggc tccccgcgcc atcatctaac   84780
ccgccaagtg atcctgacgg atctgtgcca acccaacgcg gatcgtgccg ggacgctgct   84840
tctggcgctg cggcaccccg ccgacctgcc tcacctggcc caccagcgcg ccccgccagg   84900
ccggcagacc gagcggctgg gcgaggcctg gggccagctg atggaggcga ccgccctggg   84960
gtcggggcga gccgagagcg ggtgcacgcg cgcgggcctc gtgtcgttta acttcctggt   85020
ggcggcgtgt gccgcctcgt acgacgcgcg cgacgccgcc gatgcggtac gggcccacgt   85080
cacggccaac taccgcggga cgcgggtggg ggcgcgcctg gatcgttttt ccgagtgtct   85140
gcgcgccatg gttcacacgc acgtcttccc ccacgaggtc atgcggtttt tcggggggct   85200
ggtgtcgtgg gtcacccagg acgagctagc gagcgtcacc gccgtgtgcg ccgggcccca   85260
ggaggcggcg cacaccggcc acccgggccg gccccgctcg gccgtgatcc tcccggcgtg   85320
tgcgttcgtg gacctggacg ccgagctggg gctgggggc ccgggcgcgg cgtttctgta    85380
cctggtattc acttaccgcc agcgccggga ccaggagctg tgttgtgtgt acgtgatcaa   85440
gagccagctc ccccgcgcg ggttggagcc ggccctggag cggctgtttg ggcgcctccg    85500
gatcaccaac acgattcacg gcaccgagga catgacgccc ccggccccaa accgaaaccc   85560
cgacttcccc ctcgcgggcc tggccgccaa tccccaaacc ccgcgttgct ctgctggcca   85620
ggtcacgaac ccccagttcg ccgacaggct gtaccgctgg cagccggacc tgcggggggcg  85680
ccccaccgca cgcacctgta cgtacgccgc cttttgcagag ctcggcatga tgcccgagga  85740
tagtccccgc tgcctgcacc gcaccgagcg cttttggggcg gtcagcgtcc ccgttgtcat  85800
cctggaaggc gtggtgtggc ccccggcga gtggcgggcc tgcgcgtgag cgtagcaaac    85860
gccccgccca cacaacgctc cgcccccaac cccttcccccg ctgtcactcg ttgttcgttg  85920
acccggacgt ccgccaaata aagccactga aaccgaaac gcgagtgttg taacgtcctt    85980
```

```
tgggcgggag gaagccacaa aatgcaaatg ggatacatgg aaggaacaca ccccgtgac    86040 tcaggacatc ggcgtgtcct tttgggtttc actgaaactg gcccgcgccc cacccctgcg    86100
cgatgtggat aaaaagccag cgcgggtggt ttagggtacc acaggtgggt gctttggaaa    86160
cttgtcggtc gccgtgctcc tgtgagcttg cgtccctccc cggtttcctt tgcgctcccg    86220
ccttccggac ctgctctcgc ctatcttctt tggctctcgg tgcgattcgt caggcagtgg    86280
ccttgtcgaa tctcgacccc accactcgcc ggacccgccg acgtcccctc tcgagcccgc    86340
cgaaacccgc cgcgtctgtt gaaatggcca gccgccccgc cgcatcctct cccgtcgaag    86400
cgcgggcccc ggttggggga caggaggccg cggccccag cgcagccacc caggggagg     86460 ccgccggggc ccctctcgcc cgcggccacc acgtgtactg ccagcgagtc aatggcgtga    86520
tggtgctttc cgacaagacg cccgggtccg cgtcctaccg catcagcgat agcaactttg    86580
tccaatgtgg ttccaactgc accatgatca tagacggaga cgtggtgcgc gggcgccccc    86640
aggacccggg ggccgcggca tccccgctc ccttcgttgc ggtgacaaac atcggagccg     86700
gcagcgacgg cgggaccgcc gtcgtggcat tcggggaaac cccacgtcgc tcggcgggga    86760
cgtctaccgg tacccagacg accgacgtcc ccaccgaggc ccttgggggc ccccctcctc    86820
ctccccgctt cacctgggt ggcggctgtt gttcctgtcg cgacacacgg cgccgctctg     86880
cggtattcgg gggggaggggg gatcccgtcg gccccgcgga gttcgtctcg gacgaccggt    86940
cgtccgattc cgactcggat gactcggagg acaccgactc ggagacgctg tcacacgcct    87000
cctcggacgt gtccggcggg gccacgtacg acgacgccct tgactccgat tcgtcatcgg    87060
atgactccct gcagatagat ggcccccgtgt gtcgcccgtg gagcaatgac accgcgcccc    87120
tggatgtttg ccccgggacc cccggcccgg gcgccgacgc cggtggtccc tcagcggtag    87180
acccacacgc accgacgcca ggggccggcg ctggtcttgc ggccgatccc gccgtggccc    87240
gggacgacgc ggaggggctt tcggacccc ggccacgtct gggaacgggc acggcctacc      87300 ccgtcccct ggaactcacg cccgagaacg cggaggccgt ggcgcgcttt ctgggagatg     87360
ccgtgaaccg cgaacccgcg ctcatgctgg agtacttttg ccggtgcgcc cgcgaggaaa    87420
ccaagcgtgt ccccccagg acattctgca gccccctcg cctcacggag gacgactttg      87480
ggcttctcaa ctacgcgctc gtggagatgc agcgcctgtg tctggacgtt cctccggtcc    87540
tgccgaacgc atacatgccc tattatctca gggagtatgt gacgcggctg gtcaacgggt    87600
tcaagccgct ggtgagccgg tccgctcgcc tttaccgcat cctgggggtt ctggtgcacc    87660
tgcggatccg gacccgggag gcctccttg aggagtggct gcgatccaag gaagtggccc      87720
tggactttgg cctgacggaa aggcttcgcg agcacgaagc ccagctggtg atcctggccc    87780
aggctctgga ccattacgac tgtctgatcc acagcacacc gcacacgctg tcgagcggg     87840 ggctgcaatc ggccctgaag tatgaggagt tttacctaaa gcgctttggc gggcactaca    87900
tggagtccgt cttccagatg tacacccgca tcgccggctt tttggcctgc gggccacgc     87960 gcggcatgcg ccacatcgcc ctgggggcgag aggggtcgtg gtgggaaatg ttcaagttct    88020
ttttccaccg cctctacgac caccagatcg taccgtcgac ccccgccatg ctgaacctgg    88080
ggacccgcaa ctactacacc tccagctgct acctggtaaa ccccaggcc accacaaaca     88140 aggcgaccct gcgggccatc accagcaacg tcagcgccat cctcgcccgc aacggggca     88200 tcgggctatg cgtgcaggcg tttaacgact ccggccccgg gaccgctagc gtcatacccg    88260
ccctcaaggt cctcgactcg ctggtggcgg cgcacaacaa agagagcgcg cgtccaaccg    88320
gcgcgtgcgt gtacctggag ccgtggcaca ccgacgtgcg ggccgtgctc cggatgaagg    88380
```

```
gggtcctcgc cggcgaagag gcccagcgct gcgacaatat cttcagcgcc ctctggatgc    88440
cagacctgtt tttcaagcgc ctgattcgcc acctggacgg cgagaagaac gtcacatgga    88500
ccctgttcga ccgggacacc agcatgtcgc tcgccgactt tcacggggag gagttcgaga    88560
agctctacca gcacctcgag gtcatggggt tcggcgagca gatacccatc caggagctgg    88620
cctatggcat tgtgcgcagt gcggccacga ccgggagccc cttcgtcatg ttcaaagacg    88680
cggtgaaccg ccactacatc tacgacaccc aggggcggc catcgccggc tccaacctct    88740
gcaccgagat cgtccatccg gcctccaagc gatccagtgg ggtctgcaat ctgggaagcg    88800
tgaatctggc ccgatgcgtc tccaggcaga cgtttgactt tgggcggctc cgcgacgccg    88860
tgcaggcgtg cgtgctgatg gtgaacatca tgatcgacag cacgctacaa cccacgcccc    88920
agtgcacccg cggcaacgac aacctgcggt ccatgggaat cggcatgcag ggcctgcaca    88980
cggcctgcct gaagctgggg ctggatctgg agtctgtcga atttcaggac ctgaacaaac    89040
acatcgccga ggtgatgctg ctgtcggcga tgaagaccag caacgcgctg tgcgttcgcg    89100
gggcccgtcc cttcaaccac tttaagcgca gcatgtatcg cgccggccgc tttcactggg    89160 agcgcttttcc ggacgcccgg ccgcggtacg agggcgagtg ggagatgcta cgccagagca    89220
tgatgaaaca cggcctgcgc aacagccagt ttgtcgcgct gatgcccacc gccgcctcgg    89280
cgcagatctc ggacgtcagc gagggctttg cccccctgtt caccaacctg ttcagcaagg    89340
tgacccggga cggcgagacg ctgcgcccca acacgctcct gctaaaggaa ctggaacgca    89400
cgtttagcgg gaagcgcctc ctggaggtga tggacagtct cgacgccaag cagtggtccg    89460
tggcgcaggc gctcccgtgc ctggagccca cccaccccct ccggcgattc aagaccgcgt    89520
ttgactacga ccagaagttg ctgatcgacc tgtgtgcgga ccgcgccccc tacgtcgacc    89580
atagccaatc catgaccctg tatgtcacgg agaaggcgga cgggaccctc ccagcctcca    89640
ccctggtccg ccttctggtc cacgcatata agcgcggact aaaaacaggg atgtactact    89700
gcaaggttcg caaggcgacc aacagcgggg tctttggcgg cgacgacaac attgtctgca    89760
cgagctgcgc gctgtgaccg acaaacccc tccgcgccag gcccgccgcc actgtcgtcg    89820
ccgtcccacg cgctccccg ctgccatgga ttccgcggcc ccagccctct cccccgctct    89880
gacggcccat acgggccaga gcgcgccggc ggacctggcg atccagattc caaagtgccc    89940 cgacccgag aggtacttct acacctccca gtgtcccgac attaaccacc tgcgctccct    90000
cagcatcctt aaccgctggc tggaaaccga gcttgttttc gtggggacg aggaggacgt    90060 ctccaagctt tccgagggcg agctcagctt ttaccgcttc ctcttcgctt tcctgtcggc    90120
cgccgacgac ctggttacgg aaaacctggg cggcctctcc ggcctgtttg agcagaagga    90180
cattctccac tactacgtgg agcaggaatg catcgaagtc gtacactcgc gcgtgtacaa    90240
catcatccag ctggtgcttt ttcacaacaa cgaccaggcg cgccgcgagt acgtggccgg    90300
caccatcaac cacccggcca tccgcgccaa ggtggactgg ctggaagcgc gggtgcggga    90360
atgcgcctcc gttccggaaa agttcatcct catgatcctc atcgagggca tctttttttgc    90420 cgcctcgttt gccgccatcg cctaccttcg caccaacaac cttctgcggg tcacctgcca    90480
gtcaaacgac ctcatcagcc gggacgaggc cgtgcacacg acggcctcgt gttacatcta    90540
caacaactac ctcggcgggc acgccaagcc cccgcccgac cgcgtgtacg ggctgttccg    90600
ccaggcggtc gagatcgaga tcggatttat ccgatcccag gcgccgacgg acagccatat    90660
cctgagcccg gcggcgctgg cggccatcga aaactacgtg cgattcagcg cggatcgcct    90720
```

```
gttgggcctt atccacatga agccactgtt ttccgcccca ccccccgacg ccagctttcc   90780
gctgagcctc atgtccaccg acaaacacac caattttttc gagtgtcgca gcacctccta   90840
cgccggggcg tcgtcaacg atctgtgagg tcgcggcgc gcttctaccc gtgtttgccc    90900
ataataaacc tctgaaccaa actttgggtc tcattgtgat tcttgtcagg gacgcggggg   90960
tgggagagga taaaggcgg cgcaaaaagc agtaaccagg tccgtccaga ttctgagggc    91020
ataggatacc ataattttat tggtgggtcg tttgttcggg gacaagcgcg ctcgtctgac   91080
gtttgggcta ctcgtcccag aatttggcca ggacgtcctt gtagaacgcg ggtgggggggg  91140
cctgggtccg cagctgctcc agaaacctgt cggcgatatc aggggccgtg atatgccggg   91200
tcacaataga tcgcgccagg ttttcgtcgc ggatgtcctg gtagataggc aggcgtttca   91260
gaagagtcca cggcccccgc tccttggggc cgataagcga tatgacgtac ttaatgtagc   91320
ggtgttccac cagctcggtg atggtcatgg gatcggggag ccagtccagg gactctgggg   91380
cgtcgtggat gacgtggcgt cgccggctgg ccacataact gcggtgctct tccagcagct   91440
gcgcgttcgg gacctggacg agctcggcg gggtgagtat ctccgaggag gacgacctgg    91500
ggccggggtg gcccccggta acgtcccggg gatccagggg gaggtcctcg tcgtcttcgt   91560
atccgccggc gatctgttgg gttagaattt cggtccacga gacgcgcatc tcggtgccgc   91620
cggcggccgg cggcaaaggg ggcctggttt ccgtggagcg cgagctggtg tgttcccggc   91680
ggatggcccg ccgggtctga gagcgactcg gggggtccca gtgacattcg cgcagcacat   91740
cctccacgga ggcgtaggtg ttattgggat ggaggtcggt gtggcagcgg acaaagaggg   91800
ccaggaactg ggggtagctc atcttaaagt actttagtat atcgcgacag ttgatcgtgg   91860
gaatgtagca ggcgctaata tccaacacaa tatcacagcc catcaacagg aggtcagtgt   91920
ctgtggtgta cacgtacgcg accgtgttgg tgtgatagag gttggcgcag gcatcgtccg   91980
cctccagctg acccgagtta atgtaggcgt accccagggc ccggagaacg cgaatacaga   92040
acagatgcgc cagacgcagg gccggcttcg agggcgcggc ggacggcagc gcggctccgg   92100
acccggccgt cccccgggtc cccgaggcca gagaggtgcc gcgccggcgc atgttggaaa   92160
aggcagagct gggtctggag tcggtgatgg gggaaggcgg tggagaggcg tccacgtcac   92220
tggcctcctc gtccgtccgg cattgggccg tcgtgcgggc caggatggcc ttggctccaa   92280
acacaaccgg ctccatacaa ttgaccccgc gatcggtaac gaagatgggg aaaagggact   92340
tttgggtaaa caccttaat aagcgacaga ggcagtgtag cgtaatggcc tcgcggtcgt    92400
aactggggta tcggcgctga tatttgacca ccaacgtgta catgacgttc cacaggtcca   92460
cggcgatggg ggtgaagtac ccggccgggg ccccaaggcc ctggcgcttg accagatggt   92520
gtgtgtgggc aaacttcatc atcccgaaca aacccatgtc aggtcgattg taactgcgga   92580
tcggcctaac taaggcgtgg ttggtgcgac ggtccgggac acccgagcct gtctctctgt   92640
gtatggtgac ccagacaaca acaccgcacg aagaggacaa taatccgtta ggggacgctc   92700
tttataattt cgatggccca actccacgcg gattggtgca gcaccctgca tgcgccggtg   92760
tgggccaaac ttccccccgc tcattgcctc ttccaaaagg gtgtggccta acgagctggg   92820
ggcgtattta atcaggctag cgcggcgggc ctgccgtagt ttctggctcg gtgagcgacg   92880
gtccggttgc ttgggtcccc tggctgccag caaaacccca ccctcgcagc ggcatacgcc   92940
ccctccgcgt cccgcacccg agacccggcc ccggctgccc tcaccaccga agcccacctc   93000
gtcactgtgg ggtgttccca gcccgcattg ggatgacgga ttcccctggc ggtgtggccc   93060
ccgcctcccc cgtggaggac gcgtcggacg cgtccctcgg gcagccggag gaggggcgc    93120
```

```
cctgccaggt ggtcctgcag ggcgccgaac ttaatggaat cctacaggcg tttgccccgc    93180
tgcgcacgag ccttctggac tcgcttctgg ttatgggcga ccggggcatc cttatccata    93240
acacgatctt tggggagcag gtgttcctgc ccctggaaca ctcgcaattc agtcggtatc    93300
gctggcgcgg acccacggcg gcgttcctgt ctctcgtgga ccagaagcgc tccctcctga    93360
gcgtgtttcg cgccaaccag tacccggacc tacgtcgggt ggagttggcg atcacgggcc    93420
aggccccgtt tcgcacgctg gttcagcgca tatggacgac gacgtccgac ggcgaggccg    93480
ttgagctagc cagcgagacg ctgatgaagc gcgaactgac gagctttgtg gtgctggttc    93540
cccagggaac ccccgacgtt cagttgcgcc tgacgaggcc gcagctcacc aaggtcctta    93600
acgcgaccgg ggccgatagt gccacgccca ccacgttcga gctcggggtt aacggcaaat    93660
tttccgtgtt caccacgagt acctgcgtca catttgctgc ccgcgaggag ggcgtgtcgt    93720
ccagcaccag cacccaggtc cagatcctgt ccaacgcgct caccaaggcg ggccaggcgg    93780
ccgccaacgc caagacggtg tacggggaaa atacccatcg caccttctct gtggtcgtcg    93840
acgattgcag catgcgggcg gtgctccggc gactgcaggt cgccgggggc accctcaagt    93900
tcttcctcac gaccccgtc cccagtctgt gcgtcaccgc caccggtccc aacgcggtat    93960
cggcggtatt tctcctgaaa ccccagaaga tttgcctgga ctggctgggt catagccagg    94020
ggtctccttc agccgggagc tcggcctccc gggcctctgg gagcgagcca acagacagcc    94080
aggactccgc gtcggacgcg gtcagccacg gcgatccgga agacctcgat ggcgctgccc    94140
gggcgggaga ggcgggggcc tcgcacgcct gtccgatgcc gtcgtcgacc acgcgggtca    94200
ctcccacgac caagcggggg cgctcggggg gcgaggatgc gcgcgcggac acggccctaa    94260
agaaacctaa gacggggtcg cccaccgcac ccccgcccac agatccagtc cccctggaca    94320
cggaggacga ctccgatgcg gcggacggga cggcggcccg tcccgccgct ccagacgccc    94380
ggagcggaag ccgttacgcg tgttactttc gcgacctccc gaccggagaa gcaagccccg    94440
gcgccttctc cgccttccgg gggggcccc aaaccccgta tggttttgga ttcccctgac    94500
ggggcggggc cttggcggcc gcccaactct cgcaccatcc cggggttaatg taaataaact    94560 tggtattgcc caacactctc ccgcgtgtcg cgtgtggttc atgtgtgtgc ctggcgtccc    94620
ccaccctcgg gttcgtgtat ttcctttccc tgtccttata aaagccgtat gtggggcgct    94680
gacggaacca ccccgcgtgc catcacggcc aaggcgcggg atgctccgca acgacagcca    94740
ccgggccgcg tccccggagg acggccaggg acgggtcgac gacggacggc cacacctcgc    94800
gtgcgtgggg gccctggcgc gggggttcat gcatatctgg cttcaggccg ccacgctggg    94860
ttttgcggga tcggtcgtta tgtcgcgcgg gccgtacgcg aatgccgcgt ctgggcgtt    94920 cgccgtcggg tgcgccgtgc tgggctttat gcgcgcaccc cctcccctcg cgcggcccac    94980
cgcgcggata tacgcctggc tcaaactggc ggccggtgga gcggccctttg ttctgtggag    95040 tctcggggag cccggaacgc agccgggggc cccgggcccg gccacccagt gcctggcgct    95100
gggcgccgcc tatgcggcgc tcctggtgct cgccgatgac gtctatccgc tctttctcct    95160
cgccccgggg cccctgttcg tcggcaccct ggggatggtc gtcggcgggc tgacgatcgg    95220
aggcagcgcg cgctactggt ggatcggtgg gcccgccgcg gccgccttgg ccgcggcggt    95280
gttggcgggc ccgggggcga ccaccgccag ggactgcttc tccagggcgt gccccgacca    95340
ccgccgcgtc tgcgtcatcg tcgcaggcga gtctgtttcc cgccgccccc cggaggaccc    95400
agagcgaccc ggggaccccg gccaccgtc ccccccgaca ccccaacgat cccagggggcc    95460
```

-continued

| | |
|---|---|
| gccggccgat gaggtcgcac cggccggggt agcgcggccc gaaaacgtct gggtgcccgt | 95520 |
| ggtcacctttt ctgggggcgg gcgcgctcgc cgtcaagacg gtgcgagaac atgcccggga | 95580 |
| aacgccgggc ccgggcctgc cgctgtggcc ccaggtgttt ctcggaggcc atgtggcggt | 95640 |
| ggccctgacg gagctgtgtc aggcgcttat gccctgggac cttacggacc cgctgctgtt | 95700 |
| tgttcacgcc ggactgcagg tcatcaacct cggggttggtg tttcggtttt ccgaggttgt | 95760 |
| cgtgtatgcg cgctagggg gtgccgtgtg gatttcgttg gcgcaggtgc tgggctccg | 95820 |
| gcgtcgcctg cacaggaagg accccgggga cggggcccgg ttggcggcga cgcttcgggg | 95880 |
| cctcttcttc tccgtgtacg cgctgggtt tggggtgggg gcgctgctgt gccctccggg | 95940 |
| gtcaacgggc gggtggtcgg gcgattgata tattttttcaa taaaaggcat tagtcccgaa | 96000 |
| gaccgccggt gtgtgatgat ttcgccataa cacccaaacc ccggatgggg cccgggtata | 96060 |
| aattccggaa ggggacacgg gctaccctca ctaccgaggg cgcttggtcg ggaggccgca | 96120 |
| tcgaacgcac accccccatcc ggtggtccgt gtggaggtcg ttttcagtg cccggtctcg | 96180 |
| ctttgccggg aacgctagcc gatccctcgc gaggggagg cgtcgggcat ggccccgggg | 96240 |
| cgggtgggcc ttgccgtggt cctgtggagc ctgttgtggc tcggggcggg ggtggccggg | 96300 |
| ggctcggaaa ctgcctccac cgggcccacg atcaccgcgg gagcggtgac gaacgcgagc | 96360 |
| gaggcccca catcggggtc ccccgggtca gccgccagcc cggaagtcac ccccacatcg | 96420 |
| accccaaacc ccaacaatgt cacacaaaac aaaaccaccc ccaccgagcc ggccagcccc | 96480 |
| ccaacaaccc ccaagcccac ctccacgccc aaaagccccc ccacgtccac cccgacccc | 96540 |
| aaacccaaga acaacaccac ccccgccaag tcgggccgcc ccactaaacc ccccgggccc | 96600 |
| gtgtggtgcg accgccgcga cccattggcc cggtacggct cgcgggtgca gatccgatgc | 96660 |
| cggtttcgga attccacccg catggagttc cgcctccaga tatggcgtta ctccatgggt | 96720 |
| ccgtccccc caatcgctcc ggctccgac ctagaggagg tcctgacgaa catcaccgcc | 96780 |
| ccacccggg gactcctggt gtacgacagc gcccccaacc tgacggaccc ccacgtgctc | 96840 |
| tgggcggagg gggccggccc gggcgccgac cctccgttgt attctgtcac cgggccgctg | 96900 |
| ccgacccagc ggctgattat cggcgaggtg acgcccgcga cccagggaat gtattacttg | 96960 |
| gcctgggcc ggatggacag cccgcacgag tacgggacgt gggtgcgcgt ccgcatgttc | 97020 |
| cgccccccgt ctctgacccct ccagcccac gcggtgatgg agggtcagcc gttcaaggcg | 97080 |
| acgtgcacgg ccgccgccta ctacccgcgt aacccgtgg agtttgtctg gttcgaggac | 97140 |
| gaccgccagg tgtttaaccc gggccagatc gacacgcaga cgcacgagca ccccgacggg | 97200 |
| ttcaccacag tctctaccgt gacctccgag gctgtcggcg gccaggtccc cccgcggacc | 97260 |
| ttcacctgcc agatgacgtg gcaccgcgac tccgtgatgt tctcgcgacg caatgccacc | 97320 |
| gggctggccc tggtgctgcc gcggccaacc atcaccatgg aatttggggt ccggcatgtg | 97380 |
| gtctgcacgg ccggctgcgt ccccgaggc gtgacgtttg cctggttcct ggggacgac | 97440 |
| ccctcaccgg cggctaagtc ggccgttacg gcccaggagt cgtgcgacca ccccgggctg | 97500 |
| gctacggtcc ggtccacccct gcccattttcg tacgactaca gcgagtacat ctgtcggttg | 97560 |
| accggatatc cggccgggat tcccgttcta gagcaccacg gcagtcacca gccccaccc | 97620 |
| agggacccca ccgagcggca ggtgatcgag gcgatcgagt gggtgggat tggaatcggg | 97680 |
| gttctcgcgg cggggggtcct ggtcgtaacg gcaatcgtgt acgtcgtccg cacatcacag | 97740 |
| tcgcggcagc gtcatcggcg gtaacgcgag acccccccgt taccttttta atatctatat | 97800 |
| agtttggtcc ccctctatcc cgcccaccgc tgggcgctat aaagccgcca ccctctcttc | 97860 |

```
cctcaggtca tccttggtcg atcccgaacg acacacggcg tggagcaaaa cgcctccccc    97920
tgagccgctt tcctaccaac acaacggcat gcctctgcgg gcatcggaac acgcctaccg    97980
gcccctgggc cccgggacac cccccatgcg ggctcggctc ccgccgcgg cctgggttgg     98040
cgtcgggacc atcatcgggg gagttgtgat cattgccgcg ttggtcctcg tgccctcgcg    98100
ggcctcgtgg gcactttccc catgcgacag cggatggcac gagttcaacc tcgggtgcat    98160
atcctgggat ccgaccccca tggagcacga gcaggcggtc ggcggctgta gcgcccggc    98220
gaccctgatc cccgcgcgg ctgccaaaca gctggccgcc gtcgcacgcg tccagtcggc     98280
aagatcctcg ggctactggt gggtgagcgg agacggcatt cgggcctgcc tgcggctcgt    98340
cgacggcgtc ggcggtattg accagttttg cgaggagccc gcccttcgca tatgctacta    98400
tccccgcagt cccggggct ttgttcagtt tgtaacttcg acccgcaacg cgctgggct     98460
gccgtgaggc gcgtgtactg cggtctgtct cgtctcctct tctccccttc cctcccctc     98520
cgcatcccag gatcacaccg gccaacgagg gttggggggg tccggcacgg acccaaaata    98580
ataaacacac aatcacgtgc gataaaaaga acacgcggtc ccctgtggtg tttttggtta    98640
tttttattaa atctcgtcga caaacagggg gaaaggggcg tggtctagcg acggcagcac    98700
gggcggaggc gttcaccggc tccggcgtcc ttcgcgttta agcttggtca ggagggcgct    98760
cagggcggcg acgttggtcg ggccgtcgtt ggtcagggcg ttggctcgat ggcgggcgag    98820
gacgggcgag gggctcaacg gcgggggcgg gggtccggtg cggcccgggg gggaaaatag    98880
ggcggatccc ccccagtcgt acagggggatt ttccgcctca atgtacgggg aggccggcgc   98940
tgcattcgcc gtgttcacgc agacgttttc gtagacccgc atccatggta tttcctcgta    99000
gacacgcccc ccgtcctcgc tcacggtctc gtatattgac tcgtcgtcct cgtagggggc    99060
gtgccgttcg cgggccgagg cggcgtgggt ggctttgcgg cgggcgtcgt cgtcgtcgtc    99120
gtcggccgtc agatacgtgg cttccatctg gtcgggttct ccctccgggg cgggtcccca    99180
cacccgtggc cgatcgaggc tccccagaga cgcgcgccgg acaagaaggg ggcacgtcgc    99240
cgccggcggt cgcctgtcgg gtcccgcgac gttacgggcc gggaggcgcg ggggcacctc    99300
ccccatgtgc gtgtaatacg tggccggctg tgcggccgca gcggggggct cggcgaccgg    99360
gtcgtccgca tccggaagcg gggccccgc gccgtccgca cggcgcctcc ggaaccgccg     99420
ggtggacggc gcggggtcg agtgtaggcg aggtcggggg aggggcgggg gctcgttgtc     99480
gcgccgcgcc cgctgaatct tttcccgaca ggtcccaccc ccgcgcgat gcccccgg       99540
gccgcgggcc atgtcgtccg ggggaggccc cgcggaccac gtcgtccggc gagacgccac    99600
gagccgcagg atggactcgt agtggagcga cggcgccccg ctgcggagca gatccgcggc    99660
cagggcggcc ccgaaccaag ccttgatgct caactccatc cgggcccagc tgggggcggt    99720
catcgtgggg aacaggggg cggtggtccg acagaaacgc tcctggctgt ccaccgcggc    99780
ccgcagatac tcgttgttca ggctgtcggt ggcccagacg ccgtacccgg tgagggtcgc    99840
gttgatgata tactgggcgt ggtgatggac gatcgacaga acctccaccg tggataccac    99900
ggtatccacg gtcccgtacg taccgccgct ccgcttgccg gtctgccaca ggttggctag    99960
gcacgtcagg tgggccagga cgtcgctgac cgccgccctg agcgccatgc actgcatgga   100020
gccggtcgtg ccgctgggac cccggtccag atggcgcgcg aacgtttccg cgggcgcctc   100080
cgggctgccg ccgagcggga ggaaccggcg attggaggga ctcagccggt gacatacgtg   100140
cttgtccgtc gtccacagca tccaggacgc ccaccggtac agcacggaga cgtaggccag   100200
```

```
gagctcgttg agccgcagtg cggtgtcggt gctggggcgg cttgggtccg ccgggcgcat    100260
aaagaacatg tactgctgaa tccgatggag ggcgtcgcgc aggccggcca cggtggcggc    100320
gtacttggcc gccgcggccc cgctcttgaa cggggtgcgc gccagcagct ttggcgccag    100380
ggtgggccgc agcagcacgt gaaggctggg gtcgcagtcg cccacggggt cctcggggac    100440
gtccaggccg ctgggcacca ccgtctgcag gtacttccag tactgcgtga ggatggcgcg    100500
gctcaactgg ccgccgggca gctccacctc gcccagcgcc tgggtggcgg ccgaagcgta    100560
gtgccggatg tactcgtagt gcgggtcgct ggcgagcccg tccacgatca aactctcggg    100620
aaccgtgttg tgttgccgcg cggccaaccg gacgctgcga tcggtgcagg tcagaaacgc    100680
cggctgcgcg tcgtcggagc gctgccgcaa ggcgcccacg gccgcgctaa ggagcccctc    100740
cggggtgggg agcagacacc cgccgaagat gcgccgctcg ggaacgcccg cgttgtcgcc    100800
gcggatcagg ttggcaggcg tcaggcaccg cgccagccgc agggagctcg cgccgcgcgt    100860
ccggcgctgc atggtgacgc ccgttcggtc gggacccgcc ggtcggagtt atgccgcgtc    100920
cagggccatc ggggcgcttt ttatcgggag gagcttatgg gcgtggcggg cctcccagcc    100980
cggtcgcgcg cctccccgac acgtgcgccc gcagggcggc ggcccccctcg tctcccatca    101040
gcagtttcct aaactgggac atgatgtcca ccacgcggac ccgcgggccc aacacggacc    101100
cgccgcttac ggggcggggg gggaagggct ccaggtcctt gagcagaaag gcggggtctg    101160
ccgtcccgga cacgggggcc cggggcgcgg aggaggcggg gcgcagatcc acgtgctccg    101220
cggccgcgcg gacgtccgcc cagaacttgg cggggggtggt gcgcgcgtac aggggctggg    101280
tcgctcggag gacacacgcg tagcgcaggg gggtgtacgt gcccacctcg ggggccgtga    101340
atccccgtc aaacgcggcc agtgtcacgc acgccaccac ggtgtcggca aagcccagca    101400
gccgctgcag gacgagcccg gcggccagaa tggcgcgcgt ggtcgcagcg tcgtcccggc    101460
gccggtgcgc gtccccgcac gcccgggcgt actttaaggt cactgtcgcc agggccgtgt    101520
gcagcgcgta caccgcagcg cccagcacgg cgttgagccc gctgttggcg agcagccggc    101580
gcgctgcggt gtcgcccagc gcctcgtgct cggcccccac gaccgcgggg cttcccaggg    101640
gcagggcgcg aaacagctcc tcccgcgcca cgtccgcaaa ggcggggtgg tgcacgtgcg    101700
ggtgcaggcg cgccccacg accaccgaga gccactggac cgtctgctcc gccatcaccg    101760
ccaacacatc cagcacgcgc cccaggaagg cggcctcccg cgtcaaaacg caccggacgg    101820
cgtcgggatt gaagcgggcg agcagggccc cggtggccag gtacgtcatg cggccggcat    101880
agcgggcggc cacgcgacag tcgcggtcca gcagcgcgcg caccccgggc cagtacagca    101940
gggaccccag cgagctgcga aacaccgcgg cgtcggggcc ggattggggg gacactaacc    102000
cccccgcgct cagtaacggc acggccgcgg ccccgacggg acgcaacgcc gtgaggctcg    102060
cgaactgccg cctcagctcg gcagccctgt cgtccaggtc cgacccgcgc gcctctgcgt    102120
gaaggcgcgt cccgcacacc cacccgttga tggccagccg cacgacggca tccgccaaaa    102180
agctcatcgc ctgggcgggg ctggttttg ttcgacgatc cgtcaggtca agaatcccat    102240
cgcccgtgat ataccaggcc aacgcctcgc cctgctgcag ggtttggcgg aaaaacaccg    102300
cggggttgtc gggggaggcg aagtgcatga ccccacgcg cgataacccg aacgcgctat    102360
ccggacacgg gtaaaacccg gccggatgcc ccagggctag ggcggagcgc acggactcgt    102420
cccacacggg aacctgaggg gccagtcgat ccaacgggaa tgccgcccgg agctccggrc    102480
ccggcacgcg tccctccaga acctccacct tgggcgggga acgggcccg ccgccgtcct    102540
ccggcccgac gtcttccggg tagtcgtcct cctcgtactg cagttcctct aggaacagcg    102600
```

```
gcgacggcgc acccgcgaa  ccgccgaccc gccccaaaat agcccgcgcg tcgacgggac  102660
ccaggtatcc cccctgccgg gcctgcggag daccgcgggg aacctcatca tcatcgtcca  102720
ggcgaccgcg caccgactgg ctacgggccg catcgggccc ggggcgctgc cggacgctc   102780 ggcgatggga tgaggggcggg gcttccgacg cgcgccgtcg tcgggctcgc gggccttccc 102840
gtcgacggcg cacgggcggc tcgtcgcccg ccatctcctc cagagcctct agctcgctgt  102900
cgtcatcccc gcggaacacc gcacgcaggt accccatgaa ccccacccca tcgcccgctg  102960
gctcgtccgc cacgggcgag gcgcggggggc gggtggatgc gcgcctcctg cgccccgcgg 103020
gttcgcgagc cgacatggtg gcgatagacg cgggttatcg gatgtccgct accccccaaa  103080
aaagaaaaag acccccacagc gcggatggag gtcggggtag gtgccgccgg acccctcgc   103140 gatgggaatg gacgggagcg acggggccgg cgcaaaaaac gcagtatctc ccgcgaaggc  103200
tacccgccgc cccagccccc ggccaaatgc ggaaacggtc ccgcgctctc gcctttatac  103260 gcgggccgc  ctgcgacaca atcacccgtc cgtggtttcg aatctacacg acaggcccgc   103320
agacgcggct aacacacacg ccggcaaccc agaccccagt gggttggttg cgcggtcccg  103380
tctcctggct agttctttcc cccaccacca aataatcaga cgacaaccgc aggttttttgt 103440 aatgtatgtg ctcgtgttta ttgtggatac gaaccgggga cgggagggga aacccagac   103500 ggggggatgcg ggtccggtcg cgccccctac ccaccgtact cgtcaattcc aagggcatcg  103560
gtaaacatct gctcaaactc gaagtcggcc atatccagag cgccgtaggg ggcggagtcg  103620 tgggggggtaa atcccggacc cggggaatcc ccgtcccccca acatgtccag atcgaaatcg  103680
tctagcgcgt cggcatgcgc catcgccacg tcctcgccgt ctaagtggag ctcgtccccc  103740
aggctgacat cggtcggggg ggccgtcgac agtctgcgcg tgtgtcccgc ggggagaaag  103800
gacaggcgcg gagccgccag ccccgcctct tcggggggcgt cgtcgtccgg gagatcgagc  103860
aggccctcga tggtagaccc gtaattgttt ttcgtacgcg cgcggctgta cgcgtgttcc  103920
cgcatgaccg cctcggaggg cgaggtcgtg aagctggaat acgagtccaa cttcgcccga  103980
atcaacacca taaagtaccc agaggcgcgcg gcctggttgc catgcagggt ggggagggggtc 104040 gtcaacggcg cccctggctc ctccgtagcc gcgctgcgca ccagcgggag gttaaggtgc  104100
tcgcgaatgt ggtttagctc ccgcagccgg cgggcctcga ttggcactcc ccggacggtg  104160
agcgctccgt tgacgaacat gaagggctgg aacagacccg ccaactgacg ccagctctcc  104220
aggtcgcaac agaggcagtc aaacaggtcg ggccgcatca tctgctcggc gtacgcggcc  104280
cataggatct cgcgggtcaa aaatagatac aaatgcaaaa acagaacacg cgccagacga  104340
gcggtctctc ggtagtacct gtccgcgatc gtggcgcgca gcatttctcc caggtcgcga  104400
tcgcgtccgc gcatgtgcgc ctggcggtgc agctgccgga cgctggcgcg caggtaccgg  104460
tacagggccg agcagaagtt ggccaacacg gttcgatagc tctcctcccg cgcccgtagc  104520
tcggcgtgga agaaacgaga gagcgcttcg tagtagagcc cgaggccgtc gcgggtggcc  104580
ggaagcgtcg ggaaggccac gtcgccgtgg gcgcgaatgt cgatttgggc gcgttcgggg  104640
acgtacgcgt ccccccattc caccacatcg ctgggcagcg ttgataggaa tttacactcc  104700
cggtacaggt cggcgttggt cggtaacgcc gaaaacaaat cctcgttcca ggtatcgagc  104760
atggtacata gcgcggggcc cgcgctaaag cccaagtcgt cgaggagacg gttaaagagg  104820 gcggcgggggg ggacgggcat gggcgggggag ggcatgagct gggcctggct caggcgcccc  104880
gttgcgtaca gcggaggggc cgccggggtg ttttttgggac ccccggccgg gcgggggggt  104940
```

```
ggtggcgaag cgccgtccgc gtccatgtcg gcaaacagct cgtcgaccaa gaggtccatt    105000
gggtggggtt gatacgggaa agacgatatc gggcttttga tgcgatcgtc cccgcccgcc    105060
cagagagtgt gggacgcccg acggcgcggg aagagaaaaa cccccaaacg cgttagagga    105120
ccggacggac cttatggggg gaagtgggca gcgggaaccc cgtccgttcc cgaggaatga    105180
cagcccgtgg tcgccacccc gcatttaagc aacccgcacg ggccgccccg tacctcgtga    105240
cttcccccca cattggctcc tgtcacgtga aggcaaaccg agggcggctg tccaacccac    105300
cccccgccac ccagtcacgg tccccgtcgg attgggaaac aaaggcacgc aacgccaaca    105360
ccgaatgaac ccctgttggt gctttattgt ctgggtacgg aagttttttca ctcgacgggc    105420 cgtctggggc gagaagcgga gcgggctggg gctcgaggtc gctcggtggg gcgcgacgcc    105480
gcagaacgcc ctcgagtcgc cgtggccgcg tcgacgtcct gcaccacgtc tggattcacc    105540
aactcgttgg cgcgctgaat caggttttttg ccctcgcaga ccgtcacgcg gatggtggtg    105600
atgccaagga gttcgttgag gtcttcgtct gtgcgcggac gcgacatgtc ccagagctgg    105660
accgccgcca tccgggcatg catggccgcc aggcgcccaa ccgcggcgca gaagacgcgc    105720
ttgttaaagc cggccacccg gggggtccat ggcgcgtcgg ggtttggggg ggcggtgcta    105780
aagtgcagct ttctggccag cccctgcgcg ggtgtcttgg atcgggttgg cgccgtcgac    105840 gcggggggcgt ctgggagtgc ggcggattct ggctgggccg atttcctgcc gcgggtggtc    105900
tccgccgccg gggccgcggg ggccttagtc gccacccgct gggttcgggg ggcccggggg    105960
gcggtggtgg gtgtgcgtcc ggcccctccg gacccagcgg gcggcggagg cgcccgcgca    106020 ggcccccgggg cggacaaaac cgccccggaa acgggacgcc gcgtccgggg gacctccggg    106080
tgttcgtcgt cttcggatga cgagcccccg tagagggcat aatccgactc gtcgtactgg    106140
acgaaacgga cctcgcccct tgggcgcgcg cgtgtctgta gggcgccacg gcgggaggtg    106200
tcaggcggac tatcgggact cgccatacat gaagacgggg tgtagtacag atcctcgtac    106260
tcatcgcgcg gaacctcccg cggacccgac ttcacggagc ggcgagaggt catggttcca    106320
cgaacacgct agggtcggat gcgcggacaa ttaggcctgg gttcggacgg cggggggtggt    106380 gcaggtgtgg agaggtcgag cgataggggc ggccccgggag agaagagagg gtccgcaaaa    106440
cccactgggg atgcgtgagt ggccctctgt gggcggtggg ggagagtctt ataggaagtg    106500
catataacca caacccatgg gtctaaccaa tccccagggg ccaagaaaca gacacgcccc    106560
aaacggtctc ggtttccgcg aggaagggga agtcctggga caccctccac ccccaccccct    106620 caccccacac agggcgggtt caggcgtgcc cggcagccag tagcctctgg cagatctgac    106680
agacgtgtgc gataatacac acgcccatcg aggccatgcc tacataaaag ggcaccaggg    106740
ccccccgggc agacatttgg ccagcgtttt gggtctcgca ccgcgcgccc ccgatcccat    106800
cgcgcccgcc ctcctcgccg ggcggctccc cgtgcgggcc cgcgtctccc gccgctaagg    106860
cgacgagcaa gacaaacaac aggcccgccc gacagaccct tctgggggggg cccatcgtcc    106920 ctaacaggaa gatgagtcag tggggatccg gggcgatcct tgtccagccg gacagcttgg    106980
gtcgggggta cgatggcgac tggcacacgg ccgtcgctac tcgcgggggc ggagtcgtgc    107040
aactgaacct ggtcaacagg cgcgcggtgg cttttatgcc gaaggtcagc ggggactccg    107100
gatgggccgt cgggcgcgtc tctctggacc tgcgaatggc tatgccggct gacttttgtg    107160
cgattattca cgcccccgcg ctatccagcc cagggcacca cgtaatactg ggtcttatcg    107220
actcggggta ccgcggaacc gttatggccg tggtcgtagc gcctaaaagg acgcgggaat    107280
ttgcccccgg gaccctgcgg gtcgacgtga cgttcctgga catcctggcg accccccggg    107340
```

```
ccctcaccga gccgatttcc ctgcggcagt tcccgcaact ggcgcccccc cctccaaccg 107400
gggccgggat acgcgcagat ccttggttgg aggggggcgct cggggaccca agcgtgactc 107460
ctgccctacc ggcgcgacgc cgagggcggt ccctcgtcta tgccggcgag ctgacgccgg 107520
ttcagacgga acacggggac ggcgtacgag aagccatcgc cttccttcca aaacgcgagg 107580
aggatgccgg tttcgacatt gtcgtccgtc gcccggtcac cgtcccggca acggcacca 107640 cggtcgtgca gccatccctc cgcatgctcc acgcggacgc cgggcccgcg gcctgctatg 107700
tgctggggcg gtcgtcgctc aacgcccgcg gcctcctggt cgttcctacg cgctggctcc 107760
ccgggcacgt atgtgcgttt gttgtttaca accttacggg ggttcctgtg accctcgagg 107820
ccggcgccaa ggtcgcccag ctcctggttg cggggggcgga cgctcttcct tggatccccc 107880
cggacaactt tcacgggacc aaagcgcttc gaaactaccc caggggtgtt ccggactcaa 107940
ccgccgaacc caggaacccg ccgctcctgg tgtttacgaa cgagtttgac gcggaggccc 108000
ccccgagcga gcgcgggacc gggggttttg gctctaccgg tatttagccc atagcttggg 108060
gttcgttccg ggcaataaaa aacgtttgta tctcatcttt cctgtgtgta gttgtttctg 108120
ttggatgcct gtgggtctat cacacccgcc cctccatccc acaaacacag aacacacggg 108180
ttggatgaaa acacgcattt attgacccaa aacacacgga gctgctcgag atgggccagg 108240
gcgaggtgcg gttggggagg ctgtaggtct gggaacggac acgcggggac acgattccgg 108300
tttggggtcc gggagggcgt cgccgtttcg ggcggcaggc gccagcgtaa cctccggggg 108360
cggcgtgtgg gggtgcccca aggagggcgc ctccggtcacc ccaagccccc ccgagcgggt 108420
tcccccggca accccgaagg cggagaggcc aagggcccgt tcggcgatgg ccacatcctc 108480
catgaccacg tcgctctcgg ccatgctccg aatagcctgg gagacgagca catccgcgga 108540
cttgtcagcc gcccccacgg acatgtacat ctgcaggatg gtggccatac acgtgtccgc 108600
caggcgccgc atcttgtcct gatgggccgc cacggccccg tcgatcgtgg gggcctcgag 108660
cccggggtgg tggcgcgcca gtcgttctag gttcaccatg caggcgtggt acgtgcgggc 108720
caaggcgcgg gccttcacga ggcgtcgggt gtcgtccagg gaccccaggg cgtcatcgag 108780
cgtgatgggg gcgggaagta gcgcgttaac gaccaccagg gcctcctgca gccgcggctc 108840
cgcctccgag ggcggaacgg ccgcgcggat catctcatat tgttcctcgg ggcgcgctcc 108900
ccagccacat atagccccga gaagagaagc catcgcgggc gggtactggc ccttgggcgc 108960
gcggacgcaa tggggcagga agacgggaac cgcggggaga ggcgggcggc cgggactccc 109020
gtggaggtga ccgcgcttta tgcgaccgac gggtgcgtta ttacctcttc gatcgccctc 109080
ctcacaaact ctctactggg ggccgagccg gtttatatat tcagctacga cgcatacacg 109140
cacgatggcc gtgccgacgg gcccacgag caagacaggt tcgaagagag tcgggcgctc 109200
taccaagcgt cgggcgggct aaatggcgac tccttccgag taaccttttg tttattgggg 109260
acggaagtgg gtgggaccca ccaggcccgc gggcgaaccc gacccatgtt cgtctgtcgc 109320
ttcgagcgag cggacgacgt cgccgcgcta caggacgccc tggcgcacgg gaccccgcta 109380
caaccggacc acatcgccgc caccctggac gcggaggcca cgttcgcgct gcatgcgaac 109440
atgatcctgg ctctcaccgt ggccgtcaac aacgccagcc cccgcaccgg acgcgacgcc 109500 gccgcgcgc agtatgatca gggcgcgtcc ctacgctcgc tcgtggggcg cacgtccctg 109560
ggacaacgcg gccttaccac gctatacgtc caccacgagg cgcgcgtgct ggccgcgtac 109620
cgcagggcgt attatggaag cgcgcagagt cccttctggt ttcttagcaa attcgggcct 109680
```

```
gacgaaaaaa gcctggtgct caccactcgg tactacctgc ttcaggccca gcgtctgggg    109740 ggcgcgggg  ccacgtacga cctgcaggcc atcaaggaca tctgcgccac ctacgcgatt    109800
ccccacgccc cccgccccga caccgtcagc gccgcgtccc tgacctcgtt tgccgccatc    109860
acgcggttct gttgcacgag ccagtacgcc cgcggggccg cggcggccgg gtttccgctt    109920
tacgtggagc gccgtattgc ggccgacgtc cgcgagacca gtgcgctgga gaagttcata    109980
acccacgatc gcagttgcct gcgcgtgtcc gaccgtgaat tcattacgta catttacctg    110040
gcccattttg agtgtttcag ccccccgcgc ctagccacgc atcttcgggc cgtgacgacc    110100 caggaccccca accccgcggc caacacggag cagccctcgc ccctgggcag ggaggccgtg    110160
gaacaatttt tttgccacgt gcgcgcccaa ctgaatatcg gggagtacgt caaacacaac    110220 gtgaccccccc gggagaccgt cctggatggc gatacggcca aggcctacct gcgcgctcgc    110280
acgtacgcgc ccggggccct gacgcccgcc cccgcgtatt gcggggccgt ggactccgcc    110340
accaaaatga tgggggcgttt ggcggacgcc gaaaagctcc tggtccccccg cgggtggccc    110400 gcgtttgcgc ccgccagtcc cggggaggat acggcgggcg gcacgccgcc cccacagacc    110460
tgcggaatcg tcaagcgcct cctgagactg gccgccacgg aacaacagga caccacgccc    110520
ccggcgatcg cggcgcttat ccgtaatgcg gcggtgcaga ctcccctgcc cgtctaccgg    110580
atatccatgg tccccacggg acaggcattt gccgcgctgg cctgggacga ctgggcccgc    110640
ataacgcggg acgctcgcct ggccgaagcg gtcgtgtccg ccgaagcggc ggcgcacccc    110700
gaccacggcg cgctgggcag gcggctcacg gatcgcatcc gcgcccaggg ccccgtgatg    110760 cccccctggcg gcctggatgc cggggggcag atgtacgtga atcgcaacga gatatttaac    110820
ggcgcgctgg caatcacaaa catcatcctg gatctcgaca tcgcccctgaa ggagcccgtc    110880 cccttttcgcc ggctccacga ggccctgggc cactttaggc gcggggctct ggcggcggtt    110940
cagctcctgt ttccccgcggc ccgcgtggac cccgacgcat atccctgtta ttttttttcaaa   111000 agcgcatgtc ggcccccggccc ggcgtccgtg ggttccggca gcggactcgg caacgacgac   111060
gacggggact ggtttccctg ctacgacgac gccggtgatg aggagtgggc ggaggacccg    111120
ggcgccatgg acacatccca cgatcccccg gacgacgagg ttgcctactt tgacctgtgc    111180
cacgaagtcg gccccacggc ggaacctcgc gaaacggatt cgcccgtgtg ttcctgcacc    111240
gacaagatcg gactgcgggt gtgcatgccc gtccccgccc cgtacgtcgt ccacggttct    111300
ctaacgatgc ggggggtggc acgggtcatc cagcaggcgg tgctgttgga ccgagatttt    111360
gtggaggcca tcgggagcta cgtaaaaaac ttcctgttga tcgatacggg ggtgtacgcc    111420
cacggccaca gcctgcgttt gccgtatttt gccaaaatcg cccccgacgg gcctgcgtgc    111480
ggaaggctgc tgccagtgtt tgtgatcccc cccgcctgca aagacgttcc ggcgtttgtc    111540
gccgcgcacg ccgacccgcg gcgcttccat tttcacgccc cgcccaccta tctcgcttcc    111600
ccccgggaga tccgtgtcct gcacagcctg ggtggggact atgtgagctt cttttgaaagg    111660 aaggcgtccc gcaacgcgct ggaacacttt gggcgacgcg agaccctgac ggaggtcctg    111720
ggtcggtaca acgtacagcc ggatgcgggg gggaccgtcg aggggttcgc atcggaactg    111780
ctggggcgga tagtcgcgtg catcgaaacc cactttcccg aacacgccgg cgaatatcag    111840
gccgtatccg tccggcgggc cgtcagtaag gacgactggg tcctcctaca gctagtcccc    111900
gttcgcggta ccctgcagca aagcctgtcg tgtctgcgct ttaagcacgg ccgggcgagt    111960
cgcgccacgg cgcggacatt cgtcgcgctg agcgtcgggg ccaacaaccg cctgtgcgtg    112020
tccttgtgtc agcagtgctt tgccgccaaa tgcgacagca accgcctgca cacgctgttt    112080
```

```
accattgacg ccggcacgcc atgctcgccg tccgttccct gcagcacctc tcaaccgtcg   112140
tcttgataac ggcgtacggc ctcgtgctcg tgtggtacac cgtcttcggt gccagtccgc   112200
tgcaccgatg tatttacgcg gtacgcccca ccggcaccaa caacgacacc gccctcgtgt   112260
ggatgaaaat gaaccagacc ctattgtttc tgggggcccc gacgcacccc cccaacgggg   112320
gctggcgcaa ccacgcccat atctgctacg ccaatcttat cgcgggtagg gtcgtgccct   112380
tccaggtccc acccgacgcc acgaatcgtc ggatcatgaa cgtccacgag gcagttaact   112440
gtctggagac cctatggtac acacgggtgc gtctggtggt cgtagggtgg ttcctgtatc   112500
tggcgttcgt cgccctccac caacgccgat gtatgtttgg tgtcgtgagt cccgcccaca   112560
agatggtggc cccggccacc tacctcttga actacgcagg ccgcatcgta tcgagcgtgt   112620
tcctgcagta cccctacacg aaaattaccc gcctgctctg cgagctgtcg gtccagcggc   112680
aaaacctggt tcagttgttt gagacggacc cggtcacctt cttgtaccac cgccccgcca   112740
tcggggtcat cgtaggctgc gagttgatgc tacgctttgt ggccgtgggt ctcatcgtcg   112800
gcaccgcttt catatcccgg ggggcatgtg cgatcacata cccctgtttt ctgaccatca   112860
ccacctggtt ttttgtctcc accatcggcc tgacagagct gtattgtatt ctgcggcggg   112920
gcccggcccc caagaacgca gacaaggccg ccgccccggg gcgatccaag gggctgtcgg   112980
gcgtctgcgg gcgctgttgt tccatcatcc tgtcgggcat cgcaatgcga ttgtgttata   113040
tcgccgtggt ggccggggtg gtgctcgtgg cgcttcacta cgagcaggag atccagaggc   113100
gcctgtttga tgtatgacgt cacatccagg ccggcggaaa ccggaacggc atatgcaaac   113160
tggaaactgt cctgtcttgg ggcccaccca cccgacgcgt catatgtaaa tgaaaatcgt   113220
tcccccgagg ccatgtgtag cctggatccc aacgaccccg cccatgggtc ccaattggcc   113280
gtcccgttac caagaccaac ccagccagcg tatccacccc cgcccgggtc cccgcggaag   113340
cggaacggtg tatgtgatat gctaattaaa tacatgccac gtacttatgg tgtctgattg   113400
gtccttgtct gtgccggagg tggggcgggg gccccgcccg gggggcggaa ctaggagggg   113460
tttgggagag ccggccccgg caccacgggt ataaggacat ccaccacccg gccggtggtg   113520
gtgtgcagcc gtgttccaac cacggtcacg cttcggtgcc tctccccgat tcgggcccgg   113580
tcgcttgcta ccggtgcgcc accaccagag gccatatccg acaccccagc cccgacggca   113640
gccgacagcc cggtcatggc gactgacatt gatatgctaa ttgacctcgg cctgacctc    113700 tccgacagcg atctggacga ggaccccccc gagccggcgg agagccgccg cgacgacctg   113760
gaatcggaca gcaacgggga gtgttcctcg tcggacgagg acatggaaga cccccacgga   113820
gaggacggac cggagccgat actcgacgcc gctcgcccgg cggtccgccc gtctcgtcca   113880
gaagaccccg gcgtacccag cacccagacg cctcgtccga cggagcggca gggccccaac   113940
gatcctcaac cagcgcccca cagtgtgtgg tcgcgcctcg ggcccggcg accgtcttgc    114000 tcccccgagc ggcacggggg caaggtggcc cgcctccaac ccccaccgac caaagcccag   114060
cctgcccgcg gcggacgccg tgggcgtcgc aggggtcggg gtcgcggtgg tcccggggcc   114120
gccgatggtt tgtcggaccc ccgccggcgt gccccagaa ccaatcgcaa cccgggggga    114180
ccccgccccg gggcggggtg gacggacggc cccggcgccc ccatggcga ggcgtggcgc     114240 ggaagtgagc agcccgaccc acccggaggc ccgcggacac ggagcgtgcg ccaagcaccc   114300
cccccgctaa tgacgctggc gattgccccc ccgcccgcgg accccgcgc cccggcccg     114360 gagcgaaagg cgcccgccgc cgacaccatc gacgccacca cgcggttggt cctgcgctcc   114420
```

```
atctccgagc gcgcggcggt cgaccgcatc agcgagagct tcggccgcag cgcacaggtc    114480
atgcacgacc cctttggggg gcagccgttt cccgccgcga atagccctg ggccccggtg    114540 ctggcgggcc aaggagggcc ctttgacgcc gagaccagac gggtctcctg ggaaaccttg    114600
gtcgcccacg gcccgagcct ctatcgcact tttgccggca atcctcgggc cgcatcgacc    114660
gccaaggcca tgcgcgactg cgtgctgcgc aagaaaatt tcatcgaggc gctggcctcc    114720
gccgacgaga cgctggcgtg gtgcaagatg tgcatccacc acaacctgcc gctgcgcccc    114780
caggacccca ttatcgggac ggccgcggcg gtgctggata acctcgccac gcgcctgcgg    114840 cccttctcc agtgctacct gaaggcgcga ggcctgtgcg gcctggacga actgtgttcg    114900
cggcggcgtc tggcggacat taaggacatt gcatccttcg tgtttgtcat tctggccagg    114960
ctcgccaacc gcgtcgagcg tggcgtcgcg gagatcgact acgcgaccct tggtgtcggg    115020
gtcggagaga agatgcattt ctacctcccc ggggcctgca tggcgggcct gatcgaaatc    115080
ctagacacgc accgccagga gtgttcgagt cgtgtctgcg agttgacggc cagtcacatc    115140
gtcgcccccc cgtacgtgca cggcaaatat ttttattgca actccctgtt ttaggtacaa    115200
taaaaacaaa acatttcaaa caaatcgccc cacgtgttgt ccttctttgc tcatggccgg    115260
cggggcgtgg gtcacggcag atggcggggg tgggcccggc gtacggcctg ggtgggcgga    115320
gggaactaac ccaacgtata aatccgtccc cgctccaagg ccggtgtcat agtgcccta    115380 ggagcttccc gcccgggcgc atcccccctt ttgcactatg acagcgaccc ccctcaccaa    115440
cctgttctta cgggccccgg acataaccca cgtggccccc ccttactgcc tcaacgccac    115500
ctggcaggcc gaaacggcca tgcacaccag caaaacggac tccgcttgcg tggccgtgcg    115560
gagttacctg gtccgcgcct cctgtgagac cagcggcaca atccactgct ttttctttgc    115620
ggtatacaag gacacccacc ataccctcc gctgattacc gagctccgca actttgcgga    115680
cctggttaac cacccgccgg tcctacgcga actggaggat aagcgcgggg tgcggctgcg    115740
gtgtgcgcgc ccgtttagcg tcgggacgat taaggacgtc tctgggtccg gcgcgtcctc    115800
ggcgggagag tacacgataa acgggatcgt gtaccactgc cactgtcggt atccgttctc    115860
aaaaacatgc tggatggggg cctccgcggc cctacagcac ctgcgctcca tcagctccag    115920
cggcatggcc gcccgcgcgg cagagcatcg acgcgtcaag attaaaatta aggcgtgatc    115980
tccaaccccc catgaatgtg tgtaacccc cccaaaaaaa taagagccg taacccaacc    116040 aaaccaggcg tggtgtgagt ttgtggaccc aaagccctca gagacaatgc gacaggccag    116100 tatgaccgt gatactttta tttattaact cacaggggcg cttaccgcca caggaatacc    116160
agaataatga ccaccacaat cgcgaccacc ccaaatacag catggcgcca caccacgcca    116220
caacagccct gtcgccggta tgggggcatga tcagacgagc cgcgcgccgc gcgttgggcc    116280
ctgtacagct cgcgcgaatt gaccctagga ggccgccacg cgcccgagtt ttgcgttcgt    116340
cgctggtcgt cgggcgccaa agccccggac ggctgttcgg tcgaacgaac ggccacgaca    116400
gtggcatagg ttgggggtg gtccgacata gcctcggcgt acgtcgggag gcccgacaag    116460
aggtcccttg tgatgtcggg tggggccaca agcctggttt ccggaagaaa caggggggtt    116520
gccaataacc cgccagggcc aaaactccgg cgctgcgcac gtcgttcggc gcggcgccgg    116580
gcgcgccgag cggctcgctg gcggcttgg cgtgagcggc cccgctccga cgcctcgccc    116640
tctccggagg aggttggcgg aattggcacg gacgacaggg gcccagcaga gtacggtgga    116700
ggtgggtccg tggggtgtc cagatcaata acgacaaacg gccctcgtt cctaccgac    116760 aagctatcgt aggggggcgg gggatcagca aacgcgttcc ccgcgctcca tagacccgcg    116820
```

```
tcgggttgcg ccgcctccga agccatggat gcgccccaaa gccacgactc ccgcgcgcta    116880
ggtccttggg gtaagggaaa aggccctact ccccatccaa gccagccaag ttaacgggct    116940
acgccttcgg ggatgggact ggcaccccgg cggattttgt tgggctggta cgcgtcgccc    117000
aaccgagggc cgcgtccacg ggacgcgcct tttataaccc cggggtcatt cccaacgatc    117060
acatgcaatc taactggctc ccctctcccc ccctctcccc tctcccccc  tctccctct     117120
cccccctct  cccctctccc cccctctccc ctctcccccc ctctccctc  tccccccctc    117180
tccctctcc  ccccctctcc ctctcccccc cctctcccct ctccccccct ctccctctc     117240
cccccctctc ccctgctctt tccccgtgac acccgacgct gggggcgtg  gctgccggga    117300
ggggccgcgt atgggcgggc ctactcggtc tcccgccccc ccgaaccgcc ccgccggctt    117360
tgccccccctt tgatcccctg ctaccccccac cccgtgctcg tggtgcgggg tgggggatg   117420
tgggcggggg tgcgcgggag gtgtcggtgg tggggtggt  ggtggtggtg gtagtaggaa    117480
tggtggtggg gggagggcg  ctggttggtc aaaaaaggga gggacggggg ccggcagacc    117540
gacggcgaca acgctccccg gcggccgggt cgcggctctt acgagcggcc cggcccgcgc    117600
tcccacccccc cggggccgtgt ccttgctttc ccccgtctc ccccccgcc  ttctcctcct   117660
cctcctcgtt tttccaaacc ccgcccaccc ggcccggccc ggcccggccc ggccaccgcc    117720
gcccacccac ccacctcggg ataccccagcc ccggtcccccc gttccccggg ggccgttatc   117780
tccagcgccc cgtccggcgc gccgccccccc ggcgctaaac cccatcccgc ccccgggacc   117840
ccacatataa gcccccagcc acacgcaaga acagacacgc agaacggctg tgtttattttt   117900
aaataaaccg atgtcggaat aaacaaacac aaacaccccgc gacgggggga cggaggggac   117960
ggagggaggg gggtgacggg ggacggaaac agacacaaaa aacaaccaca aaaacaacc     118020
acccaccgac accccccaccc cagtctcctc gccttctccc acccaccccca cgcccccact  118080
gagcccggtc gatcgacgag cacccccgcc cacgccccg  ccctgccccc ggcgaccccc    118140
ggcccgcacg atcccgacaa caataacaac cccaacggaa agcggcgggg tgttgggggga  118200
ggcgaggaac aaccgagggg aacgggggat ggaaggacgg gaagtggaag tcctgatacc    118260
catcctacac ccccctgcct tccacccctcc ggccccccgc gagtccaccc gccggccggc   118320
taccgagacc gaacacggcg gccaccgccg ccgccgccgc cgacaccgca gagccggcgc    118380
gcgcacacac aagcggcaga ggcagaaagg ccccgagtca ttgtttatgt ggccgcgggc    118440
cagcagacgg cccgcgacac ccccccccgc ccgtgtgggt atccggcccc ccgccccgcg    118500
ccggtccatt aagggcgcgc gtgccccgcga gatatcaatc cgttaagtgc tctgcagaca   118560
ggggcaccgc gcccggaaat ccattaggcc gcagacgagg aaaataaaat tacatcacct    118620
acccatgtgg tgctgtggcc tgttttttgct gcgtcatctg agcctttata aaagcggggg   118680
cgcggccgtg ccgatcgccg gtggtgcgaa agactttccg ggcgcgtccg ggtgccgcgg    118740
ctctccgggc ccccctgcag ccgggccggc caaggggcgt cggcgacatc ctccccctaa    118800
gcgccggccg gccgctggtc tgttttttcg ttttcccccgt ttcggggggtg gtgggggttg   118860
cggtttctgt ttcttttaacc cgtctggggt gtttttcgtt ccgtcgccgg aatgtttcgt   118920
tcgtctgtcc cctcacgggg cgaaggccgc gtacggcccg ggacgagggg ccccgaccgg    118980
cggcggtccg ggccccgtcc ggacccgctc gccggcacgc gacgcgaaaa aggcccccccg  119040
gaggcttttc cggggttcccg gcccggggcc tgagatgaac actcgggggtt accgccaacg   119100
gccggccccc gtggcggccc ggcccggggc cccggcggac ccaaggggcc ccggcccggg    119160
```

```
gccccacaac ggcccggcgc atgcgctgtg gttttttttt cctcggtgtt ctgccgggct   119220
ccgtcgcctt tcctgttctc gcttctcccc ccccccttc accccagta ccctcctccc   119280 tcccttcctc ccccgttatc ccactcgtcg agggcgcccc ggtgtcgttc aacaaagacg   119340
ccgcgtttcc aggtaggtta gacacctgct tctccccaat agagggggg ggacccaaac   119400 gacaggggc gccccagagg ctaaggtcgg ccacgccact cgcgggtggg ctcgtgttac   119460
agcacaccag cccgttattt tccccccctc ccacccttag ttagactctg ttacttaccc   119520
gtccgaccac caactgcccc cttatctaag ggccggctgg aagaccgcca ggggtcggc   119580 cggtgtcgct gtaaccccc acgccaatga cccacgtact ccaagaaggc atgtgtccca   119640
ccccgcctgt gtttttgtgc ctggctctct atgcttgggt cttactgcct ggggggggg   119700 agtgcggggg aggggggggg tgtggaagga aatgcacggc gcgtgtgtac cccccctaa   119760 agttgttcct aaagcgagga tatggaggag tggcgggtgc cgggggaccg gggtgatctc   119820
tggcacgcgg gggtgggaag ggtcggggga ggggggatg gggtaccggc ccacctggcc   119880
ggcgcgggtg cgcgtgcctt tgcacaccaa ccccacgtcc cccggcggtc tctaagaaac   119940
accgcccccc ctccttcata ccaccgagca tgcctgggtg tgggttggta accaacacgc   120000
ccatcccctc gtctcctgtg attctctggc tgcaccgcat tcttgttttc taactatgtt   120060
cctgtttctg tctccccccc cacccctccg ccccaccccc caacaccac gtctgtggtg   120120 tggccgaccc ccttttgggc gccccgtccc gccccgctac ccctcccatc ctttgttgcc   120180
ctatagtgta gttaaccccc ccccgcccc tttgtggcgg ccagaggcca ggtcagtccg   120240
ggcgggcagg cgctcgcgga aacttaacac ccacacccaa cccactgtgg ttctggctcc   120300
atgccagtgg caggatgctt tcggggatcg gtggtcaggc agcccgggcc gcggctctgt   120360
ggttaacacc agagcctgcc caacatggca ccccactcc cacgcacccc cactcccacg   120420
cacccccact cccacgcacc cccactccca cgcacccca ctcccacgca ccccactcc   120480 cacgcacccc cactcccacg cacccccact cccacgcacc cccactccca cgcaccccg   120540 cgatacatcc aacacagaca gggaaaagat acaaagtaa acctttattt cccaacagac   120600
agcaaaaatc ccctgagttt tttttattag ggccaacaca aaagaccgc tggtgtgtgg   120660 tgcccgtgtc tttcactttc cacctccccg acacggattg gctggtgtag tgggcgcggc   120720
cagagaccac ccagcgcccg accccccct cccacaaac acggggcgt cccttattgt   120780 tttccctcgt cccgggtcga cgcccctgc tccccggacc acgggtgccg agaccgcagg   120840
ctgcggaagt ccagggcgcc cactagggtg ccctggtcga acagcatgtt ccccacgggg   120900
gtcatccaga ggctgttcca ctccgacgcg ggggccgtcg ggtactcggg gggcgtcacg   120960
tggttacccg cggtctcggg gagcagggtg cggcggctcc agccggggac cgcggccgc   121020 agccgggtcg ccatgtttcc cgtctggtcc accaggacca cgtacgcccc gatgttcccc   121080
gtctccatgt ccaggatggg caggcagtcc ccgtgatcg tcttgttcac gtaaggcgac   121140
agggcgacca cgctagagac ccccgagatg ggcaggtagc gcgtgaggcc gcccgcgggg   121200
acggccccgg aagtctccgc gtggcgcgtc ttccgggcac acttcctcgg ccccgcggc   121260 ccagaagcag cgcggggcc gagggaggtt tcctcttgtc tccctcccag ggcaccgacg   121320
gccccgcccg aggaggcgga agcggaggag gacgcggccc cggtggcgga agaggtggcc   121380 ccgcgggag tcggggccga ggaggaagag gcggaggagg aagaggcgga ggccgccgag   121440
gacgtcaggg gggtcccggg ccctccctgg ccgcgccccc ccggccctga gtcggagggg   121500
gggtgcgtcg ccgcccctctt ggcccctgcc ggcgcgaggg ggggacgcgt ggactggggg   121560
```

```
gaggggtttt cctggcccga cccgcgcctc ttcctcggac gcaccgccgc ctcctgctcg   121620
acagaggcgg cggaggggag cgggggggcg ccggaggggg cggcgccgga gggggcggcg   121680
ccgcgggagg gcccgtgtcc accctccacg cccggccccc ccgagccgcg cgccaccgtc   121740
gcacgcgccc ggcacagact ctgttcttgg ttcgcggcct gagccaggga cgagtgcgac   121800
tggggcacac ggcgcgcgtc cgcggggcgg gcggccggct ccgccccggg ggccggggcg   121860 cggggccgg gccccggagg cggcgcccgc acacacgggg ccacgccgc gcgggggcgc   121920 gcggggcccg acgcggccgc ggacgcgggg ggaccggggc gggggggcgga gcctggcatg   121980 ggcgccgcgg ggggcctgtg gggagaggcc gggggggagt cgctgatcac tatgggtct    122040 ctgttgtttg caaggggggc gggtctgttg acaaggggc ccgtccggcc cctcggccgc   122100
cccgcctccg cttcaacaac cccaacccccc ccggaggggc cagacgcccc ccgcggcacc   122160
gcggctcgcg actggcggga ccgccgccg ccgctgctgt tggtggtggt gttagtgtta    122220
ctgctgccgt gtggcccgat gggcgccgag ggggcgctg tccgagccgc ggccggctgg    122280
ggggctgcgt gagacgcccc gcccgtcacg ggggcgcgg cggcgcctct gcgtgggggg   122340
gcgcggggcg tccggcgggg ggcgggcggt acgtagtctg ctgcaagaga caacgggggg    122400
cgcgatcagg ttacgcccc tccccggccc gccctttcct cgcccgcccg cccgcctatt    122460
cctccctccc ccccccctcc tcctcctccc ccagggtcct cgccgccccc ccgcctcacc    122520
gtcgtccagg tcgtcgtcat cctcgtccgt ggtgggctca gggtgggtgg gcgacagggc   122580
cctcaccgtg tgcccccca gggtcaggta ccgcggggcg aaccgctgat tgcccgtcca    122640
gataaagtcc acggccgtgc ccgccctgac ggcctcctcg gcctccatgc gggtctgggg   122700
gtcgttcacg atcgggatgg tgctgaacga cccgctgggc gtcacgccca ctatcaggta   122760
caccagcttg gcgttgcaca gcgggcaggt gttgcgcaat tgcatccagg ttttcatgca   122820
cgggatgcag aagcggtgca tgcacgggaa ggtgtcgcag cgcaggtggg gcgcgatctc   122880
atccgtgcac acggcgcaca cgtcgccctc gtcgctcccc ccgtcctctc gagggggggc   122940
gcccccgcaa ctgccggggt cttcctcgcg ggggggctc ccccccgaga ccgcccccc    123000 atccacgccc tgcggcccca gcagcccgt ctcgaacagt tccgtgtccg tgctgtccgc   123060
ctcggaggcg gagtcgtcgt catggtggtc ggcgtccccc cgccccccca cttcggtctc   123120
cgcctccgag tcgctgctgt ccggcaggtc tcggtcgcag ggaaacaccc agacatccgg    123180
ggcgggctga ggggaaaaaa ggggggggcg gtaagaatgg ggggatttcc cgcgtcaatc   123240
agcgcccacg agttcccct ccccccccgc ctcacaaagt cctgccccc tgctggcctc     123300 ggaagagggg ggagaaaggg gtctgcaacc aaaggtggtc tgggtccgtc ctttggatcc    123360 cgaccctct tcttccctct tctccgccc tccagacgca ccggagtcgg gggtcccacg     123420
gcgtccccca aatatggcgg gcggctcctc ccccacccccc tagatgcgtg tgagtaaggg    123480
ggccctgcgt atgagtcagt ggggaccacg cccctaaca cggcgacccc ggtccctgtg    123540
tgtttgttgt gggggcgtgt ctctgtgtat gagtcagggg ggtcccacgg cgaccccggg    123600
ccctgcgtct gagtcaaagg ggccatgtgt aggtgttggg ggtctgtata tataaagtca    123660
gggggtcaca tggcgacccc taacagggcg accccgtcc ctgtatatat agggtcaggg     123720
ggttccgcgc ccctaacat ggcgccccg gtccctgtat atatagtgtc acggggttcc      123780 acgccccta acatggcgcc ccaacatggc gccggctcc cgtgtatgag tgggggtccc      123840
ccaacatggc ggccggttcc agtgtaaggg tcggggggtcc cccaacatgg cgcccccaa    123900
```

```
catggcgccc cccaacatgg cgccccagac atggcgcccg gcccctcacc tcgcgctggg   123960
ggcggccctc aggccggcgg gtactcgctc cggggcgggg ctccatgggg gtcgtatgcg   124020
gctggagggt cgctgacgga gggtccctgg gggtcgcaac gtaggcgggg cttctgtggt   124080
gatgcggaga gggggcggcc cgagtctgcc tggctgctgc gtctcgctcc gagtgccgag   124140
gtgcaaatgc gaccagaccg tcgggccagg gctaacttat accccacgcc tttcccctcc   124200
ccaaggggc ggcagtgacg attcccccaa tggccgcgcg tcccagggga ggcaggccca    124260
ccgcggggcg gccccgtccc cggggaccaa cccggcgccc caaagaata tcattagcat    124320
gcacggcccg gcccccgatt tgggggacca acccggtgtc ccccaaagaa ccccattagc   124380
atgcccctcc cgccgacgca acaggggctt ggcctgcgtc ggtgcccgg ggcttcccgc    124440
cttcccgaag aaactcatta ccatacccgg aaccccaggg gaccaatgcg ggttcattga   124500
gcgacccgcg ggccaatgcg cgaggggccg tgtgttccgc caaaaaagca attaacataa   124560
cccggaaccc caggggagtg gttacgcgcg gcgcgggagg cggggaatac cggggttgcc   124620
cattaagggc cgcgggaatt gccggaagcg ggaagggcgg ccggggccgc ccattaatga   124680
gtttctaatt accataccgg gaagcggaac aaggcctctg caagttttta attaccatac   124740
cgggaagtgg gcgccccggc ccactgggcg ggagttaccg cccagtgggc cgggcccga    124800
cgactcggcg gacgctggtt ggccgggccc cgccgcgctg gcggccgccg attggccagt   124860
cccgccctcc gagggcgggc ccgcctcggg ggcgggccgg ctccaagcgt atatatgcgc   124920
ggctcctgcc atcgtctctc cggagagcgg cttggtgcgg agctcccggg agctccgcgg   124980
aagacccagg ccgcctcggg tgtaacgtta gaccgagttc gccgggccgg ctccgcgggc   125040
cagggcccgg gcacgggcct cgggcccag gcacggcccg atgaccgcct cggcctccgc    125100
caccgggcgc cggaaccgag cccggtcggc ccgctcgcgg gccacgagc cgcggcgcgc    125160
caggcgggcg gccgaggccc agaccaccag gtggcgcacc cggacgtggg gcgagaagcg   125220
cacccgcgtg ggggtcgcgg gggtcgcggg ggtcgcgggg ggcttcggcg ccccctcccc   125280
gcccgcgcgt cgcaggcgca ggcgcgccag gtgctctgcg gtgacgcgca ggcggagggc   125340
gaggcgcggg ggaaggcgga aggggcgtga gggggggtgg gaggggttag ccccgccccc   125400
cgggcccgcg ccgggcggtg gggaccgggg gcggggggcg cggcggtgg gccgggcctc    125460
tggcgccggc tcgggcgggg ggctgtccgg ccagtcgtcg tcgtcgtcgt cggacgcgga   125520
ctcgggaacg tggagccact ggcgcagcag cagcgaacaa gaaggcgggg gcccactggc   125580
ggggggcggc ggcggggcgg ccgcgggcgc gctcctgacc acgggttccg agttgggcgt   125640
ggaggttacc tgggactgtg cggttgggac cgcgcccgtg ggcccgggcg gccggggggcg  125700
gcggggggccg cgatggcggc ggcgggccat ggagacagag agcgtgccgg ggtggtagag  125760
tttgacaggc aagcatgtgc gtgcagaggc gagtagtgct tgcctgtcta actcgctagt   125820
ctcggccgcg gggggcccgg gctgcccgcc gcccgccttt aaaggccgc gcgcgacccc    125880
cggggggtgt gtttttgggg gggcccgttt ccggggtctg gccgctcctc ccccgctcct   125940
cccccgctc ctcccccgc tcctcccccc gctcctcccc ccgctcctcc cccgctcct     126000
cccccgctc ctcccccgc tcctcccccc gctcctcccc ccgctcctcc cccgctcct     126060
cccccgctc ctcccccgc tcctcccccc gctcctcccc ccgctcctcc cccgctcct     126120
cccccgctcc tccccgctc ccggccccc gccccacg cccgccgcgc gcgcacgc        126180
cgcccggacc gccgccgcc tttttgcgc gcgcgcgcgc ccgcgggggg cccgggctgc    126240
cacaggtaaa acaacaccaa caaagcacgg cgcaatccgc acgtcacacg tcacgtcatc   126300
```

```
caccacacct gcccaacaac acaactcaca gcgacaactc accgcgcaac aactcctgtt   126360
cctcatccac acgtcaccgc gcacctcccg ctcctccaga cgtacccggg cgcaacacac   126420
cgctcctgct acacaccacc gcccctcccc agcccagcc ctcccagcc ccagccctcc     126480 ccggccccag ccctcccgg ccccagccct cccggcccc agccctcccc ggcccagccc    126540
ctccccggcc ccagcctcc ccagccag ccctccccag ccgcgtcccg cgctccctcg     126600 gggggggttcg ggcatctcta cctcagtgcc gccaatctca ggtcagagat ccaaaccctc  126660
cgggggcgcc cgcgcaccac caccgcccct cgcccctcc cgcccctcgc ccctcccgc    126720 ccctcgcccc ctcccgcccc tcgcccctc ccgcccctcg ccccctcccg ccctcgcccc   126780
cctcccgccc ctcgcccct cccgccctc gcccctccc gcccctcgcc ccctcccgcc    126840
cctcgccccc tcccgcccct cgccccctcc cgccctcgc cccctcccgc ccctcgcccc   126900
ctccccgccc tcgccccctc ccgccctcg cccctccg ccctcgccc cctcccgccc    126960 ctcgccccct cccgccctc gcccctccc gccctcgcc ccctcccgcc cctcgaataa   127020
acaacgctac tgcaaaactt aatcaggtcg ttgccgttta ttgcgtcttc gggtttcaca  127080
agcgccccgc cccgtcccgg cccgttacag cacccgtcc ccctcgaacg cgccgccgtc   127140
gtcttcgtcc caggcgcctt cccagtccac aacgtcccgt cgcggggcg tggccaagcc   127200 cgcctccgcc cccagcacct ccacggcccc cgccgccgcc agcacggtgc cgctgcggcc   127260
cgtggccgag gcccagcgaa tcccgggcgg cgccggcggc agggccccg ggccgtcgtc   127320 gtcgtcgccg cgcagcacca gcgggggggc gtcgtcgtcg ggctccagca gggcgcggc   127380 gcaaaagtcc ctccgcggcc cgcgccaccg ggccgggccg gcgcgcaccg cctcgcgccc   127440
cagcgccacg tacacgggcc gcagcggcgc gcccaggccc cagcgcgcgc aggcgcggtg   127500
cgagtgggcc tcctcctcgc agaagtccgg cgcgccgggc gccatggcgt cggtggtccc   127560
cgaggccgcc gccggccgt ccagcgccgg cagcacggcc cggcggtact cgcgcgggga   127620
catgggcacc ggcgtgtccg ggccgaagcg cgtgcgcacg cggtagcgca cgttgccgcc   127680
gcggcacagg cgcagcggcg cgcgcgtcggg gtacaggcgc gcgtgcgcgg cctccacgcg   127740
cgcgaagacc cccgggccga acacgcgcc cgaggccagc accgtgcggc gcaggtcccg   127800
cgccgccggc cagcgcacgg cgcactgcac ggcgggcagc aggtcgcacg ccaggtaggc   127860
gtgctgccgc gacaccgcgg gcccgtcggc gggccagtcg caggcgcgca cggtgttgac   127920
cacgatgagc cgccggtcgc cggcgctggc gagcagcccc agaaactcca cggccccggc   127980
gaaggccagg tcccgcgtgg acagcagcag cacgccctgc gcgcccagcg ccgacacgtc   128040
gggggcgccg gtccagttgc ccgcccaggc ggccgtgtcc ggcccgcaca gccggttggc   128100
cagggccgcc agcaggcagg acagcccgcc gcgctcggcg gaccactccg gcggcccccc   128160
cgaggccccg ccgccggcca ggtcctcgcc cggcagcggc gagtacagca ccaccacgcg   128220
cacgtcctcg gggtcgggga tctggcgcat ccaggccgcc atgcggcgca gcgggcccga   128280
ggcgcgcagg gggccaaaga ggcggccccc ggcggccccg tgggggtggg ggttctcgtc   128340
gtcgtcgccg ccgcacgcgg cctgggcggc ggggcgggc ccggcgcacc gcgcggcgat   128400
cgaggccagg gcccgcgggt caaacatgag ggccggtcgc caggggacgg ggaacagcgg   128460
gtggtccgtg agctcggcca cggcgcgcgg ggagcagtag gcctccaggg cggcggccgc   128520
gggcgccgcc gtgtggctgg gccccgggg ctgccgccgc cagccgccca ggggtcggg    128580 gccctcggcg ggcggcgcg acagcgccac ggggcgcggg cgggcctgcg ccgcggcgcc   128640
```

```
ccgggccgcc gcgggctggg cggggtcggg ctcgggcccc gggggcgtgg agggggggcgc   128700 ggggagggggg gcgcggccgt ccgagccggg ggcgtccgcg ccgctcttct tcgtcttcgg   128760
gggtcgcggg ccgccgcctc cgggcggccg ggccgggccg ggactcttgc gcttgcgccc   128820
ctcccgcggc gcggcggagg cggcggcggc cgccagcgcg tcggcggcgt ccggtgcgct   128880
ggccgccgcc gccagcaggg ggcggaggct ctggttctca aacagcaggt ccgcggcggc   128940
ggcggccgcg gagctcggca ggcgcgggtc ccgcggcagc gcggggccca gggcccggcc   129000
gaccaggctc acggcgcgca cggcggccac ggcggcctcg ctgccgccgg ccacgcgcag   129060
gtccccgcgc aggcgcatga gcaccagcgc gtcgcgcacg aaccgcagct cgcgcagcca   129120
cgcgcgcagg cggggcgcgt cggcgtgcgg cggcggcggg gaagcggggc ccgcgggtcc   129180
ctccggccgc gggggggctgg cgggccgggc cccggccagc cccggacggg ccgccaggtc   129240
gccgtcgaag ccctcggcca gcgcctccag gatcccgcgg caggcggcca ggcactcgac   129300
ggccacgcgg ccggcctggg cgcggcgccc ggcgtcggcg tcggcgtggc gggcggcgtc   129360
ggggtcgtcg ccccccacgg gggaggcggg cgcggcggac agccgcccca gggcggcgag   129420
gatccccgcg gcgccgtacc cggcgggcac cgcgcgctcg cccggtgcgg cggcggcgac   129480
ggcggcgacc ccctcgtcat ctgcgccggc gccggggctc cccgcggccc ccgtcagcgc   129540
cgcgttctcg cgcgccaaca gggggcgcgta ggcgcggcgc aggctggtca gcaggaagcc   129600
cttctgcgcg cggtcgtatc ggcggctcat ggccacggcg gccgccgcgt gcgccaggcc   129660
ccagccgaag cggccggccg ccatggcgta gcccaggtgg ggcacggccc gcgccacgct   129720
gccggtgatg aaggagctgc tgttgcgcgc ggcgcccgag atccggaagc aggcctggtc   129780
cagcgccacg tccccgggga ccacgcgcgg gttctggagc caccccatgg cctccgcgtc   129840
cggggtgtac agcagccgcg tgatcagggc gtactgctgc gcggcgtcgc ccagctcggg   129900
cgcccacacg gccgccgggg cgcccgaggc ctcgaaccgg cgtcgcgcct cctccgcctc   129960
gggcgccccc cagaggcccg ggcggctgtc gcccaggccg ccgtacagca cccgcccccgg   130020 gggcgggggc ccggcgccgg gccacggctc cccgctgacg tacccgtcgc gatagcgcgc   130080
gtagaaggcg ccggaggccg cgtcggcgtc cagctcgacc cgccggggct gcccggccgt   130140
gaagcggccc gtggcgtcgc ggccggccac cgccgcgcgg gccggccggc gctcgatgcg   130200
gcccgcggag gccgcggggg tcctcgccgc cgcccggggc ttgggcgcgg cctcggagag   130260 gggggggtggc ccgggcgggg gcggcgtccg cccgggggct tccggcgccg cgctcgacgg   130320
accccgcccg acgcccgcgc cctcgcgtgc gtggtcggcc gcgtcgttgc cgtcgtcgtc   130380
ctcgtcctcg tcggacgacg aggacgaaga ggatgcggac gacgaggacg aggacccgga   130440
gtccgacgag gtcgatgacg ccgatggccg ccgccggccg tgacgacgtc tccgcggcgg   130500
ctgggccggc gggcgcggcg acaggcggtc cgtggggtcc ggatacgcgc cgcgtagcgg   130560
ggcctcccgt tcgcggcccc gggcgggggc ccggtcgccg gcggcgtcgg ctgcgtcgtc   130620
gtactcgtcc ccgtcatcgt cgtcggctag aaaggcgggg gtccggggcg gcgaggccgc   130680
ggggtcgggc gtcgggatcg tccggacggc ctcctctacc atggaggcca gcagagccag   130740
ctgtcgcgac gagacggcgt cccggccgtc ctcgccggcg tcggtgcccg ccgcggggc    130800 cctcccgtcc cgccgggcgt cgtcgaggtc gtggggtgg tcggggtcgt ggtcggggtc    130860
gtccccgccc tcctccgtct ccgcgcccca cccgagggcc cccgctcgt cgcggtctgg    130920 gctcggggtg ggcggcggcc cgtcggtggg gcccggggag ccggggcgct gcttgttctc    130980
cgacgccatc gccgatgcgg ggcgatcctc cggggatacg gctgcgacgg cggacgtagc    131040
```

```
acggtaggtc acctacggac tctcgatggg gggaggggc gagacccacg gacccccgacg   131100
accccgccg tcgacgcgga actagcgcgg accggtcgat gcttgggtgg ggaaaaagga    131160
cagggacggc cgatcccct cccgcgcttc gtccgcgtat cggcgtcccg gcgcggcgag    131220
cgtctgacgg tctgtctctg gcggtcccgc gtcgggtcgt ggatccgtgt cggcagccgc   131280
gctccgtgtg gacgatcggg gcgtcctcgg gctcatatag tcccaggggc cggcgggaag   131340
gaggagcagc ggaggccgcc ggccccccgc ccccggcgg gcccaccccg aacgaattc    131400
cattatgcac gaccccgccc cgacgccggc acgccgggg cccgtggccg cggcccgttg   131460
gtcgaacccc cggccccgcc catccgcgcc atctgccatg gacggggcgc gagggcgggt   131520
gggtccgcgc cccgcccgc atggcatctc attaccgccc gatccggcgg tttccgcttc   131580
cgttccgcat gctaacgagg aacgggcagg gggcggggcc cggccccga cttcccggtt    131640
cggcggtaat gagatacgag ccccgcgcgc ccgttggccg tccccgggcc cccggtcccg   131700
cccgccggac gccgggacca acgggacggc gggcggccct tgggccgccc gccttgccgc   131760
cccccattg gccggcgggc gggaccgccc caagggggcg gggccgccgg gtaaaagaag    131820
tgagaacgcg aagcgttcgc acttcgtccc aatatatata tattattagg gcgaagtgcg   131880
agcactggcg ccgtgcccga ctccgcgccg gccccggggg cggacccggg cggcgggggg   131940
cgggtctctc cggcgcacat aaaggccggg cgcgaccgac gcccgcagac ggcgccagcc   132000
acgaacgacg ggagcggctg cggagcacgc ggaccgggag cgggagtcgc agagggccgt   132060
cggagcggac ggcgtcggca tcgcgacgcc ccggctcggg atcgggatcg catcggaaag   132120
ggacacgcgg acgcgggggg gaaagacccg cccacccccac ccacgaaaca caggggacgc  132180
accccgggg cctccgacga cagaaaccca ccggtccgcc ttttttgcac gggtaagcac    132240
cttgggtggg cagaggaggg gggacgcggg ggcggaggag gggggacgcg ggggcggagg   132300
aggggggacg cggggggga ggagggga cgcggggcg gaggagggg gacgcgggg         132360
cggaggaggg ggctcacccg cgttcgtgcc ttccgcagg aggaacgccc tcgtcgaggc    132420
gaccggcggc gaccgttgcg tggaccgctt cctgctcgtc gggggggggg gagccactgt   132480
ggtcctccgg gacgttttct ggatggccga catttcccca ggcgcttttg tgccttgtgt   132540
aaaagcgcgg cgtcccgctc tccgatcccc gcccctgggc acgcgcaagc gcaagcgccc   132600
tgcccgcccc ctctcatcgg agtctgaggt cgaatccgag acagccttgg agtctgaggt   132660
cgaatccgag acagcatcgg attcgaccga gtctggggac caggaggaag ccccccgcat   132720
cggtggccgt aggggccccc ggaggcttgg ggggcggttt tttctggaca tgtcggcgga   132780
atccaccacg gggacggaaa cggatgcgtc ggtgtcggac gaccccgacg acacgtccga   132840
ctggtcttgt gacgacattc ccccacgacc caagcgggcc cgggtaaacc tgcggctcac   132900
tagctctccc gatcggcggg atggggttat ttttcctaag atgggcggg tccggtctac    132960
ccgggaaacg cagccccggg cccccaccc gtcggcccca agcccaaatg caatgctccg    133020
gcgctcggtg cgccaggccc agaggcggag cagcgcacga tggaccccg acctgggcta    133080
catgcgccag tgtatcaatc agctgtttcg ggtcctgcgg gtcgcccggg accccacgg    133140
cagtgccaac cgcctgcgcc acctgatacg cgactgttac ctgatgggat actgccgagc   133200
ccgtctggcc ccgcgcacgt ggtgccgctt gctgcaggtg tccggcggaa cctggggcat   133260
gcacctgcgc aacaccatac gggaggtgga ggctcgattc gacgccaccg cagaaccgt    133320
gtgcaagctt ccttgtttgg aggccagacg gtacggcccg gagtgtgatc ttagtaatct   133380
```

-continued

```
cgagattcat ctcagcgcga caagcgatga tgaaatctcc gatgccaccg atctggaggc    133440
cgccggttcg gaccacacgc tcgcgtccca gtccgacacg gaggatgccc cctcccccgt    133500
tacgctggaa accccagaac cccgcgggtc cctcgctgtg cgtctggagg atgagtttgg    133560
ggagtttgac tggaccccce aggagggctc ccagccctgg ctgtctgcgg tcgtggccga    133620
taccagctcc gtggaacgcc cgggcccatc cgattctggg gcgggtcgcg cagcagaaga    133680
ccgcaagtgt ctggacggct gccggaaaat gcgcttctcc accgcctgcc cctatccgtg    133740
cagcgacacg tttctccggc cgtgagtccg gtcgccccga ccccccttgta tgtccccaaa    133800
ataaaagacc aaaatcaaag cgtttgtccc agcgtcttaa tggcgggaag ggcggagaga    133860
aacagaccac gcgtacatgg ggggtgtttg ggggtttatt gacatcgggg ctacagggtg    133920
gtaaccggat agcagatgtg aggaagtctg ggccgttcgc cgcgaacggc gatcagaggg    133980
tccgtttctt gcggaccacg gcccggtgat gtgggttgct cgtctaaaat ctcgggcata    134040
cccatacacg cacaacacgg acgccgcacc gaatgggacg tcgtaagggg gtgggaggta    134100
gctgggtggg gtttgtgcag agcaatcagg gaccgcagcc agcgcataca atcgcgctcc    134160
cgtccgttgg tcccgggcag gaccacgccg tactggtatt cgtaccggct gagcagggtc    134220
tccagggggt ggttgggtgc cgcggggaac ggggtccacg ccacggtcca ctcgggcaaa    134280
aaccgagtcg gcacggccca cggttctccc acccacgcgt ctggggtctt gatggcgata    134340
aatcttaccc cgagccggat tttttgggcg tattcgagaa acggcacaca cagatccgcc    134400
gcgcctacca cccacaagtg gtagaggcga ggggggctgg gttggtctcg gtgcaacagt    134460
cggaagcacg ccacgcgtc cacgacctcg gtgctctcca agggggctgtc ctccgcaaac    134520
aggcccgtgg tggtgtttgg ggggcagcga caggacctag tgcgcacgat cgggcgggtg    134580
ggtttgggta agtccatcag cggctcggcc aaccgtcgaa ggttggccgg gcgaacgacg    134640
accggggtac ccaggggttc tgatgccaaa atgcggcact gcctaagcag gaagctccac    134700
agggccgggc ttgcgtcgac ggaagtccgg ggcagggcgt tgttctggtc aaggagggtc    134760
attacgttga cgacaacaac gcccatgttg gtatattaca ggcccgtgtc cggtttgggg    134820
cacttgcaga tttgtaaggc cacgcacggc ggggagacag gccgacgcgg gggctgctct    134880
aaaaatttaa gggccctacg gtccacagac ccgccttccc ggggggggccc ttggagcgac    134940
cggcagcgga ggcgtccggg ggaggggagg gttatttacg ggggggtagg tcaggggtg    135000
ggtcgtcaaa ctgccgctcc ttaaaacccc ggggcccgtc gttcggggtg ctcgttggtt    135060
ggcactcacg gtgcggcgaa tggcctgtcg taagttttgt cgcgtttacg ggggacaggg    135120
caggaggaag gaggaggccg tcccgccgga gacaaagccg tcccgggtgt ttcctcatgg    135180
ccccttttat accccagccg aggacgcgtg cctggactcc ccgcccccgg agaccccaa    135240
accttcccac accacaccac ccggcgatgc cgagcgcctg tgtcatctgc aggagatcct    135300
ggcccagatg tacggaaacc aggactaccc catagaggac gacccagcg cggatgccgc    135360
ggacgatgtc gacgaggacg ccccggacga cgtggcctat ccggaggaat acgcagagga    135420
gcttttctg cccggggacg cgaccggtcc ccttatcggg gccaacgacc acatccctcc    135480
cccgcgtggc gcatctcccc ccggtatacg acgacgcagc cggatgagga ttggggccac    135540
gggatttacc gcagaagagc tggacgccat ggacaggcag gcggctcgag ccatcagccg    135600
cggcggcaag cccccctcga ccatggccaa gctggtgact ggcatgggct ttacgatcca    135660
cggagcgctc accccaggat cggaggggtg tgtctttgac agcagccacc cagattcccc    135720
ccaacgggta atcgtgaagg cggggtggta cacgagcacg agccacgagg cgcgactgct    135780
```

```
gaggcgactg gaccacccgg cgatcctgcc cctcctggac ctgcatgtcg tctccggggt    135840
cacgtgtctg gtcctcccca agtaccaggc cgacctgtat acctatctga gtaggcgcct    135900
gaacccactg ggacgcccgc agatcgcagc ggtctcccgg cagctcctaa gcgccgttga    135960
ctacattcac cgccagggca ttatccaccg cgacattaag accgaaaata tttttattaa    136020
cacccccgag gacatttgcc tgggggactt tggtgccgcg tgcttcgtgc agggttcccg    136080
atcaagcccc ttcccctacg gaatcgccgg aaccatcgac accaacgccc ccgaggtcct    136140
ggccggggat ccgtatacca cgaccgtcga catttggagc gccggtctgg tgatcttcga    136200
gactgccgtc cacaacgcgt ccttgttctc ggcccccgc  ggcccaaaa ggggcccgtg    136260 cgacagtcag atcacccgca tcatccgaca ggcccaggtc cacgttgacg agttttcccc    136320
gcatccagaa tcgcgcctca cctcgcgcta ccgctcccgc gcggccggga caatcgccc    136380 gccttacacc cgaccggcct ggacccgcta ctacaagatg gacatagacg tcgaatatct    136440
ggtttgcaaa gccctcacct tcgacggcgc gcttcgcccc agcgccgcag agctgctttg    136500
tttgccgctg tttcaacaga aatgaccgcc cccgggggc  ggtgctgttt gcgggttggc    136560
acaaaaagac cccgacccgc gtctgtggtg ttttggcat  catgtcgccg ggcgccatgc    136620
gtgccgttgt tcccattatc ccattccttt tggttcttgt cggtgtatcg ggggttccca    136680
ccaacgtctc ctccaccacc caaccccaac tccagaccac cggtcgtccc tcgcatgaag    136740
cccccaacat gacccagacc ggcaccaccg actctcccac cgccatcagc cttaccacgc    136800
ccgaccacac cccccatg  ccaagtatcg gactggagga ggaggaggaa gaggaggagg    136860
gggccgggga tggcgaacat cttaagggg  gagatgggac ccgtgacacc ctaccccagt    136920
ccccgggtcc agccgtcccg ttggccgggg atgacgagaa ggacaaaccc aaccgtcccg    136980
tagtcccacc ccccggtccc aacaactccc ccgcgcgccc cgagaccagt cgaccgaaga    137040 cacccccac  cagtatcggg ccgctggcaa ctcgacccac gacccaactc ccctcaaagg    137100 ggcgacccctt ggttccgacg cctcaacata ccccgctgtt ctcgttcctc actgcctccc    137160
ccgccctgga caccctcttc gtcgtcagca ccgtcatcca caccttatcg tttgtgtgta    137220
ttgttgctat ggcgacacac ctgtgtggtg gttggtccag acgcgggcga cgcacacacc    137280
ctagcgtgcg ttacgtgtgc ctgccgcccg aacgcgggta gggtatgggg cggggatggg    137340
gagagcccac acgcggaaag caagaacaat aaaggcggcg ggatctagtt gatatgcgtc    137400
tctgggtgtt tttggggtgt ggtgggcgcg gggcggtcat tggacggggg tgcagttaaa    137460
tacatgcccg ggacccatga agcatgcgcg acttccgggc ctcggaaccc acccgaaacg    137520
gccaacggac gtctgagcca ggcctggcta tccggagaaa cagcacacga cttggcgttc    137580
tgtgtgtcgc gatgtctctg cgcgcagtct ggcatctggg gcttttggga agcctcgtgg    137640
gggctgttct tgccgccacc catctgggac ctgcggccaa cacaacggac cccttaacgc    137700 acgcccagt  gtccctcac  cccagccccc tgggggctt  tgccgtcccc ctcgtagtcg    137760
gtgggctgtg tgccgtagtc ctgggggcgg cgtgtctgct tgagctcctg cgtcgtacgt    137820
gccgcgggtg gggcgttac  catccctaca tggacccagt tgtcgtataa ttttttcccc    137880
cccccccttc tccgcatggg tgatgtcggg tccaaactcc cgacaccacc agctggcatg    137940
gtataaatca ccggtgcgcc ccccaaacca tgtccggcag ggggatgggg ggcgaatgcg    138000
gagggcaccc aacaacaccg ggctaaccag gaaatccgtg gccccggccc ccaacaaaga    138060
tcgcggtagc ccggccgtgt gacattatcg tccataccga ccacaccgac gaatccccta    138120
```

```
aggggagggg gccattttac gaggaggagg ggtataacaa agtctgtctt taaaaagcag    138180
gggttaggga gttgttcggt cataagcttc agtgcgaacg accaactacc ccgatcatca    138240
gttatcctta aggtctcttt tgtgtggtgc gttccggtat gggggggggct gccgccaggt    138300 tgggggccgt gattttgttt gtcgtcatag tgggcctcca tggggtccgc ggcaaatatg    138360
ccttggcgga tgcctctctc aagatggccg accccaatcg ctttcgcggc aaagaccttc    138420
cggtcctgga ccagctgacc gaccctccgg gggtccggcg cgtgtaccac atccaggcgg    138480
gcctaccgga cccgttccag ccccccagcc tcccgatcac ggtttactac gccgtgttgg    138540
agcgcgcctg ccgcagcgtg ctcctaaacg caccgtcgga ggcccccag attgtccgcg    138600 gggcctccga agacgtccgg aaacaaccct acaacctgac catcgcttgg tttcggatgg    138660
gaggcaactg tgctatcccc atcacggtca tggagtacac cgaatgctcc tacaacaagt    138720 ctctggggc ctgtcccatc cgaacgcagc cccgctggaa ctactatgac agcttcagcg    138780
ccgtcagcga ggataacctg ggttcctga tgcacgcccc cgcgtttgag accgccggca    138840
cgtacctgcg gctcgtgaag ataaacgact ggacggagat tacacagttt atcctggagc    138900
accgagccaa gggctcctgt aagtacgccc tcccgctgcg catccccccg tcagcctgcc    138960 tctccccca ggcctaccag caggggtga cggtggacag catcgggatg ctgccccgct    139020
tcatccccga gaaccagcgc accgtcgccg tatacagctt gaagatcgcc gggtggcacg    139080
ggcccaaggc cccatacacg agcaccctgc tgccccggga gctgtccgag acccccaacg    139140
ccacgcagcc agaactcgcc ccggaagacc ccgaggattc ggccctcttg gaggaccccg    139200
tggggacggt ggcgccgcaa atcccaccaa actggcacat cccgtcgatc caggacgccg    139260
cgacgcctta ccatccccg gccaccccga caacatgggg cctgatcgcc ggcgcggtgg    139320
gcggcagtct cctggcagcc ctggtcattt gcggaattgt gtactggatg caccgccgca    139380
ctcggaaagc cccaaagcgc atacgcctcc cccacatccg ggaagacgac cagccgtcct    139440
cgcaccagcc cttgttttac tagataccccc cccttaatgg gtgcgggggg gtcaggtctg    139500
cggggttggg atgggaccct aactccatat aaagcgagtc tggaagggg gaaaggcgga    139560 cagtcgataa gtcggtagcg ggggacgcgc acctgttccg cctgtcgcac ccacagcttt    139620
ttcgcgaacc gtcccgtttc gggatgccgt gccgccgtt gcagggcctg gtgctcgtgg    139680
gcctctgggt ctgtgccacc agcctggttg tccgtggccc cacggtcagt ctggtatcaa    139740
actcatttgt ggacgccggg gccttgggc ccgacggcgt agtggaggaa gacctgctta    139800
ttctcgggga gcttcgcttt gtggggggacc aggtccccca caccacctac tacgatgggg    139860
tcgtagagct gtggcactac cccatgggac acaaatgccc acgggtcgtg catgtcgtca    139920
cggtgaccgc gtgcccacgt cgcccgccg tggcatttgc cctgtgtcgc gcgaccgaca    139980
gcactcacag ccccgcatat cccaccctgg agctgaatct ggcccaacag ccgcttttgc    140040
gggtccggag ggcgacgcgt gactatgccg gggtgtacgt gttacgcgta tgggtcgggg    140100
acgcaccaaa cgccagcctg tttgtcctgg ggatggccat agccgccgaa ggtactctgg    140160
cgtacaacgg ctcggcccat ggctcctgcg acccgaaact gcttccgtct tcggcccgc    140220 gtctggcccc ggcgagcgta taccaacccg cccctaaccc ggcctccacc ccctcgacca    140280
ccacctccac cccctcgacc accatccccg ctccccaagc atcgaccaca cccttcccca    140340
cgggagaccc aaaacccaa cctcacgggg tcaaccacga accccatcg aatgccacgc    140400 gagcgacccg cgactcgcga tatgcgctaa cggtgaccca gataatccag atagccatcc    140460
ccgcgtccat tatagcccctg gtgtttctgg ggagctgtat ttgctttata cacagatgtc    140520
```

```
aacgccgcta ccgacgctcc cgccgcccga tttacagccc ccagatACCc acgggcatct  140580
catgcgcggt gaacgaagcg gccatggccc gcctcggagc cgagctcaaa tcgcatccga  140640
gcacccCCcc caaatcccgg cgccggtcgt cacgcacgcc aatgccctcc ctgacggcca  140700
tcgccgaaga gtcggagccc gcgggggcgg ctgggcttcc gacgcccccc gtgGACccca  140760
cgacatccac cccaacgcct cccctgttgg tataggtcca cggccactgg ccggGGgcac  140820
cacataaccg accgcagtca ctgagttggg aataaaccgg tattatttac ctatatccgt  140880
gtatgtccat ttctttcttc cccccccccc ccggaaacca agaaggaag caaagaatgg   140940
atgggaggag ttcaggaagc cggggagagg gcccgcggcg catttaaggc gttgttgtgt  141000
tgactttggc tcttctggcg ggttggtgcg gtgctgtttg ttgggctccc attttacccg  141060
aagatcggct gctatcccCG ggacatggat cgcggggCGg tggtggggtt tcttctcggt  141120
gtttgtgttg tatcgtgctt ggcgggaacg cccaaaacgt cctggagacg ggtgagtgtc  141180
ggcgaggacg tttcgttgct tccagctccg gggcctacgg ggcgcggccc gacccagaaa  141240
ctactatggg ccgtggaacc cctggatggg tgcggcccct tacacccgtc gtgggtctcg  141300
ctgatgcccc ccaagcaggt gcccgagacg gtcgtggatg cggcgtgcat gcgcgctccg  141360
gtcccgctgg cgatggcgta cgcccCCccg gccccatctg cgaccggggg tctacgaacg  141420
gacttcgtgt ggcaggagcg cgcggccgtg gttaaccgga gtctggttat tcacggggtc  141480
cgagagacgg acagcggcct gtataccctg tccgtgggcg acataaagga cccggctcgc  141540
caagtggcct cggtggtcct ggtggtgcaa ccggccccag ttccgacccc accccgacc   141600
ccagccgatt acgacgagga tgacaatgac gagggcgagg acgaaagtct cgccggcact  141660
cccgccagcg ggacccccCg gctcccgcct ccccccgccc cccgaggtc ttggcccagc    141720
gcccccgaag tctcacatgt gcgtggggtg accgtgcgta tggagactcc ggaagctatc  141780
ctgttttccc ccggggagac gttcagcacg aacgtctcca tccatgccat cgcccacgac  141840
gaccagacct actccatgga cgtcgtctgg ttgaggttcg acgtgccgac ctcgtgtgcc  141900
gagatgcgaa tatacgaatc gtgtctgtat cacccgcagc tcccagaatg tctgtccccg  141960
gccgacgcgc cgtgcgccgc gagtacgtgg acgtctcgcc tggccgtccg cagctacgcg  142020
gggtgttcca gaacaaaccc cccaccgcgc tgttcggccg aggctcacat ggagcccgtc  142080
ccggggctgg cgtggcaggc ggcctccgtc aatctggagt tccggGACgc gtccccacaa  142140
cactccggcc tgtatctgtg tgtggtgtac gtcaacgacc atattcacgc ctggggccac  142200
attaccatca gcaccgcggc gcagtaccgg aacgcggtgg tggaacagcc cctcccacag  142260
cgcggcgcgg atttggccga gcccacccac ccgcacgtcg gggcccctcc ccacgcgccc  142320
ccaacccacg gcgccctgcg gttagggGCg gtgatggggg ccgccctgct gctgtctgcg  142380
ctggggttgt cggtgtgggc gtgtatgacc tgttggcgca ggcgtgcctg gcgggcggtt  142440
aaaagcaggg cctcgggtaa ggggcccacg tacattcgcg tggccgacag cgagctgtac  142500
gcggactgga gctcggacag cgagggagaa cgcgaccagg tcccgtggct ggccccccg   142560
gagagacccg actctccctc caccaatgga tccggctttg agatcttatc accaacggct  142620
ccgtctgtat accccgtag cgacgggcat caatctcgcc gccagctcac aacctttgga   142680
tccggaaggc ccgatcgccg ttactcccag gcctccgatt cgtccgtctt ctggtaaggc  142740
gccccatccc gaggcccCAC gtcggtcgcc gaactgggcg accgccgcg aggtggacgt    142800
cggagacgag ctaatcgcga tttccgacga acgcggaccc ccccgacatg accgccgcc   142860
```

```
cctcgccacg tcgaccgcgc cctcgccaca cccgcgaccc ccgggctaca cggccgttgt  142920
ctccccgatg gccctccagg ctgtcgacgc ccctccctg tttgtcgcct ggctggccgc   142980
tcggtggctc cgggggcctt ccggcctggg ggccgtcctg tgtgggattg cgtggtatgt   143040
gacgtcaatt gcccgaggcg cacaaagggc cggtggtccg cctagccgca gcaaattaaa   143100
aatcgtgagt cacagcgacc gcaacttccc acccggagct ttcttccggc ctcgatgacg   143160
tcccggctct ccgatcccaa ctcctcagcg cgatccgaca tgtccgtgcc gctttatccc   143220
acggcctcgc cagtttcggt cgaagcctac tactcggaaa gcgaagacga ggcggccaac   143280
gacttcctcg tacgcatggg ccgccaacag tcggtattaa ggcgttgacg cagacgcacc   143340
cgctgcgtcg gcatggtgat cgcctgtctc ctcgtggccg ttctgtcggg cggatttggg   143400
gcgctcctga tgtggctgct ccgctaaaag accgcatcga cacgcgcgtc cttcttgtcg   143460
tctctcttcc cccccatcac cccgcaattt gcacccagcc tttaactaca ttaaattggg   143520
ttcgattggc aatgttgtct cccggttgat ttttgggtgg gtggggagtg ggtgggtggg   143580
gagtgggtgg gtggggagtg ggtgggtggg gagtgggtgg gtggggagtg ggtgggtggg   143640
gagtgggtgg gtggggagtg ggtgggtggg gagtgggtgg gtggggagtg ggtgggtggg   143700
gagtggcaag gaagaaacaa gcccgaccac cagacagaaa atgtaaccat acccaaaccg   143760
actctggggg ctgtttgtgg ggtcggaacc ataggatgaa caaaccaccc cgtacctccc   143820
gcacccaagg gtgcgggtgg ctcatcggca tctgtccggt atgggttgtt ccccacccac   143880
tcgcgttcgg acgtcttaga atcatggcgg ttttctatgc cgacatcggt tttctccccc   143940
gcaataagac acgatgcgat aaaatctgtt tgtaaaattt attaagggta caaattgccc   144000
tagcacaggg gtggggttag ggccgggtcc ccacacccaa acgcaccaaa cagatgcagg   144060
cagtgggtcg agtacagccc cgcgtacgaa cacgtcgatg cgtgtgtcag acagcaccag   144120
aaagcacagg ccatcaacag gtcgtgcatg tgtcggtggg tttggacgcg gggggccatg   144180
gtggtgataa agttaatggc cgccgtccgc cagggccaca ggggcgacgt ctcttggttg   144240
gcccggagcc actgggtgtg gaccagccgc gcgtggcggc ccaacatggc ccctgtagcc   144300
gggggcgggg gatcgcgcac gtttgcagcg cacatgcgag acacctcgac cacggttcga   144360
aagaaggccc ggtggtccgc gggcaacatc accaggtgcg caagcgcccg ggcgtccaga   144420
gggtagagcc ctgagtcatc cgaggttggc tcatcgcccg ggtcttgccg caagtgcgtg   144480
tgggttgggc ttccggtggg cgggacgcga accgcggtgt ggatcccgac gcgggcccga   144540
gcgtatgctc catcttgtgg ggagaagggg tctgggctcg ccaggggggc atacttgccc   144600
gggctataca gacccgcgag ccgtacgtgg ttcgcggggg gtgcgtgggg tccgggctc    144660 cctgggagac cggggttgtc gtggatccct ggggtcacgc ggtaccctgg ggtctctggg   144720
agctcgcggt actctgggtt ccctaggttc tcggggtggt cgcggaaccc ggggctcccg   144780
gggaacacgc ggtgtcctgg ggattgttgg cggtcggacg gcttcagatg gcttcgagat   144840
cgtagtgtcc gcaccgactc gtagtagacc cgaatctcca cattgccccg ccgcttgatc   144900
attatcaccc cgttgcgggg gtccggagat catgcgcggg tgtcctcgag gtgcgtgaac   144960
acctctgggg tgcatgccgg cggacggcac gcctttaag taaacatctg ggtcgcccgg   145020
cccaactggg gccggggggtt gggtctggct catctcgaga gacacggggg ggaaccaccc   145080
tccgcccaga gactcgggtg atggtcgtac ccgggactca acgggttacc ggattacggg   145140
gactgtcggt caccggtccg ccggttcttc gatgtgccac acccaaggat gcgttggggg   145200
cgatttcggg cagcagcccg ggagagcgca gcaggggacg ctccgggtcg tgcacggcgg   145260
```

```
ttctggccgc ctcccggtcc tcacgccccc ttttattgat ctcatcgcgt acgtcggcgt  145320
acgtcctggg cccaacccgc atgttgtcca ggaaggtgtc cgccatttcc agggcccacg  145380
acatgctttt cccccccgacg agcaggaagc ggtccacgca acggtcgccg ccggtcgcct  145440
cgacgagggc gttcctcctg cgggaaggca cgaacgcggg tgagccccct cctccgcccc  145500
cgcgtccccc ctcctccgcc cccgcgtccc ccctcctccg ccccccgcgtc cccctcctc  145560
cgcccccgcg tcccccctcc tccgccccg cgtcccccct cctctgccca cccaaggtgc  145620
ttaccgtgc aaaaaaggcg gaccggtggg tttctgtcgt cggaggcccc cggggtgcgt  145680
ccctgtgtt tcgtgggtgg ggtgggcggg tcttttccccc ccgcgtccgc gtgtcccttt  145740
ccgatgcgat cccgatcccg agccggggcg tcgcgatgcc gacgccgtcc gctccgacgg  145800
ccctctgcga ctcccgctcc cggtccgcgt gctccgcagc cgctcccgtc gttcgtggct  145860
ggcgccgtct gcgggcgtcg gtcgcgccgg gcctttatgt gcgccggaga gacccgcccc  145920
ccgccgcccg ggtccgcccc cggggccggc gcggagtcgg gcacggcgcc agtgctcgca  145980
cttcgcccta ataatatata tatattggga cgaagtgcga acgcttcgcg ttctcacttc  146040
ttttacccgg cggccccgcc cccttgggc ggtcccgccc gccggccaat ggggggggcgg  146100
caaggcgggc ggcccaaggg ccgcccgccg tcccgttggt cccggcgtcc ggcgggcggg  146160
accgggggcc cggggacggc caacgggcgc gcggggctcg tatctcatta ccgccgaacc  146220
gggaagtcgg ggcccgggcc ccgcccccctg cccgttcctc gttagcatgc ggaacggaag  146280
cggaaaccgc cggatcgggc ggtaatgaga tgccatgcgg ggcggggcgc ggacccaccc  146340
gccctcgcgc cccgtccatg gcagatggcg cggatgggcg gggccggggg ttcgaccaac  146400
gggccgcggc cacgggcccc cggcgtgccg gcgtcgggc ggggtcgtgc ataatggaat  146460
tccgttcggg gtgggcccgc cggggggcgg ggggccggcg gcctccgctg ctcctccttc  146520
ccgccggccc ctgggactat atgagcccga ggacgcccg atcgtccaca cggagcgcgg  146580
ctgccgacac ggatccacga cccgacgcgg gaccgccaga gacagaccgt cagacgctcg  146640
ccgcgccggg acgccgatac gcggacgaag cgcgggaggg ggatcggccg tccctgtcct  146700
tttttcccac ccaagcatcg accggtccgc gctagttccg cgtcgacggc gggggtcgtc  146760
ggggtccgtg ggtctcgccc cctcccccca tcgagagtcc gtaggtgacc taccgtgcta  146820
cgtccgccgt cgcagccgta tccccggagg atcgccccgc atcggcgatg gcgtcggaga  146880
acaagcagcg ccccggctcc ccgggcccca ccgacgggcc gccgccacc ccgagcccag  146940
accgcgacga gcggggggcc ctcggtgggg gcgcggagac ggaggagggc ggggacgacc  147000
ccgaccacga ccccgaccac ccccacgacc tcgacgacgc ccggcgggac gggagggccc  147060
ccgcggcggg caccgacgcc ggcgaggacg ccggggacgc cgtctcgtcg cgacagctgg  147120
ctctgctggc ctccatggta gaggaggccg tccggacgat cccgacgccc gaccccgcgg  147180
cctcgccgcc ccggaccccc gccttttctag ccgacgacga tgacgggac gagtacgacg  147240
acgcagccga cgccgccggc gaccgggccc cggcccgggg ccgcgaacgg gaggcccccgc  147300
tacgcggcgc gtatccggac cccacggacc gcctgtcgcc gcgccgccg gcccagccgc  147360
cgcggagacg tcgtcacggc cggcggcggc catcggcgtc atcgacctcg tcggactccg  147420
ggtcctcgtc ctcgtcgtcc gcatcctctt cgtcctcgtc gtccgacgag gacgaggacg  147480
acgacggcaa cgacgcggcc gaccacgcac gcgaggcgcg ggccgtcggg cggggtccgt  147540
cgagcgcggc gccggaagcc cccgggcgga cgccgccccc gcccgggcca ccccccctct  147600
```

-continued

```
ccgaggccgc gcccaagccc cggggcggcgg cgaggacccc cgcggcctcc gcgggccgca 147660
tcgagcgccg ccgggcccgc gcggcggtgg ccggccgcga cgccacgggc cgcttcacgg 147720
ccgggcagcc ccggcgggtc gagctggacg ccgacgcggc ctccggcgcc ttctacgcgc 147780
gctatcgcga cgggtacgtc agcggggagc cgtggcccgg cgccgggccc ccgccccgg 147840 ggcgggtgct gtacggcggc ctgggcgaca gccgcccggg cctctggggg gcgcccgagg 147900
cggaggaggc gcgacgccgg ttcgaggcct cgggcgcccc ggcggccgtg tgggcgcccg 147960
agctgggcga cgccgcgcag cagtacgccc tgatcacgcg gctgctgtac accccggacg 148020
cggaggccat ggggtggctc cagaacccgc gcgtggtccc cggggacgtg gcgctggacc 148080
aggcctgctt ccggatctcg ggcgccgcgc gcaacagcag ctccttcatc accggcagcg 148140
tggcgcgggc cgtgccccac ctgggctacg ccatggcggc cggccgcttc ggctgggcc 148200 tggcgcacgc ggcggccgcc gtggccatga gccgccgata cgaccgcgcg cagaagggct 148260
tcctgctgac cagcctgcgc cgcgcctacg cgccctgtt ggcgcgcgag aacgcggcgc 148320 tgacggggc cgcggggagc cccggcgccg gcgcagatga cgaggggtc gccgccgtcg 148380 ccgccgccgc accgggcgag cgcgcggtgc ccgccgggta cggcgccgcg gggatcctcg 148440
ccgccctggg gcggctgtcc gccgcgcccg cctccccgt ggggggcgac gaccccgacg 148500
ccgcccgcca cgccgacgcc gacgccgggc ccgcgccca ggccggccgc gtggccgtcg 148560
agtgcctggc cgcctgccgc gggatcctgg aggcgctggc cgagggcttc gacggcgacc 148620
tggcggccgt cccggggctg gccggggccc ggcccgccag ccccccgcgg ccggagggac 148680
ccgcgggccc cgcttccccg ccgccgccgc acgccgacgc gccccgcctg cgcgcgtggc 148740
tgcgcgagct gcggttcgtg cgcgacgcgc tggtgctcat gcgcctgcgc ggggacctgc 148800
gcgtggccgg cggcagcgag gccgccgtgg ccgccgtgcg cgccgtgagc ctggtcgccg 148860
gggccctggg ccccgcgctg ccgcgggacc cgcgcctgcc gagctccgcg gccgccgccg 148920
ccgcggacct gctgtttgag aaccagagcc tccgcccct gctggcggcg gcggccagcg 148980
caccggacgc cgccgacgcg ctggcggccg ccgccgcctc cgccgcgccg cgggaggggc 149040
gcaagcgcaa gagtcccggc ccggcccggc cgcccggagg cggcggcccg cgaccccga 149100 agacgaagaa gagcggcgcg gacgcccccg gctcggacgc ccgcgccccc ctcccgcgc 149160 cccctccac gccccggggg cccgagccca ccccgccca gccgcggcg gcccggggcg 149220 ccgcggcgca ggcccgcccg cgcccgtgg cgctgtcgcg ccggcccgcc gagggccccg 149280
accccctggg cggctggcgg cggcagcccc gggggcccag ccacacggcg cgcccgcgg 149340 ccgccgccct ggaggcctac tgctcccgc gcgccgtggc cgagctcacg gaccacccgc 149400
tgttccccgt ccctggcga ccggccctca tgtttgaccc gcgggccctg gcctcgatcg 149460
ccgcgcggtg cgcggggccc gccccgccg cccaggccgc gtggcggcgc gacgacgacg 149520
agaaccccca ccccacgggg gccgccgggg gccgcctctt tggccccctg cgcgcctcgg 149580
gcccgctgcg ccgcatggcg gcctggatgc gccagatccc cgaccccgag gacgtgcgcg 149640
tggtggtgct gtactcgccg ctgccggggcg aggacctggc cggcggcggg gcctcggggg 149700
ggccgccgga gtggtccgcc gagcgcggcg ggctgtcctg cctgctggcg gccctggcca 149760
accggctgtg cgggccggac acggccgcct gggcgggcaa ctggaccggc gccccgacg 149820 tgtcggcgct gggcgcgcag ggcgtgctgc tgctgtccac gcgggacctg gccttcgccg 149880
gggccgtgga gtttctgggg ctgctcgcca gcgccggcga ccggcggctc atcgtggtca 149940
acaccgtgcg cgcctgcgac tggcccgccg acgggcccgc ggtgtcgcgg cagcacgcct 150000
```

```
acctggcgtg cgacctgctg cccgccgtgc agtgcgccgt gcgctggccg gcggcgcggg    150060
acctgcgccg cacggtgctg gcctcgggcc gcgtgttcgg cccgggggtc ttcgcgcgcg    150120
tggaggccgc gcacgcgcgc ctgtaccccg acgcgccgcc gctgcgcctg tgccgcggcg    150180
gcaacgtgcg ctaccgcgtg cgcacgcgct tcggcccgga cacgccggtg cccatgtccc    150240
cgcgcgagta ccgccgggcc gtgctgccgg cgctggacgg ccgggcggcg gcctcgggga    150300
ccaccgacgc catggcgccc ggcgcgccgg acttctgcga ggaggaggcc cactcgcacc    150360
gcgcctgcgc gcgctggggc ctgggcgcgc cgctgcggcc cgtgtacgtg gcgctggggc    150420
gcgaggcggt gcgcgccggc ccggcccggt ggcgcgggcc gcggagggac ttttgcgccc    150480
gcgccctgct ggagcccgac gacgacgccc cccgctggt gctgcgcggc gacgacgacg     150540
acggcccggg ggcccgccg ccggcgccgc cggggattcg ctgggcctcg gccacggcc     150600
gcagcggcac cgtgctggcg gcggcggggg ccgtggaggt gctgggggcg gaggcgggct    150660
tggccacgcc cccgcgacgg gacgttgtgg actgggaagg cgcctgggac gaagacgacg    150720
gcggcgcgtt cgagggggac ggggtgctgt aacgggccgg gacggggcgg ggcgcttgtg    150780
aaacccgaag acgcaataaa cggcaacgac ctgattaagt tttgcagtag cgttgtttat    150840
tcgaggggcg ggaggggggcg aggggcggga gggggcgagg ggcgggaggg ggcgaggggc    150900
gggaggggc gaggggcggg aggggcgag gggcgggagg gggcgagggg cgggagggg      150960
cgaggggcgg gaggggcga ggggcgggag ggggcgaggg gcgggagggg gcgaggggcg     151020
ggaggggcg aggggcggga ggggcgaggg gcgggaggg ggcgaggggc gggaggggc       151080
gaggggcggg aggggcgag gggcgggagg gggcgagggg cggaggggg cgaggggcgg     151140
gagggggcga gggcgggag ggggcgaggg gcggtggtgg tgcgcgggcg ccccggagg      151200
gtttggatct ctgacctgag attggcggca ctgaggtaga gatgcccgaa ccccccgag     151260
ggagcgcggg acgcgctgg ggagggctgg ggctggggag ggctggggcc ggggagggct    151320
ggggccgggg agggctgggg ccggggaggg ctggggccgg ggagggctgg ggccggggag    151380
ggctggggct gggagggct ggggctgggg aggcggtg gtgtgtagca ggagcggtgt       151440
gttgcgccgg ggtacgtctg gaggagcggg aggtgcgcgg tgacgtgtgg atgaggaaca    151500
ggagttgttg cgcggtgagt tgtcgctgtg agttgtgttg ttgggcaggt gtggtggatg    151560
acgtgacgtg tgacgtgcgg attgcgccgt gctttgttgg tgttgtttta cctgtggcag    151620
cccgggcccc ccgcgggcgc gcgcgcgcgc aaaaaaggcg ggcggcggtc cggcggcgt     151680
gcgcgcgcgc ggcgggcgtg gggggcgggg ccgcgggagc gggggaggag cggggaggga    151740
gcgggggag gagcggggg aggagcgggg ggaggagcgg ggggaggagc gggggagga       151800
gcgggggag gagcggggg aggagcgggg ggaggagcgg ggggaggagc gggggagga       151860
gcgggggag gagcggggg aggagcgggg ggaggagcgg ggggaggagc gggggagga       151920
gcgggggagg agcggccaga ccccggaaac gggcccccc caaaacacac ccccgggg       151980
tcgcgcgcgg cccttttaaag gcgggcggcg g                                  152011
```

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ctggcaccca gcacaatg                                                    18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccgatccac acggagtact                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggacaggat gaactttgac                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgatagacat tagccaggag                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctcagagga gcctggctaa                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgacatctca attgctccag                                                  20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcacaaact ttcagagaca g                                                  21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acacagagct gcagaaatca gg                                                 22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggcagaaag cttgtctcaa                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcttcctcct tccttctggt                                                    20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acaaacccga gaaacaatga cc                                                 22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcatctgagg agtccgaaga                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acggccaggt catcactatt g                                                  21

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caagaaggaa ggctggaaaa ga                                            22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tccgagcaga gatcttcagg aa                                            22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgcaaccacc actcattctg ag                                            22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
accatgggag agaatgctga t                                             21

<210> SEQ ID NO 23
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gccaggaggt tgtgc                                                    15

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
gcaugcgacc ucuguuuga                                                19
```

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
ucaaacagag gucgcaugc                                                19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gcaugcgacc ucuguuuga                                                19

<210> SEQ ID NO 27
<211> LENGTH: 8
<212> TYPE: PRT
<213> ORGANISM: Herpes simplex virus

<400> SEQUENCE: 27

Ser Ser Ile Glu Phe Ala Arg Leu
1               5

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctttcgaagc ctttgctctg                                               20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
caccatgaat caaactgcga                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtgaggaac aagccagagc                                               20

<210> SEQ ID NO 31
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tcctgatttc tgcagctctg t                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agctcggcaa cagactcttc                                                20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcggaacagc agagacacag                                                20

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gttgtcgacg acgagcg                                                   17

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccctatggag atgacggaga                                                20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caaggcaggt ttctgaggag                                                20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
ctcatcctgc tgggtctgag                                                     20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctacgaggg ctatgctctc c                                                   21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caggagagca atttggagga                                                     20

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gctgatgcag gtacagcgt                                                      19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41 gtcagggtg gttattgcat                                                      20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaatttgggg tggaaaggtt                                                     20

<210> SEQ ID NO 43
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 43
gatgatcaaa gggatgtggc                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aagttccagg tgaaatggca                                              20

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gcacagagcc tcgcctt                                                 17

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cccagtgctg gagaaattgt                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gacctggtca ccatcagcat                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cctatggccc tcattctcac                                              20

<210> SEQ ID NO 49
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 49
tctttgatgt cacgcacgat ttc                                           23

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Cys Lys Asp Leu Glu Asp Leu Ser Gln Ile Gln Asn Arg
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Tyr Asp Asp Ala Leu Ile Ile Ser Glu His Ala Arg
1               5                   10

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ala Phe Phe His Val Cys Thr Gln Asn Pro Glu Asp Ser Glu Trp
1               5                   10                  15

Asp Arg Lys
```